United States Patent
Kim et al.

(10) Patent No.: US 12,234,516 B2
(45) Date of Patent: Feb. 25, 2025

(54) BIOMARKERS OF RESPONSE TO HIF-2-ALPHA INHIBITION IN CANCER AND METHODS FOR THE USE THEREOF

(71) Applicant: The Board of Regents of the University of Texas System, Austin, TX (US)

(72) Inventors: Min Soo Kim, Grand Prairie, TX (US); James Brugarolas, Irving, TX (US); Tae Hyun Hwang, Dallas, TX (US); Yang Xie, Coppell, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 499 days.

(21) Appl. No.: 17/206,895

(22) Filed: Mar. 19, 2021

(65) Prior Publication Data

US 2021/0222257 A1 Jul. 22, 2021

Related U.S. Application Data

(62) Division of application No. 15/761,534, filed as application No. PCT/US2016/052118 on Sep. 16, 2016, now abandoned.

(60) Provisional application No. 62/221,527, filed on Sep. 21, 2015.

(51) Int. Cl.
| | |
|---|---|
| *C12Q 1/6886* | (2018.01) |
| *A61P 35/00* | (2006.01) |
| *C12N 15/52* | (2006.01) |
| *C40B 40/08* | (2006.01) |
| *G01N 33/50* | (2006.01) |
| *G16B 25/00* | (2019.01) |
| *G16B 25/10* | (2019.01) |
| *G16B 25/20* | (2019.01) |
| *G16B 30/00* | (2019.01) |
| *G16H 50/20* | (2018.01) |
| *G16H 50/30* | (2018.01) |

(52) U.S. Cl.
CPC ........... *C12Q 1/6886* (2013.01); *A61P 35/00* (2018.01); *C12N 15/52* (2013.01); *C40B 40/08* (2013.01); *G01N 33/5091* (2013.01); *G16B 25/00* (2019.02); *G16B 25/10* (2019.02); *G16B 25/20* (2019.02); *G16B 30/00* (2019.02); *G16H 50/20* (2018.01); *G16H 50/30* (2018.01); *C12Q 2600/106* (2013.01); *C12Q 2600/112* (2013.01); *C12Q 2600/158* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 2003/0092019 A1 | 5/2003 | Meyer et al. | |
| 2005/0070474 A1* | 3/2005 | Krissansen | A61P 35/00 514/19.3 |
| 2009/0155796 A1 | 6/2009 | Ahmad et al. | |
| 2011/0166200 A1 | 7/2011 | Zhang et al. | |
| 2011/0213008 A1 | 9/2011 | Nakajima et al. | |
| 2014/0057914 A1* | 2/2014 | Jones | A61K 31/4245 548/131 |

OTHER PUBLICATIONS

Cobb et al (Crit Care Med 2002 Vol. 30 p. 2711) (Year: 2002).*
Enard et al. (Science 2002 Vol 296 p. 340) (Year: 2002).*
Bera et al., "NGEP, a gene encoding a membrane protein detected only in prostate cancer and normal prostate," *PNAS*, 101(9):3059-3064, 2004.
Chen et al., "Targeting Renal Cell Carcinoma with a HIF-2 antagonist," *Nature*, 539(7627):1-5, 2016.
Jiang et al., "Key regulators in prostate cancer identified by co-expression module analysis," *BMC Genomics*, 15(1015):1-13, 2014.
Juppner, "Functional properties of the PTH/PTHrP receptor," *Bone*, 17(2):39S-42S, 1995.
Kimbro et al., "Hypoxia-inducible factor-1 in human breast and prostate cancer," *Endocrine-Related Cancer*, 13(3):739-749, 2006.
Office Action issued in U.S. Appl. No. 15/761,534, mailed Mar. 26, 2020.
Office Action issued in U.S. Appl. No. 15/761,534, mailed Oct. 21, 2020.
Office Action issued in U.S. Appl. No. 15/761,534, mailed Sep. 20, 2019.
PCT International Preliminary Report on Patentability issued in corresponding PCT Application No. PCT/US2016/052118, mailed on Apr. 5, 2018.
PCT International Search Report and Written Opinion issued in corresponding PCT Application No. PCT/US2016/052118, mailed on Jan. 30, 2017.
Petrella et al., "PTEN suppression of YY1 induces HIF-2 activity in von hippel lindau null renal cell carcinoma," *Cancer Biology and Therapy*, 8:1389-1401, 2009.
Sandlund et al., "Hypoxia-inducible factor-2a mRNA expression in human renal cell carcinoma," *Acta Oncol.*, 48(6):909-914, 2009.
Schödel et al., "Common genetic variants at the 11q13.3 renal cance3r susceptibility locus influence binding of HIF to an enhancer of cyclin D1 expression," *Nature Genetics*, 44:420-425, 2012.
Zhao et al., "The role of hypoxia-inducible factor-2 in digestive system cancers," *Cell Death Dis.*, 2015(6):1-9, 2015.

* cited by examiner

*Primary Examiner* — Katherine D Salmon
(74) *Attorney, Agent, or Firm* — Parker Highlander PLLC

(57) ABSTRACT

Described herein are methods and systems for identifying and/or treating subjects having cancer who are more likely to respond to treatment with an inhibitor of the transcription factor HIF-2α.

5 Claims, 6 Drawing Sheets

BIOMARKERS OF RESPONSE TO HIF-2-ALPHA INHIBITION IN CANCER AND METHODS FOR THE USE THEREOF

This application is a divisional of U.S. application Ser. No. 15/761,534, filed Mar. 20, 2018, which is a national phase application under 35 U.S.C. § 371 of International Application No. PCT/US2016/052118, filed Sep. 16, 2016, which claims benefit of priority to U.S. Ser. No. 62/221,527 filed Sep. 21, 2015, the entire contents of each of which are hereby incorporated by reference.

BACKGROUND

An adequate supply of oxygen to tissues is essential in maintaining mammalian cell function and physiology. A deficiency in oxygen supply to tissues is a characteristic of a number of pathophysiologic conditions in which there is insufficient blood flow to provide adequate oxygenation, for example, ischemic disorders, cancer, and atherosclerosis. The hypoxic (low oxygen) environment of tissues activates a signaling cascade that drives the induction or repression of the transcription of a multitude of genes implicated in events such as angiogenesis (neo-vascularization), glucose metabolism, and cell survival or death. A key to this hypoxic transcriptional response lies in the transcription factors, the hypoxia-inducible factors (HIFs).

HIFs consist of an oxygen-sensitive HIFα subunit and constitutively expressed HIFβ subunit. When HIFs are activated, the HIFα and HIFβ subunits assemble a functional heterodimer (the a subunit heterodimerizes with the subunit). Both HIFα and HIFβ have two identical structural characteristics, a basic helix-loop-helix (bHLH) and PAS domains (PAS is an acronym referring to the first proteins, PER, ARNT, SIM, in which this motif was identified). There are three human HIFα subunits (HIF-1α, HIF-2α, and HIF-3α) that are oxygen sensitive. Among the three subunits, HIF-1α is the most ubiquitously expressed and induced by low oxygen concentrations in many cell and tissue types. HIF-2α exhibits more restricted tissue-specific expression, and may also be differentially regulated by nuclear translocation. HIF-3α also exhibits conservation with HIF-1α and HIF-2α in the HLH and PAS domains. HIF-1β (also referred to as ARNT—Aryl Hydrocarbon Receptor Nuclear Translocator), the dimerization partner of the HIFα subunits, is constitutively expressed in all cell types and is not regulated by oxygen concentration. HIFs are disregulated in a vast array of cancers through hypoxia-dependent and independent mechanisms and their expression is associated with poor patient prognosis.

Cancer is the second leading cause of human death. Worldwide, millions of people die from cancer every year. In the United States alone, cancer causes the death of well over a half-million people annually, with some 1.4 million new cases diagnosed per year. Deaths resulting from cancer generally are on the rise. Certain therapies are known to be more effective in some patient populations than others. Understanding these drug-responsive subtypes is of significant interest to patients and health care professionals so as to avoid a trial and error approach of treatment.

SUMMARY

As such, there is a pressing need for a method of stratifying patients into populations based on the predicted sensitivity or resistance of a patient population to a particular treatment, including treatment with HIF-2α inhibitors. The present disclosure addresses this need in the art through the assessment of biomarkers that are indicative of patient populations that would be responsive during treatment with a HIF-2α inhibitor. This allows for more timely and aggressive treatment as opposed to a trial and error approach.

In one aspect, the disclosure provides a method of treating a subject for cancer. In one embodiment, the method comprises administering an effective dose of a HIF-2α inhibitor to the subject, wherein a cancer cell of the subject exhibits (1) differential expression of one or more genes or gene products, or (2) aberrant activity of one or more gene products encoded by the one or more genes, wherein the one or more genes predict for HIF-2α inhibitor sensitivity. In some embodiments, the differential expression of the one or more genes is assessed by detecting a level of mRNA transcribed from the one or more genes. In some embodiments, the differential expression of the one or more genes is assessed by detecting a level of cDNA produced from reverse transcription of mRNA transcribed from the one or more genes. In some embodiments, the differential expression of the one or more genes is assessed by detecting a level of polypeptide encoded by the one or more genes. In some embodiments, the one or more genes are selected from Table 3. In some embodiments, the one or more genes are involved in a pathway selected from the group consisting of hypoxia signaling, DNA damage response, GPCR signaling, insulin signaling, non-canonical Wnt signaling, dopaminiergic signaling, ion and solute transport signaling, and neurotrophic growth factor signaling. In some embodiments, the differential expression comprises overexpression of the one or more genes, wherein the one or more genes are selected from Table 4. In some embodiments, the differential expression comprises underexpression of the one or more genes, wherein the one or more genes are selected from Table 5. In some embodiments, the differential expression comprises overexpression of the one or more genes, wherein the one or more genes are involved in a pathway selected from the group consisting of hypoxia signaling, GPCR signaling, dopaminiergic signaling, and neurotrophic growth factor signaling. In some embodiments, the differential expression comprises underexpression of the one or more genes, wherein the one or more genes are involved in a pathway selected from the group consisting of DNA damage response, insulin signaling, non-canonical Wnt signaling, and ion and solute transport. In some embodiments, the differential expression is assessed relative to a reference level. In some embodiments, the reference level is derived from a patient population having a known HIF-2α inhibitor treatment status.

In another aspect, the disclosure provides a method of treating a subject having cancer. In some embodiments, the method comprises: (a) screening the subject for the presence or absence of at least one biomarker for HIF-2α inhibitor response; (b) administering a HIF-2α inhibitor to the subject if the at least one biomarker for HIF-2α inhibitor response is determined to be present; and (c) applying an alternative therapy to the subject if the at least one biomarker for HIF-2α inhibitor response is determined to be absent, thereby treating the subject. In some embodiments, presence of the at least one biomarker comprises an expression level of the at least one biomarker that is equal to or above a reference level. In some embodiments, presence of the at least one biomarker comprises overexpression of one or more genes selected from Table 4. In some embodiments, absence of the at least one biomarker comprises underexpression of one or more genes selected from Table 5. In some embodiments, the alternative therapy is chemotherapy, radiotherapy, or surgery.

In another aspect, the disclosure provides a method of treating a plurality of cancer cells with a HIF-2α inhibitor. In some embodiments, the method comprises: (a) assessing, by nucleic acid hybridization assay and/or protein assay, an expression level of at least one biomarker selected from Table 4 in a biological sample comprising a cancer cell of the plurality of cells, or a portion thereof; and (b) administering an effective dose of the HIF-2α inhibitor to the plurality of cells if the at least one biomarker is present in the sample at an increased level as compared to a reference level. In some embodiments, the expression level of the at least one biomarker is assessed by detecting a level of mRNA transcribed from the at least one biomarker. In some embodiments, the expression level of the at least one biomarker is assessed by detecting a level of cDNA produced from reverse transcription of mRNA transcribed from the at least one biomarker. In some embodiments, the expression level of the at least one biomarker is assessed by detecting a level of polypeptide encoded by the at least one biomarker. In some embodiments, the at least one biomarker is present in the sample at an increased level of at least 2-fold as compared to the reference level. In some embodiments, the biological sample is a tissue sample. In some embodiments, the tissue sample is fixed, paraffin-embedded, fresh, or frozen. In some embodiments, the tissue sample is derived from fine needle, core, or other types of biopsy.

In another aspect, the disclosure provides a method of measuring a likelihood that a subject having cancer will exhibit a clinically beneficial response to treatment with a HIF-2α inhibitor. In some embodiments, the method comprises: (a) measuring, in a sample from the subject comprising a cancer cell, an expression level of a plurality of genes; (b) generating an expression profile based on a comparison between the expression level of the plurality of genes in the sample from the subject and a corresponding expression level in a control sample; and (c) calculating, using a computer system, a likelihood of response of the subject to treatment with a HIF-2α inhibitor based on the expression profile, wherein the likelihood is adjusted upward for each gene in the plurality exhibiting an increased expression level relative to the control sample, wherein each gene in the plurality is selected from Table 4, or is a gene involved in one or more of hypoxia signaling, GPCR signaling, dopaminiergic signaling, and neurotrophic growth factor signaling. In some embodiments, the expression level of the plurality of genes is measured by detecting a level of mRNA transcribed from the plurality of genes. In some embodiments, the expression level of the plurality of genes is measured by detecting a level of cDNA produced from reverse transcription of mRNA transcribed from the plurality of genes. In some embodiments, the expression level of the plurality of genes is measured by detecting a level of polypeptide encoded by the plurality of genes. In some embodiments, the method further comprises preparing a report comprising a prediction of the likelihood of response of the subject to treatment with a HIF-2α inhibitor.

In another aspect, the disclosure provides a method of selecting an anti-tumor therapy against a cancer. In some embodiments, the method comprises: (a) obtaining a pretreatment sample comprising a cancer cell; (b) measuring a biomarker in the pretreatment sample to determine whether it is overexpressed in the pretreatment sample relative to a reference level; and (c) selecting a HIF-2α inhibitor for treatment of the subject based on the measured overexpression of (b), wherein the biomarker is a predictor of HIF-2α inhibitor sensitivity. In some embodiments, the biomarker is selected from Table 4. In some embodiments, the biomarker is a gene or gene product involved in a pathway selected from the group consisting of hypoxia signaling, GPCR signaling, dopaminiergic signaling, and neurotrophic growth factor signaling. In some embodiments, the biomarker is measured by detecting a level of mRNA transcribed from the biomarker. In some embodiments, the biomarker is measured by detecting a level of cDNA produced from reverse transcription of mRNA transcribed from the biomarker. In some embodiments, the biomarker is measured by detecting a level of polypeptide encoded by the biomarker.

In another aspect, the disclosure provides a method of categorizing a cancer status of a subject. In some embodiments, the method comprises: (a) obtaining a tumor sample from the subject; (b) measuring an expression level of a plurality of genes in the tumor sample; (c) generating an expression profile based on a comparison between the expression level of the plurality of genes in the sample from the subject and a corresponding expression level obtained from a reference sample derived from a different subject having a known cancer status; and (d) categorizing the cancer status of the subject of (a) based on the expression profile. In some embodiments, a gene in the plurality predicts for sensitivity or resistance to treatment with a HIF-2α inhibitor. In some embodiments, a gene in the plurality is selected from Table 3. In some embodiments, a gene in the plurality is involved in a pathway selected from the group consisting of hypoxia signaling, DNA damage response, GPCR signaling, insulin signaling, non-canonical Wnt signaling, dopaminiergic signaling, ion and solute transport signaling, and neurotrophic growth factor signaling. In some embodiments, the cancer status is categorized as likely sensitive to treatment with a HIF-2α inhibitor if a gene in the plurality that predicts for HIF-2α inhibitor sensitivity is overexpressed, or likely resistant to treatment with a HIF-2α inhibitor if a gene in the plurality that predicts for HIF-2α inhibitor resistance is overexpressed. In some embodiments, the expression level of the plurality of genes is measured by detecting a level of mRNA transcribed from the plurality of genes. In some embodiments, the expression level of the plurality of genes is measured by detecting a level of cDNA produced from reverse transcription of mRNA transcribed from the plurality of genes. In some embodiments, the expression level of the plurality of genes is measured by detecting a level of polypeptide encoded by the plurality of genes.

In another aspect, the disclosure provides a method of assessing a likelihood of a subject having cancer exhibiting a clinically beneficial response to treatment with a HIF-2α inhibitor. In some embodiments, the method comprises: (a) assessing an expression level of a plurality of biomarkers selected from: (i) AC074091.13, ANO7, AVPR2, BCL2L11, BRCC3, C1QL1, CAMK2D, CHRDL2, CHST1, CORO6, CPE, CRYM, CXCR4, DEK, EPAS1, EPO, EXOG, EZH2, FAM180A, FAM65B, FAM65C, GFRA2, GLI1, HAGHL, HIF1A, HMGA1, HRH2, HSPB7, IGFBP1, INHBB, ITGB8, KCNIP3, KLHL3, KNDC1, LAMB1, LOX, LYPD1, MCAM, MCIDAS, MEST, MRS2, NFASC, NPTX1, PASK, PFN2, PHYHIP, PICALM, PKNOX2, PLAG1, POSTN, PPA2, PPAPDC3, PRICKLE1, PRR5, PTHLH, PTPRJ, RASGEFIB, RDH13, RGL2, SLC36A4, SLC6A3, SLCO5A1, SLITRK4, SORCS3, ST3GAL5, SVIP, TBC1D4, TMEM30B, TPST2, VGLL4, WFIKKN1, ZKSCAN3, ZKSCAN8, ZSCAN16, and ZSCAN9; and (ii) a gene or gene product involved in a pathway selected from the group consisting of hypoxia signaling, DNA damage response, GPCR signaling, insulin signaling, non-canonical Wnt signaling, dopaminiergic signaling, ion and solute transport signaling, and neurotrophic growth factor signaling; in a biological sample comprising a cancer cell; (b) calculating, using a computer system, a weighted probability of HIF-2α inhibitor responsiveness based on the expression level of the plurality of biomarkers as compared to a corresponding level in one or more control samples; (c) designating the subject as having a high probability of exhibiting a clinically beneficial response to treatment with a HIF-2α inhibitor if the weighted probability corresponds to at least 2 times a baseline probability, where the baseline probability represents a likelihood that the subject will exhibit a clinically beneficial response to treatment with a HIF-2α inhibitor before obtaining the weighted probability of (b); and (d) transmitting information concerning the likelihood to a receiver. In some embodiments, the expression level of the plurality of biomarkers is assessed by detecting a level of mRNA transcribed from the plurality of biomarkers. In some embodiments, the expression level of the plurality of biomarkers is assessed by detecting a level of cDNA produced from reverse transcription of mRNA transcribed from the plurality of biomarkers. In some embodiments, the expression level of the plurality of biomarkers is assessed by detecting a level of polypeptide encoded by the plurality of genes. In some embodiments, the method further comprises providing a recommendation based on the weighted probability. In some embodiments, the recommendation comprises further monitoring. In some embodiments, the recommendation comprises treating the subject with a HIF-2α inhibitor. In some embodiments, the recommendation comprises discontinuing therapy, chemotherapy, radiotherapy, or surgery. In some embodiments, the method further comprises selecting a treatment based on the weighted probability. In some embodiments, the method further comprises administering a HIF-2α inhibitor based on the weighted probability.

In one aspect, the disclosure provides a system for assessing a likelihood of a subject having cancer exhibiting a clinically beneficial response to treatment with a HIF-2α inhibitor. In some embodiments, the system comprises: (a) a memory unit configured to store information concerning an expression level of a plurality of biomarkers selected from: (i) AC074091.13, ANO7, AVPR2, BCL2L11, BRCC3, C1QL1, CAMK2D, CHRDL2, CHST1, CORO6, CPE, CRYM, CXCR4, DEK, EPAS1, EPO, EXOG, EZH2, FAM180A, FAM65B, FAM65C, GFRA2, GLI1, HAGHL, HIF1A, HMGA1, HRH2, HSPB7, IGFBP1, INHBB, ITGB8, KCNIP3, KLHL3, KNDC1, LAMB1, LOX, LYPD1, MCAM, MCIDAS, MEST, MRS2, NFASC, NPTX1, PASK, PFN2, PHYHIP, PICALM, PKNOX2, PLAG1, POSTN, PPA2, PPAPDC3, PRICKLE1, PRR5, PTHLH, PTPRJ, RASGEFIB, RDH13, RGL2, SLC36A4, SLC6A3, SLCO5A1, SLITRK4, SORCS3, ST3GAL5, SVIP, TBC1D4, TMEM30B, TPST2, VGLL4, WFIKKN1, ZKSCAN3, ZKSCAN8, ZSCAN16, and ZSCAN9; and (ii) a gene or gene product involved in a pathway selected from the group consisting of hypoxia signaling, DNA damage response, GPCR signaling, insulin signaling, non-canonical Wnt signaling, dopaminiergic signaling, ion and solute transport signaling, and neurotrophic growth factor signaling; in a biological sample comprising a cancer cell from the subject; and (b) one or more processors alone or in combination programmed to: (1) determine a weighted probability of HIF-2α inhibitor responsiveness based on the expression level of a plurality of biomarkers as compared to a corresponding expression level in one or more control samples; and (2) designate the subject as having a high probability of exhibiting a clinically beneficial response to treatment with a HIF-2α inhibitor if the weighted probability corresponds to at least 2 times a baseline probability, where the baseline probability represents a likelihood that the subject will exhibit a clinically beneficial response to treatment with a HIF-2α inhibitor before obtaining the weighted probability of (b)(1). In some embodiments, the expression level of the plurality of biomarkers is assessed by detecting a level of mRNA transcribed from the plurality of biomarkers. In some embodiments, the expression level of the plurality of biomarkers is assessed by detecting a level of cDNA produced from reverse transcription of mRNA transcribed from the plurality of biomarkers. In some embodiments, the expression level of the plurality of biomarkers is assessed by detecting a level of polypeptide encoded by the plurality of genes. In some embodiments, the cancer is selected from the group consisting of lung cancer, colon cancer, pancreatic cancer, liver cancer, head and neck cancer, stomach cancer, and renal cell carcinoma. In some embodiments, the renal cell carcinoma is clear cell renal cell carcinoma. In some embodiments, the subject is a human.

In one aspect, the disclosure provides a method of identifying biomarkers for sensitivity to a HIF-2α inhibitor. In some embodiments, the method comprises: (a) administering the HIF-2α inhibitor to a plurality of non-human subjects having a proliferative disorder; (b) measuring an expression level of a plurality of genes in the subjects; and (c) generating a biomarker profile for responsiveness to the HIF-2α inhibitor, wherein the biomarker profile comprises genes, and optionally associated expression levels, that are expressed at higher levels among non-human subjects in which cancer was most ameliorated by the HIF-2α inhibitor relative to corresponding levels among non-human subjects in which cancer was least ameliorated. In some embodiments, the expression level of the plurality of genes is measured by detecting a level of mRNA transcribed from the plurality of genes. In some embodiments, the expression level of the plurality of genes is measured by detecting a level of cDNA produced from reverse transcription of mRNA transcribed from the plurality of genes. In some embodiments, the expression level of the plurality of genes is measured by detecting a level of polypeptide encoded by the plurality of genes.

In practicing any of the methods described herein, the cancer may be selected from the group consisting of lung cancer, colon cancer, pancreatic cancer, liver cancer, head and neck cancer, stomach cancer, and renal cell carcinoma. In some embodiments, the renal cell carcinoma is clear cell renal cell carcinoma. Similarly, the cancer cell of any of the methods described herein may be selected from the group consisting of a lung cancer cell, a colon cancer cell, a pancreatic cancer cell, a liver cancer cell, a head and neck cancer cell, a stomach cancer cell, and a renal cell carcinoma cell. In some embodiments, the renal cell carcinoma cell is clear cell renal cell carcinoma cell. In some embodiments, the subject of a method described herein is a human. In some embodiments, the HIF-2α inhibitor is administered as monotherapy. In some embodiments, the HIF-2α inhibitor is co-administered with at least one other anti-cancer agent.

In some embodiments, the HIF-2α inhibitor is a compound of Formula I:

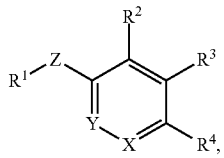

Formula I or a pharmaceutically acceptable salt or prodrug thereof, wherein:

X is $CR^5$ or N;

Y is $CR^6$ or N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl, heteroaryl, aralkyl, heteroarylalkyl, acyl or cyano;

$R^2$ is nitro, carboxaldehyde, carboxyl, ester, amido, cyano, halo, sulfonyl, alkyl, alkenyl, alkynyl or heteroalkyl;

$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;

$R^4$ is nitro, halo, cyano, alkyl, cycloalkyl, heteroaryl, carboxyl, sulfinyl, sulfonamidyl, sulfonyl or sulfoximinyl; and $R^5$, $R^6$, $R^7$ and $R^8$ are independently hydrogen, halo, hydroxy, cyano, alkyl or alkoxy.

In some embodiments of compounds of Formula I, $R^1$ is phenyl, monocyclic heteroaryl or bicyclic heteroaryl. In some embodiments, $R^1$ is phenyl or pyridyl. In yet other embodiments, $R^1$ is cycloalkyl or heterocycloalkyl. Compounds of Formula I are also provided wherein $R^1$ is substituted with at least one substituent selected from the group consisting of halo, $C_1$-$C_4$ alkyl, $C_1$-$C_4$ alkoxy and cyano.

In some embodiments of compounds of Formula I, $R^2$ and $R^3$ are independently selected from halo, cyano and alkyl. In some further embodiments, $R^3$ is —(CH$_2$)$_n$OH and n is 1, 2 or 3. In still other embodiments, n is 1.

In some embodiments of compounds of Formula I, $R^4$ is cyano, fluoroalkyl, sulfinyl, sulfonamidyl, sulfonyl or sulfoximinyl. In other embodiments, $R^4$ is fluoroalkyl or alkylsulfonyl.

In some embodiments of compounds of Formula I, $R^2$ and $R^3$ are independently selected from halo, cyano and alkyl; and $R^4$ is cyano, fluoroalkyl, sulfinyl, sulfonamidyl, sulfonyl or sulfoximinyl. In another embodiment, $R^3$ is CH$_2$OH.

In some embodiments, Z is —O—. In some embodiments, Z is —S—. In still other embodiments, Z is —N(R$^8$)—. In another embodiment, Z is —C(HR$^7$)—. In some embodiments, Z is absent. In some embodiments, X is N and Y is $CR^6$. In another embodiment, X is $CR^5$ and Y is N. In yet another embodiment, X is N and Y is N. In still another embodiment, X is $CR^5$ and Y is $CR^6$.

In some embodiments, the HIF-2α inhibitor is a compound of Formula I-C:

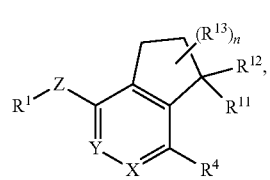

Formula I-C or a pharmaceutically acceptable salt or prodrug thereof, wherein:

X is $CR^5$ or N;

Y is $CR^6$ or N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl, heteroaryl, aralkyl, heteroarylalkyl, acyl or cyano;

$R^4$ is nitro, halo, cyano, alkyl, cycloalkyl, heteroaryl, carboxyl, sulfinyl, sulfonamidyl, sulfonyl or sulfoximinyl;

$R^5$, $R^6$, $R^7$ and $R^8$ are independently hydrogen, halo, hydroxy, cyano, alkyl or alkoxy;

$R^{11}$ is hydrogen, halo, hydroxy, alkoxy or amino;

$R^{12}$ is hydrogen, alkyl, alkenyl or alkynyl; or $R^{11}$ and $R^{12}$ in combination form oxo or oxime;

each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and n is 0, 1, 2, 3 or 4.

In some embodiments of compounds of Formula I-C, $R^1$ is phenyl, monocyclic heteroaryl or bicyclic heteroaryl. In some embodiments, $R^1$ is phenyl or pyridyl. In yet other embodiments, $R^1$ is cycloalkyl or heterocycloalkyl. Compounds of Formula I-C are also provided wherein $R^1$ is substituted with at least one substituent selected from the group consisting of halo, $C_1$-$C_4$ alkyl, $C_1$-$C_4$ alkoxy and cyano.

In some embodiments of compounds of Formula I-C, $R^4$ is cyano, fluoroalkyl, sulfinyl, sulfonamidyl, sulfonyl or sulfoximinyl. In other embodiments, $R^4$ is fluoroalkyl or alkylsulfonyl. In some other embodiments, $R^{11}$ is hydroxy or amino. In further embodiments, $R^{11}$ is hydroxy. In yet other embodiments, $R^{12}$ is hydrogen. In yet another embodiment, $R^{13}$ is fluoro and n is 1, 2 or 3.

In some embodiments of compounds of Formula I-C, $R^4$ is cyano, fluoroalkyl, sulfinyl, sulfonamidyl, sulfonyl or sulfoximinyl; $R^{11}$ is hydroxy or amino; and $R^{12}$ is hydrogen. In still another embodiment, $R^{13}$ is fluoro. In yet another embodiment, Z is —O—. In some embodiments, Z is —S—. In still other embodiments, Z is —N(R$^8$)—. In another embodiment, Z is —C(HR$^7$). In some embodiments, Z is absent.

In some embodiments of compounds of Formula I-C, $R^4$ is fluoroalkyl; n is 0, 1, 2 or 3; Z is —O—; $R^{11}$ is hydroxy; and $R^{12}$ is hydrogen. In some embodiments, $R^4$ is sulfonyl; n is 0, 1, 2 or 3; Z is —O—; $R^{12}$ is hydroxy; and $R^{12}$ is hydrogen. In some further embodiments, $R^1$ is phenyl, pyridyl, cycloalkyl or heterocycloalkyl.

In some embodiments, X is N and Y is $CR^6$. In another embodiment, X is $CR^5$ and Y is N. In yet another embodiment, X is N and Y is N. In still another embodiment, X is $CR^5$ and Y is $CR^6$.

In some embodiments, the HIF-2α inhibitor is a compound selected from Table 1.

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
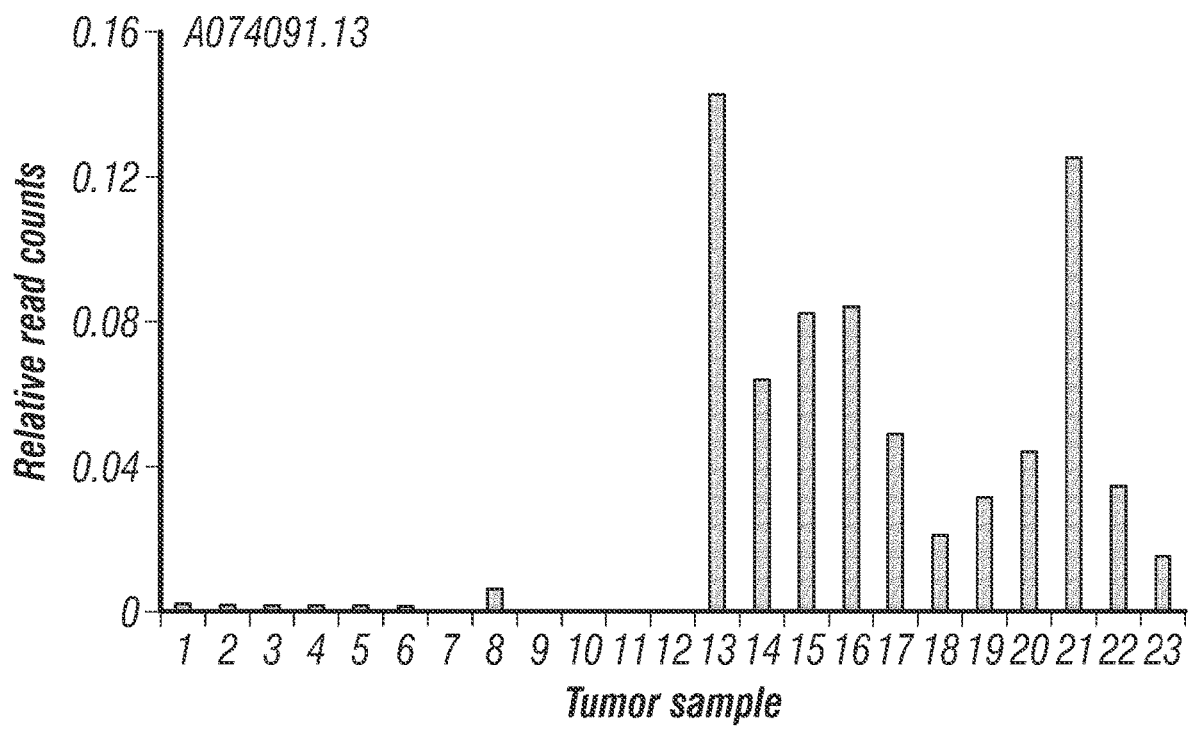
FIG. 1. Examples of genes that are differentially expressed in tumors that are sensitive or resistant to Compound 15. Data shown are relative read counts from RNA sequencing of untreated tumors. Tumors that are sensitive to Compound 15 have lower relative expression of A074091.13 and CORO6, but higher expression of C1QL1 and CPE.
Figure 1:
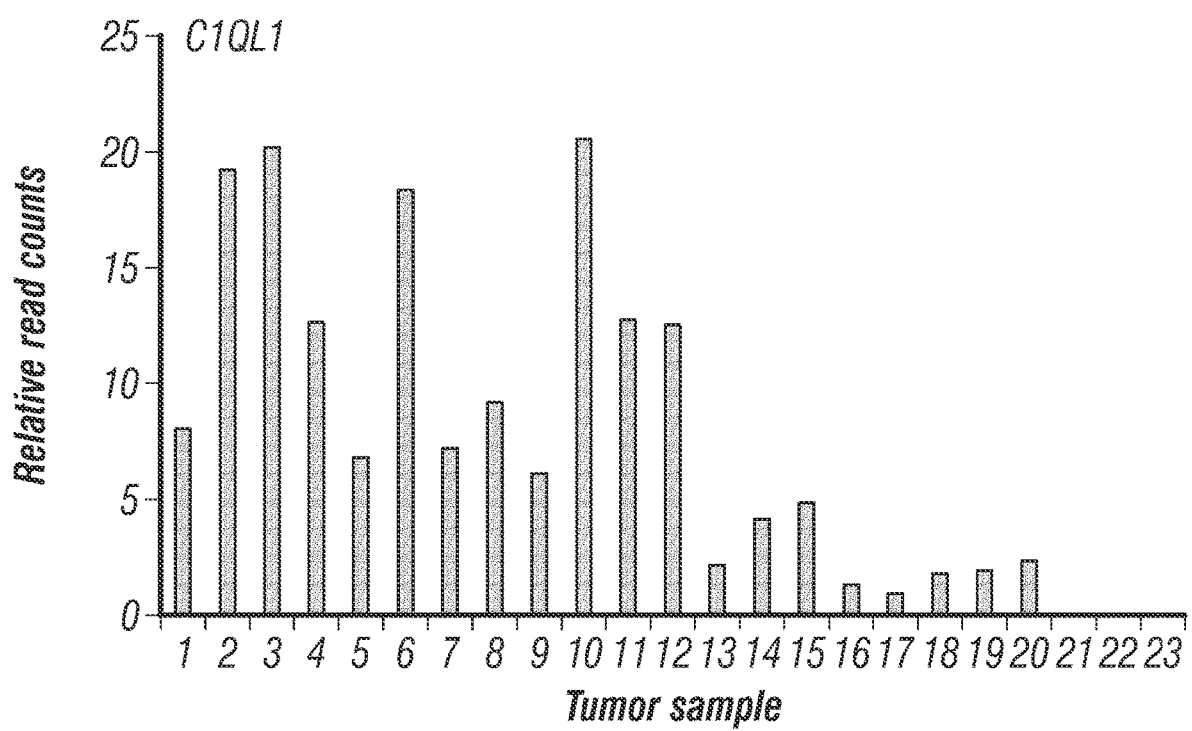
Figure 1:
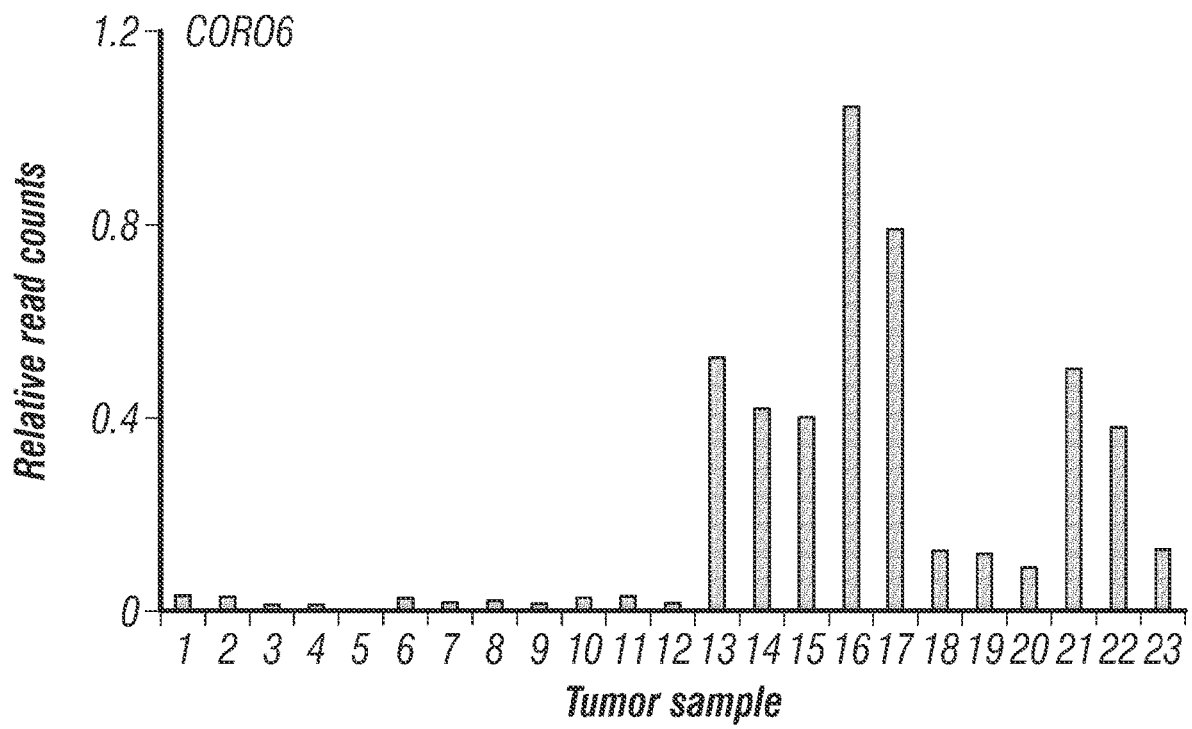
Figure 1:
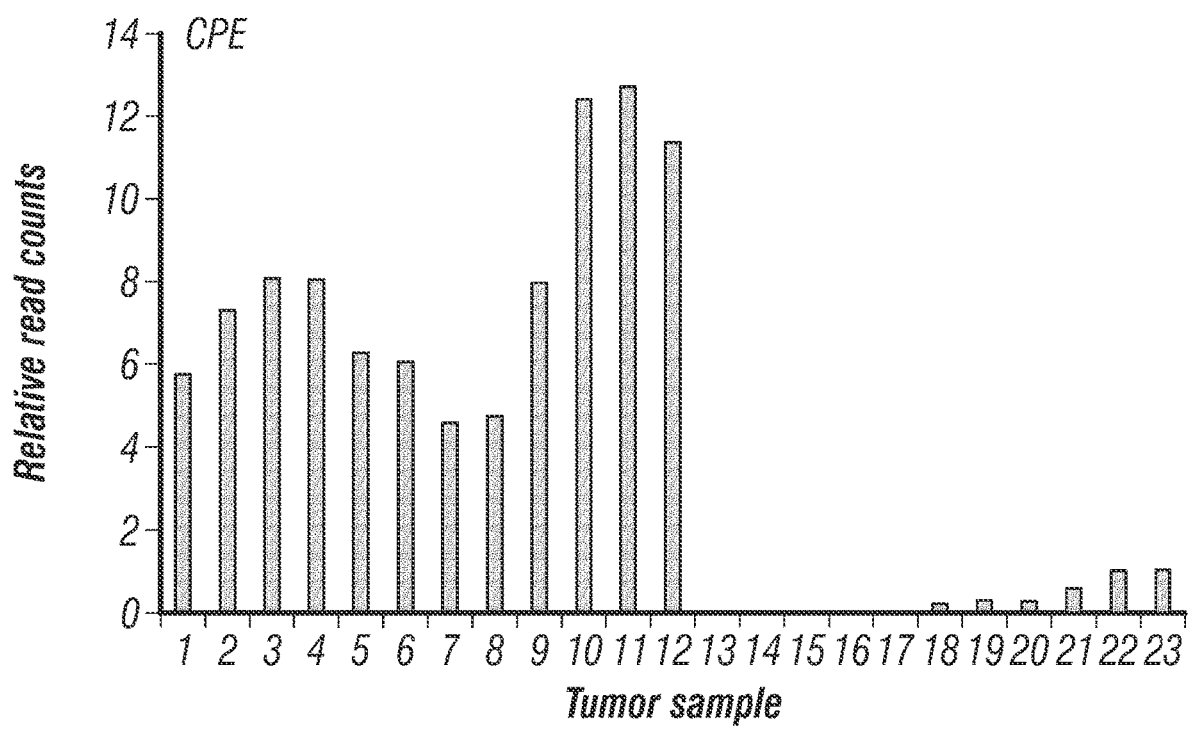

While preferred embodiments of the present disclosure have been shown and described herein, it will be obvious to those skilled in the art that such embodiments are provided by way of example only. Numerous variations, changes and substitutions will now occur to those skilled in the art without departing from the disclosure. It should be understood that various alternatives to the embodiments of the disclosure described herein may be employed in practicing the disclosure. It is intended that the appended claims define the scope of the disclosure and that methods and structures within the scope of these claims and their equivalents be covered thereby.

Unless defined otherwise, all technical and scientific terms used herein have the same meaning as is commonly understood by one of skill in the art to which this disclosure belongs. All patents and publications referred to herein are incorporated by reference.

As used in the specification and claims, the singular form "a", "an" and "the" includes plural references unless the context clearly dictates otherwise. For example, reference to "a cell" includes a plurality of cells, including mixtures thereof.

"About" as used herein when referring to a measurable value such as an amount, a duration, and the like, is meant to encompass variations of ±10% of a stated number or value.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleotide probe" or "probe" refers to a polynucleotide used for detecting or identifying its corresponding target polynucleotide in a hybridization reaction.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

As used herein, "expression" refers to the process by which a polynucleotide is transcribed into mRNA and/or the process by which the transcribed mRNA (also referred to as a "transcript") is subsequently translated into peptides, polypeptides, or proteins. The transcripts and the encoded polypeptides are collectively referred to as "gene product." If the polynucleotide is derived from genomic DNA, expression may include splicing of the mRNA in a eukaryotic cell. The level of expression (or alternatively, the "expression level") of an AVPR2 gene can be determined, for example, by determining the level of AVPR2 polynucleotides, polypeptides, and/or gene products.

"Differentially expressed" or "differential expression" as applied to a nucleotide sequence (e.g., a gene) or polypeptide sequence in a subject, refers to the differential production of the mRNA transcribed and/or translated from the nucleotide sequence or the protein product encoded by the nucleotide sequence. A differentially expressed sequence may be overexpressed or underexpressed as compared to the expression level of a control. As used herein, overexpression is an increase in expression and generally is at least 1.25 fold, or alternatively, at least 1.5 fold, or alternatively, at least 2 fold, or alternatively, at least 3 fold, or alternatively, at least 4 fold, or alternatively, at least 10 fold expression over that detected in a control. As used herein, underexpression is a reduction in expression and generally is at least 1.25 fold, or alternatively, at least 1.5 fold, or alternatively, at least 2 fold, or alternatively, at least 3 fold, or alternatively, at least 4 fold, or alternatively, at least 10 fold expression under that detected in a control. Underexpression also encompasses absence of expression of a particular sequence as evidenced by the absence of detectable expression in a test subject when compared to a control.

"Signal transduction" is a process during which stimulatory or inhibitory signals are transmitted into and within a cell to elicit an intracellular response. A molecule can mediate its signaling effect via direct or indirect interaction with downstream molecules of the same pathway or related pathway(s). For instance, HIF-2α signaling can involve a host of downstream molecules including but not limited to one or more of the following proteins: HMOX1, SFTPA1, CXCR4, PAI1, BDNF, hTERT, ATP7A, and VEGF.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "biomarker" and "marker" are used interchangeably herein to refer to a molecule which is differentially present in a sample taken from a subject of one phenotypic status (e.g., having a cancer that is sensitive to a HIF-2α inhibitor) as compared with another phenotypic status (e.g., having a cancer that is resistant to a HIF-2α inhibitor). A biomarker is differentially present between different phenotypic statuses if the mean or median expression level of the biomarker in the different groups is calculated to be statistically significant. Common tests for statistical significance include, for example, t-test, ANOVA, Kruskal-Wallis, Wilcoxon, Mann-Whitney and odds ratio. Biomarkers, alone or in combination, can provide measures of relative risk that a subject belongs to one phenotypic status or another. Therefore, they are useful as markers for disease (diagnostics), therapeutic effectiveness of a drug (theranostics) and drug toxicity. The polynucleotides and polypeptides described herein can be used as biomarkers for certain cancers described herein.

A "control" is an alternative subject or sample used in an experiment for comparison purpose.

The term "reference level" refers to a control level used to evaluate a test level. In some examples, a reference level may be a control. For example, a biomarker may be considered to be underexpressed when the expression level of that biomarker is lower than a reference level. The reference level can be determined by a plurality of methods, provided that the resulting reference level accurately provides a level of a biomarker above which exists a first group of subjects having a different probability of exhibiting a clinically beneficial response to treatment with a HIF-2α inhibitor than that of a second group of patients having levels of the biomarker below the reference level. The reference level may be determined, for example, by measuring the level of expression of a biomarker in tumorous or non-tumorous cancer cells from the same tissue as the tissue of the cancer cells to be tested. In some examples, the reference level may be a level of a biomarker determined in vitro. A reference level may be determined by comparison of the level of a biomarker in populations of subjects having the same cancer. Two or more separate groups of subjects may be determined by identification of subsets of populations of the cohort that have the same or similar levels of a biomarker. Determination of a reference level can then be made based on a level that distinguishes these separate groups. A reference level may be a single number, equally applicable to every subject, or a reference level can vary according to specific subpopulations of subjects. For example, older men may have a different reference level than younger men for the same cancer, and women may have a different reference level than men for the same cancer. Furthermore, the reference level may be some level determined for each subject individually. For example, the reference level may be a ratio of a biomarker level in a cancer cell of a subject relative to the biomarker level in a normal cell within the same subject. In some embodiments, a reference level is a numerical range of gene expression that is obtained from a statistical sampling from a population of individuals having cancer. The responsiveness of the individuals having cancer to treatment with a HIF-2α inhibitor may be known. In certain embodiments, the reference level is derived by comparing gene expression to a control gene that is expressed in the same cellular environment at relatively stable levels (e.g. a housekeeping gene such as an actin). Comparison to a reference level may be a qualitative assessment or a quantitative determination.

The terms "determining," "measuring," "evaluating," "assessing," "assaying," "testing," and "analyzing" are used interchangeably herein to refer to any form of measurement, and include determining if an analyte is present or not (e.g., detection). These terms can include both quantitative and/or qualitative determinations. Assessing may be relative or absolute. A relative amount could be, for example, high, medium or low. An absolute amount could reflect the measured strength of a signal or the translation of this signal strength into another quantitative format, such as micrograms/mL. "Detecting the presence of" can include determining the amount of something present, as well as determining whether it is present or absent.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to a subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment", "treating", "palliating" and "ameliorating" are used interchangeably. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "selective inhibition" or "selectively inhibit" as applied to a biologically active agent refers to the agent's ability to selectively reduce the target signaling activity as compared to off-target signaling activity, via direct or indirect interaction with the target.

The term "subject" includes, but is not limited to, humans of any age group, e.g., a pediatric subject (e.g., infant, child or adolescent) or adult subject (e.g., young adult, middle-aged adult or senior adult)) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. The methods described herein can be useful in both human therapeutics and veterinary applications. In some embodiments, the patient is a mammal, and in some embodiments, the patient is human.

"Radiation therapy" or "radiation treatment" means exposing a patient, using routine methods and compositions known to the practitioner, to radiation emitters such as alpha-particle emitting radionucleotides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons.

The term "in vivo" refers to an event that takes place in a subject's body.

The term "in vitro" refers to an event that takes place outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

The term "HIF-2α" refers to a monomeric protein that contains several conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, including Endothelial PAS Domain Protein 1 (EPAS1), HIF-2A, PASD2, HIF-2-Alpha, HIF-2-Alpha, HLF, Hypoxia-Inducible Factor 2-Alpha, HIF-1alpha-Like Factor, and MOP2. As a member of the bHLH/PAS family of transcription factors, "HIF-2α" forms an active heterodimeric transcription factor complex by binding to the ARNT (also known as HIF-1β) protein through non-covalent interactions. In some embodiments, "HIF-2α" may refer to a fragment of the native protein. In some further embodiments, the fragment may include residues 239 to 348 of the native protein sequence.

"HIF-2α activity" as used herein has its ordinary meaning in the art. HIF-2α activity, for example, includes activation of gene transcription mediated by HIF-2α.

The term "inhibiting HIF-2α activity", as used herein, refers to slowing, reducing, altering, as well as completely eliminating and/or preventing HIF-2α activity.

The term "alkyl" refers to a straight or branched hydrocarbon chain radical comprising carbon and hydrogen atoms, containing no unsaturation, and having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl, (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "fluoroalkyl" refers to an alkyl group substituted with one or more fluorine atoms. In some embodiments, it is a $C_1$-$C_4$ alkyl group substituted with one or more fluorine atoms. Typical fluoroalkyl groups include, but are in no way limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

The term "alkenyl" refers to a straight or branched hydrocarbon chain radical group comprising carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., $C_2$-$C_8$ alkenyl). In other embodiments, an alkenyl comprises two to five carbon atoms (i.e., $C_2$-$C_5$ alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "alkynyl" refers to a straight or branched hydrocarbon chain radical group comprising carbon and hydrogen atoms, containing at least one triple bond, and having from two to ten carbon atoms (i.e., $C_2$-$C_{10}$ alkynyl). In some embodiments, an alkynyl group may contain one or more double bonds. Whenever it appears herein, a numerical range such as "2 to 10" refers to each integer in the given range, e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., $C_2$-$C_8$ alkynyl). In other embodiments, an alkynyl has two to five carbon atoms (i.e., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "aromatic" or "aryl" refers to an aromatic radical with six to ten ring atoms (i.e., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OP$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Aralkyl" or "arylalkyl" refers to an (aryl)alkyl-radical wherein the arylalkyl moiety is attached via the alkyl portion of the moiety. Aryl and alkyl are as disclosed herein and are optionally substituted by one or more of the substituents described as suitable substituents for aryl and alkyl, respectively.

The term "heteroaryl" or, alternatively, "heteroaromatic" refers to a 5- to 18-membered aromatic radical (i.e., $C_5$-$C_{18}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl. Examples of monocylic heteroaryls include, but are not limited to, imidazolyl, pyridinyl, pyrrolyl, pyrazinyl, pyrimidinyl, thiazolyl, furanyl and thienyl.

Substituted heteroaryl also includes ring systems substituted with one or more oxide substituents, such as pyridinyl N-oxides.

"Heteroarylalkyl" refers to a moiety having a heteroaryl moiety, as described herein, connected to an alkyl moiety, as described herein, wherein the connection to the remainder of the molecule is through the alkyl group. Heteroaryl and alkyl are as disclosed herein and are optionally substituted by one or more of the substituents described as suitable substituents for heteroaryl and alkyl, respectively.

The term "acyl" refers to a —C(=O)R radical, wherein R is hydrogen, alkyl, cycloalkyl, aryl, heteroaryl, heteroalkyl, or heterocycloalkyl, which are as described herein. The R group is attached to the parent structure through the carbonyl functionality. In some embodiments, it is a $C_1$-$C_{10}$ acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "halo", "halide", or alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" refer to haloalkyl and haloalkoxy groups, respectively, in which the halo is fluoro. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$. The alkyl part of the haloalkyl radical may be optionally substituted as defined above for an alkyl group.

The term "cyano" refers to a —CN radical.

The term "alkoxy" refers to an —O-alkyl radical, including from wherein alkyl is as described herein and contains 1 to 10 carbon atoms (i.e., $C_1$-$C_{10}$ alkoxy) of a straight, branched, or cyclic configuration and combinations thereof attached to the parent structure through an oxygen. Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. Examples include methoxy, ethoxy, propoxy, isopropoxy, cyclopropyloxy, cyclohexyloxy and the like. Unless stated otherwise specifically in the specification, an alkoxy moiety may be substituted by one or more of the substituents described as suitable substituents for an alkyl radical.

The term "sp³ hybridized carbon" refers to a carbon atom that is bonded to four other atoms. sp³ hybridization results from the combination of the s orbital and all three p orbitals in the second energy level of carbon. It results in four equivalent orbitals and the geometric arrangement of those four orbitals is tetrahedral.

The term "sulfonyl" refers to a —S(=O)$_2$R$^a$ radical, wherein R$^a$ is selected from the group consisting of alkyl, amino, cycloalkyl, aryl, heteroalkyl, heteroaryl (bonded through a ring carbon) and heterocycloalkyl (bonded through a ring carbon). Unless stated otherwise specifically in the specification, the R$^a$ group may be substituted by one or more of the substituents described as suitable substituents for an alkyl, an aryl or a heteroaryl radical.

The term "sulfoximinyl" refers to a —S(=O)(=NR$^a$)R$^b$ radical, wherein R$^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and R$^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R$^a$ and R$^b$ groups may be substituted by one or more of the substituents described as suitable substituents for an alkyl, an aryl or a heteroaryl radical.

"Sulfonamide," "sulfonamidyl" or "sulfonamido" refers to a —S(=O)$_2$N(R$^a$)$_2$ radical, wherein each R$^a$ is selected independently from the group consisting of hydrogen, alkyl, heteroalkyl, cycloalkyl, aryl, heteroaryl and heterocycloalkyl. The R$^a$ groups in —N(R$^a$)$_2$ of the —S(=O)$_2$—N(R$^a$)$_2$ radical may be taken together with the nitrogen to which it is attached to form a 4-, 5-, 6-, or 7-membered ring. In some embodiments, it is a $C_1$-$C_{10}$ sulfonamido, wherein each R$^a$ in sulfonamido contains 1 carbon, 2 carbons, 3 carbons or 4 carbons total. A sulfonamido group is optionally substituted by one or more of the substituents described for alkyl, cycloalkyl, aryl and heteroaryl, respectively.

The term "fluoroalkylsulfonyl" refers to a —S(=O)$_2$R$^a$ radical, wherein R$^a$ is fluoroalkyl. In some embodiments, R$^a$ is $C_1$-$C_4$ alkyl, substituted with one or more fluorines.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "heterocyclyl" or "heterocycloalkyl" refers to a stable 3- to 18-membered nonaromatic ring (e.g., $C_3$-$C_{18}$ heterocycloalkyl) radical that comprises two to twelve ring carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur and nitrogen, as well as combinations comprising at least one of the foregoing heteroatoms; the other ring, usually with 3 to 7 ring atoms, optionally contains 1-3 heteroatoms independently selected form oxygen, sulfur and nitrogen and is not aromatic.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, $C_3$-$C_4$ heteroalkyl has a chain length of 3-4 atoms. For example, a —$CH_2OCH_2CH_3$ radical is referred to as a "$C_4$ heteroalkyl", which includes the heteroatom in the atom chain length description. Connection to the rest of the molecule may be through either a heteroatom or a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —$OC(=O)R^a$, —$OC(=O)OR^a$, —$OC(=O)N(R^a)_2$, —$N(R^a)_2$, —$C(=O)OR^a$, —$C(=O)R^a$, —$C(=O)N(R^a)_2$, —$N(R^a)C(=O)OR^a$, —$N(R^a)C(=O)N(R^a)_2$, —$N(R^a)C(NR^a)N(R^a)_2$, —$N(R^a)C(=O)R^a$, —$N(R^a)S(=O)_tR^a$ (where t is 1 or 2), —$N(R^a)S(=O)_tN(R^a)_2$ (where t is 1 or 2), —$S(=O)_tR^a$ (where t is 1 or 2), —$S(=O)_tN(R^a)_2$ (where t is 1 or 2), —$PO_3(R^a)_2$, —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amino" or "amine" refers to a —$N(R^a)_2$ radical group, where each $R^a$ is independently hydrogen, alkyl, heteroalkyl, fluoroalkyl, cycloalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ other than hydrogen, they can be combined with the nitrogen atom to form a 3-, 4-, 5-, 6-, 7- or 8-membered ring. For example, —$N(R^a)_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —$OC(=O)R^a$, —$OC(=O)OR^a$, —$OC(=O)N(R^a)_2$, —$N(R^a)_2$, —$C(=O)OR^a$, —$C(=O)R^a$, —$C(=O)N(R^a)_2$, —$N(R^a)C(=O)OR^a$, —$N(R^a)C(=O)N(R^a)_2$, —$N(R^a)C(NR^a)N(R^a)_2$, —$N(R^a)C(=O)R^a$, —$N(R^a)S(=O)_tR^a$ (where t is 1 or 2), —$N(R^a)S(=O)_tN(R^a)_2$ (where t is 1 or 2), —$S(=O)_tR^a$ (where t is 1 or 2), —$S(=O)_tN(R^a)_2$ (where t is 1 or 2), —$PO_3(R^a)_2$, —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "substituted amino" also refers to N-oxides of the groups —$NHR^a$ and $N(R^a)_2$, each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "acyloxy" refers to a RC(=O)O— radical wherein R is alkyl, cycloalkyl, aryl, heteroalkyl, heteroaryl or heterocycloalkyl, which are as described herein. In some embodiments, it is a $C_1$-$C_4$ acyloxy radical, which refers to the total number of chain or ring atoms of the alkyl, cycloalkyl, aryl, heteroalkyl, heteroaryl or heterocycloalkyl portion of the acyloxy group plus the carbonyl carbon of acyl, i.e., the other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —$OC(=O)R^a$, —$OC(=O)OR^a$, —$OC(=O)N(R^a)_2$, —$N(R^a)_2$, —$C(=O)OR^a$, —$C(=O)R^a$, —$C(=O)N(R^a)_2$, —$N(R^a)C(=O)OR^a$, —$N(R^a)C(=O)N(R^a)_2$, —$N(R^a)C(NR^a)N(R^a)_2$, —$N(R^a)C(=O)R^a$, —$N(R^a)S(=O)_tR^a$ (where t is 1 or 2), —$N(R^a)S(=O)_tN(R^a)_2$ (where t is 1 or 2), —$S(=O)_tR^a$ (where t is 1 or 2), —$S(=O)_tN(R^a)_2$ (where t is 1 or 2), —$PO_3(R^a)_2$, —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amide" or "amido" refers to a chemical moiety with formula —$C(=O)N(R^a)_2$ or —$NR^aC(=O)R^a$, wherein each of $R^a$ is independently selected from the group consisting of hydrogen, alkyl, cycloalkyl, aryl, heteroaryl (bonded through a ring carbon) and heterocycloalkyl. Two $R^a$s may optionally be taken together with the nitrogen to which it is attached to form a 4-10 membered ring. In some embodiments, it is a $C_1$-$C_4$ amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound having an amine or a carboxylic acid moiety, thereby forming a prodrug. Any amine, hydroxy or carboxyl side chain on the compounds described herein can be amidified. The procedures and specific groups to make such amides are known to those of skilled in the art and can readily be found in reference sources such as Wuts, *Greene's Protective Groups in Organic Synthesis*, 5$^{th}$Ed., Wiley, New York, N.Y., 2014, which is incorporated herein by reference in its entirety.

"Carboxaldehyde" refers to a —C(=O)H radical.

"Carboxyl" refers to a —C(=O)OH radical.

"Ester" refers to a chemical radical of formula —C(=O)OR, where R is selected from the group consisting of alkyl, cycloalkyl, aryl, heteroaryl (bonded through a ring carbon) and heterocycloalkyl (bonded through a ring carbon). Any amine, hydroxy, or carboxyl side chain on the compounds described herein can be esterified. The procedures and specific groups to make such esters are known to those skilled in the art and can readily be found in reference sources such as Wuts, *Greene's Protective Groups in Organic Synthesis*, 5$^{th}$ Ed., Wiley, New York, N.Y., 2014, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R)S(=O)$_t$R$^a$ (where t is 1 or 2), —N(R)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Imino" refers to a =N—R$^a$ radical, wherein R$^a$ is hydrogen, alkyl, heteroalkyl, cycloalkyl, cyano, aryl, heterocycloalkyl or heteroaryl.

"Isocyanato" refers to a —NCO radical.

"Isothiocyanato" refers to a —NCS radical.

"Mercaptyl" refers to an —S(alkyl) or —SH radical.

"Methylene" refers to a =CH$_2$ radical.

"Hydroxy" refers to a —OH radical.

"Oxa" refers to a —O— radical.

"Oxo" refers to a =O radical.

"Nitro" refers to a —NO$_2$ radical.

"Oxime" refers to a =N(—OR) radical, where R is hydrogen or alkyl.

"Sulfinyl" refers to a —S(=O)R radical, where R is selected from the group consisting of alkyl, cycloalkyl, aryl, heteroalkyl, heteroaryl (bonded through a ring carbon) and heterocycloalkyl (bonded through a ring carbon). In some embodiments, R is fluoroalkyl.

"Sulfoxyl" refers to a —S(=O)$_2$OH radical.

"Sulfonate" refers to a —S(=O)$_2$OR radical, where R is selected from the group consisting of alkyl, cycloalkyl, aryl, heteroalkyl, heteroaryl (bonded through a ring carbon) and heteroalkyl (bonded through a ring carbon). The R group is optionally substituted by one or more of the substituents described for alkyl, heteroalkyl, cycloalkyl, heterocycloalkyl, aryl, and heteroaryl, respectively.

"Thiocyanato" refers to a —CNS radical.

"Thioxo" refers to a =S radical.

"Moiety" refers to a specific segment or functional group of a molecule. Chemical moieties are often recognized chemical entities embedded in or appended to a molecule.

"Substituted" means that the referenced group may be substituted with one or more additional group(s) individually and independently selected from acyl, alkyl, alkylaryl, heteroalkyl, cycloalkyl, aralkyl, heterocycloalkyl, aryl, carbohydrate, carbonate, heteroaryl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamide, sulfoxyl, sulfonate, urea, and amino, including mono- and di-substituted amino groups and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Wuts, *Greene's Protective Groups in Organic Synthesis*, 5$^{th}$ Ed., Wiley, New York, N.Y., 2014.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*, Vol. 7, Wiley, ISBN-10: 0471495018, published on Mar. 14, 2001.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "enantiomeric excess," as used herein, is the percent excess of one enantiomer compared to that of the other enantiomer in a mixture, and can be calculated using the following equation: enantiomeric excess=((R−S)/(R+S))×100=% (R*)−% (S*), wherein R and S are the number of moles of each enantiomer in the mixture, and R* and S* are the respective mole fractions of the enantiomers in the mixture. For example, for a mixture with 87% R enantiomer and 13% S enantiomer, the enantiomeric excess is 74%.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in Wuts, *Greene's Protective Groups in Organic Synthesis*, 5$^{th}$ Ed., Wiley, New York, N.Y., 2014. For example, a hydroxy protected form is where at least one of the hydroxy groups present in a compound is protected with a hydroxy protecting group. Likewise, amines and other reactive groups may similarly be protected.

"Solvate" refers to a compound in physical association with one or more molecules of a pharmaceutically acceptable solvent. It will be understood that the present chemical entities encompass the present chemical entities and solvates of the compound, as well as mixtures thereof.

"Solvent," "organic solvent," and "inert solvent" each means a solvent inert under the conditions of the reaction being described in conjunction therewith, including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diasteroisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers;

or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Abbreviations used herein have their conventional meaning within the chemical and biological arts.

When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

When " $\backslash$ " is drawn across a bond, it denotes where a bond disconnection or attachment occurs. For example, in the chemical structure

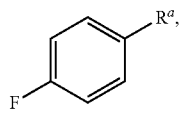

$R^a$ is attached to the para position of a fluorophenyl ring through a single bond. When $R^a$ is phenyl, it can also be drawn as

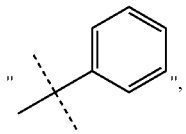

The waved line " $\sim$ " means a bond with undefined stereochemistry. For example,

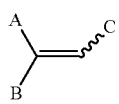

represents a mixture of

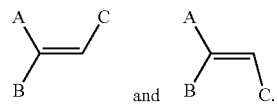

When a bond is drawn across a ring, it means substitution at a non-specific ring atom or position. For example, in the structure shown below,

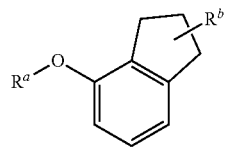

$R^b$ may be attached to any one of the —$CH_2$— in the five-membered ring.

When a bold bond " ╱ " appears two or more times in the same chemical structure, a mixture of the two cis isomers of the compound is described. For example,

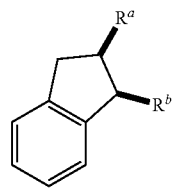

represents a mixture of the two isomers

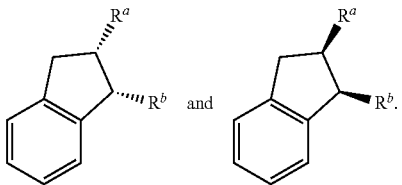

The present inventors have discovered certain genes and/or pathways that are differentially expressed in cancerous cells that are sensitive to therapy with a HIF-2α inhibitor. Methods of using these genes and/or the gene expression products to identify cancerous cells that will likely respond to therapy with a HIF-2α inhibitor as well as methods of identifying subjects having cancer that are predicted to exhibit a clinically beneficial response to treatment with a HIF-2α inhibitor are described herein. In particular, elevated levels of the genes or the corresponding gene products may be indicative of sensitivity to therapy with a HIF-2α inhibitor.

The inventors have additionally discovered certain genes and/or pathways that are differentially expressed in cancerous cells that are resistant to therapy with a HIF-2α inhibitor. Methods of using these genes and/or the gene expression products to identify cancerous cells that will likely be resistant to therapy with a HIF-2α inhibitor as well as methods of identifying subjects having cancer that are predicted to be resistant to treatment with a HIF-2α inhibitor are described herein. In particular, elevated levels of the genes or the corresponding gene products may be indicative of resistance to therapy with a HIF-2α inhibitor.

In one aspect, the disclosure provides a method of treating a subject for cancer. In one embodiment, the method comprises administering an effective dose of a HIF-2α inhibitor to the subject. In some embodiments, a cancer cell of the subject exhibits (1) differential expression of one or more genes or gene products, or (2) aberrant activity of one or more gene products encoded by the one or more genes. The one or more genes or gene products may predict for sensitivity to treatment with a HIF-2α inhibitor. In some embodiments, an alternative therapy is applied to the subject if the one or more genes or gene products predict for resistance to treatment with a HIF-2α inhibitor, and treatment with the HIF-2α inhibitor is discontinued.

In another aspect, the disclosure provides a method of treating a subject having cancer. In one embodiment, the method comprises (a) screening the subject for the presence or absence of at least one biomarker for HIF-2α inhibitor response and (b) administering a HIF-2α inhibitor to the subject if the at least one biomarker for HIF-2α inhibitor response is determined to be present. A method of the disclosure may further comprise (c) applying an alternative therapy to the subject if the at least one biomarker for HIF-2α inhibitor response is determined to be absent.

In yet another aspect, the disclosure provides a method of treating a plurality of cancer cells with a HIF-2α inhibitor. In one embodiment, the method comprises (a) assessing an expression level of at least one biomarker in a biological sample comprising a cancer cell of the plurality of cells, or a portion thereof; and (b) administering an effective dose of the HIF-2α inhibitor to the plurality of cells if the at least one biomarker is present in the sample at an increased level as compared to a control sample and/or a reference level. The at least one biomarker may be a predictor of HIF-2α inhibitor sensitivity. In some embodiments, the expression level of the at least one biomarker is assessed by nucleic acid hybridization assay and/or protein assay.

In still another aspect, the disclosure provides a method of measuring a likelihood that a subject having cancer will exhibit a clinically beneficial response to treatment with a HIF-2α inhibitor. In one embodiment, the method comprises (a) measuring, in a sample from the subject comprising a cancer cell, an expression level of a plurality of genes. In some embodiments, a method of the disclosure further comprises (b) generating an expression profile based on a comparison between the expression level of the plurality of genes in the sample from the subject and a corresponding expression level in a control sample. The expression level of the plurality of genes may be compared to a reference level to generate the expression profile. In some embodiments, a method of the disclosure further comprises calculating, using a computer system and/or a computational algorithm, a likelihood of response of the subject to treatment with a HIF-2α inhibitor based on the expression profile. The likelihood of response may be adjusted upward for each gene in the plurality exhibiting an increased expression level relative to the control sample or reference level. Each gene in the plurality may be a predictor of HIF-2α inhibitor sensitivity as described herein. In some embodiments, a gene in the plurality is associated with one or more pathways that may be predictors of HIF-2α inhibitor sensitivity. In a further embodiment, the likelihood of response may be adjusted downward for each gene in the plurality that is a predictor of HIF-2α inhibitor resistance exhibiting an increased expression level relative to the control sample or reference level.

In another aspect, the disclosure provides a method of selecting an anti-tumor therapy against a cancer. In one embodiment, the method comprises (a) obtaining a pretreatment sample comprising a cancer cell; (b) measuring a biomarker in the pretreatment sample to determine whether it is overexpressed in the pretreatment sample relative to a control sample and/or a reference level; and (c) selecting a HIF-2α inhibitor for treatment of the subject based on the measured overexpression of (b). In some embodiments, the biomarker is a predictor of HIF-2α inhibitor sensitivity. The biomarker may be a pathway, e.g. a signaling pathway in a cell that is frequently active in a cell that is sensitive to a HIF-2α inhibitor. If the measured overexpression predicts a likelihood of resistance to treatment with a HIF-2α inhibitor, an alternative therapy may be selected.

In a still further aspect, the disclosure provides a method of categorizing a cancer status of a subject. In one embodiment, the method comprises (a) obtaining a sample from the subject; (b) measuring an expression level of a plurality of genes in the sample; (c) generating an expression profile based on a comparison between the expression level of the plurality of genes in the sample from the subject and a corresponding expression level obtained from a reference sample derived from a different subject having a known cancer status; and (d) categorizing the cancer status of the subject of (a) based on the expression profile. In some embodiments, a gene in the plurality predicts for sensitivity or resistance to treatment with a HIF-2α inhibitor. In some embodiments, the sample is a tumor sample. In some embodiments, the sample comprises plasma or circulating cancer cells.

In yet another aspect, the disclosure provides a method of assessing a likelihood of a subject having cancer exhibiting a clinically beneficial response to treatment with a HIF-2α inhibitor. In one embodiment, the method comprises (a) assessing an expression level of a plurality of biomarkers in a biological sample comprising a cancer cell, wherein the plurality of biomarkers predict for sensitivity or resistance to treatment with a HIF-2α inhibitor. In some embodiments, a biomarker in the plurality is a pathway that is frequently active in a cell that is sensitive to treatment with a HIF-2α inhibitor. In some embodiments, a method of the disclosure further comprises (b) calculating, using a computer system, a weighted probability of HIF-2α inhibitor responsiveness based on the expression level of the plurality of biomarkers. The expression level of the plurality of biomarkers may be compared to (1) a corresponding level in one or more control samples or (2) a reference level. In some embodiments, a method of the disclosure further comprises (c) designating the subject as having a high probability of exhibiting a clinically beneficial response to treatment with a HIF-2α inhibitor if the weighted probability corresponds to at least 2 times a baseline probability, where the baseline probability represents a likelihood that the subject will exhibit a clinically beneficial response to treatment with a HIF-2α inhibitor before obtaining the weighted probability of (b). In some embodiments, a method of the disclosure further comprises (d) transmitting information concerning the likelihood to a receiver. A recommendation may be made based on the weighted probability, for example, a recommendation to continue monitoring the subject, a recommendation to treat the subject with a HIF-2α inhibitor, a recommendation to discontinue therapy, or a recommendation to treat the subject with an alternative therapy, e.g. chemotherapy, radiotherapy or surgery. In some embodiments, a treatment is selected based on the weighted probability, e.g., administering a HIF-2α inhibitor based on the weighted probability.

Certain embodiments contemplate a human subject such as a subject that has been diagnosed as having or being at risk for developing or acquiring cancer. Certain other embodiments contemplate a non-human subject, for example a non-human primate such as a macaque, chimpanzee, gorilla, vervet, orangutan, baboon or other non-human primate, including such non-human subjects that can be known to the art as preclinical models. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present disclosure, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Any cancer may be analyzed and/or treated according to the methods of the disclosure. Many kinds of cancers are known in the art. Examples of types of cancers include, without limitation, cancers originating from epithelial cell tissue (carcinomas), blood cells (leukemias, lymphomas, myelomas), connective tissue (sarcomas), or glial or supportive cells (gliomas). In some embodiments, the target cancers are carcinomas. In some embodiments, the target cancers are lung tumors, breast tumors, ovarian tumors, pancreatic tumors, glioblastoma tumors, and/or sarcomas. Cancers may comprise solid and/or non-solid tumors. Cancers may comprise primary and/or secondary tumors. Non-limiting examples of cancers that may be analyzed according to the methods of the disclosure include acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basal-like carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathy-associated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, glomus tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, nonmelanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof. In some embodiments, the methods of the disclosure are applied to cancers of the adrenal glands, blood, bone marrow, brain, breast, cervix, colon, head and neck, kidney, liver, lung, ovary, pancreas, plasma cells, rectum, retina, skin, spine, throat or any combination thereof. In some embodiments, the cancer is selected from the group consisting of lung cancer, colon cancer, pancreatic cancer, liver cancer, head and neck cancer, stomach cancer, renal cell carcinoma, breast cancer, glioblastoma, and neuroblastoma. In another embodiment, the cancer is renal cell carcinoma, e.g., clear cell renal cell carcinoma.

Typically, a sample of a subject comprises cancerous or pre-cancerous cells. The sample may be a solid biological sample, for example, a tumor biopsy. A biopsy may be fixed, paraffin-embedded, fresh, or frozen. Samples may be obtained by any suitable means, including but not limited to needle aspiration, fine needle aspiration, core needle biopsy, vacuum assisted biopsy, large core biopsy, incisional biopsy, excisional biopsy, punch biopsy, shave biopsy, skin biopsy, and venipuncture. A sample may be derived from fine needle, core, or other types of biopsy, or may comprise circulating tumor cells. A sample may be analyzed directly for its contents, or may be processed to purify one or more of its contents for analysis. Methods of direct analysis of samples are known in the art and include, without limitation, mass spectrometry and histological staining procedures. In some embodiments, one or more components are purified from the sample for the detection of a biomarker for HIF-2α inhibitor response. In some embodiments, the purified component of the sample is a nucleic acid, such as DNA (e.g. genomic DNA) or RNA (e.g. total RNA or mRNA). In some embodiments, the purified component of the sample is protein (e.g. total protein, cytoplasmic protein, or membrane protein).

Methods for the extraction, purification, and amplification of nucleic acids are known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the disclosure, such as to remove excess or unwanted reagents, reactants, or products.

In some embodiments, sample polynucleotides are fragmented into a population of fragmented DNA molecules of one or more specific size range(s). In some embodiments, fragments are generated from about or at least about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average length from about 10 to about 10,000 nucleotides. In some embodiments, the fragments have an average length from about 50 to about 2,000 nucleotides. In some embodiments, the fragments have an average or median length from about 100-2,500, 10-1,000, 10-800, 10-500, 50-500, 50-250, or 50-150 nucleotides. In some embodiments, the fragmentation is accomplished mechanically comprising subjection sample polynucleotides to acoustic sonication. In some embodiments, the fragmentation comprises treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods such as column purification or isolation from an agarose gel.

In some embodiments, one or more polynucleotides from a sample of a subject are amplified. In general, amplification comprises generating one or more copies of all or a portion of polynucleotides in a template-dependent manner. Amplification may be primer-dependent, or primer-independent. When primer-dependent, amplification may be directed to one or more specific polynucleotides in a sample or portions thereof, such as one or more regions (e.g. about or more than about 1, 5, 10, 15, 20, 25, 30, 35, 40, 45, 50, 75, 100, 200, 500, or more regions), each region comprising one or more sequences of interest, and having a length of about, less than about, or more than about 1, 5, 10, 25, 50, 100, 150, 200, 250, 350, 500, 1000, 2000, or more nucleotides. Amplification may be linear or non-linear (e.g. exponential). Amplification may comprise directed changes in temperature, or may be isothermal. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles.

Differential expression of a biomarker may be assessed by any appropriate method. The expression level of a biomarker may be assessed by detecting a level of mRNA transcribed from the biomarker, by detecting a level of cDNA produced from reverse transcription of mRNA transcribed from the biomarker, or by detecting a level of polypeptide encoded by the biomarker. Regulation of a target gene or gene transcript can also be determined indirectly, such as by measuring the effect on a phenotypic indicator of the gene or gene transcript activity, such as by cellular assay. Methods of detecting gene expression products are known in the art, examples of which are described herein. These methods can be performed on a sample by sample basis or modified for high throughput analysis, for example, using Affymetrix™ U133 microarray chips.

Detection of nucleic acids may involve the use of a hybridization reaction, such as between a target nucleic acid and an oligonucleotide probe or primer (e.g., a nucleic acid hybridization assay). In some embodiments, the oligonucleotide probe is immobilized on a substrate. Substrates include, but are not limited to, arrays, microarrays, wells of a multi-well plate, and beads (e.g. non-magnetic, magnetic, paramagnetic, hydrophobic, and hydrophilic beads). Examples of materials useful as substrates include but are not limited to nitrocellulose, glass, silicon, and a variety of gene arrays. A preferred hybridization assay is conducted on high-density gene chips as described in U.S. Pat. No. 5,445,934.

The expression level of a gene may be determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization may be quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). PCR conditions used for each application reaction are empirically determined. A number of parameters influence the success of a reaction. Among them are annealing temperature and time, extension time, $Mg^{2+}$ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

The hybridized nucleic acids may be detected by detecting one or more labels attached to the sample nucleic acids. The labels can be incorporated by any of a number of means well known to those of skill in the art. However, in one embodiment, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Suitable detectable labels may include any composition detectable by spectroscopic, photochemical, biochemical, immunochemical, electrical, optical or chemical means. Useful labels include, for example, biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters. Fluorescent markers may be detected using a photodetector to detect emitted light. Enzymatic labels are typically detected by providing the enzyme with a substrate and detecting the reaction product produced by the action of the enzyme on the substrate. Calorimetric labels may be detected by simply visualizing the colored label.

The biomarker may be detected in a biological sample using a microarray. Differential gene expression can also be identified, or confirmed using the microarray technique. Thus, the expression profile biomarkers can be measured in either fresh or fixed tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. The source of mRNA typically is total RNA isolated from a biological sample, and corresponding normal tissues or cell lines may be used to determine differential expression.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the microarray chip is scanned by a device, such as confocal laser microscopy, or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair-wise to the array. The relative abundance of the transcripts from the two sources corresponding to each specified gene is thus determined simultaneously. Microarray analysis can be performed by commercially available equipment, following manufacturer's protocols.

The biomarker may be detected in a biological sample using qRT-PCR, which can be used to compare mRNA levels in different sample populations, in normal and tumor tissues, with or without drug treatment, to characterize patterns of gene expression, to discriminate between closely related mRNAs, and to analyze RNA structure. The first step in gene expression profiling by RT-PCR is extracting RNA from a biological sample followed by the reverse transcription of the RNA template into cDNA and amplification by a PCR reaction. The reverse transcription reaction step is generally primed using specific primers, random hexamers, or oligo-dT primers, depending on the goal of expression profiling. The two commonly used reverse transcriptases are avilo myeloblastosis virus reverse transcriptase (AMV-RT) and Moloney murine leukemia virus reverse transcriptase (MLV-RT).

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan™ PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Differential expression of a biomarker can also be determined by examining protein expression or the protein product of the biomarker, for example, using a suitable protein assay. Determining the protein level involves measuring the amount of any immunospecific binding that occurs between an antibody that selectively recognizes and binds to the polypeptide of the biomarker in a test sample and comparing this to the amount of immunospecific binding of at least one biomarker in a control sample. The amount of protein expression of the biomarker may be increased or reduced when compared with control expression. Alternatively, all of the biomarkers disclosed herein may be assayed for as a single set.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), western blot analysis, immunoprecipitation assays, immunofluorescent assays, flow cytometry, immunohistochemistry, confocal microscopy, enzymatic assays, surface plasmon resonance and PAGE-SDS.

The present disclosure provides for methods for detecting biomarkers in biological samples. Useful analyte capture agents that can be used with the present disclosure include but are not limited to antibodies, such as crude serum containing antibodies, purified antibodies, monoclonal antibodies, polyclonal antibodies, synthetic antibodies, antibody fragments (for example, Fab fragments); antibody interacting agents, such as protein A, carbohydrate binding proteins, and other interactants; protein interactants (for example avidin and its derivatives); peptides; and small chemical entities, such as enzyme substrates, cofactors, metal ions/chelates, and haptens. Antibodies may be modified or chemically treated to optimize binding to targets or solid surfaces (e.g. biochips and columns).

In one embodiment of the disclosure the biomarker can be detected in a biological sample using an immunoassay. Immunoassays are assays that use an antibody that specifically bind to or recognizes an antigen (e.g. site on a protein or peptide, biomarker target). The method includes the steps of contacting the biological sample with the antibody and allowing the antibody to form a complex with the antigen in the sample, washing the sample and detecting the antibody-antigen complex with a detection reagent. In one embodiment, antibodies that recognize the biomarkers may be commercially available. In another embodiment, an antibody that recognizes the biomarkers may be generated by known methods of antibody production.

Alternatively, the marker in the sample can be detected using an indirect assay, wherein, for example, a second, labeled antibody is used to detect bound marker-specific antibody. Exemplary detectable labels include magnetic beads (e.g., DYNABEADS™) fluorescent dyes, radiolabels, enzymes (e.g., horse radish peroxide, alkaline phosphatase and others commonly used), and calorimetric labels such as colloidal gold or colored glass or plastic beads. The marker in the sample can be detected using and/or in a competition or inhibition assay wherein, for example, a monoclonal antibody which binds to a distinct epitope of the marker is incubated simultaneously with the mixture.

The conditions to detect an antigen using an immunoassay will be dependent on the particular antibody used. Also, the incubation time will depend upon the assay format, marker, volume of solution, concentrations and the like. In general, the immunoassays will be carried out at room temperature, although they can be conducted over a range of temperatures, such as 10 degrees, to 40 degrees Celsius depending on the antibody used.

There are various types of immunoassay known in the art that as a starting basis can be used to tailor the assay for the detection of the biomarkers of the present disclosure. Useful assays can include, for example, an enzyme immune assay (EIA) such as enzyme-linked immunosorbent assay (ELISA). There are many variants of these approaches, but those are based on a similar idea. For example, if an antigen can be bound to a solid support or surface, it can be detected by reacting it with a specific antibody and the antibody can be quantitated by reacting it with either a secondary antibody or by incorporating a label directly into the primary antibody. Alternatively, an antibody can be bound to a solid surface and the antigen added. A second antibody that recognizes a distinct epitope on the antigen can then be added and detected. This is frequently called a 'sandwich assay' and can frequently be used to avoid problems of high background or non-specific reactions. These types of assays are sensitive and reproducible enough to measure low concentrations of antigens in a biological sample.

Proximity ligation assay (PLA) is another type of immunoassay known in the art useful for the detection of the biomarkers of the present disclosure. The term "proximity ligation assay" or "PLA" as used herein refers to an immunoassay utilizing so-called PLA probes—affinity reagents such as antibodies modified with DNA oligonucleotides—for detecting and reporting the presence of proteins either in solution or in situ. When two PLA probes bind the same or two interacting target molecules, the attached oligonucleotides are brought in close proximity. A proximity ligation assay may be tailored to detect the biomarkers disclosed herein.

Immunoassays can be used to determine presence or absence of a marker in a sample as well as the quantity of a marker in a sample. Methods for measuring the amount of, or presence of, antibody-marker complex include but are not limited to, fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). In general these regents are used with optical detection methods, such as various forms of microscopy, imaging methods and non-imaging methods. Electrochemical methods include voltametry and amperometry methods. Radio frequency methods include multipolar resonance spectroscopy.

Biochips can be designed with immobilized nucleic acid molecules, full-length proteins, antibodies, affibodies (small molecules engineered to mimic monoclonal antibodies), aptamers (nucleic acid-based ligands) or chemical compounds. A chip could be designed to detect multiple macromolecule types on one chip. For example, a chip could be designed to detect nucleic acid molecules, proteins and metabolites on one chip. The biochip is used to and designed to simultaneously analyze a panel biomarker in a single sample, producing a subject's profile for these biomarkers. The use of the biochip allows for the multiple analyses to be performed reducing the overall processing time and the amount of sample required.

Protein microarrays are a particular type of biochip which can be used with the present disclosure. The chip consists of a support surface such as a glass slide, nitrocellulose membrane, bead, or microtitre plate, to which an array of capture proteins are bound in an arrayed format onto a solid surface. Protein array detection methods must give a high signal and a low background. Detection probe molecules, typically labeled with a fluorescent dye, are added to the array. Any reaction between the probe and the immobilized protein emits a fluorescent signal that is read by a laser scanner. Such protein microarrays are rapid, automated, and offer high sensitivity of protein biomarker read-outs for diagnostic tests. However, it would be immediately appreciated to those skilled in the art that they are a variety of detection methods that can be used with this technology.

The present disclosure provides for the detection of biomarkers using mass spectrometry. Mass spectrometry (MS) is an analytical technique that measures the mass-to-charge ratio of charged particles. It is primarily used for determining the elemental composition of a sample or molecule, and for elucidating the chemical structures of molecules, such as peptides and other chemical compounds. MS works by ionizing chemical compounds to generate charged molecules or molecule fragments and measuring their mass-to-charge ratios MS instruments typically consist of three modules (1) an ion source, which can convert gas phase sample molecules into ions (or, in the case of electrospray ionization, move ions that exist in solution into the gas phase) (2) a mass analyzer, which sorts the ions by their masses by applying electromagnetic fields and (3) a detector, which measures the value of an indicator quantity and thus provides data for calculating the abundances of each ion present.

Suitable mass spectrometry methods to be used with the present disclosure include but are not limited to, one or more of electrospray ionization mass spectrometry (ESI-MS), ESI-MS/MS, ESI-MS/(MS)$_n$, matrix-assisted laser desorption ionization time-of-flight mass spectrometry (MALDI-TOF-MS), surface-enhanced laser desorption/ionization time-of-flight mass spectrometry (SELDI-TOF-MS), tandem liquid chromatography-mass spectrometry (LC-MS/MS) mass spectrometry, desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$_n$, atmospheric pressure_photoionization mass spectrometry (APPI-MS), APPI-MS/MS, and APPI-(MS)$_n$, quadrupole mass spectrometry, Fourier transform mass spectrometry (FTMS), and ion trap mass spectrometry, where n is an integer greater than zero.

To gain insight into the underlying proteomics of a sample, LC-MS is commonly used to resolve the components of a complex mixture. LC-MS method generally involves protease digestion and denaturation (usually involving a protease, such as trypsin and a denaturant such as, urea to denature tertiary structure and iodoacetamide to cap cysteine residues) followed by LC-MS with peptide mass fingerprinting or LC-MS/MS (tandem MS) to derive sequence of individual peptides. LC-MS/MS is most commonly used for proteomic analysis of complex samples where peptide masses may overlap even with a high-resolution mass spectrometer. Samples of complex biological fluids like human serum may be first separated on an SDS-PAGE gel or HPLC-SCX and then run in LC-MS/MS allowing for the identification of over 1000 proteins.

In some applications, HPLC and UHPLC can be coupled to a mass spectrometer. A number of other peptide and protein separation techniques can be performed prior to mass spectrometric analysis. Some exemplary separation techniques which can be used for separation of the desired analyte (e.g., peptide or protein) from the matrix background include but are not limited to Reverse Phase Liquid Chromatography (RP-LC) of proteins or peptides, offline Liquid Chromatography (LC), 1 dimensional gel separation, 2-dimensional gel separation, Strong Cation Exchange (SCX) chromatography, Strong Anion Exchange (SAX) chromatography, Weak Cation Exchange (WCX), and Weak Anion Exchange (WAX). One or more of the above techniques can be used prior to mass spectrometric analysis.

In some embodiments, a method of the disclosure comprises a group of biomarkers that is differentially expressed in cancer cells. The relative expression of these biomarkers may be used to identify cells that are more likely to respond to treatment with a HIF-2α inhibitor. In some embodiments, a method of the disclosure comprises a biomarker that is a predictor of HIF-2α inhibitor sensitivity, including, for example, AC074091.13, ANO7, AVPR2, BCL2L11, BRCC3, C1QL1, CAMK2D, CHRDL2, CHST1, CORO6, CPE, CRYM, CXCR4, DEK, EPAS1, EPO, EXOG, EZH2, FAM180A, FAM65B, FAM65C, GFRA2, GLI1, HAGHL, HIF1A, HMGA1, HRH2, HSPB7, IGFBP1, INHBB, ITGB8, KCNIP3, KLHL3, KNDC1, LAMB1, LOX, LYPD1, MCAM, MCIDAS, MEST, MRS2, NFASC, NPTX1, PASK, PFN2, PHYHIP, PICALM, PKNOX2, PLAG1, POSTN, PPA2, PPAPDC3, PRICKLE1, PRR5, PTHLH, PTPRJ, RASGEFIB, RDH13, RGL2, SLC36A4, SLC6A3, SLCO5A1, SLITRK4, SORCS3, ST3GAL5, SVIP, TBC1D4, TMEM30B, TPST2, VGLL4, WFIKKN1, ZKSCAN3, ZKSCAN8, ZSCAN16, and ZSCAN9. In some embodiments, the biomarker that is a predictor of HIF-2α inhibitor sensitivity is a gene or gene product associated with a cellular pathway, including, for example, hypoxia signaling, DNA damage response, GPCR signaling, insulin signaling, non-canonical Wnt signaling, dopaminiergic signaling, ion and solute transport, and neurotrophic growth factor signaling pathways. The pathway may be a signaling pathway that is aberrantly active in a cell that is sensitive to a HIF-2α inhibitor.

In some embodiments, a method of the disclosure comprises a biomarker that, if overexpressed, is a predictor of HIF-2α inhibitor sensitivity, including, for example, AVPR2, C1QL1, CHRDL2, CHST1, CPE, CXCR4, EPAS1, EPO, FAM180A, GFRA2, GLI1, HRH2, HSPB7, IGFBP1, INHBB, KNDC1, LOX, NFASC, NPTX1, PKNOX2, POSTN, PTHLH, RDH13, SLC6A3, SORCS3, TMEM30B, TPST2, and WFIKKN1. In some embodiments, the overexpression of EPAS1, CPE, LOX, GLI1, and/or HRH2 predict sensitivity to a HIF-2α inhibitor. The biomarker that, when overexpressed, is a predictor of HIF-2α inhibitor sensitivity may be a gene or gene product associated with a pathway selected from the group consisting of hypoxia signaling, GPCR signaling, dopaminiergic signaling, and neurotrophic growth factor signaling.

In some embodiments, a method of the disclosure comprises a biomarker that, if underexpressed, is a predictor of HIF-2α inhibitor sensitivity, including, for example, AC074091.13, ANO7, BCL2L11, BRCC3, CAMK2D, CORO6, CRYM, DEK, EXOG, EZH2, FAM65B, FAM65C, HAGHL, HIF1A, HMGA1, ITGB8, KCNIP3, KLHL3, LAMB1, LYPD1, MCAM, MCIDAS, MEST, MRS2, PASK, PFN2, PHYHIP, PICALM, PLAG1, PPA2, PPAPDC3, PRICKLE1, PRR5, PTPRJ, RASGEFIB, RGL2, SLC36A4, SLCO5A1, SLITRK4, ST3GAL5, SVIP, TBC1D4, VGLL4, ZKSCAN3, ZKSCAN8, ZSCAN16, and ZSCAN9. In some embodiments, the underexpression of HIF1A, A074091.13, CORO6, FAM65B, KLHL3, and/or PPAPDC3 predict sensitivity to a HIF-2α inhibitor. The biomarker that, when underexpressed, is a predictor of HIF-2α inhibitor sensitivity may be a gene or gene product associated with a pathway selected from the group consisting of DNA damage response, insulin signaling, non-canonical Wnt signaling, and ion and solute transport.

In some embodiments, a method of the disclosure comprises a biomarker that, if overexpressed, is a predictor of HIF-2α inhibitor resistance, including, for example, AC074091.13, ANO7, BCL2L11, BRCC3, CAMK2D, CORO6, CRYM, DEK, EXOG, EZH2, FAM65B, FAM65C, HAGHL, HIF1A, HMGA1, ITGB8, KCNIP3, KLHL3, LAMB1, LYPD1, MCAM, MCIDAS, MEST, MRS2, PASK, PFN2, PHYHIP, PICALM, PLAG1, PPA2, PPAPDC3, PRICKLE1, PRR5, PTPRJ, RASGEFIB, RGL2, SLC36A4, SLCO5A1, SLITRK4, ST3GAL5, SVIP, TBC1D4, VGLL4, ZKSCAN3, ZKSCAN8, ZSCAN16, and ZSCAN9. In some embodiments, the overexpression of HIF1A, A074091.13, CORO6, FAM65B, KLHL3, and/or PPAPDC3 predict resistance to a HIF-2α inhibitor. The biomarker that, when overexpressed, is a predictor of HIF-2α inhibitor resistance may be a gene or gene product associated with a pathway selected from the group consisting of DNA damage response, insulin signaling, non-canonical Wnt signaling, and ion and solute transport.

In some embodiments, a method of the disclosure comprises a biomarker that, if underexpressed, is a predictor of HIF-2α inhibitor resistance, including, for example, AVPR2, C1QL1, CHRDL2, CHST1, CPE, CXCR4, EPAS1, EPO, FAM180A, GFRA2, GLI1, HRH2, HSPB7, IGFBP1, INHBB, KNDC1, LOX, NFASC, NPTX1, PKNOX2, POSTN, PTHLH, RDH13, SLC6A3, SORCS3, TMEM30B, TPST2, and WFIKKN1. In some embodiments, the underexpression of EPAS1, CPE, LOX, GLI1, and/or HRH2 predict resistance to a HIF-2α inhibitor. The biomarker that, when underexpressed, is a predictor of HIF-2α inhibitor resistance may be a gene or gene product associated with a pathway selected from the group consisting of hypoxia signaling, GPCR signaling, dopaminiergic signaling, and neurotrophic growth factor signaling.

The methods described herein for qualifying or quantifying the expression of polypeptides and/or polynucleotides provide information which can be correlated with pathological conditions, predisposition to disease, therapeutic monitoring, risk stratification, among others. In some embodiments, a method of the disclosure is particularly useful for diagnosing conditions, evaluating whether a HIF-2α inhibitor will have a desired effect, i.e., predicting responsiveness to a HIF-2α inhibitor, and determining prognoses. The present methods may be used for the optimization of treatment protocols. In this context, evaluation of the expression profile of the biomarkers disclosed herein can be used to gain information on the treatment potential of a tissue sample with a HIF-2α inhibitor.

In some embodiments, the disclosure provides methods for measuring a likelihood that a subject having cancer will exhibit a clinically beneficial response to treatment with a HIF-2α inhibitor based on an expression profile of a plurality of genes or gene products. An "expression profile" refers to a pattern of expression of at least one biomarker that recurs in multiple samples and reflects a property shared by those samples, such as tissue type, response to treatment with a HIF-2α inhibitor, or activation of a particular biological process or pathway in the cells. Furthermore, an expression profile differentiates between samples that share that common property and those that do not with better accuracy than would likely be achieved by assigning the samples to the two groups at random. An expression profile may be used to predict whether samples of unknown status share that common property or not. Some variation between the levels of at least one biomarker and the typical profile is to be expected, but the overall similarity of the expression levels to the typical profile is such that it is statistically unlikely that the similarity would be observed by chance in samples not sharing the common property that the expression profile reflects.

An expression profile may be generated based on a comparison between the expression level of a plurality of biomarkers in a sample from a test subject and a corresponding reference level. The plurality of biomarkers may comprise a single biomarker that is a predictor of HIF-2α inhibitor sensitivity. In some embodiments, an expression profile is generated based on the expression of 2 or more, 3 or more, 4 or more, 5 or more, 6 or more, 7 or more, 8 or more, 9 or more, 10 or more, 15 or more, 20 or more, 25 or more, 30 or more, 40 or more, 50 or more, 60 or more, 70 or more, 80 or more, 90 or more, or 100 or more biomarkers. For example, expression levels of all of the biomarkers in Table 4 can be used to generate an expression profile, or only a subset of 10 biomarkers thereof may be used. The expression profile may comprise expression levels of biomarkers that predict sensitivity of a cancer to a HIF-2α inhibitor, expression levels of biomarkers that predict resistance of a cancer to a HIF-2α inhibitor, or a combination thereof. For example, the expression profile may comprise expression levels of HIF1A, A074091.13, CORO6, FAM65B, KLHL3, PPAPDC3, EPAS1, CPE, LOX, GLI1, and HRH2.

In some embodiments, the expression profile is used in a method of the disclosure to assess a likelihood of response to treatment with a HIF-2α inhibitor. The likelihood of response may be adjusted upward for each biomarker that is a predictor of HIF-2α inhibitor sensitivity that is overexpressed. Similarly, the likelihood of response may be adjusted upward for each biomarker that is a predictor of HIF-2α inhibitor resistance that is underexpressed. In some embodiments, the likelihood of response may be adjusted downward for each biomarker that is a predictor of HIF-2α inhibitor sensitivity that is underexpressed. The likelihood of response may be adjusted downward for each biomarker that is a predictor of HIF-2α inhibitor resistance that is overexpressed. The magnitude of under- or over-expression may be used to weight the amount of adjustment to the likelihood of response. In some embodiments, a method of the disclosure provides a reference level above or below which a biomarker must be expressed to be considered in assessing the likelihood of response to treatment with a HIF-2α inhibitor. The biomarker may be differentially expressed at least 1.1 fold, at least 1.2 fold, at least 1.3 fold, at least 1.4 fold, at least 1.5 fold, at least 2.0 fold, at least 2.25 fold, at least 2.5 fold, at least 2.75 fold, at least 3.0 fold, at least 3.5 fold, at least 4.0 fold, at least 5.0, or even at least 10 fold higher or lower relative to a reference level to be considered in adjusting the likelihood of response. In some embodiments, the reference level is a numerical range of biomarker expression that is obtained from a statistical sampling from a population of individuals having cancer that is resistant to treatment with a HIF-2α inhibitor. In some embodiments, the reference level is a numerical range of biomarker expression that is obtained from a statistical sampling from a population of individuals having cancer that is sensitive to treatment with a HIF-2α inhibitor. The reference level may be a numerical range of biomarker expression that is obtained from a statistical sampling from a population of individuals having cancer, e.g., the same cancer as the test subject. In some embodiments, the reference level is derived by comparison of sensitive and resistant populations.

In some embodiments, one or more steps in the assessment and/or reporting of a likelihood of response to treatment with a HIF-2α inhibitor is performed with the aid of a processor, such as with a computer system executing instructions contained in computer-readable media. In one aspect, the disclosure provides a system for of assessing a likelihood of a subject having cancer exhibiting a clinically beneficial response to treatment with a HIF-2α inhibitor. In one embodiment, the system comprises (a) a memory unit configured to store information concerning an expression level of a plurality of biomarkers in a biological sample comprising a cancer cell from the subject, wherein the plurality of biomarkers predict for sensitivity or resistance to treatment with a HIF-2α inhibitor. In some embodiments, the biomarker in the plurality is a gene or gene product associated with a pathway that is frequently active in a cell that is sensitive to treatment with a HIF-2α inhibitor. In some embodiments, the system further comprises (b) one or more processors alone or in combination programmed to (1) determine a weighted probability of HIF-2α inhibitor responsiveness based on the expression level of a plurality of biomarkers as compared to a corresponding expression level in one or more control samples and (2) designate the subject as having a high probability of exhibiting a clinically beneficial response to treatment with a HIF-2α inhibitor if the weighted probability corresponds to at least 2 times a baseline probability, where the baseline probability represents a likelihood that the subject will exhibit a clinically beneficial response to treatment with a HIF-2α inhibitor before obtaining the weighted probability of (b)(1). In some embodiments, a processor or computational algorithm may aid in the assessment of a likelihood of a subject having cancer exhibiting a clinically beneficial response to treatment with a HIF-2α inhibitor. For example, one or more steps of methods or systems described herein may be implemented in hardware. Alternatively, one or more steps may be implemented in software stored in, for example, one or more memories or other computer readable medium and implemented on one or more processors. As is known, the processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, a remote server (e.g. the cloud), or other storage medium, as is also known. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A computer system may be involved in one or more of sample collection, sample processing, data analysis, expression profile assessment, calculation of weighted probabilities, calculation of baseline probabilities, comparison of a weighted probability to a reference level and/or control sample, determination of a subject's absolute or increased probability, generating a report, and reporting results to a receiver.

A client-server, relational database architecture can be used in embodiments of the disclosure. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers), workstations, or mobile computing devices (e.g., a tablets or smart phones) on which users run applications, as well as example output devices as disclosed herein. Client computers may rely on server computers for resources, such as files, devices, and even processing power. In some embodiments of the disclosure, the server computer handles all of the database functionality. The client computer can have software that handles all the front-end data management and can also receive data input from users.

In some embodiments, the computer system is connected to an analysis system by a network connection. The computer system may be understood as a logical apparatus that can read instructions from media and/or a network port, which can optionally be connected to server having fixed media. The system can include a CPU, disk drives, optional input devices such as keyboard and/or mouse, and optional monitor. Data communication can be achieved through the indicated communication medium to a server at a local or a remote location. The communication medium can include any means of transmitting and/or receiving data. For example, the communication medium can be a network connection, a wireless connection, or an internet connection. Such a connection can provide for communication over the World Wide Web. In some embodiments, a physical report is generated and delivered to a receiver.

In some embodiments there is provided a computer readable medium encoded with computer executable software that includes instructions for a computer to execute functions associated with the identified biomarkers. Such computer system may include any combination of such codes or computer executable software, depending upon the types of evaluations desired to be completed. The system can have code for calculating a weighted probability of HIF-2α inhibitor responsiveness, and optionally for calculating an aggregated probability based on a plurality of weighted probabilities. In some embodiments, the weighted probability of HIF-2α inhibitor responsiveness is increased if a cancer or cancer cell (1) overexpresses one or more biomarkers that predict for HIF-2α inhibitor sensitivity or (2) underexpresses one or more biomarkers that predict for HIF-2α inhibitor resistance. The weighted probability of HIF-2α inhibitor responsiveness is decreased if a cancer or cancer cell (1) underexpresses one or more biomarkers that predict for HIF-2α inhibitor sensitivity or (2) overexpresses one or more biomarkers that predict for HIF-2α inhibitor resistance. A cancer or cancer cell may express predictors of both sensitivity and resistance. In calculating a weighted probability, the computer system or computational algorithm may consider the expression of 1 or more, 2 or more, 3 or more, 4 or more, 5 or more, 6 or more, 7 or more, 8 or more, 9 or more, 10 or more, 15 or more, 20 or more, 25 or more, 30 or more, 40 or more, 50 or more, 60 or more, 70 or more, 80 or more, 90 or more, or 100 or more biomarkers. For example, expression levels of all of the biomarkers in Table 4 can be used to generate an expression profile. The system can further comprise code for conducting genetic analysis based on specific panel(s) of biomarkers chosen. The system can also have code for one or more of the following: conducting, analyzing, organizing, or reporting the results, as described herein. The system can also have code for generating a report. In some embodiments, the test subject may be designated as having a high probability of exhibiting a clinically beneficial response to treatment with a HIF-2α inhibitor if the weighted probability corresponds to at least about 0.55, at least about 0.6, at least about 0.65, at least about 0.7, at least about 0.75, at least about 0.8, at least about 0.85, at least about 0.9, at least about 0.95, or at least about 0.99. In some embodiments, the test subject may be designated as having a low probability of exhibiting a clinically beneficial response to treatment with a HIF-2α inhibitor if the weighted probability corresponds to less than about 0.45, less than about 0.4, less than about 0.35, less than about 0.3, less than about 0.25, less than about 0.2, less than about 0.15, less than about 0.1, less than about 0.05, less than about 0.01.

The system may further comprise code for comparing a weighted probability to a baseline probability, a threshold value, and/or a reference level, and assigning a fold-baseline probability based on whether or not the baseline probability, threshold value, or reference level is exceeded. Assessing a weighted probability, threshold value, or reference level can be linked to at least one recommendation. Exceeding a weighted probability, threshold value, or reference level may be linked to a recommendation of treatment with a HIF-2α inhibitor. In some embodiments, the baseline probability represents the average probability of a subject having cancer exhibiting a clinically beneficial response to treatment with a HIF-2α inhibitor, either in general or for a specific population. In some embodiments, the baseline probability represents a pre-test likelihood that a particular subject will exhibit a clinically beneficial response to treatment with a HIF-2α inhibitor before applying a method of the disclosure to determine a post-test risk. A weighted probability above a baseline probability may correspond to a specified fold-baseline probability, whatever the pre-test baseline for the subject may be. In some embodiments, the test subject may be designated as having a high probability of exhibiting a clinically beneficial response to treatment with a HIF-2α inhibitor if the weighted probability corresponds to about or at least about 1.1-times, 1.2-times, 1.3-times, 1.4-times, 1.5-times, 1.8-times, 2-times, 2.5-times, 3-times, 4-times, 5-times, 6-times, 7-times, 8-times, 9-times, 10-times, 25-times, 50-times, or 100-times the baseline probability. In some embodiments, the test subject may be designated as having a low probability of exhibiting a clinically beneficial response to treatment with a HIF-2α inhibitor if the weighted probability corresponds to about or at less than about 0.9-times, 0.8-times, 0.7-times, 0.6-times, 0.5-times, 0.4-times, 0.3-times, 0.2-times, 0.1-times, 0.05-times, 0.01-times the baseline probability.

After performing a calculation, a processor can provide the output, such as from a calculation, back to, for example, the input device or storage unit, to another storage unit of the same or different computer system, or to an output device. Output from the processor can be displayed by data display. A data display can be a display screen (for example, a monitor or a screen on a digital device), a print-out, a data signal (for example, a packet), an alarm (for example, a flashing light or a sound), a graphical user interface (for example, a webpage), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a tablet, a flash memory drive, a light source, a sound generator, a fax machine, a computer, a computer monitor, a printer, an iPod, and a webpage. The user station may be in communication with a printer or a display monitor to output the information processed by the server.

It is envisioned that data relating to the present disclosure can be transmitted over a network or connections for reception and/or review by a receiver. The receiver can be but is not limited to an individual; the subject to whom the report pertains; a health care provider, manager, other healthcare professional, or other caretaker; an oncologist; a genetic counselor; a person or entity that performed and/or ordered the biomarker expression analysis; or a local or remote system for storing such reports (e.g. servers or other systems of a "cloud computing" architecture). In one embodiment, a computer-readable medium includes a medium suitable for transmission of a result of an analysis of a biological sample, such as analysis of one or more biomarkers. The medium can include a result regarding one or more biomarker expression levels of an individual, probability (such as fold-baseline probability) of having a cancer that is sensitive to treatment with a HIF-2α inhibitor, and/or a treatment plan for the individual, wherein such a result is derived using the methods described herein.

In some embodiments, the subject or a third party (e.g. a heath care provider, health care manager, other health professional, or other caretaker) is alerted if a subject is designated as having a "high probability" of having a beneficial response to treatment with a HIF-2α inhibitor. The analysis generated can be reviewed and further analyzed by a medical professional such as a managing doctor or licensed physician, or other third party. The medical professional or other third party can meet with the subject to discuss the results, analysis, and report. Information provided can include recommendations, such as treatment (e.g., with a HIF-2α inhibitor or an alternative therapy).

In some embodiments, the method further comprises providing a recommendation for treatment based on an assessment of the likelihood that a subject having cancer will exhibit a clinically beneficial response to treatment with a HIF-2α inhibitor, such as designation as having high probability. A recommendation may form part of a report generated based on biomarker expression analysis, or may be made by a receiver on the basis of such report. A recommendation may be for further action on the part of the subject and/or for a third party, such as a heath care provider, health care manager, other health professional, or other caretaker. Recommendations may include, but are not limited to, treatment with a HIF-2α inhibitor; continued monitoring of the subject; screening exams or laboratory tests that may further characterize the cancer; prescription and/or administration of one or more therapeutic agents that are not HIF-2α inhibitors; discontinued therapy; and treatment with an alternative therapy, e.g. chemotherapy, radiotherapy, or surgery.

In some embodiments, the disclosure provides a method of categorizing a cancer status of a subject. The cancer status of the subject may be categorized based on an expression profile of a tumor sample from the subject. A cancer status may be categorized as likely sensitive to treatment with a HIF-2α inhibitor or likely resistant to treatment with a HIF-2α inhibitor. A "likely sensitive" categorization may be assigned to a cancer or cancer cell having (1) overexpression of one or more biomarkers that predict for HIF-2α inhibitor sensitivity and/or (2) underexpression of one or more biomarkers that predict for HIF-2α inhibitor resistance. A "likely resistant" categorization may be assigned to a cancer or cancer cell having (1) underexpression of one or more biomarkers that predict for HIF-2α inhibitor sensitivity and/or (2) overexpression of one or more biomarkers that predict for HIF-2α inhibitor resistance. A cancer or cancer cell may have an expression profile having predictors of both sensitivity and resistance. In some embodiments, a cancer or cancer cell may be categorized as sensitive if at least 1 more, at least 2 more, at least 3 more, at least 4 more, at least 5 more, at least 6 more, at least 7 more, at least 8 more, at least 9 more, at least 10 more, at least 15 more, at least 20 more, at least 25 more, at least 30 more, at least 40 more, or at least 50 more biomarkers predict for sensitivity to HIF-2α inhibitor treatment than predict for resistance to HIF-2α inhibitor treatment. For example, a cancer cell having overexpression of LOX, GLI1, RDH13, and TPST2 (predictors of sensitivity) and overexpression of ANO7 (a predictor of resistance) may be categorized as likely sensitive, as three more biomarkers predict for sensitivity than for resistance to HIF-2α inhibitor treatment.

In some embodiments, a method of the disclosure provides a reference level above or below which a biomarker must be expressed to be considered in assessing the likelihood of response to treatment with a HIF-2α inhibitor. The biomarker may be differentially expressed at least 1.1 fold, at least 1.2 fold, at least 1.3 fold, at least 1.4 fold, at least 1.5 fold, at least 2.0 fold, at least 2.25 fold, at least 2.5 fold, at least 2.75 fold, at least 3.0 fold, at least 3.5 fold, at least 4.0 fold, at least 5.0, or even at least 10 fold higher or lower relative to a reference level to be considered in adjusting the likelihood of response. In some embodiments, the reference level is a numerical range of biomarker expression that is obtained from a statistical sampling from a population of individuals having cancer that is resistant to treatment with a HIF-2α inhibitor. In some embodiments, the reference level is a numerical range of biomarker expression that is obtained from a statistical sampling from a population of individuals having cancer that is sensitive to treatment with a HIF-2α inhibitor. The reference level may be a numerical range of biomarker expression that is obtained from a statistical sampling from a population of individuals having cancer, e.g., the same cancer as the test subject. In some embodiments, the reference level is derived by comparison of sensitive and resistant populations.

In some embodiments, a method of the disclosure provides applying an alternative therapy to the subject if at least one biomarker for HIF-2α inhibitor response is determined to be absent. An alternative therapy may be applied to the subject if a biomarker that predicts for sensitivity to a HIF-2α inhibitor is underexpressed and/or if a biomarker that predicts for resistance to a HIF-2α inhibitor is overexpressed. The alternative therapy may comprise any treatment that is not a HIF-2α inhibitor, for example, chemotherapy, radiotherapy, or surgery.

In a further embodiment, the present disclosure provides a method of treating a cancer condition, wherein the HIF-2α inhibitor is effective in one or more of inhibiting proliferation of cancer cells, inhibiting metastasis of cancer cells, killing cancer cells and reducing severity or incidence of symptoms associated with the presence of cancer cells. In some other embodiments, said method comprises administering to the cancer cells a therapeutically effective amount of a HIF-2α inhibitor. In some embodiments, the administration takes place in vitro. In other embodiments, the administration takes place in vivo.

Hypoxia-inducible factors (HIFs), like HIF-2α, are transcription factors that respond to changes in available oxygen in the cellular environment (e.g. a decrease in oxygen, or hypoxia). The HIF signaling cascade mediates the effects of hypoxia, the state of low oxygen concentration, on the cell. Hypoxia often keeps cells from differentiating. However, hypoxia promotes the formation of blood vessels, and is important for the formation of a vascular system in embryos, and cancer tumors. The hypoxia in wounds also promotes the migration of keratinocytes and the restoration of the epithelium. A HIF-2α inhibitor of the present disclosure may be administered in an amount effective in reducing any one or more of such effects of HIF-2α activity.

HIF-2α activity can be inhibited by inhibiting heterodimerization of HIF-2α to HIF-1β (ARNT). A variety of methods for measuring HIF-2α dimerization are available. In some embodiments, the HIF-2α inhibitor binds the PAS-B domain cavity of HIF-2α.

Inhibition of heterodimerization of HIF-2α to HIF-1β (ARNT) may also be determined by a reduction in HIF-2α target gene mRNA expression. mRNA quantitation can be performed using real-time PCR technology (Wong, et al, "Real-time PCR for mRNA quantitation", 2005. BioTechniques 39, 1: 1-1.). Yet another method for determining inhibition of heterodimerization of HIF-2α to HIF1β (ARNT) is by co-immunoprecipitation.

As described herein, HIF-2α is a transcription factor that plays important roles in regulating expression of target genes. Non-limiting examples of HIF-2α target gene include HMOX1, SFTPA1, CXCR4, PAI1, BDNF, hTERT, ATP7A, and VEGF. For instance, HIF-2α is an activator of VEGF. A HIF-2α inhibitor of the present disclosure may be administered in an amount effective in reducing expression of any one or more of genes induced by HIF-2α activity. A variety of methods is available for the detection of gene expression levels, and includes the detection of gene transcription products (polynucleotides) and translation products (polypeptides). For example, gene expression can be detected and quantified at the DNA, RNA or mRNA level. Various methods that have been used to quantify mRNA include in situ hybridization techniques, fluorescent in situ hybridization techniques, reporter genes, RNase protection assays, Northern blotting, reverse transcription (RT)-PCR, SAGE, DNA microarray, tiling array, and RNA-seq. Examples of methods for the detection of polynucleotides include, but are not limited to selective colorimetric detection of polynucleotides based on the distance-dependent optical properties of gold nanoparticles, and solution phase detection of polynucleotides using interacting fluorescent labels and competitive hybridization. Examples for the detection of proteins include, but are not limited to microscopy and protein immunostaining, protein immunoprecipitation, immunoelectrophoresis, western blot, BCA assay, spectrophotometry, mass spectrophotometry and enzyme assay.

In some embodiments, inhibition of HIF-2α is characterized by a decrease in VEGF gene expression. The decrease may be measured by any of a variety of methods, such as those described herein. As a further example, the mRNA expression level of VEGF can be measured by quantitative PCR (QT-PCR), microarray, RNA-seq and nanostring. As another example, an ELISA assay can be used to measure the level VEGF protein secretion.

A "HIF-2α inhibitor" suitable for use in the subject methods can be selected from a variety of types of molecules. For example, the HIF-2α inhibitor can be a biological or chemical compound, such as a simple or complex organic or inorganic molecule, peptide, peptide mimetic, protein (e.g. antibody), liposome, or a polynucleotide (e.g. small interfering RNA, microRNA, anti-sense, aptamer, ribozyme, or triple helix). Some exemplary classes of chemical compounds suitable for use in the subject methods include compounds disclosed herein. A HIF-2α inhibitor for use in the present disclosure can be any HIF-2α inhibitor that is known in the art, and can include any chemical entity that, upon administration to a patient, results in inhibition of HIF-2α in the patient.

In general, a HIF-2α inhibitor is a compound that inhibits one or more biological effects of HIF-2α. Examples of biological effects of HIF-2α include, but are not limited to, heterodimerization of HIF-2α to HIF-1β, HIF-2α target gene expression, VEGF gene expression, and VEGF protein secretion. In some embodiments, the HIF-2α inhibitor is selective for HIF-2α, such that the inhibitor inhibits heterodimerization of HIF-2α to HIF-1β but not heterodimerization of HIF-1α to HIF-1β. Such biological effects may be inhibited by about or more than about 10%, 20%, 30%, 40%, 50%, 60%, 70%, 80%, 90%, 95%, or more.

Exemplary HIF-2α inhibitors: In one aspect, the disclosure provides a compound which is an inhibitor of HIF-2α of Formula I:

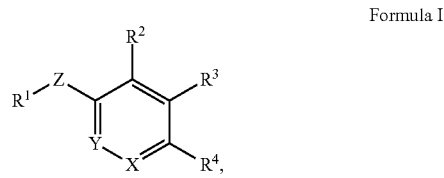

Formula I or a pharmaceutically acceptable salt or prodrug thereof, wherein:

X is CR⁵ or N;
Y is CR⁶ or N;
Z is —O—, —S—, —S(O)—, —S(O)₂—, —C(O)—, —C(HR⁷)—, —N(R⁸)—, $C_1$-$C_3$ alkylene, $C_1$-$C_3$ heteroalkylene, $C_1$-$C_3$ alkenylene or absent;
R¹ is alkyl, heteroalkyl, cycloalkyl, heterocycloalkyl, aryl, heteroaryl, aralkyl, heteroarylalkyl, acyl or cyano;
R² is nitro, carboxaldehyde, carboxyl, ester, amido, cyano, halo, sulfonyl, alkyl, alkenyl, alkynyl or heteroalkyl;
R³ is hydrogen, halo, cyano, alkyl, heteroalkyl, alkenyl, alkynyl, amino, carboxaldehyde, carboxylic acid, oxime, ester, amido or acyl; or R² and R³ taken together form a cyclic moiety;
R⁴ is nitro, halo, cyano, alkyl, cycloalkyl, heteroaryl, carboxyl, sulfinyl, sulfonamidyl, sulfonyl or sulfoximinyl; and
R⁵, R⁶, R⁷ and R⁸ are independently hydrogen, halo, hydroxy, cyano, alkyl or alkoxy.

In some embodiments, R¹ is phenyl or monocyclic heteroaryl. In some further embodiments, R¹ is phenyl or pyridyl, optionally substituted with one or more substituents selected from the group consisting of halo, alkyl, alkoxy and cyano. In a further embodiment, the substituent(s) is selected from the group consisting of halo, $C_1$-$C_4$ alkyl, $C_1$-$C_4$ alkoxy and cyano.

In some embodiments, R¹ is bicyclic heteroaryl. In a further embodiment, the bicyclic heteroaryl is substituted with one or more substituents selected from the group consisting of halo, $C_1$-$C_4$ alkyl, $C_1$-$C_4$ alkoxy and cyano.

In some embodiments, R¹ is pyridyl N-oxide. In a further embodiment, the pyridyl N-oxide is substituted with one or more substituents selected from the group consisting of halo, $C_1$-$C_4$ alkyl, $C_1$-$C_4$ alkoxy and cyano.

In some embodiments, R¹ is

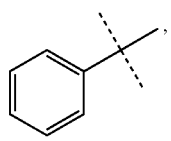

wherein the aryl ring may optionally be substituted with one or more substituents selected from the group consisting of cyano, halo, alkyl and alkoxy. In a further embodiment, the substituent(s) is selected from the group consisting of halo, $C_1$-$C_4$ alkyl, $C_1$-$C_4$ alkoxy and cyano.

In some embodiments, R¹ is

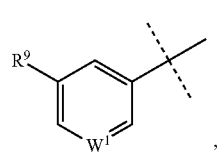

wherein W¹ is N or CR¹⁰, R⁹ is cyano, halo, alkyl or alkoxy, and R¹⁰ is hydrogen, cyano, halo, alkyl or alkoxy. In a further embodiment, R⁹ is cyano, halo, $C_1$-$C_4$ alkyl or $C_1$-$C_4$ alkoxy, and R¹⁰ is hydrogen, cyano, halo, $C_1$-$C_4$ alkyl or $C_1$-$C_4$ alkoxy.

In some embodiments, R¹ is selected from the group consisting of:

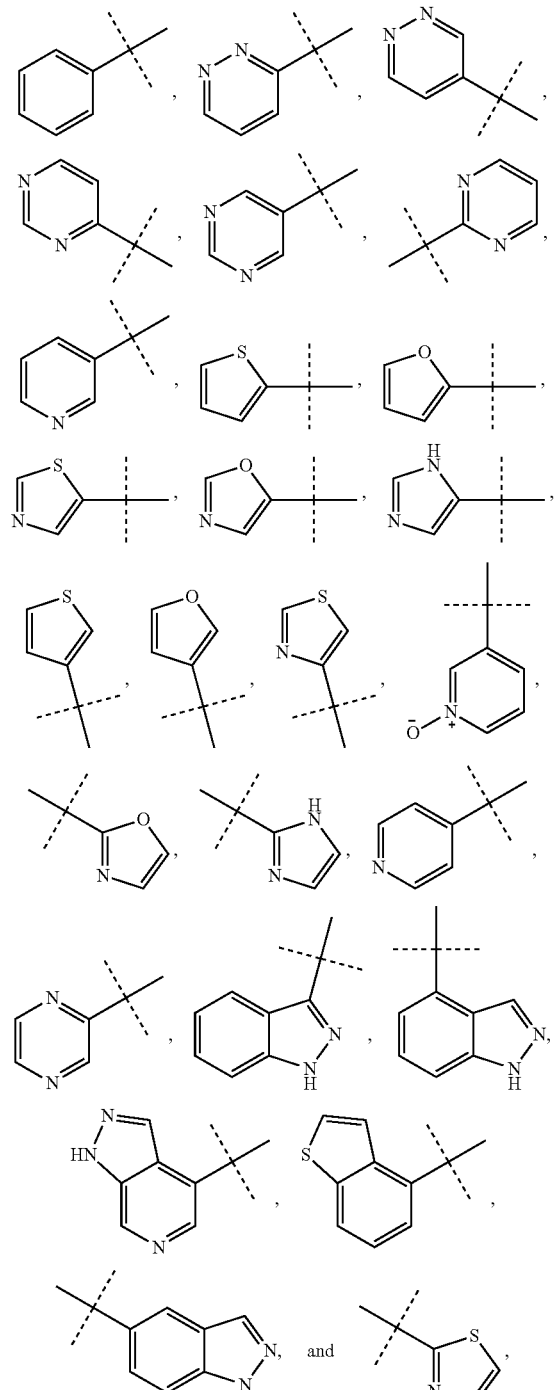

and the rings specified for R¹ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

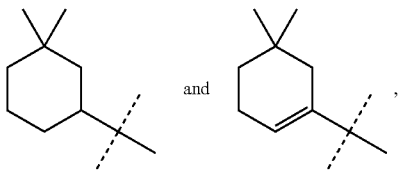

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

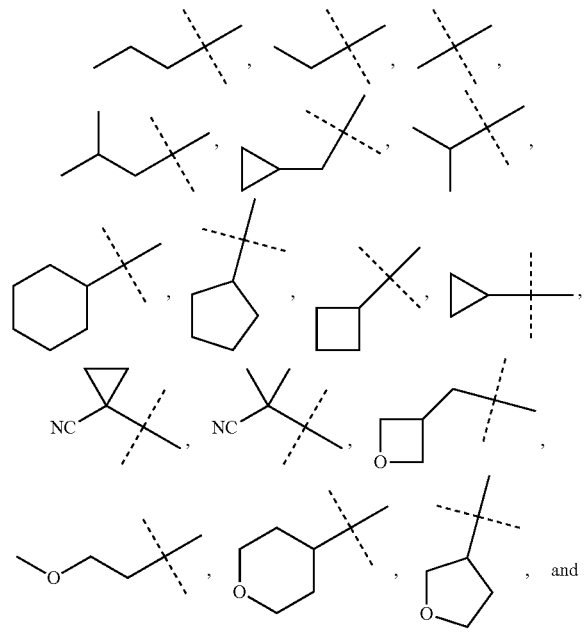

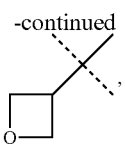

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —$CH_2F$, —$CHF_2$ or —$CF_3$. In another embodiment, $R^2$ is hydrogen. In some other embodiments, $R^2$ is heteroalkyl, alkenyl or alkynyl.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —$(CH_2)_n$OH, wherein n is 1, 2 or 3. In still a further embodiment, $R^3$ is —$CH_2OH$.

In some embodiments, $R^2$ and $R^3$ taken together with the atoms to which they are attached form a 5- or 6-membered carbocycle with at least one $sp^3$ hybridized carbon. Representative compounds with the carbocycle include, but are not limited to, the following:

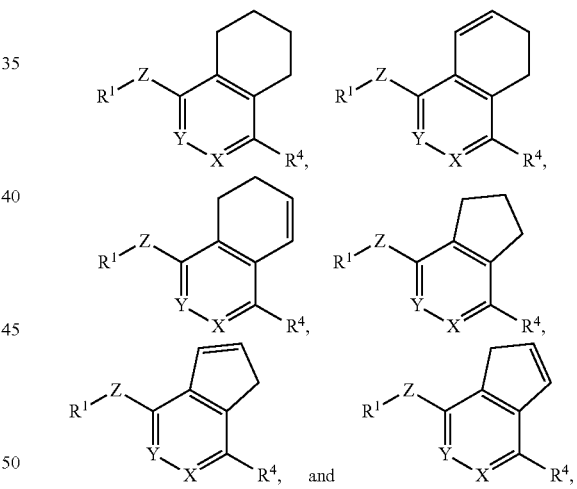

wherein the carbocycle formed by linking R and R may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl, sulfoximinyl or fluoroalkylsulfonyl. In a further embodiment, $R^4$ is fluoroalkyl. In yet another embodiment, $R^4$ is sulfonyl. In still another embodiment, $R^4$ is alkylsulfonyl.

In some embodiments, $R^4$ is —S(=O)$_2$R$^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=NR$^b$)R$^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^3$ is hydrogen, $R^4$ is —S(=O)$_2$R$^a$ or —S(=O)(=NR$^b$)R$^c$, wherein $R^a$ is fluoroalkyl, $R^b$ is hydrogen, cyano or alkyl and $R^c$ is alkyl. In a further embodiment, $R^1$ is selected from the group consisting of

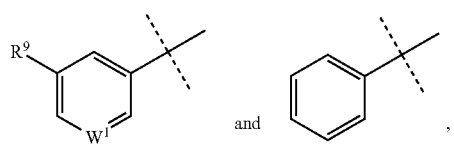

wherein $W^1$ is N or CR$^{10}$, $R^9$ is cyano, halo, alkyl or alkoxy, and $R^{10}$ is hydrogen, cyano, halo, alkyl or alkoxy; and

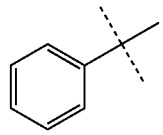

may optionally be substituted with one or more substituents selected from the group consisting of cyano, halo, alkyl and alkoxy. In a further embodiment, the alkyl is $C_1$-$C_4$ alkyl. In another further embodiment, the alkoxy is $C_1$-$C_4$ alkoxy.

In some embodiments, each of $R^2$ and $R^3$ is independently alkyl and $R^4$ is cyano, fluoroalkyl, sulfonamidyl, sulfinyl, sulfonyl, sulfoximinyl or fluoroalkylsulfonyl.

In some embodiments, $R^3$ is —CH$_2$OH. In a further embodiment, $R^4$ is cyano, fluoroalkyl, sulfonamidyl, sulfinyl, sulfonyl, sulfoximinyl or fluoroalkylsulfonyl and $R^5$ is hydrogen. In still a further embodiment, $R^2$ is cyano, halo or alkyl.

In some embodiments, $R^1$ is phenyl or monocyclic heteroaryl; $R^2$ is nitro, halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$. In still a further embodiment, $R^5$ is hydrogen.

In some embodiments, $R^1$ is bicyclic heteroaryl; $R^2$ is nitro, halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl; and $R^5$ is hydrogen.

In some embodiments, $R^1$ is phenyl, monocyclic heteroaryl or bicyclic heteroaryl; $R^2$ is halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl; and $R^5$ is hydrogen.

In some embodiments, $R^2$ and $R^3$ together with the atoms to which they are attached form a 5- or 6-membered carbocycle with at least one sp$^3$ hybridized carbon; $R^4$ is cyano, fluoroalkyl, sulfonamidyl, sulfinyl, sulfonyl, sulfoximinyl or fluoroalkylsulfonyl; and $R^5$ is hydrogen. In a further embodiment, $R^1$ is phenyl or monocyclic heteroaryl. In another further embodiment, $R^1$ is bicyclic heteroaryl.

In some embodiments, X is N and Y is CR$^6$. In other embodiments, X is CR and Y is N. In still other embodiments, X is N and Y is N. In yet other embodiments, X is CR$^5$ and Y is CR$^6$.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In another aspect, the disclosure provides a compound of Formula I-A:

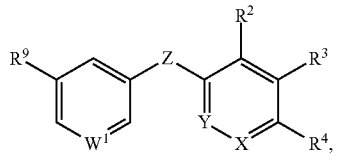

or a pharmaceutically acceptable salt or prodrug thereof, wherein:
X is $CR^5$ or N;
Y is $CR^6$ or N;
Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy.
$W^1$ is N or $CR^{10}$;
$R^9$ is cyano, halo, alkyl or alkoxy; and
$R^{10}$ is hydrogen, cyano, halo, alkyl or alkoxy.
In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —CH$_2$F, —CHF$_2$ or —CF$_3$.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —(CH$_2$)$_n$OH, wherein n is 1, 2 or 3. In still a further embodiment, $R^3$ is —CH$_2$OH.

In some embodiments, $R^2$ and $R^3$ taken together with the atoms to which they are attached form a 5- or 6-membered carbocycle with at least one sp$^3$ hybridized carbon. Representative compounds with the carbocycle include, but are not limited to, the following:

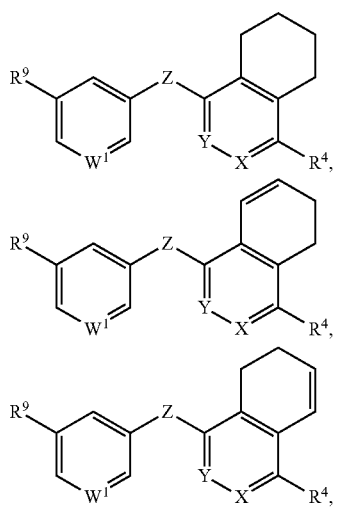

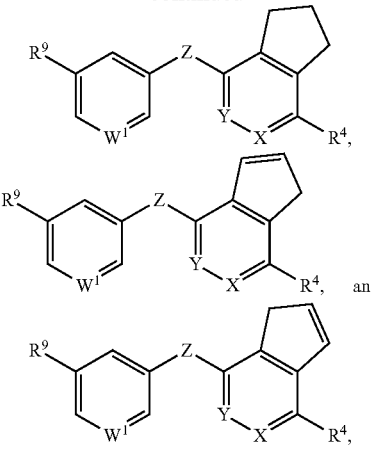

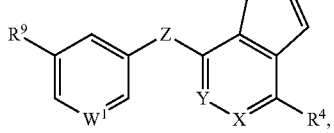

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is alkylsulfonyl.

In some embodiments, $R^4$ is —S(=O)$_2$R$^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=NR$^b$)R$^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^9$ is cyano, halo, $C_1$-$C_4$ alkyl or $C_1$-$C_4$ alkoxy.

In some embodiments, $R^{10}$ is hydrogen, cyano, halo, $C_1$-$C_4$ alkyl or $C_1$-$C_4$ alkoxy.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl.

In some embodiments, $R^3$ is —CH$_2$OH and $R^4$ is cyano, fluoroalkyl, sulfonamidyl, sulfonyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is CH$_2$OH; $R^4$ is cyano, fluoroalkyl, sulfonamidyl, sulfonyl or sulfoximinyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR and Y is N. In still other embodiments, X is N and Y is N. In yet other embodiments, X is CR$^5$ and Y is CR$^6$.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In another aspect, the disclosure provides a compound of Formula I-B:

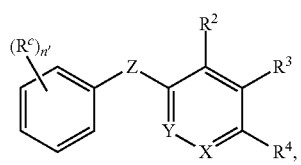

or a pharmaceutically acceptable salt or prodrug thereof, wherein:

X is CR$^5$ or N;

Y is CR$^6$ or N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^2$ is nitro, carboxaldehyde, carboxylic acid, ester, amido, cyano, halo, sulfonyl or alkyl;

$R^3$ is hydrogen, halo, cyano, alkyl, heteroalkyl, alkenyl, alkynyl, amino, oxime or acyl; or $R^2$ and $R^3$ taken together form a cyclic moiety;

$R^4$ is nitro, halo, cyano, alkyl, sulfinyl, sulfonamidyl, sulfonyl or sulfoximinyl;

$R^5$, $R^6$, $R^7$ and $R^8$ are independently hydrogen, halo, hydroxy, cyano, alkyl or alkoxy.

$R^c$ is hydrogen, cyano, halo, alkyl or alkoxy; and n' is 0, 1, 2, 3 or 4.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —CH$_2$F, —CHF$_2$ or —CF$_3$.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —(CH$_2$)$_n$OH, wherein n is 1, 2 or 3.

In some embodiments, $R^2$ and $R^3$ taken together with the atoms to which they are attached form a 5- or 6-membered carbocycle with at least one sp$^3$ hybridized carbon. Representative compounds with the carbocycle include, but are not limited to, the following:

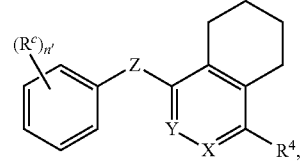

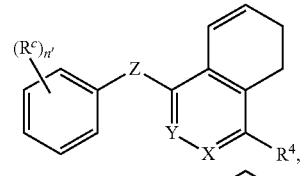

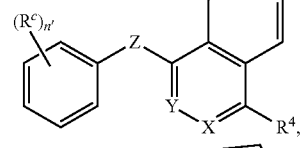

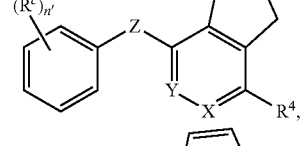

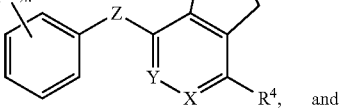
and

-continued

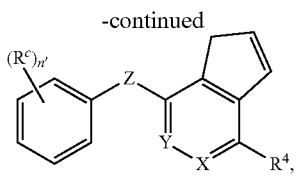

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^3$ is hydrogen, $R^4$ is —S(=O)$_2$R$^a$ or —S(=O)(=NR$^b$)R$^d$, wherein R$^a$ is fluoroalkyl, R$^b$ is hydrogen, cyano or alkyl and R$^d$ is alkyl.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is alkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$—N(R$^a$)$_2$, wherein each R$^a$ is independently hydrogen, alkyl, heteroalkyl, cycloalkyl or heterocycloalkyl, and at least one R$^a$ is hydrogen. In a further embodiment, both R$^a$s are hydrogen. In another further embodiment, one R$^a$ is hydrogen and the other R$^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^3$ is —CH$_2$OH and $R^4$ is fluoroalkyl, sulfonamidyl, sulfonyl, sulfinyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is CH$_2$OH; $R^4$ is fluoroalkyl, sulfonamidyl, sulfonyl, sulfinyl or sulfoximinyl. In a further embodiment, $R^4$ is selected from the group consisting of —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR and Y is N. In still other embodiments, X is N and Y is N. In yet other embodiments, X is CR$^5$ and Y is CR$^6$.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In some embodiments, R$^c$ is cyano, halo, $C_1$-$C_4$ alkyl or $C_1$-$C_4$ alkoxy.

In yet another aspect, the disclosure provides a compound of Formula I-C:

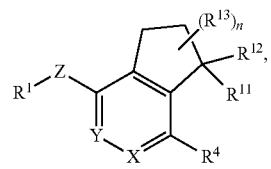

or a pharmaceutically acceptable salt or prodrug thereof, wherein:

X is CR$^5$ or N;
Y is CR$^6$ or N;
Z is —O—, —S—, —S(O)—, —S(O)$_2$—, —C(O)—, —C(HR$^7$)—, —N(R$^8$)—, C$_1$-C$_3$ alkylene, C$_1$-C$_3$ heteroalkylene, C$_1$-C$_3$ alkenylene or absent;
R$^1$ is alkyl, heteroalkyl, cycloalkyl, heterocycloalkyl, aryl, heteroaryl, aralkyl, heteroarylalkyl, acyl or cyano;
R$^4$ is nitro, halo, cyano, alkyl, cycloalkyl, heteroaryl, carboxyl, sulfinyl, sulfonamidyl, sulfonyl or sulfoximinyl; and
R$^5$, R$^6$, R$^7$ and R$^8$ are independently hydrogen, halo, hydroxy, cyano, alkyl or alkoxy;
R$^{11}$ is hydrogen, halo, hydroxy, alkoxy or amino;
R$^{12}$ is hydrogen, alkyl, alkenyl or alkynyl; or R$^{11}$ and R$^{12}$ in combination form oxo or oxime;
each of R$^{13}$ is independently selected from the group consisting of hydrogen, fluoro, chloro, hydroxy, alkyl and heteroalkyl, with the proviso that when R$^{13}$ is hydroxy, n is 1 or 2; or two R$^{13}$s and the carbon atom(s) to which they are attached form a 3- to 8-membered cycloalkyl or heterocycloalkyl moiety; and
n is 0, 1, 2, 3 or 4.

In some embodiments, R$^1$ is phenyl or monocyclic heteroaryl. In some further embodiments, R$^1$ is phenyl or pyridyl, optionally substituted with one or more substituents selected from the group consisting of halo, alkyl, alkoxy and cyano. In a further embodiment, R$^1$ is

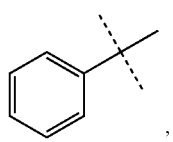

wherein the aryl ring is optionally substituted with one or more substituents selected from the group consisting of cyano, halo, alkyl and alkoxy. In another further embodiment, R$^1$ is

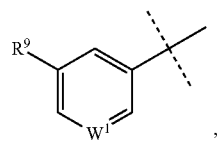

wherein W$^1$ is N or CR$^{10}$, R$^9$ is cyano, halo, alkyl or alkoxy, and R$^{10}$ is hydrogen, cyano, halo, alkyl or alkoxy.

In some embodiments, R$^1$ is bicyclic heteroaryl.

In some embodiments. R$^1$ is selected from the group consisting of:

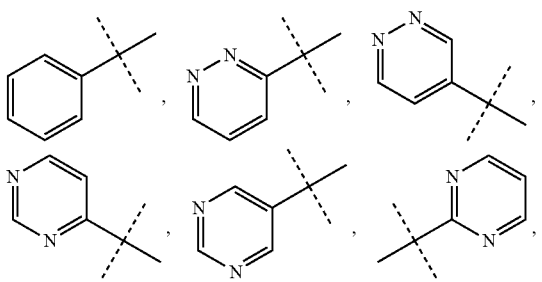

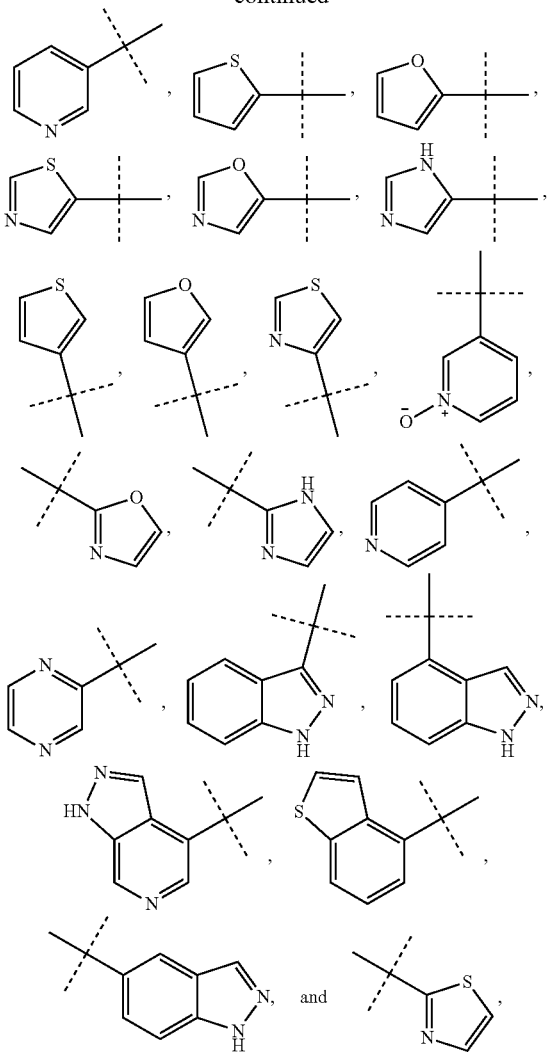

and the rings specified for R$^1$ may optionally be substituted with one or more substituents described for aryl and heteroaryl. In a further embodiment, the substituent(s) is selected from the group consisting of halo, C$_1$-C$_4$ alkyl, C$_1$-C$_4$ alkoxy and cyano.

In some embodiments, R$^1$ is selected from the group consisting of:

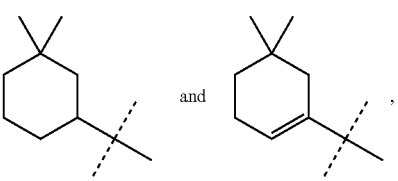

and the rings specified for R$^1$ may optionally be substituted with one or more substituents described for cycloalkyl. In a further embodiment, the substituent(s) is selected from the group consisting of halo, hydroxy, C$_1$-C$_4$ alkyl, C$_1$-C$_4$ alkoxy, cyano and oxo.

In some embodiments, R$^1$ is cycloalkyl. In other embodiments, R$^1$ is heterocycloalkyl. In a further embodiment, R$^1$ is C$_3$-C$_6$ cycloalkyl or C$_3$-C$_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

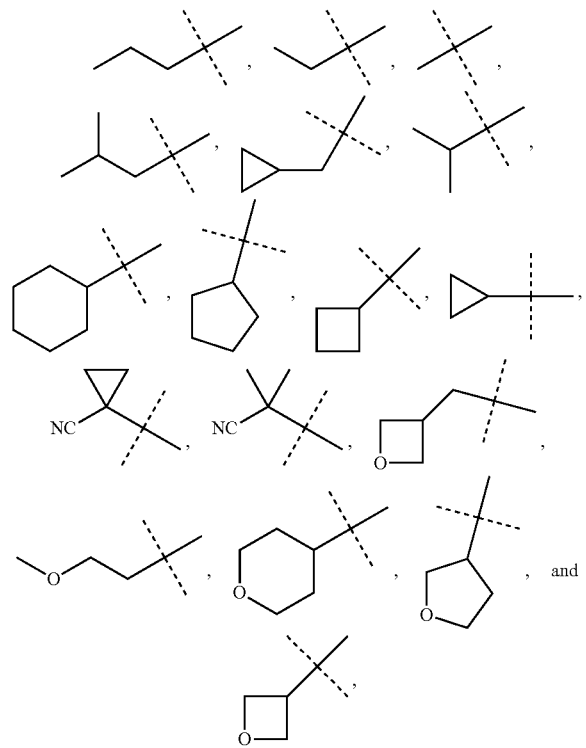

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is alkylsulfonyl.

In some embodiments, $R^4$ is —S(=O)$_2$$R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=N$R^b$)$R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N($R^a$)$_2$, wherein each $R^a$ is independently hydrogen, alkyl, heteroalkyl, cycloalkyl or heterocycloalkyl, and at least one $R^a$ is hydrogen. In another further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy or amino. In a further embodiment, $R^{11}$ is hydroxy. In another further embodiment, $R^{11}$ is amino.

In some embodiments, $R^{12}$ is hydrogen. In some other embodiments, $R^{12}$ is alkyl or alkenyl.

In some embodiments, $R^{13}$ is fluoro. In a further embodiment, n is 1, 2 or 3. In a further embodiment, two $R^{13}$s in combination form oxo, oxime or methylene. In still further embodiments, two $R^{13}$s and the carbon atom(s) to which they are attached form a 3- to 8-membered cycloalkyl or heterocycloalkyl moiety.

In some embodiments, $R^1$ is monocyclic aryl or monocyclic heteroaryl and $R^{11}$ is hydroxy or amino. In a further embodiment, $R^{13}$ is fluoro. In still a further embodiment, n is 1, 2 or 3.

In some embodiments, $R^1$ is phenyl or monocyclic heteroaryl, $R^{11}$ is hydroxy or amino, $R^{13}$ is fluoro, n is 1, 2 or 3, and $R^5$ is hydrogen.

In some embodiments, $R^1$ is bicyclic heteroaryl and $R^{11}$ is hydroxy or amino. In a further embodiment, $R^{13}$ is fluoro. In still a further embodiment, n is 1, 2 or 3.

In some embodiments, $R^1$ is bicyclic heteroaryl, $R^{11}$ is hydroxy or amino, $R^{13}$ is fluoro, n is 1, 2 or 3, and $R^5$ is hydrogen.

In some embodiments, $R^4$ is cyano, fluoroalkyl, sulfonamidyl, sulfinyl, sulfonyl, sulfoximinyl or fluoroalkylsulfonyl, and $R^{11}$ is hydroxy or amino. In a further embodiment, $R^{12}$ is hydrogen. In another further embodiment, $R^{13}$ is fluoro. In still a further embodiment, n is 1, 2 or 3.

In some embodiments, $R^4$ is cyano, fluoroalkyl, sulfonamidyl, sulfinyl, sulfonyl, sulfoximinyl or fluoroalkylsulfonyl; $R^{11}$ is hydroxy or amino; $R^{13}$ is fluoro; n is 1, 2 or 3; and $R^5$ is hydrogen. In a further embodiment, $R^{12}$ is hydrogen.

In some embodiments $R^{11}$ is hydroxy or amino and $R^{12}$ is hydrogen. In a further embodiment, $R^{13}$ is fluoro. In still a further embodiment, n is 1, 2 or 3.

In some embodiments $R^{11}$ is hydroxy or amino, $R^{12}$ is hydrogen, $R^{13}$ is fluoro, n is 1, 2 or 3, and $R^5$ is hydrogen. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^4$ is fluoroalkyl; n is 0, 1, 2 or 3; Z is —O—; $R^{11}$ is hydroxy; and $R^{12}$ is hydrogen.

In some embodiments, $R^4$ is sulfonyl or fluoroalkylsulfonyl; n is 0, 1, 2 or 3; Z is —O—; $R^{11}$ is hydroxy; and $R^{12}$ is hydrogen.

In some embodiments, X is N and Y is $CR^6$. In other embodiments, X is CR and Y is N. In still other embodiments, X is N and Y is N. In yet other embodiments, X is $CR^5$ and Y is $CR^6$.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In still another aspect, the disclosure provides a compound of Formula I-D, I-E, I-F or I-G:

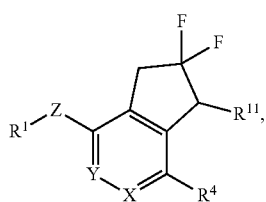

I-D

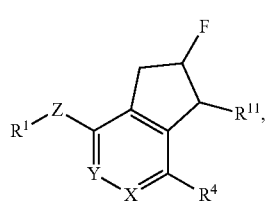

I-E

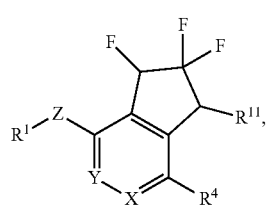

I-F

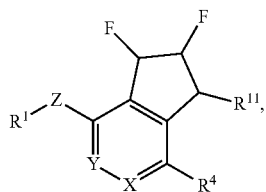

I-G or a pharmaceutically acceptable salt or prodrug thereof, wherein:

X is $CR^5$ or N;

Y is $CR^6$ or N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl heteroaryl, aralkyl, or heteroarylalkyl;

$R^4$ is nitro, halo, cyano, alkyl, cycloalkyl, heteroaryl, carboxyl, sulfinyl, sulfonamidyl, sulfonyl or sulfoximinyl; and $R^5$, $R^6$, $R^7$ and $R^8$ are independently hydrogen, halo, hydroxy, cyano, alkyl or alkoxy; and $R^{11}$ is hydrogen, halo, hydroxy, alkoxy or amino.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

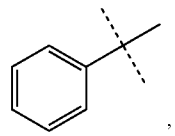

wherein the aryl ring is optionally substituted with one or more substituents selected from the group consisting of cyano, halo, alkyl and alkoxy. In another further embodiment, $R^1$ is

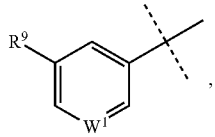

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl having at least one N atom.

In some embodiments, $R^1$ is selected from the group consisting of:

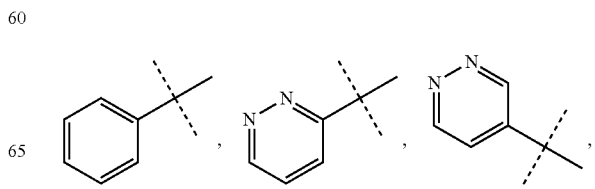

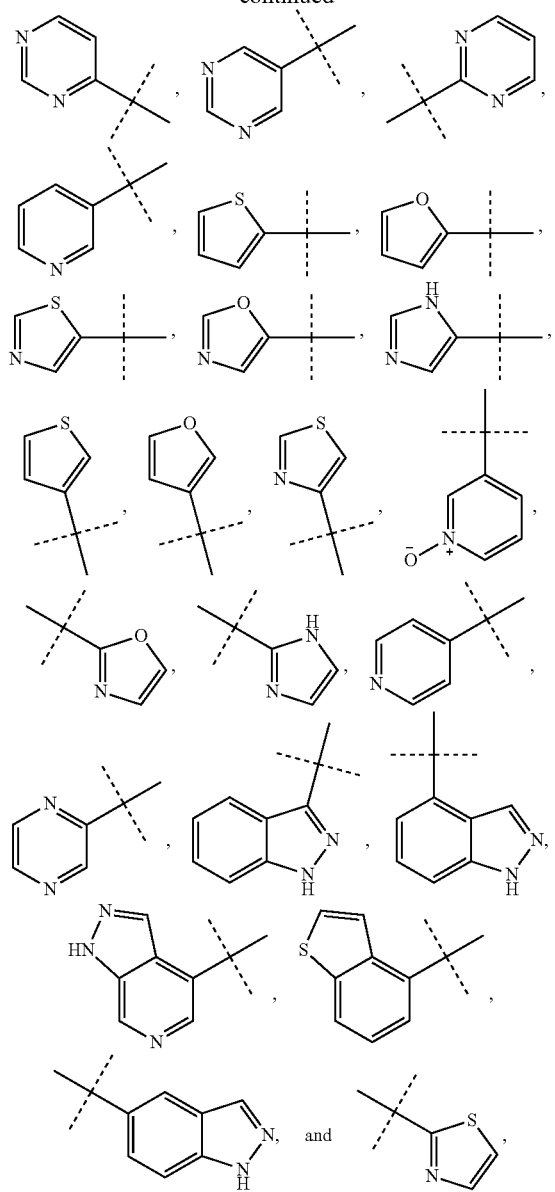

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, IV is selected from the group consisting of:

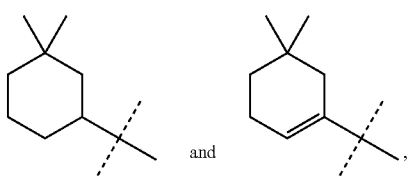

and the rings specified for IV may optionally be substituted with one or more substituents described for cycloalkyl.

In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

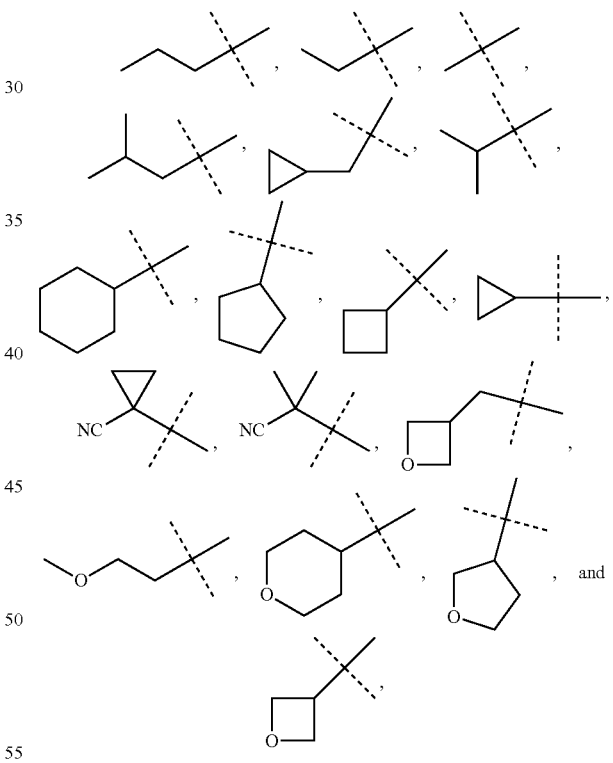

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In some embodiments, $R^4$ is fluoroalkyl, sulfonamidyl, sulfinyl, sulfonyl or sulfoximinyl. In a further embodiment, $R^4$ is fluoroalkyl. In yet another embodiment, $R^4$ is sulfonyl. In still another embodiment, $R^4$ is alkylsulfonyl.

In some embodiments, $R^4$ is $—S(=O)_2R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, $—CH_2F$, $—CHF_2$, $—CF_3$, $—CH_2CF_3$, $—CH_2CHF_2$, $—CH_2CH_2F$, $—CHFCH_3$ and $—CF_2CH_3$.

In some embodiments, $R^4$ is $—S(=O)(=NR^b)R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, $—CH_2F$, $—CHF_2$, $—CF_3$, $—CH_2CF_3$, $—CH_2CHF_2$, $—CH_2CH_2F$, $—CHFCH_3$ and $—CF_2CH_3$.

In some embodiments, $R^4$ is $—S(=O)_2N(R^a)_2$, wherein each $R^a$ is independently hydrogen, alkyl, heteroalkyl, cycloalkyl or heterocycloalkyl, and at least one $R^a$ is hydrogen. In another further embodiment, both $R^a$s are hydrogen. In a further embodiment, one $R^a$ is hydrogen and the other $R^a$ is $C_1$-$C_4$ alkyl.

In some embodiments, $R^4$ is selected from the group consisting of $—CN$, $—CF_3$, $—S(=O)CH_3$, $—S(=O)_2CH_3$, $—S(=O)_2CH_2F$, $—S(=O)_2CHF_2$, $—S(=O)_2CF_3$, $—S(=O)_2NH_2$, $—S(=O)_2NHCH_3$, $—S(=O)(=NH)CH_3$, $—S(=O)(=NH)CH_2F$, $—S(=O)(=NH)CHF_2$, $—S(=O)(=NH)CF_3$, $—S(=O)(=N—CN)CH_3$, $—S(=O)(=N—CN)CH_2F$, $—S(=O)(=N—CN)CHF_2$ and $—S(=O)(=N—CN)CF_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino. In a further embodiment, X is $CR^5$ and $R^5$ is hydrogen. In another further embodiment, $R^5$ is alkyl. In still a further embodiment, $R^5$ is $C_1$-$C_4$ alkyl.

In some embodiments $R^1$ is bicyclic heteroaryl and $R^4$ is cyano, fluoroalkyl, sulfinyl, sulfonamidyl, sulfonyl or sulfoximinyl. In a further embodiment, X is $CR^5$ and $R^5$ is hydrogen. In another further embodiment, $R^4$ is selected from the group consisting of $—CN$, $—CF_3$, $—S(=O)CH_3$, $—S(=O)_2CH_3$, $—S(=O)_2CH_2F$, $—S(=O)_2CHF_2$, $—S(=O)_2CF_3$, $—S(=O)_2NH_2$, $—S(=O)_2NHCH_3$, $—S(=O)(=NH)CH_3$, $—S(=O)(=NH)CH_2F$, $—S(=O)(=NH)CHF_2$, $—S(=O)(=NH)CF_3$, $—S(=O)(=N—CN)CH_3$, $—S(=O)(=N—CN)CH_2F$, $—S(=O)(=N—CN)CHF_2$ and $—S(=O)(=N—CN)CF_3$.

In some embodiments $R^1$ is bicyclic heteroaryl; $R^4$ is cyano, fluoroalkyl, sulfinyl, sulfonamidyl, sulfonyl or sulfoximinyl; $R^{11}$ is hydroxy or amino; and X is $CR^5$ or N; and $R^5$ is hydrogen. In a further embodiment, $R^{11}$ is hydroxy. In another further embodiment, $R^4$ is selected from the group consisting of $—CN$, $—CF_3$, $—S(=O)CH_3$, $—S(=O)_2CH_3$, $—S(=O)_2CH_2F$, $—S(=O)_2CHF_2$, $—S(=O)_2CF_3$, $—S(=O)_2NH_2$, $—S(=O)_2NHCH_3$, $—S(=O)(=NH)CH_3$, $—S(=O)(=NH)CH_2F$, $—S(=O)(=NH)CHF_2$, $—S(=O)(=NH)CF_3$, $—S(=O)(=N—CN)CH_3$, $—S(=O)(=N—CN)CH_2F$, $—S(=O)(=N—CN)CHF_2$ and $—S(=O)(=N—CN)CF_3$.

In some embodiments $R^1$ is phenyl or monocyclic heteroaryl and $R^4$ is cyano, fluoroalkyl, sulfinyl, sulfonamidyl, sulfonyl or sulfoximinyl. In a further embodiment, X is $CR^5$ and $R^5$ is hydrogen. In another further embodiment, $R^4$ is selected from the group consisting of $—CN$, $—CF_3$, $—S(=O)CH_3$, $—S(=O)_2CH_3$, $—S(=O)_2CH_2F$, $—S(=O)_2CHF_2$, $—S(=O)_2CF_3$, $—S(=O)_2NH_2$, $—S(=O)_2NHCH_3$, $—S(=O)(=NH)CH_3$, $—S(=O)(=NH)CH_2F$, $—S(=O)(=NH)CHF_2$, $—S(=O)(=NH)CF_3$, $—S(=O)(=N—CN)CH_3$, $—S(=O)(=N—CN)CH_2F$, $—S(=O)(=N—CN)CHF_2$ and $—S(=O)(=N—CN)CF_3$.

In some embodiments $R^1$ is phenyl or monocyclic heteroaryl; $R^4$ is cyano, fluoroalkyl, sulfinyl, sulfonamidyl, sulfonyl or sulfoximinyl; $R^{11}$ is hydroxy or amino; and X is $CR^5$ or N; and $R^5$ is hydrogen. In a further embodiment, $R^{11}$ is hydroxy. In another further embodiment, $R^4$ is selected from the group consisting of $—CN$, $—CF_3$, $—S(=O)CH_3$, $—S(=O)_2CH_3$, $—S(=O)_2CH_2F$, $—S(=O)_2CHF_2$, $—S(=O)_2CF_3$, $—S(=O)_2NH_2$, $—S(=O)_2NHCH_3$, $—S(=O)(=NH)CH_3$, $—S(=O)(=NH)CH_2F$, $—S(=O)(=NH)CHF_2$, $—S(=O)(=NH)CF_3$, $—S(=O)(=N—CN)CH_3$, $—S(=O)(=N—CN)CH_2F$, $—S(=O)(=N—CN)CHF_2$ and $—S(=O)(=N—CN)CF_3$.

In some embodiments, X is N and Y is $CR^6$. In other embodiments, X is $CR^5$ and Y is N. In still other embodiments, X is N and Y is N. In yet other embodiments, X is $CR^5$ and Y is $CR^6$.

In some embodiments, Z is $—O—$, $—S—$, $—S(O)—$, $—S(O)_2—$, $—S(O_2)N(R^8)—$, $—C(O)—$, $—C(O)O—$, $—C(HR^7)—$, $—N(R^8)—$, $—C(O)N(R^8)—$, alkylene, alkenylene, alkynylene, heteroalkylene, or absent. In some embodiments, Z is $—O—$, $—S—$, $—S(O)—$, $—S(O)_2—$, $—C(O)—$, $—C(HR^7)—$, $—N(R)—$, $C_1$-$C_3$ alkylene, $C_1$-$C_3$ heteroalkylene, $C_1$-$C_3$ alkenylene or absent. In some embodiments, Z is $—O—$. In other embodiments, Z is $—S—$. In further embodiments, Z is $—C(HR^7)—$. In yet other embodiments, Z is $—N(R^8)—$. In some embodiments, Z is absent.

In a further aspect, the disclosure provides a compound of Formula I-H, I-I, I-J or I-K:

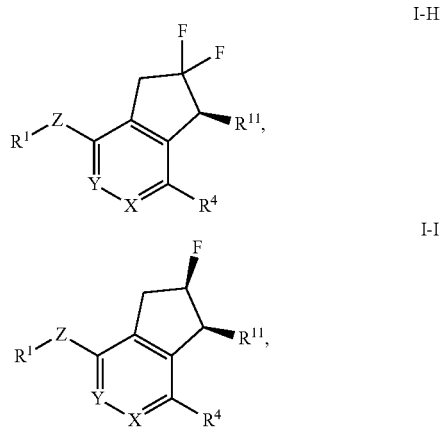

-continued

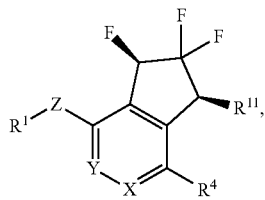
I-J

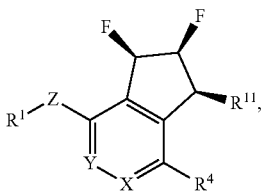
I-K or a pharmaceutically acceptable salt or prodrug thereof, wherein:

X is $CR^5$ or N;

Y is $CR^6$ or N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl heteroaryl, aralkyl, or heteroarylalkyl;

$R^4$ is nitro, halo, cyano, alkyl, cycloalkyl, heteroaryl, carboxyl, sulfinyl, sulfonamidyl, sulfonyl or sulfoximinyl; and $R^5$, $R^6$, $R^7$ and $R^8$ are independently hydrogen, halo, hydroxy, cyano, alkyl or alkoxy; and $R^{11}$ is hydroxy or amino.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

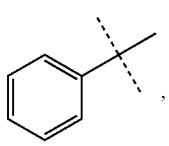

wherein the aryl ring is optionally substituted with one or more substituents selected from the group consisting of cyano, halo, alkyl and alkoxy. In another further embodiment, $R^1$ is

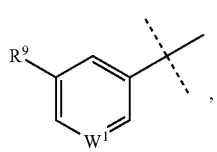

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

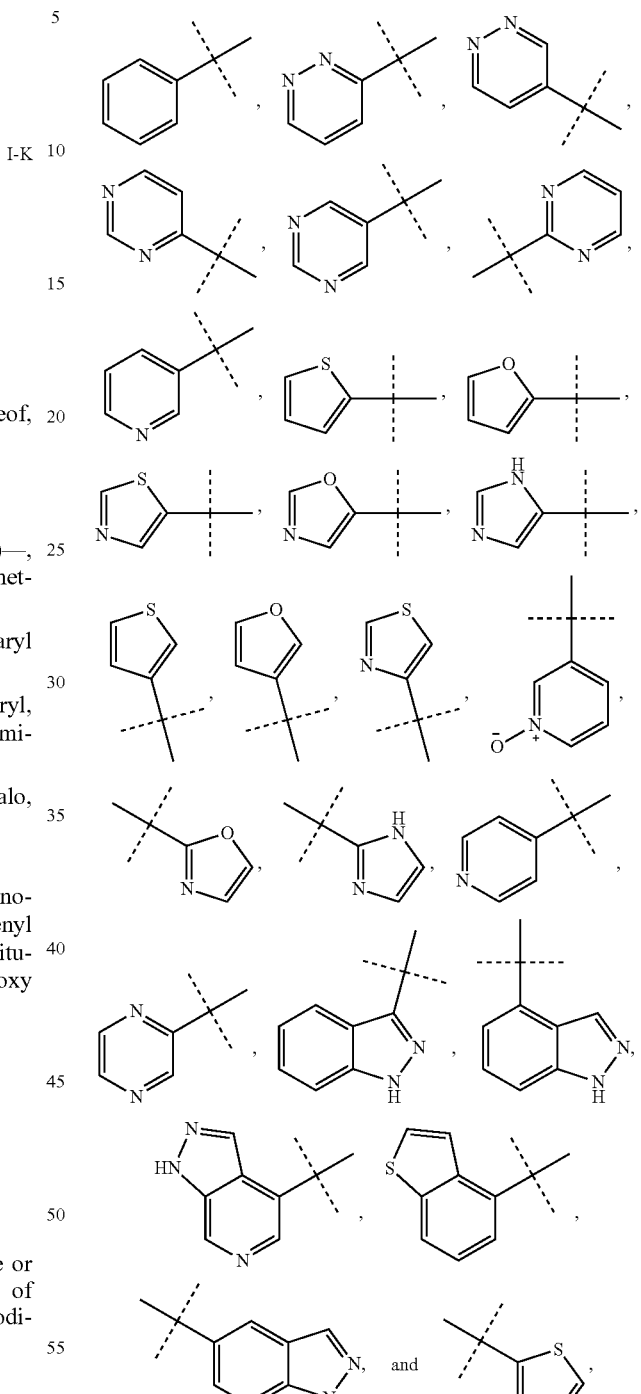

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

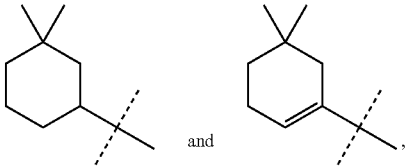

and

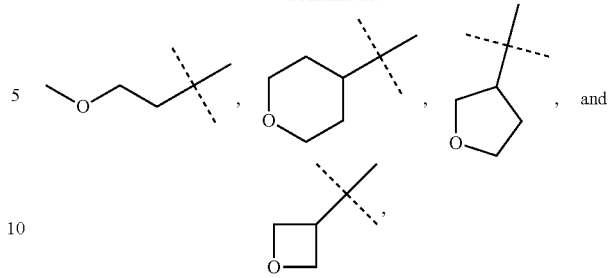

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

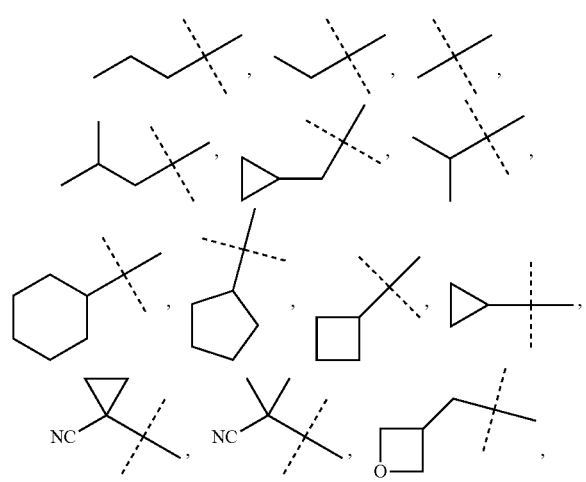

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^4$ is cyano, fluoroalkyl, sulfinyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is alkylsulfonyl.

In some embodiments, $R^4$ is —S(=O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(=O)(=NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, both R$^a$s are hydrogen. In a further embodiment, one R$^a$ is hydrogen and the other R$^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino. In a further embodiment, X is $CR^5$ and $R^5$ is hydrogen. In another further embodiment, $R^5$ is alkyl. In still a further embodiment, $R^5$ is $C_1$-$C_4$ alkyl.

In some embodiments $R^1$ is bicyclic heteroaryl and $R^4$ is cyano, fluoroalkyl, sulfinyl, sulfonamidyl, sulfonyl or sulfoximinyl. In a further embodiment, X is $CR^5$ and $R^5$ is hydrogen. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is bicyclic heteroaryl; $R^4$ is cyano, fluoroalkyl, sulfinyl, sulfonamidyl, sulfonyl or sulfoximinyl; $R^{11}$ is hydroxy or amino; and X is $CR^5$ or N; and $R^5$ is hydrogen. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is phenyl or monocyclic heteroaryl and $R^4$ is cyano, fluoroalkyl, sulfinyl, sulfonamidyl, sulfonyl or sulfoximinyl. In a further embodiment, X is $CR^5$ and $R^5$ is hydrogen. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments $R^1$ is phenyl or monocyclic heteroaryl; $R^4$ is cyano, fluoroalkyl, sulfinyl, sulfonamidyl, sulfonyl or sulfoximinyl; $R^{11}$ is hydroxy or amino; and X is $CR^5$ or N; and $R^5$ is hydrogen. In a further embodiment, $R^{11}$ is hydroxy. In another further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is $CR^6$. In other embodiments, X is $CR^5$ and Y is N. In still other embodiments, X is N and Y is N. In yet other embodiments, X is $CR^5$ and Y is $CR^6$.

In some embodiments, Z is —O—, —S—, —S(O)—, —S(O)$_2$—, —S(O$_2$)N($R^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$)—. In some embodiments, Z is absent.

In some embodiments, a compound of any one of Formulae I-H-I-K may have an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae I-H-I-K may have an enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99%.

In yet another aspect, the disclosure provides a compound of Formula II:

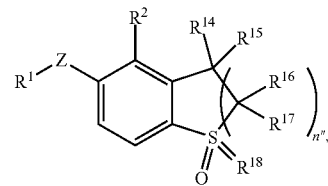

or a pharmaceutically acceptable salt or prodrug thereof, wherein:

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl, heteroaryl, aralkyl, heteroarylalkyl, acyl or cyano;

$R^2$ is hydrogen, alkyl, heteroalkyl, alkenyl, alkynyl, nitro, carboxaldehyde, carboxylic acid, ester, amido, cyano, halo or sulfonyl;

$R^{14}$ is hydrogen, deuterium or alkyl;

$R^{15}$ is hydrogen, hydroxy or amino; or $R^{14}$ and $R^{15}$ in combination form oxo or methylene;

$R^{16}$ and $R^{17}$ are independently selected from the group consisting of hydrogen, halo, alkyl, heteroalkyl and cycloalkyl; or $R^{16}$ and $R^{17}$ and the carbon to which they are attached form $C_3$-$C_8$ cycloalkyl or $C_5$-$C_8$ heterocycloalkyl;

$R^{18}$ is O or $NR^{19}$, wherein $R^{19}$ is selected from the group consisting of hydrogen, alkyl and cyano;

n" is 1 or 2; and $R^7$ and $R^8$ are independently hydrogen, halo, hydroxy, cyano, alkyl or alkoxy.

In some embodiments, $R^1$ is alkyl, cycloalkyl, heterocycloalkyl, aryl or heteroaryl. In some embodiments, $R^1$ is cycloalkyl, heterocycloalkyl, aryl or heteroaryl. In some embodiments, $R^1$ is heterocycloalkyl, aryl or heteroaryl. In some embodiments, $R^1$ is cycloalkyl, aryl or heteroaryl. In some embodiments, $R^1$ is aryl or heteroaryl. In a further embodiment, $R^1$ is phenyl. In another further embodiment, $R^1$ is pyridyl. In a still further embodiment, the phenyl or pyridyl is substituted with at least one substituent selected from the group consisting of halo, alkoxy, cyano and alkyl.

In some embodiments, $R^1$ is selected from the group consisting of cyclobutyl, cyclohexyl, tetrahydrofuranyl and tetrahydropyranyl.

In some embodiments, $R^1$ is

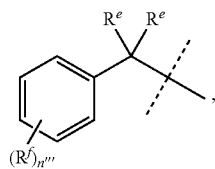

wherein each of $R^e$ is independently hydrogen or $C_1$-$C_4$ alkyl, or two $R^e$s and the carbon atom to which they are attached form a 4- to 8-membered cyclic moiety; each of $R^f$ is independently selected from the group consisting of halo, alkoxy, cyano and alkyl; and n' is 0, 1, 2, 3 or 4. In some further embodiments, the 4- to 8-membered cyclic moiety is an all carbon or heterocyclic ring system.

In some embodiments, $R^1$ is selected from the group consisting of:

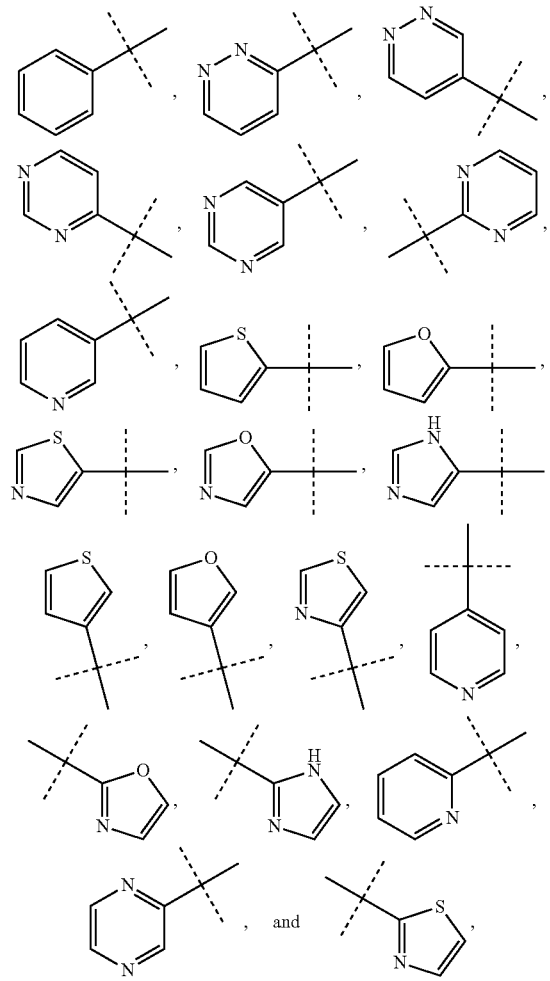

and the rings specified for $R^1$ may optionally be substituted by one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

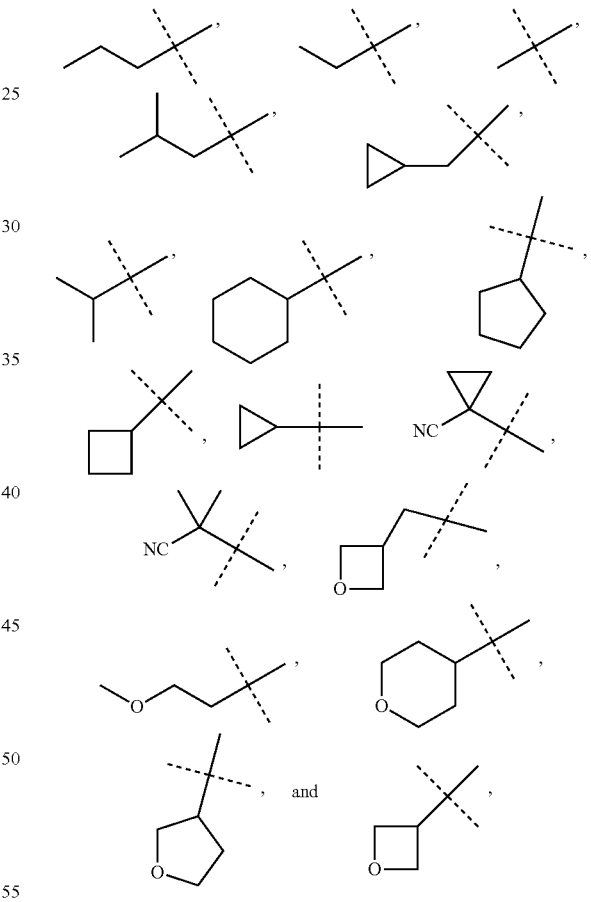

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is nitro, cyano, halo, alkyl, heteroalkyl, alkynyl or alkenyl. In some embodiments, $R^2$ is cyano, halo, alkyl, heteroalkyl or alkynyl. In some embodiments, $R^2$ is cyano, halo or alkyl. In some embodiments, $R^2$ is halo or alkyl. In a further embodiment, $R^2$ is fluoroalkyl. In a still further embodiment, $R^2$ is $C_1$-$C_4$ fluoroalkyl.

Exemplary $C_1$-$C_4$ fluoroalkyl includes, but is not limited to, —$CH_2F$, —$CHF_2$, —$CF_2CH_3$ and the like.

In some embodiments, $R^{14}$ is hydrogen or deuterium. In some embodiments, $R^{14}$ is alkyl. In a further embodiment, $R^{14}$ is $C_1$-$C_4$ alkyl.

In some embodiments, $R^{15}$ is hydroxy or amino. In some embodiments, $R^{15}$ is hydroxy. In some embodiments, $R^{15}$ is amino. In a further embodiment, $R^{15}$ is $NH_2$.

In some embodiments, each of $R^{16}$ and $R^{17}$ is independently hydrogen or fluoro. In some embodiments, each of $R^{16}$ and $R^{17}$ is hydrogen. In some embodiments, each of $R^{16}$ and $R^{17}$ is fluoro. In some embodiments, at least one of $R^{16}$ and $R^{17}$ is fluoro.

In some embodiments, $R^{18}$ is O, N—CN, or NH. In some embodiments, $R^{18}$ is O. In some embodiments, $R^{18}$ is NH. In some embodiments, $R^{18}$ is N—CN.

In some embodiments, $R^{14}$ is hydrogen and $R^{15}$ is hydroxy or amino. In some further embodiments, $R^1$ is aryl or heteroaryl. In a further embodiment, $R^2$ is cyano, halo or alkyl. In a still further embodiment, $R^{16}$ and $R^{17}$ are fluoro.

In some embodiments, $R^{15}$ is hydroxy or amino and $R^2$ is cyano, halo or alkyl. In a further embodiment, $R^2$ is fluoroalkyl. In a still further embodiment, at least one $R^{16}$ and $R^{17}$ is fluoro. In a yet still further embodiment, n" is 1.

In some embodiments, $R^{18}$ is O or NH and $R^{14}$ is hydrogen. In some further embodiments, $R^1$ is aryl or heteroaryl. In a further embodiment, $R^2$ is cyano, halo or alkyl. In a still further embodiment, at least one of $R^{16}$ and $R^{17}$ is fluoro.

In some embodiments, n" is 1. In some further embodiments, $R^{15}$ is hydroxy or amino and $R^{16}$ and $R^{17}$ are fluoro. In a further embodiment, $R^1$ is aryl or heteroaryl. In a still further embodiment, $R^1$ is phenyl or pyridyl, optionally substituted with one or more substituents selected from the group consisting of halo, alkoxy, cyano and alkyl.

In some embodiments, Z is —O—, —S—, —S(O)—, —$S(O)_2$—, —$S(O_2)N(R^8)$—, —C(O)—, —C(O)O—, —$C(HR^7)$—, —$N(R^8)$—, —$C(O)N(R^8)$—, alkylene, alkenylene, alkynylene, heteroalkylene, or absent. In some embodiments, Z is —O—, —S—, —S(O)—, —$S(O)_2$—, —C(O)—, —$C(HR^7)$—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —$C(HR^7)$—. In yet other embodiments, Z is —$N(R^8)$—. In some embodiments, Z is absent.

In another aspect, the disclosure provides a compound of Formula II-A:

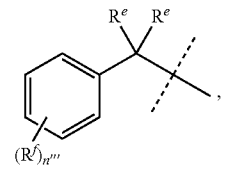

or a pharmaceutically acceptable salt or prodrug thereof, wherein:
Z is —O—, —S—, —S(O)—, —$S(O)_2$—, —C(O)—, —$C(HR^7)$—, —$N(R^8)$—, $C_1$-$C_3$ alkylene, $C_1$-$C_3$ heteroalkylene, $C_1$-$C_3$ alkenylene or absent;
$R^1$ is alkyl, heteroalkyl, cycloalkyl, heterocycloalkyl, aryl, heteroaryl, aralkyl, heteroarylalkyl, acyl or cyano;
$R^2$ is hydrogen, alkyl, heteroalkyl, alkenyl, alkynyl, nitro, carboxaldehyde, carboxylic acid, ester, amido, cyano, halo or sulfonyl;
$R^{14}$ is hydrogen, deuterium or alkyl;
$R^{15}$ is hydrogen, hydroxy or amino; or $R^{14}$ and $R^{15}$ in combination form oxo or methylene;
$R^{18}$ is O or $NR^{19}$, wherein $R^{19}$ is selected from the group consisting of hydrogen, alkyl and cyano; and
$R^7$ and $R^8$ are independently hydrogen, halo, hydroxy, cyano, alkyl or alkoxy.

In some embodiments, $R^1$ is alkyl, cycloalkyl, heterocycloalkyl, aryl or heteroaryl. In some embodiments, $R^1$ is cycloalkyl, heterocycloalkyl, aryl or heteroaryl. In some embodiments, $R^1$ is heterocycloalkyl, aryl or heteroaryl. In some embodiments, $R^1$ is cycloalkyl, aryl or heteroaryl. In some embodiments, $R^1$ is aryl or heteroaryl. In a further embodiment, $R^1$ is phenyl. In another further embodiment, $R^1$ is pyridyl. In a still further embodiment, the phenyl or pyridyl is substituted with at least one substituent selected from the group consisting of halo, alkoxy, cyano and alkyl.

In some embodiments, $R^1$ is selected from the group consisting of cyclobutyl, cyclohexyl, tetrahydrofuranyl and tetrahydropyranyl.

In some embodiments, $R^1$ is

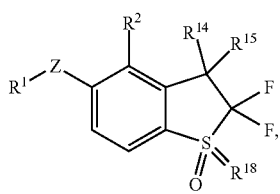

wherein each of $R^e$ is independently hydrogen or $C_1$-$C_4$ alkyl, or two $R^e$s and the carbon atom to which they are attached form a 4- to 8-membered cyclic moiety; each of $R^f$ is independently selected from the group consisting of halo, alkoxy, cyano and alkyl; and n''' is 0, 1, 2, 3 or 4. In some further embodiments, the 4- to 8-membered cyclic moiety is an all carbon or heterocyclic ring system.

In some embodiments, $R^1$ is selected from the group consisting of:

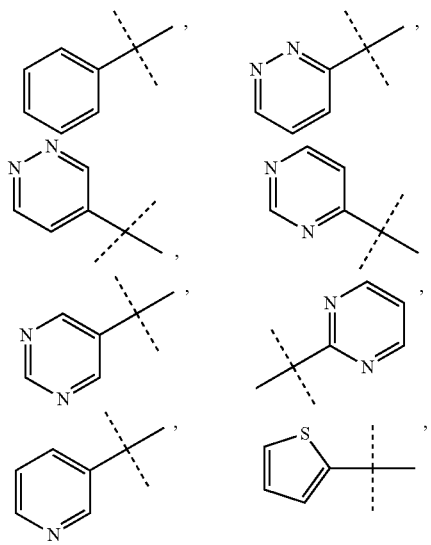

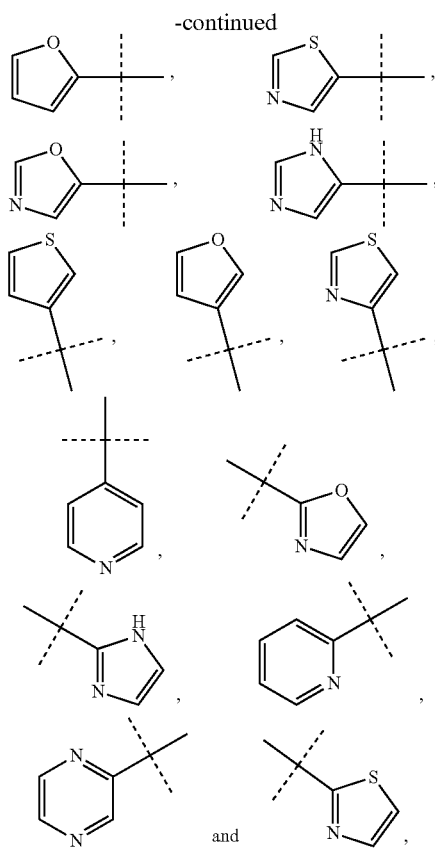

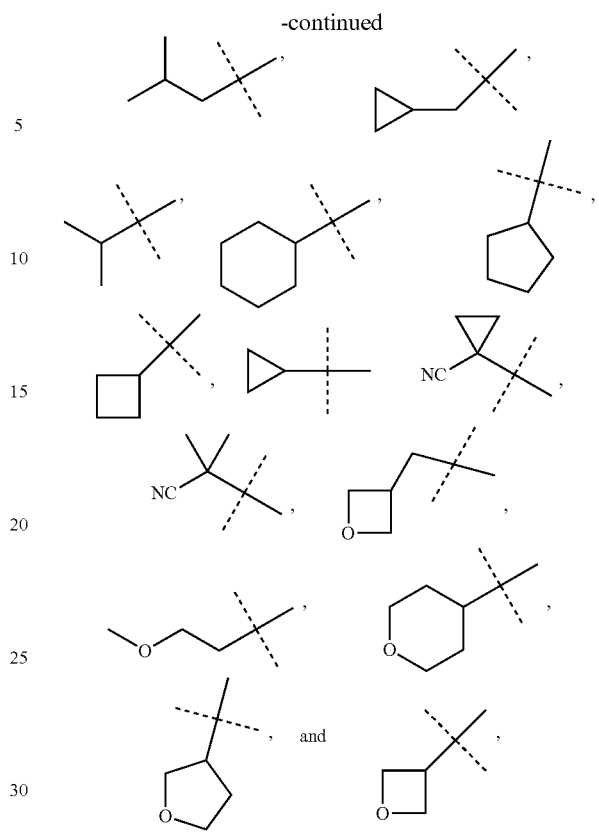

and the rings specified for $R^1$ may optionally be substituted by one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

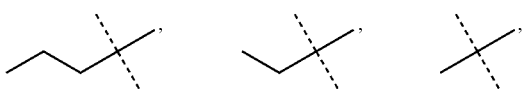

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is nitro, cyano, halo, alkyl, heteroalkyl, alkynyl or alkenyl. In some embodiments, $R^2$ is cyano, halo, alkyl, heteroalkyl or alkynyl. In some embodiments, $R^2$ is cyano, halo or alkyl. In some embodiments, $R^2$ is halo or alkyl. In a further embodiment, $R^2$ is fluoroalkyl. In a still further embodiment, $R^2$ is $C_1$-$C_4$ fluoroalkyl. Exemplary $C_1$-$C_4$ fluoroalkyl includes, but is not limited to, —$CH_2F$, —$CHF_2$, —$CF_2CH_3$ and the like.

In some embodiments, $R^{14}$ is hydrogen or deuterium. In some embodiments, $R^{14}$ is alkyl. In a further embodiment, $R^{14}$ is $C_1$-$C_4$ alkyl.

In some embodiments, $R^{15}$ is hydroxy or amino. In some embodiments, $R^{15}$ is hydroxy. In some embodiments, $R^{15}$ is amino. In a further embodiment, $R^{15}$ is $NH_2$.

In some embodiments, $R^{18}$ is O, N—CN, or NH. In some embodiments, $R^{18}$ is O. In some embodiments, $R^{18}$ is NH. In some embodiments, $R^{18}$ is N—CN.

In some embodiments, $R^{18}$ is O or NH and $R^{14}$ is hydrogen. In some further embodiments, $R^1$ is aryl or heteroaryl. In a further embodiment, $R^2$ is cyano, halo or alkyl. In a still further embodiment, at least one of $R^{16}$ and $R^{17}$ is fluoro.

In some embodiments, Z is —O—, —S—, —S(O)—, —S(O)$_2$—, —S(O$_2$)N($R^8$)—, —C(O)—, —C(O)O—, —C(H$R^7$)—, —N($R^8$)—, —C(O)N($R^8$)—, alkylene, alkenylene, alkynylene, heteroalkylene, or absent. In some embodiments, Z is —O—, —S—, —S(O)—, —S(O)$_2$—, —C(O)—, —C(H$R^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR⁷)—. In yet other embodiments, Z is —N(R⁸). In some embodiments, Z is absent.

In still another aspect, the disclosure provides a compound of Formula II-B:

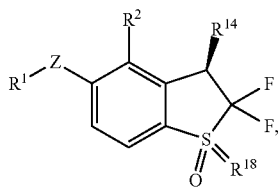

or a pharmaceutically acceptable salt or prodrug thereof, wherein:

Z is —O—, —S—, —S(O)—, —S(O)$_2$—, —C(O)—, —C(HR⁷)—, —N(R⁸)—, $C_1$-$C_3$ alkylene, $C_1$-$C_3$ heteroalkylene, $C_1$-$C_3$ alkenylene or absent;

R¹ is alkyl, heteroalkyl, cycloalkyl, heterocycloalkyl, aryl, heteroaryl, aralkyl, heteroarylalkyl, acyl or cyano;

R² is hydrogen, alkyl, heteroalkyl, alkenyl, alkynyl, nitro, carboxaldehyde, carboxylic acid, ester, amido, cyano, halo or sulfonyl;

R¹⁵ is hydroxy or amino;

R¹⁸ is O or NR¹⁹, wherein R¹⁹ is selected from the group consisting of hydrogen, alkyl and cyano; and R⁷ and R⁸ are independently hydrogen, halo, hydroxy, cyano, alkyl or alkoxy.

In some embodiments, R¹ is alkyl, cycloalkyl, heterocycloalkyl, aryl or heteroaryl. In some embodiments, R¹ is cycloalkyl, heterocycloalkyl, aryl or heteroaryl. In some embodiments, R¹ is heterocycloalkyl, aryl or heteroaryl. In some embodiments, R¹ is cycloalkyl, aryl or heteroaryl. In some embodiments, R¹ is aryl or heteroaryl. In a further embodiment, R¹ is phenyl. In another further embodiment, R¹ is pyridyl. In a still further embodiment, the phenyl or pyridyl is substituted with at least one substituent selected from the group consisting of halo, alkoxy, cyano and alkyl.

In some embodiments, R¹ is selected from the group consisting of cyclobutyl, cyclohexyl, tetrahydrofuranyl and tetrahydropyranyl.

In some embodiments, R¹ is

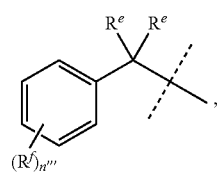

wherein each of $R^e$ is independently hydrogen or $C_1$-$C_4$ alkyl, or two $R^e$s and the carbon atom to which they are attached form a 4- to 8-membered cyclic moiety; each of $R^f$ is independently selected from the group consisting of halo, alkoxy, cyano and alkyl; and n''' is 0, 1, 2, 3 or 4. In some further embodiments, the 4- to 8-membered cyclic moiety is an all carbon or heterocyclic ring system.

In some embodiments, R¹ is selected from the group consisting of:

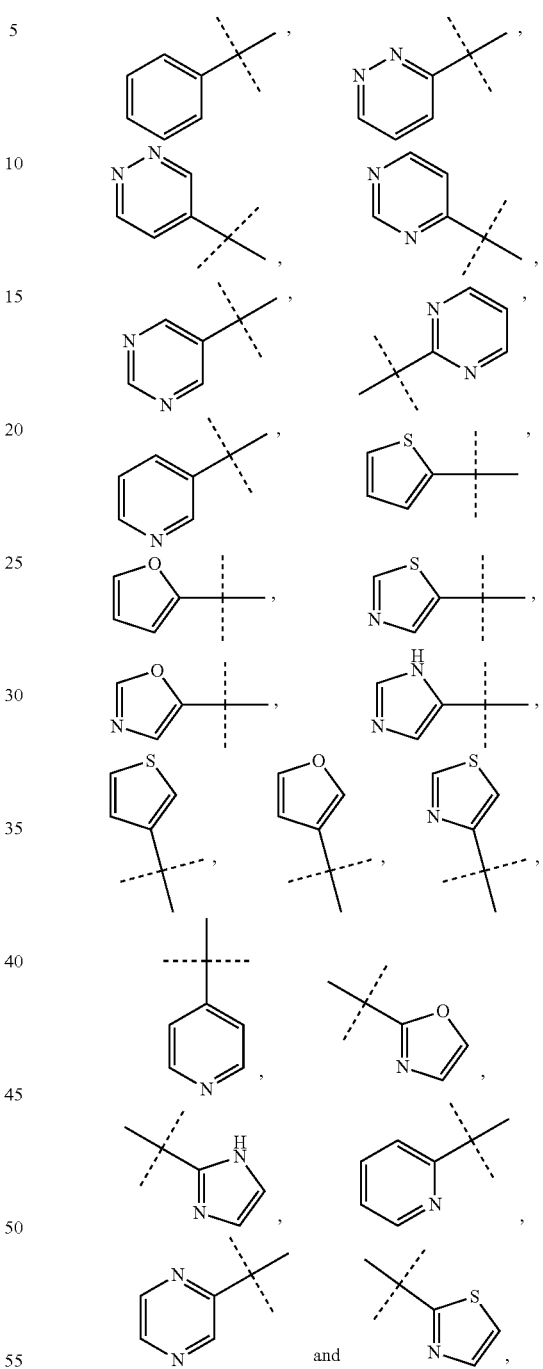

and the rings specified for R¹ may optionally be substituted by one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, R¹ is cycloalkyl. In other embodiments, R¹ is heterocycloalkyl. In a further embodiment, R¹ is $C_3$-$C_6$ cycloalkyl or $C_3$-$C_6$ heterocycloalkyl. In yet a further embodiment, R¹ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

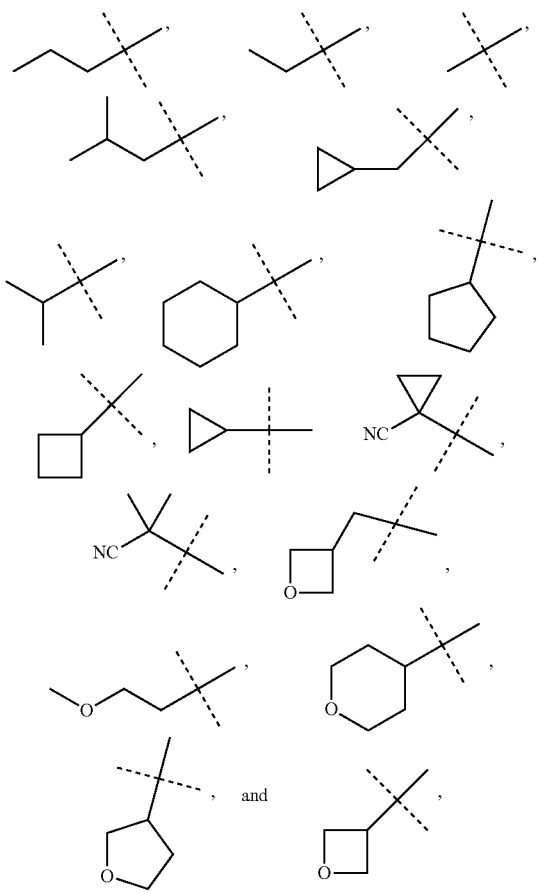

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is nitro, cyano, halo, alkyl, heteroalkyl, alkynyl or alkenyl. In some embodiments, $R^2$ is cyano, halo, alkyl, heteroalkyl or alkynyl. In some embodiments, $R^2$ is cyano, halo or alkyl. In some embodiments, $R^2$ is halo or alkyl. In a further embodiment, $R^2$ is fluoroalkyl. In a still further embodiment, $R^2$ is $C_1$-$C_4$ fluoroalkyl. Exemplary $C_1$-$C_4$ fluoroalkyl includes, but is not limited to, —$CH_2F$, —$CHF_2$, —$CF_2CH_3$ and the like.

In some embodiments, $R^{15}$ is hydroxy. In some embodiments, $R^{15}$ is amino. In a further embodiment, $R^{15}$ is $NH_2$.

In some embodiments, $R^{18}$ is O, N—CN, or NH. In some embodiments, $R^{18}$ is O. In some embodiments, $R^{18}$ is NH. In some embodiments, $R^{18}$ is N—CN.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In some embodiments, a compound of Formula II-B may have an enantiomeric excess of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99%. In a further embodiment, the compound has an enantiomeric excess of at least about 90%.

In another aspect, the present disclosure provides a compound or pharmaceutically acceptable salt or prodrug thereof, selected from the group consisting of the compounds given in Table 1.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-27, the steps in some cases may be performed in a different order than the order shown in Schemes 1-27. Various modifications to these synthetic reaction schemes may be made and will be suggested to one skilled in the art having referred to the disclosure contained in this Application.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

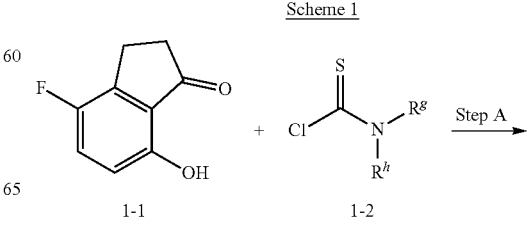

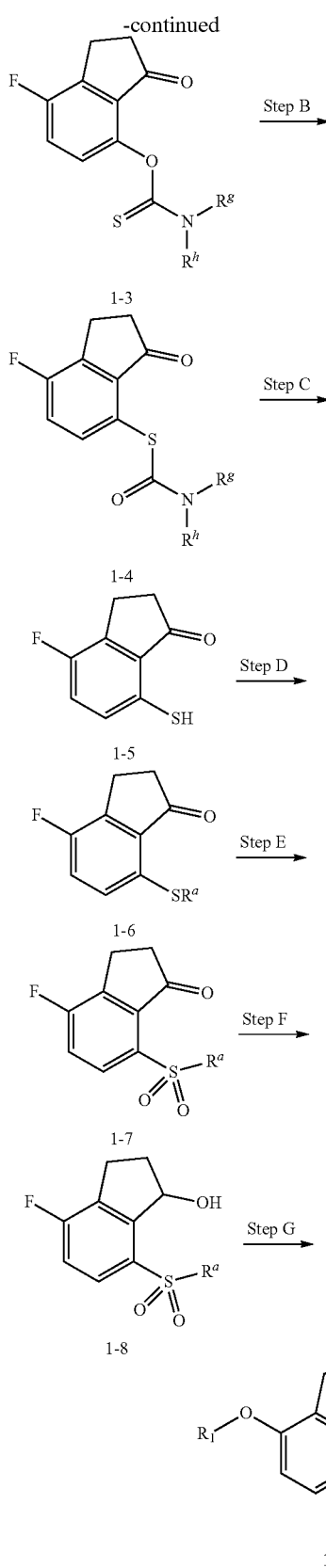

chloride 1-2 (wherein $R^g$ and $R^h$ are independently alkyl) provides intermediate 1-3. The reaction may be carried out in a suitable organic solvent in the presence of a base. Suitable bases for the reaction include, but are not limited to, organic bases, for example, triethylamine, N,N-diisopropylethylamine, 1,4-diazabicyclo[2.2.2]octane, and inorganic bases, for example, sodium hydroxide, cesium carbonate, cesium bicarbonate, sodium carbonate, and potassium carbonate. A compound of Formula 1-3 is then subjected to a rearrangement reaction to give a compound of Formula 1-4. Elevated temperature may be needed for the rearrangement to occur. The temperature may be in a range of 100° C. to 300° C. In some embodiments, the temperature is in a range of 180° C. to 240° C. Hydrolysis of a compound of Formula 1-4 provides thiophenol 1-5, which is alkylated to provide a compound if Formula 1-6. A variety of alkyl groups may be introduced in Step D. In some embodiments, $R^a$ is a $C_1$-$C_4$ alkyl. In a further embodiment, $R^a$ is a $C_1$-$C_4$ fluoroalkyl. Oxidation of a compound of Formula 1-6 may be accomplished by a variety of methods known in the art, including, but not limited to, $RuCl_3$ catalyzed oxidation in the presence of $NaIO_4$, oxidation with m-chloroperoxybenzoic acid (mCPBA) and oxidation with Oxone®. Ketone 1-7 is then reduced to give alcohol 1-8, which then undergoes a nucleophilic aromatic substitution (SNAr) reaction with a suitable substrate $R^1OH$ to give a compound of Formula 1-9. Temperatures for carrying out the SNAr reaction may depend on the reactivity of both ROH and/or compound 1-8. The reaction may be carried out in a temperature range from about room temperature to 200° C. In some embodiments, the temperature range is from room temperature to 60° C. In some other embodiments, the temperature range is from 60° C. to 100° C. In some other embodiments, the temperature range is from 100° C. to 200° C.

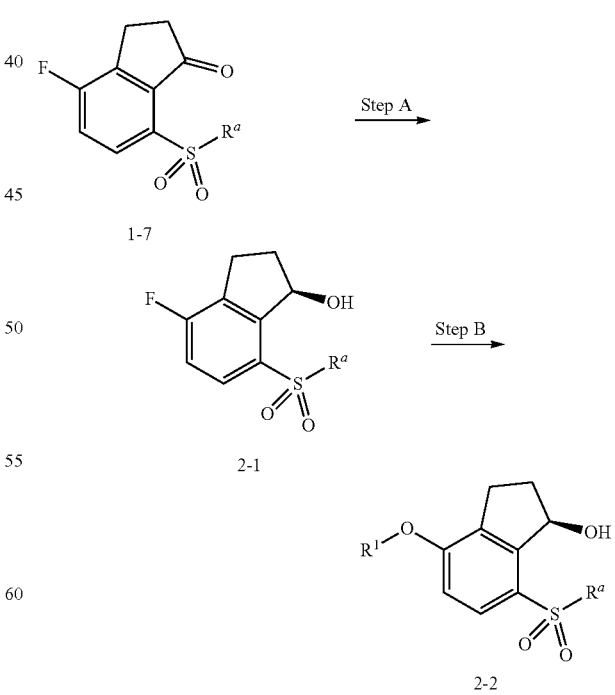

Scheme 2

In some embodiments, a compound of Formula 1-9 can be prepared according to steps outlined in Scheme 1. The synthesis starts with phenol 1-1. Reaction of 1-1 with In some other embodiments, a compound of Formula 1-9 can be prepared asymmetrically to give a compound of Formula 2-2 (Scheme 2). For example, direct asymmetric reduction of ketone 1-7 (Step A) may be accomplished chemically or enzymatically. For a recent review on enzymatic reduction of ketones, see Moore, et al. *Acc. Chem. Res.* 40: 1412-1419, 2007. Examples of chemical asymmetric reduction of ketones include, but are not limited to, Corey-Bakshi-Shibata (CBS) reduction, asymmetric hydrogenation and asymmetric transfer hydrogenation. In some embodiments, the asymmetric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R, R configuration):

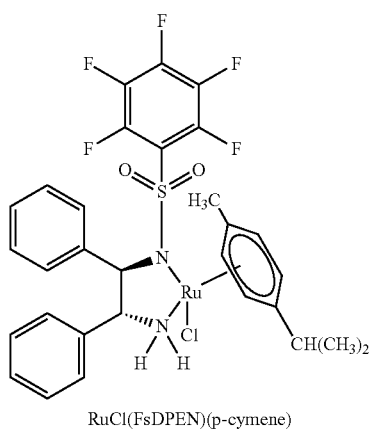

RuCl(FsDPEN)(p-cymene)

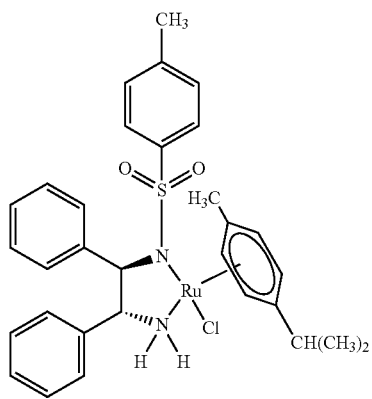

RuCl(TsDPEN)(p-cymene)

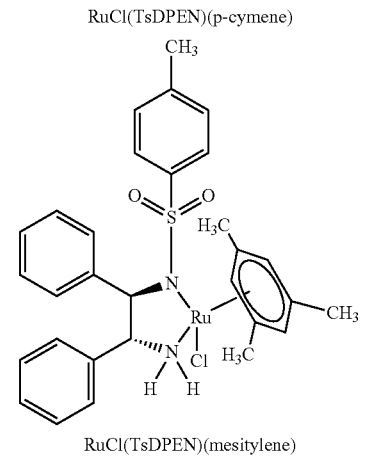

RuCl(TsDPEN)(mesitylene)

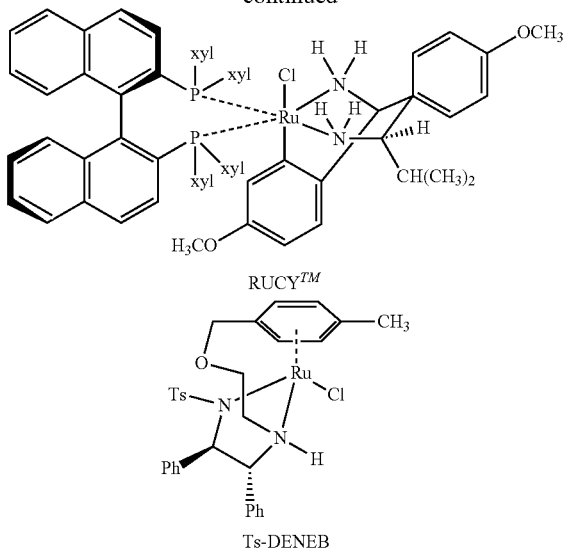

RUCY™

Ts-DENEB

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration. Chiral alcohol 2-1 can be coupled with a suitable substrate, for example, a phenol, to give a compound of Formula 2-2 without significant loss of enantiomeric excess. The loss of enantiomeric excess (ee) in the coupling step for 2-2 may be less than about 1%, less than about 2%, less than about 3%, less than about 4%, less than about 5%, less than about 6% or less than about 8%.

Scheme 3

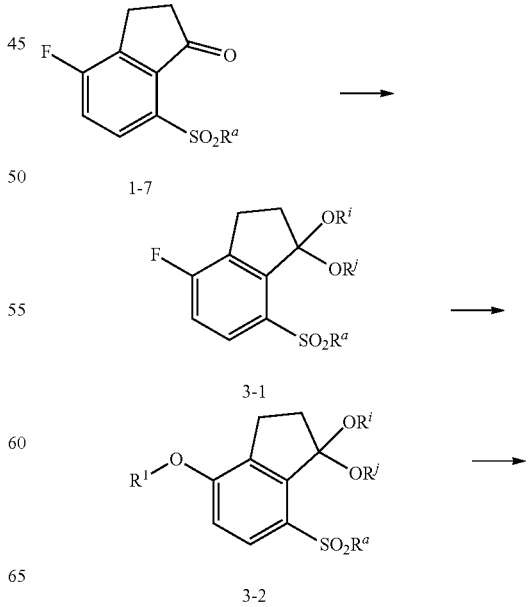

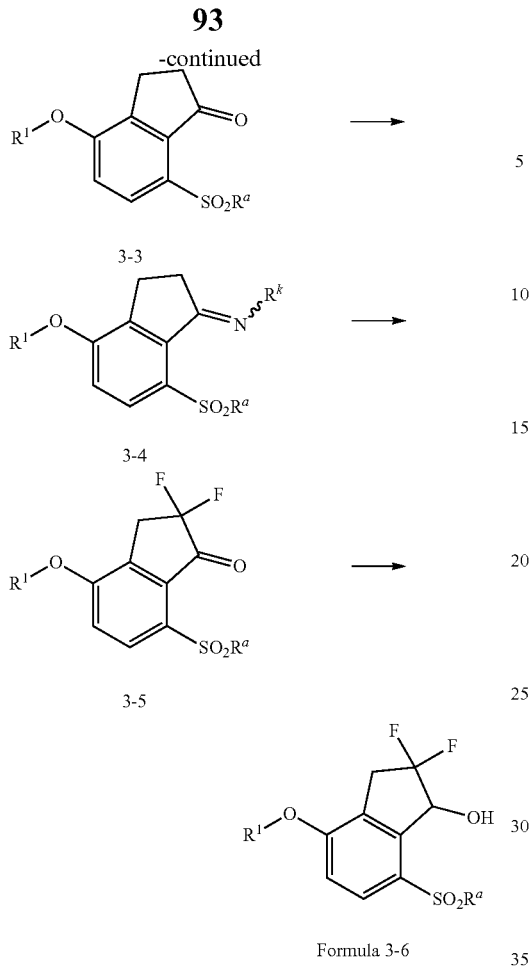

3-3

3-4

3-5

Formula 3-6

In some embodiments, a compound of Formula 3-6 may be prepared according to Scheme 3. The ketone in 1-7 is protected as a ketal to give a compound of Formula 3-1, wherein each of $R^i$ and $R^j$ is independently an alkyl group. In addition, $R^i$ and $R^j$ may optionally be connected to form a cyclic ketal. Exemplary structures of ketal 3-1 include, but are not limited to, the following:

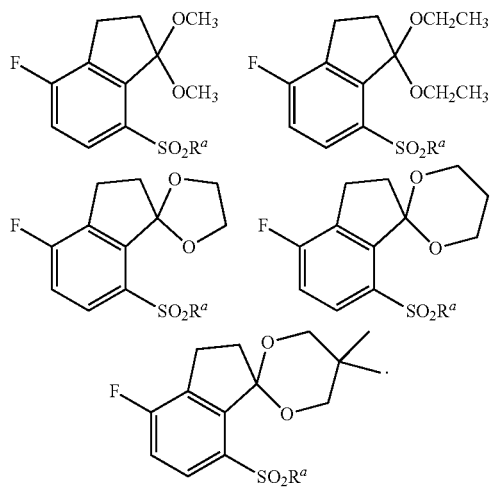

A compound of Formula 3-1 and a suitable $R^1OH$ may undergo a nucleophilic aromatic substitution reaction (SNAr) to give biaryl ether 3-2. As described in Step G of Scheme 1, the reaction temperature of the SNAr reaction may depend on the reactivity of the aryl halide (i.e. compound 3-1) and/or $R^1OH$. Ketone 3-3, resulting from the deprotection of ketal 3-2, is condensed with an amine to form imine 3-4, wherein $R^k$ is alkyl. The imine functional group in a compound of Formula 3-4 may exist as a mixture of E and Z isomers. Fluorination of 3-4 can be accomplished with a fluorinating reagent, for example, 1-(chloromethyl)-4-fluoro-1,4-diazoniabicyclo[2.2.2]octane ditetrafluoroborate, to give difluoroketone 3-5 after acid hydrolysis. Finally, reduction of ketone 3-5 with a hydride donor gives a compound of Formula 3-6.

Scheme 4

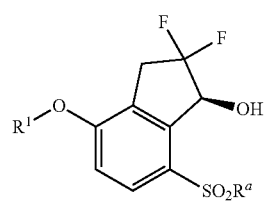

3-5

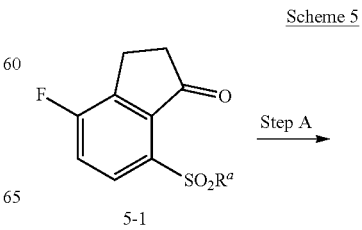

Formula 4-1

A compound of Formula 4-1 (Scheme 4) can be prepared asymmetrically following the general procedure described above in Scheme 2. In some embodiments, the asymmetric reduction gives a compound of Formula 4-1 with an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or even higher. The enantiomeric excess of a compound of Formula 2-2 or 4-1 may be determined by chrial HPLC or Mosher ester analysis. For determination of ee with Mosher ester, see Hoye, et al. *Natural Protocol*, 2: 2451, 2007.

Scheme 5

5-1

Step A

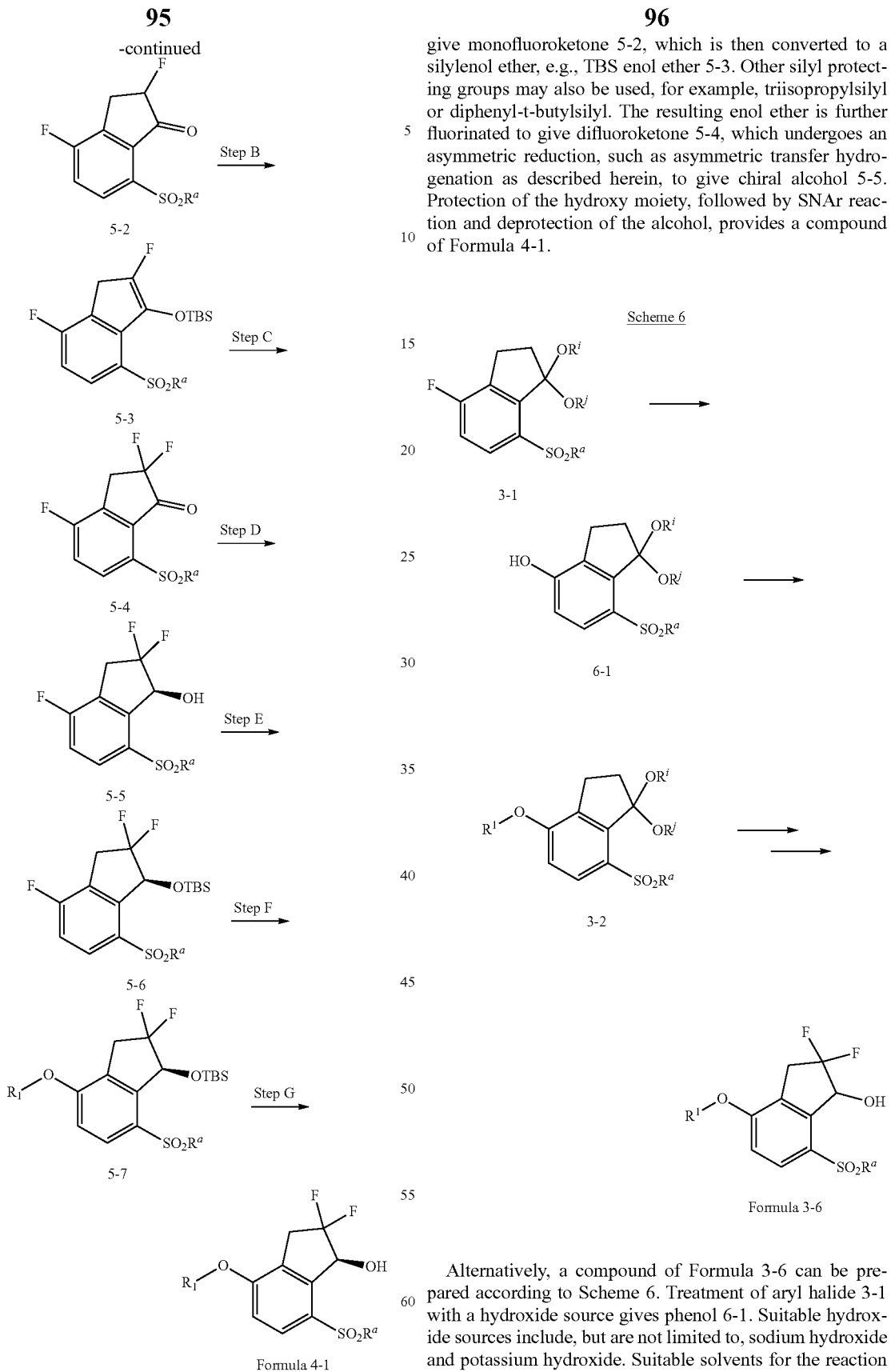

give monofluoroketone 5-2, which is then converted to a silylenol ether, e.g., TBS enol ether 5-3. Other silyl protecting groups may also be used, for example, triisopropylsilyl or diphenyl-t-butylsilyl. The resulting enol ether is further fluorinated to give difluoroketone 5-4, which undergoes an asymmetric reduction, such as asymmetric transfer hydrogenation as described herein, to give chiral alcohol 5-5. Protection of the hydroxy moiety, followed by SNAr reaction and deprotection of the alcohol, provides a compound of Formula 4-1.

Alternatively, a compound of Formula 4-1 may be prepared according to Scheme 5. Ketone 5-1 is fluorinated to Alternatively, a compound of Formula 3-6 can be prepared according to Scheme 6. Treatment of aryl halide 3-1 with a hydroxide source gives phenol 6-1. Suitable hydroxide sources include, but are not limited to, sodium hydroxide and potassium hydroxide. Suitable solvents for the reaction include, but are not limited to, DMSO, DMA, DMF and EtOH. Phenol 6-1 can react with a suitable halide via an SNAr reaction to give ether 3-2, which can be converted to a compound of Formula 3-6 as described in Scheme 3.

Scheme 7

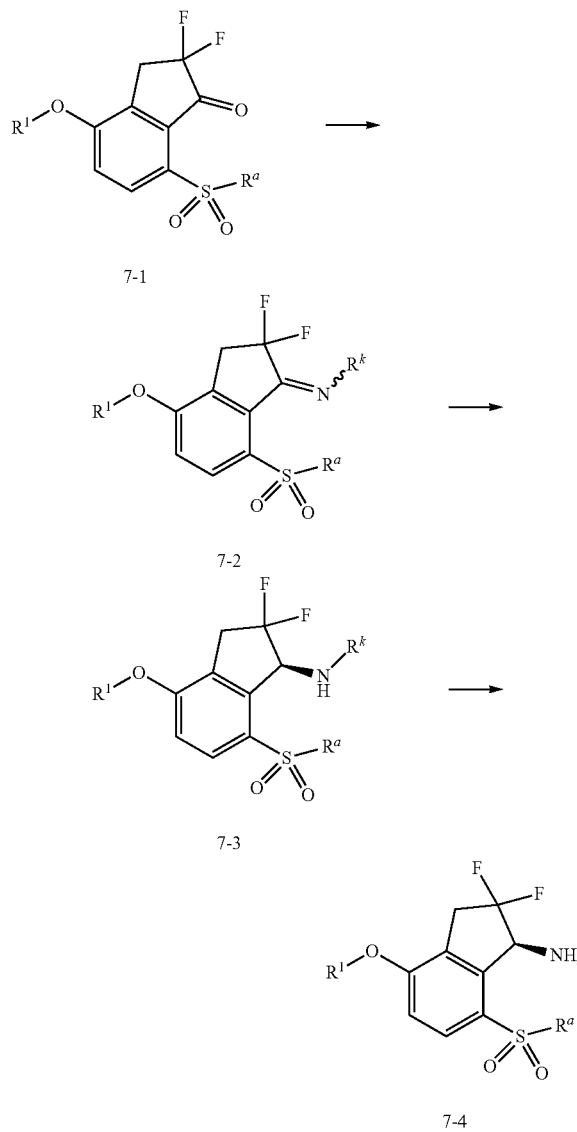

Compounds of Formulae 7-3 and 7-4 may be prepared according to Scheme 7. For example, condensation of $NH_2R^k$ with difluoroketone 7-1, wherein $R^a$ is aryl, heteroaryl, alkyl, heteroalkyl, heterocycle, or cycloalkyl, gives intermediate 7-2. In some embodiments, $R^k$ is a chiral auxiliary. Exemplary chiral auxiliaries include, but are not limited to:

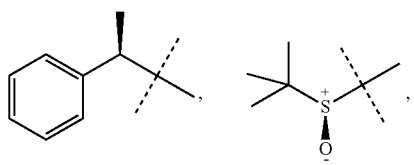

and enantiomers thereof. Hydride reduction of intermediate 7-2 yields 7-3. At this stage, the chiral auxiliary may be cleaved under appropriate conditions, e.g., hydrogenation or acid treatment, to give chiral secondary amine 7-4. In some other embodiments, when a compound of Formula 7-3 is desirable and $R^k$ is not hydrogen, asymmetric hydrogenation or asymmetric transfer hydrogenation is applied on intermediate 7-2 to give a compound of Formula 7-3. For a review on asymmetric hydrogenation and asymmetric transfer hydrogenation, see Iwao Ojima ed. *Catalytic Asymmetric Synthesis*, Wiley-VCH, Inc., 2000, ISBN 0-471-29805-0.

Scheme 8

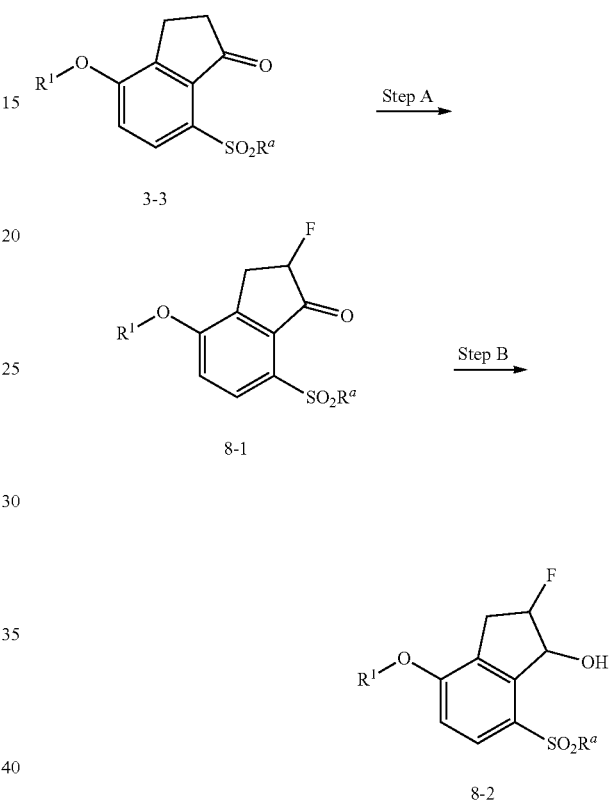

In some embodiments, a compound of Formula 8-2 can be prepared according to Scheme 8. For example, ketone 3-3 is monofluorinated to give a monofluoroketone of Formula 8-1. The monofluorination can be achieved with a variety of fluorinating reagents, e.g., N-Fluoro-O-benzenedisulfonimide, acetyl hypofluorite, Accufluor®, Selectfluor®, Selectfluor® II, or N-fluorobenzenesulfonimide, in the presence or absence of a base. A compound of Formula 8-1 is reduced to give a compound of Formula 8-2. In some cases, the reduction is highly diastereoselective to give a compound of Formula 8-2 with greater than 80%, greater than 82%, greater than 84%, greater than 86%, greater than 88%, greater than 90%, greater than 92%, greater than 94%, greater than 96% or even greater than 96% diastereoselectivity. In some cases, the reduction is highly enantioselective to give a compound of Formula 8-2 with greater than 80%, greater than 82%, greater than 84%, greater than 86%, greater than 88%, greater than 90%, greater than 92%, greater than 94%, greater than 96% or even greater than 96% enantioselectivity. Reduction conditions to achieve high enantioselectivity include, but are not limited to, asymmetric transfer hydrogenation and enzymatic reduction as described herein.

Scheme 9

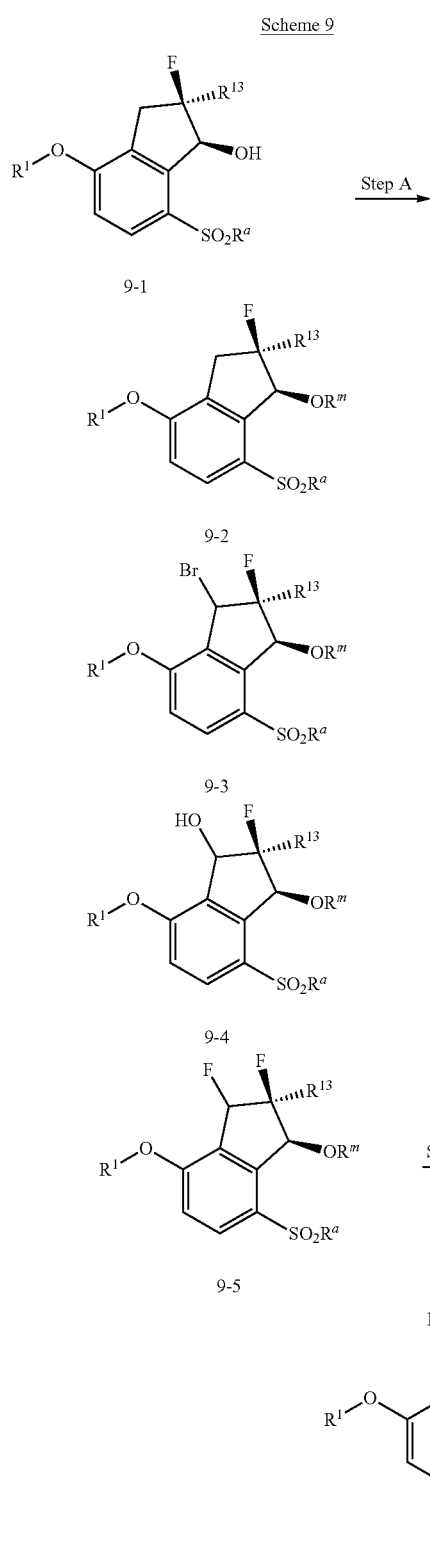

a bromide source, e.g., N-bromosuccinimide, in the presence of a radical initiator, e.g., 2,2'-azobis(2-methylpropionitrile) (AIBN) or benzyol peroxide. The bromide of compound 9-3 can be replaced with a hydroxy group in a solvent comprising water in the presence of a silver salt, e.g., $Ag_2CO_3$ or $AgClO_4$ or $AgBF_4$. Finally, fluorination of a compound of Formula 9-4 followed by deprotection gives a compound of Formula 9-6. In some cases, direct benzylic oxidation may be used for converting a compound of Formula 9-2 to a compound of Formula 9-4, thus bypassing an intermediate bromination step.

Scheme 10

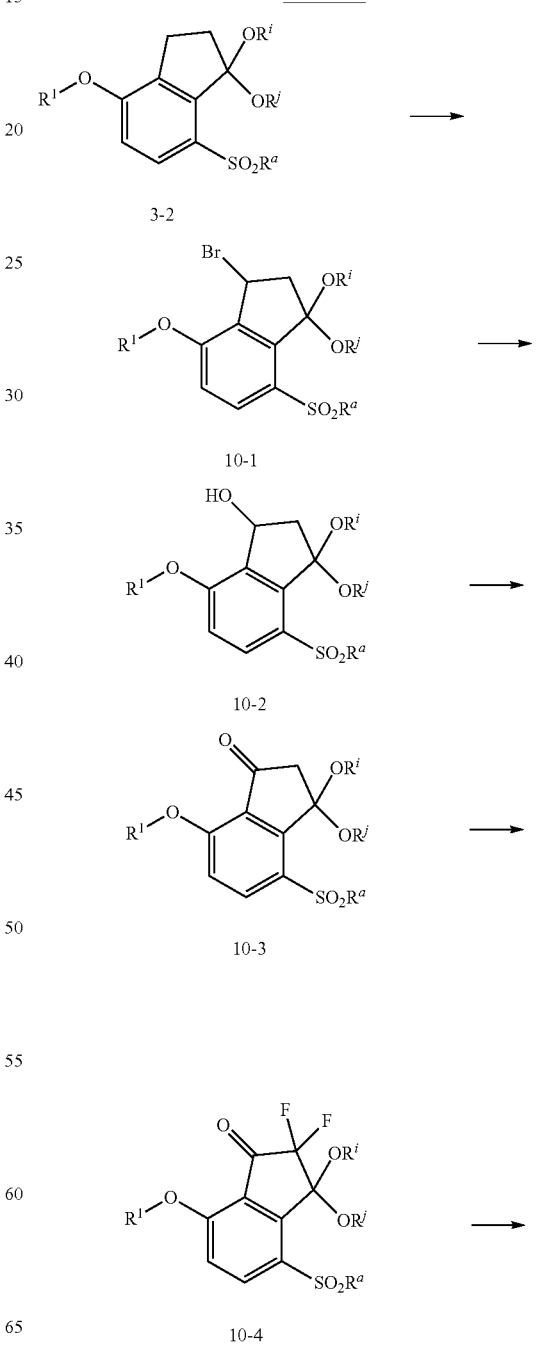

In some embodiments, a compound of Formula 9-6 may be prepared according to Scheme 9, wherein $R^{13}$ is hydrogen, alkyl or fluoro. The hydroxy group of compound 9-1 may be protected, for example, with an acyl or methoxymethyl ether (MOM) group, to give a compound of Formula 9-2. Benzylic bromination in Step B may be carried out with

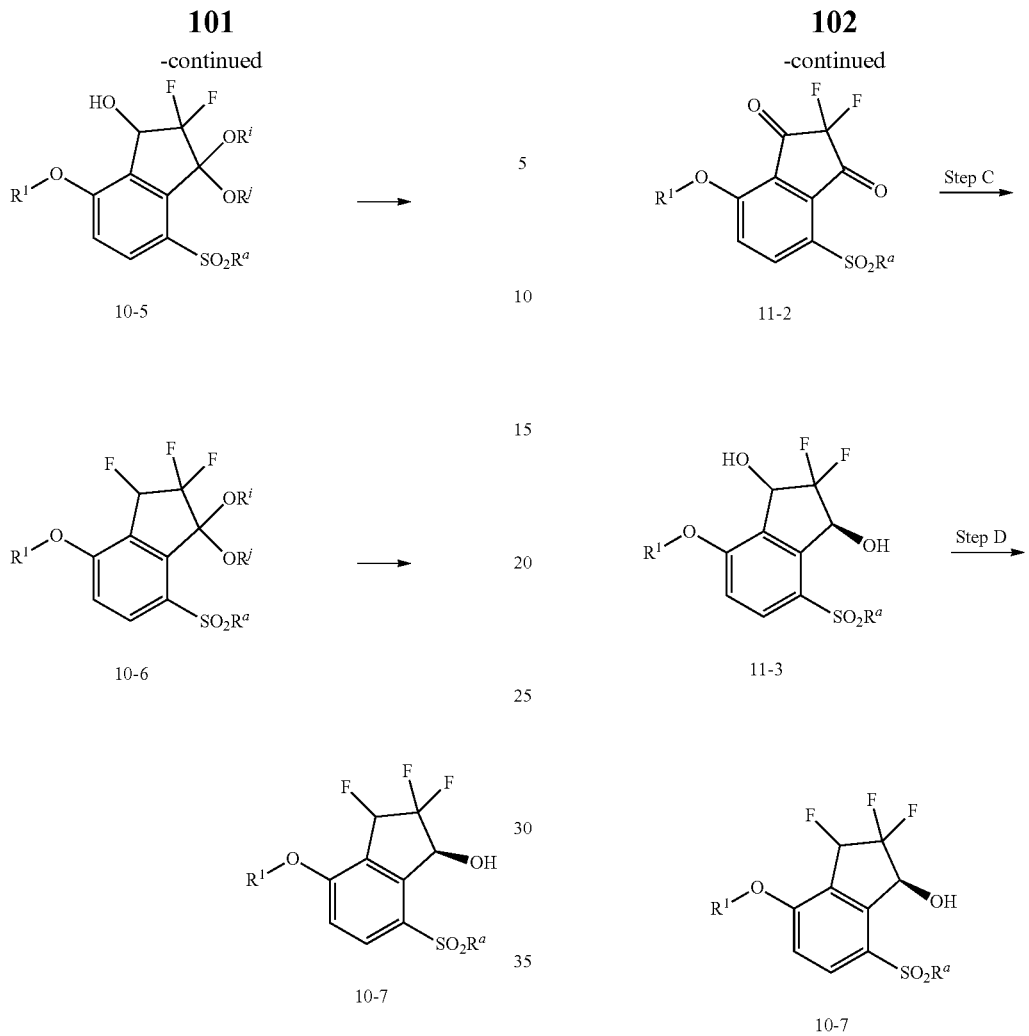

In some embodiments, a compound of Formula 10-7 can be prepared according to Scheme 10. For example, a compound of Formula 10-3 may be prepared from a compound of Formula 3-2 following a similar sequence as outlined in Scheme 9. Further functional group manipulations lead to a compound of Formula 10-7.

Alternatively, a compound of Formula 10-3 can be deprotected to give diketone 11-1, which is fluorinated to give difluorodiketone 11-2. Asymmetric reduction of 11-2 provides diol 11-3. In some embodiments, a fluorination step is performed to give a compound of Formula 10-7.

Scheme 11

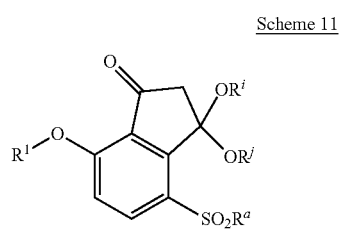

Scheme 12

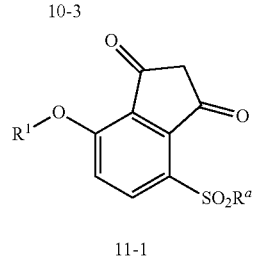

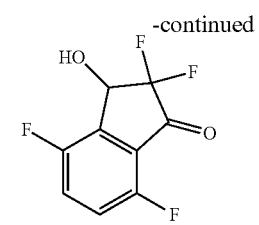

12-3

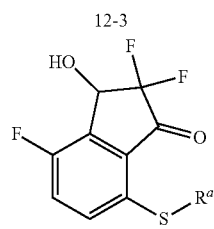

12-4

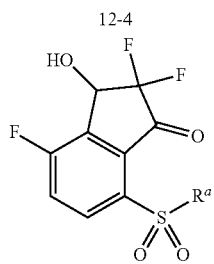

12-5

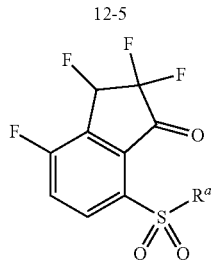

12-6

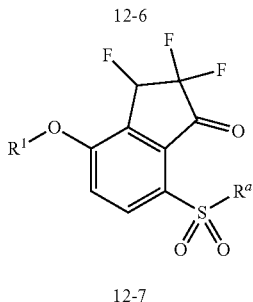

12-7

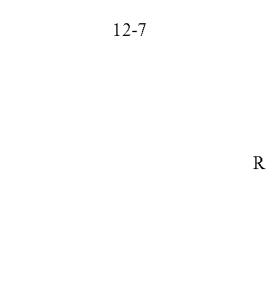

10-7

Alternatively, a compound of Formula 10-7 may be prepared according to Scheme 12. For example, difluoroketone 12-2 is reduced to give hydroxyketone 12-3. The reduction may be enantioselective under transfer hydrogenation conditions with a Ru-catalysis as described herein. One of the aryl fluorines may be selectively displaced with an alkyl thiol to give a compound of Formula 12-4. Oxidation, fluorination, nucleophilic aromatic substitution (SNAr) and asymmetric reduction give a compound of Formula 10-7.

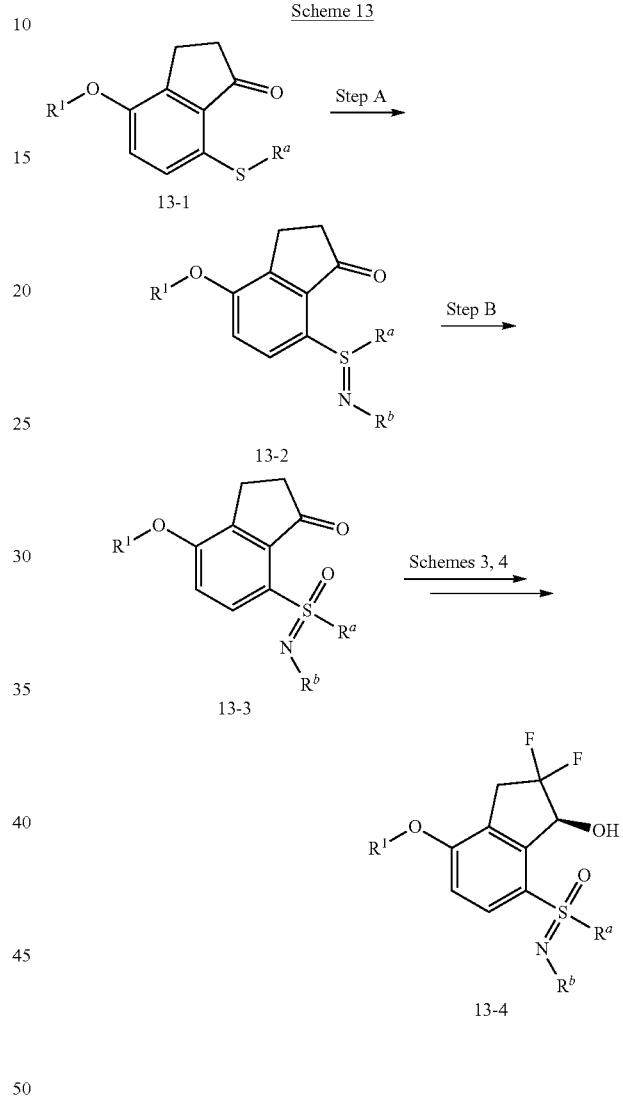

In some embodiments, a compound of Formula 13-4 can be prepared according to Scheme 13. An aryl sulfide of Formula 13-1 is treated with $H_2N$—$R^b$ and an oxidant, e.g., diacetoxyiodobenzene or dipivaloyloxyiodobenzene, in a suitable solvent, such as acetonitrile, to obtain aryl sulfinimide 13-2. In some embodiments, wherein $R^a$ is fluoroalkyl, the addition of rhodium(II) acetate or $R^h{}_2(esp)_2$ catalyst along with magnesium oxide is helpful in Step A. Oxidation of aryl sulfinimide 13-2 to substituted sulfoximine 13-3 may be accomplished with catalytic ruthenium(III) chloride and sodium periodate in a suitable solvent, such as a mixture of water, acetonitrile, and carbon tetrachloride. Substituted sulfoximine 13-3 is then manipulated similarly as described in Schemes 3 and 4 to afford sulfoximines of Formula 13-4 as a diastereomeric mixture. The diastereomers may be separated by column chromatography.

Scheme 14

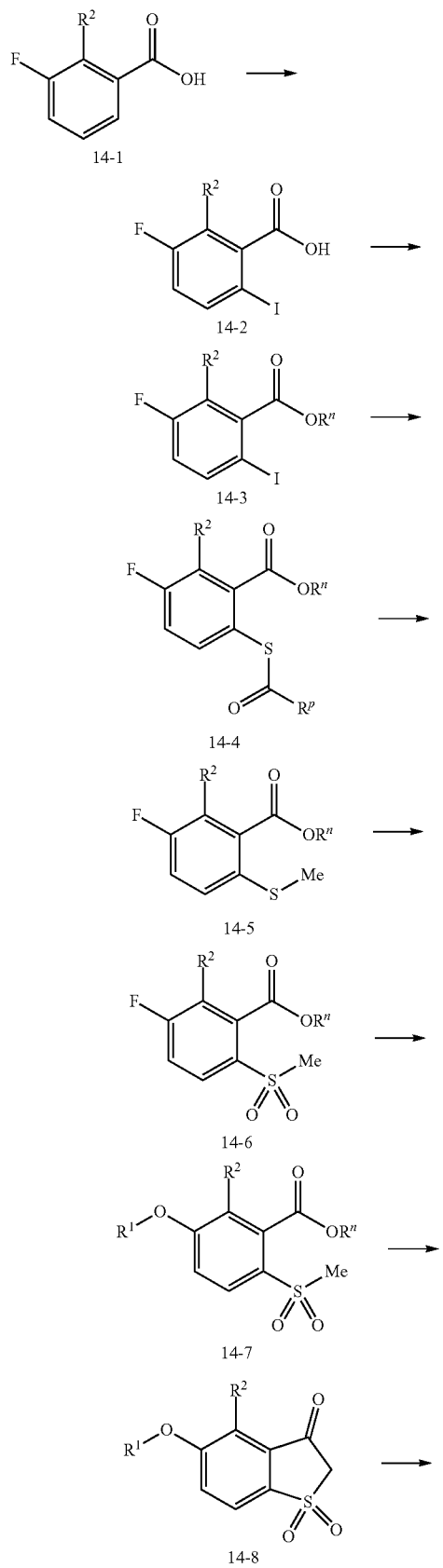

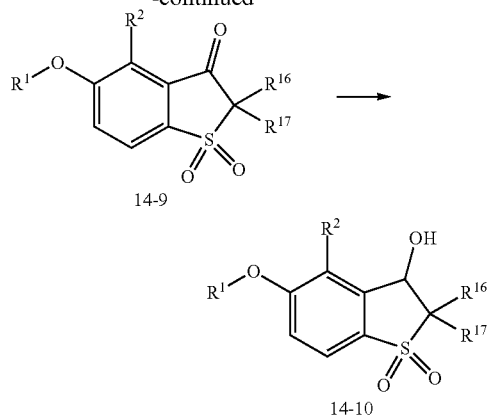

In some embodiments, a compound of Formula 14-10 can be prepared according to steps outlined in Scheme 14, wherein $R^1$ is alkyl, heteroalkyl, cycloalkyl, heterocycloalkyl, aryl or heteroaryl; $R^2$ is halo, cyano, alkyl, alkenyl or alkynyl; and $R^{16}$ and $R^{17}$ are fluoro or alkyl, or $R^{16}$ and $R^{17}$ and the carbon to which they are attached form $C_3$-$C_8$ cycloalkyl or $C_5$-$C_8$ heterocycloalkyl. The synthesis commences with compounds of Formula 14-1. Orthoiodination of 14-1 provides compound 14-2. The reaction may be carried out in a suitable organic solvent in the presence of iodine and a palladium catalyst at an elevated temperature, if needed. After esterification of 14-2, the resulting ester 14-3 may undergo a transition-metal catalyzed coupling reaction with a thioate, e.g., potassium ethanethioate or sodium ethanethioate, to give compounds of Formula 14-4. Suitable transition-metal catalysts include, but are not limited to, Pd(PPh$_3$)$_4$, Pd$_2$(dba)$_3$ chloroform complex or Pd(OAc)$_2$, in the presence or absence of a suitable ligand. Hydrolysis of a compound of Formula 14-4 followed by alkylation of the resulting thiophenol intermediate with an alkyl halide, e.g., methyl iodide, gives a compound of Formula 14-5. The hydrolysis and alkylation may be carried out in a one-pot procedure without purification. In some embodiments, this is carried out by treating a compound of Formula 14-4 with a carbonate base in a suitable solvent at or near room temperature for a period ranging from 0.1 to 24 hours, followed by addition of an alkyl halide. Carbonate bases include, but are not limited to, sodium carbonate, potassium carbonate, cesium carbonate, potassium bicarbonate and cesium bicarbonate. Oxidation of a compound of Formula 14-5 to give a compound of Formula 14-6 may be accomplished by a variety of methods known in the art, including, but not limited to, RuCl$_3$ catalyzed oxidation in the presence of NaIO$_4$, oxidation with m-chloroperoxybenzoic acid (mCPBA), and oxidation with Oxone®. A compound of Formula 14-6 is then subjected to a nucleophilic aromatic substitution (SNAr) reaction with $R^1$OH (wherein $R^1$ is alkyl, aryl or heteroaryl) to give a compound of Formula 14-7. Temperature for carrying out the SNAr reaction may depend on the reactivity of both $R^1$OH and/or a compound of Formula 14-6. The reaction may be carried out at a temperature ranging from −10° C. to 200° C. In some embodiments, the temperature range is from 30° C. to 120° C. In some other embodiments, the temperature range is from 0° C. to room temperature. Cyclization of a compound of Formula 14-7 may be effected with a base, e.g., sodium hydride, in a suitable solvent to yield a compound of Formula 14-8. After the cyclization, a variety of $R^{16}$ and $R^{17}$ groups may be introduced. In some embodiments, a compound of Formula 14-8 is difluorinated to give a compound of Formula 14-9, formed by treatment with a fluorinating agent, e.g., 1-(chloromethyl)-4-fluoro-1,4-diazo niabicyclo[2.2.2]octane ditetrafluoroborate (Selectfluor©), in the presence of suitable base, e.g., sodium carbonate. Reduction of a compound of Formula 14-9 yields a compound of Formula 14-10. In some embodiments, the reduction is carried out with a hydride, e.g., sodium borohydride and sodium triacetoxyborohydride, to give a racemic mixture. In some embodiments, an asymmetric reduction is carried out as described above (see Scheme 2) to give an enantiomer having an enantiomeric excess as disclosed herein.

the electrophile is N,N-dimethylformamide and $R^2$ is —CHO. In a further embodiment, —CHO is converted to —CHF$_2$ through addition of a fluorinating reagent, e.g., diethylaminosulfur trifluoride. One of the fluorines in a compound of Formula 15-2 may be selectively displaced with a thiomethoxide, e.g., sodium thiomethoxide, to give compounds of Formula 15-3. The reaction temperature may be in a range of −50 to 40° C. In some embodiments, the temperature is at or about 0° C. Oxidation of a compound of Formula 15-3, followed by SNAr reaction with $R^1$OH and base-mediated cyclization provides a compound of Formula 14-8.

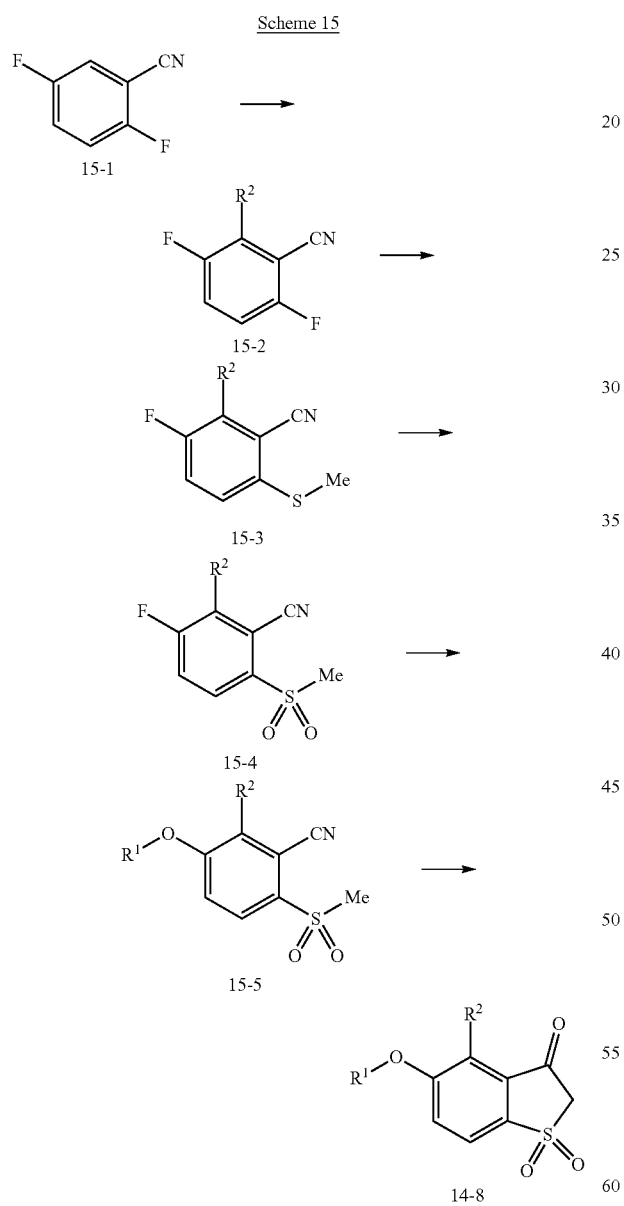

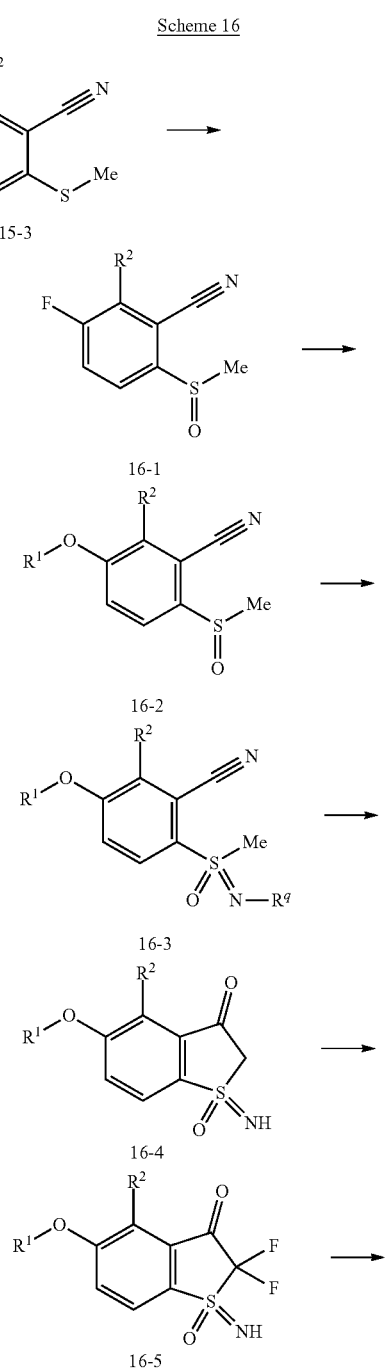

Alternatively, a compound of Formula 14-8 may be prepared according to Scheme 15. For example, lithiation of a compound of Formula 15-1 followed by trapping of the resulting lithio intermediate with a suitable electrophile gives a compound of Formula 15-2. In some embodiments,

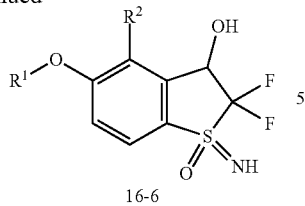

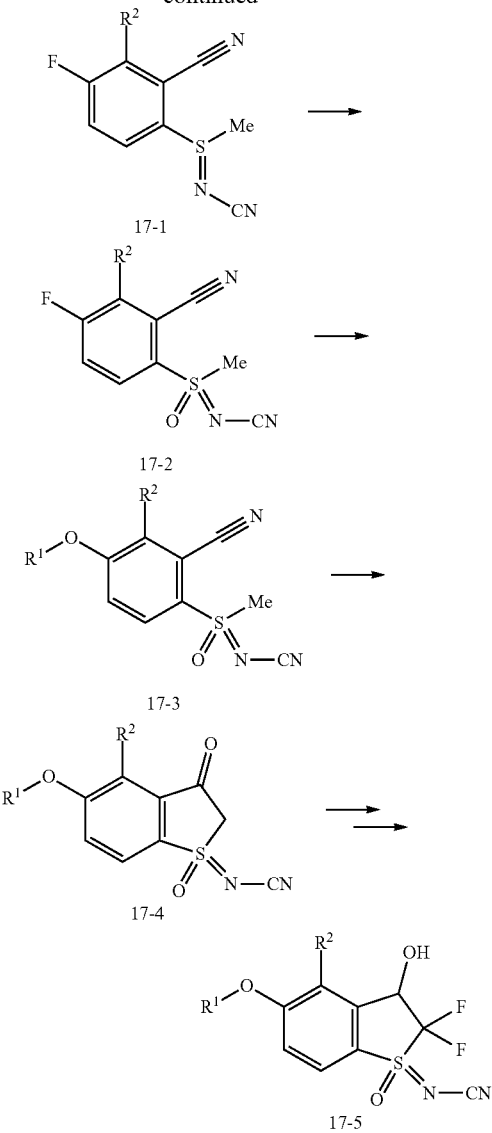

In some embodiments, a compound of Formula 16-6 may be prepared according to Scheme 16. Oxidation of a compound of Formula 15-3 gives a compound of Formula 16-1. The oxidation may be accomplished with Oxone® or mCPBA. The amount of oxidant used for the oxidation may be about 1.5 equivalent, about 1.4 equivalent, about 1.3 equivalent, about 1.2 equivalent, about 1.1 equivalent or about 1.0 equivalent. SNAr reaction of a compound of Formula 16-1 with $R^1OH$ (wherein $R^1$ is alkyl, heteroalkyl, cycloalkyl, heterocycloalkyl, aryl or heteroaryl) in the presence of a base gives a compound of Formula 16-2. At this stage, a sulfoximine moiety may be installed to give a compound of Formula 16-3 through a transition-metal catalyzed insertion of a suitable nitrogen donor. Suitable transition-metal catalysts include, but are not limited to, copper and rhodium catalysts, e.g., bis(rhodium($\alpha,\alpha,\alpha',\alpha'$-tetramethyl-1,3-benzenedipropionic acid)) and dirhodium tetraacetate. Suitable nitrogen donors include, but are not limited to, PhI=NNs, cyanamide, and fluoroalkylamines, e.g., trifluoromethyl acetamide. Cyclization of a compound of Formula 16-3 to give a compound of Formula 16-4 may be achieved with a base, e.g., sodium hydride, at about room temperature. Finally, reduction of a compound of Formula 16-5 as outlined in Scheme 14 provides a compound of Formula 16-6. A compound of Formula 16-6 may exist as a mixture of diastereomers and/or enantiomers. Diastereomers may be separated by conventional column chromatography, while enantiomers may be separated by chiral column chromatography.

Scheme 17

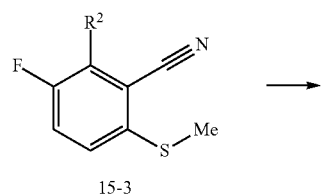

In some embodiments, a compound of Formula 17-5 can be prepared according to Scheme 17. Reaction of a compound of Formula 15-3 with cyanamide in the presence of an oxidant, e.g., (diacetoxyiodo)benzene, affords a compound of Formula 15-1. Further oxidation of a compound of Formula 15-1 provides a compound of Formula 15-2, which undergoes SNAr reaction, cyclization and reduction to give a compound of Formula 17-5.

Scheme 18

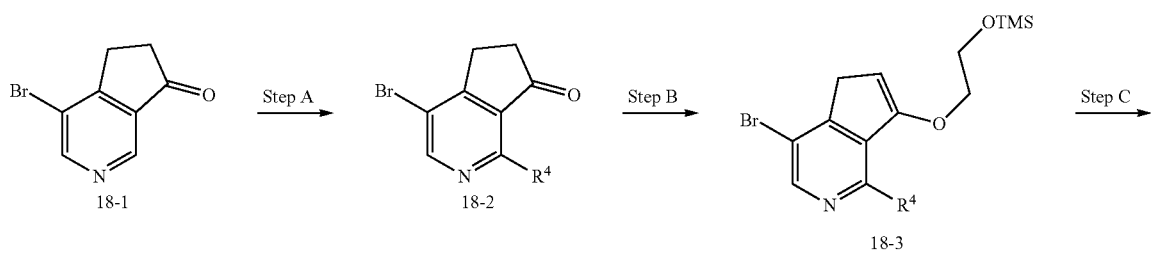

-continued

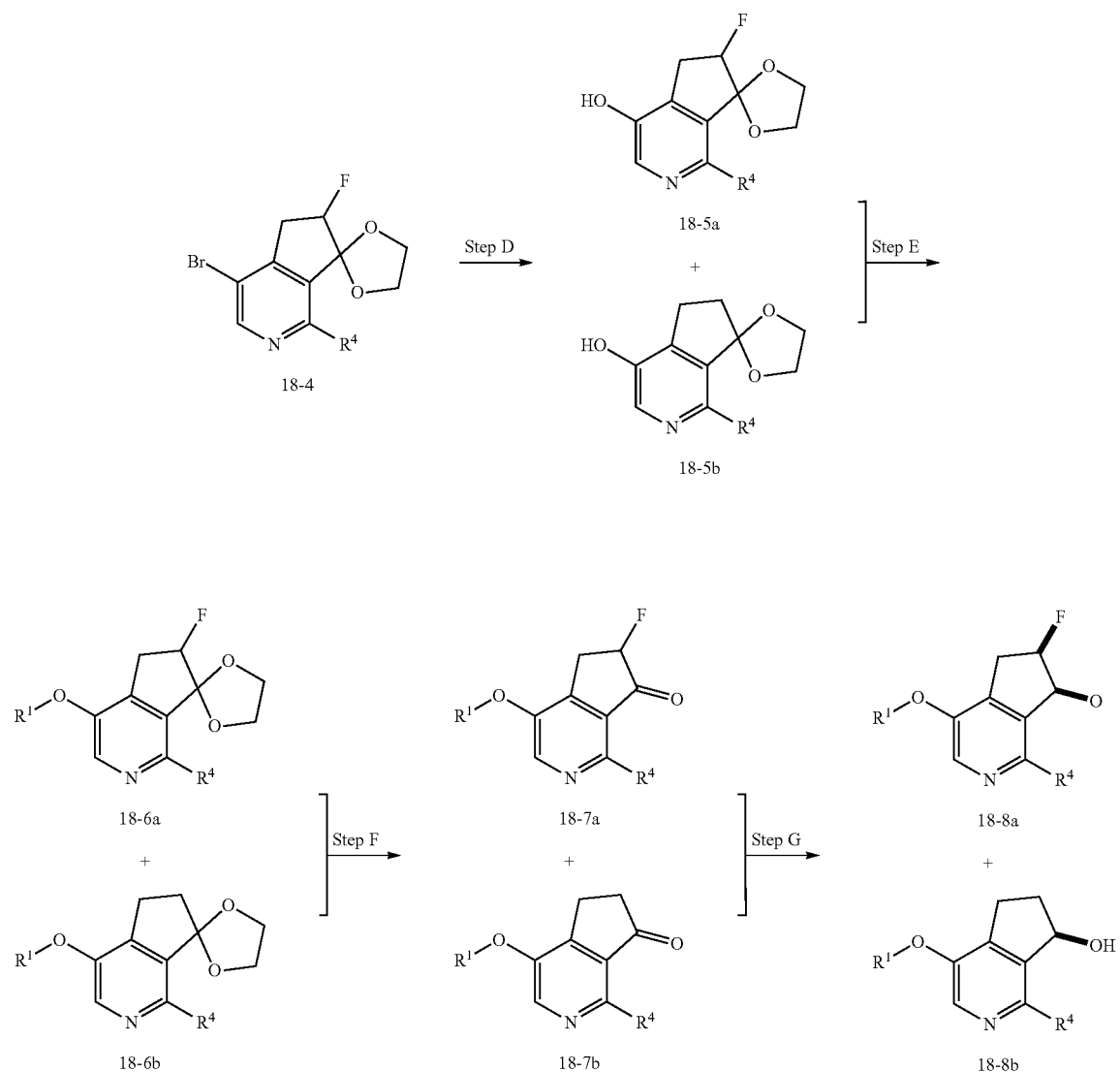

In some embodiments, compounds of Formula 18-8a and 18-8b may be prepared according to Scheme 18. For example, pyridine 18-1 may be converted to alkylaryl derivative 18-2 in Step A, wherein $R^4$ is, for example, trifluoromethyl. The ketone may be converted to protected enol ether 18-3, then fluorinated to give fluoroketal 18-4. Treatment of a compound of Formula 18-4 with a suitable hydroxide source as described in Scheme 6 gives a mixture of phenols 18-5a and 18-5b. The phenols can undergo an SNAr reaction with a suitable halide to give aryl ethers of Formulae 18-6a and 18-6b, which may be deprotected to give the resultant ketones. In some embodiments, a compound of Formula 18-7 is reduced with a hydride source to give a racemic mixture. In other embodiments, an asymmetric reduction is carried out as described in Scheme 2, affording alcohols 18-8a and 18-8b, separable by methods known to one skilled in the art, such as, for example, conventional column chromatography.

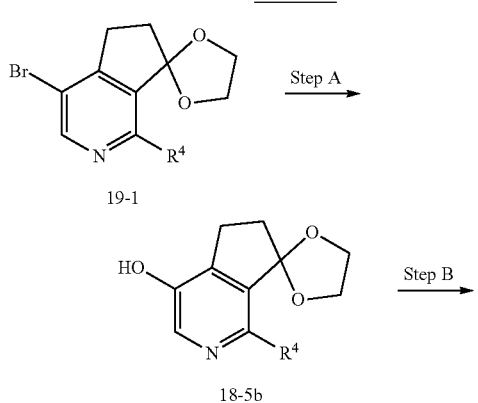

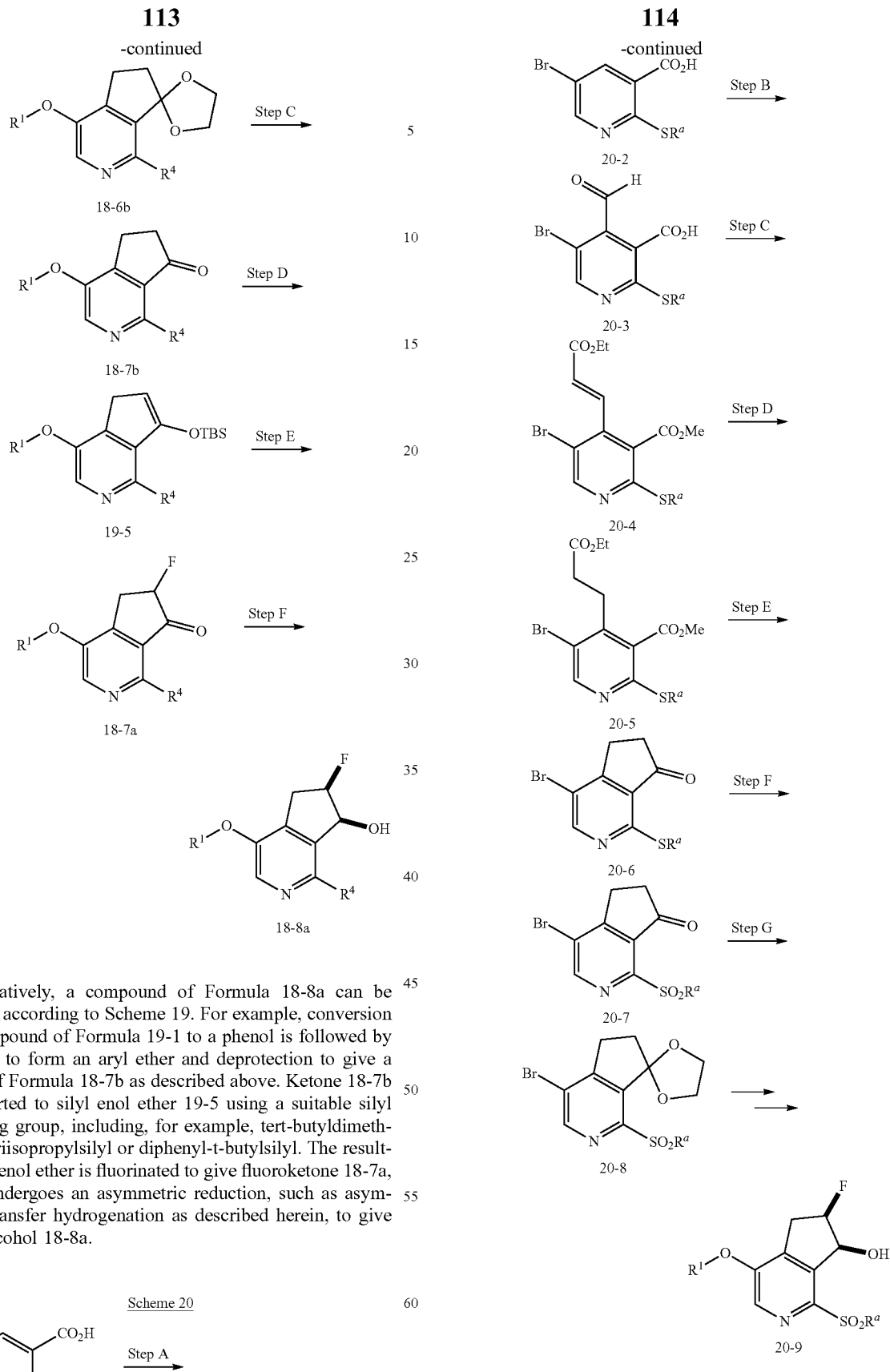

Alternatively, a compound of Formula 18-8a can be prepared according to Scheme 19. For example, conversion of a compound of Formula 19-1 to a phenol is followed by coupling to form an aryl ether and deprotection to give a ketone of Formula 18-7b as described above. Ketone 18-7b is converted to silyl enol ether 19-5 using a suitable silyl protecting group, including, for example, tert-butyldimethylsilyl, triisopropylsilyl or diphenyl-t-butylsilyl. The resulting silyl enol ether is fluorinated to give fluoroketone 18-7a, which undergoes an asymmetric reduction, such as asymmetric transfer hydrogenation as described herein, to give chiral alcohol 18-8a.

A compound of Formula 20-9 can be prepared following the general procedure outlined in Scheme 20, wherein the aryl fluoride of a compound of Formula 20-1 is displaced with an alkyl thiol to give 20-2. Formation of benzaldehyde 20-3 may be followed by, for example, a Wittig reaction, to give alkene 20-4, which is reduced to an alkane of Formula 20-5 under suitable conditions. In some embodiments, a Dieckmann condensation reaction is followed by a decarboxylation to give ketone 20-6. Oxidation of a compound of Formula 20-6 to give a compound of Formula 20-7 may be accomplished by a variety of methods known in the art, including, but not limited to, RuCl₃ catalyzed oxidation in the presence of NaIO₄, oxidation with m-chloroperoxybenzoic acid (mCPBA) and oxidation with Oxone®. Protection of the ketone, for example, as the cyclic ketal (20-8) is followed by the general procedure outlined in Scheme 19 to give a compound of Formula 20-9.

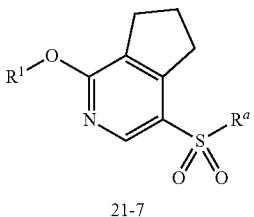

In some embodiments, a compound of Formula 21-7 may be prepare according to Scheme 21. Formation of a chloropyridine of Formula 21-2 may be followed by an SNAr reaction with a suitable alcohol of formula $R^1OH$ as described above to give a compound of Formula 21-3. Aryl bromide 21-3 may undergo a transition-metal catalyzed coupling reaction with a thioate to give a compound of Formula 21-4, analogously to the procedure detailed in Scheme 14. Hydrolysis, alkylation with a suitable alkyl halide and oxidation affords a compound of Formula 21-7.

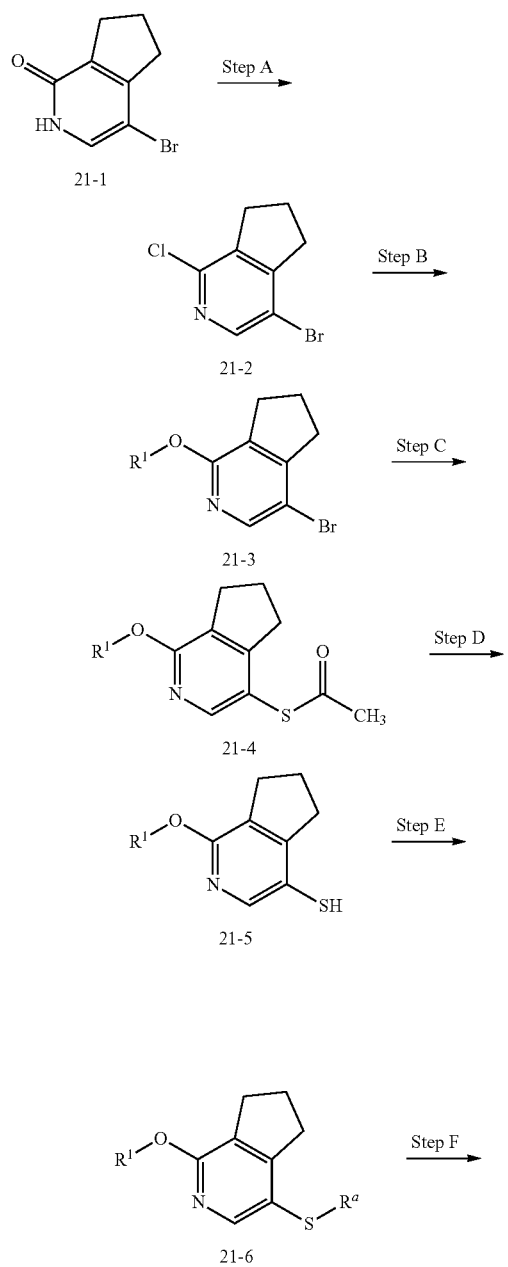

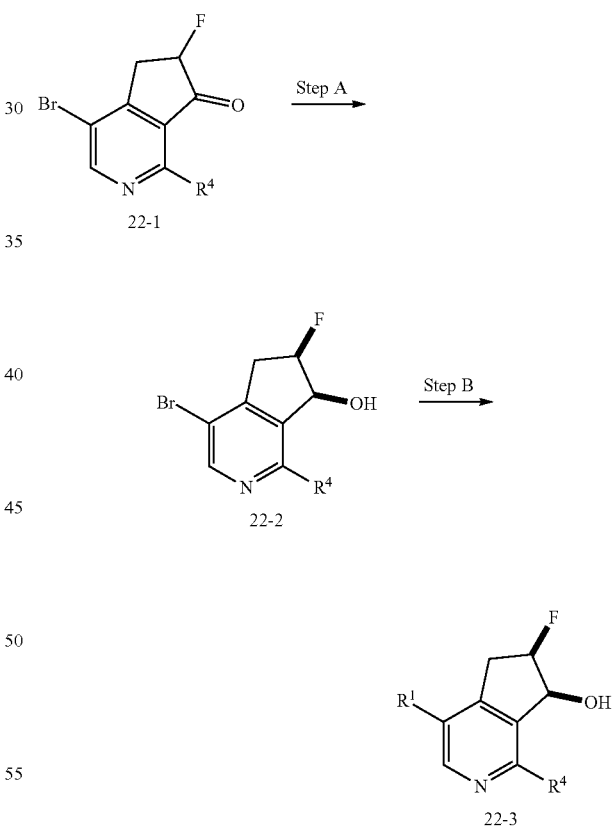

In some embodiments, a ketone of Formula 22-1 may be reduced to give 22-2, optionally with high enantioselectivity using asymmetric transfer hydrogenation or enzymatic reduction conditions as described herein. A compound of Formula 22-2 and a suitable coupling partner, including, but not limited to, a boronic acid of formula $R^1B(OH)_2$, may undergo a coupling reaction to give a compound of Formula 22-3.

Scheme 23

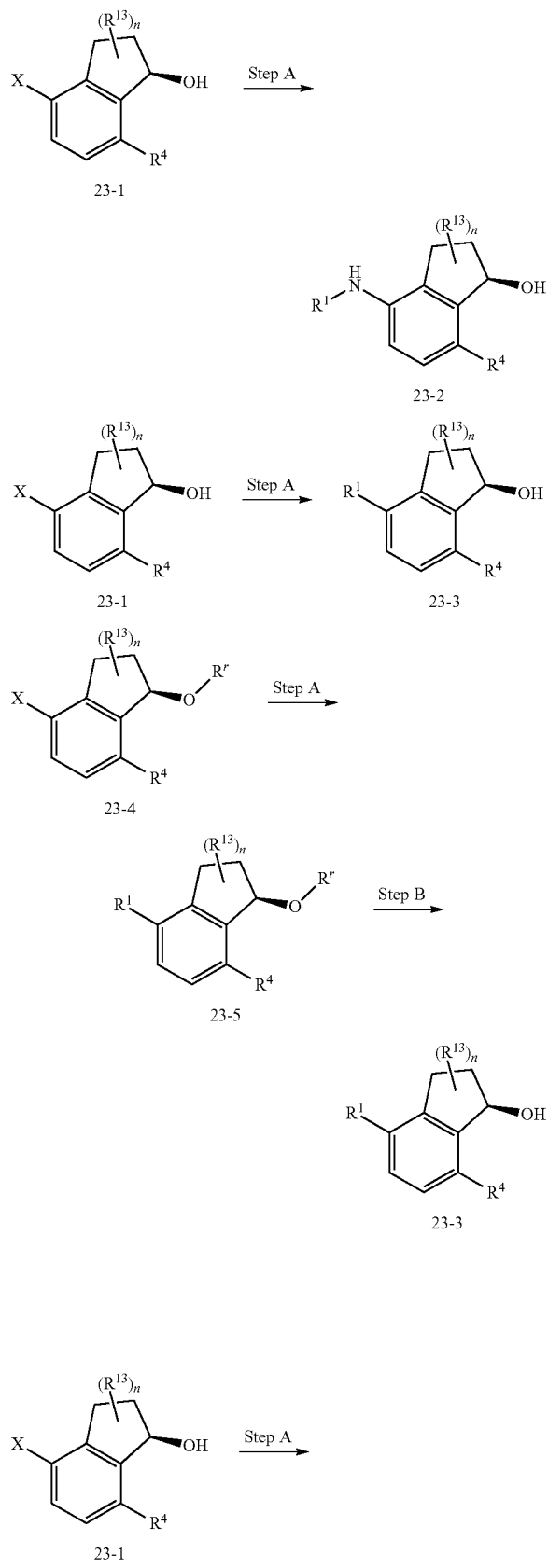

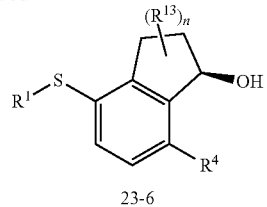

In some embodiments, $R^1$ can be coupled to a compound of Formula 23-1 or 23-4 via a reaction scheme represented generally in Scheme 23. In some embodiments, wherein Z is $-N(R^8)$, an aryl halide of Formula 23-1 is coupled to a suitably substituted amine, i.e. $NHR^1R^8$, via a Buchwald-Hartwig amination to give a compound of Formula 23-2. In a further embodiment, Step A is a cross coupling reaction, including, but not limited to, a Stille, Negishi or Suzuki reaction, wherein an aryl halide of Formula 23-1 is combined with an appropriate reactant containing $R^1$ and a suitable catalyst to afford a compound of Formula 23-3. In other embodiments, a compound of Formula 23-4 undergoes an SNAr reaction and a subsequent deprotection to give a compound of Formula 23-3. $R^1$ in a compound of Formula 23-5 may be, for example, morpholine, wherein a C—N bond connects said morpholine to the aryl ring. In still other embodiments, Z is —S—, and $R^1S$— is attached to a compound of Formula 23-1 via an SNAr reaction to give a compound of Formula 23-6.

Scheme 24

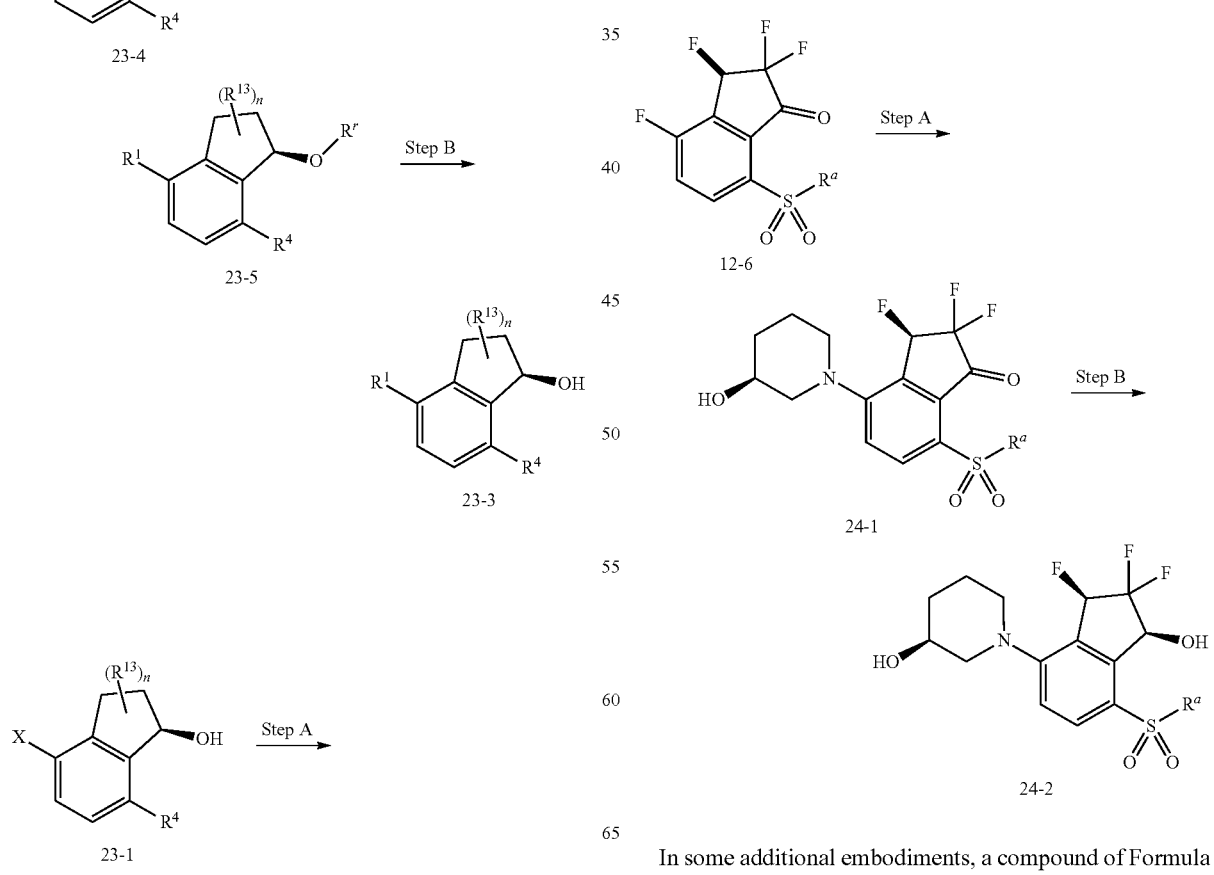

In some additional embodiments, a compound of Formula 24-2 can be prepared according to steps outlined in Scheme 24. A compound of Formula 12-6 is prepared via an asymmetric variation of the sequence presented in Scheme 12, then reacted with an amine, i.e. (3S)-3-piperidinol hydrochloride, to give a compound of Formula 24-1. Asymmetric reduction as described above gives a compound of Formula 24-2.

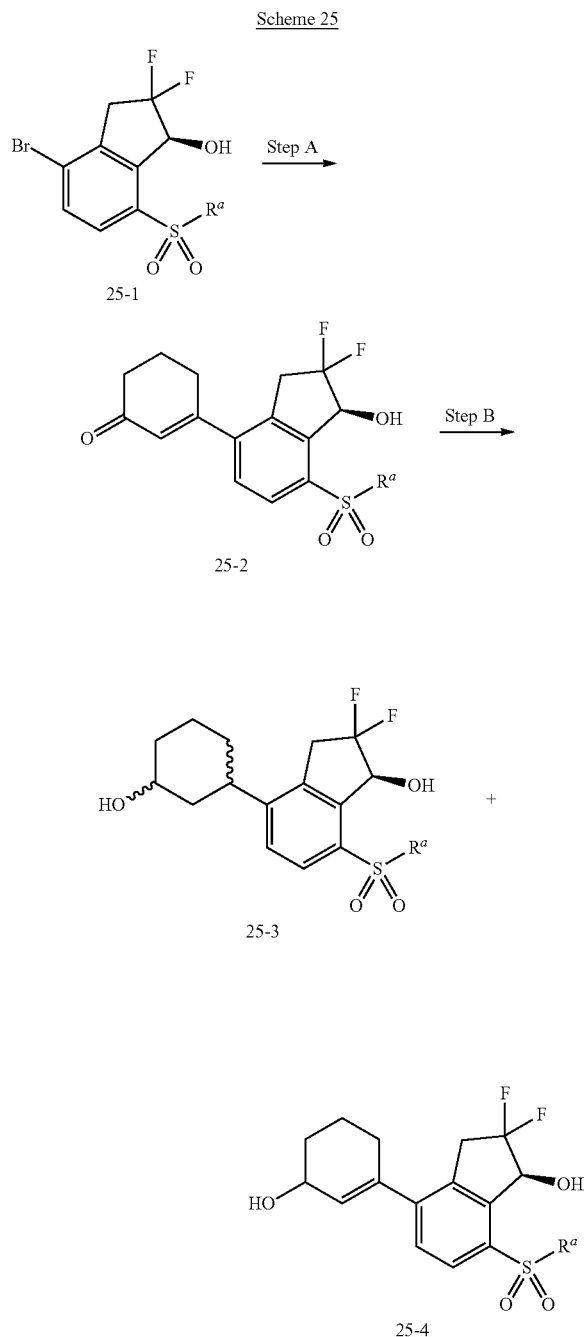

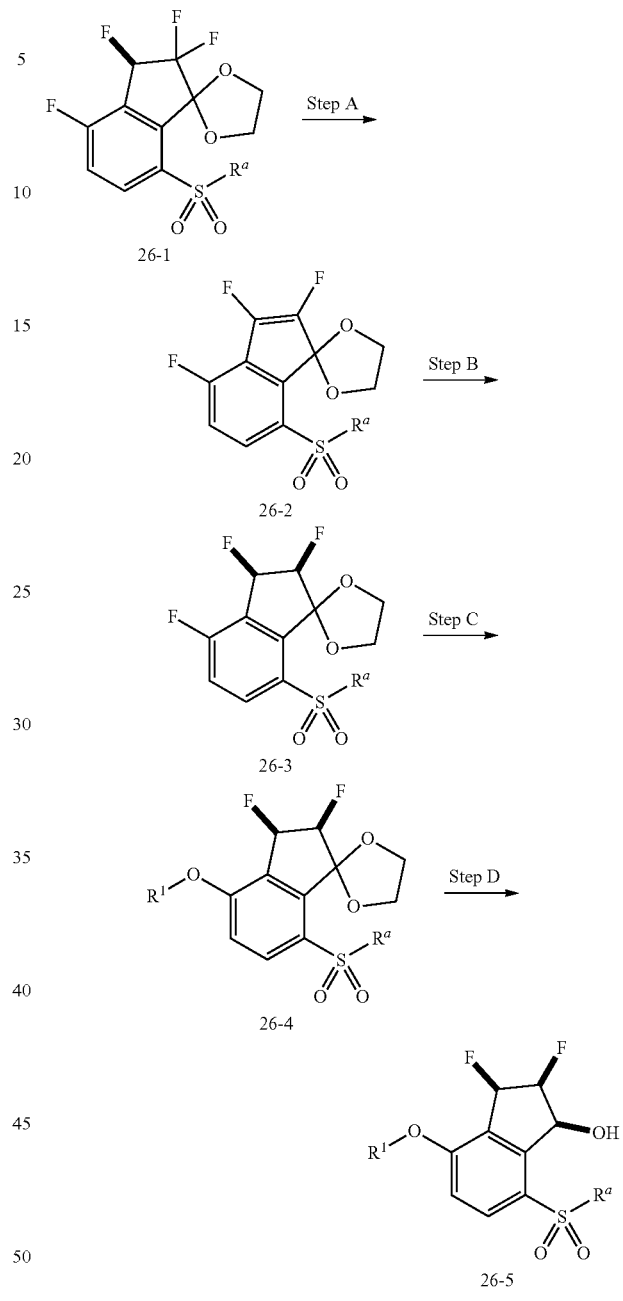

In some embodiments, a compound of Formula 25-3 or 25-4 may be prepared according to steps outlined in Scheme 25. For example, 25-2 may be prepared via a cross coupling reaction, i.e., a Suzuki reaction with a boronic acid of formula $R^1B(OH)_2$. Hydride reduction of 25-2 gives a mixture of alcohols 25-3 and unsaturated alcohol 25-4.

In some embodiments, a compound of Formula 26-5 can be synthesized according to Scheme 26. For example, treatment of compound 26-1 with base can provides difluoroalkene 26-2. The amount of base may be about 1 equivalent to avoid byproduct formation. The olefin in 26-2 may be hydrogenated to give a compound of Formula 26-3 with cis difluoro configuration. At this stage, an alkoxy group can be introduced by displacement of the aryl fluoride in 26-3 by an alcohol in the presence of a base. Finally, deprotection followed by reduction of the resulting ketone provides a compound of Formula 26-5. Intermediate 26-3 may be separated, for example, by chiral column chromatography, to give both enantiomers, each of which can be functionalized as outlined in Scheme 26 to provide either enantiomer of a compound of Formula 26-5.

Scheme 27

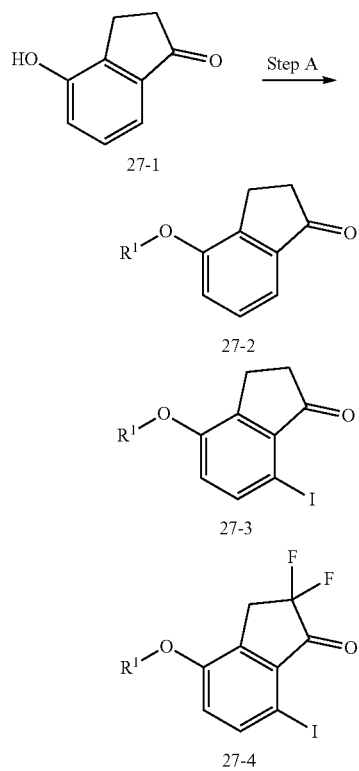

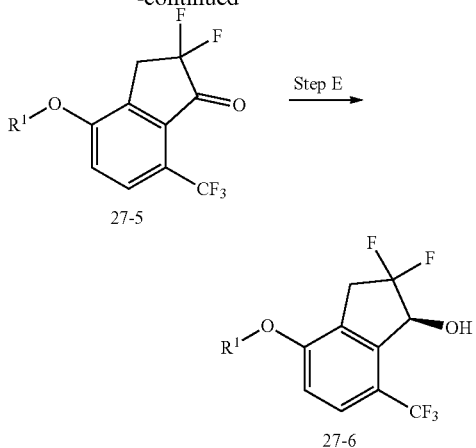

In some embodiments, a compound of Formula 27-6 may be synthesized according to Scheme 27. For example, alkylation of compound 27-1 provides a compound of Formula 27-2, wherein $R^1$ is alkyl, cycloalkyl, or heterocycloalkyl. A compound of Formula 27-2 can be selectively iodinated to give aryl iodide 27-3. A compound of Formula 27-3 can be difluorinated as previously described. Installation of a $CF_3$ group followed by asymmetric reduction provides a compound of Formula 27-6.

In some other embodiments, a compound of a formula given in Table 1 is synthesized according to one of the general routes outlined in Schemes 1-27, Examples 1-14 or by methods generally known in the art.

TABLE 1

| No. | Structure | Mass Characterization | $^1$H NMR Data |
|---|---|---|---|
| 1 | ![structure] | 393 (M + H) | (400 MHz, CDCl$_3$): δ 7.81 (d, 1H), 7.00-6.89 (m, 3H), 6.73-6.71 (m, 1H), 6.35 (t, 1H), 5.66-5.65 (m, 1H), 3.19-3.13 (m, 2H), 2.96-2.90 (m, 1H), 2.50-2.40 (m, 1H), 2.30-2.24 (m, 1H) |
| 2 | ![structure] | 377 (M + H) | (400 MHz, CDCl$_3$): δ 7.81 (d, 1H), 6.96 (d, 1H), 6.73-6.68 (m, 1H), 6.62-6.61 (m, 2H), 6.36 (t, 1H), 5.66-5.65 (m, 1H), 3.22-3.10 (m, 2H), 2.96-2.90 (m, 1H), 2.50-2.40 (m, 1H), 2.29-2.24 (m, 1H) |
| 3 | ![structure] | 376, 378 (M + H) | (400 MHz, CDCl$_3$): δ 8.49 (s, 1H), 8.36 (s, 1H), 7.81 (d, 1H), 7.44-7.43 (m, 1H), 6.89 (d, 1H), 6.36 (t, 1H), 5.67-5.66 (m, 1H), 3.23-3.16 (m, 2H), 2.99-2.92 (m, 1H), 2.51-2.42 (m, 1H), 2.32-2.25 (m, 1H) |

TABLE 1-continued

| No. | Structure | Mass Characterization | ¹H NMR Data |
|---|---|---|---|
| 4 | 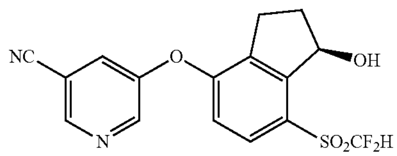 | 367 (M + H) | (400 MHz, CDCl₃): δ 8.76 (s, 1H), 8.66 (s, 1H), 7.86 (d, 1H), 7.65-7.64 (m, 1H), 6.93 (d, 1H), 6.38 (t, 1H), 5.71-5.65 (m, 1H), 3.20-3.16 (m, 2H), 2.96-2.90 (m, 1H), 2.50-2.42 (m, 1H), 2.37-2.24 (m, 1H) |
| 5 | 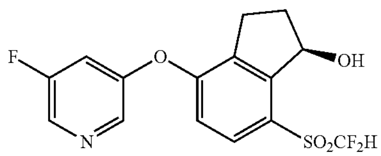 | 360 (M + H) | (400 MHz, CDCl₃): δ 8.41 (s, 1H), 8.32 (s, 1H), 7.82 (d, 1H), 7.22-7.17 (m, 1H), 6.92 (d, 1H), 6.37 (t, 1H), 5.70-5.60 (m, 1H), 3.23-3.18 (m, 2H), 2.99-2.97 (m, 1H), 2.54-2.40 (m, 1H), 2.34-2.22 (m, 1H) |
| 6 | 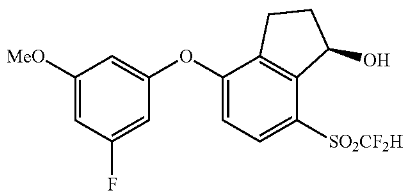 | 433 (M − H + 46) | (400 MHz, CDCl₃): δ 7.77 (d, 1H), 6.91 (d, 1H), 6.54-6.50 (m, 1H), 6.42-6.38 (m, 2H), 6.39 (t, 1H), 5.67-5.63 (m, 1H), 3.80 (s, 3H), 3.23-3.15 (m, 2H), 2.99-2.92 (m, 1H), 2.50-2.45 (m, 1H), 2.30-2.23 (m, 1H) |
| 7 | Compound 7a<br><br>Compound 7b | 7a, 429, 431 (M + Na)<br>7b, 429, 431 (M + Na) | 7a: (400 MHz, CDCl₃): δ 7.81 (d, 1H), 7.01-6.98 (m, 1H), 6.91-6.89 (m, 2H), 6.75-6.71 (m, 1H), 6.34 (t, 1H), 5.58-5.53 (m, 1H), 3.48-3.40 (m, 1H), 3.22 (d, 1H), 2.66-2.59 (m, 1), 1.98-1.93 (m, 1H), 1.46 (d, 3H)<br>7b: (400 MHz, CDCl₃): δ 7.81 (d, 1H), 7.01-6.97 (m, 1H), 6.92 (d, 1H), 6.89-6.88 (m, 1H), 6.73-6.69 (m, 1H), 6.38 (t, 1H), 5.70-5.67 (m, 1H), 3.71-3.64 (m, 1H), 3.25 (d, 1H), 2.47-2.41 (m, 1H), 2.14-2.06 (m, 1H), 1.36 (d, 3H) |
| 8 | 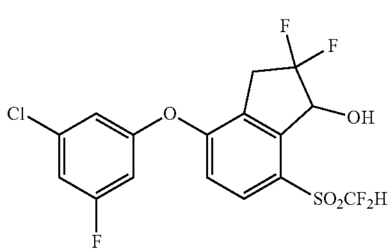 | 429, 431 (M + H) | (400 MHz, CDCl₃): δ 7.90 (d, 1H), 7.06-7.03 (m, 1H), 6.98 (d, 1H), 6.94-6.92 (m, 1H), 6.78-6.74 (m, 1H), 6.42 (t, 1H), 5.50 (d, 1H), 3.61-3.43 (m, 2H), 3.24 (s, 1H) |
| 9 | 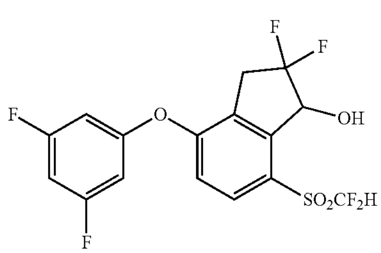 | 413 (M + H) | (400 MHz, CDCl₃): δ 7.90 (d, 1H), 7.01 (d, 1H), 6.80-6.73 (m, 1H), 6.70-6.63 (m, 2H), 6.43 (t, 1H), 5.50 (m, 1H), 3.60-3.43 (m, 2H), 3.30 (d, 1H) |

TABLE 1-continued

| No. | Structure | Mass Characterization | ¹H NMR Data |
|---|---|---|---|
| 10 | 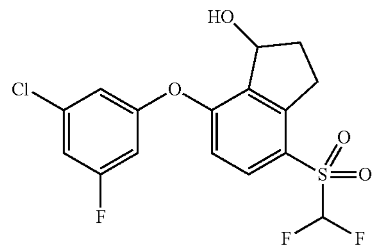 [SMILES: O=S(=O)(c1ccc(Oc2cc(F)cc(Cl)c2)c2c1CCC2O)C(F)F] | 375, 377 (M − OH) | (400 MHz, CDCl$_3$): δ 7.85 (d, 1H), 7.04-7.00 (m, 1H), 6.97-6.95 (m, 1H), 6.84-6.77 (m, 2H), 6.18 (t, 1H), 5.58-5.53 (m, 1H), 3.59-3.50 (m, 1H), 3.34-3.26 (m, 1H), 2.60-2.50 (m, 1H), 2.31 (d, 1H), 2.21-2.13 (m, 1H) |
| 11 | 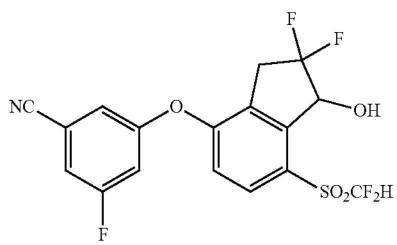 | 437 (M + NH$_4$) | (400 MHz, CDCl$_3$): δ 7.94 (d, 1H), 7.33-7.29 (m, 1H), 7.23-7.21 (m, 1H), 7.13-7.09 (m, 1H), 7.00 (d, 1H), 6.43 (t, 1H), 5.51 (d, 1H), 3.60-3.43 (m, 2H), 3.30 (br s, 1H) |
| 12 | 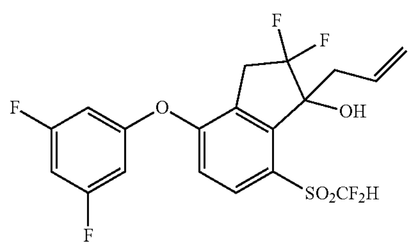 | 451 (M − H) | (400 MHz, CDCl$_3$): δ 8.01 (d, 1H), 6.97 (d, 1H), 6.82-6.55 (m, 4H), 5.76-5.64 (m, 1H), 5.35-5.26 (m, 2H), 3.54-3.44 (m, 2H), 3.31-3.18 (m, 1H), 3.06-2.96 (m, 2H) |
| 13 | 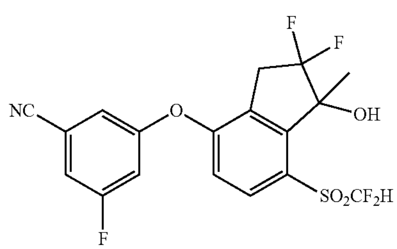 | 451 (M + NH$_4$) | (400 MHz, CDCl$_3$): δ 8.0 (d, 1H), 7.33-7.30 (m, 1H), 7.23-7.21 (m, 1H), 7.13-7.09 (m, 1H), 6.92 (d, 1H), 6.62 (m, 1H), 3.58-3.49 (m, 2H), 3.34-3.20 (m, 1H), 1.84-1.82 (m, 3H) |
| 14 | 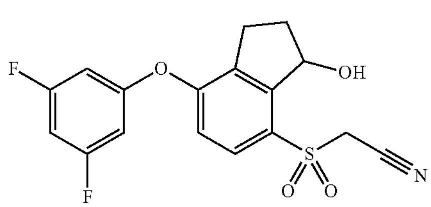 [SMILES: N#CCS(=O)(=O)c1ccc(Oc2cc(F)cc(F)c2)c2c1C(O)CC2] | 364 (M − H) | (400 MHz, CDCl$_3$): δ 7.9 (d, 1H), 6.97 (d, 1H), 6.73-6.67 (m 1H), 6.64-6.58 (m, 1H), 5.83-5.79 (m, 1H), 6.57-6.53 (m, 1H), 4.22 (d, 1H), 3.20-3.10 (m, 1H), 2.95-2.85 (m, 2H), 2.60-2.50 (m, 1H), 2.25-2.16 (m, 1H) |
| 15 | 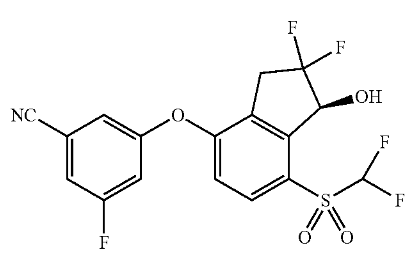 [SMILES: N#Cc1cc(F)cc(Oc2ccc(S(=O)(=O)C(F)F)c3c2CC(F)(F)[C@H]3O)c1] | 420 (M + H) | (400 MHz, CDCl$_3$): δ 7.94 (d, 1H), 7.33-6.98 (m, 4H), 6.44 (t, 1H), 5.51 (d, 1H), 3.61-3.45 (m, 2H) |

TABLE 1-continued

| No. | Structure | Mass Characterization | ¹H NMR Data |
|---|---|---|---|
| 16 | 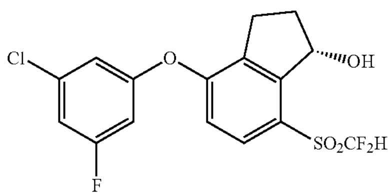 | 437/439 (M − H + 46) | (400 MHz, CDCl₃): δ 7.81 (d, 1H), 7.00-6.98 (m, 1H), 6.94 (d, 1H), 6.89-6.88 (m, 1H), 6.74-6.71 (m, 1H), 6.35 (t, 1H), 5.67-5.65 (m, 1H), 3.21-3.13 (m, 2H), 2.96-2.89 (m, 1H), 2.50-2.41 (m, 1H), 2.30-2.23 (m, 1H) |
| 17 | 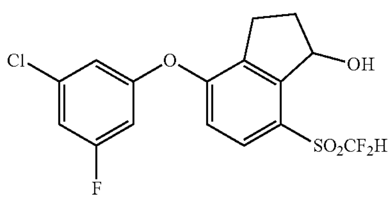 | 393 (M + H) | |
| 18 | 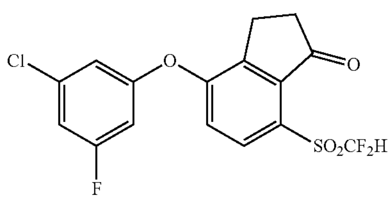 | 391, 393 (M + H) | (400 MHz, CDCl₃): δ 8.15 (d, 1H), 7.14 (d, 1H), 7.12 (t, 1H), 7.07-7.04 (m, 1H), 6.96-6.93 (m, 1H), 6.80-6.76 (m, 1H), 3.23-3.20 (m, 2H), 2.90-2.87 (m, 2H) |
| 19 | 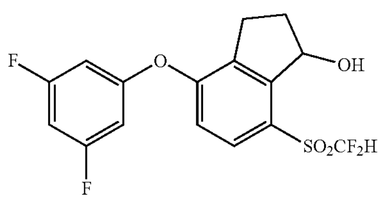 | 376 (M + H) | (400 MHz, CDCl₃): δ 7.81 (d, 1H), 6.92 (d, 1H), 6.72-6.67 (m, 1H), 6.62 (t, 1H), 6.63-6.59 (m, 2H), 4.96-4.94 (m, 1H), 3.18-3.10 (m, 1H), 2.99-2.92 (m, 1H), 2.51-2.41 (m, 1H), 2.30-2.00 (m, 3H) |
| 20 | 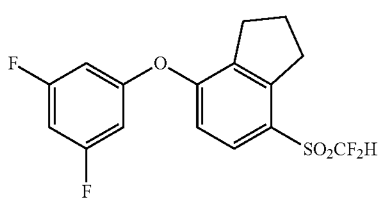 | 361 (M + H) | (400 MHz, CDCl₃): δ 7.76 (d, 1H), 6.87 (d, 1H), 6.69-6.63 (m, 1H), 6.60-6.55 (m, 2H), 6.18 (t, 1H), 3.37 (t, 2H), 2.93 (t, 2H), 2.20-2.17 (m, 2H) |
| 21 | 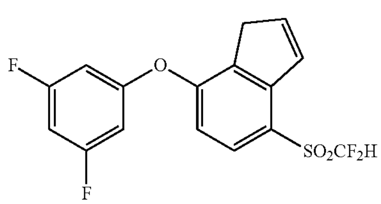 | 359 (M + H) | (400 MHz, CDCl₃): δ 7.88 (d, 1H), 7.47-7.45 (m, 1H), 6.93-6.90 (m, 2H), 6.71-6.60 (m, 3H), 6.22 (t, 1H), 3.49-3.48 (m, 1H) |
| 22 | 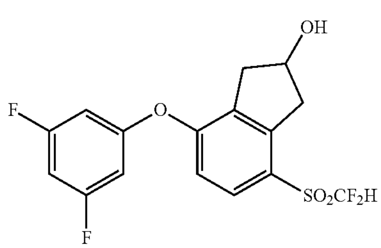 | 421 (M − H + 46) | (400 MHz, CDCl₃): δ 7.79 (d, 1H), 6.90 (d, 1H), 6.72-6.66 (m, 1H), 6.64-6.57 (m, 2H), 6.19 (t, 1H), 4.85-4.81 (m, 1H), 3.60-3.44 (m, 3H), 3.21-2.99 (m, 2H) |

TABLE 1-continued

| No. | Structure | Mass Characterization | ¹H NMR Data |
|---|---|---|---|
| 23 | 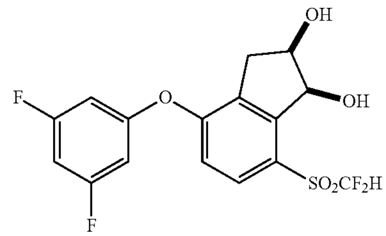 | 437 (M − H + 46) | (400 MHz, CDCl$_3$): δ 7.83 (d, 1H), 6.98 (d, 1H), 6.74-6.69 (m, 1H), 6.64-6.62 (m, 2H), 6.36 (t, 1H), 5.37 (brs, 1H), 4.65-4.63 (m, 1H), 3.45-3.39 (m, 2H), 2.92-2.88 (m, 1H) |
| 24 | 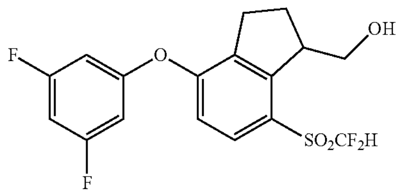 | 391 (M + H) | (400 MHz, CDCl$_3$): δ 7.77 (d, 1H), 6.90 (d, 1H), 6.71-6.65 (m, 1H), 6.62-6.36 (m, 2H), 6.23 (t, 1H), 3.94-3.71 (m, 3H), 2.97-2.89 (m, 2H), 2.84 (s, 1H), 2.40-2.22 (m, 2H) |
| 25 | 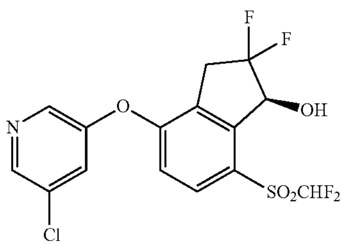 | 410, 412 (M + H) | (400 MHz, CDCl$_3$) δ 8.55-8.54 (m, 1H), 8.40-8.39 (m, 1H), 7.91 (d, 1H), 7.52-7.49 (m, 1H), 6.93 (d, 1H), 6.44 (t, 1H), 5.53-5.49 (m, 1H), 3.64-3.48 (m, 2H), 3.35 (d, 1H) |
| 26 | 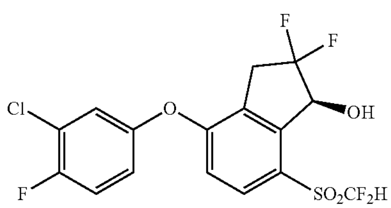 | 473, 475 (M − H + 46) | (400 MHz, CDCl$_3$): δ 7.86 (d, 1H), 7.26-7.22 (m, 2H), 7.05-6.95 (m, 1H), 6.86 (d, 1H), 6.41 (t, 1H), 5.51-5.47 (m, 1H), 3.58-3.51 (m, 2H), 3.26 (brd s, 1H) |
| 27 | 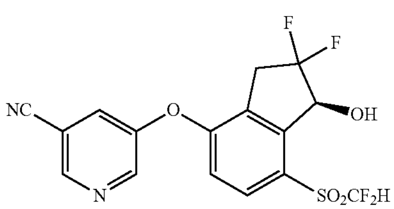 | 403 (M + H) | (400 MHz, CDCl$_3$): δ 8.82 (s, 1H), 8.71 (s, 1H), 7.95 (d, 1H), 7.73-7.71 (m, 1H), 6.95 (d, 1H), 6.44 (t, 1H), 5.55-5.50 (m, 1H), 3.60-3.51 (m, 2H), 3.29 (d, 1H) |
| 28 | 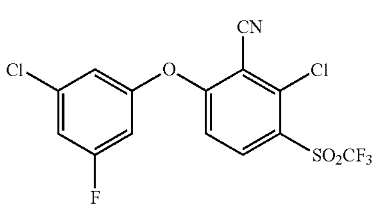 | 412, 414 (M − H) | (400 MHz, CDCl$_3$): δ 8.27 (d, 1H), 7.17-7.14 (m, 1H), 7.03-7.02 (m, 1H), 6.97 (d, 1H), 6.88-6.85 (m, 1H) |
| 29 | 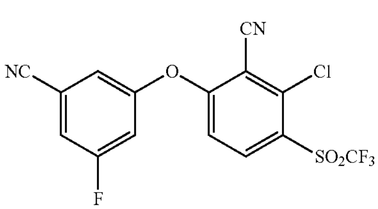 | 403/405 (M − H) | (400 MHz, CDCl$_3$): δ 8.31 (d, 1H), 7.44-7.41 (m, 1H), 7.32-7.31 (m, 1H), 7.24-7.20 (m, 1H), 6.97 (d, 1H) |

TABLE 1-continued

| No. | Structure | Mass Characterization | ¹H NMR Data |
|---|---|---|---|
| 30 | 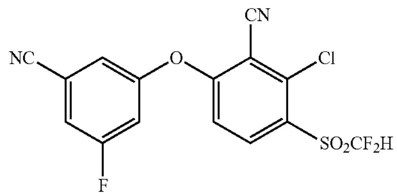 | 385, 387 (M − H) | (400 MHz, CDCl$_3$): δ 8.28 (d, 1H), 7.42-7.40 (m, 1H), 7.31-7.26 (m, 1H), 7.22-7.19 (m, 1H), 6.97 (d, 1H), 6.45 (t, 1H) |
| 31 | 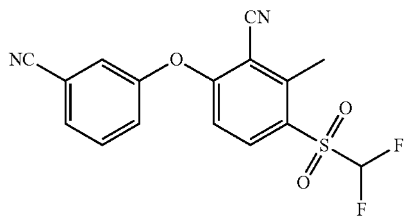 [SMILES: Cc1c(S(=O)(=O)C(F)F)ccc(Oc2cccc(C#N)c2)c1C#N] | [M − H] 374 | (400 MHz, CDCl$_3$): δ 8.14 (d, 1H), 7.67-7.61 (m, 2H), 7.48-7.47 (m, 1H), 6.80 (d, 1H), 6.24 (t, 1H), 2.98 (s, 3H) |
| 32 | 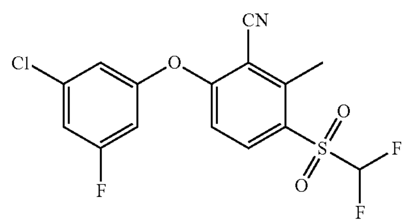 [SMILES: Cc1c(S(=O)(=O)C(F)F)ccc(Oc2cc(F)cc(Cl)c2)c1C#N] | [M − 1] 374 | (400 MHz, CDCl$_3$): δ 8.15 (d, 1H), 7.12-7.08 (m, 1H), 7.01-6.99 (m, 1H), 6.89 (d, 1H), 6.85-6.81 (m, 1H), 6.24 (t, 1H), 2.97 (s, 3H) |
| 33 | 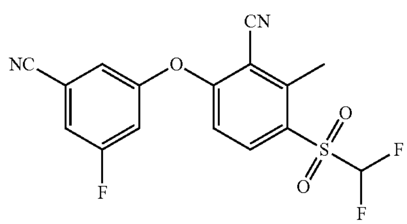 [SMILES: Cc1c(S(=O)(=O)C(F)F)ccc(Oc2cc(F)cc(C#N)c2)c1C#N] | [M − H] 365 | (400 MHz, CDCl$_3$): δ 8.20 (d, 1H), 7.39-7.35 (m, 1H), 7.29-7.27 (m, 1H), 7.20-7.16 (m, 1H), 6.90 (d, 1H), 6.26 (t, 1H), 2.90 (s, 3H) |
| 34 | 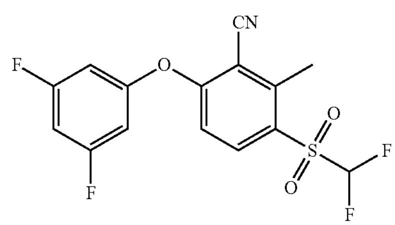 [SMILES: Cc1c(S(=O)(=O)C(F)F)ccc(Oc2cc(F)cc(F)c2)c1C#N] | [M − H] 358 | (400 MHz, CDCl$_3$): δ 8.15 (d, 1H), 6.91 (d, 1H), 6.85-6.79 (m, 1H), 6.77-6.70 (m, 2H), 6.24 (t, 1H), 2.97 (s, 3H) |
| 35 | 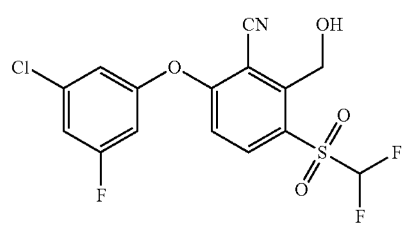 [SMILES: N#Cc1c(Oc2cc(F)cc(Cl)c2)ccc(S(=O)(=O)C(F)F)c1CO] | [M − H] 391 | (400 MHz, CDCl$_3$): δ 8.07 (d, 1H), 7.13-7.05 (m, 1H), 7.04-6.95 (m, 2H), 6.89-6.85 (m, 1H), 6.26 (t, 1H), 5.60 (s, 2H) |
| 36 | 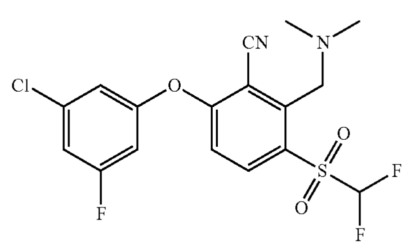 [SMILES: CN(C)Cc1c(S(=O)(=O)C(F)F)ccc(Oc2cc(F)cc(Cl)c2)c1C#N] | [M + H] 419 | (400 MHz, CDCl$_3$): δ 8.29 (d, 1H), 7.13-7.09 (m, 1H), 7.02 (t, 1H), 7.01-6.99 (m, 1H), 6.96 (d, 1H), 6.86-6.82 (m, 1H), 4.11 (s, 2H), 2.34 (s, 6H) |

TABLE 1-continued

| No. | Structure | Mass Characterization | ¹H NMR Data |
|---|---|---|---|
| 37 | 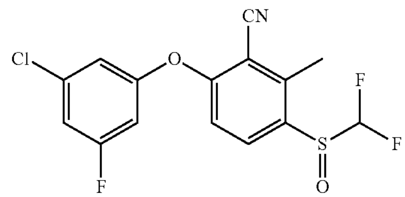 [SMILES: Cc1c(S(=O)C(F)F)ccc(Oc2cc(F)cc(Cl)c2)c1C#N] | [M − H] 358 | (400 MHz, CDCl$_3$): δ 8.07 (d, 1H), 7.07-7.03 (m, 1H), 7.01 (d, 1H), 6.96-6.94 (m, 1H), 6.81-6.77 (m, 1H), 6.15 (t, 1H), 2.68 (s, 3H) |
| 38 | 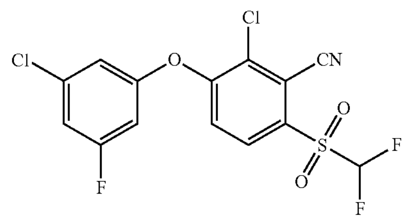 [SMILES: N#Cc1c(S(=O)(=O)C(F)F)ccc(Oc2cc(F)cc(Cl)c2)c1Cl] | [M − H + 18] 413 | (400 MHz, CDCl$_3$): δ 8.03 (d, 1H), 7.24 (d, 1H), 7.12-7.08 (m, 1H), 6.96-6.94 (m, 1H), 6.81-6.77 (m, 1H), 6.41 (t, 1H) |
| 39 | 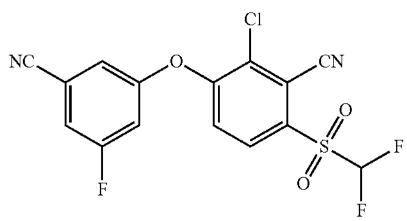 [SMILES: N#Cc1cc(F)cc(Oc2ccc(S(=O)(=O)C(F)F)c(C#N)c2Cl)c1] | [M − H + 18] 404 | (400 MHz, CDCl$_3$): δ 8.09 (d, 1H), 7.37-7.34 (m, 1H), 7.29 (d, 1H), 7.22-7.21 (m, 1H), 7.14-7.10 (m, 1H), 6.43 (t, 1H) |
| 40 | 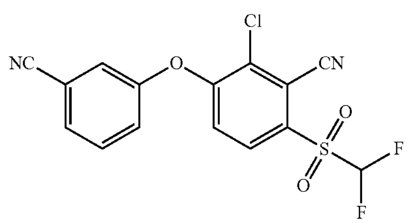 [SMILES: N#Cc1cccc(Oc2ccc(S(=O)(=O)C(F)F)c(C#N)c2Cl)c1] | [M − H + 18] 386 | (400 MHz, CDCl$_3$): δ 8.03 (d, 1H), 7.68-7.62 (m, 2H), 7.45-7.43 (m, 1H), 7.40-7.36 (m, 1H), 7.17 (d, 1H), 6.41 (t, 1H) |
| 41 | 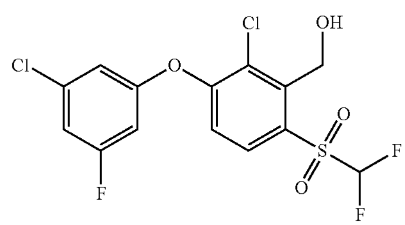 [SMILES: O=S(=O)(c1ccc(Oc2cc(F)cc(Cl)c2)c(Cl)c1CO)C(F)F] | [M − H + 46] 445 | (400 MHz, CDCl$_3$): δ 8.01 (d, 1H), 7.06 (d, 1H), 7.04-7.01 (m, 1H), 6.91-6.88 (m, 1H), 6.76-6.71 (m, 1H), 6.47 (t, 1H), 5.21 (d, 2H), 2.69 (t, 1H) |
| 42 | 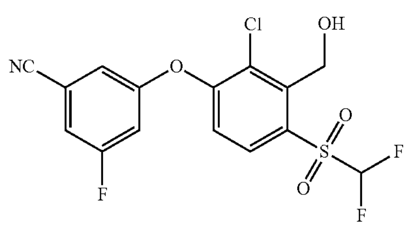 [SMILES: N#Cc1cc(F)cc(Oc2ccc(S(=O)(=O)C(F)F)c(CO)c2Cl)c1] | [M − H + 46] 436 | (400 MHz, CDCl$_3$): δ 8.06 (d, 1H), 7.28-7.25 (m, 1H), 7.15-7.12 (m, 2H), 7.07-7.03 (m, 1H), 6.50 (t, 1H), 5.21 (d, 2H), 2.70 (t, 1H) |
| 43 | 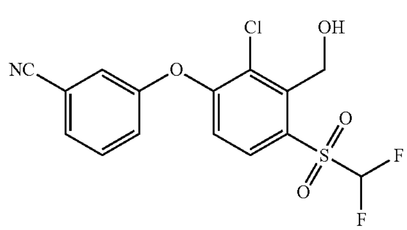 [SMILES: N#Cc1cccc(Oc2ccc(S(=O)(=O)C(F)F)c(CO)c2Cl)c1] | [M − H + 46] 418 | (400 MHz, CDCl$_3$): δ 8.00 (d, 1H), 7.59-7.56 (m, 1H), 7.38-7.37 (m, 1H), 7.36-7.31 (m, 1H), 7.00 (d, 1H), 6.48 (t, 1H), 5.22 (d, 2H), 2.71 (t, 1H) |

TABLE 1-continued

| No. | Structure | Mass Characterization | $^1$H NMR Data |
|---|---|---|---|
| 44 | 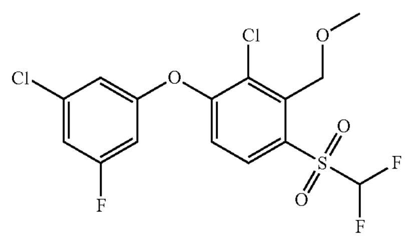 [SMILES: COCc1c(S(=O)(=O)C(F)F)ccc(Oc2cc(F)cc(Cl)c2)c1Cl] | [M − H + 46] 445 | (400 MHz, CDCl$_3$): δ 8.01 (d, 1H), 7.06 (d, 1H), 7.04-7.01 (m, 1H), 6.91-6.88 (m, 1H), 6.76-6.71 (m, 1H), 6.47 (t, 1H), 5.21 (d, 2H), 2.69 (t, 1H) |
| 45 | 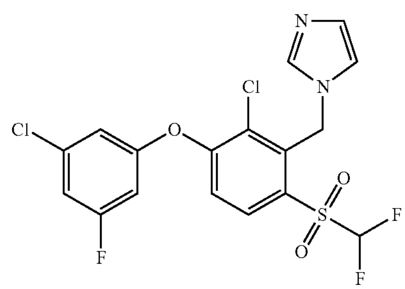 [SMILES: O=S(=O)(c1ccc(Oc2cc(F)cc(Cl)c2)c(Cl)c1Cn1ccnc1)C(F)F] | [M + H] 451 | (400 MHz, CDCl$_3$): δ 8.06 (d, 1H), 7.67 (s, 1H), 7.12-7.03 (m, 4H), 6.93 (s, 1H), 6.77 (br d, 1H), 5.92 (t, 1H), 5.76 (d, 2H) |
| 46 | 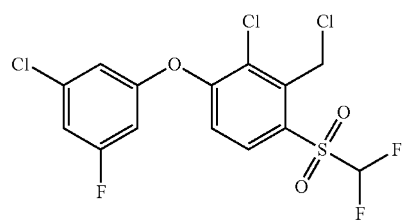 [SMILES: O=S(=O)(c1ccc(Oc2cc(F)cc(Cl)c2)c(Cl)c1CCl)C(F)F] | [M − H + 46] 463 | (400 MHz, CDCl$_3$): δ 8.03 (d, 1H), 7.07 (d, 1H), 7.06-7.03 (m, 1H), 6.93-6.91 (m, 1H), 6.78-6.74 (m, 1H), 6.42 (t, 1H), 5.26 (d, 2H) |
| 47 | 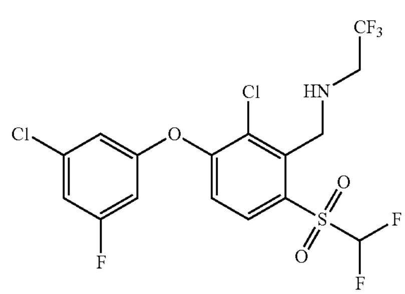 [SMILES: O=S(=O)(c1ccc(Oc2cc(F)cc(Cl)c2)c(Cl)c1CNCC(F)(F)F)C(F)F] | [M + H] 482 | (400 MHz, CDCl$_3$): δ 8.04 (d, 1H), 7.05-7.01 (m, 2H), 6.90-6.89 (m, 1H), 6.75-6.71 (m, 1H), 6.67 (s, 1H), 6.43 (t, 1H), 4.50 (br s, 2H) 3.40-3.30 (m, 2H) |
| 48 | 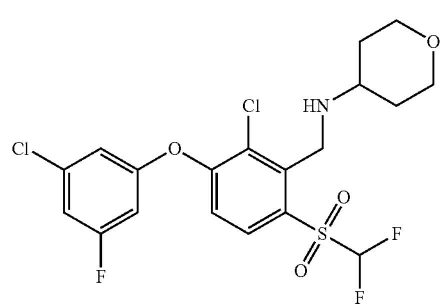 [SMILES: O=S(=O)(c1ccc(Oc2cc(F)cc(Cl)c2)c(Cl)c1CNC1CCOCC1)C(F)F] | [M + H] 484 | (400 MHz, CDCl$_3$): δ 8.04 (d, 1H), 7.07 (t, 2H), 7.03-6.99 (m, 2H), 6.89-6.87 (m, 1H), 6.74-6.70 (m, 1H), 4.40 (s, 2H), 4.05-3.98 (m, 2H) 3.48-3.40 (m, 2H), 2.89-2.81 (m, 1H), 1.97-1.90 (m, 2H), 1.52-1.41 (m, 3H) |

TABLE 1-continued

| No. | Structure | Mass Characterization | ¹H NMR Data |
|---|---|---|---|
| 49 | 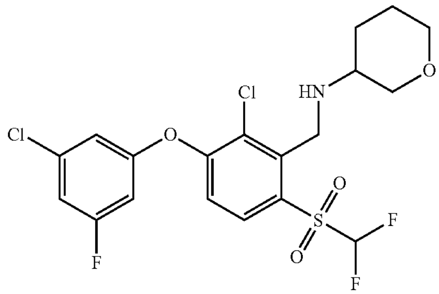 [SMILES: O=S(=O)(c1ccc(Oc2cc(F)cc(Cl)c2)c(Cl)c1CNC1CCCOC1)C(F)F] | [M + H] 484 | (400 MHz, CDCl$_3$): δ 8.04 (d, 1H), 7.09 (t, 2H), 7.03-7.00 (m, 2H), 6.89-6.88 (m, 1H), 6.74-6.70 (m, 1H), 4.40 (s, 2H), 3.94-3.89 (m, 1H) 3.78-3.71 (m, 1H), 3.56-3.49 (m, 1H), 3.39-3.33 (m, 1H), 2.86-2.79 (m, 1H), 2.06-1.97 (m, 1H), 1.80-1.72 (m, 1H), 1.66-1.46 (m, 3H) |
| 50 | 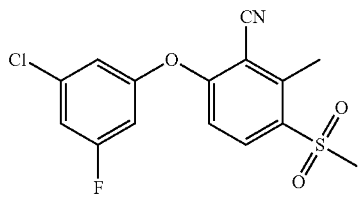 [SMILES: Cc1c(S(C)(=O)=O)ccc(Oc2cc(F)cc(Cl)c2)c1C#N] | [M − H] 338 | (400 MHz, CDCl$_3$): δ 8.20 (d, 1H), 7.08-7.04 (m, 1H), 6.96-6.94 (m, 1H), 6.87 (d, 1H), 6.81-6.77 (m, 1H), 3.12 (s, 3H), 2.97 (s, 3H) |
| 51 | 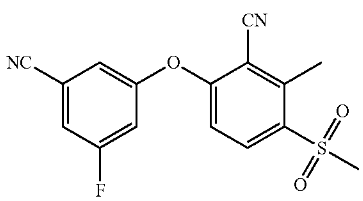 [SMILES: Cc1c(S(C)(=O)=O)ccc(Oc2cc(F)cc(C#N)c2)c1C#N] | [M − H] 329 | (400 MHz, CDCl$_3$): δ 8.25 (d, 1H), 7.33-7.30 (m, 1H), 7.22-7.20 (m, 1H), 7.16-7.12 (m, 1H), 6.93-6.89 (m, 1H), 3.13 (s, 3H), 2.98 (s, 3H) |
| 52 | 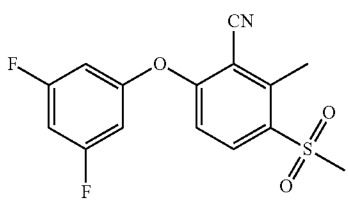 [SMILES: Cc1c(S(C)(=O)=O)ccc(Oc2cc(F)cc(F)c2)c1C#N] | [M − H] 322 | (400 MHz, CDCl$_3$): δ 8.20 (d, 1H), 6.91-6.88 (m, 1H), 6.81-6.75 (m, 1H), 6.72-6.65 (m, 2H), 3.12 (s, 3H), 2.97 (s, 3H) |
| 53 | 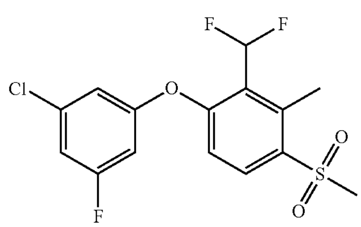 [SMILES: Cc1c(S(C)(=O)=O)ccc(Oc2cc(F)cc(Cl)c2)c1C(F)F] | [M − H] 363 | (400 MHz, CDCl$_3$): δ 8.18 (br d, 1H), 7.26 (t, 1H), 7.01-6.97 (m, 1H), 6.89-6.84 (m, 2H), 6.71-6.67 (m, 1H), 3.15 (s, 3H), 2.95 (t, 3H) |
| 54 | 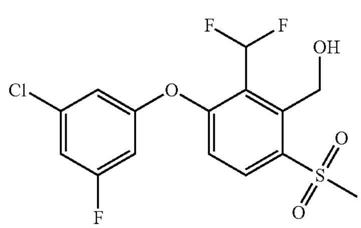 [SMILES: CS(=O)(=O)c1ccc(Oc2cc(F)cc(Cl)c2)c(C(F)F)c1CO] | [M − H + 46] 425 | (400 MHz, CDCl$_3$): δ 8.21 (d, 1H), 7.31 (t, 1H), 7.03-6.98 (m, 2H), 6.89-6.87 (m, 1H), 6.74-6.70 (m, 1H), 5.27 (d, 2H), 3.30 (s, 3H), 2.96-2.91 (m, 1H) |

TABLE 1-continued

| No. | Structure | Mass Characterization | ¹H NMR Data |
|---|---|---|---|
| 55 | 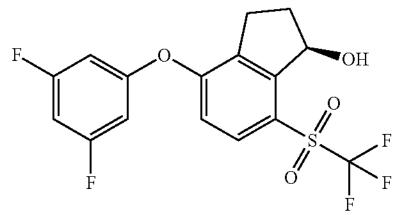 [SMILES: O=S(=O)(c1ccc(Oc2cc(F)cc(F)c2)c2c1[C@H](O)CC2)C(F)(F)F] | [M − H] 393 | (400 MHz, CDCl$_3$): δ 7.84 (d, 1H), 6.95 (d, 1H), 6.76-6.70 (m, 1H), 6.66-6.60 (m, 2H), 5.65-5.60 (m, 1H), 3.25-3.15 (m, 2H), 3.00-2.92 (m, 1H) 2.47-2.28 (m, 2H) |
| 56 | 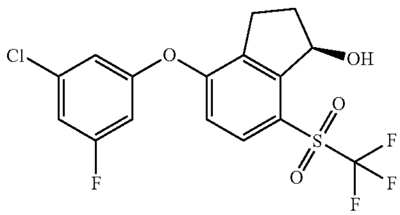 [SMILES: O=S(=O)(c1ccc(Oc2cc(F)cc(Cl)c2)c2c1[C@H](O)CC2)C(F)(F)F] | [M − H + 46] 455 | (400 MHz, CDCl$_3$): δ 7.84 (d, 1H), 7.03-6.99 (m, 1H), 6.93 (d, 1H), 6.92-6.90 (m, 1H), 6.75-6.71 (m, 1H), 5.65-5.61 (m, 1H), 3.24-3.15 (m, 2H), 3.01-2.92 (m, 1H) 2.47-2.28 (m, 2H) |
| 57 | 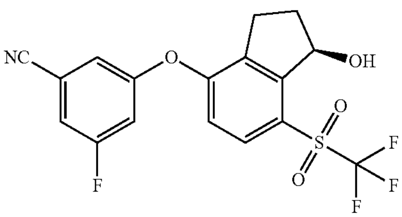 [SMILES: N#Cc1cc(F)cc(Oc2ccc(S(=O)(=O)C(F)(F)F)c3c2CC[C@H]3O)c1] | [M − H + 46] 446 | (400 MHz, CDCl$_3$): δ 7.88 (d, 1H), 7.28-7.25 (m, 2H), 7.19-7.17 (m, 1H), 7.09-7.05 (m, 1H), 6.96 (d, 1H), 5.66-5.62 (m, 1H), 3.23-3.13 (m, 2H), 2.99-2.90 (m, 1H) 2.47-2.29 (m, 2H) |
| 58 | 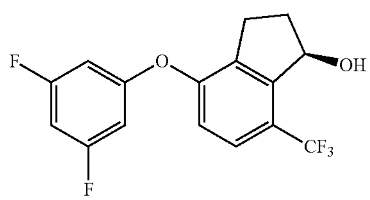 [SMILES: O[C@@H]1CCc2c(Oc3cc(F)cc(F)c3)ccc(C(F)(F)F)c21] | [M − H] 329 | (400 MHz, CDCl$_3$): δ 7.53-7.49 (m, 1H), 6.98-6.95 (m, 1H), 6.62-6.55 (m, 1H), 6.53-6.46 (m, 2H), 5.53 (br s, 1H), 3.11-3.01 (m, 1H), 2.84-2.76 (m, 1H), 2.41-2.31 (m, 1H) 2.25-2.18 (m, 1H), 2.04 (br s, 1H) |
| 59 | 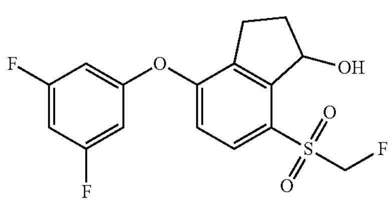 [SMILES: O=S(=O)(CF)c1ccc(Oc2cc(F)cc(F)c2)c2c1C(O)CC2] | [M − H + 46] 403 | (400 MHz, CDCl$_3$): δ 7.81 (d, 1H), 6.97 (d, 1H), 6.70-6.64 (m, 1H), 6.61-6.55 (m, 2H), 5.70-5.66 (m, 1H), 5.41-5.14 (m, 2H), 3.29 (d, 1H), 3.18-3.09 (m, 1H), 2.92-2.83 (m, 1H), 2.51-2.42 (m, 1H) 2.27-2.19 (m, 1H) |
| 60 | 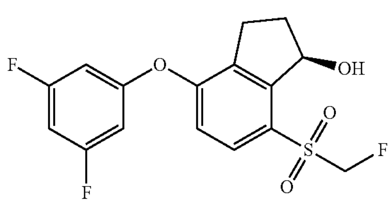 [SMILES: O=S(=O)(CF)c1ccc(Oc2cc(F)cc(F)c2)c2c1[C@H](O)CC2] | [M − H + 46] 403 | (400 MHz, CDCl$_3$): δ 7.81 (d, 1H), 6.97 (d, 1H), 6.70-6.64 (m, 1H), 6.61-6.55 (m, 2H), 5.70-5.66 (m, 1H), 5.42-5.13 (m, 2H), 3.30 (d, 1H), 3.18-3.09 (m, 1H), 2.92-2.83 (m, 1H), 2.51-2.42 (m, 1H) 2.27-2.19 (m, 1H) |
| 61 | 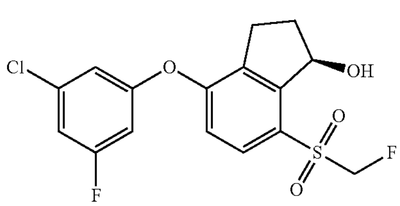 [SMILES: O=S(=O)(CF)c1ccc(Oc2cc(F)cc(Cl)c2)c2c1[C@H](O)CC2] | [M − H + 46] 419 | (400 MHz, CDCl$_3$): δ 7.81 (d, 1H), 6.97-6.93 (m, 2H), 6.87-6.85 (m, 1H), 6.71-6.67 (m, 1H), 5.71-5.66 (m, 1H), 5.42-5.13 (m, 2H), 3.30 (d, 1H), 3.18-3.09 (m, 1H), 2.92-2.84 (m, 1H), 2.51-2.41 (m, 1H) 2.28-2.19 (m, 1H) |

TABLE 1-continued

| No. | Structure | Mass Characterization | ¹H NMR Data |
|---|---|---|---|
| 62 | 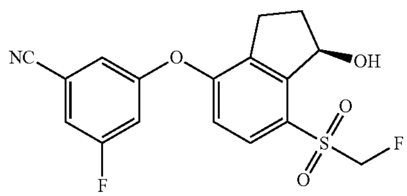 [SMILES: N#Cc1cc(F)cc(Oc2ccc(S(=O)(=O)CF)c3c2CC[C@H]3O)c1] | [M − H + 46] 410 | (400 MHz, CDCl₃): δ 7.85 (d, 1H), 7.23-7.19 (m, 2H), 7.13-7.11 (m, 1H), 7.04-7.00 (m, 1H), 6.98 (d, 1H), 5.72-5.67 (m, 1H), 5.44-5.12 (m, 2H), 3.29 (d, 1H), 3.16-3.07 (m, 1H), 2.90-2.81 (m, 1H), 2.52-2.42 (m, 1H), 2.29-2.20 (m, 1H) |
| 63 | 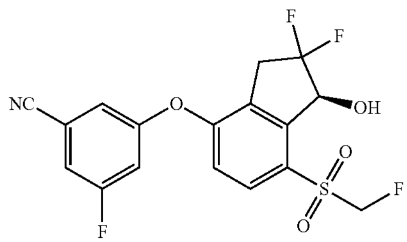 [SMILES: N#Cc1cc(F)cc(Oc2ccc(S(=O)(=O)CF)c3c2CC(F)(F)[C@H]3O)c1] | [M − H + 46] 446 | (400 MHz, CDCl₃): δ 7.93 (d, 1H), 7.30-7.26 (m, 1H), 7.20-7.19 (m, 1H), 7.10-7.07 (m, 1H), 7.00 (d, 1H), 5.59-5.13 (m, 3H), 3.58-3.38 (m, 1H) |
| 64 | 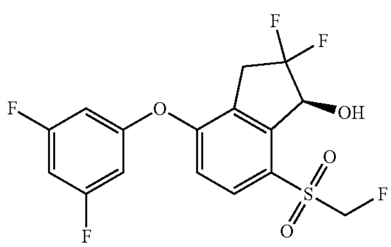 [SMILES: O=S(=O)(CF)c1ccc(Oc2cc(F)cc(F)c2)c2c1[C@H](O)C(F)(F)C2] | [M − H + 46] 439 | (400 MHz, CDCl₃): δ 7.90 (d, 1H), 7.01 (d, 1H), 6.77-6.71 (m, 1H), 6.67-6.60 (m, 2H), 5.58-5.12 (m, 3H), 3.58-3.38 (m, 3H) |
| 65 | 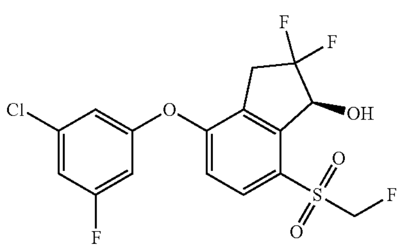 [SMILES: O=S(=O)(CF)c1ccc(Oc2cc(F)cc(Cl)c2)c2c1[C@H](O)C(F)(F)C2] | [M − H + 46] 455 | (400 MHz, CDCl₃): δ 7.90 (d, 1H), 7.03-7.00 (m, 1H), 6.98 (d, 1H), 6.91-6.90 (m, 1H), 6.76-6.72 (m, 1H), 5.58-5.12 (m, 3H), 3.59-3.39 (m, 3H) |
| 66 | 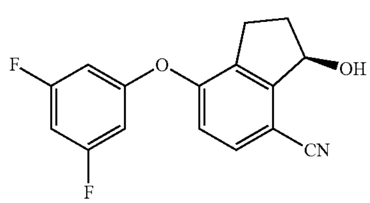 [SMILES: N#Cc1ccc(Oc2cc(F)cc(F)c2)c2c1[C@H](O)CC2] | [M − H] 286 | (400 MHz, CDCl₃): δ 7.55-7.52 (m, 1H), 6.90 (d, 1H), 6.65-6.60 (m, 1H), 6.55-6.49 (m, 2H), 5.56-5.51 (m, 1H), 3.08-3.00 (m, 1H), 2.80-2.71 (m, 1H), 2.68-2.64 (m, 1H) 2.60-2.50 (m, 1H), 2.17-2.08 (m, 1H) |
| 67 | 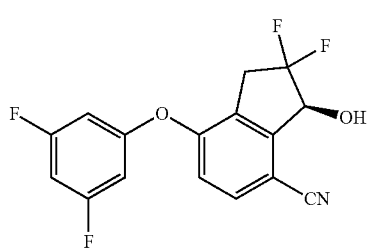 [SMILES: N#Cc1ccc(Oc2cc(F)cc(F)c2)c2c1[C@H](O)C(F)(F)C2] | [M − H + 46] 368 | (400 MHz, CDCl₃): δ 7.62 (d, 1H), 6.94 (d, 1H), 6.72-6.67 (m, 1H), 6.61-6.54 (m, 2H), 5.36-5.30 (m, 1H), 3.54-3.30 (m, 2H), 3.13-3.10 (m, 1H) |

TABLE 1-continued

| No. | Structure | Mass Characterization | ¹H NMR Data |
|---|---|---|---|
| 68 | 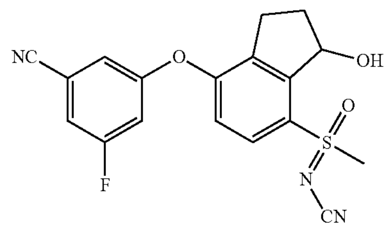 [SMILES: CS(=O)(=NC#N)c1ccc(Oc2cc(F)cc(C#N)c2)c2c1C(O)CC2] | [M + H] 372 | (400 MHz, CDCl$_3$): δ 7.87 (d, 1H), 7.25-7.22 (m, 1H), 7.15-7.13 (m, 1H), 7.08-6.97 (m, 2H), 5.86-5.80 (m, 1H), 3.51 (s, 3H), 3.19-3.06 (m, 2H), 2.95-2.78 (m, 1H), 2.65-2.55 (m, 1H), 2.27-2.14 (m, 1H) |
| 69 | 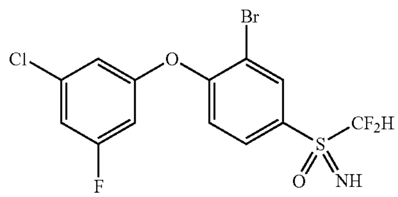 [SMILES: N=S(=O)(c1ccc(Oc2cc(F)cc(Cl)c2)c(Br)c1)C(F)F] | 414, 416, 418 (M + H) | (400 MHz, CDCl$_3$): δ 8.34 (d, 1H), 7.96 (m, 1H), 7.08 (d, 1H), 6.99 (m, 1H), 6.86 (m, 1H), 6.70 (m, 1 H), 6.16 (t, 1H), 3.35 (br s, 1H) |
| 70 | 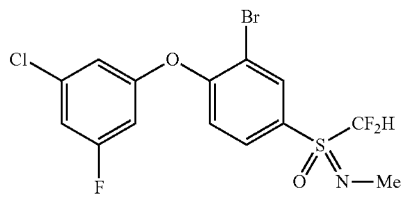 [SMILES: CN=S(=O)(c1ccc(Oc2cc(F)cc(Cl)c2)c(Br)c1)C(F)F] | 428, 430, 432 (M + H) | (400 MHz, CDCl$_3$): δ 8.26 (d, 1H), 7.87 (m, 1H), 7.07 (d, 1H), 6.98 (m, 1H), 6.86 (m, 1H), 6.70 (m, 1H), 6.22 (t, 1H), 2.98 (s, 3H) |
| 71 | 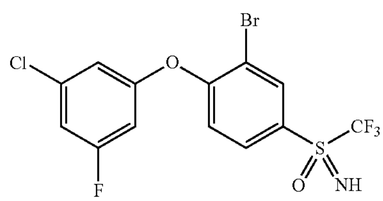 [SMILES: N=S(=O)(c1ccc(Oc2cc(F)cc(Cl)c2)c(Br)c1)C(F)(F)F] | 430, 432, 434 (M − H) | (400 MHz, CDCl$_3$): δ 8.42 (d, 1H), 8.03 (m, 1H), 7.07 (d, 1H), 7.01 (m, 1H), 6.89 (m, 1H), 6.73 (m, 1 H), 3.65 (br s, 1H) |
| 72 | 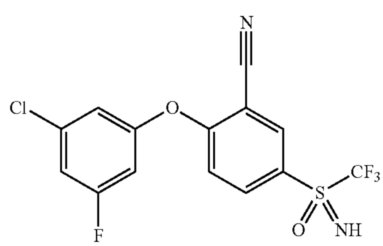 [SMILES: N#Cc1cc(S(=N)(=O)C(F)(F)F)ccc1Oc1cc(F)cc(Cl)c1] | 377, 379 (M − H) | (400 MHz, CDCl$_3$): δ 8.47 (d, 1H), 8.23 (m, 1H), 7.12 (m, 1H), 7.07 (d, 1H), 7.00 (m, 1H), 6.84 (m, 1 H), 3.74 (br s, 1H) |
| 73 | 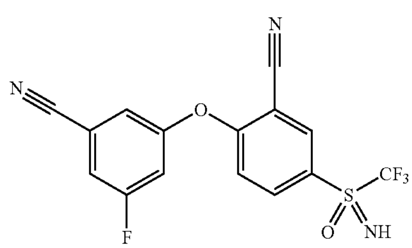 [SMILES: N#Cc1cc(F)cc(Oc2ccc(S(=N)(=O)C(F)(F)F)cc2C#N)c1] | 368 (M − H) | (400 MHz, CDCl$_3$): δ 8.50 (d, 1H), 8.28 (m, 1H), 7.38 (m, 1H), 7.30 (m, 1H), 7.20 (m, 1H), 7.09 (d, 1 H), 3.78 (br s, 1H) |
| 74 | 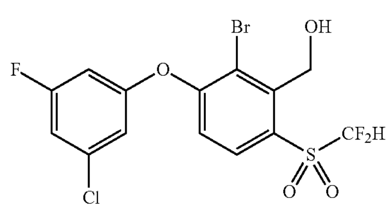 [SMILES: O=S(=O)(c1ccc(Oc2cc(F)cc(Cl)c2)c(Br)c1CO)C(F)F] | 462, 464, 466 (M + NH$_4$) | (400 MHz, CDCl$_3$): δ 8.06 (d, 1H), 7.04-6.99 (m, 2H), 6.90 (m, 1H), 6.73 (m, 1H), 6.48 (t, 1H), 5.25 (d, 2 H), 2.69 (t, 1H) |

TABLE 1-continued
| No. | Structure | Mass Characterization | ¹H NMR Data |
|---|---|---|---|
| 75 | 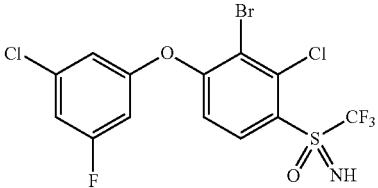 [SMILES: N=S(=O)(c1ccc(Oc2cc(F)cc(Cl)c2)c(Br)c1Cl)C(F)(F)F] | 464, 466, 468 (M − H) | (400 MHz, CDCl$_3$): δ 8.33 (d, 1H), 7.03 (m, 1H), 6.98 (d, 1H), 6.90 (m, 1H), 6.74 (m, 1H), 3.88 (br s, 1H) |
| 76 | 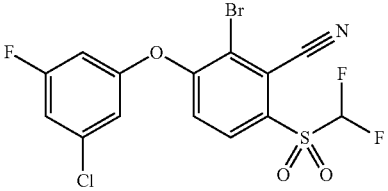 [SMILES: N#Cc1c(S(=O)(=O)C(F)F)ccc(Oc2cc(F)cc(Cl)c2)c1Br] | 441, 443, 445 (M + H) | (400 MHz, CDCl$_3$): δ 8.00 (d, 1H), 7.36 (d, 1H), 7.03 (m, 1H), 6.87 (m, 1H), 6.72 (m, 1H), 6.33 (t, 1H) |
| 77 | 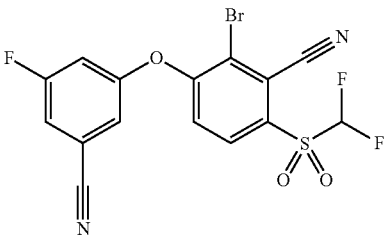 [SMILES: N#Cc1cc(F)cc(Oc2ccc(S(=O)(=O)C(F)F)c(C#N)c2Br)c1] | 432, 434 (M + H) | (400 MHz, CDCl$_3$): δ 8.06 (d, 1H), 7.42 (d, 1H), 7.28 (m, 1H), 7.12 (m, 1H), 7.03 (m, 1H), 6.36 (t, 1H) |
| 78 | 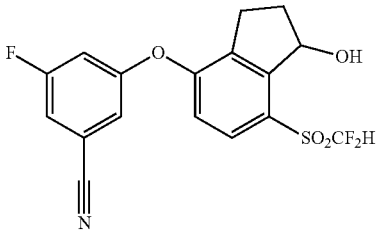 | 401 (M + NH$_4$) | (400 MHz, CDCl$_3$): δ 7.86 (d, 1H), 7.16 (m, 1H), 7.04 (m, 1H), 6.97 (d, 1H), 6.37 (t, 1H), 5.69-5.65 (m, 1H), 3.21-3.11 (m, 2H), 2.92 (m, 1H), 2.51-2.41 (m, 1H), 2.32-2.23 (m, 1H) |
| 79 | 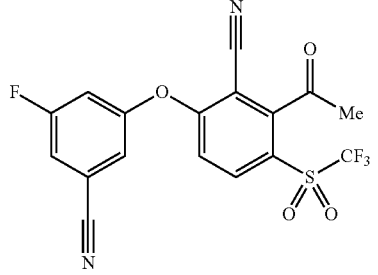 [SMILES: CC(=O)c1c(S(=O)(=O)C(F)(F)F)ccc(Oc2cc(F)cc(C#N)c2)c1C#N] | | (400 MHz, CDCl$_3$): δ 8.16 (d, 1H), 7.43 (m, 1H), 7.34-7.32 (m, 1H), 7.24-7.21 (m, 1H), 7.06 (d, 1H), 2.79 (s, 3H) |
| 80 | 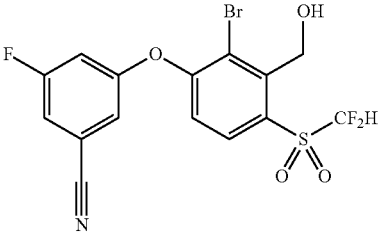 [SMILES: N#Cc1cc(F)cc(Oc2ccc(S(=O)(=O)C(F)F)c(CO)c2Br)c1] | 453, 455 (M + NH$_4$) | (400 MHz, CDCl$_3$): δ 8.11 (d, 1H), 7.28-7.23 (m, 1H), 7.15-7.13 (m, 1H), 7.09 (d, 1H), 7.05 (m, 1H), 6.50 (t, 1H), 5.25 (d, 2H), 2.69 (t, 1H) |

TABLE 1-continued

| No. | Structure | Mass Characterization | ¹H NMR Data |
|---|---|---|---|
| 81 | 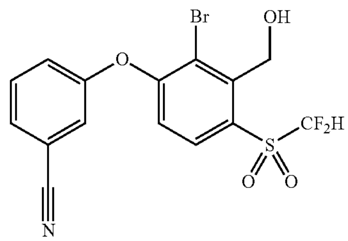 [SMILES: N#Cc1cccc(Oc2ccc(S(=O)(=O)C(F)F)c(CO)c2Br)c1] | 435, 437 (M + NH$_4$) | (400 MHz, CDCl$_3$): δ 8.05 (d, 1H), 7.59-7.56 (m, 2H), 7.39-7.37 (m, 1H), 7.36-7.31 (m, 1H), 6.95 (d, 1H), 6.48 (t, 1H), 5.26 (d, 2H), 2.70 (t, 1H) |
| 82 | 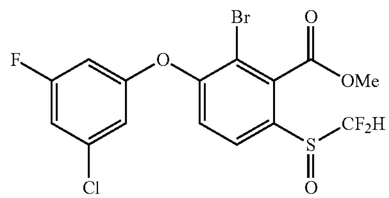 [SMILES: COC(=O)c1c(S(=O)C(F)F)ccc(Oc2cc(F)cc(Cl)c2)c1Br] | 457, 459, 461 (M + H) | (400 MHz, CDCl$_3$): δ 8.05 (d, 1H), 7.28 (d, 1H), 6.96 (m, 1H), 6.83-6.81 (m, 1H), 6.66 (m, 1H), 6.58 (m, 1H), 4.04 (t, 3H) |
| 83 | 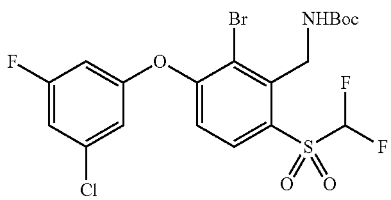 [SMILES: CC(C)(C)OC(=O)NCc1c(S(=O)(=O)C(F)F)ccc(Oc2cc(F)cc(Cl)c2)c1Br] | 488, 490, 492 [MH$^+$ − C$_4$H$_8$] | (400 MHz, CDCl$_3$): δ 8.04 (d, 1H), 7.02 (m, 1H), 6.99 (d, 1H), 6.90-6.88 (m, 1H), 6.73 (m, 1H), 6.62 (br t, 1H), 5.22 (br s, 1H), 4.95 (d, 2H), 1.45 (s, 9H) |
| 84 | 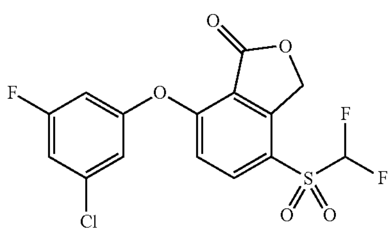 [SMILES: O=C1OCc2c(S(=O)(=O)C(F)F)ccc(Oc3cc(F)cc(Cl)c3)c21] | 393, 395 (M + H) | (400 MHz, CDCl$_3$): δ 8.07 (d, 1H), 7.11 (m, 1H), 7.04-6.99 (m, 2H), 6.87 (m, 1H), 6.26 (t, 1H), 5.61 (d, 2H) |
| 85 | 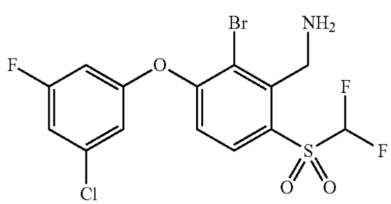 [SMILES: NCc1c(S(=O)(=O)C(F)F)ccc(Oc2cc(F)cc(Cl)c2)c1Br] | 444, 446, 448 (M + H) | (400 MHz, CDCl$_3$): δ 8.04 (d, 1H), 7.02 (m, 1H), 6.97 (d, 1H), 6.89 (m, 1H), 6.73 (m, 1H), 6.66 (t, 1H), 4.45 (br s, 2H) |
| 86 | 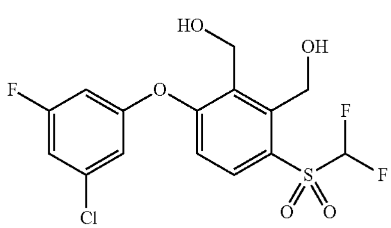 [SMILES: O=S(=O)(c1ccc(Oc2cc(F)cc(Cl)c2)c(CO)c1CO)C(F)F] | 486, 488, 490 (M + H) | (400 MHz, CDCl$_3$): δ 8.04 (d, 1H), 7.03 (m, 1H), 6.99 (d, 1H), 6.90 (m, 1H), 6.74 (m, 1H), 6.66 (t, 1H), 6.11 (br s, 1H), 5.05 (d, 2H), 2.00 (s, 3H) |
| 87 | 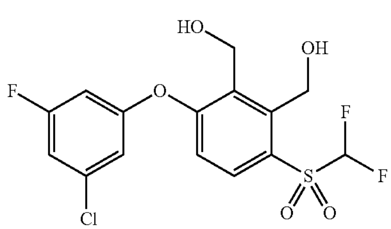 [SMILES: O=S(=O)(c1ccc(Oc2cc(F)cc(Cl)c2)c(CO)c1CO)C(F)F] | 379, 381 (M + H − 16) | (400 MHz, CDCl$_3$): δ 8.07 (d, 1H), 7.02 (d, 1H), 7.00 (m, 1H), 6.90-6.88 (m, 1H), 6.75-6.71 (m, 1H), 6.46 (t, 1H), 5.18 (d, 2H), 5.01 (d, 2H), 3.01 (t, 1H), 2.76 (t, 1H) |

TABLE 1-continued

| No. | Structure | Mass Characterization | ¹H NMR Data |
|---|---|---|---|
| 88 | 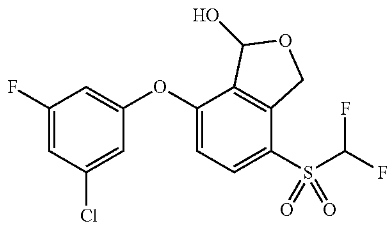 [SMILES: O=S(=O)(c1ccc(Oc2cc(F)cc(Cl)c2)c2c1COC2O)C(F)F] | 377, 379 (M + H − 16) | (400 MHz, CDCl$_3$): δ 7.89 (d, 1H), 7.03 (m, 1H), 6.97-6.94 (m, 2H), 6.80 (m, 1H), 6.67 (m, 1H), 6.20 (t, 1H), 5.57 (m, 1H), 5.39 (d, 1H), 3.33 (d, 1H) |
| 89 | 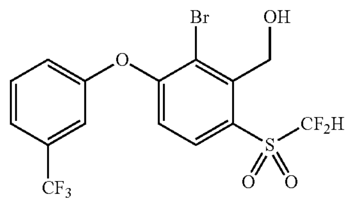 [SMILES: O=S(=O)(c1ccc(Oc2cccc(C(F)(F)F)c2)c(Br)c1CO)C(F)F] | 478, 480 (M + NH$_4$) | (400 MHz, CDCl$_3$): δ 8.01 (d, 1H), 7.63-7.55 (m, 2H), 7.41-7.38 (m, 1H), 7.28 (m, 1H), 6.90 (d, 1H), 6.47 (t, 1H), 5.26 (d, 2H), 2.73 (t, 1H) |
| 90 | 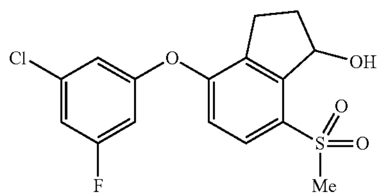 [SMILES: CS(=O)(=O)c1ccc(Oc2cc(F)cc(Cl)c2)c2c1C(O)CC2] | 339, 341 (M + H − 16) | (400 MHz, CDCl$_3$): δ 7.80 (d, 1H), 6.95 (d, 1H), 6.93 (m, 1H), 6.84-6.82 (m, 1H), 6.66 (m, 1H), 5.68 (m, 1H), 3.64 (d, 1H), 3.20 (s, 3H), 3.15-3.06 (m, 1H), 2.83 (m, 1H), 2.53-2.43 (m, 1H), 2.27-2.18 (m, 1H) |
| 91 | 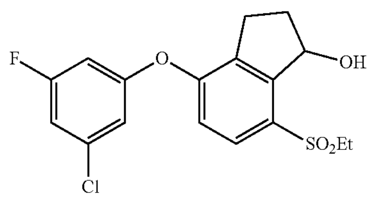 | 353, 355 (M − OH) | (400 MHz, CDCl$_3$): δ 7.74 (d, 1H), 6.95-6.92 (m, 2H), 6.84-6.82 (m, 1H), 6.66 (m, 1H), 5.65-5.60 (m, 1H), 3.70 (d, 1H), 3.35-3.19 (m, 2H), 3.15-3.06 (m, 1H), 2.83 (m, 1H), 2.49-2.39 (m, 1H), 2.27-2.19 (m, 1H), 1.34 (t, 3H) |
| 92 | 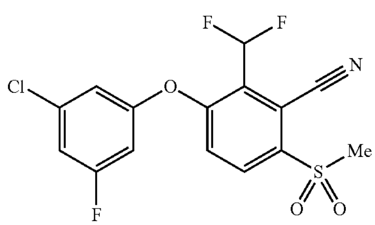 [SMILES: CS(=O)(=O)c1ccc(Oc2cc(F)cc(Cl)c2)c(C(F)F)c1C#N] | 393, 395 (M + NH$_4$) | (400 MHz, CDCl$_3$): δ 8.29-8.25 (m, 1H), 7.27-7.23 (m, 1H), 7.22 (t, 1H), 7.10-7.06 (m, 1H), 6.93-6.91 (m, 1H), 6.76 (m, 1H), 3.35 (s, 3H) |
| 93 | 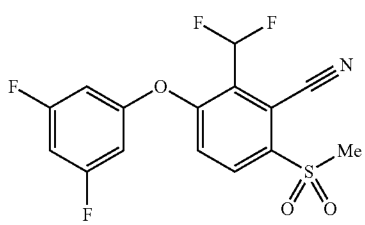 [SMILES: CS(=O)(=O)c1ccc(Oc2cc(F)cc(F)c2)c(C(F)F)c1C#N] | 377 (M + NH$_4$) | (400 MHz, CDCl$_3$): δ 8.29-8.25 (m, 1H), 7.29-7.25 (m, 1H), 7.22 (t, 1H), 6.80 (tt, 1H), 6.69-6.63 (m, 2H), 3.35 (s, 3H) |
| 94 | 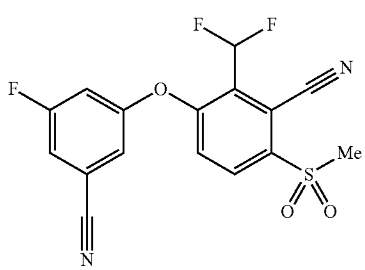 [SMILES: CS(=O)(=O)c1ccc(Oc2cc(F)cc(C#N)c2)c(C(F)F)c1C#N] | 384 (M + NH$_4$) | (400 MHz, CDCl$_3$): δ 8.34-8.30 (m, 1H), 7.35-7.32 (m, 1H), 7.29-7.25 (m, 1H), 7.21 (t, 1H), 7.21-7.18 (m, 1H), 7.11 (m, 1H), 3.36 (s, 3H) |

TABLE 1-continued

| No. | Structure | Mass Characterization | ¹H NMR Data |
|---|---|---|---|
| 95 | 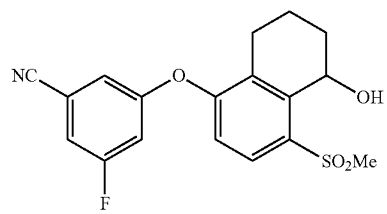 [SMILES: CS(=O)(=O)c1ccc(Oc2cc(F)cc(C#N)c2)c2c1C(O)CCC2] | 379 (M + NH$_4$) | (400 MHz, CDCl$_3$): δ 7.98 (d, 1H), 7.17 (m, 1H), 7.05-7.03 (m, 1H), 6.97 (m, 1H), 6.95 (d, 1H), 5.44-5.39 (m, 1H), 3.72 (m, 1H), 3.25 (s, 3H), 3.04-2.95 (m, 1H), 2.58-2.47 (m, 1H), 2.29-2.22 (m, 1H), 2.16-2.03 (m, 1H), 1.91-1.73 (m, 2H) |
| 96 | 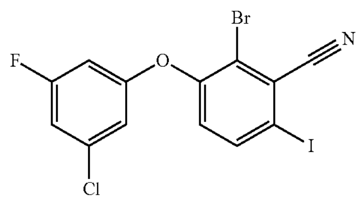 [SMILES: N#Cc1c(I)ccc(Oc2cc(F)cc(Cl)c2)c1Br] | | (400 MHz, CDCl$_3$): δ 7.85 (d, 1H), 6.94 (d, 1H), 6.93-6.90 (m, 1H), 6.74-6.73 (m, 1H), 6.61-6.57 (m, 1H) |
| 97 | 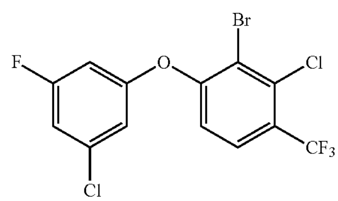 [SMILES: Fc1cc(Cl)cc(Oc2ccc(C(F)(F)F)c(Cl)c2Br)c1] | | (400 MHz, CDCl$_3$): δ 7.68 (d, 1H), 6.99-6.94 (m, 2H), 6.85-6.84 (m, 1H), 6.71-6.67 (m, 1H) |
| 98 | 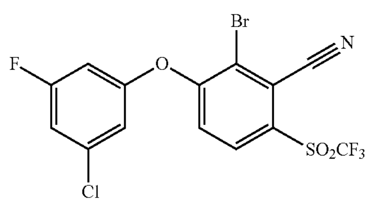 | (M − H) 456, 458 | (400 MHz, CDCl$_3$): δ 8.12 (d, 1H), 7.18 (d, 1H), 7.14-7.11 (m, 1H), 6.97-6.96 (m, 1H), 6.82-6.79 (m, 1H) |
| 99 | 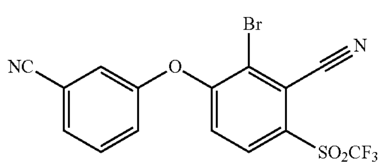 | (M + NH$_4$) 448 | (400 MHz, CDCl$_3$): δ 8.12 (d, 1H), 7.69-7.63 (m, 2H), 7.46-7.45 (m, 1H), 7.41-7.38 (m, 1H), 7.11 (d, 1H) |
| 100 | 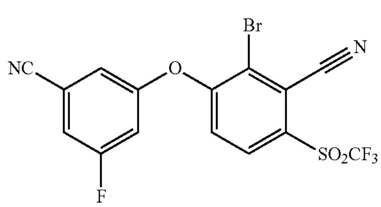 | (M + NH$_4$) 466 | (400 MHz, CDCl$_3$): δ 8.17 (d, 1H), 7.39-7.36 (m, 1H), 7.24-7.23 (m, 1H), 7.22 (d, 1H), 7.16-7.13 (m, 1H) |
| 101 | 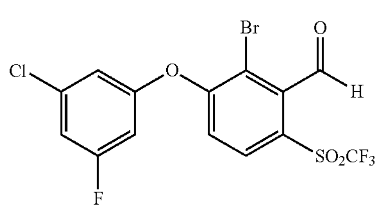 | | (400 MHz, CDCl$_3$): δ 10.31 (s, 1H), 7.99 (d, 1H), 7.10 (d, 1H), 7.10-7.07 (m, 1H), 6.96-6.94 (m, 1H), 6.81-6.77 (m, 1H) |

TABLE 1-continued

| No. | Structure | Mass Characterization | ¹H NMR Data |
|---|---|---|---|
| 102 | 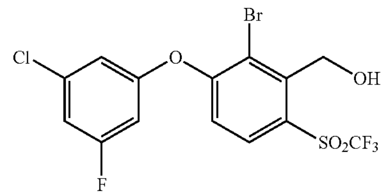 | | (400 MHz, CDCl$_3$): δ 7.77 (d, 1H), 7.16 (d, 1H), 7.00-6.97 (m, 1H), 6.83-6.82 (m, 1H), 6.70-6.67 (m, 1H), 5.43 (s, 2H) |
| 103 | 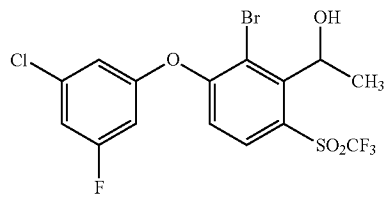 | (M − H) 475, 477 | (400 MHz, CDCl$_3$): δ 8.11 (d, 1H), 7.06-7.03 (m, 1H), 6.95 (d, 1H), 6.92-6.91 (m, 1H), 6.77-6.74 (m, 1H), 5.88 (m, 1H), 3.38 (d, 1H), 1.81 (d, 3H) |
| 104 | 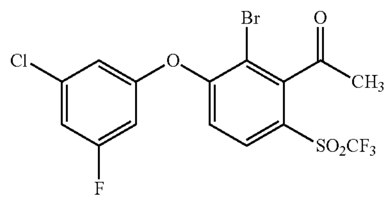 | (M + H) 474.8/ 476.7 | (400 MHz, CDCl$_3$): δ 7.97-7.94 (m, 1H), 7.10-7.07 (m, 1H), 7.01 (d, 1H), 6.80-6.77 (m, 1H), 2.71 (s, 3H) |
| 105 | 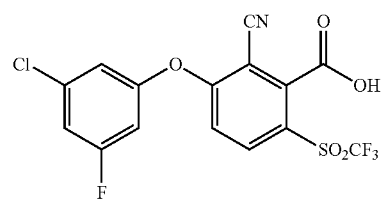 | (M + H) 424, 426 | (400 MHz, CDCl$_3$): δ 8.35 (d, 1H), 7.84 (brd s, 1H), 7.26 (d, 1H), 7.15-7.12 (m, 1H), 7.04-7.03 (m, 1H), 6.89-6.86 (m, 1H) |
| 106 | 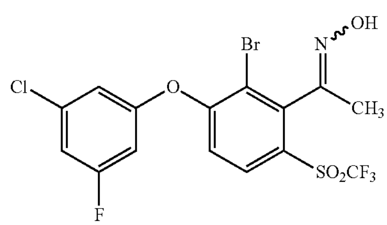 | (M + H) 492, 494 | (400 MHz, CDCl$_3$): δ 7.95-7.94 (m, 1H), 7.09-7.06 (m, 1H), 7.01 (d, 1H), 6.96-6.95 (m, 1H), 6.80-6.77 (m, 1H), 2.70 (s, 3H) |
| 107 | 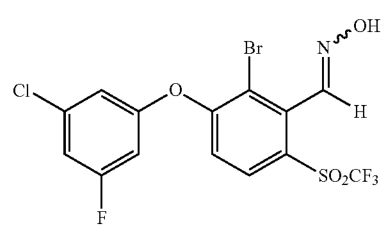 | (M + H) 476, 478 | (400 MHz, CDCl$_3$): δ 8.39 (s, 1H), 8.07 (d, 1H), 7.07 (d, 1H), 7.07-7.04 (m, 1H), 6.94-6.93 (m, 1H), 6.79-6.76 (m, 1H) |
| 108 | 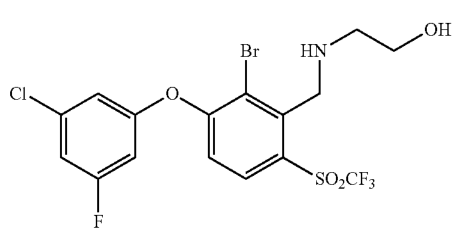 | (M + H) 506, 508 | (400 MHz, CDCl$_3$): δ 8.07 (d, 1H), 7.06-7.03 (m, 1H), 6.98 (d, 1H), 6.93-6.92 (m, 1H), 6.78-6.74 (m, 1H), 4.32 (s, 2H), 3.72 (t, 2H), 2.97 (t, 2H) |

TABLE 1-continued

| No. | Structure | Mass Characterization | $^1$H NMR Data |
|---|---|---|---|
| 109 | 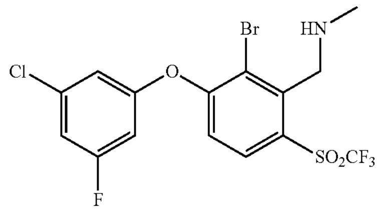 | (M + H) 476, 478 | (400 MHz, CDCl$_3$): δ 8.06 (d, 1H), 7.05-7.02 (m, 1H), 6.97 (d, 1H), 6.91-6.90 (m, 1H), 6.76-6.72 (m, 1H), 4.25 (s, 2H), 2.57 (s, 3H) |
| 110 | 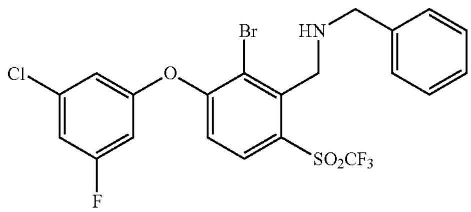 | (M + H) 552, 554 | (400 MHz, CDCl$_3$): δ 8.04 (d, 1H), 7.39-7.31 (m, 4H), 7.28-7.23 (m, 1H), 7.05-7.02 (m, 1H), 6.94 (d, 1H), 6.91-6.89 (m, 1H), 6.75-6.72 (m, 1H), 4.30 (s, 2H), 3.96 (s, 2H). |
| 111 | 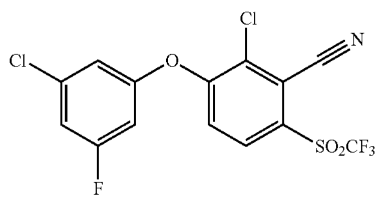 | (M + NH$_4$) 431, 433 | (400 MHz, CDCl$_3$): δ 8.08 (d, 1H), 7.23 (d, 1H), 7.14-7.11 (m, 1H), 6.98-6.96 (m, 1H), 6.83-6.79 (m, 1H) |
| 112 | 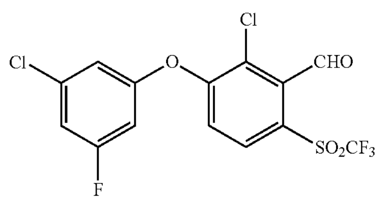 | | (400 MHz, CDCl$_3$): δ 10.43 (s, 1H), 7.96 (d, 1H), 7.15 (d, 1H), 7.09-7.07 (m, 1H), 6.95-6.94 (m, 1H), 6.80-6.77 (m, 1H) |
| 113 | 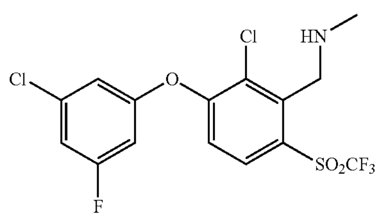 | (M + H) 432, 434 | (400 MHz, CDCl$_3$): δ 8.02 (d, 1H), 7.05-7.02 (m, 1H), 7.01 (d, 1H), 6.91-6.90 (m, 1H), 6.76-6.72 (m, 1H), 4.22 (s, 2H), 2.56 (s, 3H) |
| 114 | 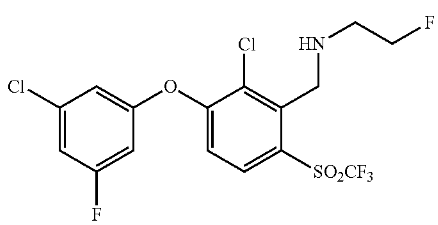 | (M + H) 464, 466 | (400 MHz, CDCl$_3$): δ 8.02 (d, 1H), 7.06-7.03 (m, 1H), 7.01 (d, 1H), 6.92 (m, 1H), 6.77-6.73 (m, 1H), 4.64 (t, 1H), 4.52 (t, 1H), 4.34 (s, 2H), 3.11-3.09 (m, 1H), 3.04-3.02 (m, 1H) |
| 115 | 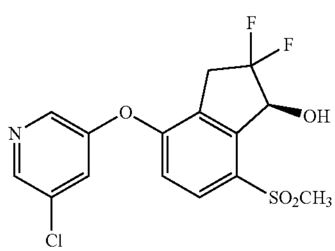 [SMILES: CS(=O)(=O)c1ccc(Oc2cncc(Cl)c2)c2c1[C@H](O)C(F)(F)C2] | (M + H) 376, 378 | (400 MHz, CDCl$_3$): δ 8.50-8.49 (m, 1H), 8.36-8.35 (m, 1H), 7.89 (d, 1H), 7.43 (t, 1H), 6.93 (d, 1H), 5.62-5.58 (m, 1H), 3.62-3.40 (m, 3H), 3.22 (s, 3H) |

TABLE 1-continued

| No. | Structure | Mass Characterization | ¹H NMR Data |
|---|---|---|---|
| 116 | 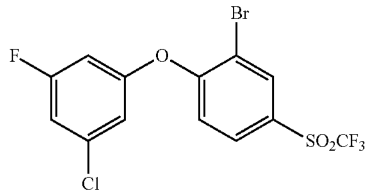 | 431 (M − H) | (400 MHz, CDCl$_3$): δ 8.30 (d, 1 H), 7.93 (m, 1 H), 7.08-7.02 (m, 2 H), 6.93-6.91 (m, 1 H), 6.78-6.74 (m, 1 H) |
| 117 | 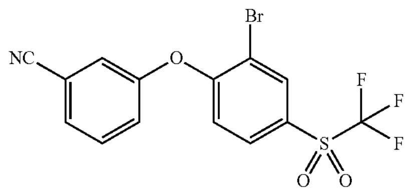 [SMILES: N#Cc1cccc(Oc2ccc(S(=O)(=O)C(F)(F)F)cc2Br)c1] | 404 (M − H) | |
| 118 | 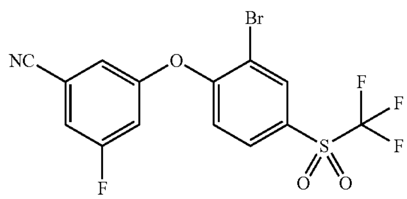 [SMILES: N#Cc1cc(F)cc(Oc2ccc(S(=O)(=O)C(F)(F)F)cc2Br)c1] | 422 (M − H) | |
| 119 | 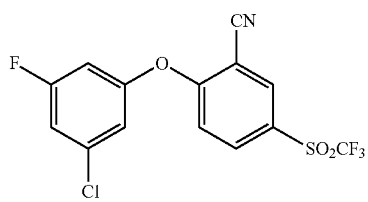 | 379 (M − H) | (400 MHz, CDCl$_3$): δ 8.35 (d, 1 H), 8.13 (m, 1 H), 7.16-7.13 (m, 1 H), 7.11 (d, 1 H), 7.03-7.01 (m, 1 H), 6.88-6.85 (m, 1 H) |
| 120 | 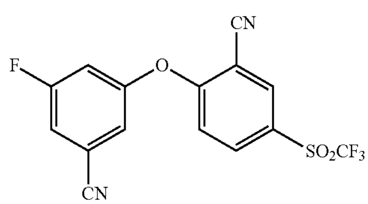 | 369 (M − H) | |
| 121 | 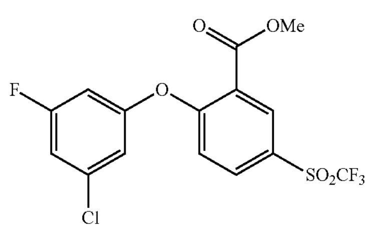 | 411 (M − H) | (400 MHz, CDCl$_3$): δ 8.58 (d, 1 H), 8.10-8.07 (m, 1 H), 7.14 (d, 1 H), 7.03-7.00 (m, 1 H), 6.91-6.90 (m, 1 H), 6.77-6.73 (m, 1 H), 3.94 (s, 3 H) |
| 122 | 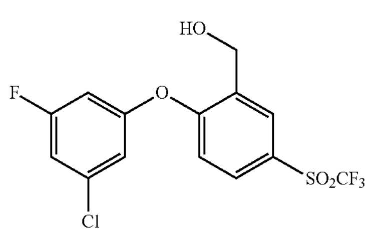 | 383 (M − H) | |

TABLE 1-continued

| No. | Structure | Mass Characterization | $^1$H NMR Data |
|---|---|---|---|
| 123 | 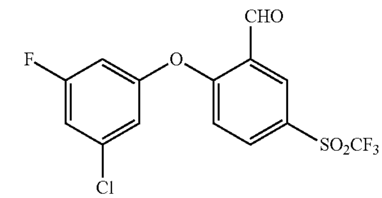 | | |
| 124 | 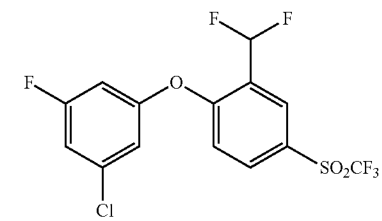 | | (400 MHz, CDCl$_3$): δ 8.35-8.34 (m, 1 H), 8.09-8.05 (m, 1 H), 7.17-6.90 (m, 4 H), 6.82-6.78 (m, 1 H) |
| 125 | 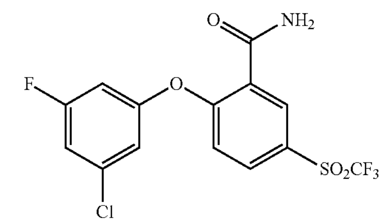 | 396 (M − H) | (400 MHz, CDCl$_3$): δ 8.95 (d, 1 H), 8.07-8.04 (m, 1 H), 7.21 (br s, 1 H), 7.15-7.12 (m, 1 H), 7.05 (d, 1 H), 7.02-7.01 (m, 1 H), 6.86-6.83 (m, 1 H), 6.01 (br s, 1 H) |
| 126 | 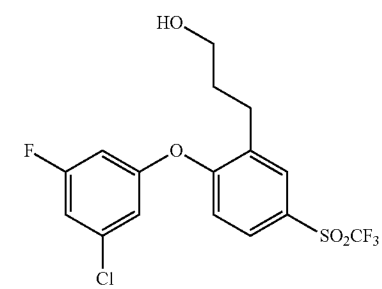 | 457 (M + HCO$_2^-$) | (400 MHz, CDCl$_3$): δ 7.96 (d, 1 H), 7.84 (m, 1 H), 7.02-6.98 (m, 2 H), 6.88-6.87 (m, 1 H), 6.73-6.69 (m, 1 H), 3.74-3.60 (m, 2 H), 2.91-2.87 (m, 2 H), 1.97-1.90 (m, 2 H), 1.40-1.37 (m, 1 H) |
| 127 | 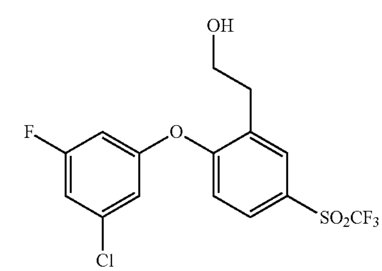 | 397 (M − H) | (400 MHz, CDCl$_3$): δ 8.02 (d, 1 H), 7.86 (m, 1 H), 7.02-6.99 (m, 2 H), 6.89-6.87 (m, 1 H), 6.74-6.70 (m, 1 H), 3.98-3.93 (m, 2 H), 3.06 (t, 2 H), 1.50-1.47 (m, 1 H) |
| 128 | 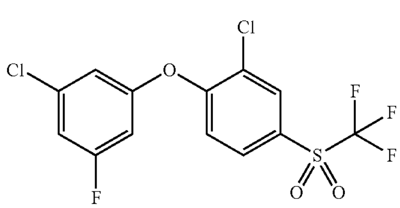 [SMILES: O=S(=O)(c1ccc(Oc2cc(F)cc(Cl)c2)c(Cl)c1)C(F)(F)F] | 387 (M − H) | |

TABLE 1-continued

| No. | Structure | Mass Characterization | ¹H NMR Data |
|---|---|---|---|
| 129 | 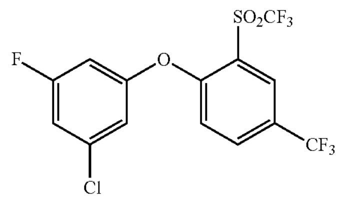 | 421 (M − H) | (400 MHz, CDCl$_3$): δ 8.39-8.38 (m, 1 H), 7.98-7.95 (m, 1 H), 7.15 (d, 1 H), 7.08-7.05 (m, 1 H), 6.95-6.94 (m, 1 H), 6.80-6.77 (m, 1 H) |
| 130 | 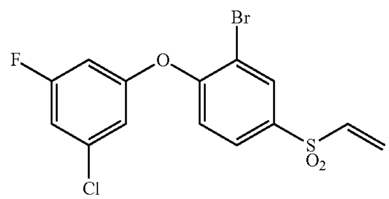 [SMILES: C=CS(=O)(=O)c1ccc(Oc2cc(F)cc(Cl)c2)c(Br)c1] | 389 (M − H) | (400 MHz, CDCl$_3$): δ 8.18 (d, 1 H), 7.83-7.80 (m, 1 H), 7.07 (d, 1 H), 6.97-6.94 (m, 1 H), 6.82-6.81 (m, 1 H), 6.70-6.64 (m, 2 H), 6.54-6.50 (m, 1H), 6.13-6.11 (m, 1H) |
| 131 | 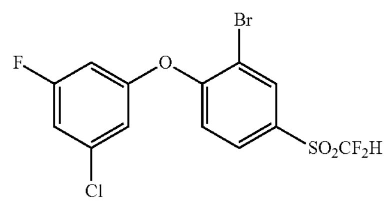 | 413 (M − H) | (400 MHz, CDCl$_3$): δ 8.26 (d, 1 H), 7.89-7.87 (m, 1 H), 7.07 (d, 1 H), 7.04-7.00 (m, 1 H), 6.90-6.89 (m, 1 H), 6.75-6.72 (m, 1 H), 6.21 (t, 1 H) |
| 132 | 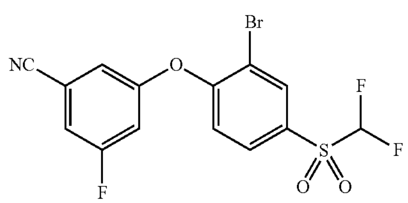 [SMILES: N#Cc1cc(F)cc(Oc2ccc(S(=O)(=O)C(F)F)cc2Br)c1] | 404 (M − H) | (400 MHz, CDCl$_3$): δ 8.30 (d, 1 H), 7.95-7.93 (m, 1 H), 7.27-7.25 (m, 1 H), 7.15-7.13 (m, 2 H), 7.06-7.03 (m, 1 H), 6.24 (t, 1 H) |
| 133 | 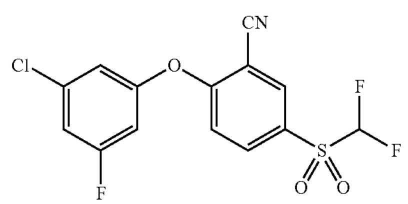 [SMILES: N#Cc1cc(S(=O)(=O)C(F)F)ccc1Oc1cc(F)cc(Cl)c1] | 360 (M − H) | (400 MHz, CDCl$_3$): δ 8.34 (d, 1 H), 8.15-8.12 (m, 1 H), 7.40-7.37 (m, 1 H), 7.31-7.29 (m, 1 H), 7.22-7.19 (m, 1 H), 7.10 (d, 1 H), 6.26 (t, 1 H) |
| 134 | 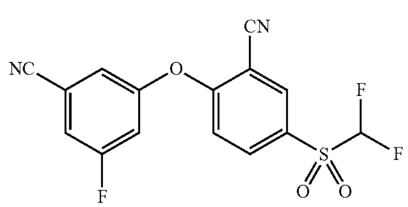 [SMILES: N#Cc1cc(F)cc(Oc2ccc(S(=O)(=O)C(F)F)cc2C#N)c1] | 351 (M − H) | (400 MHz, CDCl$_3$): δ 8.34 (d, 1 H), 8.15-8.12 (m, 1 H), 7.40-7.37 (m, 1 H), 7.31-7.29 (m, 1 H), 7.22-7.19 (m, 1 H), 7.10 (d, 1 H), 6.26 (t, 1 H) |
| 135 | 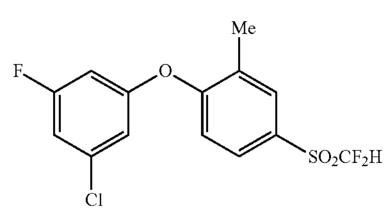 | 349 (M − H) | (400 MHz, CDCl$_3$): δ 7.86 (d, 1 H), 7.80-7.77 (m, 1 H), 7.01 (d, 1 H), 6.98-6.95 (m, 1 H), 6.84-6.83 (m, 1 H), 6.69-6.65 (m, 1 H), 6.19 (t, 1 H), 2.39 (s, 3 H) |

TABLE 1-continued

| No. | Structure | Mass Characterization | $^1$H NMR Data |
|---|---|---|---|
| 136 | 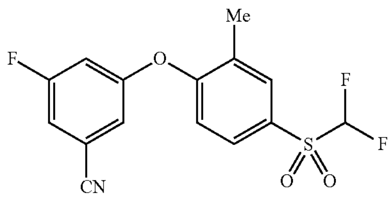 [SMILES: Cc1cc(S(=O)(=O)C(F)F)ccc1Oc1cc(F)cc(C#N)c1] | 340 (M − H) | (400 MHz, CDCl$_3$): δ 7.93 (d, 1 H), 7.85-7.82 (m, 1 H), 7.23-7.20 (m, 1H), 7.11-7.09 (m, 1 H), 7.04 (d, 1 H), 7.03-6.98 (m, 1 H), 6.21 (t, 1 H), 2.39 (s, 3 H) |
| 137 | 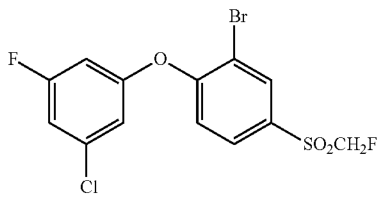 | 395 (M − H) | (400 MHz, CDCl$_3$): δ 8.25 (d, 1 H), 7.89-7.86 (m, 1 H), 7.09 (d, 1 H), 7.00-6.97 (m, 1 H), 6.87-6.86 (m, 1 H), 6.72-6.69 (m, 1 H), 5.17 (d, 2 H) |
| 138 | 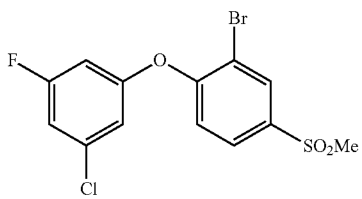 [SMILES: CS(=O)(=O)c1ccc(Oc2cc(F)cc(Cl)c2)c(Br)c1] | 377 (M − H) | |
| 139 | 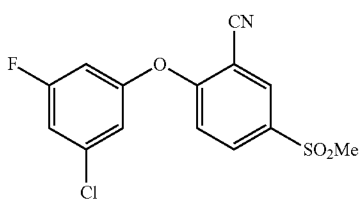 [SMILES: CS(=O)(=O)c1ccc(Oc2cc(F)cc(Cl)c2)c(C#N)c1] | 370 (M + HCO$_2^-$) | (400 MHz, CDCl$_3$): δ 8.29-8.28 (m, 1 H), 8.09-8.06 (m, 1 H), 7.10-7.06 (m, 2 H), 6.97-6.96 (m, 1 H), 6.83-6.79 (m, 1 H), 3.10 (s, 3 H) |
| 140 | 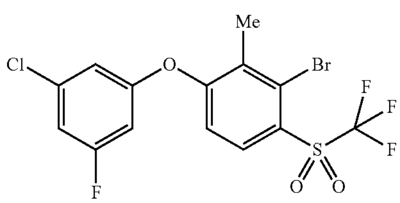 [SMILES: Cc1c(Oc2cc(F)cc(Cl)c2)ccc(S(=O)(=O)C(F)(F)F)c1Br] | 445 (M − H) | (400 MHz, CDCl$_3$): δ 8.07 (d, 1 H), 7.03-7.00 (m, 1 H), 6.94 (d, 1 H), 6.87-6.86 (m, 1 H), 6.72-6.68 (m, 1 H), 2.52 (s, 3 H) |
| 141 | 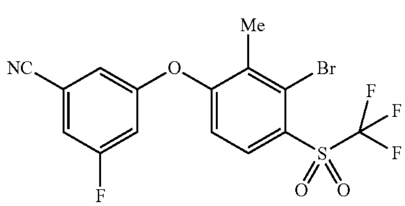 [SMILES: Cc1c(Oc2cc(F)cc(C#N)c2)ccc(S(=O)(=O)C(F)(F)F)c1Br] | 438 (M + H) | |
| 142 | 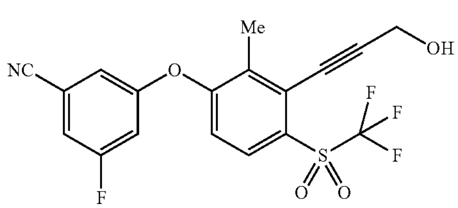 [SMILES: Cc1c(Oc2cc(F)cc(C#N)c2)ccc(S(=O)(=O)C(F)(F)F)c1C#CCO] | 412 (M − H) | (400 MHz, CDCl$_3$): δ 8.00 (d, 1 H), 7.26-7.23 (m, 1 H), 7.12-7.11 (m, 1 H), 7.03-6.99 (m, 1 H), 6.97 (d, 1 H), 4.62 (d, 2 H), 2.49 (s, 3 H), 1.96-1.91 (m, 1 H) |

TABLE 1-continued

| No. | Structure | Mass Characterization | ¹H NMR Data |
|---|---|---|---|
| 143 | 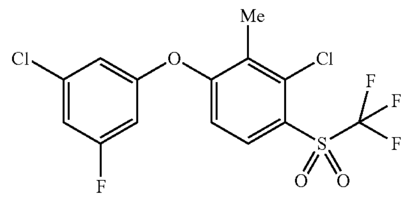 [SMILES: Cc1c(Oc2cc(F)cc(Cl)c2)ccc(S(=O)(=O)C(F)(F)F)c1Cl] | 401 (M − H) | (400 MHz, CDCl$_3$): δ 8.03 (d, 1 H), 7.03-7.00 (m, 1 H), 6.90 (d, 1 H), 6.88-6.86 (m, 1 H), 6.72-6.69 (m, 1 H), 2.47 (s, 3 H) |
| 144 | 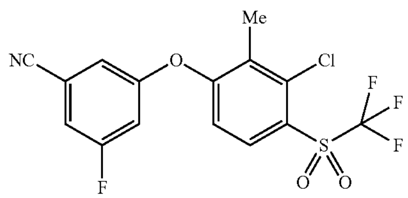 [SMILES: Cc1c(Oc2cc(F)cc(C#N)c2)ccc(S(=O)(=O)C(F)(F)F)c1Cl] | 392 (M − H) | (400 MHz, CDCl$_3$): δ 8.05 (m, 1 H), 7.29-7.26 (m, 1 H), 7.14 (s, 1 H), 7.05-7.02 (m, 1 H), 6.94-6.91 (m, 1 H), 2.46 (s, 3 H) |
| 145 | 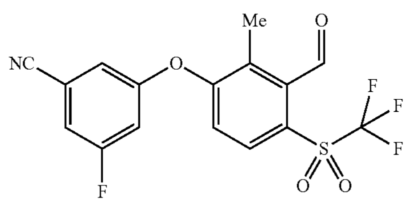 [SMILES: Cc1c(Oc2cc(F)cc(C#N)c2)ccc(S(=O)(=O)C(F)(F)F)c1C=O] | 386 (M − H) | (400 MHz, CDCl$_3$): δ 10.62 (s, 1 H), 7.97 (d, 1 H), 7.30-7.27 (m, 1 H), 7.16-7.15 (m, 1 H), 7.10 (d, 1 H), 7.07-7.03 (m, 1 H), 2.40 (s, 3 H) |
| 146 | 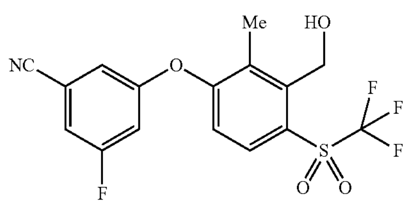 [SMILES: Cc1c(Oc2cc(F)cc(C#N)c2)ccc(S(=O)(=O)C(F)(F)F)c1CO] | 434 (M + HCO$_2^-$) | (400 MHz, CDCl$_3$): δ 8.01 (d, 1 H), 7.26-7.23 (m, 1 H), 7.12-7.11 (m, 1 H), 7.03-6.99 (m, 2 H), 4.99 (d, 2 H), 2.50 (s, 3 H) |
| 147 | 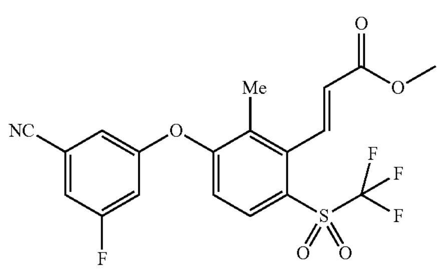 [SMILES: COC(=O)/C=C/c1c(S(=O)(=O)C(F)(F)F)ccc(Oc2cc(F)cc(C#N)c2)c1C] | 442 (M − H) | (400 MHz, CDCl$_3$): δ 8.02 (s, 1 H), 7.99 (d, 1 H), 7.28-7.25 (m, 1 H), 7.16-7.15 (m, 1 H), 7.07-7.05 (m, 1 H), 6.98 (d, 1 H), 6.03 (d, 1 H), 3.85 (s, 3 H), 2.34 (s, 3 H) |
| 148 | 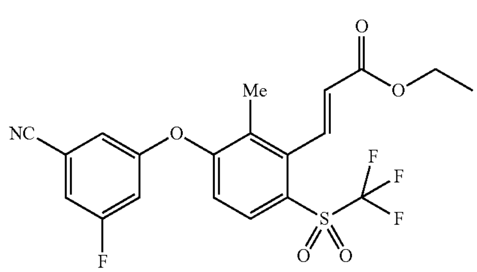 [SMILES: CCOC(=O)/C=C/c1c(S(=O)(=O)C(F)(F)F)ccc(Oc2cc(F)cc(C#N)c2)c1C] | 458 (M + H) | (400 MHz, CDCl$_3$): δ 8.02 (s, 1 H), 7.99 (d, 1 H), 7.28-7.25 (m, 1 H), 7.16-7.15 (m, 1 H), 7.07-7.03 (m, 1 H), 6.98 (d, 1 H), 6.02 (d, 1 H), 4.31 (q, 2 H), 2.34 (s, 3 H), 1.36 (t, 3 H) |

TABLE 1-continued

| No. | Structure | Mass Characterization | ¹H NMR Data |
|---|---|---|---|
| 149 | 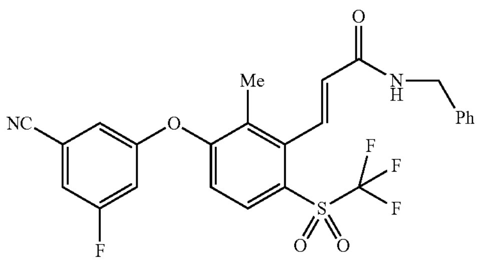 [SMILES: Cc1c(Oc2cc(F)cc(C#N)c2)ccc(S(=O)(=O)C(F)(F)F)c1/C=C/C(=O)NCc1ccccc1] | 519 (M + H) | (400 MHz, CDCl₃): δ 8.01 (d, 1 H), 7.79 (d, 1 H), 7.39-7.29 (m, 5 H), 7.27-7.24 (m, 1 H), 7.14-7.13 (m, 1 H), 7.06-7.03 (m, 1 H), 6.97 (d, 1 H), 6.06-6.02 (m, 2 H), 4.60 (d, 2 H), 2.33 (s, 3 H) |
| 150 | 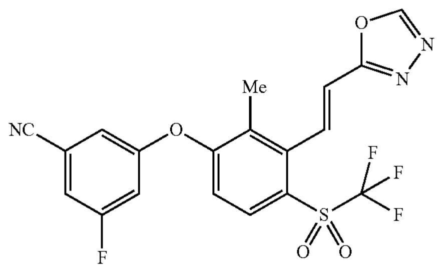 [SMILES: Cc1c(Oc2cc(F)cc(C#N)c2)ccc(S(=O)(=O)C(F)(F)F)c1/C=C/c1nnco1] | 454 (M + H) | (400 MHz, CDCl₃): δ 8.47 (d, 1 H), 8.05 (d, 1 H), 7.98 (d, 1 H), 7.31-7.27 (m, 1 H), 7.19-7.18 (m, 1 H), 7.10-7.07 (m, 1 H), 7.01 (d, 1 H), 6.72 (d, 1 H), 2.42 (s, 3 H) |
| 151 | 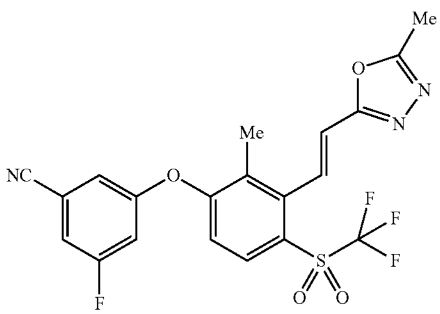 [SMILES: Cc1nnc(/C=C/c2c(S(=O)(=O)C(F)(F)F)ccc(Oc3cc(F)cc(C#N)c3)c2C)o1] | 468 (M + H) | (400 MHz, CDCl₃): δ 8.03 (d, 1 H), 7.85 (d, 1 H), 7.30-7.27 (m, 1 H), 7.18-7.17 (m, 1 H), 7.09-7.05 (m, 1 H), 6.99 (d, 1 H), 6.62 (d, 1 H), 2.63 (s, 3 H), 2.40 (s, 3 H) |
| 152 | 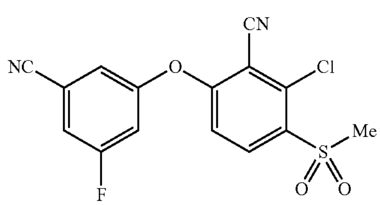 [SMILES: CS(=O)(=O)c1ccc(Oc2cc(F)cc(C#N)c2)c(C#N)c1Cl] | 349 (M − H) | (400 MHz, CDCl₃): δ 8.32 (d, 1 H), 7.38-7.35 (m, 1 H), 7.26-7.25 (m, 1 H), 7.18-7.15 (m, 1 H), 6.97 (d, 1 H), 3.30 (s, 3 H) |
| 153 | 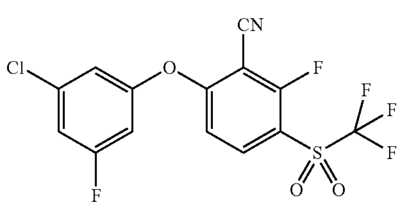 [SMILES: N#Cc1c(Oc2cc(F)cc(Cl)c2)ccc(S(=O)(=O)C(F)(F)F)c1F] | 396 (M − H) | (400 MHz, CDCl₃): δ 8.01 (d, 1 H), 7.22 (d, 1 H), 7.09-7.05 (m, 1 H), 6.94-6.92 (m, 1 H), 6.80-6.77 (m, 1 H) |
| 154 | 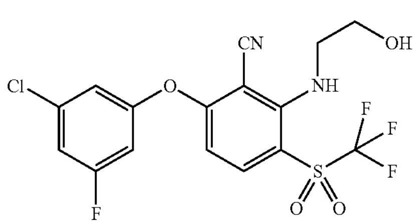 [SMILES: N#Cc1c(Oc2cc(F)cc(Cl)c2)ccc(S(=O)(=O)C(F)(F)F)c1NCCO] | 437 (M − H) | (400 MHz, CDCl₃): δ 7.44-7.40 (m, 1 H), 7.33 (m, 1 H), 7.15 (d, 1 H), 6.91-6.88 (m, 1 H), 6.74-6.73 (m, 1 H), 6.62-6.58 (m, 1 H), 3.95-3.91 (m, 2 H), 3.44-3.40 (m, 2 H), 1.71-1.69 (m, 1 H) |

TABLE 1-continued

| No. | Structure | Mass Characterization | $^1$H NMR Data |
|---|---|---|---|
| 155 | 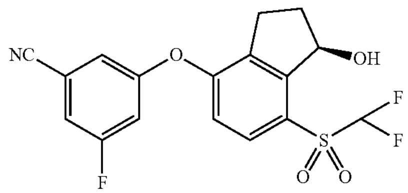 [SMILES: N#Cc1cc(F)cc(Oc2ccc(S(=O)(=O)C(F)F)c3c2CC[C@H]3O)c1] | 428 (M + HCO$_2^-$) | (400 MHz, CDCl$_3$): δ 7.85 (d, 1 H), 7.26-7.24 (m, 1 H), 7.17-7.15 (m, 1 H), 7.06-7.03 (m, 1 H), 6.97 (d, 1 H), 6.37 (t, 3 H), 5.68-5.65 (m, 1 H), 3.20-3.11 (m, 2 H), 2.94-2.87 (m, 1 H), 2.51-2.41 (m, 1 H), 2.31-2.25 (m, 1 H) |
| 156 | 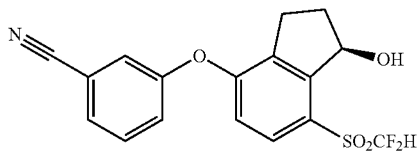 | 410 (M + HCO$_2^-$) | (400 MHz, CDCl$_3$): δ 7.80 (d, 1 H), 7.56-7.54 (m, 2 H), 7.39-7.30 (m, 2 H), 6.88-6.84 (m, 1 H), 6.38 (t, 1 H), 5.68-5.66 (m, 1 H), 3.22-3.13 (m, 2 H), 2.98-2.90 (m, 1 H), 2.50-2.41 (m, 1 H), 2.32-2.22 (m, 1 H) |
| 157 | 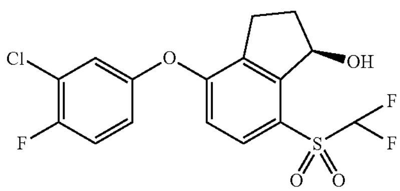 [SMILES: O=S(=O)(c1ccc(Oc2ccc(F)c(Cl)c2)c2c1[C@H](O)CC2)C(F)F] | 437 (M + HCO$_2^-$) | |
| 158 | 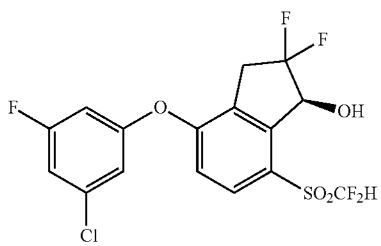 | 473 (M + HCO$_2^-$) | (400 MHz, CDCl$_3$): δ 7.90 (d, 1 H), 7.06-7.03 (m, 1 H), 6.99 (d, 1 H), 6.94-6.93 (m, 1 H), 6.78-6.75 (m, 1 H), 6.43 (t, 1 H), 5.52-5.48 (m, 1 H), 3.64-3.43 (m, 2 H), 3.29 (s, 1 H) |
| 159 | 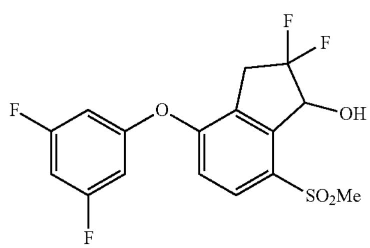 [SMILES: CS(=O)(=O)c1ccc(Oc2cc(F)cc(F)c2)c2c1C(O)C(F)(F)C2] | 421 (M + HCO$_2^-$) | (400 MHz, CDCl$_3$): δ 7.89 (d, 1 H), 7.01 (d, 1 H), 6.74-6.68 (m, 1 H), 6.62-6.58 (m, 2 H), 5.61-5.57 (m, 1H), 3.54-3.40 (m, 3 H), 3.22 (s, 3 H) |
| 160 | 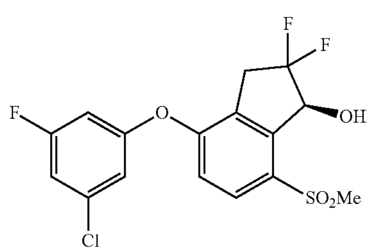 [SMILES: CS(=O)(=O)c1ccc(Oc2cc(F)cc(Cl)c2)c2c1[C@H](O)C(F)(F)C2] | 393 (M + H) | (400 MHz, CDCl$_3$): δ 7.90-7.87 (m, 1 H), 7.01-6.97 (m, 2 H), 6.88-6.87 (m, 1 H), 6.73-6.69 (m, 1 H), 5.61-5.57 (m, 1 H), 3.57-3.37 (m, 3 H), 3.22 (s, 3 H) |
| 161 | 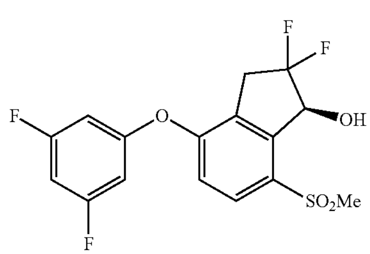 [SMILES: CS(=O)(=O)c1ccc(Oc2cc(F)cc(F)c2)c2c1[C@H](O)C(F)(F)C2] | 421 (M + HCO$_2^-$) | (400 MHz, CDCl$_3$): δ 7.89 (d, 1 H), 7.01 (d, 1 H), 6.74-6.68 (m, 1 H), 6.62-6.58 (m, 2 H), 5.61-5.57 (m, 1H), 3.54-3.40 (m, 3 H), 3.22 (s, 3 H) |

TABLE 1-continued

| No. | Structure | Mass Characterization | $^1$H NMR Data |
|---|---|---|---|
| 162 | 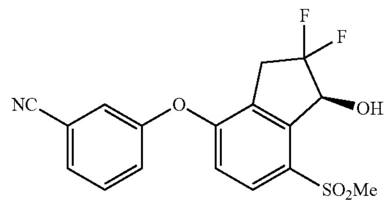 [SMILES: CS(=O)(=O)c1ccc(Oc2cccc(C#N)c2)c2c1[C@H](O)C(F)(F)C2] | 410 (M + HCO$_2^-$) | |
| 163 | 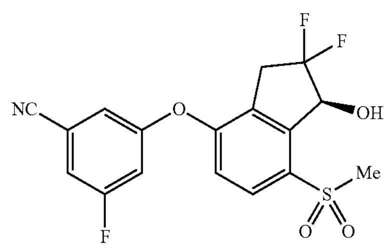 [SMILES: CS(=O)(=O)c1ccc(Oc2cc(F)cc(C#N)c2)c2c1[C@H](O)C(F)(F)C2] | 428 (M + HCO$_2^-$) | (400 MHz, CDCl$_3$): δ 7.93 (d, 1 H), 7.27-7.24 (m, 1 H), 7.15-7.14 (m, 1 H), 7.07-7.03 (m, 1 H), 7.00 (d, 1 H), 5.63-5.58 (m, 1 H), 3.56-3.35 (m, 3 H), 3.24 (s, 3 H) |
| 164 | 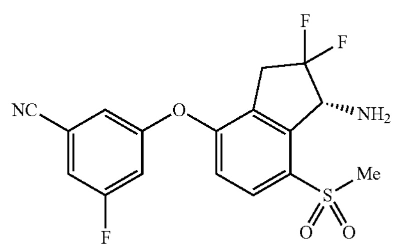 [SMILES: CS(=O)(=O)c1ccc(Oc2cc(F)cc(C#N)c2)c2c1[C@@H](N)C(F)(F)C2] | 383 (M + H) | (400 MHz, CDCl$_3$): δ 7.93-7.91 (m, 1 H), 7.25-7.22 (m, 1 H), 7.14-7.13 (m, 1 H), 7.06-7.02 (m, 1 H), 6.96 (d, 1 H), 4.97-4.93 (m, 1 H), 3.55-3.37 (m, 2 H), 3.32 (s, 3 H) |
| 165 | 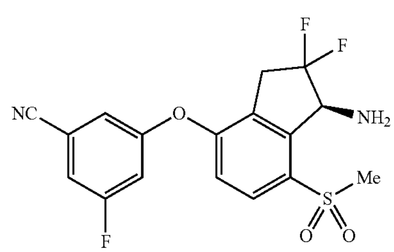 [SMILES: CS(=O)(=O)c1ccc(Oc2cc(F)cc(C#N)c2)c2c1[C@H](N)C(F)(F)C2] | 383 (M + H) | (400 MHz, CDCl$_3$): δ 7.93-7.91 (m, 1 H), 7.25-7.22 (m, 1 H), 7.14-7.13 (m, 1 H), 7.06-7.02 (m, 1 H), 6.96 (d, 1 H), 4.97-4.93 (m, 1 H), 3.55-3.37 (m, 2 H), 3.32 (s, 3 H) |
| 166 | 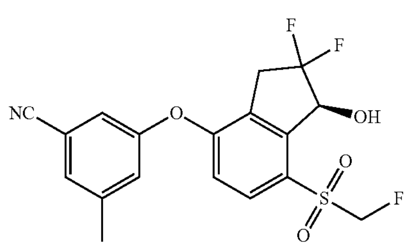 [SMILES: Cc1cc(C#N)cc(Oc2ccc(S(=O)(=O)CF)c3c2CC(F)(F)[C@H]3O)c1] | [M − H + 46]: 442 | (400 MHz, CDCl$_3$) δ 7.87 (d, 1H), 7.38 (br s, 1H), 7.16 (br d, 1H), 6.88 (d, 1H), 5.58-5.12 (m, 3H), 3.59-3.44 (m, 3H) |
| 167 | 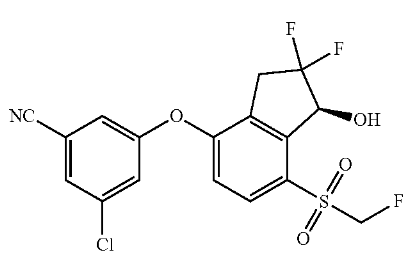 [SMILES: N#Cc1cc(Cl)cc(Oc2ccc(S(=O)(=O)CF)c3c2CC(F)(F)[C@H]3O)c1] | [M − H + 46]: 462 | (400 MHz, CDCl$_3$) δ 7.92 (d, 1H), 7.36-7.33 (m, 1H), 7.32-7.27 (m, 1H), 6.97 (d, 1H), 5.58-5.12 (m, 3H), 3.62-3.38 (m, 3H) |

TABLE 1-continued

| No. | Structure | Mass Characterization | ¹H NMR Data |
|---|---|---|---|
| 168 | 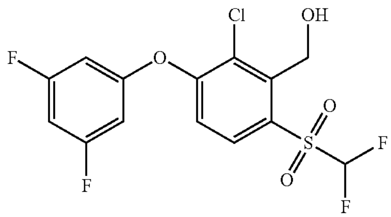 [SMILES: O=S(=O)(c1ccc(Oc2cc(F)cc(F)c2)c(Cl)c1CO)C(F)F] | [M − H + 46]: 429 | (400 MHz, CDCl$_3$) δ 8.01 (d, 1H), 7.09 (d, 1H), 6.77-6.67 (m, 1H), 6.64-6.61 (m, 2H), 6.47 (t, 1H), 5.21 (d, 2H), 2.70 (t, 1H) |
| 169 | 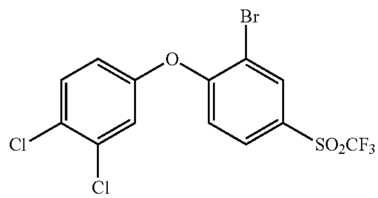 | | (400 MHz, CDCl$_3$): δ 8.30 (d, 1H), 7.89 (d, 1H), 7.54 (d, 1H), 7.26 (s, 1H), 6.99 (m, 2H) |
| 170 | 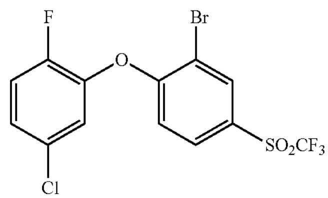 | | (400 MHz, CDCl$_3$): δ 8.30 (s, 1H), 7.88 (d, 1H), 7.21-7.31 (m, 3H), 6.90 (d, 1H) |
| 171 | 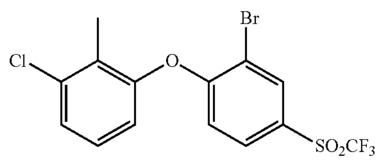 | | (400 MHz, d$_6$-DMSO): δ 8.40 (d, 1H), 8.02 (d, 1H), 7.45 (d, 1H), 7.35 (t, 1H), 7.20 (d, 1H), 6.95 (d, 1H), 2.13 (s, 3H) |
| 172 | 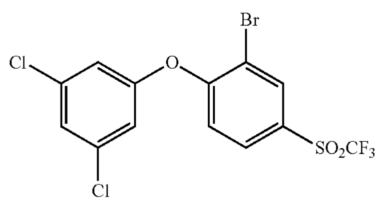 | | (400 MHz, CDCl$_3$): δ 8.30 (d, 1H), 7.93 (d, 1H), 7.31 (d, 1H), 7.04 (m, 3H) |
| 173 | 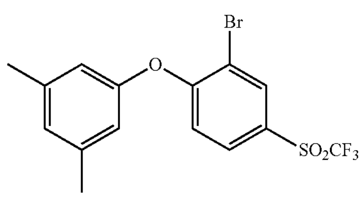 | | (400 MHz, CDCl$_3$): δ 8.26 (d, 1H), 7.81 (d, 1H), 6.95 (s, 1H), 6.91 (d, 1H), 6.74 (s, 2H), 2.35 (s, 6H) |
| 174 | 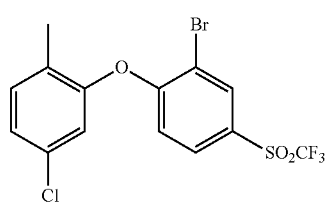 | | (400 MHz, CDCl$_3$): δ 8.29 (d, 1H), 7.84 (d, 1H), 7.22-7.27 (m, 2H), 7.06 (s, 1H), 6.78 (d, 1H), 2.16 (s, 3H) |
| 175 | 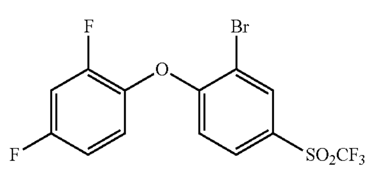 | | (400 MHz, d$_6$-DMSO): δ 8.40 (s, 1H), 8.03 (d, 1H), 7.58 (m, 2H), 7.23 (m, 1H), 7.11 (d, 1H) |

TABLE 1-continued

| No. | Structure | Mass Characterization | $^1$H NMR Data |
|---|---|---|---|
| 176 | 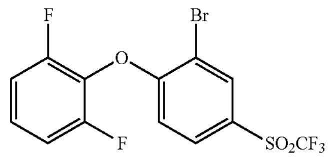 | | (400 MHz, d$_6$-DMSO): δ 8.30 (s, 1H), 7.88 (d, 1H), 7.27-7.32 (m, 1H), 7.08-7.14 (m, 2H), 6.85 (d, 1H) |
| 177 | 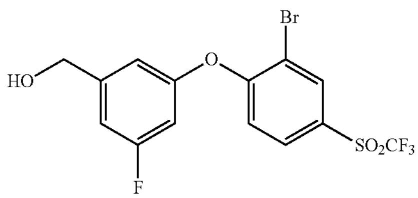 | | (400 MHz, CDCl$_3$): δ 8.29 (d, 1H), 7.87 (m, 1H), 7.06 (d, 1H), 7.02 (d, 1H), 6.94 (d, 1H), 6.77 (m, 1H), 4.75 (d, 2H), 1.83 (t, 1H) |
| 178 | 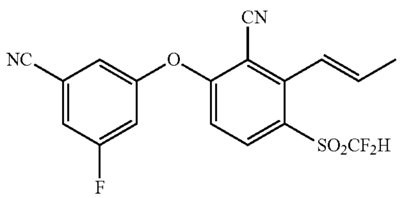 | 391 (M − H) | (400 MHz, CDCl$_3$): δ 8.18 (d, 1H), 7.38-7.35 (m, 1H), 7.29-7.27 (m, 1H), 7.21-7.18 (m, 1H), 7.07-7.02 (m, 1H), 6.90 (d, 1H), 6.56-6.47 (m, 1H), 6.22 (t, 1H), 2.08-2.06 (m, 1H) |
| 179 | 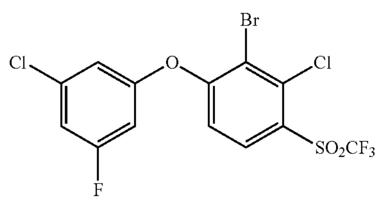 | | (400 MHz, CDCl$_3$): δ 8.13 (d, 1H), 7.08-7.05 (m, 1H), 6.95-6.93 (m, 2H), 6.79-6.76 (m, 1H) |
| 180 | 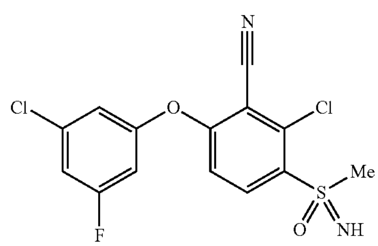 [SMILES: CS(=N)(=O)c1ccc(Oc2cc(F)cc(Cl)c2)c(C#N)c1Cl] | 359, 361 (M + H) | (400 MHz, CDCl$_3$): δ 8.33 (d, 1H), 7.09 (m, 1H), 6.97-6.95 (m, 1H), 6.94 (d, 1H), 6.81 (m, 1H), 3.32 (s, 3H), 2.94 (br s, 1H) |
| 181 | 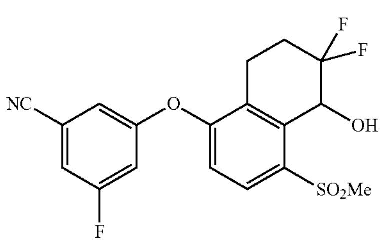 [SMILES: CS(=O)(=O)c1ccc(Oc2cc(F)cc(C#N)c2)c2c1C(O)C(F)(F)CC2] | 359, 361 (M + H) | (400 MHz, CDCl$_3$): δ 8.04 (d, 1H), 7.23 (m, 1H), 7.12-7.10 (m, 1H), 7.03-6.99 (m, 1H), 6.07 (d, 1H), 5.54-5.49 (m, 1H), 3.68 (m, 1H), 3.26 (s, 3H), 3.20 (m, 1H), 2.97-2.86 (m, 1H), 2.63-2.45 (m, 1H), 2.35-2.25 (m, 1H) |
| 182 | 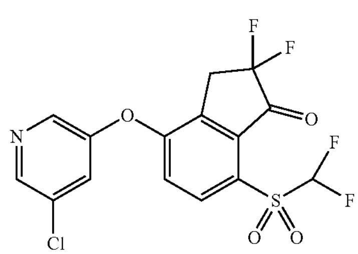 [SMILES: O=C1c2c(S(=O)(=O)C(F)F)ccc(Oc3cncc(Cl)c3)c2CC1(F)F] | (M + H) 410/412 | |

TABLE 1-continued

| No. | Structure | Mass Characterization | ¹H NMR Data |
|---|---|---|---|
| 183 | 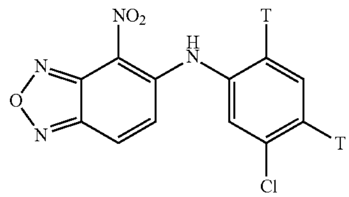 | 478 mCi | |
| 184 | 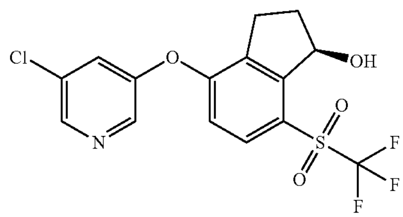 [SMILES: O=S(=O)(c1ccc(Oc2cncc(Cl)c2)c2c1[C@H](O)CC2)C(F)(F)F] | [M + H] 394 | (400 MHz, CDCl$_3$): δ 8.47 (d, 1H), 8.35 (d, 1H), 7.82 (d, 1H), 7.45 (t, 1H), 6.88 (d, 1H), 5.64-5.59 (m, 1H), 3.30-3.15 (m, 2H), 3.02-2.93 (m, 1H) 2.46-2.26 (m, 2H) |
| 185 | 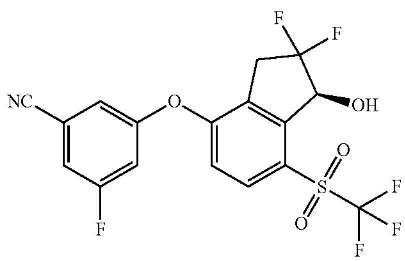 [SMILES: N#Cc1cc(F)cc(Oc2ccc(S(=O)(=O)C(F)(F)F)c3c2CC(F)(F)[C@H]3O)c1] | [M − H] 436 | (400 MHz, CDCl$_3$): δ 7.95 (d, 1H), 7.35-7.31 (m, 1H), 7.26-7.23 (m, 1H), 7.15-7.11 (m, 1H), 6.99 (d, 1H), 5.46-5.39 (m, 1H), 3.63-3.41 (m, 2H), 3.36 (d, 1H) |
| 186 | 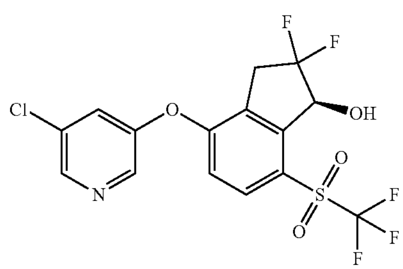 [SMILES: O=S(=O)(c1ccc(Oc2cncc(Cl)c2)c2c1[C@H](O)C(F)(F)C2)C(F)(F)F] | [M + H] 430 | (400 MHz, CDCl$_3$): δ 8.55 (d, 1H), 8.40 (d, 1H), 7.91 (d, 1H), 7.52 (t, 1H), 6.94 (d, 1H), 5.46-5.40 (m, 1H), 3.85 (d, 1H), 3.66-3.47 (m, 2H) |
| 187 | 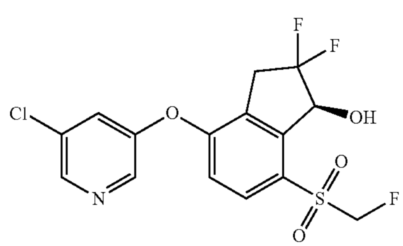 [SMILES: O=S(=O)(CF)c1ccc(Oc2cncc(Cl)c2)c2c1[C@H](O)C(F)(F)C2] | [M + H] 394 | (400 MHz, CDCl$_3$): δ 8.51 (d, 1H), 8.37 (d, 1H), 7.90 (d, 1H), 7.48 (t, 1H), 6.93 (d, 1H), 5.61-5.11 (m, 3H), 3.94 (d, 1H), 3.62-3.42 (m, 2H) |
| 188 | 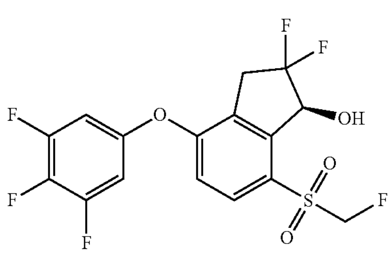 [SMILES: O=S(=O)(CF)c1ccc(Oc2cc(F)c(F)c(F)c2)c2c1[C@H](O)C(F)(F)C2] | [M − H + 46] 457 | (400 MHz, CDCl$_3$): δ 7.89 (d, 1H), 6.94 (d, 1H), 6.82-6.71 (m, 2H), 5.59-5.11 (m, 3H), 3.59-3.38 (m, 3H) |

TABLE 1-continued

| No. | Structure | Mass Characterization | ¹H NMR Data |
|---|---|---|---|
| 189 | 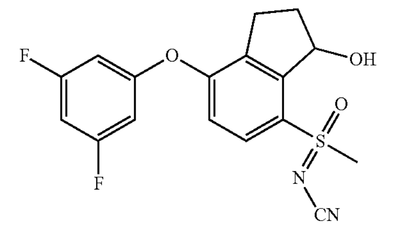 [SMILES: CS(=O)(=NC#N)c1ccc(Oc2cc(F)cc(F)c2)c2c1C(O)CC2] | [M + H] 365 | (400 MHz, CDCl$_3$): δ 7.88-7.80 (m, 1H), 6.97 (d, 1H), 6.72-6.65 (m, 1H), 6.63-6.55 (m, 2H), 5.83-5.76 (m, 1H), 3.57 (s, 1H), 3.51 (s, 3H), 3.18-3.07 (m, 1H), 2.93-2.79 (m, 1H), 2.60-2.47 (m, 1H), 2.23-2.11 (m, 1H) |
| 190 | 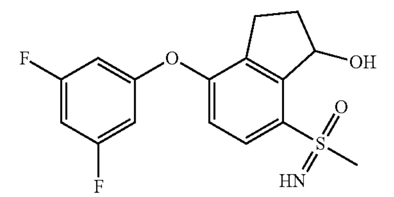 [SMILES: CS(=N)(=O)c1ccc(Oc2cc(F)cc(F)c2)c2c1C(O)CC2] | [M + H] 340 | (400 MHz, CDCl$_3$): δ 7.89-7.81 (m, 1H), 6.99-6.94 (m, 1H), 6.66-6.60 (m, 1H), 6.57-6.51 (m, 2H), 5.66-5.59 (m, 1H), 3.28 (s, 3H), 3.24 (s, 1H), 3.15-3.01 (m, 1H), 2.87-2.71 (m, 1H), 2.55-2.41 (m, 1H), 2.27-2.13 (m, 1H) |
| 191 | 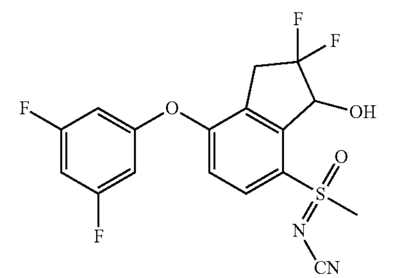 [SMILES: CS(=O)(=NC#N)c1ccc(Oc2cc(F)cc(F)c2)c2c1C(O)C(F)(F)C2] | [M + H] 401 | (400 MHz, CDCl$_3$): δ 7.98-7.91 (m, 1H), 7.04-7.01 (m, 1H), 6.80-6.73 (m, 1H), 6.69-6.61 (m, 2H), 5.73-5.63 (m, 1H), 3.60 (s, 1H), 3.58-3.40 (m, 5H) |
| 192 | 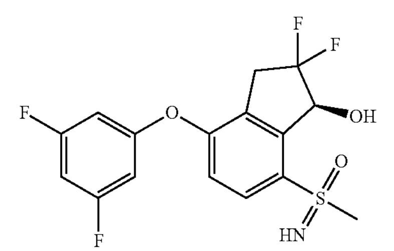 [SMILES: CS(=N)(=O)c1ccc(Oc2cc(F)cc(F)c2)c2c1[C@H](O)C(F)(F)C2] | [M + H] 376 | (400 MHz, CDCl$_3$): δ 7.96-7.89 (m, 1H), 7.03-6.98 (m, 1H), 6.73-6.66 (m, 1H), 6.63-6.55 (m, 2H), 5.62-5.56 (m, 1H), 5.47-5.41 (m, 1H), 3.57-3.30 (m, 2H), 3.28 (s, 3H) 3.24-2.88 (m, 1H) |
| 193 | 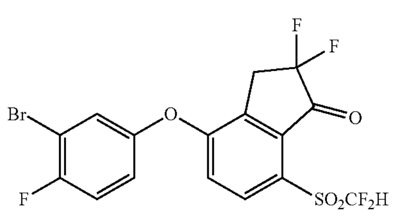 | | (400 MHz, CDCl$_3$) δ 8.18 (d, 1H), 7.41-7.39 (m, 1H), 7.30-7.26 (m, 1H), 7.13-7.05 (m, 2H), 6.91 (t, 1H), 3.67 (t, 2H) |
| 194 | 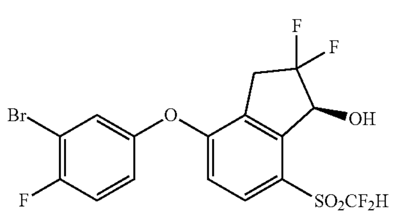 | (M + HCOOH − H): 517, 519 | (400 MHz, CDCl$_3$) δ 7.86 (d, 1H), 7.37-7.35 (m, 1H), 7.25-7.21 (m, 1H), 7.08-7.04 (m, 1H), 6.86 (d, 1H), 6.41 (t, 1H), 5.51-5.47 (m, 1H), 3.63-3.47 (m, 2H), 3.25 (d, 1H) |

TABLE 1-continued

| No. | Structure | Mass Characterization | ¹H NMR Data |
|---|---|---|---|
| 195 | 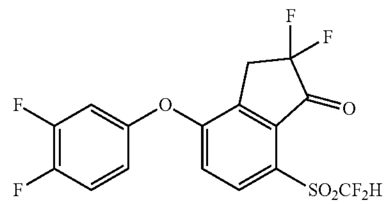 | | (400 MHz, CDCl₃) δ 8.16 (d, 1H), 7.32 (q, 1H), 7.13 (d, 1H), 7.06-7.02 (m, 1H), 6.93-6.91 (m, 1H), 6.90 (t, 1H), 3.67 (t, 2H) |
| 196 | 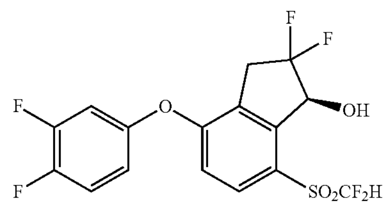 | (M + HCOOH − H) 457 | (400 MHz, CDCl₃) δ 7.86 (d, 1H), 7.30-7.24 (m, 1H), 7.02-6.97 (m, 1H), 6.89-6.86 (m, 2H), 6.41 (t, 1H), 5.51-5.47 (m, 1H), 3.63-3.47 (m, 2H), 3.27 (d, 1H) |
| 197 | 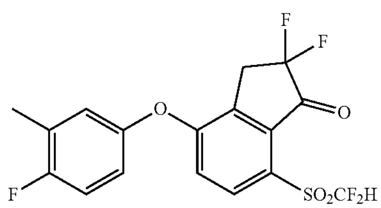 | | (400 MHz, CDCl₃) δ 8.14 (d, 1H), 7.15-7.05 (m, 2H), 6.99-6.91 (m, 2H), 6.92 (t, 1H), 3.67 (t, 2H), 2.33 (m, 3H) |
| 198 | 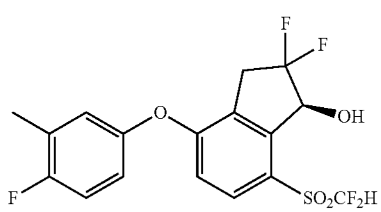 | (M + HCOOH − H) 453 | (400 MHz, CDCl₃) δ 7.82 (d, 1H), 7.09 (t, 1H), 6.93-6.88 (m, 2H), 6.82 (d, 1H), 6.40 (t, 1H), 5.48 (m, 1H), 3.63-3.48 (m, 2H), 3.25 (d, 1H), 2.31 (m, 3H) |
| 199 | 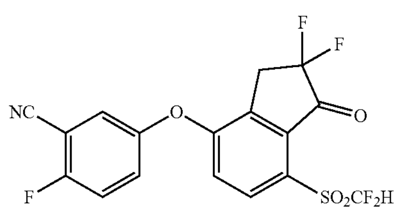 | | (400 MHz, CDCl₃) δ 8.20 (d, 1H), 7.47-7.38 (m, 3H), 7.11 (d, 1H), 6.92 (t, 1H), 3.68 (t, 2H) |
| 200 | 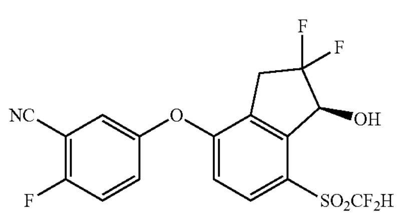 | (M + HCOOH − H) 464 | (400 MHz, CDCl₃) δ 7.89 (d, 1H), 7.41-7.32 (m, 3H), 6.85 (d, 1H), 6.43 (t, 1H), 5.57-5.48 (m, 1H), 3.59-3.49 (m, 2H), 3.29 (d, 1H) |
| 201 | 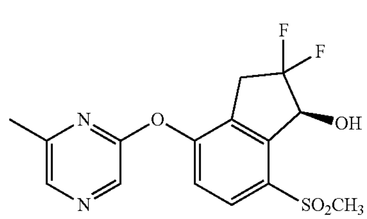 | (M + HCOOH − H) 401 | (400 MHz, CDCl₃) δ 8.31 (s, 1H), 8.28 (s, 1H), 7.94 (d, 1H), 7.33 (d, 1H), 5.61-5.58 (m, 1H), 3.57 (d, 1H), 3.51-3.28 (m, 2H), 3.24 (s, 3H), 2.44 (s, 3H) |

TABLE 1-continued

| No. | Structure | Mass Characterization | $^1$H NMR Data |
|---|---|---|---|
| 202 | 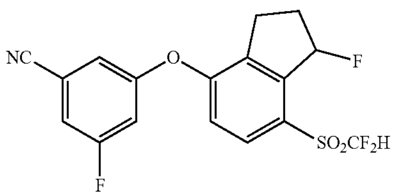 | (M + HCOOH − H) 428 | (400 MHz, CDCl$_3$) δ 7.95 (d, 1H), 7.28-7.26 (m, 1H), 7.18 (brd s, 1H), 7.08-7.03 (m, 2H), 6.64-6.47 (m, 1H), 6.34 (t, 1H), 3.23-3.14 (m, 1H), 3.04-2.95 (m, 1H), 2.57-2.42 (m, 2H) |
| 203 | 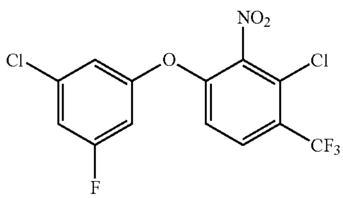 [SMILES: O=[N+]([O-])c1c(Oc2cc(F)cc(Cl)c2)ccc(C(F)(F)F)c1Cl] | | (400 MHz, CDCl$_3$) δ 7.78-7.75 (m, 1H), 7.05-7.02 (m, 1H), 7.00-6.98 (m, 1H), 6.93-6.92 (m, 1H), 6.78-6.75 (m, 1H) |
| 204 | 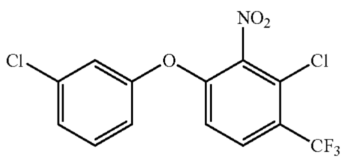 [SMILES: O=[N+]([O-])c1c(Oc2cccc(Cl)c2)ccc(C(F)(F)F)c1Cl] | 350, 352, 354 (M − H) | (400 MHz, CDCl$_3$): δ 7.71 (d, 1H), 7.38 (t, 1H), 7.31-7.26 (m, 1H), 7.14 (t, 1H), 7.03-7.00 (m, 1H), 6.91 (d, 1H) |
| 205 | 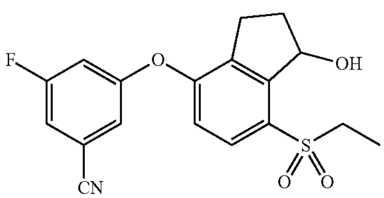 [SMILES: CCS(=O)(=O)c1ccc(Oc2cc(F)cc(C#N)c2)c2c1C(O)CC2] | | (400 MHz, CDCl$_3$): δ 7.79 (d, 1H), 7.18 (d, 1H), 7.09 (s, 1H), 6.98 (m, 2H), 5.65 (m, 1H), 3.69 (d, 1H), 3.29 (m, 2H), 3.08 (m, 1H), 2.83 (m, 1H), 2.45 (m, 1H), 2.24 (m, 1H), 1.36 (t, 3H) |
| 206 | 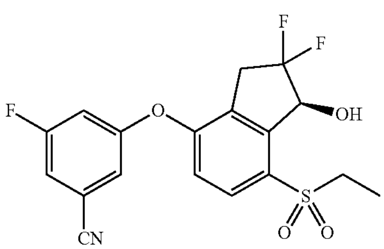 | 442 (M + HCO2) | (400 MHz, CDCl$_3$): δ 7.86 (m, 1 H), 7.27-7.24 (m, 1 H), 7.16-7.14 (m, 1 H), 7.07-7.04 (m, 1 H), 6.99 (d, 1 H), 5.55-5.51 (m, 1 H), 3.61-3.27 (m, 5 H), 1.35 (t, 3 H) |
| 207 | 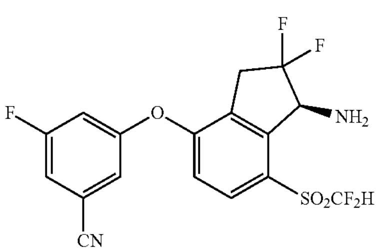 | 419 (M + H) | (400 MHz, CDCl$_3$): δ 7.94 (d, 1H), 7.32-7.28 (m, 1H), 7.22-7.19 (m, 1H), 7.12-7.07 (m, 1H), 6.94 (d, 1H), 6.83 (t, 1H), 4.91 (d, 1H), 3.60-3.40 (m, 2H), 1.91 (br s, 2H) |
| 208 | 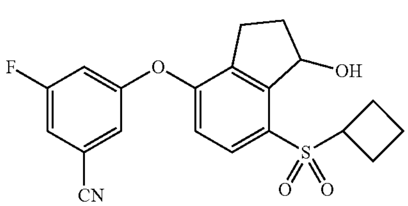 [SMILES: N#Cc1cc(F)cc(Oc2ccc(S(=O)(=O)C3CCC3)c3c2CCC3O)c1] | | (400 MHz, CDCl$_3$): δ 7.73 (d, 1H), 7.18 (d, 1H), 7.08 (s, 1H), 6.95 (m, 2H), 5.62 (m, 1H), 4.02 (m, 1H), 3.77 (s, 1H), 3.07 (m, 1H), 2.81 (m, 1H), 2.61 (m, 2H), 2.45 (m 1H), 2.26 (m, 3H), 2.06 (m, 2H) |

TABLE 1-continued

| No. | Structure | Mass Characterization | ¹H NMR Data |
|---|---|---|---|
| 209 | 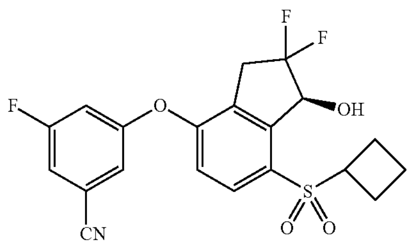 [SMILES: N#Cc1cc(F)cc(Oc2ccc(S(=O)(=O)C3CCC3)c3c2CC(F)(F)[C@H]3O)c1] | 468 (M + HCO2) | (400 MHz, CDCl₃): δ 7.81 (d, 1 H), 7.27-7.24 (m, 1 H), 7.15-7.14 (m, 1 H), 7.06-7.03 (m, 1 H), 6.96 (d, 1 H), 5.50-5.45 (m, 1 H), 3.70 (d, 1 H), 3.55-3.34 (m, 2 H), 2.67-2.50 (m, 2 H), 2.29-2.17 (m, 2 H), 2.08-2.01 (m, 2 H) |
| 210 | 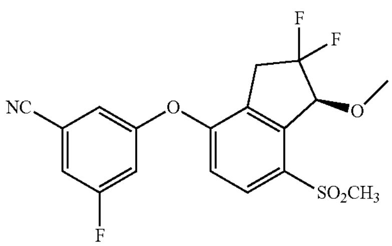 [SMILES: CO[C@H]1c2c(S(C)(=O)=O)ccc(Oc3cc(F)cc(C#N)c3)c2CC1(F)F] | 398 (M + H) | (400 MHz, CDCl₃): δ 7.95 (d, 1H), 7.24 (d, 1H), 7.13 (br s, 1H), 7.05-7.01 (m, 1H), 6.99 (d, 1H), 5.31 (d, 1H), 3.78 (s, 3H), 3.53-3.32 (m, 2H), 3.19 (s, 3H) |
| 211 | 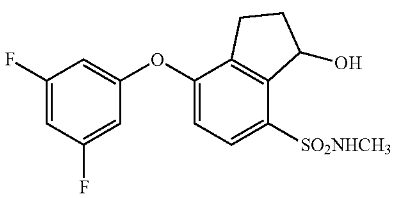 | 354 (M − H) | (400 MHz, CDCl₃): δ 7.75 (d, 1H), 6.94 (d, 1H), 6.65-6.60 (m, 1H), 6.54-6.52 (m, 2H), 5.77-5.71 (m, 1H), 5.02-4.95 (m, 1H), 3.23-3.18 (m, 1H), 3.12-3.04 (m, 1H), 2.84-2.70 (m, 1H), 2.65 (d, 3H), 2.57-2.47 (m, 1H), 2.19-2.11 (m, 1H) |
| 212 | 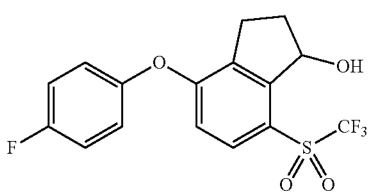 [SMILES: O=S(=O)(c1ccc(Oc2ccc(F)cc2)c2c1C(O)CC2)C(F)(F)F] | | (400 MHz, CDCl₃): δ 7.77 (d, 1H), 7.05-7.26 (m, 4H), 6.75 (d, 1H), 5.62 (m, 1H), 3.17-3.30 (m, 2H), 2.98-3.07 (m, 1H), 2.40-2.47 (m, 1H), 2.28-2.37 (m, 1H) |
| 213 | 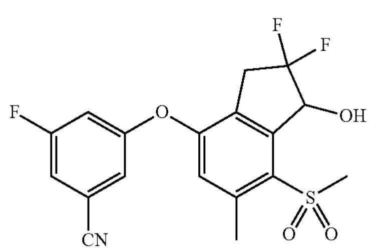 [SMILES: Cc1cc(Oc2cc(F)cc(C#N)c2)c2c(c1S(C)(=O)=O)C(O)C(F)(F)C2] | | (400 MHz, CDCl₃): δ 7.22-7.25 (m, 1H), 7.08 and 7.12 (m 1H), 6.98-7.04 (m 1H), 6.80 (s, 1H), 5.58 and 5.78 (m 1H), 3.69 (d, 1H), 3.20 and 3.23 (s, 3H), 3.08-3.47 (m, 2H), 2.68 (s, 3H) |
| 214 | 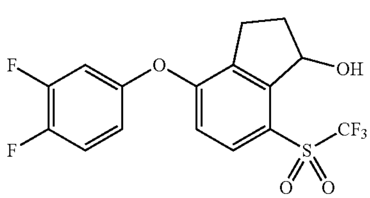 [SMILES: O=S(=O)(c1ccc(Oc2ccc(F)c(F)c2)c2c1C(O)CC2)C(F)(F)F] | | (400 MHz, d₆-DMSO): 7.87 (d, 1H), 7.51-7.64 (m, 2H), 7.11-7.16 (m, 1H), 6.96 (d, 1H), 5.51 (m, 1H), 5.30 (d, 1H), 3.04-3.31 (m, 1H), 2.87-2.95 (m, 1H), 2.11-2.30 (m, 1H), 1.99-2.09 (m, 1H) |

TABLE 1-continued

| No. | Structure | Mass Characterization | ¹H NMR Data |
|---|---|---|---|
| 215 | 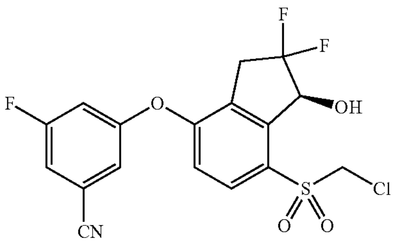 [SMILES: N#Cc1cc(F)cc(Oc2ccc(S(=O)(=O)CCl)c3c2CC(F)(F)[C@H]3O)c1] | | (400 MHz, CDCl$_3$): 7.92 (d, 1H), 7.27 (m, 2H), 7.08 (d, 1H), 6.99 (d, 1H), 5.63 (dd, 1H), 4.92 (d, 1H), 4.65 (d, 1H), 3.34-3.49 (m, 2H), 3.21 (s, 1H) |
| 216 | 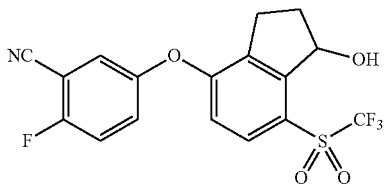 [SMILES: N#Cc1cc(Oc2ccc(S(=O)(=O)C(F)(F)F)c3c2CCC3O)ccc1F] | | (400 MHz, CDCl$_3$): 7.83 (d, 1H), 7.26-7.38 (m, 3H), 6.81 (d, 1H), 5.64 (dd, 1H), 3.16-3.25 (m, 2H), 3.00-3.04 (m 1H), 2.34-2.42 (m, 2H) |
| 217 | 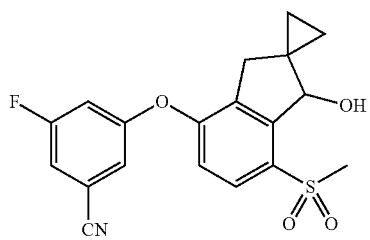 | 418 (M + HCO$_2^-$) | (400 MHz, CDCl$_3$): 7.88 (d, 1H), 7.17 (d, 1H), 7.09 (s, 1H), 7.06 (m, 2H), 5.07 (d, 1H), 3.20 (m, 5H), 2.60 (d, 1H), 1.18-1.32 (m, 2H), 0.68-0.87 (m, 2H) |
| 218 | 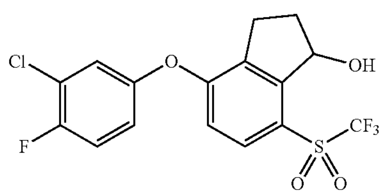 [SMILES: O=S(=O)(c1ccc(Oc2ccc(F)c(Cl)c2)c2c1C(O)CC2)C(F)(F)F] | | (400 MHz, CDCl$_3$): 7.80 (d, 1H), 7.18-7.23 (m, 2H), 6.97-7.01 (m, 1H), 6.80 (d, 1H), 5.63 (m 1H), 3.16-3.29 (m, 2H), 2.96-3.05 (m 1H), 2.29-2.46 (m, 2H) |
| 219 | 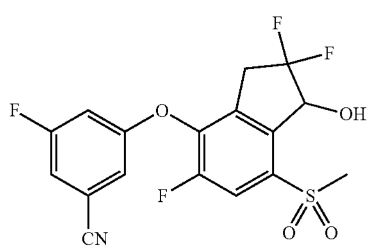 [SMILES: CS(=O)(=O)c1cc(F)c(Oc2cc(F)cc(C#N)c2)c2c1C(O)C(F)(F)C2] | | (400 MHz, d6-DMSO): δ 7.85 (d, 1H), 7.67 (m, 1H), 7.46 (d, 1H), 6.85 (d, 1H), 5.38 (dd, 1H), 3.40-3.49 (m, 2H), 3.40 (s, 3H) |
| 220 | 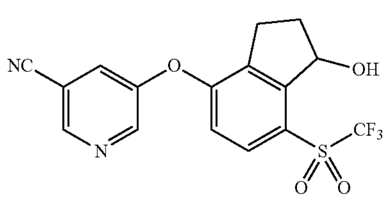 [SMILES: N#Cc1cncc(Oc2ccc(S(=O)(=O)C(F)(F)F)c3c2CCC3O)c1] | | |
| 221 | 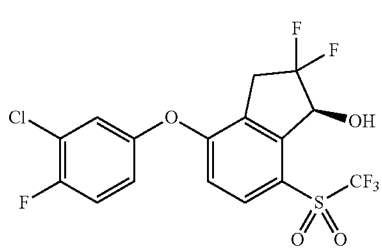 [SMILES: O=S(=O)(c1ccc(Oc2ccc(F)c(Cl)c2)c2c1[C@H](O)C(F)(F)C2)C(F)(F)F] | 445, 447 (M − H) | (400 MHz, CDCl$_3$): δ 7.97 (d, 1 H), 7.28-7.22 (m, 2 H), 7.02 (d, 1 H), 6.87 (d, 1 H), 5.43-5.39 (m, 1 H), 3.64-3.47 (m, 2 H), 3.26 (d, 1 H) |

TABLE 1-continued

| No. | Structure | Mass Characterization | ¹H NMR Data |
|---|---|---|---|
| 222 | 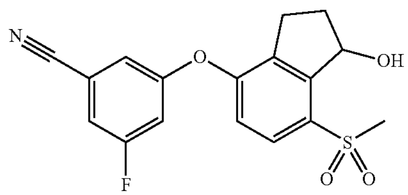 | 392 (M + HCO₂⁻) | (400 MHz, CDCl₃): δ 7.84 (d, 1 H), 7.19-7.17 (m, 1 H), 7.08 (s, 1 H), 7.00-6.97 (m, 2 H), 5.71-5.68 (m, 1 H), 3.64 (d, 1 H), 3.21 (s, 3 H), 3.12-3.04 (m, 1 H), 2.84-2.76 (m, 1 H), 2.52-2.43 (m, 1 H), 2.27-2.19 (m, 1 H) |
| 223 | 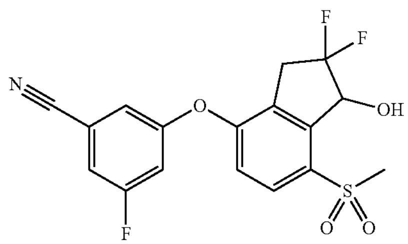 | 428 (M + HCO₂⁻) | (400 MHz, CDCl₃): δ 7.93 (d, 1 H), 7.27-7.24 (m, 1 H), 7.15-7.14 (m, 1 H), 7.07-7.03 (m, 1 H), 7.00 (d, 1 H), 5.63-5.58 (m, 1 H), 3.56-3.35 (m, 3 H), 3.24 (s, 3 H) |
| 224 | 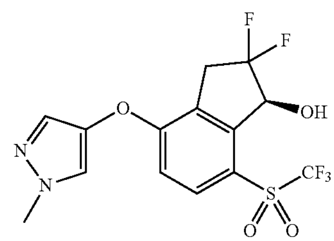 [SMILES: Cn1cc(Oc2ccc(S(=O)(=O)C(F)(F)F)c3c2CC(F)(F)[C@H]3O)cn1] | 399 (M + H) | (400 MHz, CDCl₃): δ 7.87 (d, 1 H), 7.40 (s, 1 H), 7.36 (s, 1 H), 7.08 (d, 1 H), 5.42-5.38 (m, 1 H), 3.94 (s, 3 H), 3.59-3.52 (m, 2 H), 3.21 (d, 1 H) |
| 225 | 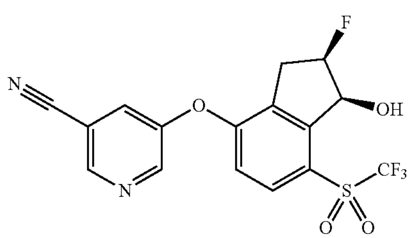 [SMILES: N#Cc1cncc(Oc2ccc(S(=O)(=O)C(F)(F)F)c3c2C[C@@H](F)[C@H]3O)c1] | 401 (M − H) | (400 MHz, CDCl₃): δ 8.82 (d, 1 H), 8.70 (d, 1 H), 7.95 (d, 1 H), 7.71-7.69 (m, 1 H), 6.94 (d, 1 H), 5.64-5.59 (m, 1 H), 5.46-5.31 (m, 1 H), 3.36-3.27 (m, 2 H), 3.19 (d, 1 H) |
| 226 | 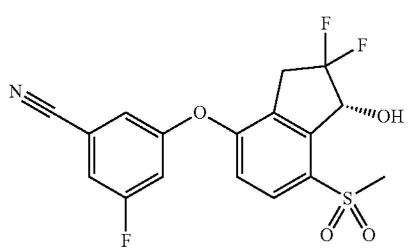 | 428 (M + HCO₂⁻) | (400 MHz, CDCl₃): δ 7.93 (d, 1 H), 7.27-7.24 (m, 1 H), 7.15-7.14 (m, 1 H), 7.07-7.03 (m, 1 H), 7.00 (d, 1 H), 5.63-5.58 (m, 1 H), 3.56-3.35 (m, 3 H), 3.24 (s, 3 H) |
| 227 | 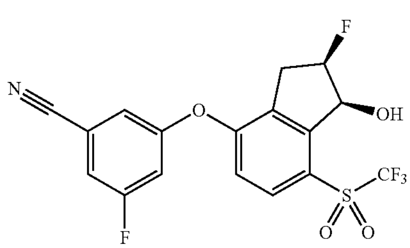 [SMILES: N#Cc1cc(F)cc(Oc2ccc(S(=O)(=O)C(F)(F)F)c3c2C[C@@H](F)[C@H]3O)c1] | 428 (M + HCO₂⁻) | (400 MHz, CDCl₃): δ 7.93 (d, 1 H), 7.27-7.24 (m, 1 H), 7.15-7.14 (m, 1 H), 7.07-7.03 (m, 1 H), 7.00 (d, 1 H), 5.63-5.58 (m, 1 H), 3.56-3.35 (m, 3 H), 3.24 (s, 3 H) |

| No. | Structure | Mass Characterization | ¹H NMR Data |
|---|---|---|---|
| 228 | 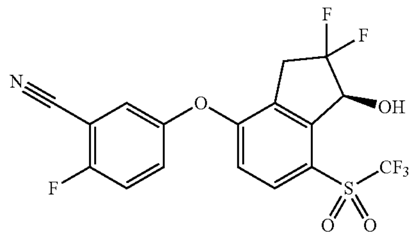 [SMILES: N#Cc1cc(Oc2ccc(S(=O)(=O)C(F)(F)F)c3c2CC(F)(F)[C@H]3O)ccc1F] | 436 (M − H) | (400 MHz, CDCl$_3$): δ 7.90 (d, 1 H), 7.42-7.30 (m, 3 H), 6.86 (d, 1 H), 5.42 (dd, 1 H), 3.58-3.47 (m, 2 H), 3.32 (d, 1 H) |
| 229 | 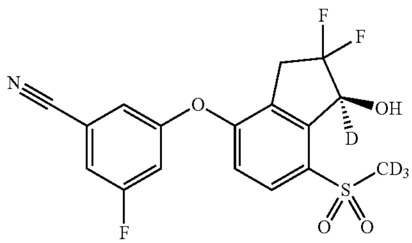 [SMILES: [2H]C([2H])([2H])S(=O)(=O)c1ccc(Oc2cc(F)cc(C#N)c2)c2c1[C@]([2H])(O)C(F)(F)C2] | 432 (M + HCO$_2^-$) | (400 MHz, CDCl$_3$): δ 7.92 (d, 1 H), 7.26-7.24 (m, 1 H), 7.15 (s, 1 H), 7.06-7.03 (m, 1 H), 7.01 (d, 1 H), 3.56-3.35 (m, 3 H) |
| 230 | 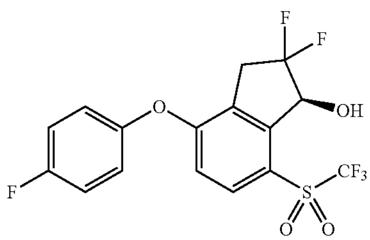 [SMILES: O=S(=O)(c1ccc(Oc2ccc(F)cc2)c2c1[C@H](O)C(F)(F)C2)C(F)(F)F] | 411 (M − H) | (400 MHz, CDCl$_3$): δ 7.85 (d, 1 H), 7.19-7.08 (m, 4 H), 6.83 (d, 1 H), 5.42 (dd, 1 H), 3.65-3.49 (m, 2 H), 3.25 (dd, 1 H) |
| 231 | 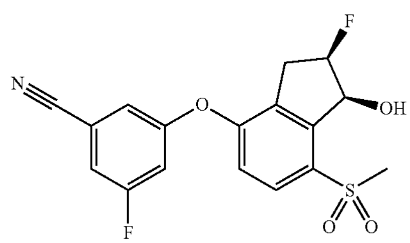 [SMILES: CS(=O)(=O)c1ccc(Oc2cc(F)cc(C#N)c2)c2c1[C@H](O)[C@H](F)C2] | 383 (M + NH$_4^+$) | (400 MHz, CDCl$_3$): δ 7.92 (d, 1 H), 7.21-7.20 (m, 1 H), 7.12-7.11 (m, 1 H), 7.03-6.98 (m, 2 H), 5.71-5.65 (m, 1 H), 5.46-5.33 (m, 1 H), 3.66 (dd, 1 H), 3.31 (s, 3 H), 3.27-3.05 (m, 2 H) |
| 232 | 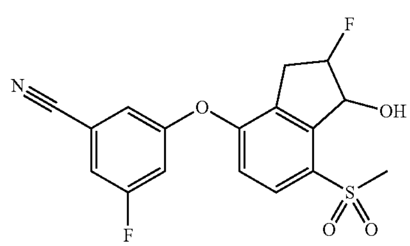 [SMILES: CS(=O)(=O)c1ccc(Oc2cc(F)cc(C#N)c2)c2c1C(O)C(F)C2] | 383 (M + NH$_4^+$) | (400 MHz, CDCl$_3$): δ 7.92 (d, 1 H), 7.21-7.20 (m, 1 H), 7.12-7.11 (m, 1 H), 7.03-6.98 (m, 2 H), 5.71-5.65 (m, 1 H), 5.46-5.33 (m, 1 H), 3.66 (dd, 1 H), 3.31 (s, 3 H), 3.27-3.05 (m, 2 H) |
| 233 | 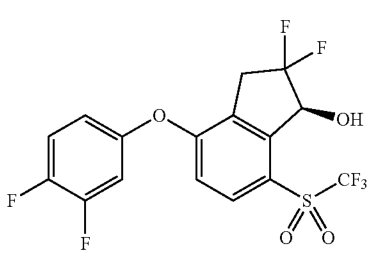 [SMILES: O=S(=O)(c1ccc(Oc2ccc(F)c(F)c2)c2c1[C@H](O)C(F)(F)C2)C(F)(F)F] | 429 (M − H) | (400 MHz, CDCl$_3$): δ 7.88 (d, 1 H), 7.32-7.25 (m, 1 H), 7.03-6.98 (m, 1 H), 6.91-6.86 (m, 2 H), 5.42 (dd, 1 H), 3.64-3.47 (m, 2 H), 3.22 (d, 1 H) |

TABLE 1-continued

| No. | Structure | Mass Characterization | ¹H NMR Data |
|---|---|---|---|
| 234 | 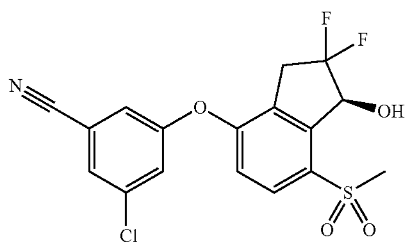 | 444 (M + HCO₂⁻) | (400 MHz, CDCl₃): δ 7.92 (d, 1 H), 7.52-7.51 (m, 1 H), 7.32-7.31 (m, 1 H), 7.25-7.24 (m, 1 H), 6.98 (d, 1 H), 5.62-5.58 (m, 1 H), 3.56-3.35 (m, 3 H), 3.24 (s, 3 H) |
| 235 | 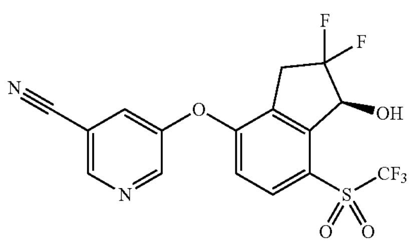 [SMILES: N#Cc1cncc(Oc2ccc(S(=O)(=O)C(F)(F)F)c3c2CC(F)(F)[C@H]3O)c1] | 419 (M − H) | (400 MHz, CDCl₃): δ 8.84 (d, 1 H), 8.73 (d, 1 H), 7.96 (d, 1 H), 7.75-7.74 (m, 1 H), 6.95 (d, 1 H), 5.45 (dd, 1 H), 3.64-3.48 (m, 2 H), 3.31 (d, 1 H) |
| 236 | 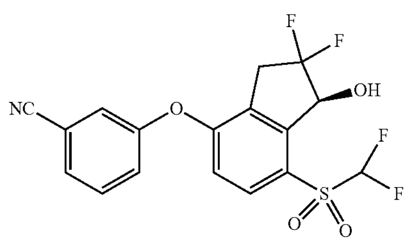 [SMILES: N#Cc1cccc(Oc2ccc(S(=O)(=O)C(F)F)c3c2CC(F)(F)[C@H]3O)c1] | 419 (M + NH4) | (400 MHz, CDCl₃): δ 7.89 (d, 1H), 7.62-7.57 (m, 2H), 7.42 (s, 1H), 7.39-7.34 (m, 1H), 6.90 (d, 1H), 6.44 (t, 1H), 5.51 (dd, 1H), 5.63-5.45 (m, 2H), 3.37 (d, 1H) |
| 237 | 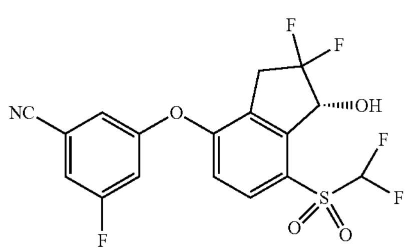 [SMILES: N#Cc1cc(F)cc(Oc2ccc(S(=O)(=O)C(F)F)c3c2CC(F)(F)[C@@H]3O)c1] | | |
| 238 | 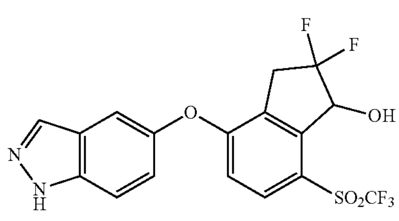 | [M + H] 435 | (400 MHz, CDCl₃): δ 10.35 (br s, 1H), 8.14 (s, 1H), 7.82 (d, 1H), 7.61 (d, 1H), 7.51 (d, 1H), 7.21-7.17 (m, 1H), 6.82 (d, 1H), 5.44 (d, 1H), 3.70-3.57 (m, 2H), 3.40 (br s, 1H) |
| 239 | 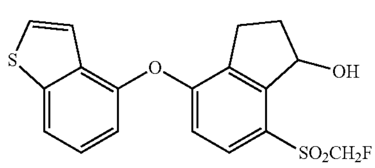 | [M + formic acid] 459 | (400 MHz, CDCl₃): δ 7.78 (d, 1H), 7.68 (d, 1H), 7.44 (d, 1H), 7.37 (t, 1H), 7.23 (d, 1H), 7.00 (d, 1H), 6.71 (d, 1H), 5.73-5.68 (m, 1H), 5.38-5.12 (m, 2H), 3.37-3.33 (m, 1H), 3.32-3.22 (m, 1H) 3.07-2.99 (m, 1H), 2.56-2.46 (m, 1H), 2.35-2.24 (m, 1H) |

TABLE 1-continued

| No. | Structure | Mass Characterization | ¹H NMR Data |
|---|---|---|---|
| 240 | 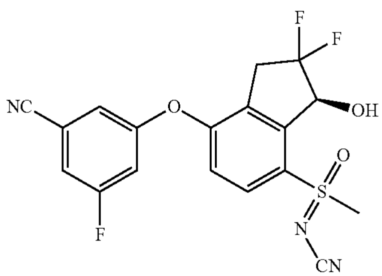 [SMILES: CS(=O)(=NC#N)c1ccc(Oc2cc(F)cc(C#N)c2)c2c1[C@H](O)C(F)(F)C2] | [M + H] 408 | (400 MHz, CD₃OD): δ 8.01 (d, 1H), 7.54-7.49 (m, 1H), 7.46-7.44 (m, 1H), 7.40-7.36 (m, 1H), 7.20-7.14 (m, 1H), 5.56 (d, 1H), 3.78-3.61 (m, 1H), 3.62 (s, 3H), 3.55-3.47 (m, 1H) |
| 241 | 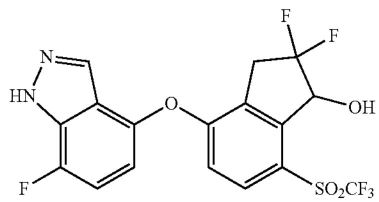 | [M + 1] 453 | (400 MHz, CDCl₃): δ 10.55 (br s, 1H), 7.94 (d, 1H), 7.83 (d, 1H), 7.16-7.10 (m, 1H), 6.86 (d, 1H), 6.83-6.78 (m, 1H), 5.46 (d, 1H), 3.72-3.59 (m, 2H), 3.34 (br s, 1H) |
| 242 | 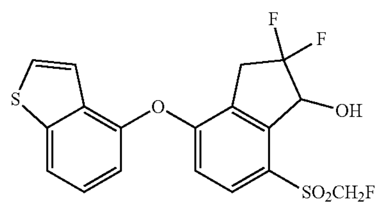 | [M + formic acid] 459 | (400 MHz, CDCl₃): δ 7.83-7.76 (m, 2H), 7.47 (d, 1H), 7.40 (t, 1H), 7.21-7.19 (m, 1H), 7.05 (d, 1H), 6.76 (d, 1H), 5.61-5.11 (m, 3H), 3.71-3.57 (m, 2H), 3.30 (br s, 1H) |
| 243 | 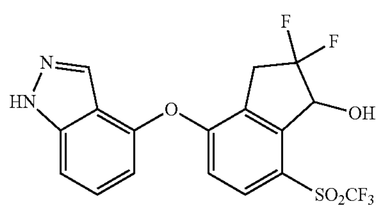 | [M + H] 435 | (400 MHz, CDCl₃): δ 10.45 (br s, 1H), 7.93 (s, 1H), 7.84 (d, 1H), 7.48-7.41 (m, 2H), 6.92 (d, 1H), 6.86 (dd, 1H), 5.46 (d, 1H), 3.72-3.59 (m, 2H), 3.44 (br s, 1H) |
| 244 | 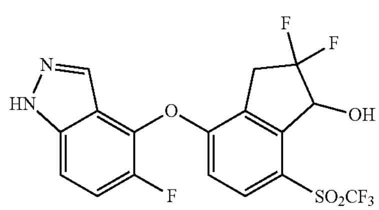 | [M + H] 453 | (400 MHz, CDCl₃): δ 10.35 (br s, 1H), 7.96 (s, 1H), 7.84 (d, 1H), 7.47-7.43 (m, 1H), 7.39-7.33 (m, 1H), 6.81 (dd, 1H), 5.46 (d, 1H), 3.74-3.59 (m, 2H), 3.36 (br s, 1H) |
| 245 | 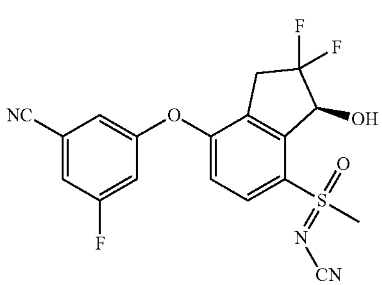 [SMILES: CS(=O)(=NC#N)c1ccc(Oc2cc(F)cc(C#N)c2)c2c1[C@H](O)C(F)(F)C2] | [M + H] 408 | (400 MHz, CDCl₃): δ 8.01 (d, 1H), 7.32-7.28 (m, 1H), 7.22-7.20 (m, 1H), 7.14-7.09 (m, 1H), 7.02 (d, 1H), 5.67 (d, 1H), 4.22 (br s, 1H), 3.65 (s, 3H), 3.60-3.40 (m, 2H) |

TABLE 1-continued

| No. | Structure | Mass Characterization | ¹H NMR Data |
|---|---|---|---|
| 246 | 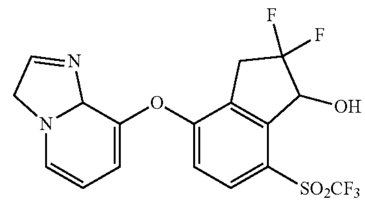 | [M + H] 435 | (400 MHz, CDCl₃): δ 8.15 (d, 1H), 7.82 (d, 1H), 7.72 (s, 1H), 7.65 (s, 1H), 6.99 (d, 1H), 6.88-6.81 (m, 2H), 5.43 (d, 1H), 3.76-3.63 (m, 2H), 3.51 (br s, 1H) |
| 247 | 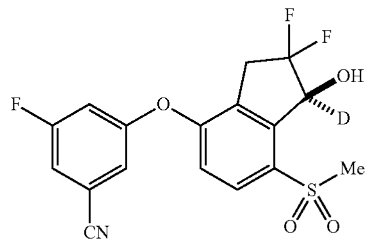 [SMILES: [2H][C@]1(O)c2c(S(C)(=O)=O)ccc(Oc3cc(F)cc(C#N)c3)c2CC1(F)F] | (M + H) 385 | (400 MHz, CDCl₃): δ 7.93 (d, 1H), 7.27-7.23 (m, 1H), 7.16-7.13 (m, 1H), 7.07-6.98 (m, 2H), 3.56-3.34 (m, 3H), 3.24 (s, 3H) |
| 248 | 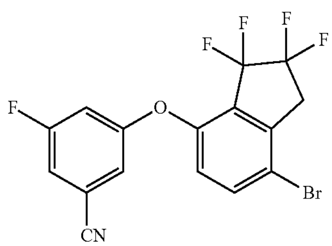 [SMILES: N#Cc1cc(F)cc(Oc2ccc(Br)c3c2C(F)(F)C(F)(F)C3)c1] | (M − H) 402, 404 | (400 MHz, CDCl₃): δ 7.70 (d, 1H), 7.20-7.15 (m, 1H), 7.10-7.08 (m, 1H), 7.02 (dt, 1H), 6.86 (d, 1H), 3.50 (t, 2H) |
| 249 | 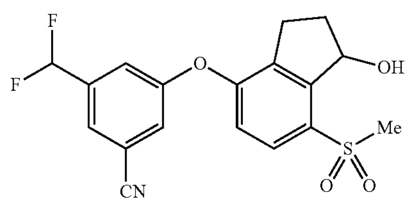 [SMILES: CS(=O)(=O)c1ccc(Oc2cc(C#N)cc(C(F)F)c2)c2c1C(O)CC2] | (M + NH₄) 397 | (400 MHz, CDCl₃): δ 7.83 (d, 1H), 7.60 (s, 1H), 7.41 (s, 1H), 7.37 (s, 1H), 6.94 (d, 1H), 6.65 (t, 1H), 5.72-5.68 (m, 1H), 3.64 (br d, 1H), 3.22 (s, 3H), 3.14-3.04 (m, 1H), 2.81 (ddd, 1H), 2.54-2.43 (m, 1H), 2.28-2.19 (m, 1H) |
| 250 | 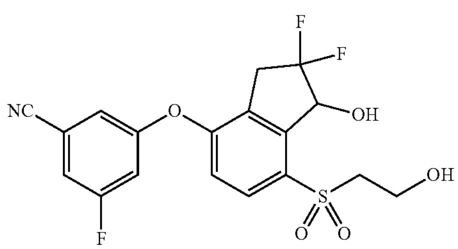 [SMILES: N#Cc1cc(F)cc(Oc2ccc(S(=O)(=O)CCO)c3c2CC(F)(F)C3O)c1] | 414 (M + H) | (400 MHz, CDCl₃): δ 7.90 (d, 1 H), 7.27-7.24 (m, 1 H), 7.16 (br s, 1 H), 7.06 (d, 1 H), 7.00 (d, 1 H), 5.62 (d, 1 H), 4.00-4.16 (m, 2 H), 3.30-3.74 (m, 4 H) |
| 251 | 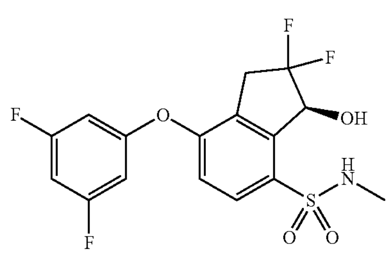 [SMILES: CNS(=O)(=O)c1ccc(Oc2cc(F)cc(F)c2)c2c1[C@H](O)C(F)(F)C2] | 392 (M + H) | (400 MHz, CDCl₃): δ 7.82 (d, 1H), 6.97 (d, 1H), 6.69 (t, 1H), 6.64-6.54 (m, 2H), 5.62 (d, 1H), 5.04-4.96 (m, 1H), 3.50-3.30 (m, 2H), 2.64 (d, 3H) |

TABLE 1-continued

| No. | Structure | Mass Characterization | ¹H NMR Data |
|---|---|---|---|
| 252 | 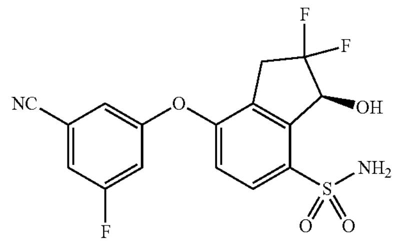 [SMILES: N#Cc1cc(F)cc(Oc2ccc(S(N)(=O)=O)c3c2CC(F)(F)[C@H]3O)c1] | 383 (M − H) | (400 MHz, CDCl$_3$): δ 7.93 (d, 1H), 7.26-7.20 (m, 1H), 7.12 (br s, 1H), 7.04-6.96 (m, 2H), 5.74-5.66 (m, 1H), 5.28 (br s, 2H), 3.50-3.32 (m, 2H) |
| 253 | 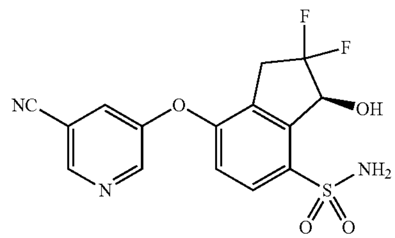 [SMILES: N#Cc1cncc(Oc2ccc(S(N)(=O)=O)c3c2CC(F)(F)[C@H]3O)c1] | 368 (M + H) | (400 MHz, CDCl$_3$): δ 8.67 (s, 1H), 8.58 (s, 1H), 7.85 (d, 1H), 7.58 (s, 1H), 6.89 (d, 1H), 5.54 (d, 2H), 3.50-3.24 (m, 2H) |
| 254 | 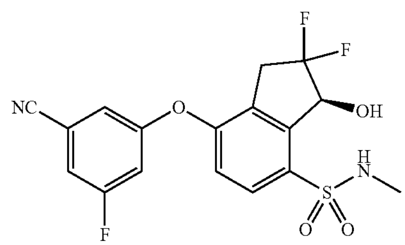 [SMILES: CNS(=O)(=O)c1ccc(Oc2cc(F)cc(C#N)c2)c2c1[C@H](O)C(F)(F)C2] | 399 (M + H) | (400 MHz, CDCl$_3$): δ 7.85 (d, 1H), 7.25-7.18 (m, 1H), 7.13 (brs, 1H), 7.08-6.92 (m, 2H), 5.68-5.56 (m, 1H), 5.05 (br s, 1H), 3.58-3.30 (m, 2H), 2.65 (s, 3H) |
| 255 | 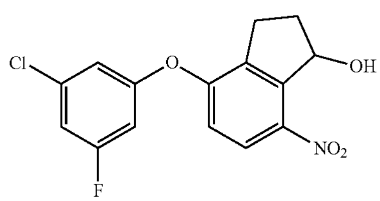 [SMILES: O=[N+]([O-])c1ccc(Oc2cc(F)cc(Cl)c2)c2c1C(O)CC2] | 322 (M − H) | (400 MHz, CDCl$_3$): δ 8.06 (d, 1H), 6.97-6.93 (m, 1H), 6.85-6.83 (m, 1H), 6.69-6.66 (m, 1H), 3.37 (d, 1H), 3.20-3.12 (m, 1H), 2.93-2.85 (m, 1H), 2.52-2.43 (m, 1H), 2.32-2.25 (m, 1H) |
| 256 | 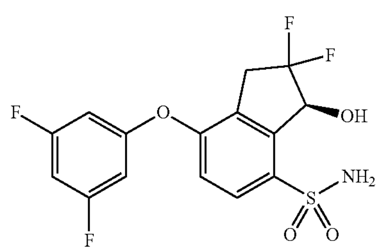 [SMILES: NS(=O)(=O)c1ccc(Oc2cc(F)cc(F)c2)c2c1[C@H](O)C(F)(F)C2] | 378 (M + H) | (400 MHz, CDCl$_3$): δ 7.89 (d, 1H), 6.98 (d, 1H), 6.72-6.60 (m, 1H), 6.62-6.52 (m, 2H), 5.72-5.64 (m, 1H), 5.29 (br s, 2H), 3.56-3.34 (m, 2H) |
| 257 | 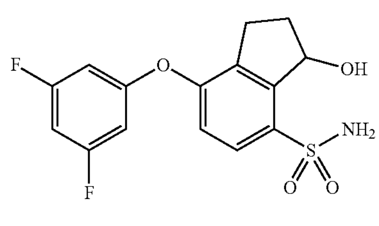 [SMILES: NS(=O)(=O)c1ccc(Oc2cc(F)cc(F)c2)c2c1C(O)CC2] | 340 (M − H) | (400 MHz, CDCl$_3$): δ 7.82 (d, 1H), 6.95 (d, 1H), 6.62 (t, 1H), 6.55-6.50 (m, 2H), 5.84-5.80 (m, 1H), 5.34 (br s, 2H), 3.11-3.03 (m, 1H), 2.83-2.75 (m, 1H), 2.61-2.52 (m, 1H), 2.19-2.10 (m, 1H) |

TABLE 1-continued

| No. | Structure | Mass Characterization | $^1$H NMR Data |
|---|---|---|---|
| 258 | 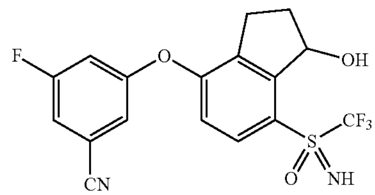 [SMILES: N#Cc1cc(F)cc(Oc2ccc(S(=N)(=O)C(F)(F)F)c3c2CCC3O)c1] | (M − H) 399 | (400 MHz, CDCl$_3$): δ 7.96 (d, 1H), 7.27-7.22 (m, 1H), 7.18-7.15 (m, 1H), 7.07-7.03 (m, 1H), 6.97 (d, 1H), 5.59 (d, 1H), 4.59 (s, 1H), 3.89 (s, 1H), 3.18 (dt, 1H), 2.96 (ddd, 1H), 2.43-2.27 (m, 2H) |
| 259 | 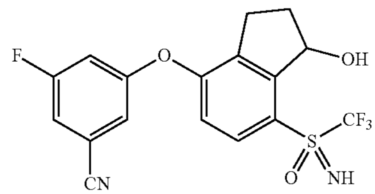 [SMILES: N#Cc1cc(F)cc(Oc2ccc(S(=N)(=O)C(F)(F)F)c3c2CCC3O)c1] | (M − H) 399 | (400 MHz, CDCl$_3$): δ 8.01 (d, 1H), 7.25-7.21 (m, 1H), 7.17-7.14 (m, 1H), 7.06-7.01 (m, 1H), 6.96 (d, 1H), 5.78-5.73 (m, 1H), 3.96-3.93 (m, 1H), 3.73 (s, 1H), 3.13 (dt, 1H), 2.87 (ddd, 1H), 2.52-2.41 (m, 1H), 2.31-2.23 (m, 1H) |
| 260 | 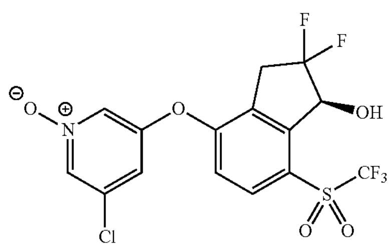 [SMILES: O=S(=O)(c1ccc(Oc2cc(Cl)c[n+](O)c2)c2c1[C@H](O)C(F)(F)C2)C(F)(F)F] | (M + H) 446, 448 | (400 MHz, CDCl$_3$): δ 8.17 (s, 1H), 8.03 (s, 1H), 7.99 (d, 1H), 7.11 (d, 1H), 7.08 (s, 1H), 5.44 (dd, 1H), 3.64-3.42 (m, 3H) |
| 261 | 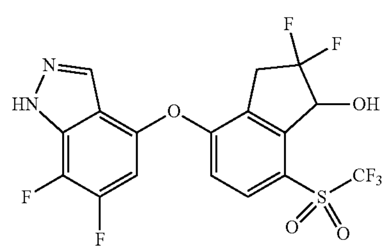 [SMILES: O=S(=O)(c1ccc(Oc2cc(F)c(F)c3[nH]ncc23)c2c1C(O)C(F)(F)C2)C(F)(F)F] | (M + H) 471 | (400 MHz, CDCl$_3$): δ 7.95 -7.87 (m, 2H), 6.95 (d, 1H), 6.77 (dd, 1H), 5.46 (d, 1H), 3.66-3.58 (m, 2H), 3.25 (m, 1H) |
| 262 | 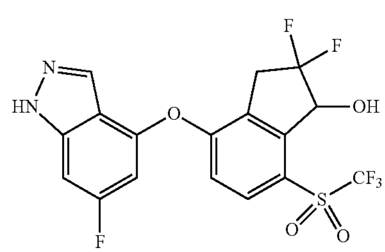 [SMILES: O=S(=O)(c1ccc(Oc2cc(F)cc3[nH]ncc23)c2c1C(O)C(F)(F)C2)C(F)(F)F] | (M + H) 453 | (400 MHz, CDCl$_3$): δ 7.91 -7.88 (m, 2H), 7.12 (d, 1H), 7.03 (d, 1H), 6.66 (d, 1H), 6.46 (d, 1H), 3.66-3.56 (m, 2H), 3.26 (br s, 1H) |
| 263 | 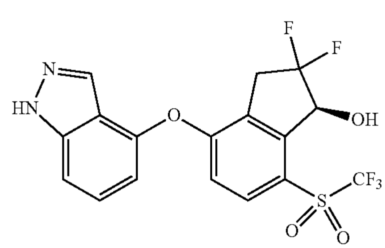 [SMILES: O=S(=O)(c1ccc(Oc2cccc3[nH]ncc23)c2c1[C@H](O)C(F)(F)C2)C(F)(F)F] | (M + H) 435 | (400 MHz, CDCl$_3$): δ 7.92 (s, 1H), 7.84 (d, 1H), 7.48-7.42 (m, 2H), 6.92 (d, 1H), 6.86 (d, 1H), 5.46 (d, 1H), 3.68-3.59 (m, 2H), 3.28 (br s, 1H) |

TABLE 1-continued

| No. | Structure | Mass Characterization | $^1$H NMR Data |
|---|---|---|---|
| 264 | 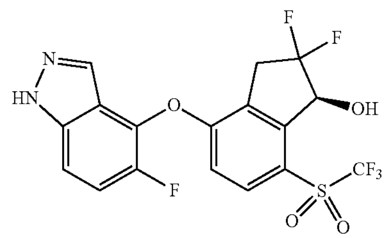 [SMILES: O=S(=O)(c1ccc(Oc2c(F)ccc3[nH]ncc23)c2c1[C@H](O)C(F)(F)C2)C(F)(F)F] | (M + H) 453 | (400 MHz, CDCl$_3$): δ 7.93 (d, 1H), 7.84 (d, 1H), 7.13 (t, 1H), 6.81 (d, 1H), 6.86 (d, 1H), 5.46 (d, 1H), 3.68-3.69 (m, 2H), 3.29 (br s, 1H) |
| 265 | 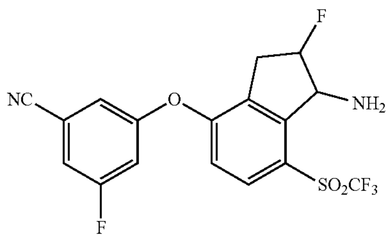 | 419 (M + H) | (400 MHz, CDCl$_3$): δ 7.90 (d, 1 H), 7.30-7.28 (m, 1 H), 7.19 (br s, 1 H), 7.10-7.06 (m, 1 H), 6.92 (d, 1 H), 5.44-5.26 (m, 1 H), 4.93 (t, 1 H), 3.40-3.24 (m, 2 H), 1.95 (br s, 2H) |
| 266 | 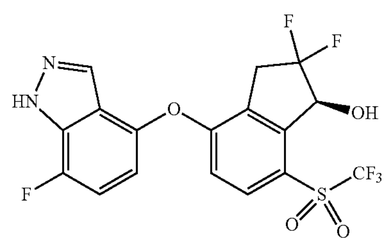 [SMILES: O=S(=O)(c1ccc(Oc2ccc(F)c3[nH]ncc23)c2c1[C@H](O)C(F)(F)C2)C(F)(F)F] | (M + H) 453 | (400 MHz, CDCl$_3$): δ 7.96 (s, 1H), 7.83 (d, 1H), 7.36 (t, 1H), 6.81 (d, 1H), 6.68 (d, 1H), 5.47 (d, 1H), 3.74-3.65 (m, 2H), 3.28 (br s, 1H) |
| 267 | 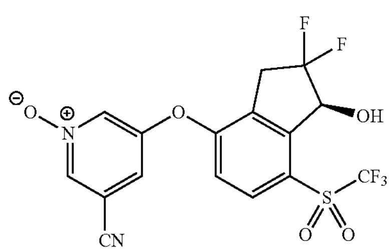 [SMILES: N#Cc1cc(Oc2ccc(S(=O)(=O)C(F)(F)F)c3c2CC(F)(F)[C@H]3O)c[n+](O)c1] | (M − H) 435 | (400 MHz, CDCl$_3$): δ 8.32 (s, 1H), 8.23 (s, 1H), 8.03 (d, 1H), 7.23 (s, 1H), 7.13 (d, 1H), 5.46 (dd, 1H), 3.64-3.42 (m, 2H), 3.25 (d, 1H) |
| 268 | 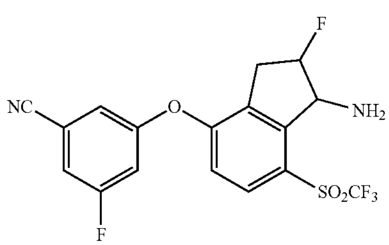 | 419 (M + H) | (400 MHz, CDCl$_3$): δ 7.90 (d, 1 H), 7.30-7.28 (m, 1 H), 7.22 (br s, 1 H), 7.12-7.08 (m, 1 H), 6.95 (d, 1 H), 5.25-5.12 (m, 1 H), 4.95 (d, 1 H), 3.52-3.46 (m, 1 H), 3.29-3.18 (m, 1H), 1.73 (br s, 2H) |
| 269 | 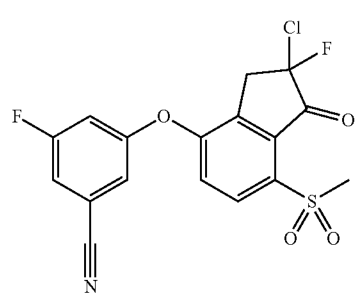 [SMILES: CS(=O)(=O)c1ccc(Oc2cc(F)cc(C#N)c2)c2c1C(=O)C(F)(Cl)C2] | 398/400 (M + NH$_4^+$) | (400 MHz, CDCl$_3$): δ 8.23-8.21 (m, 1 H), 7.35-7.32 (m, 1 H), 7.26-7.24 (m, 1 H), 7.23-7.21 (m, 1 H), 7.14-7.10 (m, 1 H), 3.97-3.78 (m, 2 H), 3.43 (s, 3 H) |

TABLE 1-continued

| No. | Structure | Mass Characterization | ¹H NMR Data |
|---|---|---|---|
| 270 | 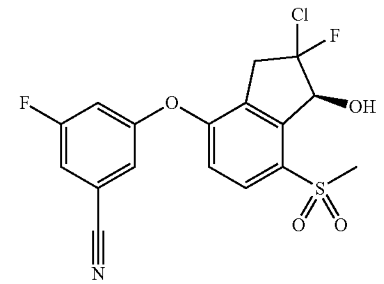 [SMILES: CS(=O)(=O)c1ccc(Oc2cc(F)cc(C#N)c2)c2c1[C@H](O)C(F)(Cl)C2] | 417/419 (M + NH₄⁺) | (400 MHz, CDCl₃): δ 7.95-7.91 (m, 1 H), 7.26-7.23 (m, 1 H), 7.14-7.13 (m, 1 H), 7.06-7.00 (m, 2 H), 5.80-5.78 (m, 0.5 H), 5.65-5.61 (m, 0.5 H), 3.81-3.55 (m, 3.5 H), 3.25 (s, 1.5 H), 3.24 (s, 1.5 H) |
| 271 | 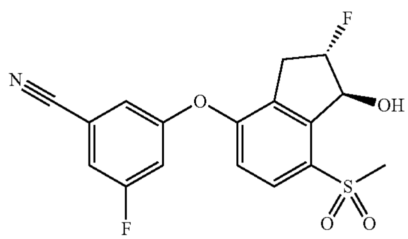 [SMILES: CS(=O)(=O)c1ccc(Oc2cc(F)cc(C#N)c2)c2c1[C@H](O)[C@@H](F)C2] | 383 (M + NH₄⁺) | (400 MHz, CDCl₃): δ 7.87 (d, 1 H), 7.23-7.21 (m, 1 H), 7.13-7.12 (m, 1 H), 7.05-7.00 (m, 2 H), 5.62-5.56 (m, 1 H), 5.44-5.29 (m, 1 H), 3.66 (dd, 1 H), 3.49-3.35 (m, 1 H), 3.20 (s, 3 H), 3.17-3.06 (m, 1 H) |
| 272 | 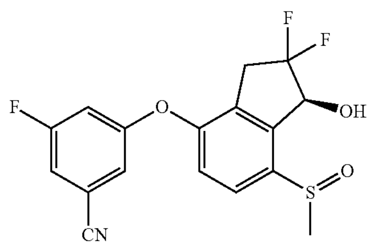 [SMILES: CS(=O)c1ccc(Oc2cc(F)cc(C#N)c2)c2c1[C@H](O)C(F)(F)C2] | [M + H] 368 | (400 MHz, CDCl₃): δ 7.84-7.80 (m, 1H), 7.19-7.16 (m, 1H), 7.10 (d, 1H), 7.08-7.06 (m, 1H), 7.00-6.96 (m, 1H), 5.40 (d, 1H), 4.48-4.36 (m, 1H), 3.49-3.27 (m, 2H), 2.93 (s, 3H) |
| 273 | 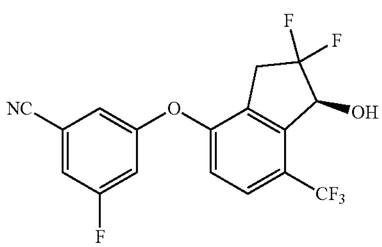 [SMILES: N#Cc1cc(F)cc(Oc2ccc(C(F)(F)F)c3c2CC(F)(F)[C@H]3O)c1] | [M + formate − H] 418 | (400 MHz, CDCl₃): δ 7.63 (d, 1H), 7.21-7.18 (m, 1H), 7.11-7.09 (m, 1H), 7.03-6.97 (m, 2H), 5.29 (d, 1H), 3.51-3.28 (m, 2H), 2.76 (br s, 1H) |
| 274 | 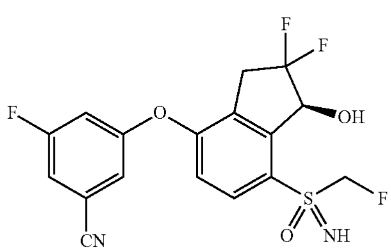 [SMILES: N#Cc1cc(F)cc(Oc2ccc(S(=N)(=O)CF)c3c2CC(F)(F)[C@H]3O)c1] | (M + H) 401 | (400 MHz, CDCl₃): δ 7.95 (d, 1H), 7.28-7.25 (m, 1H), 7.17-7.15 (m, 1H), 7.06 (dt, 1H), 7.00 (d, 1H), 5.62-5.56 (m, 1H), 5.37 (dd, 1H), 5.24 (dd, 1H), 4.26 (d, 1H), 3.57-3.34 (m, 2H), 3.20 (br d, 1H) |
| 275 | 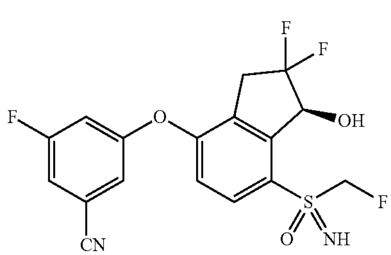 [SMILES: N#Cc1cc(F)cc(Oc2ccc(S(=N)(=O)CF)c3c2CC(F)(F)[C@H]3O)c1] | (M + H) 401 | (400 MHz, CDCl₃): δ 7.96 (d, 1H), 7.28-7.25 (m, 1H), 7.18-7.16 (m, 1H), 7.06 (dt, 1H), 7.01 (d, 1H), 5.42 (dd, 1H), 5.27 (dd, 1H), 5.15 (dd, 1H), 5.04-5.02 (m, 1H), 3.62-3.38 (m, 2H), 3.33 (br s, 1H) |

TABLE 1-continued

| No. | Structure | Mass Characterization | ¹H NMR Data |
|---|---|---|---|
| 276 | 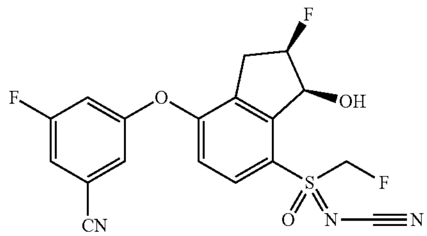 [SMILES: N#CN=S(=O)(CF)c1ccc(Oc2cc(F)cc(C#N)c2)c2c1[C@H](O)[C@H](F)C2] | (M + H) 408 | (400 MHz, CDCl$_3$): δ 8.00 (d, 1H), 7.30 (ddd, 1H), 7.21-7.19 (m, 1H), 7.09 (dt, 1H), 6.99 (d, 1H), 5.92 (dd, 1H), 5.76-5.69 (m, 1H), 5.65 (dd, 1H), 5.55-5.37 (m, 1H), 3.43-3.18 (m, 2H), 3.22 (dd, 1H) |
| 277 | 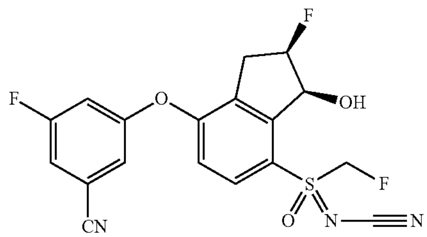 [SMILES: N#CN=S(=O)(CF)c1ccc(Oc2cc(F)cc(C#N)c2)c2c1[C@H](O)[C@H](F)C2] | (M + H) 408 | (400 MHz, CDCl$_3$): δ 8.04 (d, 1H), 7.31 (ddd, 1H), 7.24-7.22 (m, 1H), 7.11 (dt, 1H), 7.00 (d, 1H), 6.27 (dd, 1H), 5.75-5.69 (m, 1H), 5.55 (dd, 1H), 5.56-5.39 (m, 1H), 3.45-3.22 (m, 2H), 3.12 (t, 1H) |
| 278 | 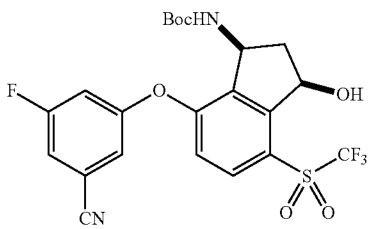 [SMILES: CC(C)(C)OC(=O)N[C@H]1C[C@@H](O)c2c(S(=O)(=O)C(F)(F)F)ccc(Oc3cc(F)cc(C#N)c3)c21] | (M + Cl⁻) 551, 553 | (400 MHz, CDCl$_3$): δ 7.97 (d, 1H), 7.27-7.23 (m, 1H), 7.17-7.13 (m, 1H), 7.07 (dt, 1H), 7.02 (d, 1H), 5.54 (dd, 1H), 5.49-5.41 (m, 1H), 5.12 (br d, 1H), 3.33 (br s, 1H), 2.73-2.64 (m, 1H), 2.22 (d, 1H), 1.35 (s, 9H) |
| 279 | 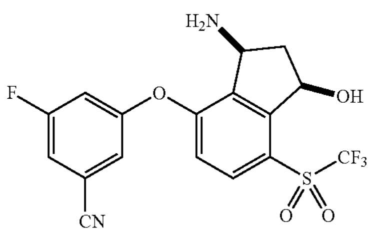 [SMILES: N#Cc1cc(F)cc(Oc2ccc(S(=O)(=O)C(F)(F)F)c3c2[C@@H](N)C[C@H]3O)c1] | (M + H) 417 | (400 MHz, CDCl$_3$): δ 7.93 (d, 1H), 7.31 (ddd, 1H), 7.26-7.24 (m, 1H), 7.16 (dt, 1H), 6.94 (d, 1H), 5.53 (d, 1H), 4.59 (d, 1H), 2.69-2.61 (m, 1H), 2.35-1.95 (m, 4H) |
| 280 | 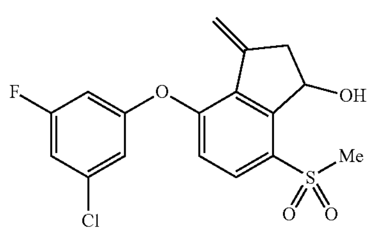 [SMILES: C=C1CC(O)c2c(S(C)(=O)=O)ccc(Oc3cc(F)cc(Cl)c3)c21] | (M + H) 369, 371 | (400 MHz, CDCl$_3$): δ 7.79 (d, 1H), 6.98 (ddd, 1H), 6.91 (d, 1H), 6.91-6.89 (m, 1H), 6.74 (dt, 1H), 5.97 (t, 1H), 5.68 (dt, 1H), 5.41 (t, 1H), 3.75 (d, 1H), 3.26-3.17 (m, 1H), 3.20 (s, 3H), 2.91-2.84 (m, 1H) |
| 281 | 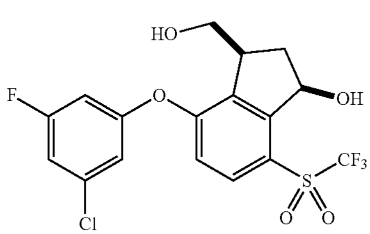 [SMILES: O=S(=O)(c1ccc(Oc2cc(F)cc(Cl)c2)c2c1[C@H](O)C[C@@H]2CO)C(F)(F)F] | (M + H) 387, 389 | (400 MHz, CDCl$_3$): δ 7.85 (d, 1H), 6.95 (ddd, 1H), 6.92 (d, 1H), 6.88-6.85 (m, 1H), 6.70 (dt, 1H), 5.65 (d, 1H), 4.24-4.06 (br m, 1H), 4.08 (dd, 1H), 3.88 (dd, 1H), 3.64-3.59 (m, 1H), 3.26 (s, 3H), 2.69 (ddd, 1H), 2.66-2.48 (br m, 1H), 2.12 (d, 1H) |

TABLE 1-continued

| No. | Structure | Mass Characterization | ¹H NMR Data |
|---|---|---|---|
| 282 | 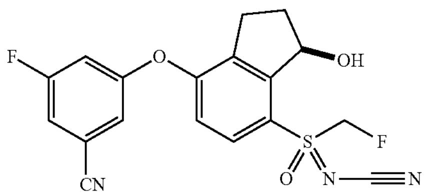 [SMILES: N#CN=S(=O)(CF)c1ccc(Oc2cc(F)cc(C#N)c2)c2c1[C@H](O)CC2] | (M + H) 390 | (400 MHz, CDCl₃): δ 7.93 (d, 1H), 7.27 (ddd, 1H), 7.20-7.18 (m, 1H), 7.08 (dt, 1H), 7.00 (d, 1H), 5.98 (dd, 1H), 5.80-5.75 (m, 1H), 5.49 (dd, 1H), 3.17 (dt, 1H), 2.94 (ddd, 1H), 2.86 (d, 1H), 2.62-2.51 (m, 1H), 2.29-2.20 (m, 1H) |
| 283 | 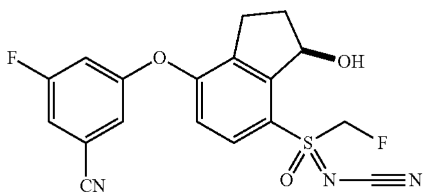 [SMILES: N#CN=S(=O)(CF)c1ccc(Oc2cc(F)cc(C#N)c2)c2c1[C@H](O)CC2] | (M + H) 390 | (400 MHz, CDCl₃): δ 7.91 (d, 1H), 7.27 (ddd, 1H), 7.19-7.16 (m, 1H), 7.06 (dt, 1H), 6.98 (d, 1H), 5.85-5.79 (m, 1H), 5.72 (dd, 1H), 5.61 (dd, 1H), 3.15 (ddd, 1H), 2.97 (d, 1H), 2.89 (ddd, 1H), 2.62-2.52 (m, 1H), 2.27-2.18 (m, 1H) |
| 284 | 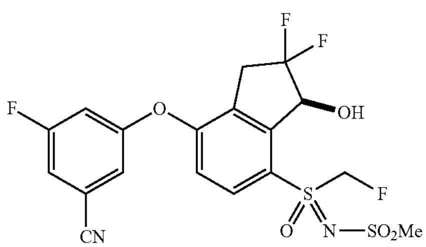 [SMILES: CS(=O)(=O)N=S(=O)(CF)c1ccc(Oc2cc(F)cc(C#N)c2)c2c1[C@H](O)C(F)(F)C2] | (M + H) 479 | (400 MHz, CDCl₃): δ 8.04 (d, 1H), 7.30 (ddd, 1H), 7.22-7.19 (m, 1H), 7.10 (dt, 1H), 7.01 (d, 1H), 5.97 (dd, 1H), 5.70 (dd, 1H), 5.60 (dd, 1H), 3.68 (d, 1H), 3.61-3.39 (m, 2H), 3.23 (s, 3H) |
| 285 | 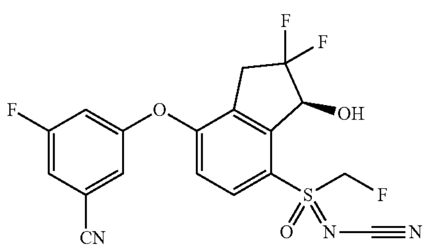 [SMILES: N#CN=S(=O)(CF)c1ccc(Oc2cc(F)cc(C#N)c2)c2c1[C@H](O)C(F)(F)C2] | (M + H) 426 | (400 MHz, CDCl₃): δ 8.01 (d, 1H), 7.34 (ddd, 1H), 7.25-7.22 (m, 1H), 7.12 (dt, 1H), 7.01 (d, 1H), 5.75 (dd, 1H), 5.71-5.65 (m, 1H), 5.61 (dd, 1H), 3.64-3.45 (m, 2H), 3.14 (dd, 1H) |
| 286 | 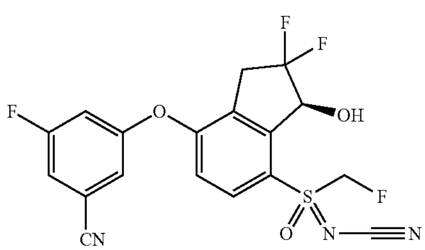 [SMILES: N#CN=S(=O)(CF)c1ccc(Oc2cc(F)cc(C#N)c2)c2c1[C@H](O)C(F)(F)C2] | (M + H) 426 | (400 MHz, CDCl₃): δ 8.03 (d, 1H), 7.34 (ddd, 1H), 7.26-7.24 (m, 1H), 7.14 (dt, 1H), 7.02 (d, 1H), 6.02 (dd, 1H), 5.65-5.59 (m, 1H), 5.54 (dd, 1H), 3.66-3.48 (m, 2H), 3.30 (dd, 1H) |
| 287 | 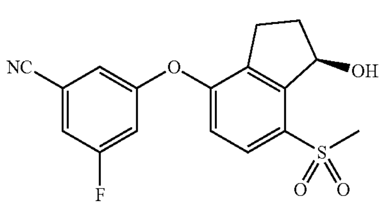 | 392 (M + HCO₂⁻) | (400 MHz, CDCl₃): δ 7.83 (d, 1H), 7.19-7.16 (m, 1H), 7.09-7.07 (m, 1H), 7.01-6.96 (m, 2H), 5.71-5.67 (m, 1H), 3.64 (d, 1H), 3.21 (s, 3H), 3.12-3.02 (m, 1H), 2.84-2.75 (m, 1H), 2.52-2.42 (m, 1H), 2.27-2.18 (m, 1H) |

TABLE 1-continued

| No. | Structure | Mass Characterization | ¹H NMR Data |
|---|---|---|---|
| 288 | 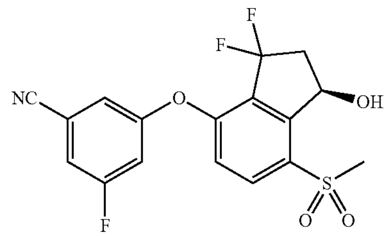 | 428 (M + HCO₂⁻) | (400 MHz, CDCl₃): δ 8.08 (d, 1H), 7.29-7.23 (m, 1H), 7.19 (brs, 1H), 7.15-7.08 (m, 1H), 7.02 (d, 1H), 5.78-5.70 (m, 1H), 3.89 (d, 1H), 3.23 (s, 3H), 3.17-3.02 (m, 1H), 2.80-2.64 (m, 1H) |
| 289 | 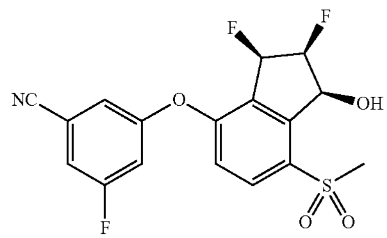 [SMILES: CS(=O)(=O)c1ccc(Oc2cc(F)cc(C#N)c2)c2c1[C@H](O)[C@H](F)[C@@H]2F] | 384 (M + H) | (400 MHz, CDCl₃): δ 8.13 (d, 1H), 7.31-7.25 (m, 1H), 7.23-7.19 (m, 1H), 7.14-7.09 (m, 1H), 7.04 (d, 1H), 6.09-5.91 (m, 1H), 5.87-5.80 (m, 1H), 5.25-5.05 (m, 1H), 3.32 (s, 3H), 2.95 (d, 1H) |
| 290 | 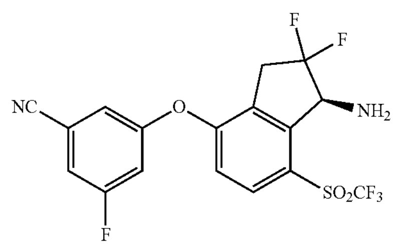 | 437 (M + H) | (400 MHz, CDCl₃): δ 7.92 (d, 1H), 7.34-7.30 (m, 1H), 7.24-7.22 (m, 1H), 7.14-7.10 (m, 1H), 6.94 (d, 1H), 4.85 (d, 1H), 3.65-3.41 (m, 2H) |
| 291 | 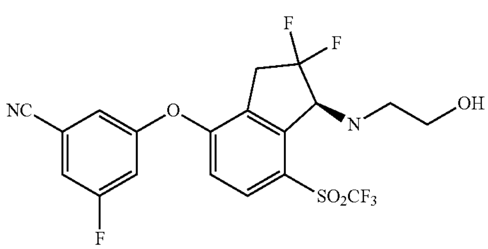 | 481 (M + H) | (400 MHz, CDCl₃): δ 7.95 (d, 1H), 7.35-7.31 (m, 1H), 7.24-7.22 (m, 1H), 7.14-7.10 (m, 1H), 6.95 (d, 1H), 4.59 (d, 1H), 3.77-3.52 (m, 2H), 3.42 (t, 2H), 3.06 (t, 2H) |
| 292 | 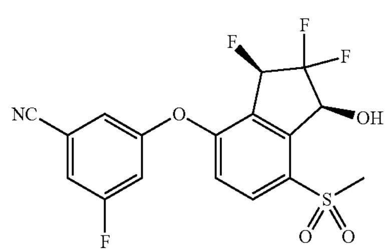 [SMILES: CS(=O)(=O)c1ccc(Oc2cc(F)cc(C#N)c2)c2c1[C@H](O)C(F)(F)[C@@H]2F] | 419 (M + NH4⁺) | (400 MHz, CDCl₃): δ 8.14-8.11 (m, 1H), 7.33-7.29 (m, 1H), 7.25-7.23 (m, 1H), 7.16-7.12 (m, 1H), 7.05 (d, 1H), 5.91-5.75 (m, 1H), 5.71-5.65 (m, 1H), 3.39 (d, 1H), 3.25 (s, 3H) |
| 293 | 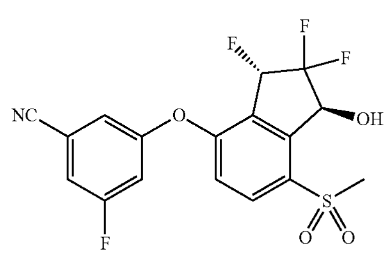 [SMILES: CS(=O)(=O)c1ccc(Oc2cc(F)cc(C#N)c2)c2c1[C@H](O)C(F)(F)[C@H]2F] | 419 (M + NH4⁺) | (400 MHz, CDCl₃): δ 8.10-8.07 (m, 1H), 7.32-7.28 (m, 1H), 7.23-7.20 (m, 1H), 7.15-7.10 (m, 1H), 7.02 (d, 1H), 6.07-5.90 (m, 1H), 5.87-5.80 (m, 1H), 3.95 (d, 1H), 3.26 (s, 3H) |

TABLE 1-continued

| No. | Structure | Mass Characterization | $^1$H NMR Data |
|-----|-----------|----------------------|----------------|
| 294 | 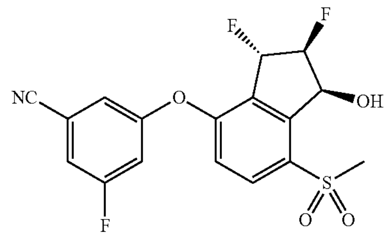 [SMILES: CS(=O)(=O)c1ccc(Oc2cc(F)cc(C#N)c2)c2c1[C@H](O)[C@H](F)[C@H]2F] | 384 (M + H) | (400 MHz, CDCl$_3$): δ 8.09-8.06 (m, 1H), 7.27-7.24 (m, 1H), 7.19-7.17 (m, 1H), 7.10-7.07 (m, 1H), 7.04 (d, 1H), 6.30-6.12 (m, 1H), 5.96-5.89 (m, 1H), 5.46-5.27 (m, 1H), 3.53-3.51 (m, 1H), 3.27 (s, 3H |
| 295 | 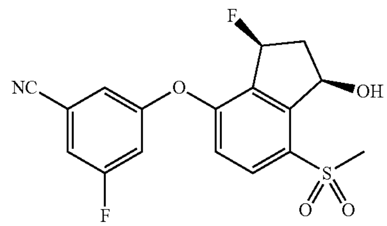 [SMILES: CS(=O)(=O)c1ccc(Oc2cc(F)cc(C#N)c2)c2c1[C@H](O)C[C@@H]2F] | 383 (M + NH4$^+$) | (400 MHz, CDCl$_3$): δ 8.04-8.01 (m, 1H), 7.25-7.22 (m, 1H), 7.18-7.16 (m, 1H), 7.11-7.06 (m, 1H), 7.00 (d, 1H), 6.09-5.79 (m, 1H), 5.69-5.61 (m, 1H), 3.54 (d, 1H), 3.23 (s, 3H), 2.94-2.80 (m, 1H), 2.52-2.41 (m, 1H) |
| 296 | 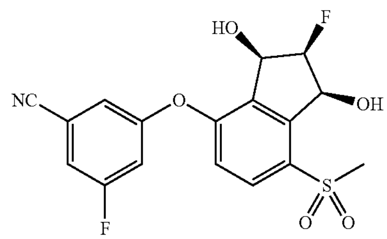 | 399 (M + NH4$^+$) | (400 MHz, CDCl$_3$): δ 8.05 (d, 1H), 7.26-7.22 (m, 1H), 7.19-7.17 (m, 1H), 7.12-7.07 (m, 1H), 7.05 (d, 1H), 5.76-5.70 (m, 1H), 5.30-5.24 (m, 1H), 5.18-5.01 (m, 1H), 3.29 (s, 3H) |
| 297 | 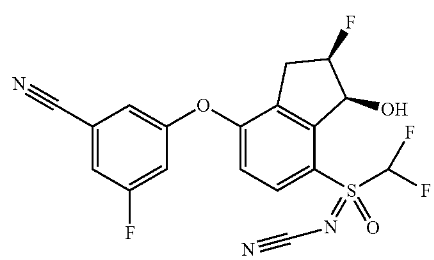 [SMILES: N#CN=S(=O)(c1ccc(Oc2cc(F)cc(C#N)c2)c2c1[C@H](O)[C@H](F)C2)C(F)F] | 426 (M + H) | (400 MHz, CDCl$_3$): δ 8.04 (d, 1H), 7.34-7.30 (m, 1H), 7.25-7.22 (m, 1H), 7.23 (t, J = 54 Hz, 1H), 7.14-7.10 (m, 1H), 7.00 (d, 1H), 5.71-5.63 (m, 1H), 5.56-5.52 (m, 0.5H), 5.43-5.39 (m, 0.5H), 3.59 (t, 1H), 3.46-3.18 (m, 2H) |
| 298 | 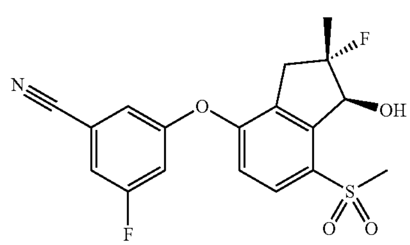 [SMILES: C[C@]1(F)Cc2c(Oc3cc(F)cc(C#N)c3)ccc(S(C)(=O)=O)c2[C@@H]1O] | 397 (M + NH$_4$) | (400 MHz, CDCl$_3$): δ 7.85 (d, 1H), 7.22-7.19 (m, 1H), 7.12-7.09 (m, 1H), 7.03-6.98 (m, 2H), 5.29-5.23 (m, 1H), 3.57-3.53 (m, 1H), 3.26-3.04 (m, 2H), 3.19 (s, 3H), 1.70 (d, J = 22 Hz, 3H) |
| 299 | 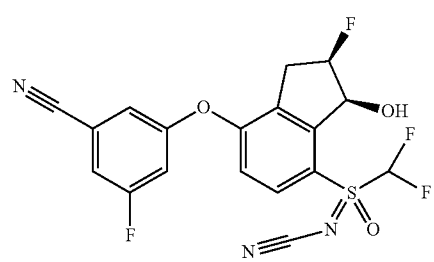 [SMILES: N#CN=S(=O)(c1ccc(Oc2cc(F)cc(C#N)c2)c2c1[C@H](O)[C@H](F)C2)C(F)F] | 426 (M + H) | (400 MHz, CDCl$_3$): δ 8.03 (d, 1H), 7.34-7.30 (m, 1H), 7.23-7.21 (m, 1H), 7.13-7.09 (m, 1H), 7.01 (t, J = 53 Hz, 1H), 6.99 (d, 1H), 5.73-5.66 (m, 1H), 5.56-5.52 (m, 0.5H), 5.43-5.39 (m, 0.5H), 3.45-3.34 (m, 1H), 3.35-3.19 (m, 2H) |

TABLE 1-continued

| No. | Structure | Mass Characterization | ¹H NMR Data |
|---|---|---|---|
| 300 | 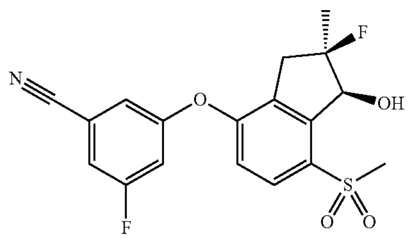 [SMILES: C[C@@]1(F)Cc2c(Oc3cc(F)cc(C#N)c3)ccc(S(C)(=O)=O)c2[C@@H]1O] | 397 (M + NH₄) | (400 MHz, CDCl₃): δ 7.90 (d, 1H), 7.21-7.19 (m, 1H), 7.10-7.08 (m, 1H), 6.99 (dt, 1H), 6.98 (d, 1H), 5.40-5.35 (m, 1H), 3.79-3.77 (m, 1H), 3.36-3.27 (m, 1H), 3.32 (s, 3H), 2.95-2.84 (m, 1H), 1.70 (d, 3H) |
| 301 | 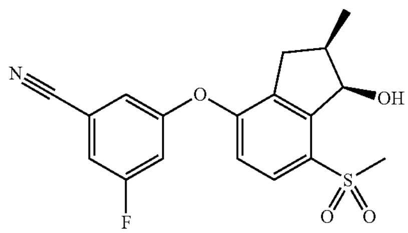 [SMILES: C[C@@H]1Cc2c(Oc3cc(F)cc(C#N)c3)ccc(S(C)(=O)=O)c2[C@@H]1O] | 379 (M + NH₄) | (400 MHz, CDCl₃): δ 7.84 (d, 1H), 7.19-7.15 (m, 1H), 7.07-7.06 (m, 1H), 6.98 (d, 1H), 6.97 (dt, 1H), 5.46-5.43 (m, 1H), 3.12 (s, 3H), 3.08 (d, 1H), 2.97-2.91 (m, 1H), 2.68-2.53 (m, 2H), 1.25 (d, 3H) |
| 302 | 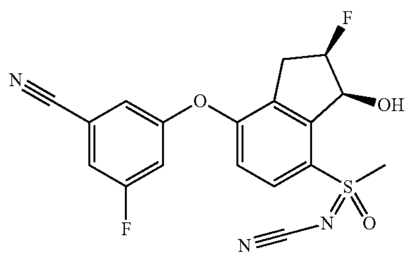 [SMILES: CS(=O)(=NC#N)c1ccc(Oc2cc(F)cc(C#N)c2)c2c1[C@H](O)[C@H](F)C2] | 390 (M + H) | (400 MHz, CDCl₃): δ 8.00 (d, J = 8.7 Hz, 0.5H), 7.95 (d, J = 8.7 Hz, 0.5H), 7.29-7.25 (m, 1H), 7.19-7.16 (m, 1H), 7.10-7.05 (m, 1H), 7.01 (d, 1H), 5.78-5.69 (m, 1H), 5.54-5.50 (m, 0.5H), 5.40-5.37 (m, 0.5H), 3.50 (d, J = 42 Hz, 3H), 3.39-3.11 (m, 3H) |
| 303 | 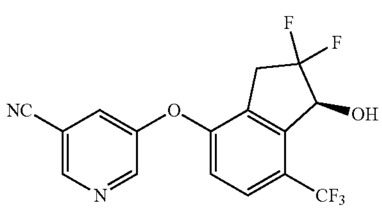 [SMILES: N#Cc1cncc(Oc2ccc(C(F)(F)F)c3c2CC(F)(F)[C@H]3O)c1] | [M + H] = 357 | (400 MHz, CDCl₃): δ 8.72 (s, 1H), 8.64 (s, 1H), 7.64 (d, 1H), 7.59-7.57 (m, 1H), 6.97 (d, 1H), 5.33-5.28 (m, 1H), 3.55-3.32 (m, 2H), 2.86-2.82 (m, 1H) |
| 304 | 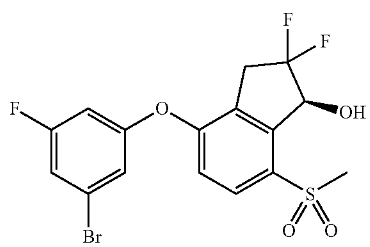 [SMILES: CS(=O)(=O)c1ccc(Oc2cc(F)cc(Br)c2)c2c1[C@H](O)C(F)(F)C2] | 437, 439 (M + H⁺) | (400 MHz, CDCl₃): δ 7.88 (d, 1 H), 7.17-7.13 (m, 1 H), 7.04-7.02 (m, 1 H), 6.98 (d, 1 H), 6.77-6.74 (m, 1 H), 5.61-5.56 (m, 1 H), 3.57-3.36 (m 3 H), 3.22 (s, 3 H) |
| 305 | 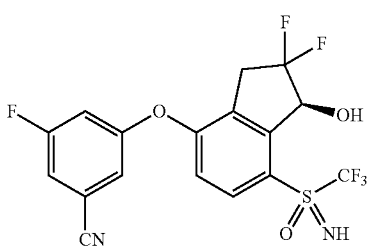 [SMILES: N#Cc1cc(F)cc(Oc2ccc(S(=N)(=O)C(F)(F)F)c3c2CC(F)(F)[C@H]3O)c1] | (M + H) 437 | (400 MHz, CDCl₃): δ 8.01 (d, 1H), 7.32 (ddd, 1H), 7.24-7.22 (m, 1H), 7.12 (dt, 1H), 6.99 (d, 1H), 5.35 (dd, 1H), 4.73-4.71 (m, 1H), 3.97 (br s, 1H), 3.63-3.46 (m, 2H) |

TABLE 1-continued

| No. | Structure | Mass Characterization | ¹H NMR Data |
|---|---|---|---|
| 306 | 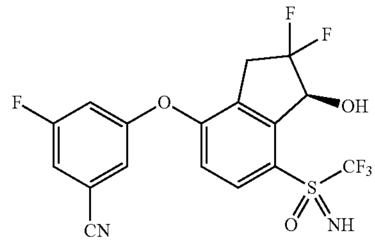 [SMILES: N#Cc1cc(F)cc(Oc2ccc(S(=N)(=O)C(F)(F)F)c3c2CC(F)(F)[C@H]3O)c1] | (M + H) 437 | (400 MHz, CDCl₃): δ 8.07 (d, 1H), 7.30 (ddd, 1H), 7.23-7.21 (m, 1H), 7.11 (dt, 1H), 6.98 (d, 1H), 5.59 (ddd, 1H), 3.97 (d, 1H), 3.81 (br s, 1H), 3.61-3.39 (m, 2H) |
| 307 | 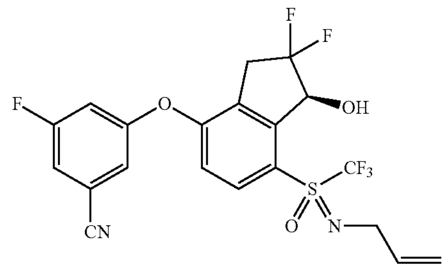 [SMILES: C=CCN=S(=O)(c1ccc(Oc2cc(F)cc(C#N)c2)c2c1[C@H](O)C(F)(F)C2)C(F)(F)F] | (M + H) 477 | (400 MHz, CDCl₃): δ 7.99 (d, 1H), 7.30 (ddd, 1H), 7.23-7.20 (m, 1H), 7.10 (dt, 1H), 6.98 (d, 1H), 6.04-5.93 (m, 1H), 5.35-5.28 (m, 2H), 5.21 (dq, 1H), 4.87 (br s, 1H), 4.16-4.09 (m, 1H), 4.04-3.96 (m, 1H), 3.61-3.44 (m, 2H) |
| 308 | 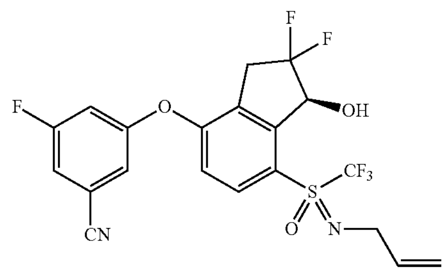 [SMILES: C=CCN=S(=O)(c1ccc(Oc2cc(F)cc(C#N)c2)c2c1[C@H](O)C(F)(F)C2)C(F)(F)F] | (M + H) 477 | (400 MHz, CDCl₃): δ 8.04 (d, 1H), 7.29 (ddd, 1H), 7.21-7.19 (m, 1H), 7.09 (dt, 1H), 6.97 (d, 1H), 5.98 (ddt, 1H), 5.58 (dd, 1H), 5.34 (dq, 1H), 5.19 (dq, 1H), 4.13-4.05 (m, 1H), 4.03-3.95 (m, 1H), 3.59-3.33 (m, 3H) |
| 309 | 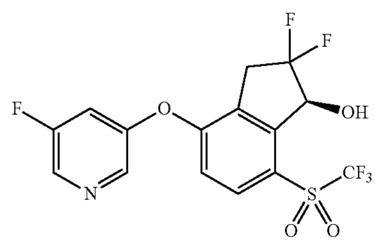 [SMILES: O=S(=O)(c1ccc(Oc2cncc(F)c2)c2c1[C@H](O)C(F)(F)C2)C(F)(F)F] | (M + H) 414 | (400 MHz, CDCl₃): δ 8.49 (d, 1H), 8.37 (d, 1H), 7.93 (d, 1H), 7.26 (dt, 1H), 6.95 (d, 1H), 5.44 (dd, 1H), 3.67-3.48 (m, 2H), 3.42 (d, 1H). |
| 310 | 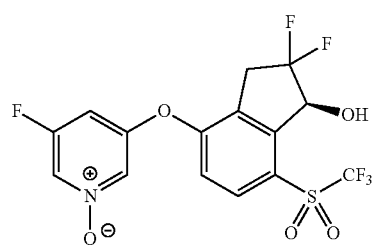 [SMILES: O=S(=O)(c1ccc(Oc2cc(F)c[n+]([O-])c2)c2c1[C@H](O)C(F)(F)C2)C(F)(F)F] | (M + H) 430 | (400 MHz, CDCl₃): δ 8.11-8.08 (m, 1H), 8.01-7.97 (m, 2H), 7.14 (d, 1H), 6.90 (dt, 1H), 5.43 (dd, 1H), 3.95 (d, 1H), 3.62-3.41 (m, 2H) |
| 311 | 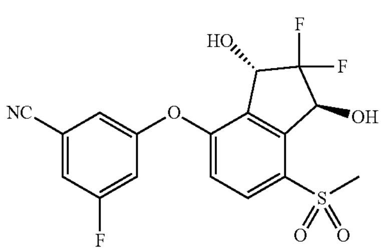 [SMILES: CS(=O)(=O)c1ccc(Oc2cc(F)cc(C#N)c2)c2c1[C@H](O)C(F)(F)[C@H]2O] | 400 (M + H) | (400 MHz, CDCl₃): δ 8.00 (d, 1H), 7.27-7.25 (m, 1H), 7.20-7.18 (m, 1H), 7.12-7.07 (m, 1H), 7.03 (d, 1H), 5.81-5.74 (m, 1H), 5.43-5.36 (m, 1H), 3.81 (d, 1H), 3.25 (s, 3H), 2.71 (m, 1H) |

TABLE 1-continued

| No. | Structure | Mass Characterization | ¹H NMR Data |
|---|---|---|---|
| 312 | 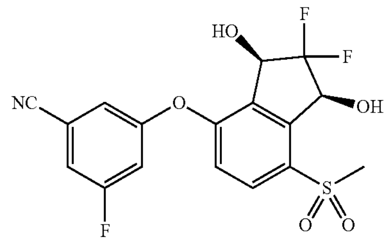 [SMILES: CS(=O)(=O)c1ccc(Oc2cc(F)cc(C#N)c2)c2c1[C@H](O)C(F)(F)[C@@H]2O] | 400 (M + H) | (400 MHz, CDCl₃): δ 8.05 (d, 1H), 7.29-7.20 (m, 2H), 7.15-7.10 (m, 1H), 7.05 (d, 1H), 5.63-5.57 (m, 1H), 5.22-5.15 (m, 1H), 3.53-3.48 (m, 1H), 3.24 (s, 3H), 2.73 (d, 1H) |
| 313 | 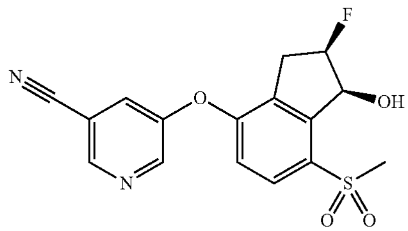 [SMILES: CS(=O)(=O)c1ccc(Oc2cncc(C#N)c2)c2c1[C@H](O)[C@H](F)C2] | 349 (M + H) | (400 MHz, CDCl₃): δ 8.75-8.72 (m, 1H), 8.66-8.64 (m, 1H), 7.92 (d, 1H), 7.61-7.59 (m, 1H), 6.95 (d, 1H), 5.73-5.65 (m, 1H), 5.51-5.47 (m, 0.5H), 5.38-5.34 (m, 0.5H), 3.71-3.68 (m, 1H), 3.36-3.38 (m, 2H), 3.31 (s, 3H) |
| 314 | 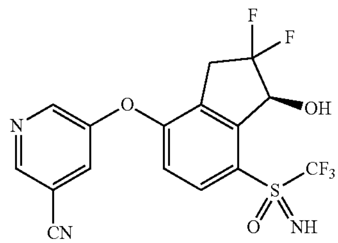 [SMILES: N#Cc1cncc(Oc2ccc(S(=N)(=O)C(F)(F)F)c3c2CC(F)(F)[C@H]3O)c1] | (M + H) 420 | (400 MHz, CDCl₃): δ 8.83 (d, 1H), 8.72 (d, 1H), 8.02 (d, 1H), 7.73 (dd, 1H), 6.95 (d, 1H), 5.35 (dd, 1H), 4.73-4.70 (m s, 1H), 3.99 (br s, 1H), 3.67-3.49 (m, 2H) |
| 315 | 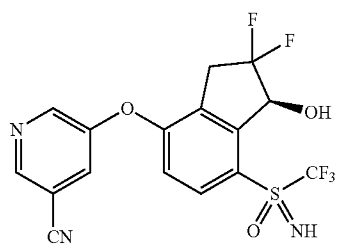 [SMILES: N#Cc1cncc(Oc2ccc(S(=N)(=O)C(F)(F)F)c3c2CC(F)(F)[C@H]3O)c1] | (M + H) 420 | (400 MHz, CDCl₃): δ 8.82 (d, 1H), 8.71 (d, 1H), 8.08 (d, 1H), 7.72 (dd, 1H), 6.93 (d, 1H), 5.63-5.57 (m, 1H), 3.97 (d, 1H), 3.82 (br s, 1H), 3.65-3.43 (m, 2H) |
| 316 | 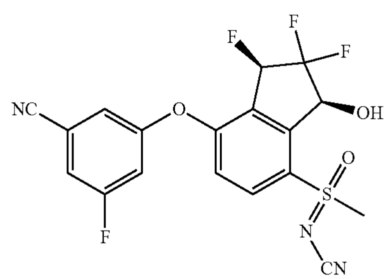 [SMILES: CS(=O)(=NC#N)c1ccc(Oc2cc(F)cc(C#N)c2)c2c1[C@H](O)C(F)(F)[C@@H]2F] | [M + H] 426 | (400 MHz, CD₃OD): δ 8.21 (dd, 1H), 7.59-7.56 (m, 1H), 7.54-7.53 (m, 1H), 7.46 (dt, 1H), 7.25 (d, 1H), 6.00 (dd, 1H), 5.60-5.56 (m, 1H), 3.64 (s, 3H) |
| 317 | 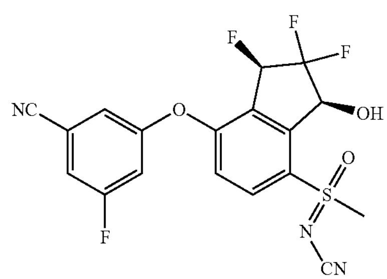 [SMILES: CS(=O)(=NC#N)c1ccc(Oc2cc(F)cc(C#N)c2)c2c1[C@H](O)C(F)(F)[C@@H]2F] | [M + H] 426 | (400 MHz, CDCl₃): δ 8.23-8.20 (m, 1H), 7.38-7.34 (m, 1H), 7.30-7.28 (m, 1H), 7.21-7.17 (m, 1H), 7.09 (d, 1H), 5.90 (dd, 1H), 5.71-5.66 (m, 1H), 3.90-3.88 (m, 1H), 3.64 (s, 3H) |

TABLE 1-continued

| No. | Structure | Mass Characterization | ¹H NMR Data |
|---|---|---|---|
| 318 | 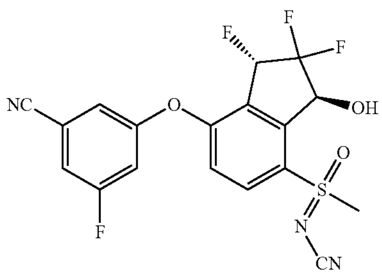 [SMILES: CS(=O)(=NC#N)c1ccc(Oc2cc(F)cc(C#N)c2)c2c1[C@H](O)C(F)(F)[C@H]2F] | [M + H] 426 | (400 MHz, CDCl$_3$): δ 8.13 (dd, 1H), 7.37-7.33 (m, 1H), 7.28-7.27 (m, 1H), 7.19-7.15 (m, 1H), 7.05 (d, 1H), 6.08-5.84 (m, 2H), 4.08 (d, 1H), 3.54 (s, 3H) |
| 319 | 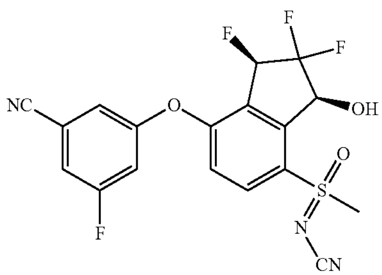 | [M + H] 409 | (400 MHz, CD$_3$COCD$_3$): δ 8.95 (d, 1H), 8.94 (d, 1H), 8.34-8.32 (m, 1H), 8.23-8.20 (m, 1H), 7.45 (d, 1H), 6.43-6.40 (m, 1H), 6.15 (dd, 1H), 5.72-5.66 (m, 1H), 3.69 (s, 3H) |
| 320 | 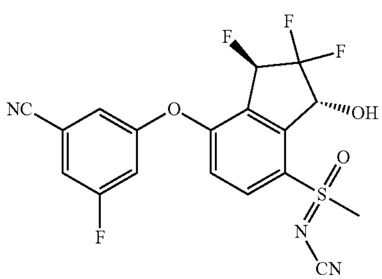 | [M + H] 409 | (400 MHz, CD$_3$COCD$_3$): δ 8.96-8.95 (m, 1H), 8.94-8.92 (m, 1H), 8.34-8.32 (m, 1H), 8.24-8.20 (m, 1H), 7.44-7.41 (m, 1H), 6.51-6.31 (m, 2H), 5.90-5.83 (m, 1H), 3.81 (s, 3H) |
| 321 | 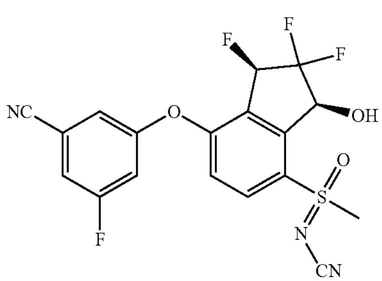 | [M + H] 409 | (400 MHz, CD$_3$COCD$_3$): δ 8.97-8.96 (m, 1H), 8.96-8.94 (m, 1H), 8.35 (dd, 1H), 8.25 (dd, 1H), 7.45 (d, 1H), 6.50 (brs, 1H), 6.16 (dd, 1H), 5.68-5.30 (m, 1H), 3.80 (s, 3H) |
| 322 | 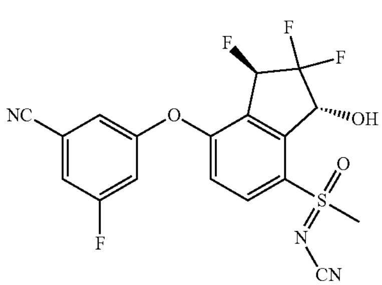 | [M + H] 409 | (400 MHz, CD$_3$COCD$_3$): δ 8.95-8.94 (m, 1H), 8.94-8.92 (m, 1H), 8.33 (dd, 1H), 8.19 (dd, 1H), 7.41 (d, 1H), 6.50-6.28 (m, 2H), 5.90-5.85 (m, 1H), 3.70 (s, 3H) |

TABLE 1-continued

| No. | Structure | Mass Characterization | ¹H NMR Data |
|---|---|---|---|
| 323 | 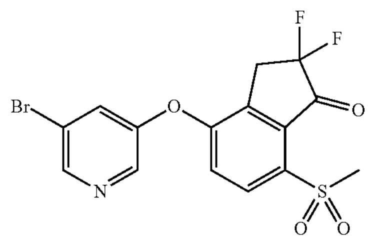 [SMILES: CS(=O)(=O)c1ccc(Oc2cncc(Br)c2)c2c1C(=O)C(F)(F)C2] | 418, 420 (M + H) | (400 MHz, CD₃COCD₃): δ 8.65-8.63 (m, 1H), 8.60-8.59 (m, 1H), 8.15-8.12 (m, 1H), 8.02-8.00 (m, 1H), 7.60-7.57 (m, 1H), 3.86-3.79 (m, 2H), 3.39 (s, 3H) |
| 324 | 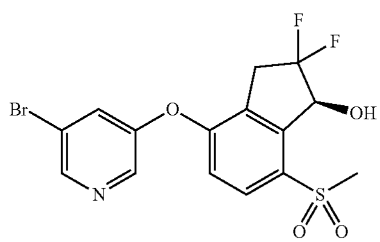 [SMILES: CS(=O)(=O)c1ccc(Oc2cncc(Br)c2)c2c1[C@H](O)C(F)(F)C2] | 420, 422 (M + H) | (400 MHz, CDCl₃): δ 8.61-8.59 (m, 1H), 8.41-8.39 (m, 1H), 7.91-7.87 (d, 1H), 7.61-7.58 (m, 1H), 6.95-6.9 (d, 1H), 5.63-5.57 (m, 1H), 3.61-3.40 (m, 3H), 3.23 (s, 3H) |
| 325 | 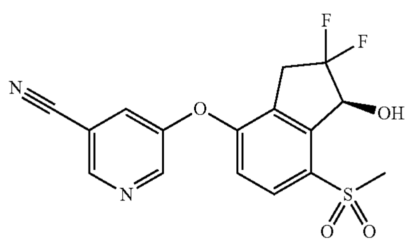 [SMILES: CS(=O)(=O)c1ccc(Oc2cncc(C#N)c2)c2c1[C@H](O)C(F)(F)C2] | 367 (M + H) | (400 MHz, CDCl₃): δ 8.76-8.75 (m, 1H), 8.67-8.66 (m, 1H), 7.95 (d, 1H), 7.70-7.68 (m, 1H), 6.98 (d, 1H), 5.60 (d, 1H), 3.57-3.35 (m, 3H), 3.22 (s, 3H) |
| 326 | 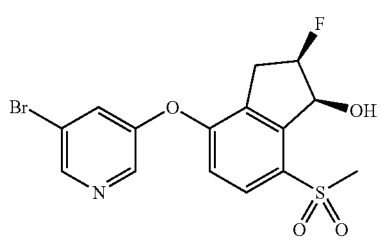 [SMILES: CS(=O)(=O)c1ccc(Oc2cncc(Br)c2)c2c1[C@H](O)[C@H](F)C2] | 402, 404 (M + H) | (400 MHz, CDCl₃): δ 8.57-8.56 (m, 1H), 8.39-8.38 (m, 1H), 7.88 (d, 1H), 7.56-7.54 (m, 1H), 6.91 (d, 1H), 5.72-5.65 (m, 1H), 5.51-5.47 (m, 0.5H), 5.38-5.34 (m, 0.5H), 3.71-3.69 (m, 1H), 3.38-3.09 (m, 3H), 3.29 (s, 3H) |
| 327 | 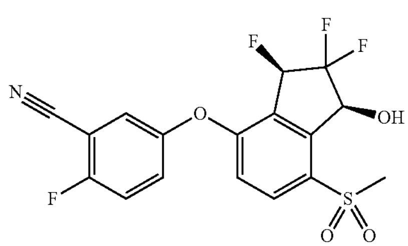 [SMILES: CS(=O)(=O)c1ccc(Oc2ccc(F)c(C#N)c2)c2c1[C@H](O)C(F)(F)[C@@H]2F] | 402 (M + H) | (400 MHz, CDCl₃): δ 8.10-8.06 (m, 1H), 7.44-7.32 (m, 3H), 6.91 (d, 1H), 5.95-5.91 (m, 0.5H), 5.81-5.78 (m, 0.5H), 5.70-5.64 (m, 1H), 4.00-3.97 (m, 1H), 3.24 (s, 3H) |
| 328 | 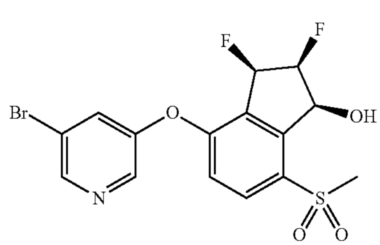 [SMILES: CS(=O)(=O)c1ccc(Oc2cncc(Br)c2)c2c1[C@H](O)[C@H](F)[C@@H]2F] | 420, 422 (M + H) | (400 MHz, CDCl₃): δ 8.63-8.61 (m, 1H), 8.45-8.43 (m, 1H), 8.11-8.07 (m, 1H), 7.66-7.64 (m, 1H), 6.96 (d, 1H), 6.13-6.11 (m, 0.5H), 5.99-5.97 (m, 0.5H), 5.86-5.82 (m, 1H), 5.24-5.04 (m, 1H), 3.30 (s, 3H), 3.03-3.00 (m, 1H) |

TABLE 1-continued

| No. | Structure | Mass Characterization | ¹H NMR Data |
|---|---|---|---|
| 329 | 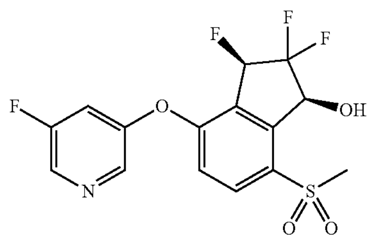 [SMILES: CS(=O)(=O)c1ccc(Oc2cncc(F)c2)c2c1[C@H](O)C(F)(F)[C@@H]2F] | 378 (M + H) | (400 MHz, CDCl₃): δ 8.49-8.47 (m, 1H), 8.39-8.37 (m, 1H), 8.11-8.07 (m, 1H), 7.29-7.25 (m, 1H), 7.00 (d, 1H), 5.96-5.93 (m, 0.5H), 5.83-5.79 (m, 0.5H), 5.71-5.65 (m, 1H), 3.65-3.63 (m, 1H), 3.24 (s, 3H) |
| 330 | 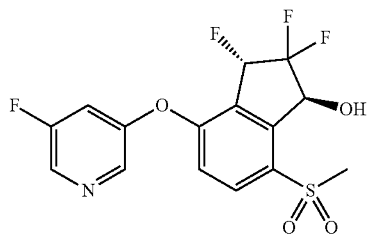 [SMILES: CS(=O)(=O)c1ccc(Oc2cncc(F)c2)c2c1[C@H](O)C(F)(F)[C@H]2F] | 378 (M + H) | (400 MHz, CDCl₃): δ 8.49-8.46 (m, 1H), 8.39-8.36 (m, 1H), 8.08-8.04 (m, 1H), 8.28-8.24 (m, 1H), 6.98 (d, 1H), 6.12-6.08 (m, 0.5H), 5.99-5.95 (m, 0.5H), 5.88-5.81 (m, 1H), 4.10-4.06 (m, 1H), 3.26 (s, 3H) |
| 331 | 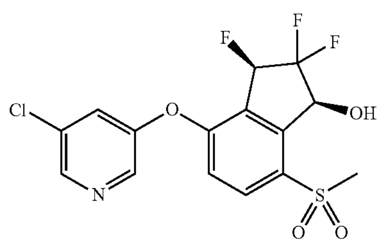 [SMILES: CS(=O)(=O)c1ccc(Oc2cncc(Cl)c2)c2c1[C@H](O)C(F)(F)[C@@H]2F] | 394, 396 (M + H) | (400 MHz, CDCl₃): δ 8.56-8.55 (m, 1H), 8.44-8.43 (m, 1H), 8.11-8.08 (m, 1H), 7.54-7.52 (m, 1H), 6.99 (d, 1H), 5.96-5.92 (m, 0.5H), 5.83-5.79 (m, 0.5H), 5.71-5.65 (m, 1H), 3.66-3.64 (m, 1H), 3.25 (s, 3H) |
| 332 | 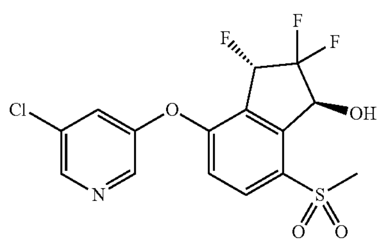 [SMILES: CS(=O)(=O)c1ccc(Oc2cncc(Cl)c2)c2c1[C@H](O)C(F)(F)[C@H]2F] | 394, 396 (M + H) | (400 MHz, CDCl₃): δ 8.56-8.54 (m, 1H), 8.43-8.41 (m, 1H), 8.08-8.04 (m, 1H), 7.52-7.50 (m, 1H), 6.96 (d, 1H), 6.12-6.08 (m, 0.5H), 5.98-5.94 (m, 0.5H), 5.88-5.81 (m, 1H), 4.02-3.99 (m, 1H), 3.26 (s, 3H) |
| 333 | 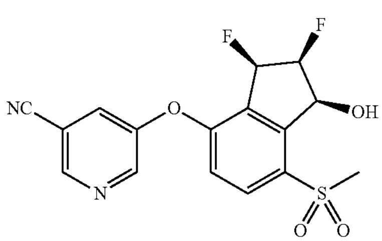 [SMILES: CS(=O)(=O)c1ccc(Oc2cncc(C#N)c2)c2c1[C@H](O)[C@H](F)[C@@H]2F] | 367 (M + H) | (400 MHz, CD₃COCD₃): δ 8.88-8.86 (m, 1H), 8.82-8.80 (m, 1H), 8.13-8.08 (m, 2H), 7.33 (d, 1H), 6.21-6.18 (m, 0.5H), 6.07-6.04 (m, 0.5H), 5.83-5.79 (m, 1H), 5.36-5.29 (m, 0.5H), 5.25-5.16 (m, 0.5H), 5.07-5.04 (m, 1H), 3.33 (s, 3H) |
| 334 | 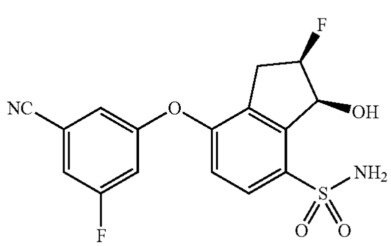 [SMILES: N#Cc1cc(F)cc(Oc2ccc(S(N)(=O)=O)c3c2C[C@@H](F)[C@H]3O)c1] | 365 (M − H) | (400 MHz, CD₃OD): δ 7.87 (d, 1H), 7.42-7.35 (m, 1H), 7.26-7.13 (m, 2H), 7.08 (d, 1H), 5.63-5.51 (m, 1H), 5.40-5.18 (m, 1H), 3.20-3.15 (m, 2H) |

TABLE 1-continued

| No. | Structure | Mass Characterization | ¹H NMR Data |
|---|---|---|---|
| 335 | 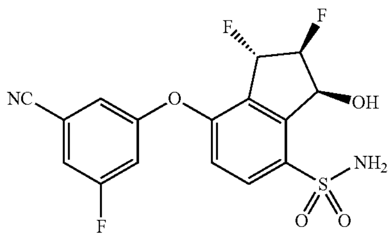 [SMILES: N#Cc1cc(F)cc(Oc2ccc(S(N)(=O)=O)c3c2[C@H](F)[C@@H](F)[C@H]3O)c1] | 383 (M − H) | (400 MHz, CD$_3$OD): δ 8.04 (d, 1H), 7.45-7.41 (m, 1H), 7.31-7.29 (m, 1H), 7.26-7.21 (m, 1H), 7.18 (d, 1H), 6.30-6.11 (m, 1H), 5.80 (t, 1H), 5.37-5.17 (m, 1H) |
| 336 | 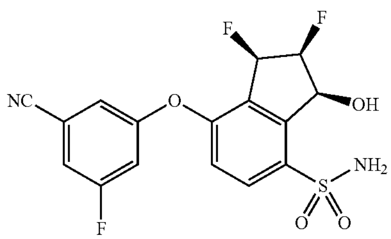 [SMILES: N#Cc1cc(F)cc(Oc2ccc(S(N)(=O)=O)c3c2[C@@H](F)[C@@H](F)[C@H]3O)c1] | 383 (M − H) | |
| 337 | 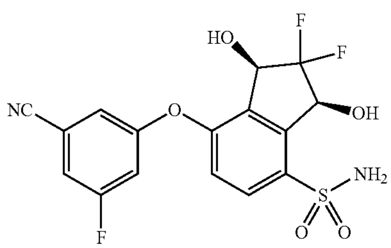 [SMILES: N#Cc1cc(F)cc(Oc2ccc(S(N)(=O)=O)c3c2[C@@H](O)C(F)(F)[C@H]3O)c1] | 399 (M − H) | (400 MHz, CD$_3$OD): δ 8.00 (d, 1H), 7.44-7.41 (m, 1H), 7.35-7.32 (m, 1H), 7.29-7.24 (m, 1H), 7.14 (d, 1H), 5.46 (d, 1H), 5.06 (d, 1H) |
| 338 | 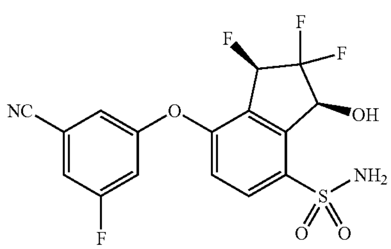 [SMILES: N#Cc1cc(F)cc(Oc2ccc(S(N)(=O)=O)c3c2[C@@H](F)C(F)(F)[C@H]3O)c1] | 401 (M − H) | (400 MHz, CD$_3$OD): δ 8.03-8.00 (m, 1H), 7.24-7.20 (m, 1H), 7.17-7.15 (m, 1H), 7.08-7.04 (m, 1H), 6.96 (d, 1H), 5.82-5.65 (m, 1H), 5.54-5.48 (m, 1H) |
| 339 | 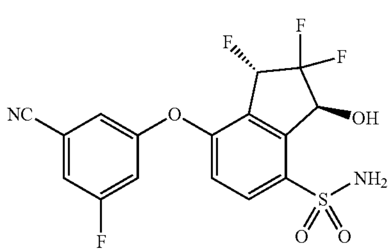 [SMILES: N#Cc1cc(F)cc(Oc2ccc(S(N)(=O)=O)c3c2[C@H](F)C(F)(F)[C@H]3O)c1] | 401 (M − H) | (400 MHz, CD$_3$OD): δ 8.09-8.05 (m, 1H), 7.50-7.46 (m, 1H), 7.39-7.38 (m, 1H), 7.33-7.29 (m, 1H), 7.14 (d, 1H), 6.19-6.02 (m, 1H), 5.72-5.65 (m, 1H) |
| 340 | 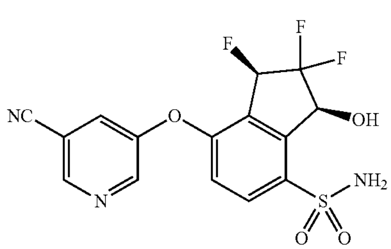 [SMILES: N#Cc1cncc(Oc2ccc(S(N)(=O)=O)c3c2[C@@H](F)C(F)(F)[C@H]3O)c1] | 384 (M − H) | (400 MHz, CD$_3$OD): δ 8.81 (d, 1H), 8.73 (d, 1H), 8.11-8.07 (m, 1H), 8.06-8.04 (m, 1H), 7.18 (d, 1H), 6.04-5.86 (m, 1H), 5.57-5.51 (m, 1H) |

TABLE 1-continued

| No. | Structure | Mass Characterization | ¹H NMR Data |
|---|---|---|---|
| 341 | 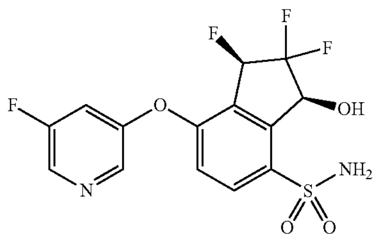 [SMILES: NS(=O)(=O)c1ccc(Oc2cncc(F)c2)c2c1[C@H](O)C(F)(F)[C@@H]2F] | 377 (M − H) | (400 MHz, CD₃OD): δ 8.43 (d, 1H), 8.35 (d, 1H), 8.10-8.06 (m, 1H), 7.59-7.54 (m, 1H), 7.15 (d, 1H), 6.03-5.85 (m, 1H), 5.56-5.50 (m, 1H) |
| 342 | 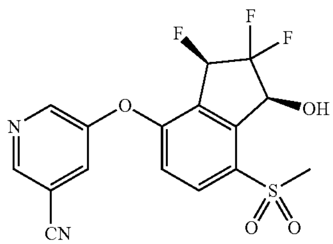 [SMILES: CS(=O)(=O)c1ccc(Oc2cncc(C#N)c2)c2c1[C@H](O)C(F)(F)[C@@H]2F] | (M + H) 385 | (400 MHz, CDCl₃): δ 8.82 (d, 1H), 8.74 (d, 1H), 8.14 (dd, 1H), 7.74 (dd, 1H), 7.02 (d, 1H), 5.87 (dd, 1H), 5.73-5.66 (m, 1H), 3.58 (d, 1H), 3.26 (s, 3H) |
| 343 | 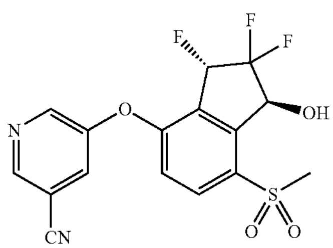 [SMILES: CS(=O)(=O)c1ccc(Oc2cncc(C#N)c2)c2c1[C@H](O)C(F)(F)[C@H]2F] | (M + H) 385 | (400 MHz, (CD₃)₂CO): δ 8.89 (dd, 1H), 8.86 (d, 1H), 8.21 (dd, 1H), 8.11 (dd, 1H), 7.36 (d, 1H), 6.36 (ddd, 1H), 6.10 (d, 1H), 5.87-5.80 (m, 1H), 3.31 (s, 3H) |
| 344 | 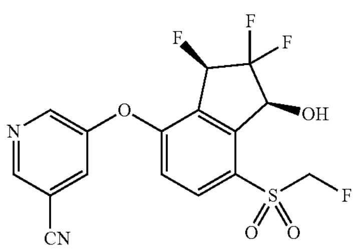 [SMILES: N#Cc1cncc(Oc2ccc(S(=O)(=O)CF)c3c2[C@@H](F)C(F)(F)[C@H]3O)c1] | (M + H) 403 | (400 MHz, CDCl₃): δ 8.84 (d, 1H), 8.75 (d, 1H), 8.15 (dd, 1H), 7.77 (dd, 1H), 7.02 (d, 1H), 5.83 (dd, 1H), 5.68-5.62 (m, 1H), 5.43 (dd, 1H), 5.31 (dd, 1H), 3.43 (dd, 1H) |
| 345 | 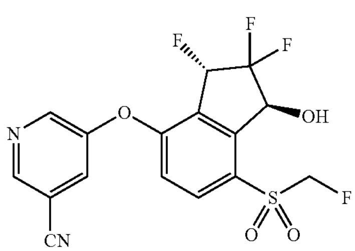 [SMILES: N#Cc1cncc(Oc2ccc(S(=O)(=O)CF)c3c2[C@H](F)C(F)(F)[C@H]3O)c1] | (M + H) 403 | (400 MHz, (CD₃)₂CO): δ 8.93 (dd, 1H), 8.90 (dd, 1H), 8.26 (dd, 1H), 8.13 (dd, 1H), 7.38 (d, 1H), 6.39 (ddd, 1H), 5.73 (dd, 1H), 5.80 (ddd, 1H), 5.61 (dd, 1H) |
| 346 | 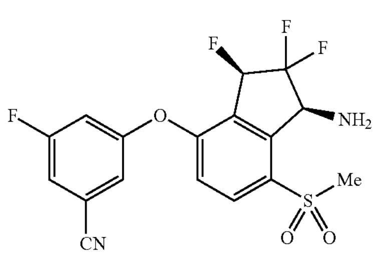 [SMILES: CS(=O)(=O)c1ccc(Oc2cc(F)cc(C#N)c2)c2c1[C@H](N)C(F)(F)[C@@H]2F] | (M + H) 401 | (400 MHz, CDCl₃): δ 8.14 (dd, 1H), 7.30 (ddd, 1H), 7.24-7.22 (m, 1H), 7.14 (dt, 1H), 6.98 (d, 1H), 5.77 (dd, 1H), 5.10-5.01 (m, 1H), 3.45 (s, 3H), 1.82 (br d, 2H) |

TABLE 1-continued

| No. | Structure | Mass Characterization | ¹H NMR Data |
|---|---|---|---|
| 347 | 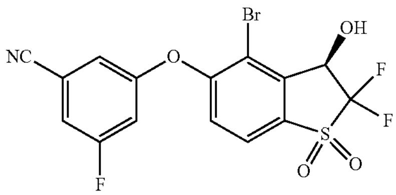 [SMILES: N#Cc1cc(F)cc(Oc2ccc3c(c2Br)[C@@H](O)C(F)(F)S3(=O)=O)c1] | | (400 MHz, CDCl₃): δ 7.86 (d, 1H), 7.27 (d, 1H), 7.27-7.24 (m, 1H), 7.13-7.11 (m, 1H), 7.04-7.00 (m, 1H), 5.41-5.37 (m, 1H), 3.06 (d, 1H) |
| 348 | 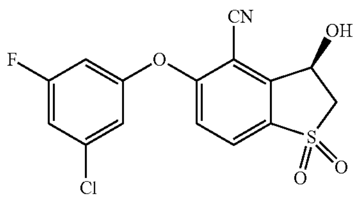 [SMILES: N#Cc1c(Oc2cc(F)cc(Cl)c2)ccc2c1[C@@H](O)CS2(=O)=O] | 352, 354 (M − H) | (CDCl₃, 400 MHz) δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H) |
| 349 | 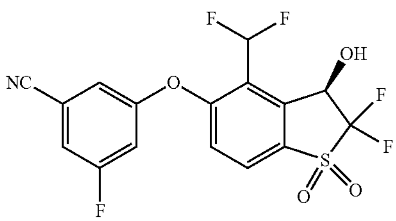 [SMILES: N#Cc1cc(F)cc(Oc2ccc3c(c2C(F)F)[C@@H](O)C(F)(F)S3(=O)=O)c1] | 404 (M − H) | (400 MHz, CDCl₃): δ 7.98 (d, 1H), 7.33-7.30 (m, 1H), 7.23 (t, 1H), 7.22-7.18 (m, 2H), 7.10-7.06 (m, 1H), 5.69-5.65 (m, 1H), 3.23 (d, 1H) |
| 350 | 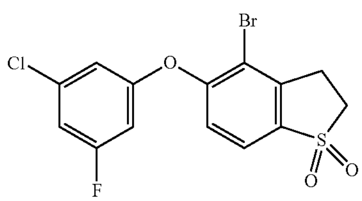 [SMILES: O=S1(=O)CCc2c1ccc(Oc1cc(F)cc(Cl)c1)c2Br] | 391, 393, 395 (M + H) | (400 MHz, CDCl₃): δ 7.70 (d, 1H), 7.10 (d, 1H), 6.93 (ddd, 1H), 6.78-6.76 (m, 1H), 6.63 (dt, 1H), 3.62-3.58 (m, 2H), 3.42-3.37 (m, 2H) |
| 351 | 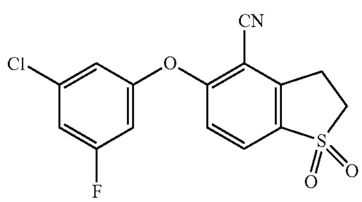 [SMILES: N#Cc1c(Oc2cc(F)cc(Cl)c2)ccc2c1CCS2(=O)=O] | 336, 338 (M + H) | (400 MHz, CDCl₃): δ 7.87 (d, 1H), 7.06 (dt, 1H), 7.03 (d, 1H), 6.94-6.92 (m, 1H), 6.78 (dt, 1H), 3.66-3.61 (m, 2H), 3.60-3.55 (m, 2H) |
| 352 | 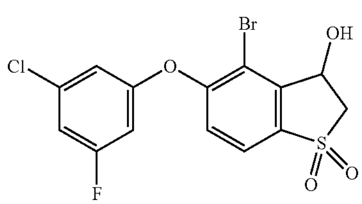 [SMILES: O=S1(=O)CC(O)c2c1ccc(Oc1cc(F)cc(Cl)c1)c2Br] | 424, 426, 428 (M + NH₄) | (400 MHz, CDCl₃): δ 7.72 (d, 1H), 7.19 (d, 1H), 6.98-6.94 (ddd, 1H), 6.82-6.80 (m, 1H), 6.67 (dt, 1H), 5.60 (td, 1H), 3.80 (dd, 1H), 3.68 (dd, 1H), 2.89 (d, 1H) |
| 353 | 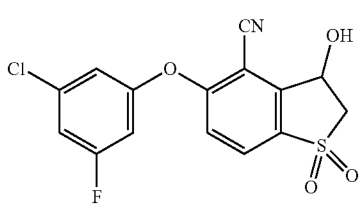 [SMILES: N#Cc1c(Oc2cc(F)cc(Cl)c2)ccc2c1C(O)CS2(=O)=O] | 352, 354 (M − H) | (400 MHz, CDCl₃): δ 7.89 (d, 1H), 7.13 (d, 1H), 7.07 (ddd, 1H), 6.97-6.94 (m, 1H), 6.80 (dt, 1H), 5.79-5.72 (m, 1H), 3.91 (dd, 1H), 3.64 (dd, 1H), 3.57 (br d, 1H) |

TABLE 1-continued
| No. | Structure | Mass Characterization | ¹H NMR Data |
|---|---|---|---|
| 354 | 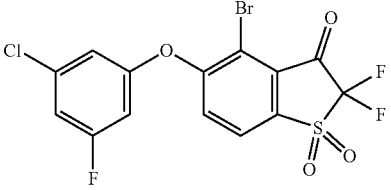 [SMILES: O=C1c2c(ccc(Oc3cc(F)cc(Cl)c3)c2Br)S(=O)(=O)C1(F)F] | | (400 MHz, CDCl$_3$): δ 7.89 (d, 1H), 7.50 (d, 1H), 7.06 (ddd, 1H), 6.89-6.86 (m, 1H), 6.73 (dt, 1H) |
| 355 | 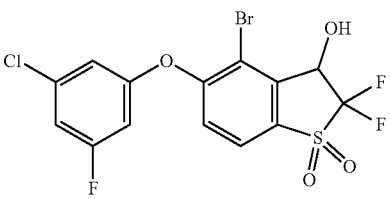 [SMILES: O=S1(=O)c2ccc(Oc3cc(F)cc(Cl)c3)c(Br)c2C(O)C1(F)F] | 425, 427, 429 (M − OH) | (400 MHz, CDCl$_3$): δ 7.80 (d, 1H), 7.22 (d, 1H), 7.01 (dt, 1H), 6.87-6.85 (m, 1H), 6.71 (dt, 1H), 5.38 (d, 1H), 2.98 (br s, 1H) |
| 356 | 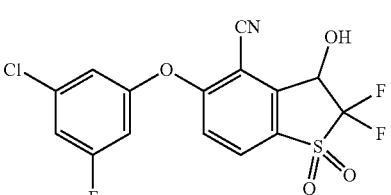 | 388, 390 (M − H) | (400 MHz, CDCl$_3$): δ 7.97 (d, 1H), 7.19 (d, 1H), 7.12 (ddd, 1H), 6.99-6.97 (m, 1H), 6.83 (dt, 1H), 5.58-5.51 (m, 1H), 3.51 (br d, 1H) |
| 357 | 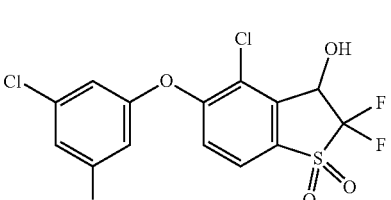 | 397, 399 (M − H) | (400 MHz, CDCl$_3$): δ 7.76 (d, 1H), 7.26 (d, 1H), 7.01 (ddd, 1H), 6.87-6.85 (m, 1H), 6.71 (dt, 1H), 5.44 (dd, 1H), 2.94 (d, 1H) |
| 358 | 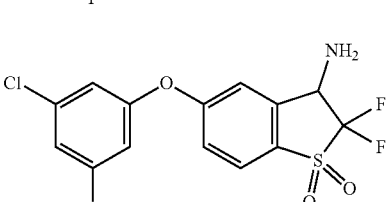 | 364, 366 (M + H) | (400 MHz, CDCl$_3$): δ 7.81 (d, 1H), 7.36 (dd, 1H), 7.20 (ddd, 1H), 6.99 (ddd, 1H), 6.89-6.86 (m, 1H), 6.71 (dt, 1H), 4.73-4.61 (m, 1H), 1.79 (br d, 2H) |
| 359 | 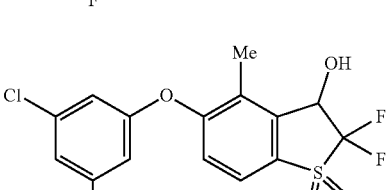 | 377, 379 (M − H) | (400 MHz, CDCl$_3$): δ 7.70 (d, 1H), 7.16 (d, 1H), 6.95 (ddd, 1H), 6.80-6.78 (m, 1H), 6.64 (dt, 1H), 5.30 (dd, 1H), 2.72 (dd, 1H), 2.43 (s, 3H) |
| 360 | 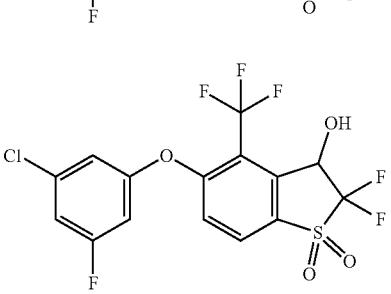 | 431, 433 (M − H) | (400 MHz, CDCl$_3$): δ 8.00 (d, 1H), 7.29 (d, 1H), 7.04 (ddd, 1H), 6.91-6.89 (m, 1H), 6.74 (dt, 1H), 5.58 (d, 1H), 3.16 (br s, 1H) |

TABLE 1-continued

| No. | Structure | Mass Characterization | $^1$H NMR Data |
|---|---|---|---|
| 361 | 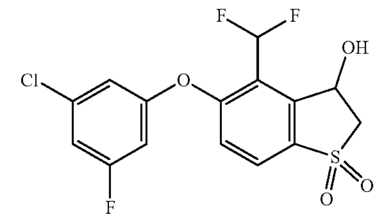 [SMILES: O=S1(=O)CC(O)c2c1ccc(Oc1cc(F)cc(Cl)c1)c2C(F)F] | 377, 379 (M − H) | (400 MHz, CDCl$_3$): δ 7.85 (d, 1H), 7.22 (t, 1H), 7.14 (dt, 1H), 7.01 (ddd, 1H), 6.87-6.85 (m, 1H), 6.71 (dt, 1H), 5.90-5.85 (m, 1H), 3.77 (ddd, 1H), 3.67 (dd, 1H), 2.87 (t, 1H) |
| 362 | 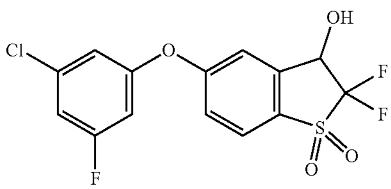 [SMILES: O=S1(=O)c2ccc(Oc3cc(F)cc(Cl)c3)cc2C(O)C1(F)F] | 363, 365 (M − H) | (400 MHz, CDCl$_3$): δ 7.84 (d, 1H), 7.27-7.23 (m, 2H), 7.01 (dt, 1H), 6.90-6.88 (m, 1H), 6.72 (dt, 1H), 5.35 (q, 1H), 2.79 (dd, 1H) |
| 363 | 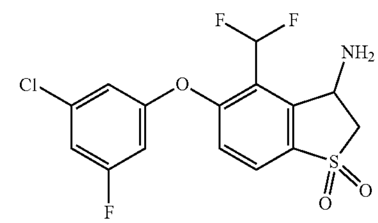 [SMILES: NC1CS(=O)(=O)c2ccc(Oc3cc(F)cc(Cl)c3)c(C(F)F)c21] | 378, 380 (M + H) | (400 MHz, CDCl$_3$): δ 7.80 (d, 1H), 7.22 (t, 1H), 7.06 (dt, 1H), 7.00 (dt, 1H), 6.87-6.84 (m, 1H), 6.70 (dt, 1H), 5.16-5.03 (br s, 1H), 3.75 (dd, 1H), 3.49 (dd, 1H), 2.20-1.97 (br s, 2H) |
| 364 | 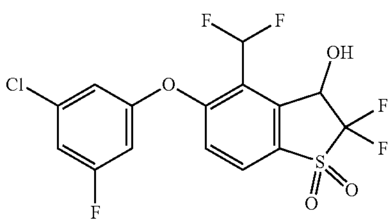 [SMILES: O=S1(=O)c2ccc(Oc3cc(F)cc(Cl)c3)c(C(F)F)c2C(O)C1(F)F] | 413, 415 (M − H) | (400 MHz, CDCl$_3$): δ 7.93 (d, 1H), 7.25 (t, 1H), 7.21-7.17 (m, 1H), 7.06 (ddd, 1H), 6.92-6.89 (m, 1H), 6.75 (dt, 1H), 5.67 (dd, 1H), 3.10 (dd, 1H) |
| 365 | 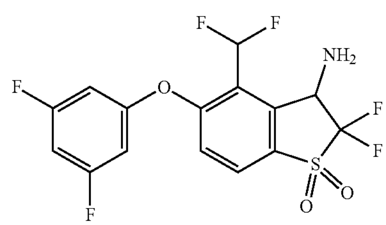 [SMILES: NC1c2c(ccc(Oc3cc(F)cc(F)c3)c2C(F)F)S(=O)(=O)C1(F)F] | 398 (M + H) | (400 MHz, CDCl$_3$): δ 7.90 (d, 1H), 7.28 (dd, 1H), 7.18-7.14 (m, 1H), 6.76 (tt, 1H), 6.67-6.60 (m, 2H), 4.98 (dt, 1H), 2.01 (br d, 2H) |
| 366 | 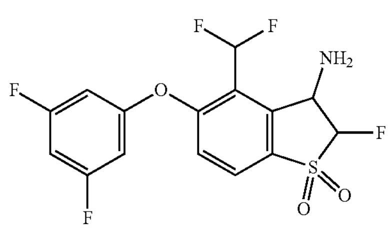 [SMILES: NC1c2c(ccc(Oc3cc(F)cc(F)c3)c2C(F)F)S(=O)(=O)C1F] | 380 (M + H) | (400 MHz, CDCl$_3$): δ 7.87 (d, 1H), 7.44 (dd, 1H), 7.15 (d, 1H), 6.73 (tt, 1H), 6.64-6.57 (m, 2H), 5.58 (dd, 1H), 5.17-5.07 (m, 1H), 2.02-1.93 (m, 2H) |
| 367 | 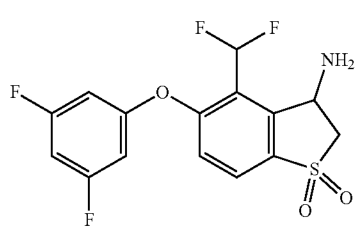 [SMILES: NC1CS(=O)(=O)c2ccc(Oc3cc(F)cc(F)c3)c(C(F)F)c21] | 362 (M + H) | (400 MHz, CDCl$_3$): δ 7.81 (d, 1H), 7.22 (t, 1H), 7.10-7.06 (m, 1H), 6.72 (tt, 1H), 6.63-6.56 (m, 2H), 5.14-5.07 (m, 1H), 3.75 (dd, 1H), 3.49 (dd, 1H), 2.12-2.04 (m, 2H) |

TABLE 1-continued

| No. | Structure | Mass Characterization | ¹H NMR Data |
|-----|-----------|----------------------|-------------|
| 368 | 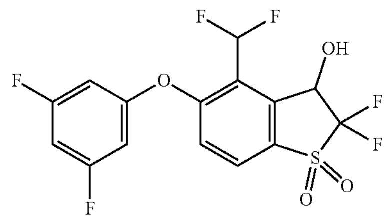 [SMILES: O=S1(=O)c2ccc(Oc3cc(F)cc(F)c3)c(C(F)F)c2C(O)C1(F)F] | 397 (M − H) | (400 MHz, CDCl$_3$): δ 7.93 (d, 1H), 7.25 (t, 1H), 7.23-7.19 (m, 1H), 6.78 (tt, 1H), 6.68-6.61 (m, 2H), 5.67 (dd, 1H), 3.09 (dd, 1H) |
| 369 | 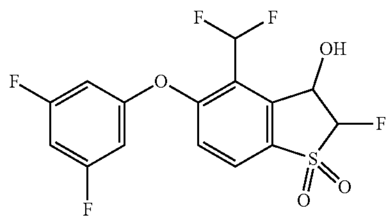 [SMILES: O=S1(=O)c2ccc(Oc3cc(F)cc(F)c3)c(C(F)F)c2C(O)C1F] | 379 (M − H) | (400 MHz, CDCl$_3$): δ 7.89 (d, 1H), 7.29 (t, 1H), 7.19 (d, 1H), 6.74 (tt, 1H), 6.65-6.58 (m, 2H), 5.87-5.80 (m, 1H), 5.66 (dd, 1H), 2.98 (ddd, 1H) |
| 370 | 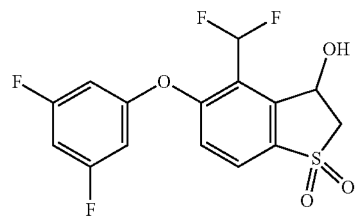 | 363 (M + H) | (400 MHz, CDCl$_3$): δ 7.85 (d, 1H), 7.25 (t, 1H), 7.16 (dt, 1H), 6.73 (tt, 1H), 6.63-6.56 (m, 1H), 5.90-5.86 (m, 1H), 5.90-5.85 (m, 1H), 3.78 (ddd, 1H), 3.67 (dd, 1H), 2.89 (t, 1H) |
| 371 | 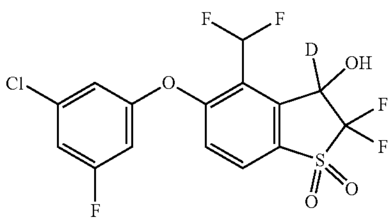 [SMILES: [2H]C1(O)c2c(ccc(Oc3cc(F)cc(Cl)c3)c2C(F)F)S(=O)(=O)C1(F)F] | 414, 416 (M − H) | (400 MHz, CDCl$_3$): δ 7.95-7.92 (m, 1H), 7.25 (t, 1H), 7.21-7.17 (m, 1H), 7.06 (ddd, 1H), 6.92-6.89 (m, 1H), 6.75 (dt, 1H), 3.07 (d, 1H) |
| 372 | 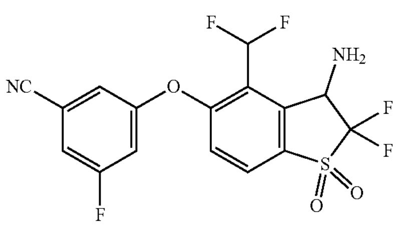 [SMILES: N#Cc1cc(F)cc(Oc2ccc3c(c2C(F)F)C(N)C(F)(F)S3(=O)=O)c1] | 405 (M + H) | (400 MHz, CDCl$_3$): δ 7.95 (d, 1H), 7.31-7.27 (m, 1H), 7.30 (dd, 1H), 7.19-7.14 (m, 2H), 7.07 (dt, 1H), 5.00-4.92 (m, 1H), 2.03 (d, 2H) |
| 373 | 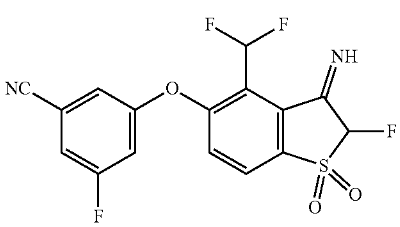 [SMILES: N#Cc1cc(F)cc(Oc2ccc3c(c2C(F)F)C(=N)C(F)S3(=O)=O)c1] | 385 (M + H) | (400 MHz, CDCl$_3$): δ 11.26-11.22 (m, 1H), 8.09 (dd, 1H), 8.06 (d, 1H), 7.04 (d, 1H), 7.27-7.23 (m, 1H), 7.15-7.13 (m, 1H), 7.06 (dt, 1H), 5.87 (dd, 1H) |
| 374 | 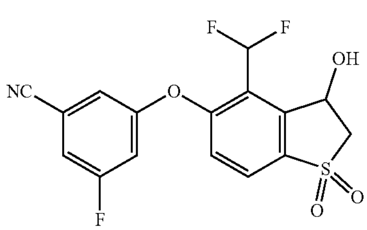 [SMILES: N#Cc1cc(F)cc(Oc2ccc3c(c2C(F)F)C(O)CS3(=O)=O)c1] | 370 (M − H) | (400 MHz, CDCl$_3$): δ 7.89 (d, 1H), 7.28-7.25 (m, 1H), 7.20 (t, 1H), 7.17-7.13 (m, 2H), 7.04 (dt, 1H), 5.90-5.85 (m, 1H), 3.79 (dd, 1H), 3.69 (dd, 1H), 2.93 (t, 1H) |

TABLE 1-continued

| No. | Structure | Mass Characterization | ¹H NMR Data |
|---|---|---|---|
| 375 | 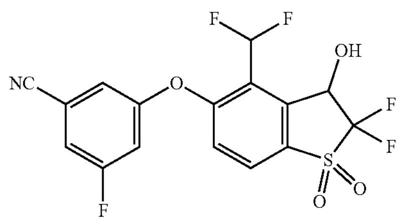 | 404 (M − H) | (400 MHz, CDCl₃): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H) |
| 376 | 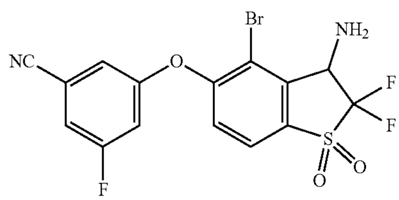 [SMILES: N#Cc1cc(F)cc(Oc2ccc3c(c2Br)C(N)C(F)(F)S3(=O)=O)c1] | 426, 428 (M + H) | (400 MHz, CDCl₃): δ 7.78 (d, 1H), 7.18 (d, 1H), 6.72 (tt, 1H), 6.63-6.54 (m, 2H), 4.70 (dt, 1H), 1.92 (d, 2H) |
| 377 | 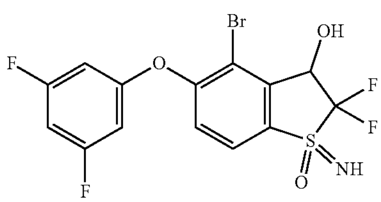 [SMILES: N=S1(=O)c2ccc(Oc3cc(F)cc(F)c3)c(Br)c2C(O)C1(F)F] | 426, 428 (M + H) | (400 MHz, CDCl₃): δ 7.88 (d, 1H), 7.22 (d, 1H), 6.71 (tt, 1H), 6.62-6.55 (m, 2H), 5.31 (dd, 1H), 3.43 (br s, 1H), 3.03 (d, 1H) |
| 378 | 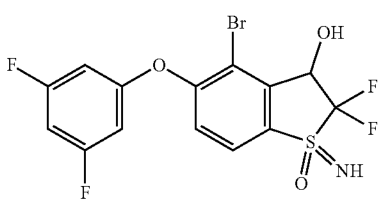 [SMILES: N=S1(=O)c2ccc(Oc3cc(F)cc(F)c3)c(Br)c2C(O)C1(F)F] | 426, 428 (M + H) | (400 MHz, CDCl₃): δ 7.81 (d, 1H), 7.22 (d, 1H), 6.70 (tt, 1H), 6.61-6.54 (m, 2H), 5.35 (t, 1H), 3.75 (br s, 1H), 3.27 (d, 1H) |
| 379 | 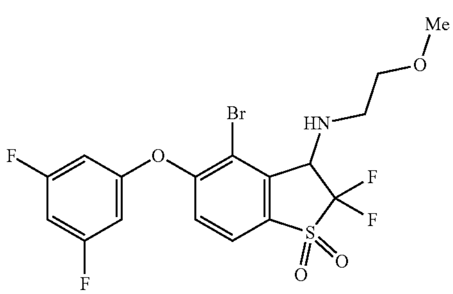 [SMILES: COCCNC1c2c(ccc(Oc3cc(F)cc(F)c3)c2Br)S(=O)(=O)C1(F)F] | 484, 486 (M + H) | (400 MHz, CDCl₃): δ 7.75 (d, 1H), 7.16 (d, 1H), 6.71 (tt, 1H), 6.62-6.55 (m, 2H), 4.60 (dd, 1H), 3.55 (t, 2H), 3.35 (s, 3H), 3.21-3.06 (m, 2H), 2.10-2.03 (m, 1H) |
| 380 | 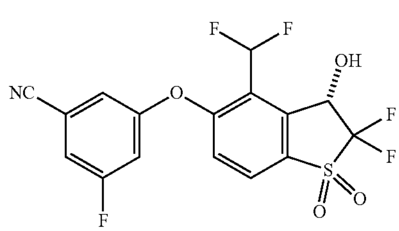 [SMILES: N#Cc1cc(F)cc(Oc2ccc3c(c2C(F)F)[C@H](O)C(F)(F)S3(=O)=O)c1] | 404 (M − H) | (400 MHz, CDCl₃): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H) |

TABLE 1-continued

| No. | Structure | Mass Characterization | ¹H NMR Data |
|---|---|---|---|
| 381 | 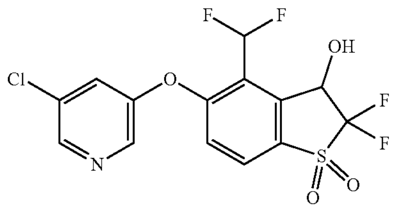 [SMILES: O=S1(=O)c2ccc(Oc3cncc(Cl)c3)c(C(F)F)c2C(O)C1(F)F] | 398, 400 (M + H) | (400 MHz, CDCl$_3$): δ 8.55 (d, 1H), 8.38 (d, 1H), 7.96 (d, 1H), 7.46 (t, 1H), 7.29 (t, 1H), 7.16-7.13 (m, 1H), 5.67 (dd, 1H), 3.24 (dd, 1H) |
| 382 | 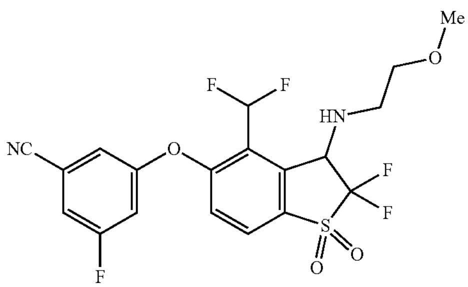 [SMILES: COCCNC1c2c(ccc(Oc3cc(F)cc(C#N)c3)c2C(F)F)S(=O)(=O)C1(F)F] | 463 (M + H) | (400 MHz, CDCl$_3$): δ 7.91 (d, 1H), 7.39 (t, 1H), 7.29-7.24 (m, 1H), 7.19-7.14 (m, 2H), 7.05 (dt, 1H), 4.94-4.87 (m, 1H), 3.53 (t, 2H), 3.37 (s, 3H), 3.17-3.07 (m, 2H), 2.28-2.20 (m, 1H) |
| 383 | 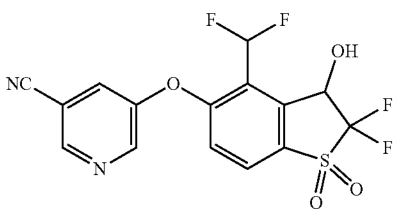 [SMILES: N#Cc1cncc(Oc2ccc3c(c2C(F)F)C(O)C(F)(F)S3(=O)=O)c1] | 389 (M + H) | (400 MHz, CD$_3$OD): δ 8.81 (d, 1H), 8.71 (d, 1H), 8.08 (d, 1H), 8.04 (dd, 1H), 7.42 (d, 1H), 7.38 (t, 1H), 5.69 (d, 1H) |
| 384 | 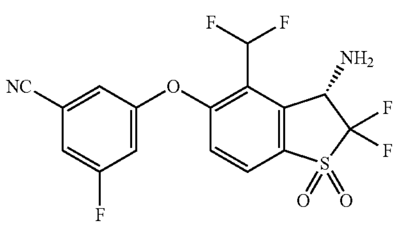 [SMILES: N#Cc1cc(F)cc(Oc2ccc3c(c2C(F)F)[C@H](N)C(F)(F)S3(=O)=O)c1] | 405 (M + H) | (400 MHz, CDCl$_3$): δ 7.95 (d, 1H), 7.31-7.27 (m, 1H), 7.30 (dd, 1H), 7.19-7.14 (m, 2H), 7.07 (dt, 1H), 5.01-4.91 (dd, 1H), 2.06-1.99 (m, 2H) |
| 385 | 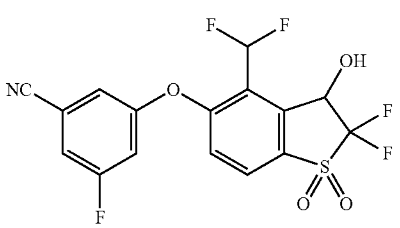 [SMILES: N#Cc1cc(F)cc(Oc2ccc3c(c2C(F)F)C(O)C(F)(F)S3(=O)=O)c1] | | (400 MHz, (CD$_3$)$_2$SO): δ 8.79 (s, 2H), 8.27 (d, 1H), 7.78-7.73 (m, 1H), 7.72 (t, 1H), 7.55-7.47 (m, 3H) |
| 386 | 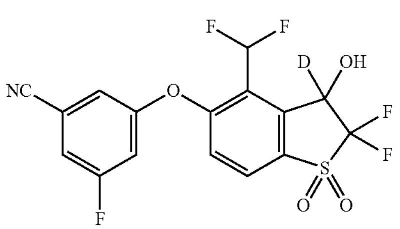 [SMILES: [2H]C1(O)c2c(ccc(Oc3cc(F)cc(C#N)c3)c2C(F)F)S(=O)(=O)C1(F)F] | 405 (M − H) | (400 MHz, CDCl$_3$): δ 7.98 (d, 1H), 7.33-7.30 (m, 1H), 7.23 (t, 1H), 7.22-7.18 (m, 2H), 7.08 (dt, 1H), 3.12 (s, 1H) |

TABLE 1-continued

| No. | Structure | Mass Characterization | $^1$H NMR Data |
|---|---|---|---|
| 387 | 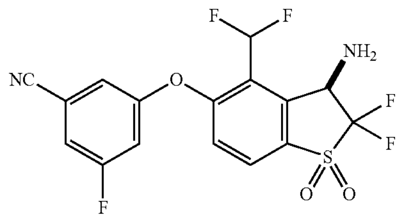 [SMILES: N#Cc1cc(F)cc(Oc2ccc3c(c2C(F)F)[C@@H](N)C(F)(F)S3(=O)=O)c1] | 405 (M + H) | (400 MHz, CDCl$_3$): δ 7.94 (d, 1H), 7.30 (d, 1H), 7.31-7.27 (m, 1H), 7.19-7.14 (m, 2H), 7.08 (dt, 1H), 5.02-4.89 (m, 1H), 2.12-1.92 (m, 2H) |
| 388 | 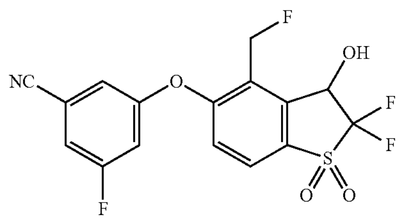 [SMILES: N#Cc1cc(F)cc(Oc2ccc3c(c2CF)C(O)C(F)(F)S3(=O)=O)c1] | 405 (M + NH$_4$) | (400 MHz, CDCl$_3$): δ 7.90 (d, 1H), 7.29-7.25 (m, 1H), 7.19 (d, 1H), 7.16-7.14 (m, 1H), 7.06-7.01 (m, 1H), 5.75 (d, 2H), 5.58 (br d, 1H), 3.30-3.22 (m, 1H) |
| 389 | 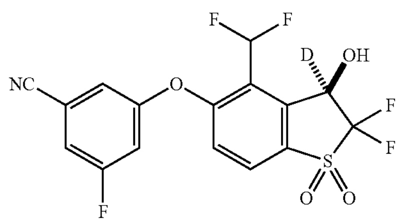 [SMILES: [2H][C@@]1(O)c2c(ccc(Oc3cc(F)cc(C#N)c3)c2C(F)F)S(=O)(=O)C1(F)F] | 405 (M − H) | (400 MHz, CDCl$_3$): δ 7.98 (d, 1H), 7.33-7.30 (m, 1H), 7.23 (t, 1H), 7.22-7.18 (m, 2H), 7.08 (dt, 1H), 3.12 (s, 1H) |
| 390 | 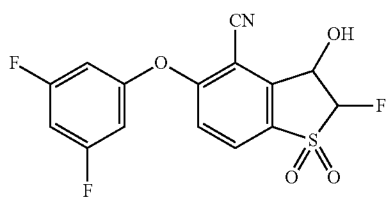 [SMILES: N#Cc1c(Oc2cc(F)cc(F)c2)ccc2c1C(O)C(F)S2(=O)=O] | 373 (M + NH$_4$) | (400 MHz, CD$_3$CN): δ 8.02 (d, 1H), 7.27 (d, 1H), 7.01-6.87 (m, 3H), 5.88-5.73 (m, 2H), 4.91 (d, 1H) |
| 391 | 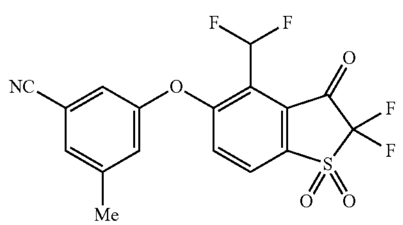 [SMILES: Cc1cc(C#N)cc(Oc2ccc3c(c2C(F)F)C(=O)C(F)(F)S3(=O)=O)c1] | | (400 MHz, CDCl$_3$): δ 8.13 (d, 1H), 7.67 (t, 1H), 7.53 (d, 1H), 7.43 (s, 1H), 7.21 (s, 1H), 7.15 (s, 1H), 2.45 (s, 3H) |
| 392 | 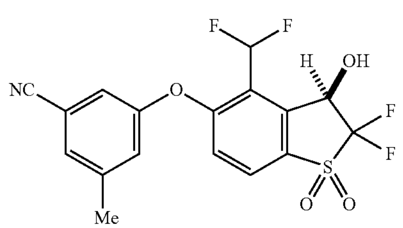 [SMILES: Cc1cc(C#N)cc(Oc2ccc3c(c2C(F)F)[C@@H](O)C(F)(F)S3(=O)=O)c1] | 419 (M + NH$_4$) | (400 MHz, CDCl$_3$): δ 7.91 (d, 1H), 7.41 (s, 1H), 7.27 (t, 1H), 7.21 (s, 1H), 7.13 (s, 1H), 7.10 (d, 1H), 5.71-5.64 (m, 1H), 3.04 (br d, 1H), 2.44 (s, 3H) |
| 393 | 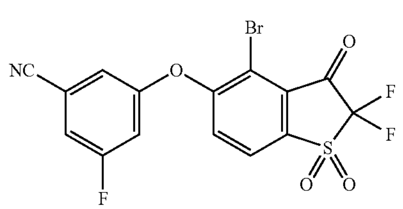 [SMILES: N#Cc1cc(F)cc(Oc2ccc3c(c2Br)C(=O)C(F)(F)S3(=O)=O)c1] | 467, 469 (M + H$_2$O + NH$_4$) | (400 MHz, CDCl$_3$): δ 8.05 (d, 1H), 7.55 (d, 1H), 7.30 (d, 1H), 7.13 (s, 1H), 7.07-7.02 (m, 1H) |

TABLE 1-continued

| No. | Structure | Mass Characterization | ¹H NMR Data |
|---|---|---|---|
| 394 | 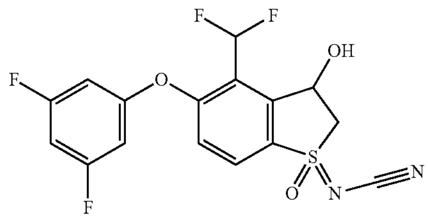 [SMILES: N#CN=S1(=O)CC(O)c2c1ccc(Oc1cc(F)cc(F)c1)c2C(F)F] | 387 (M + H) | (400 MHz, CDCl$_3$): δ 8.01 (d, 1H), 7.28 (t, 1H), 7.21 (d, 1H), 6.83-6.76 (m, 1H), 6.69-6.63 (m, 2H), 6.03-5.97 (m, 1H), 4.20 (dd, 1H), 3.88 (dd, 1H), 3.15-3.11 (m, 1H) |
| 395 | 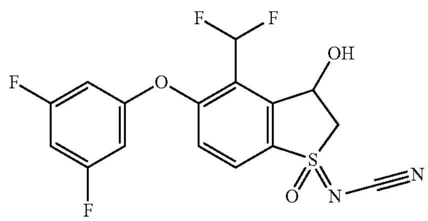 [SMILES: N#CN=S1(=O)CC(O)c2c1ccc(Oc1cc(F)cc(F)c1)c2C(F)F] | 387 (M + H) | (400 MHz, CDCl$_3$): δ 7.97 (d, 1H), 7.26 (t, 1H), 7.21 (d, 1H), 6.83-6.76 (m, 1H), 6.70-6.63 (m, 2H), 5.99 (t, 1H), 4.08-4.02 (m, 1H), 3.98 (dd, 1H), 3.20-3.15 (m, 1H) |
| 396 | 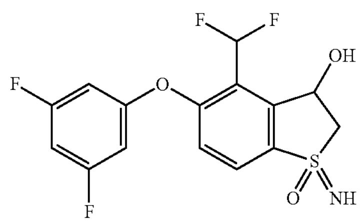 [SMILES: N=S1(=O)CC(O)c2c1ccc(Oc1cc(F)cc(F)c1)c2C(F)F] | 362 (M + H) | (400 MHz, CDCl$_3$): δ 7.80 (d, 1H), 7.17 (t, 1H), 7.12 (d, 1H), 6.74-6.67 (m, 1H), 6.62-6.55 (m, 2H), 5.80-5.74 (m, 1H), 3.80 (dd, 1H), 3.75-3.69 (m, 2H), 3.41-3.34 (m, 1H) |
| 397 | 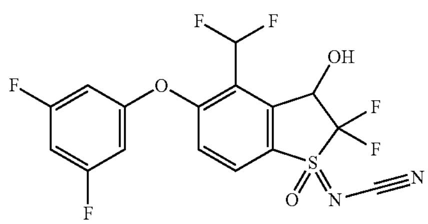 [SMILES: N#CN=S1(=O)c2ccc(Oc3cc(F)cc(F)c3)c(C(F)F)c2C(O)C1(F)F] | 423 (M + H) | (400 MHz, CDCl$_3$): δ 8.07-8.00 (m, 1H), 7.42-7.13 (m, 2H), 6.87-6.80 (m, 1H), 6.73-6.66 (m, 2H), 5.83-5.76 (m, 1H), 3.78-3.66 (m, 1H) |
| 398 | 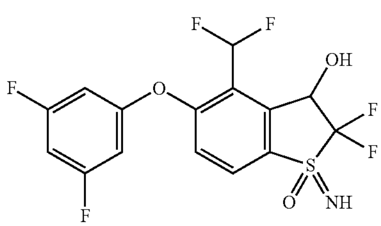 [SMILES: N=S1(=O)c2ccc(Oc3cc(F)cc(F)c3)c(C(F)F)c2C(O)C1(F)F] | 398 (M + H) | (400 MHz, CDCl$_3$): δ 8.02 (d, 1H), 7.22 (t, 1H), 7.19 (d, 1H), 6.79-6.72 (m, 1H), 6.66-6.59 (m, 2H), 5.60 (t, 1H), 3.39 (br s, 1H), 3.12 (d, 1H) |
| 399 | 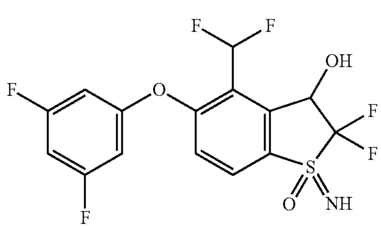 [SMILES: N=S1(=O)c2ccc(Oc3cc(F)cc(F)c3)c(C(F)F)c2C(O)C1(F)F] | 398 (M + H) | (400 MHz, CDCl$_3$): δ 7.95 (d, 1H), 7.23 (t, 1H), 7.19 (d, 1H), 6.79-6.72 (m, 1H), 6.66-6.59 (m, 2H), 5.64 (t, 1H), 3.68 (br s, 1H), 3.33 (d, 1H) |
| 400 | 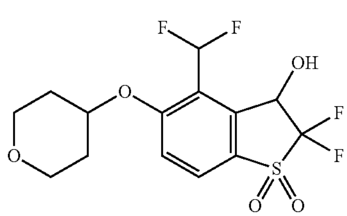 [SMILES: O=S1(=O)c2ccc(OC3CCOCC3)c(C(F)F)c2C(O)C1(F)F] | 387 (M + H) | (400 MHz, CD$_3$OD): δ 7.99 (d, 1H), 7.57 (d, 1H), 7.26 (t, 1H), 5.57-5.52 (m, 1H), 4.95-4.88 (m, 1H), 3.98-3.91 (m, 2H), 3.67-3.60 (m, 2H), 2.32-2.03 (m, 2H), 1.86-1.76 (m, 2H) |

TABLE 1-continued

| No. | Structure | Mass Characterization | ¹H NMR Data |
|---|---|---|---|
| 401 | 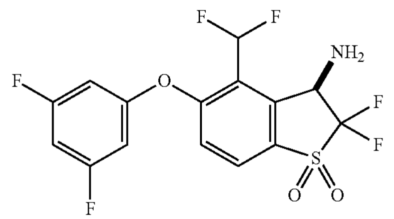 [SMILES: N[C@@H]1c2c(ccc(Oc3cc(F)cc(F)c3)c2C(F)F)S(=O)(=O)C1(F)F] | 398 (M + H) | (400 MHz, CDCl$_3$): δ 7.90 (d, 1H), 7.29 (t, 1H), 7.16 (d, 1H), 6.76 (tt, 1H), 6.67-6.60 (m, 2H), 5.02-4.93 (m, 1H), 2.01 (br d, 2H) |
| 402 | 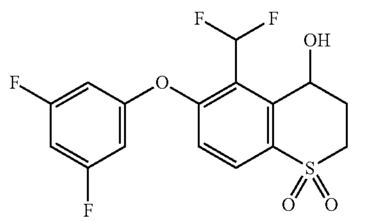 [SMILES: O=S1(=O)CCC(O)c2c1ccc(Oc1cc(F)cc(F)c1)c2C(F)F] | 394 (M + NH$_4$) | (400 MHz, CDCl$_3$): δ 8.08 (d, 1H), 7.31 (t, 1H), 7.10 (d, 1H), 6.71 (tt, 1H), 6.61-6.54 (m, 2H), 5.52-5.48 (m, 1H), 4.05 (td, 1H), 3.32 (ddd, 1H), 2.84-2.74 (m, 1H), 2.73-2.64 (m, 2H) |
| 403 | 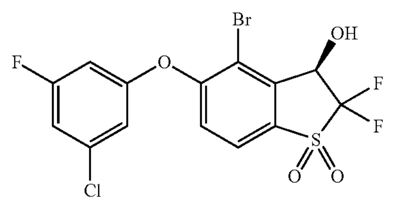 [SMILES: O=S1(=O)c2ccc(Oc3cc(F)cc(Cl)c3)c(Br)c2[C@@H](O)C1(F)F] | 441, 443, 445 (M − H) | (CDCl$_3$, 400 MHz) δ: 7.80 (d, 1H), 7.22 (d, 1H), 7.02-7.00 (m, 1H), 6.87-6.86 (m, 1H), 6.72 (dt, 1H), 5.38 (d, 1H) |
| 404 | 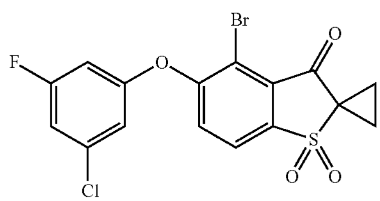 [SMILES: O=C1c2c(ccc(Oc3cc(F)cc(Cl)c3)c2Br)S(=O)(=O)C12CC2] | 475, 477, 479 (M + HCO$_2^-$) | (CDCl$_3$, 400 MHz) δ: 8.00 (d, 1H), 7.46 (d, 1H), 6.99-6.96 (m, 1H), 6.81-6.80 (m, 1H), 6.67 (dt, 1H), 2.08-2.04 (m, 2H), 1.96-1.93 (m, 2H) |
| 405 | 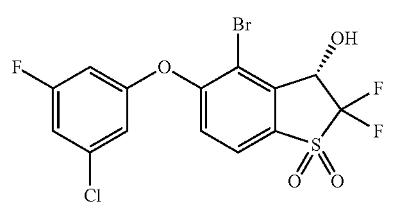 [SMILES: O=S1(=O)c2ccc(Oc3cc(F)cc(Cl)c3)c(Br)c2[C@H](O)C1(F)F] | 441, 443, 445 (M − H) | (CDCl$_3$, 400 MHz): δ 7.80 (d, 1H), 7.22 (d, 1H), 7.02-7.00 (m, 1H), 6.87-6.86 (m, 1H), 6.72 (dt, 1H), 5.38 (d, 1H) |
| 406 | 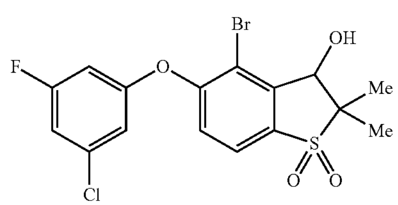 [SMILES: CC1(C)C(O)c2c(ccc(Oc3cc(F)cc(Cl)c3)c2Br)S1(=O)=O] | 479, 481, 483 (M + HCO$_2^-$) | (CDCl$_3$, 400 MHz): δ 7.73 (dd, 1H), 7.16 (d, 1H), 6.98-6.95 (m, 1H), 6.83-6.82 (m, 1H), 6.66 (dt, 1H), 1.65 (s, 3H), 1.40 (s, 3H) |
| 407 | 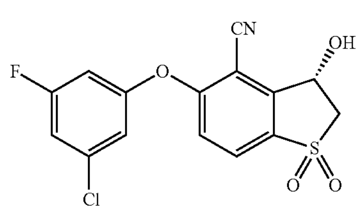 [SMILES: N#Cc1c(Oc2cc(F)cc(Cl)c2)ccc2c1[C@H](O)CS2(=O)=O] | 352, 354 (M − H) | (CDCl$_3$, 400 MHz): δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H) |

TABLE 1-continued

| No. | Structure | Mass Characterization | ¹H NMR Data |
|---|---|---|---|
| 408 | 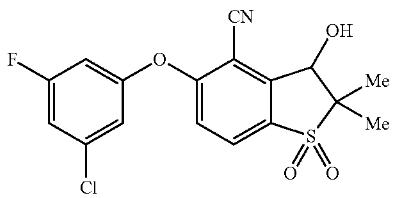 [SMILES: CC1(C)C(O)c2c(ccc(Oc3cc(F)cc(Cl)c3)c2C#N)S1(=O)=O] | 380, 382 (M − H) | (CDCl₃, 400 MHz): δ 7.91 (d, 1H), 7.10-7.06 (m, 2H), 6.97-6.96 (m, 1H), 6.81 (dt, 1H), 1.55 (s, 3H), 1.49 (s, 3H) |
| 409 | 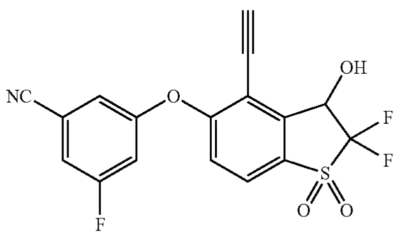 [SMILES: C#Cc1c(Oc2cc(F)cc(C#N)c2)ccc2c1C(O)C(F)(F)S2(=O)=O] | 397 (M + NH₄) | (400 MHz, CDCl₃): δ 7.85 (d, 1H), 7.27-7.23 (m, 2H), 7.15 (s, 1H), 7.04 (d, 1H), 5.46 (dd, 1H), 3.69 (s, 1H), 3.13 (d, 1H) |
| 410 | 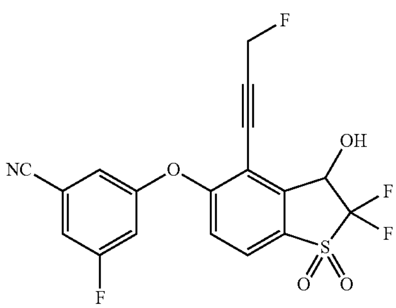 [SMILES: N#Cc1cc(F)cc(Oc2ccc3c(c2C#CCF)C(O)C(F)(F)S3(=O)=O)c1] | 410 (M − H) | (400 MHz, CDCl₃): δ 7.85 (d, 1H), 7.28-7.25 (m, 1H), 7.23 (d, 1H), 7.16-7.14 (m, 1H), 7.05 (dt, 1H), 5.43 (d, 1H), 5.19 (d, 2H), 3.27 (s, 1H) |
| 411 | 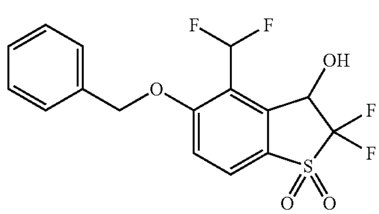 [SMILES: O=S1(=O)c2ccc(OCc3ccccc3)c(C(F)F)c2C(O)C1(F)F] | 394 (M + NH₄) | (400 MHz, CDCl₃): δ 7.92 (d, 1H), 7.46-7.10 (m, 7H), 5.61 (d, 1H), 5.26 (s, 2H), 3.00 (s, 1H) |
| 412 | 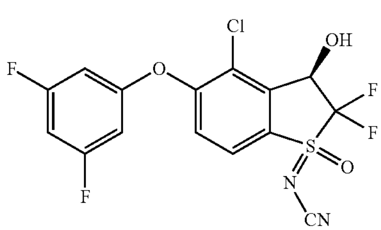 [SMILES: N#CN=S1(=O)c2ccc(Oc3cc(F)cc(F)c3)c(Cl)c2[C@@H](O)C1(F)F] | 407, 409 (M + H) | (400 MHz, CDCl₃): δ 7.89-7.81 (m, 1H), 7.31-7.26 (m, 1H), 6.78 (t, 1H), 6.65 (d, 2H), 5.59-5.51 (m, 1H), 4.60-4.38 (br s, 1H) |
| 413 | 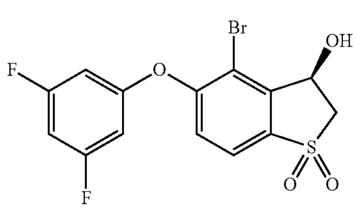 [SMILES: O=S1(=O)C[C@H](O)c2c1ccc(Oc1cc(F)cc(F)c1)c2Br] | | (400 MHz, CDCl₃): δ 7.72 (d, 1H), 7.21 (d, 1H), 6.71-6.64 (m, 1H), 6.57-6.52 (m, 2H), 5.60 (t, 1H), 3.83-3.78 (m, 1H), 3.71-3.67 (m, 1H), 2.88 (d, 1H) |

TABLE 1-continued

| No. | Structure | Mass Characterization | $^1$H NMR Data |
|---|---|---|---|
| 414 | 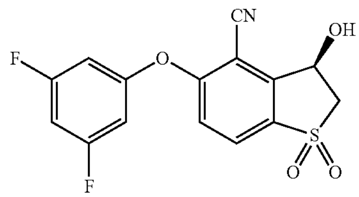 [SMILES: N#Cc1c(Oc2cc(F)cc(F)c2)ccc2c1[C@@H](O)CS2(=O)=O] | | (400 MHz, CDCl$_3$): δ 7.89 (d, 1H), 7.15 (d, 1H), 6.83-6.76 (m, 1H), 6.71-6.67 (m, 2H), 5.78-5.74 (m, 1H), 3.94-3.89 (m, 1H), 3.67-3.63 (m, 1H), 3.27-3.24 (m, 1H) |
| 415 | 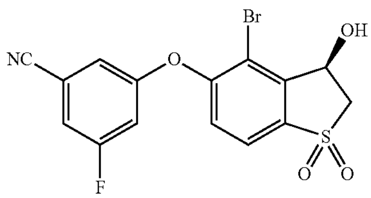 [SMILES: N#Cc1cc(F)cc(Oc2ccc3c(c2Br)[C@@H](O)CS3(=O)=O)c1] | | (400 MHz, CDCl$_3$): δ 7.77 (d, 1H), 7.25 (d, 1H), 7.22-7.19 (m, 1H), 7.06-7.05 (m, 1H), 6.99-6.96 (m, 1H), 5.62-5.59 (m, 1H), 3.85-3.80 (m, 1H), 3.71-3.69 (m, 1H), 2.90 (d, 1H) |
| 416 | 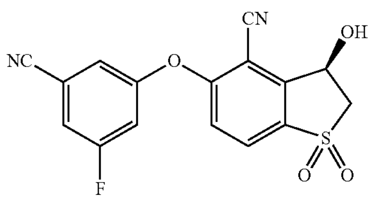 [SMILES: N#Cc1cc(F)cc(Oc2ccc3c(c2C#N)[C@@H](O)CS3(=O)=O)c1] | | (400 MHz, CDCl$_3$): δ 7.94 (d, 1H), 7.35-7.31 (m, 1H), 7.24-7.22 (m, 1H), 7.16 (d, 1H), 7.16-7.12 (m, 1H), 5.80-5.73 (m, 1H), 3.96-3.90 (m, 1H), 3.68-3.63 (m, 1H), 3.48-3.46 (m, 1H) |
| 417 | 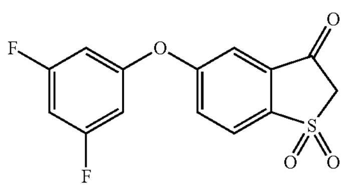 [SMILES: O=C1CS(=O)(=O)c2ccc(Oc3cc(F)cc(F)c3)cc21] | | (400 MHz, CDCl$_3$): δ 8.24 (d, 1H), 7.89-7.86 (dd, 1H), 7.11 (d, 1H), 6.70-6.65 (m, 1H), 6.59-6.51 (m, 2H), 3.10 (s, 2H) |
| 418 | 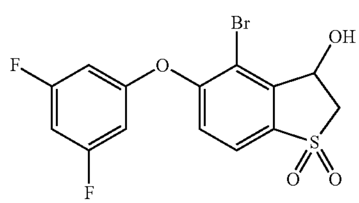 [SMILES: O=S1(=O)CC(O)c2c1ccc(Oc1cc(F)cc(F)c1)c2Br] | | (400 MHz, CDCl$_3$): δ 7.72 (d, 1H), 7.20 (d, 1H), 6.70-6.65 (m, 1H), 6.58-6.52 (m, 2H), 5.62-5.58 (m, 1H), 3.83-3.78 (m, 1H), 3.71-3.67 (m, 1H), 2.93 (d, 1H) |
| 419 | 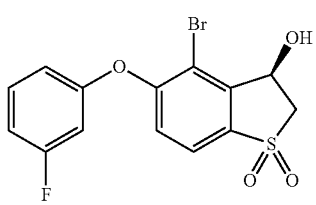 [SMILES: O=S1(=O)C[C@H](O)c2c1ccc(Oc1cccc(F)c1)c2Br] | | (400 MHz, CDCl$_3$): δ 7.66 (d, 1H), 7.40-7.35 (m, 1H), 7.10 (d, 1H), 6.97-6.93 (m, 1H), 6.83-6.76 (m, 2H), 5.62-5.59 (m, 1H), 3.82-3.77 (m, 1H), 3.70-3.66 (m, 1H), 2.96 (d, 1H) |
| 420 | 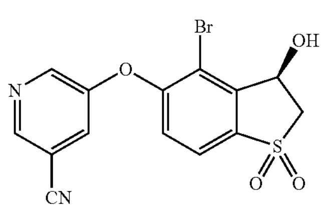 [SMILES: N#Cc1cncc(Oc2ccc3c(c2Br)[C@@H](O)CS3(=O)=O)c1] | | (400 MHz, CDCl$_3$ + CD$_3$OD): δ 8.69 (d, 1H), 8.61-8.60 (d, 1H), 7.79 (d, 1H), 7.55-7.54 (m, 1H), 7.29 (d, 1H), 5.57 (d, 1H), 3.84-3.79 (m, 1H), 3.70-3.66 (m, 1H) |

TABLE 1-continued

| No. | Structure | Mass Characterization | ¹H NMR Data |
|---|---|---|---|
| 421 | 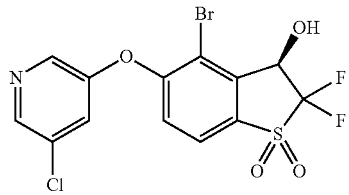 [SMILES: O=S1(=O)c2ccc(Oc3cncc(Cl)c3)c(Br)c2[C@@H](O)C1(F)F] | | (400 MHz, CDCl₃): δ 8.50 (s, 1H), 8.33 (s, 1H), 7.81 (d, 1H), 7.41-7.40 (m, 1H), 7.19 (d, 1H), 5.41-5.37 (m, 1H), 3.45-3.40 (m, 1H) |
| 422 | 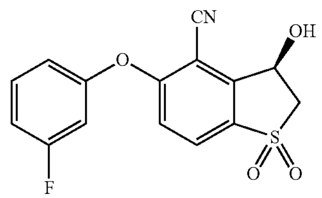 [SMILES: N#Cc1c(Oc2cccc(F)c2)ccc2c1[C@@H](O)CS2(=O)=O] | | (400 MHz, CDCl₃): δ 7.83 (d, 1H), 7.48-7.42 (m, 1H), 7.08-7.03 (m, 1H), 7.06 (d, 1H), 6.94-6.87 (m, 2H), 5.78-5.73 (m, 1H), 3.93-3.88 (m, 1H), 3.66-3.62 (m, 1H), 3.56 (d, 1H) |
| 423 | 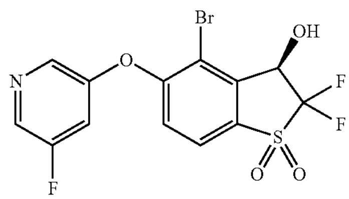 [SMILES: O=S1(=O)c2ccc(Oc3cncc(F)c3)c(Br)c2[C@@H](O)C1(F)F] | | (400 MHz, CDCl₃): δ 8.43 (d, 1H), 8.29 (d, 1H), 7.82 (d, 1H), 7.21 (d, 1H), 7.18-7.14 (dt, 1H), 5.41-5.37 (m, 1H), 3.29-3.28 (m, 1H) |
| 424 | 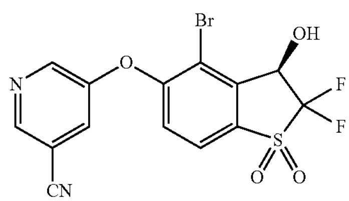 [SMILES: N#Cc1cncc(Oc2ccc3c(c2Br)[C@@H](O)C(F)(F)S3(=O)=O)c1] | | (400 MHz, CDCl₃): δ 8.76 (s, 1H), 8.64 (d, 1H), 7.87 (d, 1H), 7.59-7.58 (m, 1H), 7.27 (d, 1H), 5.42-5.36 (m, 1H), 3.36-3.32 (m, 1H) |
| 425 | 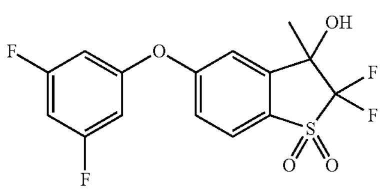 | 407 (M + HCOOH − H) | (400 MHz, CDCl₃): δ 7.81 (d, 1H), 7.28 (d, 1H), 7.24-7.21 (m, 1H), 6.76-6.70 (1H), 6.65-6.95 (m, 2H), 2.80 (m, 1H), 1.75 (m, 3H) |
| 426 | 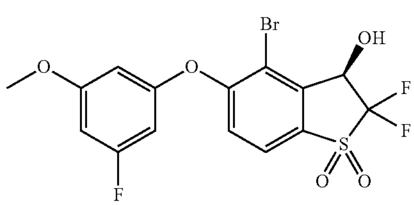 [SMILES: COc1cc(F)cc(Oc2ccc3c(c2Br)[C@@H](O)C(F)(F)S3(=O)=O)c1] | 437, 439 (M − H) | (400 MHz, CDCl₃) δ 7.75 (d, 1H), 7.17 (d, 1H), 6.56-6.51 (m, 1H), 6.42-6.37 (m, 2H), 5.42-5.35 (m, 1H), 3.80 (s, 3H), 2.99-2.95 (m, 1H) |
| 427 | 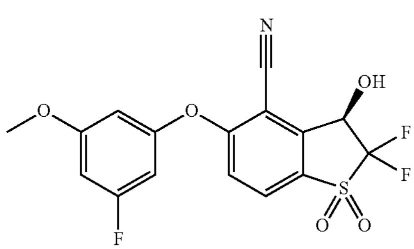 [SMILES: COc1cc(F)cc(Oc2ccc3c(c2C#N)[C@@H](O)C(F)(F)S3(=O)=O)c1] | 384 (M − H) | (400 MHz, CDCl₃) δ 7.92 (d, 1H), 7.17 (d, 1H), 6.64-6.60 (m, 1H), 6.50-6.45 (m, 2H), 6.57-6.51 (m, 1H), 3.82 (s, 3H), 3.80-3.74 (m, 1H) |

TABLE 1-continued

| No. | Structure | Mass Characterization | ¹H NMR Data |
|---|---|---|---|
| 428 | 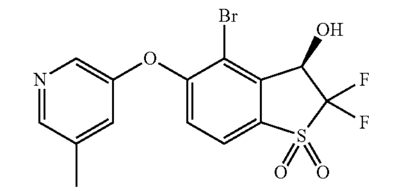 [SMILES: Cc1cncc(Oc2ccc3c(c2Br)[C@@H](O)C(F)(F)S3(=O)=O)c1] | | (400 MHz, CDCl$_3$): δ 8.38-8.36 (m, 1H), 8.14 (d, 1H), 7.72 (d, 1H), 7.24-7.22 (m, 1H), 7.01 (d, 1H), 5.41-5.37 (m, 1H), 4.14-4.08 (m, 1H), 2.40 (s, 3H) |
| 429 | 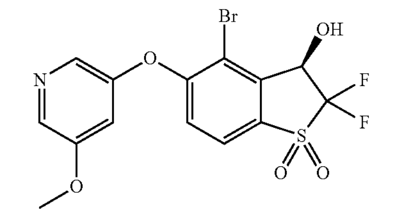 [SMILES: COc1cncc(Oc2ccc3c(c2Br)[C@@H](O)C(F)(F)S3(=O)=O)c1] | | (400 MHz, CDCl$_3$): δ 8.26-8.23 (m, 1H), 7.95-7.93 (m, 1H), 7.73 (d, 1H), 7.06 (d, 1H), 6.95-6.92 (m, 1H), 5.42-5.35 (m, 1H), 4.03-3.97 (m, 1H), 3.88 (s, 3H) |
| 430 | 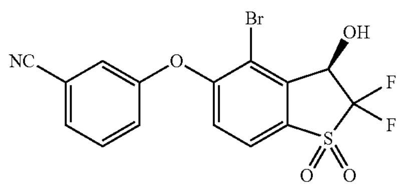 [SMILES: N#Cc1cccc(Oc2ccc3c(c2Br)[C@@H](O)C(F)(F)S3(=O)=O)c1] | | (400 MHz, CDCl$_3$): δ 7.80 (d, 1H), 7.59-7.54 (m, 2H), 7.37-7.35 (m, 1H), 7.32-7.27 (m, 1H), 7.15 (d, 1H), 5.42-5.37 (m, 1H), 3.11 (d, 1H) |
| 431 | 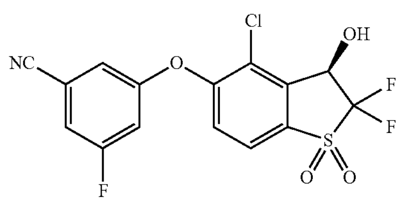 [SMILES: N#Cc1cc(F)cc(Oc2ccc3c(c2Cl)[C@@H](O)C(F)(F)S3(=O)=O)c1] | 388, 390 (M − H) | (400 MHz, CDCl$_3$): δ 7.82 (d, 1H), 7.32 (d, 1H), 7.25-7.23 (m, 1H), 7.12-7.10 (m, 1H), 7.03-7.00 (dt, 1H), 5.44 (d, 1H), 3.39-3.25 (m, 1H) |
| 432 | 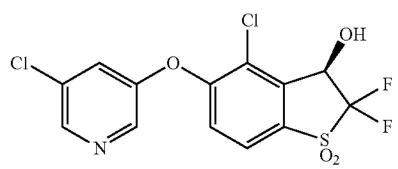 [SMILES: O=S1(=O)c2ccc(Oc3cncc(Cl)c3)c(Cl)c2[C@@H](O)C1(F)F] | | (400 MHz, CDCl$_3$): δ 8.50 (d, 1H), 8.33 (d, 1H), 7.78 (d, 1H), 7.41-7.40 (m, 1H), 7.22 (d, 1H), 5.47-5.42 (m, 1H), 3.45 (d, 1H) |
| 433 | 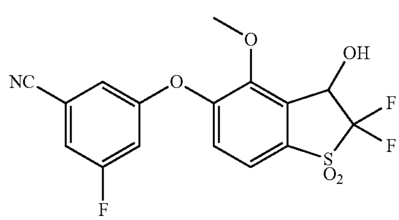 | 430 (M + HCOOH − H) | (400 MHz, CDCl$_3$): δ 7.62 (d, 1H), 7.32 (d, 1H), 7.21-7.18 (m, 1H), 7.08-7.06 (m, 1H), 6.97-6.93 (m, 1H), 5.47-5.43 (m, 1H), 4.02 (s, 3H), 3.10-3.08 (m, 1H) |
| 434 | 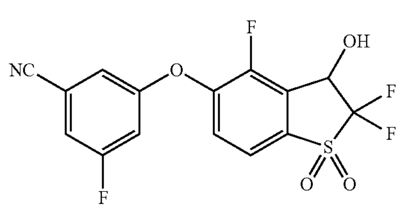 [SMILES: N#Cc1cc(F)cc(Oc2ccc3c(c2F)C(O)C(F)(F)S3(=O)=O)c1] | 418 (M + HCOOH − H) | (400 MHz, CDCl$_3$): δ 7.72 (d, 1H), 7.44-7.40 (m, 1H), 7.25-7.22 (m, 1H), 7.13-7.10 (m, 1H), 7.05-7.01 (m, 1H), 5.51 (d, 1H) |

TABLE 1-continued

| No. | Structure | Mass Characterization | $^1$H NMR Data |
|---|---|---|---|
| 435 | 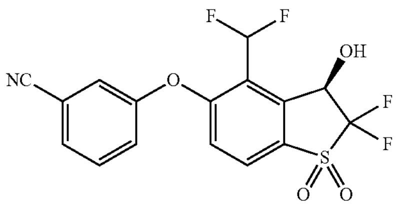 [SMILES: N#Cc1cccc(Oc2ccc3c(c2C(F)F)[C@@H](O)C(F)(F)S3(=O)=O)c1] | | (400 MHz, CDCl$_3$): δ 7.92 (d, 1H), 7.62-7.57 (m, 2H), 7.42-7.40 (m, 1H), 7.35-7.31 (m, 1H), 7.28 (t, J = 53 Hz, 1H), 7.11 (d, 1H), 5.69-5.65 (m, 1H), 3.33-3.32 (m, 1H) |
| 436 | 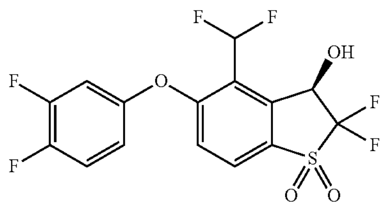 [SMILES: O=S1(=O)c2ccc(Oc3ccc(F)c(F)c3)c(C(F)F)c2[C@@H](O)C1(F)F] | | (400 MHz, CDCl$_3$ + CD$_3$OD): δ 7.80 (d, 1H), 7.23-7.15 (m, 1H), 7.20 (t, 1H), 7.02 (d, 1H), 6.94-6.88 (m, 1H), 6.80-6.75 (m, 1H), 5.50 (d, 1H) |
| 437 | 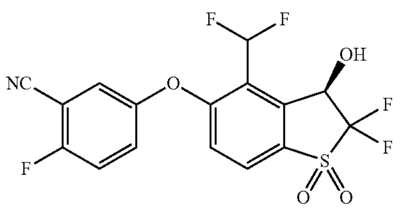 [SMILES: N#Cc1cc(Oc2ccc3c(c2C(F)F)[C@@H](O)C(F)(F)S3(=O)=O)ccc1F] | | (400 MHz, CDCl$_3$ + CD$_3$OD): δ 7.83 (d, 1H), 7.33-7.23 (m, 3H), 7.18 (t, 1H), 7.01 (d, 1H), 5.51-5.48 (m, 1H) |
| 438 | 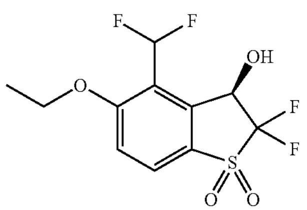 [SMILES: CCOc1ccc2c(c1C(F)F)[C@@H](O)C(F)(F)S2(=O)=O] | | (400 MHz, CDCl$_3$): δ 7.93 (d, 1H), 7.24 (d, 1H), 7.21 (t, 1H), 5.63-5.58 (m, 1H), 4.23 (q, 2H), 2.94-2.89 (m, 1H), 1.51 (t, 3H) |
| 439 | 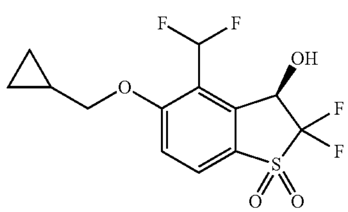 [SMILES: O=S1(=O)c2ccc(OCC3CC3)c(C(F)F)c2[C@@H](O)C1(F)F] | | (400 MHz, CDCl$_3$): δ 7.92 (d, 1H), 7.26 (t, 1H), 7.21 (d, 1H), 5.63-5.59 (m, 1H), 4.01-3.98 (m, 2H), 2.95-2.92 (m, 1H), 1.37-1.27 (m, 1H), 0.74-0.70 (m, 2H), 0.42-0.38 (m, 2H) |
| 440 | 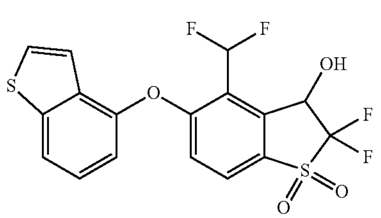 [SMILES: O=S1(=O)c2ccc(Oc3cccc4sccc34)c(C(F)F)c2C(O)C1(F)F] | | (400 MHz, CDCl$_3$): δ 7.85 (d, 1H), 7.78 (d, 1H), 7.50 (d, 1H), 7.47 (t, 1H), 7.42 (t, 1H), 7.17 (dd, 1H), 7.05 (dd, 1H), 6.96 (d, 1H), 5.73-5.67 (m, 1H), 3.20-3.13 (br s, 1H) |
| 441 | 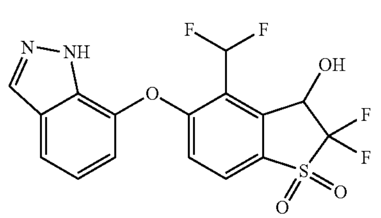 [SMILES: O=S1(=O)c2ccc(Oc3cccc4cn[nH]c34)c(C(F)F)c2C(O)C1(F)F] | | (400 MHz, CDCl$_3$): δ 8.17 (s, 1H), 7.83 (d, 1H), 7.72 (d, 1H), 7.42 (t, 1H), 7.22 (t, 1H), 7.12-7.07 (m, 2H), 5.69 (d, 1H) |

TABLE 1-continued

| No. | Structure | Mass Characterization | $^1$H NMR Data |
|---|---|---|---|
| 442 | 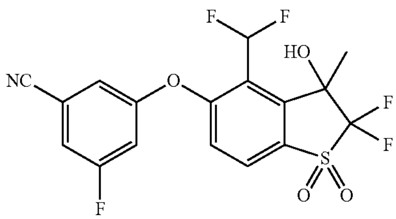 [SMILES: CC1(O)c2c(ccc(Oc3cc(F)cc(C#N)c3)c2C(F)F)S(=O)(=O)C1(F)F] | 418 (M − H) | (400 MHz, CDCl$_3$): δ 7.95-7.90 (d, 1H), 7.65 (t, 1H), 7.25-7.22 (m, 1H), 7.22-7.18 (d, 1H), 7.13-7.11 (m, 1H), 7.08-7.04 (m, 1H), 3.73 (brd s, 1H), 1.91-1.88 (m, 3H) |
| 443 | 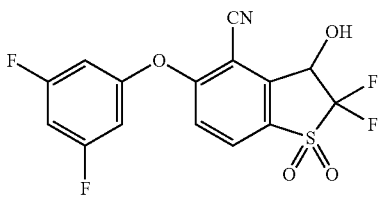 [SMILES: N#Cc1c(Oc2cc(F)cc(F)c2)ccc2c1C(O)C(F)(F)S2(=O)=O] | 372 (M − H) | (400 MHz, CDCl$_3$): δ 7.97 (d, 1H), 7.20 (d, 1H), 6.87-6.81 (m, 1H), 6.76-6.69 (m, 2H), 5.55 (dd, 1H) |
| 444 | 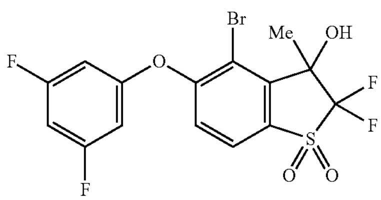 [SMILES: CC1(O)c2c(ccc(Oc3cc(F)cc(F)c3)c2Br)S(=O)(=O)C1(F)F] | 439, 441 (M − H) | (400 MHz, CDCl$_3$): δ 7.78 (d, 1H), 7.16 (d, 1H), 6.75-6.69 (m, 1H), 6.62-6.54 (m, 2H), 3.04-2.98 (m, 1H), 1.95 (d, 3H) |
| 445 | 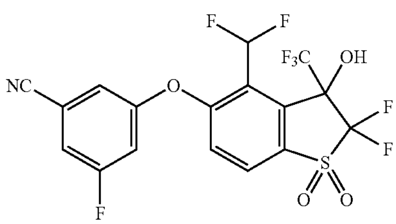 [SMILES: N#Cc1cc(F)cc(Oc2ccc3c(c2C(F)F)C(O)(C(F)(F)F)C(F)(F)S3(=O)=O)c1] | 472 (M − H) | (400 MHz, CDCl$_3$): δ 8.03 (d, 1H), 7.57 (t, 1H), 7.37 (d, 1H), 7.29-7.25 (m, 1H), 7.17-7.14 (m, 1H), 7.08 (dt, 1H), 5.40-5.10 (m, 1H) |
| 446 | 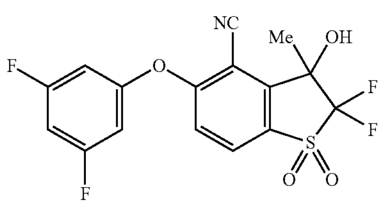 [SMILES: CC1(O)c2c(ccc(Oc3cc(F)cc(F)c3)c2C#N)S(=O)(=O)C1(F)F] | 386 (M − H) | (400 MHz, CDCl$_3$): δ 7.93 (d, 1H), 7.13 (d, 1H), 6.83 (tt, 1H), 6.75-6.68 (m, 2H), 3.54 (s, 1H), 1.97 (d, 3H) |
| 447 | 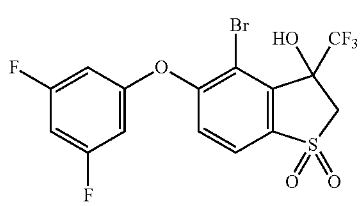 [SMILES: O=S1(=O)CC(O)(C(F)(F)F)c2c1ccc(Oc1cc(F)cc(F)c1)c2Br] | 457, 459 (M − H) | (400 MHz, CDCl$_3$): δ 7.79 (d, 1H), 7.27 (d, 1H), 6.72 (tt, 1H), 6.62-6.55 (m, 2H), 4.71 (s, 1H), 4.16 (d, 1H), 3.83 (d, 1H) |
| 448 | 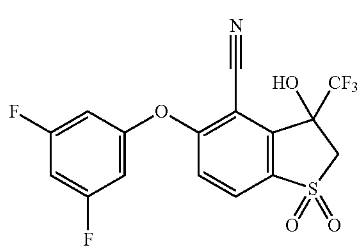 [SMILES: N#Cc1c(Oc2cc(F)cc(F)c2)ccc2c1C(O)(C(F)(F)F)CS2(=O)=O] | 404 (M − H) | (400 MHz, CDCl$_3$): δ 7.94 (d, 1H), 7.26 (d, 1H), 6.83 (tt, 1H), 6.76-6.69 (m, 2H), 4.26 (br s, 1H), 4.18 (d, 1H), 3.81 (d, 1H) |

TABLE 1-continued

| No. | Structure | Mass Characterization | $^1$H NMR Data |
|---|---|---|---|
| 449 | 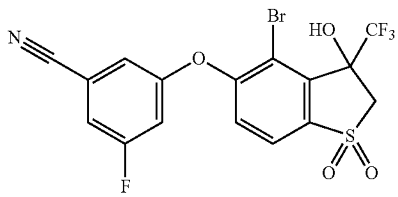 [SMILES: N#Cc1cc(F)cc(Oc2ccc3c(c2Br)C(O)(C(F)(F)F)CS3(=O)=O)c1] | 464, 466 (M − H) | (400 MHz, CDCl$_3$): δ 7.84 (d, 1H), 7.30 (d, 1H), 7.27-7.24 (m, 1H), 7.12-7.10 (m, 1H), 7.00 (dt, 1H), 4.63 (s, 1H), 4.18 (d, 1H), 3.85 (d, 1H) |
| 450 | 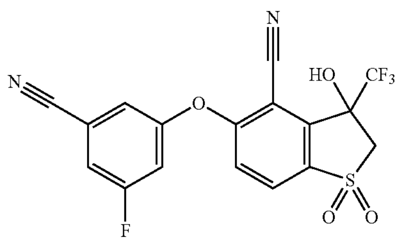 [SMILES: N#Cc1cc(F)cc(Oc2ccc3c(c2C#N)C(O)(C(F)(F)F)CS3(=O)=O)c1] | 411 (M − H) | (400 MHz, CDCl$_3$): δ 7.99 (d, 1H), 7.38-7.34 (m, 1H), 7.29-7.24 (m, 2H), 7.20-7.16 (dt, 1H), 4.75 (br s, 1H), 4.20 (d, 1H), 3.82 (d, 1H) |
| 451 | 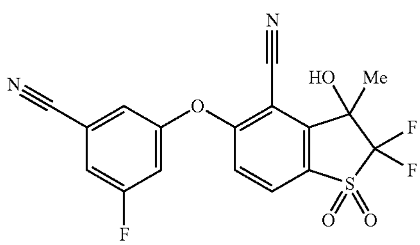 [SMILES: CC1(O)c2c(ccc(Oc3cc(F)cc(C#N)c3)c2C#N)S(=O)(=O)C1(F)F] | 393 (M − H) | (400 MHz, CDCl$_3$): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H) |
| 452 | 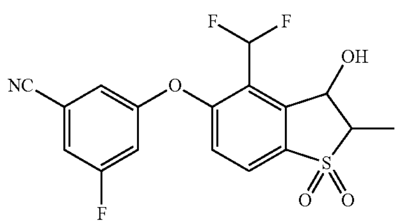 [SMILES: CC1C(O)c2c(ccc(Oc3cc(F)cc(C#N)c3)c2C(F)F)S1(=O)=O] | 401 (M + NH$_4^+$) | (400 MHz, CDCl$_3$): δ 7.89 (d, 1H), 7.27-7.24 (m, 1H), 7.21 (t, 1H), 7.16-7.11 (m, 2H), 7.06-7.02 (m, 1H), 5.34 (br s, 1H), 3.66-3.58 (m, 1H), 3.13 (br s, 1H), 1.55 (d, 3H) |
| 453 | 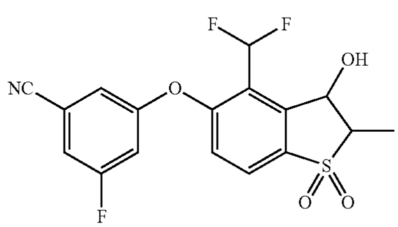 [SMILES: CC1C(O)c2c(ccc(Oc3cc(F)cc(C#N)c3)c2C(F)F)S1(=O)=O] | 401 (M + NH$_4^+$) | (400 MHz, DMSO-d$_6$): δ 7.99 (d, 1H), 7.75-7.71 (m, 1H), 7.52-7.49 (m, 1H), 7.48-7.44 (m, 1H), 7.36 (d, 1H), 7.29 (t, 1H), 6.23 (d, 1H), 5.52 (t, 1H), 3.76-3.68 (m, 1H), 1.35 (d, 3H) |
| 454 | 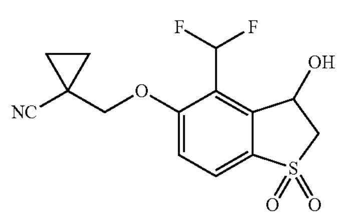 [SMILES: N#CC1(COc2ccc3c(c2C(F)F)C(O)CS3(=O)=O)CC1] | 347 (M + NH$_4^+$) | (400 MHz, CDCl$_3$): δ 7.84 (d, 1H), 7.31 (t, 1H), 7.09 (d, 1H), 5.87-5.79 (m, 1H), 4.17-4.04 (m, 2H), 3.75-3.68 (m, 1H), 3.65-3.59 (m, 1H), 2.91-2.84 (m, 1H), 1.54-1.48 (m, 2H), 1.22-1.14 (m, 2H) |
| 455 | 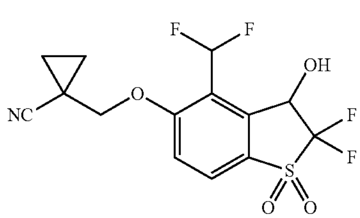 [SMILES: N#CC1(COc2ccc3c(c2C(F)F)C(O)C(F)(F)S3(=O)=O)CC1] | 410 (M + HCO$_2^-$) | (400 MHz, CDCl$_3$): δ 7.86 (d, 1H), 7.19 (t, 1H), 7.14 (d, 1H), 5.47 (d, 1H), 4.15-4.03 (m, 2H), 3.15 (s, 1H), 1.47-1.39 (m, 2H), 1.19-1.12 (m, 2H) |

TABLE 1-continued

| No. | Structure | Mass Characterization | ¹H NMR Data |
|---|---|---|---|
| 456 | 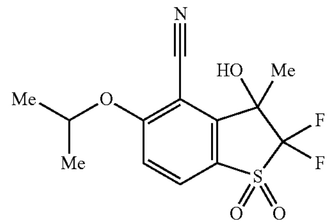 [SMILES: CC(C)Oc1ccc2c(c1C#N)C(C)(O)C(F)(F)S2(=O)=O] | 316 (M − H) | (400 MHz, CDCl₃): δ 7.92 (d, 1H), 7.18 (d, 1H), 4.81 (m, 1H), 3.18 (s, 1H), 1.92 (d, 3H), 1.48 (t, 6H) |
| 457 | 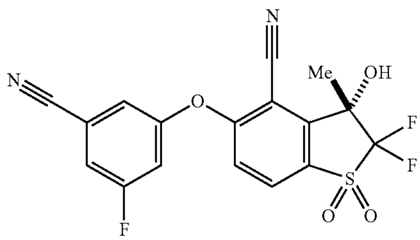 [SMILES: C[C@]1(O)c2c(ccc(Oc3cc(F)cc(C#N)c3)c2C#N)S(=O)(=O)C1(F)F] | 393 (M − H) | (400 MHz, CDCl₃): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H) |
| 458 | 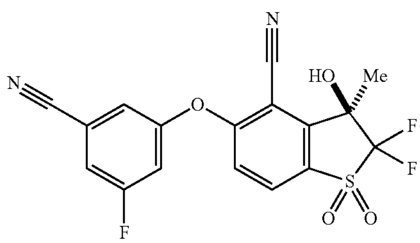 [SMILES: C[C@@]1(O)c2c(ccc(Oc3cc(F)cc(C#N)c3)c2C#N)S(=O)(=O)C1(F)F] | 393 (M − H) | (400 MHz, CDCl₃): δ 7.98 (d, 1H), 7.39-7.35 (m, 1H), 7.27-7.25 (m, 1H), 7.17 (dt, 1H), 7.13 (d, 1H), 3.27 (d, 1H), 1.99 (d, 3H) |
| 459 | 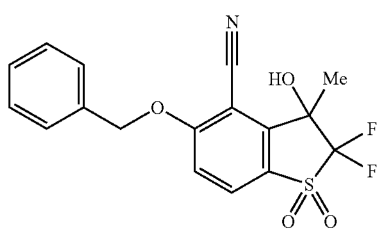 [SMILES: CC1(O)c2c(ccc(OCc3ccccc3)c2C#N)S(=O)(=O)C1(F)F] | 410 (M + HCO₂⁻) | (400 MHz, (CD₃)₂CO): δ 8.23 (d, 1H), 7.74 (d, 1H), 7.57 (d, 2H), 7.48-7.36 (m, 3H), 6.54 (d, 1H), 5.54 (s, 2H), 1.86 (d, 3H) |
| 460 | 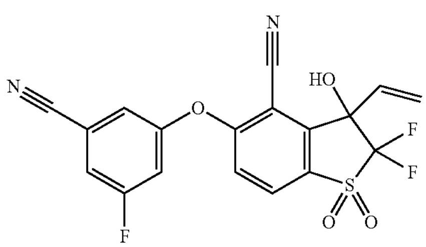 [SMILES: C=CC1(O)c2c(ccc(Oc3cc(F)cc(C#N)c3)c2C#N)S(=O)(=O)C1(F)F] | 405 (M − H) | (400 MHz, CDCl₃): δ 8.00 (d, 1H), 7.39-7.35 (m, 1H), 7.26-7.24 (m, 1H), 7.18-7.13 (m, 2H), 6.12 (ddd, 1H), 5.86 (d, 1H), 5.73 (d, 1H), 3.45 (d, 1H) |
| 461 | 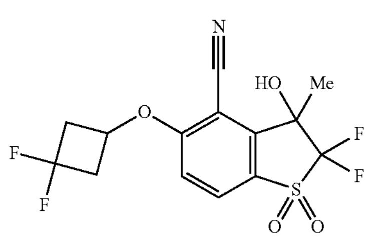 [SMILES: CC1(O)c2c(ccc(OC3CC(F)(F)C3)c2C#N)S(=O)(=O)C1(F)F] | 364 (M − H) | (400 MHz, CDCl₃): δ 7.97 (d, 1H), 7.02 (d, 1H), 4.90-4.81 (m, 1H), 3.29-3.17 (m, 2H), 3.10 (d, 1H), 3.02-2.87 (m, 2H), 1.93 (d, 3H) |

TABLE 1-continued

| No. | Structure | Mass Characterization | ¹H NMR Data |
|---|---|---|---|
| 462 | 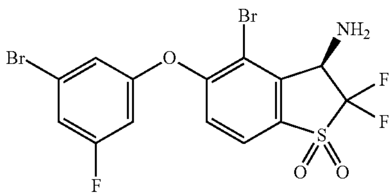 [SMILES: N[C@@H]1c2c(ccc(Oc3cc(F)cc(Br)c3)c2Br)S(=O)(=O)C1(F)F] | 486, 488, 490 (M + H) | (400 MHz, (CD$_3$)$_2$SO): δ 8.15 (d, 1H), 7.48 (d, 1H), 7.47 (ddd, 1H), 7.29-7.27 (m, 1H), 7.18 (dt, 1H), 5.04 (d, 1H) |
| 463 | 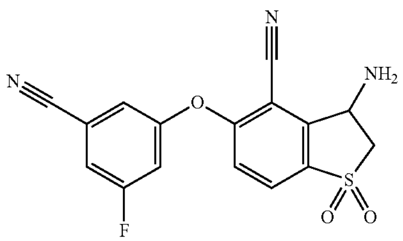 [SMILES: N#Cc1cc(F)cc(Oc2ccc3c(c2C#N)C(N)CS3(=O)=O)c1] | 342 (M − H) | (400 MHz, (CD$_3$)$_2$CO): δ 7.99 (d, 1H), 7.66-7.61 (m, 2H), 7.56 (dt, 1H), 7.42 (d, 1H), 5.03 (br s, 1H), 3.95 (dd, 1H), 3.48 (dd, 1H), 2.40 (br s, 2H) |
| 464 | 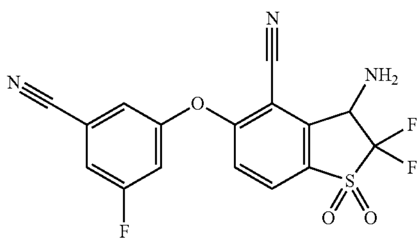 [SMILES: N#Cc1cc(F)cc(Oc2ccc3c(c2C#N)C(N)C(F)(F)S3(=O)=O)c1] | 380 (M + H) | (400 MHz, (CD$_3$)$_2$CO): δ 8.20 (d, 1H), 7.62 (ddd, 1H), 7.55-7.53 (m, 1H), 7.45 (dt, 1H), 7.39 (d, 1H), 5.14-5.04 (m, 1H), 2.42 (br d, 2H) |
| 465 | 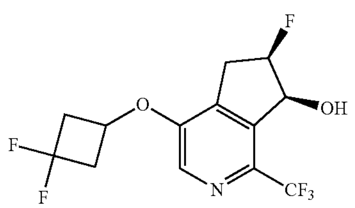 [SMILES: O[C@H]1c2c(C(F)(F)F)ncc(OC3CC(F)(F)C3)c2C[C@H]1F] | (M + H) 328 | (400 MHz, CDCl$_3$): δ 8.04 (s, 1H), 5.46-5.26 (m, 2H), 4.89-4.79 (m, 1H), 3.36-3.08 (m, 4H), 2.91-2.74 (m, 2H), 2.60 (dd, 1H) |
| 466 | 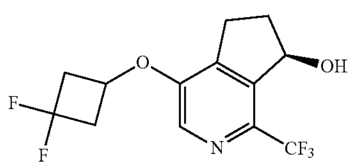 [SMILES: O[C@@H]1CCc2c(OC3CC(F)(F)C3)cnc(C(F)(F)F)c21] | (M + H) 310 | (400 MHz, CDCl$_3$): δ 7.98 (s, 1H), 5.59-5.54 (m, 1H), 4.88-4.79 (m, 1H), 3.24-3.07 (m, 3H), 2.89 (dd, 1H), 2.89-2.74 (m, 2H), 2.44-2.34 (m, 1H), 2.28-2.21 (m, 1H), 2.12-2.09 (m, 1H) |
| 467 | 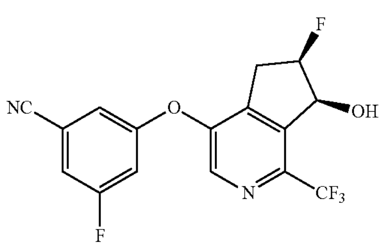 [SMILES: N#Cc1cc(F)cc(Oc2cnc(C(F)(F)F)c3c2C[C@@H](F)[C@H]3O)c1] | (M + H) 357 | (400 MHz, CDCl$_3$): δ 8.33 (s, 1H), 7.22 (ddd, 1H), 7.10-7.08 (m, 1H), 6.99 (dt, 1H), 5.54-5.46 (m, 1H), 5.46-5.28 (m, 1H), 3.26 (ddd, 1H), 3.11 (ddd, 1H), 2.67 (dd, 1H) |
| 468 | 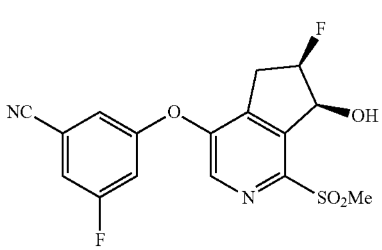 [SMILES: CS(=O)(=O)c1ncc(Oc2cc(F)cc(C#N)c2)c2c1[C@H](O)[C@H](F)C2] | (M + H) 367 | (400 MHz, CDCl$_3$): δ 8.27 (s, 1H), 7.25 (ddd, 1H), 7.14 (m, 1H), 7.03 (dt, 1H), 5.69 (dt, 1H), 5.53-5.36 (m, 1H), 4.24 (d, 1H), 3.34 (s, 3H), 3.31-3.24 (m, 1H), 3.09 (ddd, 1H) |

TABLE 1-continued
| No. | Structure | Mass Characterization | ¹H NMR Data |
|---|---|---|---|
| 469 | 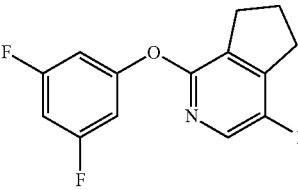 | 326/328 (M + H) | |
| 470 | 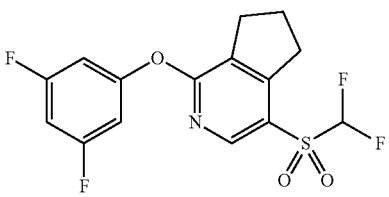 [SMILES: O=S(=O)(c1cnc(Oc2cc(F)cc(F)c2)c2c1CCC2)C(F)F] | 362 (M + H) | (400 MHz, CDCl₃): δ 7.49 (s, 1H), 6.80-6.71 (m, 3H), 6.19 (t, 1H), 3.36 (t, 2H), 3.06 (t, 2H), 2.31-2.23 (m, 2H) |
| 471 | 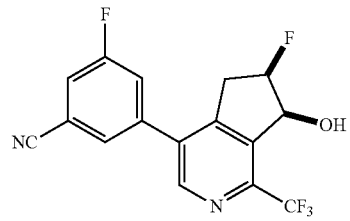 | (M + H) 341 | (400 MHz, CDCl₃): δ 8.65 (s, 1H), 7.53-7.48 (m, 2H), 7.40 (ddd, 1H), 5.56-5.48 (m, 1H), 5.35 (ddt, 1H), 3.41 (ddd, 1H), 3.21 (ddd, 1H), 2.65 (dd, 1H) |
| 472 | 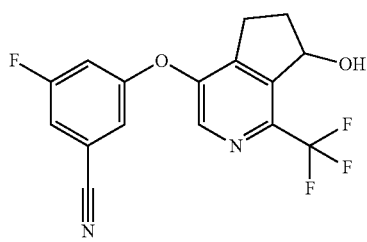 [SMILES: N#Cc1cc(F)cc(Oc2cnc(C(F)(F)F)c3c2CCC3O)c1] | 339 (M + H) | |
| 473 | 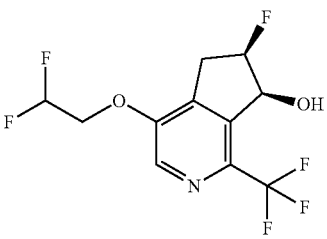 [SMILES: O[C@H]1c2c(C(F)(F)F)ncc(OCC(F)F)c2C[C@H]1F] | 302 (M + H) | |
| 474 | 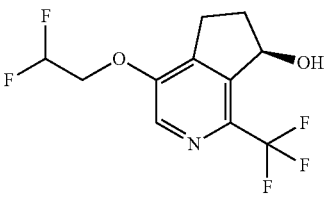 [SMILES: O[C@@H]1CCc2c(OCC(F)F)cnc(C(F)(F)F)c21] | 284 (M + H) | |
| 475 | 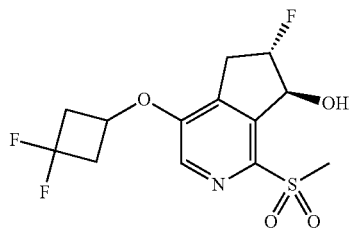 [SMILES: CS(=O)(=O)c1ncc(OC2CC(F)(F)C2)c2c1[C@H](O)[C@@H](F)C2] | 338 (M + H) | |

TABLE 1-continued

| No. | Structure | Mass Characterization | ¹H NMR Data |
|---|---|---|---|
| 476 | 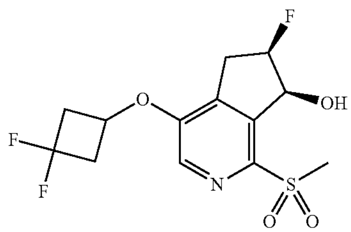 [SMILES: CS(=O)(=O)c1ncc(OC2CC(F)(F)C2)c2c1[C@H](O)[C@H](F)C2] | 338 (M + H) | |
| 477 | 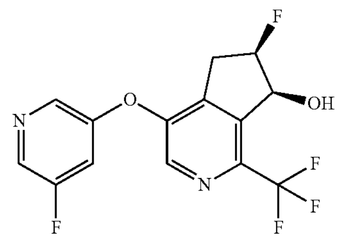 [SMILES: O[C@H]1c2c(C(F)(F)F)ncc(Oc3cncc(F)c3)c2C[C@H]1F] | 333 (M + H) | |
| 478 | 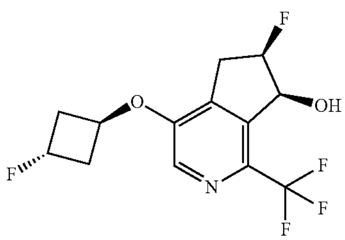 [SMILES: O[C@H]1c2c(C(F)(F)F)ncc(O[C@H]3C[C@H](F)C3)c2C[C@H]1F] | 310 (M + H) | |
| 479 | 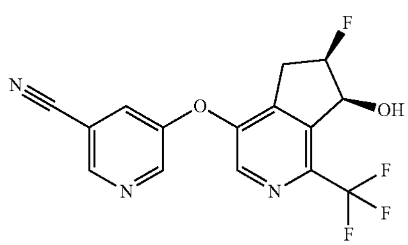 [SMILES: N#Cc1cncc(Oc2cnc(C(F)(F)F)c3c2C[C@@H](F)[C@H]3O)c1] | 340 (M + H) | |
| 480 | 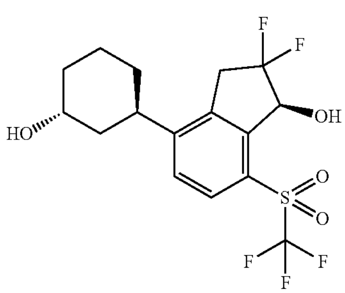 [SMILES: O=S(=O)(c1ccc([C@@H]2CCC[C@@H](O)C2)c2c1[C@H](O)C(F)(F)C2)C(F)(F)F] | (M + HCO₂⁻) 445 | (400 MHz, CDCl₃): δ 7.92 (d, 1H), 7.52 (d, 1H), 5.40 (dd, 1H), 4.33-4.28 (m, 1H), 3.59 (ddd, 1H), 3.49 (t, 1H), 3.22-3.13 (m, 2H), 1.97-1.82 (m, 4H), 1.75-1.58 (m, 3H), 1.46 (dd, 1H), 1.42-1.37 (m, 1H) |
| 481 | 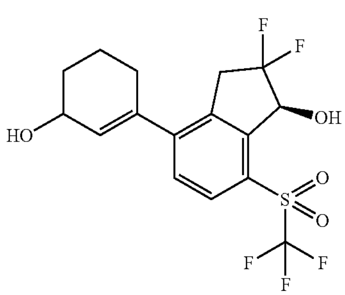 [SMILES: O=S(=O)(c1ccc(C2=CC(O)CCC2)c2c1[C@H](O)C(F)(F)C2)C(F)(F)F] | (M − OH) 381 | (400 MHz, CDCl₃): δ 7.93 (d, 1H), 7.50 (d, 1H), 5.91-5.88 (m, 1H), 5.39 (dd, 1H), 4.49-4.43 (m, 1H), 3.64 (ddd, 1H), 3.39 (t, 1H), 3.18 (dd, 1H), 2.49-2.39 (m, 1H), 2.22-2.11 (m, 1H), 2.09-1.92 (m, 2H), 1.81-1.59 (m, 3H) |

TABLE 1-continued

| No. | Structure | Mass Characterization | $^1$H NMR Data |
|---|---|---|---|
| 482 | 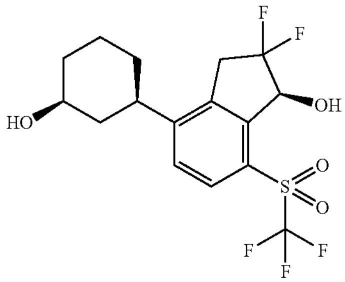 [SMILES: O=S(=O)(c1ccc([C@@H]2CCC[C@H](O)C2)c2c1[C@H](O)C(F)(F)C2)C(F)(F)F] | (M + HCO$_2^-$) 445 | (400 MHz, CDCl$_3$): δ 7.94 (d, 1H), 7.55 (d, 1H), 5.41 (dd, 1H), 3.82-3.72 (m, 1H), 3.56 (ddd, 1H), 3.42 (t, 1H), 3.20 (dd, 1H), 2.67 (tt, 1H), 2.17-2.08 (m, 2H), 2.01-1.94 (m, 1H), 1.82-1.75 (m, 1H), 1.60-1.42 (m, 3H), 1.40-1.27 (m, 2H) |
| 483 | 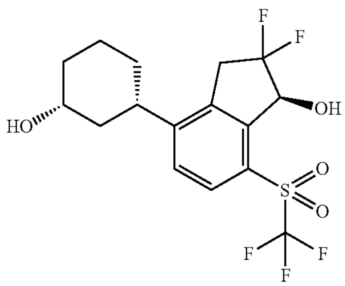 [SMILES: O=S(=O)(c1ccc([C@H]2CCC[C@@H](O)C2)c2c1[C@H](O)C(F)(F)C2)C(F)(F)F] | (M + HCO$_2^-$) 445 | (400 MHz, CDCl$_3$): δ 7.94 (d, 1H), 7.55 (d, 1H), 5.41 (dd, 1H), 3.82-3.72 (m, 1H), 3.58 (ddd, 1H), 3.40 (t, 1H), 3.18 (d, 1H), 2.67 (tt, 1H), 2.16-2.06 (m, 2H), 2.02-1.95 (m, 1H), 1.86-1.78 (m, 1H), 1.58-1.28 (m, 5H) |
| 484 | 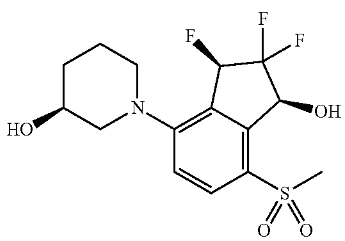 [SMILES: CS(=O)(=O)c1ccc(N2CCC[C@H](O)C2)c2c1[C@H](O)C(F)(F)[C@@H]2F] | 366 (M + H) | |
| 485 | 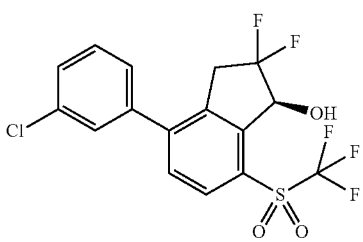 [SMILES: O=S(=O)(c1ccc(-c2cccc(Cl)c2)c2c1[C@H](O)C(F)(F)C2)C(F)(F)F] | (M − H) 411/ 413 | |
| 486 | 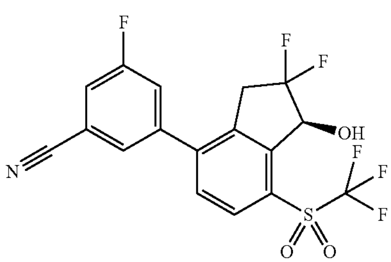 [SMILES: N#Cc1cc(F)cc(-c2ccc(S(=O)(=O)C(F)(F)F)c3c2CC(F)(F)[C@H]3O)c1] | (M − H) 420 | |
| 487 | 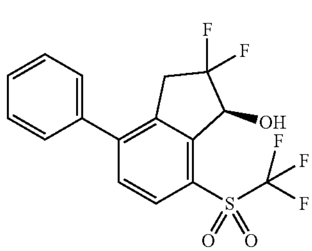 [SMILES: O=S(=O)(c1ccc(-c2ccccc2)c2c1[C@H](O)C(F)(F)C2)C(F)(F)F] | (M − H) 377 | |

TABLE 1-continued

| No. | Structure | Mass Characterization | ¹H NMR Data |
|---|---|---|---|
| 488 | 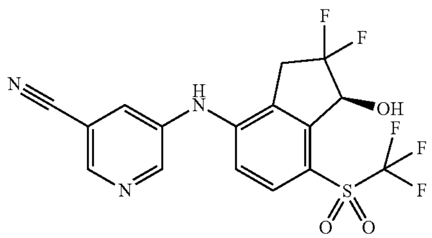 [SMILES: N#Cc1cncc(Nc2ccc(S(=O)(=O)C(F)(F)F)c3c2CC(F)(F)[C@H]3O)c1] | (M + H) 420 | |
| 489 | 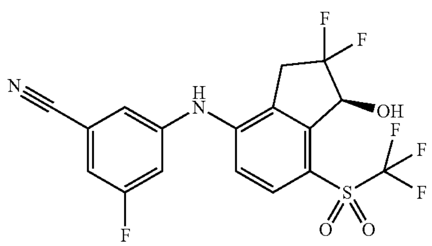 [SMILES: N#Cc1cc(F)cc(Nc2ccc(S(=O)(=O)C(F)(F)F)c3c2CC(F)(F)[C@H]3O)c1] | (M − H) 435 | |
| 490 | 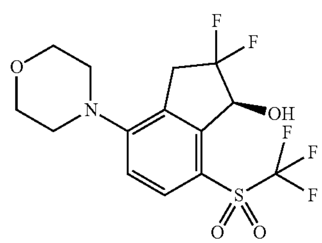 [SMILES: O=S(=O)(c1ccc(N2CCOCC2)c2c1[C@H](O)C(F)(F)C2)C(F)(F)F] | (M + H) 388 | |
| 491 | 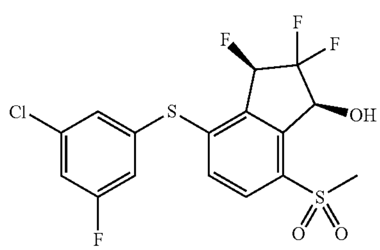 [SMILES: CS(=O)(=O)c1ccc(Sc2cc(F)cc(Cl)c2)c2c1[C@H](O)C(F)(F)[C@@H]2F] | (M + Na) 449 | |
| 492 | 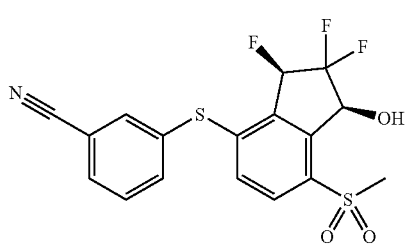 [SMILES: CS(=O)(=O)c1ccc(Sc2cccc(C#N)c2)c2c1[C@H](O)C(F)(F)[C@@H]2F] | (M + Na) 422 | |
| 493 | 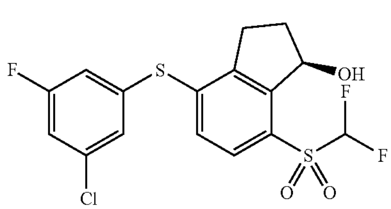 [SMILES: O=S(=O)(c1ccc(Sc2cc(F)cc(Cl)c2)c2c1[C@H](O)CC2)C(F)F] | 453/455 (M + HCO$_2$) | |

TABLE 1-continued

| No. | Structure | Mass Characterization | ¹H NMR Data |
|---|---|---|---|
| 494 | 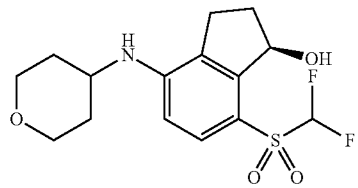 [SMILES: O=S(=O)(c1ccc(NC2CCOCC2)c2c1[C@H](O)CC2)C(F)F] | 346 (M − H) | |
| 495 | 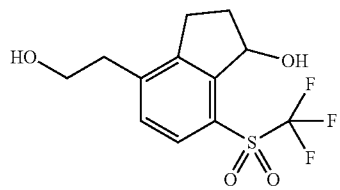 [SMILES: O=S(=O)(c1ccc(CCO)c2c1C(O)CC2)C(F)(F)F] | 309 (M − H) | |
| 496 | 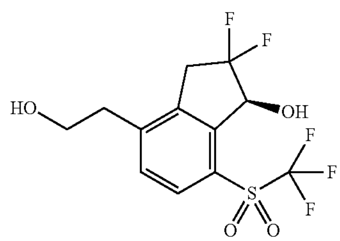 [SMILES: O=S(=O)(c1ccc(CCO)c2c1[C@H](O)C(F)(F)C2)C(F)(F)F] | 345 (M − H) | |
| 497 | 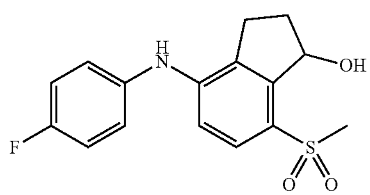 [SMILES: CS(=O)(=O)c1ccc(Nc2ccc(F)cc2)c2c1C(O)CC2] | 320 (M − H) | |
| 498 | 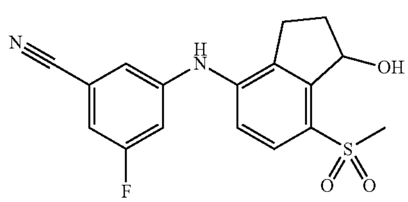 [SMILES: CS(=O)(=O)c1ccc(Nc2cc(F)cc(C#N)c2)c2c1C(O)CC2] | 345 (M − H) | |
| 499 | 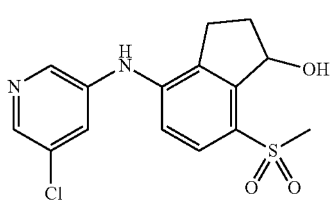 [SMILES: CS(=O)(=O)c1ccc(Nc2cncc(Cl)c2)c2c1C(O)CC2] | 337 (M − H) | |
| 500 | 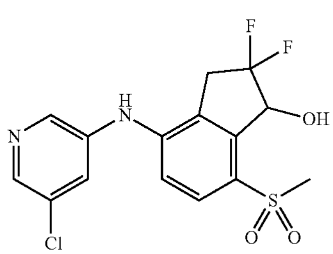 [SMILES: CS(=O)(=O)c1ccc(Nc2cncc(Cl)c2)c2c1C(O)C(F)(F)C2] | 373 (M − H) | |

TABLE 1-continued

| No. | Structure | Mass Characterization | $^1$H NMR Data |
|---|---|---|---|
| 501 | 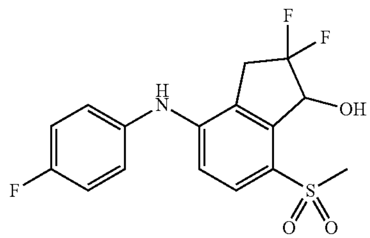 [SMILES: CS(=O)(=O)c1ccc(Nc2ccc(F)cc2)c2c1C(O)C(F)(F)C2] | 356 (M − H) | |
| 502 | 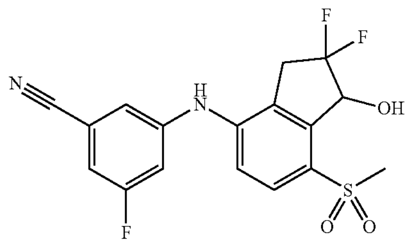 [SMILES: CS(=O)(=O)c1ccc(Nc2cc(F)cc(C#N)c2)c2c1C(O)C(F)(F)C2] | 381 (M − H) | |
| 503 | 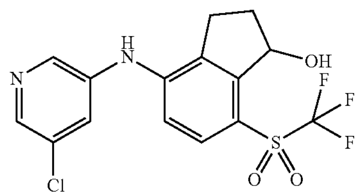 [SMILES: O=S(=O)(c1ccc(Nc2cncc(Cl)c2)c2c1C(O)CC2)C(F)(F)F] | 391 (M − H) | |
| 504 | 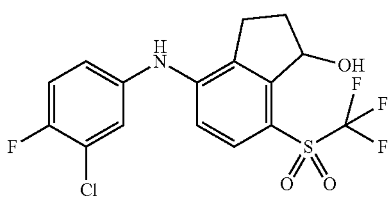 [SMILES: O=S(=O)(c1ccc(Nc2ccc(F)c(Cl)c2)c2c1C(O)CC2)C(F)(F)F] | 408 (M − H) | |
| 505 | 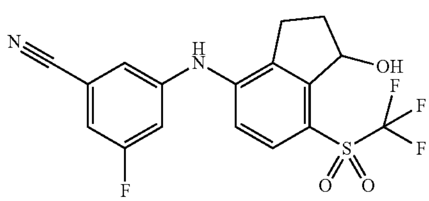 [SMILES: N#Cc1cc(F)cc(Nc2ccc(S(=O)(=O)C(F)(F)F)c3c2CCC3O)c1] | 399 (M − H) | |
| 506 | 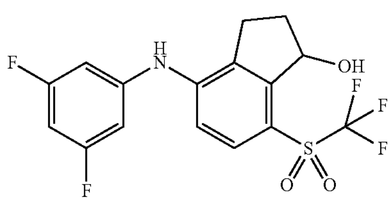 [SMILES: O=S(=O)(c1ccc(Nc2cc(F)cc(F)c2)c2c1C(O)CC2)C(F)(F)F] | 392 (M − H) | |
| 507 | 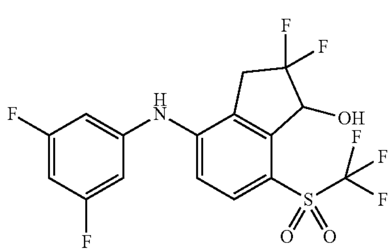 [SMILES: O=S(=O)(c1ccc(Nc2cc(F)cc(F)c2)c2c1C(O)C(F)(F)C2)C(F)(F)F] | | $^1$HNMR (300 MHz, CDCl$_3$): δ 7.83 (d, 1H), 7.30 (d, 1H), 6.77 (m, 2H), 6.67 (m, 1H), 6.10 (s, 1H), 5.36 (m, 1H), 3.45 (m, 1H), 3.27 (m, 2H). |

TABLE 1-continued

| No. | Structure | Mass Characterization | ¹H NMR Data |
|---|---|---|---|
| 508 | 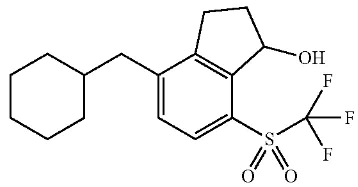 [SMILES: O=S(=O)(c1ccc(CC2CCCCC2)c2c1C(O)CC2)C(F)(F)F] | 361 (M − H) | |
| 509 | 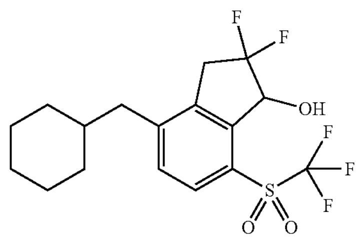 [SMILES: O=S(=O)(c1ccc(CC2CCCCC2)c2c1C(O)C(F)(F)C2)C(F)(F)F] | 397 (M − H) | |
| 510 | 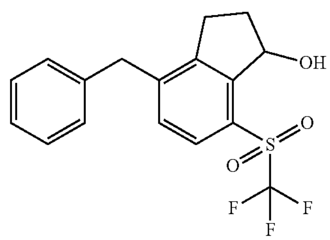 [SMILES: O=S(=O)(c1ccc(Cc2ccccc2)c2c1C(O)CC2)C(F)(F)F] | 355 (M − H) | |
| 511 | 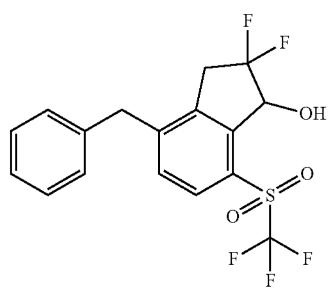 [SMILES: O=S(=O)(c1ccc(Cc2ccccc2)c2c1C(O)C(F)(F)C2)C(F)(F)F] | 391 (M − H) | |
| 512 | 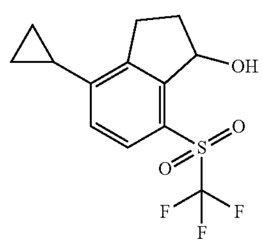 [SMILES: O=S(=O)(c1ccc(C2CC2)c2c1C(O)CC2)C(F)(F)F] | | ¹HNMR (300 MHz, CDCl$_3$): δ 8.76 (d, 1H), 6.97 (d, 1H), 5.62 (m, 1H), 3.29 (m, 1H), 3.09 (m, 1H), 3.05 (m, 1H), 2.36 (m, 2H), 1.98 (m, 1H), 1.17 (m, 2H), 0.85 (m, 2H). |
| 513 | 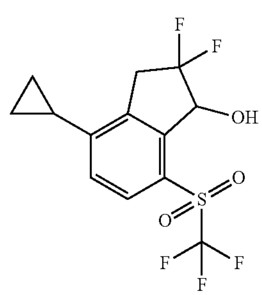 [SMILES: O=S(=O)(c1ccc(C2CC2)c2c1C(O)C(F)(F)C2)C(F)(F)F] | 341 (M − H) | |

TABLE 1-continued

| No. | Structure | Mass Characterization | ¹H NMR Data |
|-----|-----------|----------------------|-------------|
| 514 | 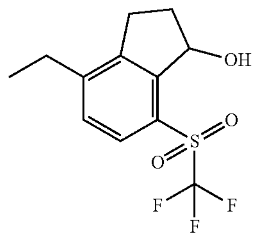 [SMILES: CCc1ccc(S(=O)(=O)C(F)(F)F)c2c1CCC2O] | 294 (M − H) | |
| 515 | 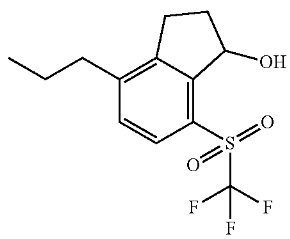 [SMILES: CCCc1ccc(S(=O)(=O)C(F)(F)F)c2c1CCC2O] | 307 (M − H) | |
| 516 | 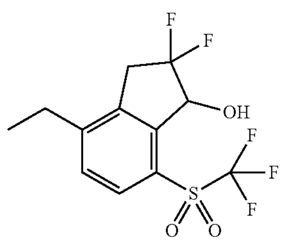 [SMILES: CCc1ccc(S(=O)(=O)C(F)(F)F)c2c1CC(F)(F)C2O] | 329 (M − H) | |
| 517 | 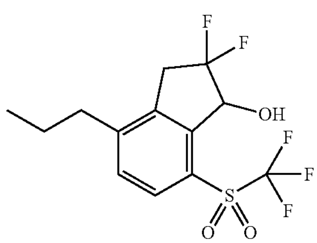 [SMILES: CCCc1ccc(S(=O)(=O)C(F)(F)F)c2c1CC(F)(F)C2O] | 343 (M − H) | |
| 518 | 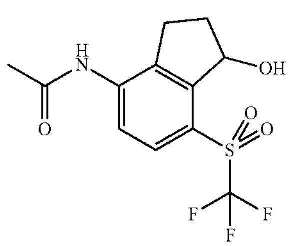 [SMILES: CC(=O)Nc1ccc(S(=O)(=O)C(F)(F)F)c2c1CCC2O] | 322 (M − H) | |
| 519 | 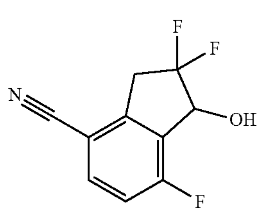 [SMILES: N#Cc1ccc(F)c2c1CC(F)(F)C2O] | 214 (M + H) | |

TABLE 1-continued

| No. | Structure | Mass Characterization | ¹H NMR Data |
|---|---|---|---|
| 520 | 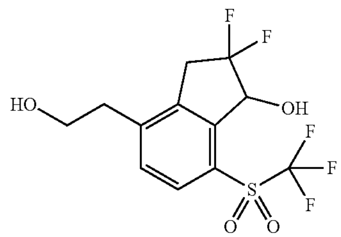 [SMILES: O=S(=O)(c1ccc(CCO)c2c1C(O)C(F)(F)C2)C(F)(F)F] | 345 (M − H) | |
| 521 | 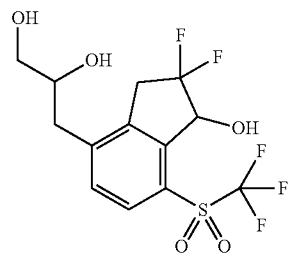 [SMILES: O=S(=O)(c1ccc(CC(O)CO)c2c1C(O)C(F)(F)C2)C(F)(F)F] | 375 (M − H) | |
| 522 | 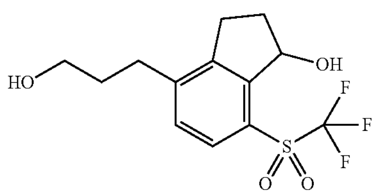 [SMILES: O=S(=O)(c1ccc(CCCO)c2c1C(O)CC2)C(F)(F)F] | 323 (M − H) | |
| 523 | 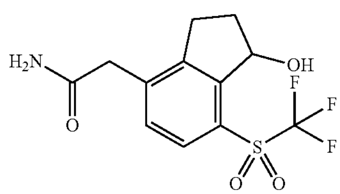 [SMILES: NC(=O)Cc1ccc(S(=O)(=O)C(F)(F)F)c2c1CCC2O] | 322 (M − H) | |
| 524 | 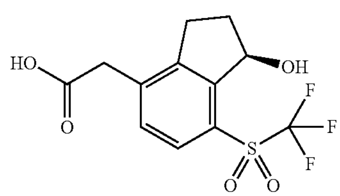 [SMILES: O=C(O)Cc1ccc(S(=O)(=O)C(F)(F)F)c2c1CC[C@H]2O] | 323 (M − H) | |
| 525 | 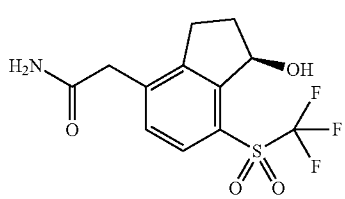 [SMILES: NC(=O)Cc1ccc(S(=O)(=O)C(F)(F)F)c2c1CC[C@H]2O] | 323 (M − H) | |
| 526 | 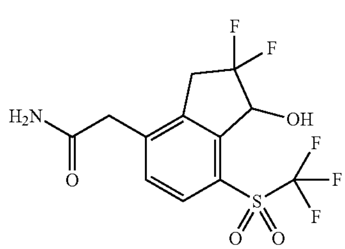 [SMILES: NC(=O)Cc1ccc(S(=O)(=O)C(F)(F)F)c2c1CC(F)(F)C2O] | 360 (M + H) | |

TABLE 1-continued

| No. | Structure | Mass Characterization | ¹H NMR Data |
|---|---|---|---|
| 527 | 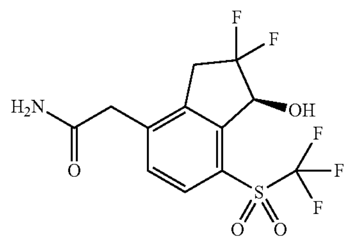 [SMILES: NC(=O)Cc1ccc(S(=O)(=O)C(F)(F)F)c2c1CC(F)(F)[C@H]2O] | 360 (M + H) | |
| 528 | 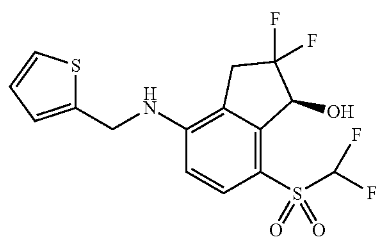 [SMILES: O=S(=O)(c1ccc(NCc2cccs2)c2c1[C@H](O)C(F)(F)C2)C(F)F] | | (400 MHz, CDCl₃): δ 7.79 (d, 1H), 7.29 (d, 1H), 7.07-7.00 (m, 2H), 6.78 (d, 1H), 6.33 (t, 1H), 5.40 (d, 1H), 4.66 (d, 2H), 4.64-4.58 (m, 1H), 3.38-3.24 (m, 2H), 3.14 (t, 1H) |
| 529 | 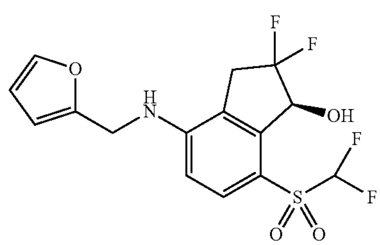 [SMILES: O=S(=O)(c1ccc(NCc2ccco2)c2c1[C@H](O)C(F)(F)C2)C(F)F] | | (400 MHz, CDCl₃): δ 7.79 (d, 1H), 7.40 (s, 1H), 6.80 (d, 1H), 6.46-6.20 (m, 3H), 5.39 (d, 1H), 4.64 (t, 1H), 4.47 (d, 2H), 3.46-3.24 (m, 2H), 3.14 (t, 1H) |
| 530 | 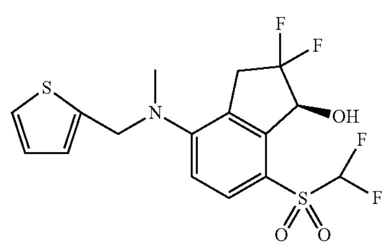 [SMILES: CN(Cc1cccs1)c1ccc(S(=O)(=O)C(F)F)c2c1CC(F)(F)[C@H]2O] | | (400 MHz, CDCl₃): δ 7.79 (d, 1H), 7.28 (d, 1H), 7.01-6.94 (m, 3H), 6.35 (t, 1H), 5.38 (d, 1H), 4.61 (m, 2H), 3.70-3.58 (m, 1H), 3.52-3.44 (m, 1H), 3.23 (br s, 1H), 3.00 (s, 3H) |
| 531 | 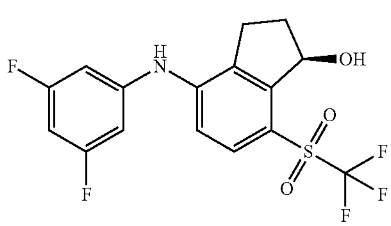 [SMILES: O=S(=O)(c1ccc(Nc2cc(F)cc(F)c2)c2c1[C@H](O)CC2)C(F)(F)F] | [M − H]⁻ 392 | |
| 532 | 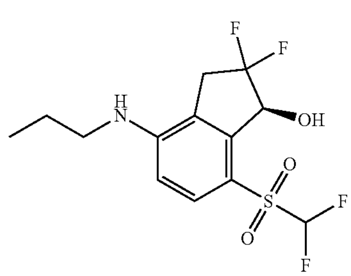 [SMILES: CCCNc1ccc(S(=O)(=O)C(F)F)c2c1CC(F)(F)[C@H]2O] | [M + H]⁺ 343 | |

TABLE 1-continued

| No. | Structure | Mass Characterization | ¹H NMR Data |
|---|---|---|---|
| 533 | 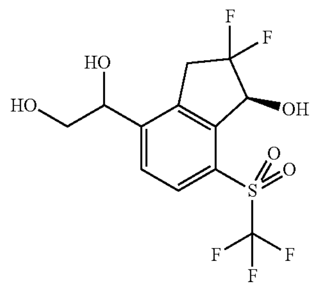 [SMILES: O=S(=O)(c1ccc(C(O)CO)c2c1[C@H](O)C(F)(F)C2)C(F)(F)F] | | (400 MHz, CDCl$_3$): δ 8.00 (dd, 1H), 7.84 (dd, 1H), 5.41 (dd, 1H), 5.00-4.93 (m, 1H), 3.83 (ddd, 1H), 3.72-3.43 (m, 4H) |
| 534 | 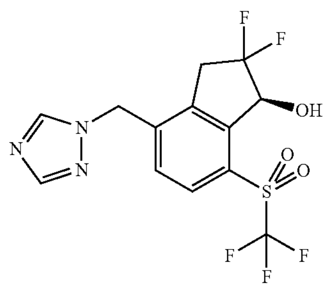 [SMILES: O=S(=O)(c1ccc(Cn2cncn2)c2c1[C@H](O)C(F)(F)C2)C(F)(F)F] | [M − H]⁻ 382 | |
| 535 | 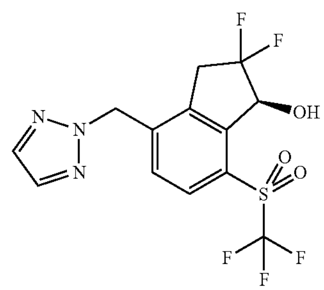 [SMILES: O=S(=O)(c1ccc(Cn2nccn2)c2c1[C@H](O)C(F)(F)C2)C(F)(F)F] | [M − H]⁻ 382 | |
| 536 | 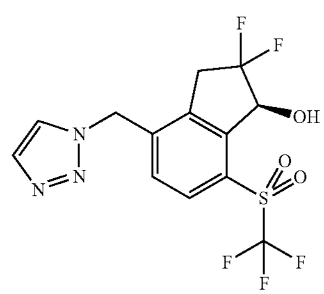 [SMILES: O=S(=O)(c1ccc(Cn2ccnn2)c2c1[C@H](O)C(F)(F)C2)C(F)(F)F] | [M − H]⁻ 382 | |
| 537 | 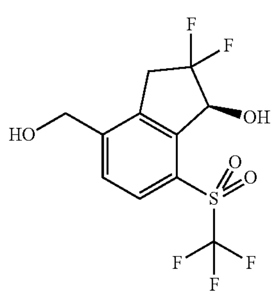 [SMILES: O=S(=O)(c1ccc(CO)c2c1[C@H](O)C(F)(F)C2)C(F)(F)F] | [M − H]⁻ 331 | |

TABLE 1-continued

| No. | Structure | Mass Characterization | ¹H NMR Data |
|---|---|---|---|
| 538 | 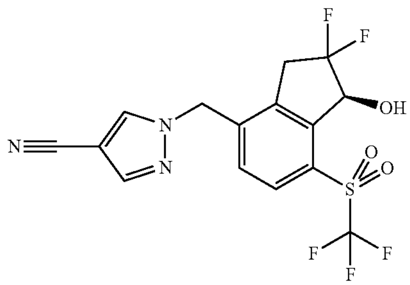 [SMILES: N#Cc1cnn(Cc2ccc(S(=O)(=O)C(F)(F)F)c3c2CC(F)(F)[C@H]3O)c1] | [M − H]⁻ 406 | |
| 539 | 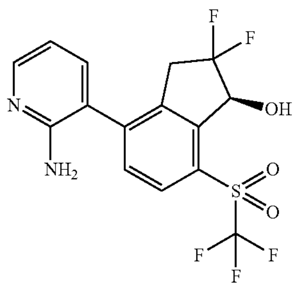 [SMILES: Nc1ncccc1-c1ccc(S(=O)(=O)C(F)(F)F)c2c1CC(F)(F)[C@H]2O] | [M + H]⁺ 395 | |
| 540 | 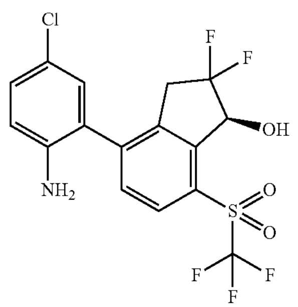 [SMILES: Nc1ccc(Cl)cc1-c1ccc(S(=O)(=O)C(F)(F)F)c2c1CC(F)(F)[C@H]2O] | [M + H]⁺ 428/ 430 | |
| 541 | 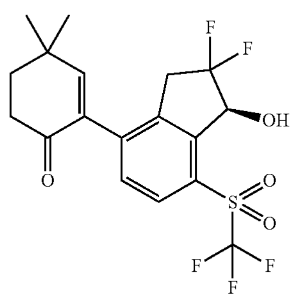 [SMILES: CC1(C)C=C(c2ccc(S(=O)(=O)C(F)(F)F)c3c2CC(F)(F)[C@H]3O)C(=O)CC1] | [M + H]⁺ 425 | |
| 542 | 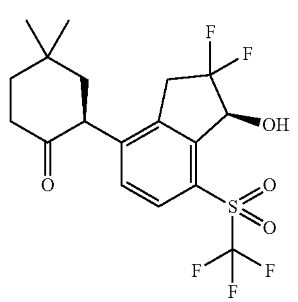 [SMILES: CC1(C)CCC(=O)[C@H](c2ccc(S(=O)(=O)C(F)(F)F)c3c2CC(F)(F)[C@H]3O)C1] | [M + NH₄]⁺ 444 | |

TABLE 1-continued

| No. | Structure | Mass Characterization | ¹H NMR Data |
|---|---|---|---|
| 543 | 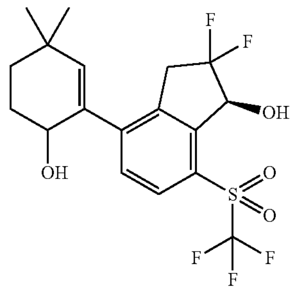 [SMILES: CC1(C)C=C(c2ccc(S(=O)(=O)C(F)(F)F)c3c2CC(F)(F)[C@H]3O)C(O)CC1] | [M − OH]⁺ 409 | |
| 544 | 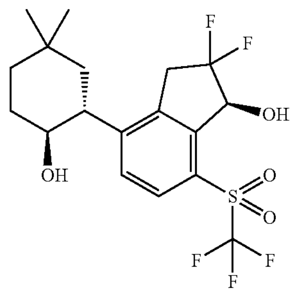 [SMILES: CC1(C)CC[C@H](O)[C@@H](c2ccc(S(=O)(=O)C(F)(F)F)c3c2CC(F)(F)[C@H]3O)C1] | [M + Cl]⁻ 463/465 | |
| 545 | 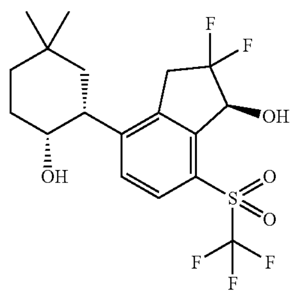 [SMILES: CC1(C)CC[C@@H](O)[C@@H](c2ccc(S(=O)(=O)C(F)(F)F)c3c2CC(F)(F)[C@H]3O)C1] | [M + Cl]⁻ 463/465 | |
| 546 | 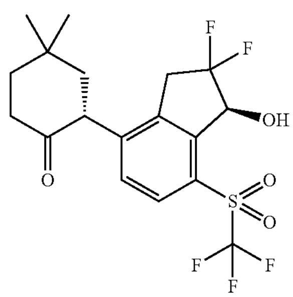 [SMILES: CC1(C)CCC(=O)[C@@H](c2ccc(S(=O)(=O)C(F)(F)F)c3c2CC(F)(F)[C@H]3O)C1] | [M + NH₄]⁺ 444 | |
| 547 | 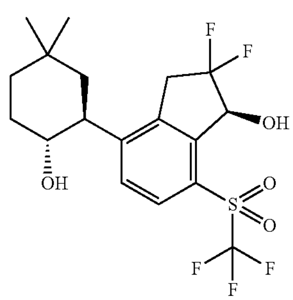 [SMILES: CC1(C)CC[C@@H](O)[C@H](c2ccc(S(=O)(=O)C(F)(F)F)c3c2CC(F)(F)[C@H]3O)C1] | [M + Cl]⁻ 463/465 | |

TABLE 1-continued

| No. | Structure | Mass Characterization | ¹H NMR Data |
|-----|-----------|----------------------|-------------|
| 548 | 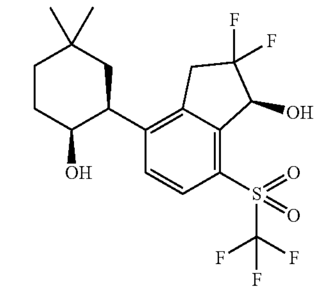 [SMILES: CC1(C)CC[C@H](O)[C@H](c2ccc(S(=O)(=O)C(F)(F)F)c3c2CC(F)(F)[C@H]3O)C1] | [M + NH$_4$]$^+$ 446 | |
| 549 | 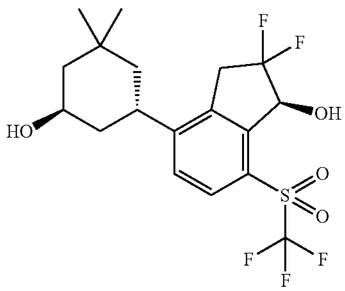 [SMILES: CC1(C)C[C@H](O)C[C@@H](c2ccc(S(=O)(=O)C(F)(F)F)c3c2CC(F)(F)[C@H]3O)C1] | [M + NH$_4$]$^+$ 446 | |
| 550 | 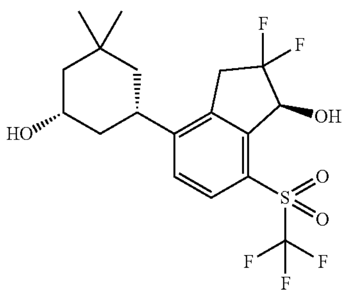 [SMILES: CC1(C)C[C@@H](O)C[C@@H](c2ccc(S(=O)(=O)C(F)(F)F)c3c2CC(F)(F)[C@H]3O)C1] | [M + NH$_4$]$^+$ 446 | |
| 551 | 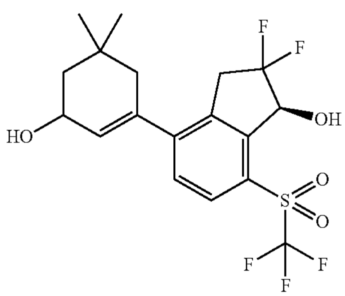 [SMILES: CC1(C)CC(c2ccc(S(=O)(=O)C(F)(F)F)c3c2CC(F)(F)[C@H]3O)=CC(O)C1] | [M − OH]$^+$ 409 | |
| 552 | 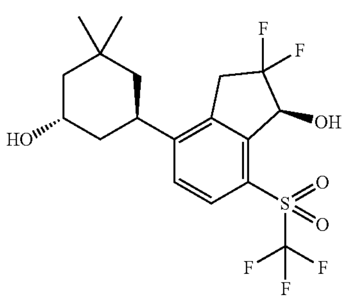 [SMILES: CC1(C)C[C@@H](O)C[C@H](c2ccc(S(=O)(=O)C(F)(F)F)c3c2CC(F)(F)[C@H]3O)C1] | [M + NH$_4$]$^+$ 446 | |

TABLE 1-continued

| No. | Structure | Mass Characterization | ¹H NMR Data |
|---|---|---|---|
| 553 | 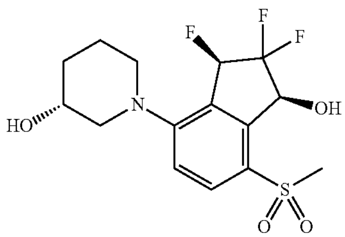 [SMILES: CS(=O)(=O)c1ccc(N2CCC[C@@H](O)C2)c2c1[C@H](O)C(F)(F)[C@@H]2F] | [M + H]⁺ 366 | |
| 554 | 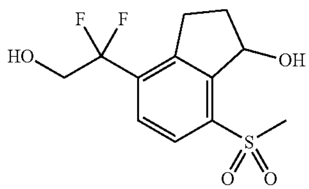 [SMILES: CS(=O)(=O)c1ccc(C(F)(F)CO)c2c1C(O)CC2] | [M + NH₄]⁺ 310 | |
| 555 | 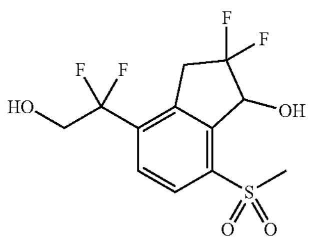 [SMILES: CS(=O)(=O)c1ccc(C(F)(F)CO)c2c1C(O)C(F)(F)C2] | [M + NH₄]⁺ 346 | |
| 556 | 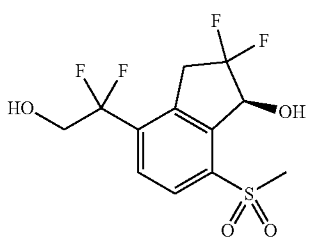 [SMILES: CS(=O)(=O)c1ccc(C(F)(F)CO)c2c1[C@H](O)C(F)(F)C2] | [M + NH₄]⁺ 346 | |
| 557 | 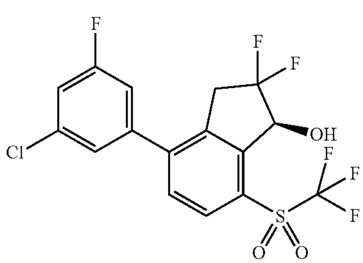 [SMILES: O=S(=O)(c1ccc(-c2cc(F)cc(Cl)c2)c2c1[C@H](O)C(F)(F)C2)C(F)(F)F] | [M + Na]⁺ 454 | |
| 558 | 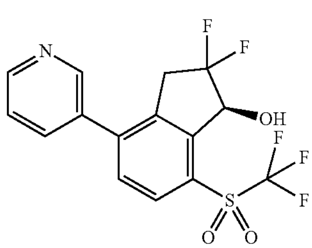 [SMILES: O=S(=O)(c1ccc(-c2cccnc2)c2c1[C@H](O)C(F)(F)C2)C(F)(F)F] | [M + H]⁺ 380 | |

TABLE 1-continued

| No. | Structure | Mass Characterization | ¹H NMR Data |
|---|---|---|---|
| 559 | 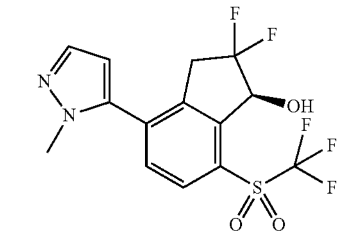 [SMILES: Cn1nccc1-c1ccc(S(=O)(=O)C(F)(F)F)c2c1CC(F)(F)[C@H]2O] | [M + H]⁺ 383 | |
| 560 | 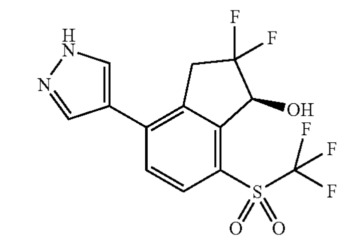 [SMILES: O=S(=O)(c1ccc(-c2cn[nH]c2)c2c1[C@H](O)C(F)(F)C2)C(F)(F)F] | [M + H]⁺ 369 | |
| 561 | 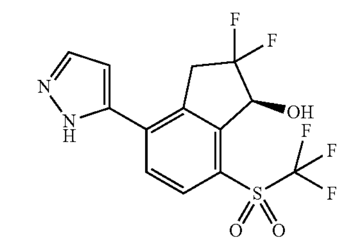 [SMILES: O=S(=O)(c1ccc(-c2ccn[nH]2)c2c1[C@H](O)C(F)(F)C2)C(F)(F)F] | [M + H]⁺ 369 | |
| 562 | 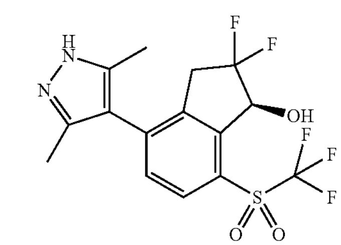 [SMILES: Cc1n[nH]c(C)c1-c1ccc(S(=O)(=O)C(F)(F)F)c2c1CC(F)(F)[C@H]2O] | [M + H]⁺ 397 | |
| 563 | 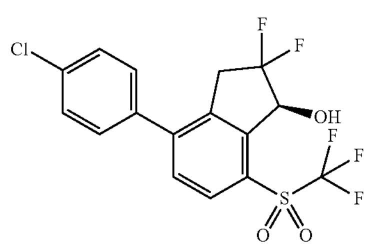 [SMILES: O=S(=O)(c1ccc(-c2ccc(Cl)cc2)c2c1[C@H](O)C(F)(F)C2)C(F)(F)F] | [M + Na]⁺ 436/ 438 | |
| 564 | 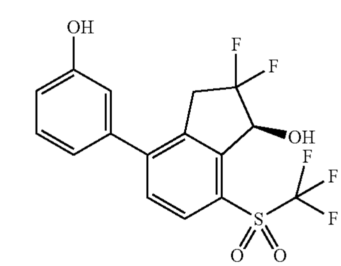 [SMILES: O=S(=O)(c1ccc(-c2cccc(O)c2)c2c1[C@H](O)C(F)(F)C2)C(F)(F)F] | [M − H]⁻ 393 | |

TABLE 1-continued

| No. | Structure | Mass Characterization | ¹H NMR Data |
|---|---|---|---|
| 565 | 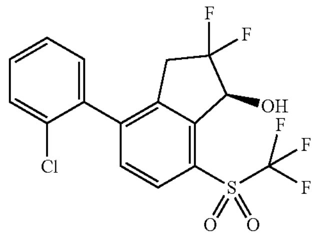 [SMILES: O=S(=O)(c1ccc(-c2ccccc2Cl)c2c1[C@H](O)C(F)(F)C2)C(F)(F)F] | [M + Na]⁺ 436/438 | |
| 566 | 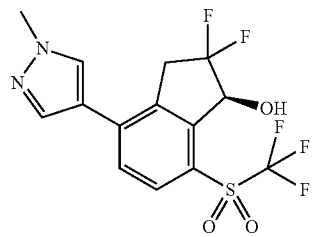 [SMILES: Cn1cc(-c2ccc(S(=O)(=O)C(F)(F)F)c3c2CC(F)(F)[C@H]3O)cn1] | [M + H]⁺ 383 | |
| 567 | 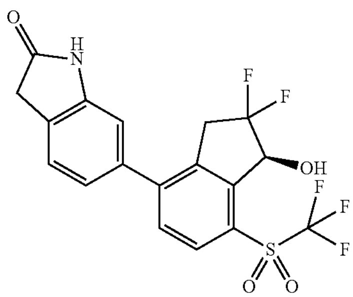 [SMILES: O=C1Cc2ccc(-c3ccc(S(=O)(=O)C(F)(F)F)c4c3CC(F)(F)[C@H]4O)cc2N1] | [M + H]⁺ 434 | |
| 568 | 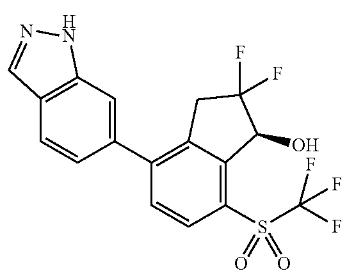 [SMILES: O=S(=O)(c1ccc(-c2ccc3cn[nH]c3c2)c2c1[C@H](O)C(F)(F)C2)C(F)(F)F] | [M + H]⁺ 419 | |
| 569 | 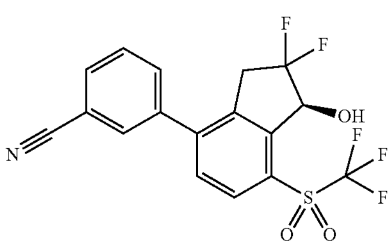 [SMILES: N#Cc1cccc(-c2ccc(S(=O)(=O)C(F)(F)F)c3c2CC(F)(F)[C@H]3O)c1] | [M − H]⁻ 402 | |
| 570 | 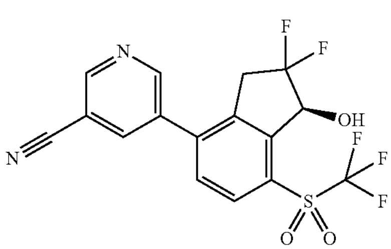 [SMILES: N#Cc1cncc(-c2ccc(S(=O)(=O)C(F)(F)F)c3c2CC(F)(F)[C@H]3O)c1] | [M + H]⁺ 405 | |

TABLE 1-continued

| No. | Structure | Mass Characterization | ¹H NMR Data |
|---|---|---|---|
| 571 | 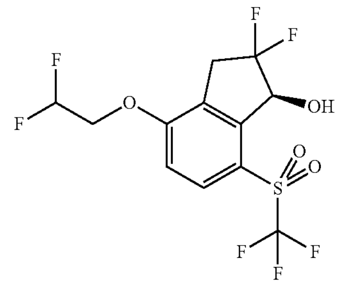 | (M − H) 381 | |
| 572 | 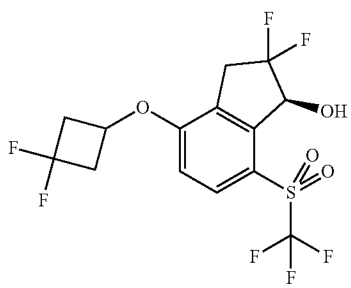 [SMILES: O=S(=O)(c1ccc(OC2CC(F)(F)C2)c2c1[C@H](O)C(F)(F)C2)C(F)(F)F] | (M − H) 407 | |
| 573 | 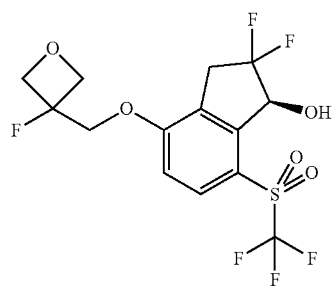 [SMILES: O=S(=O)(c1ccc(OCC2(F)COC2)c2c1[C@H](O)C(F)(F)C2)C(F)(F)F] | (M − H) 405 | |
| 574 | 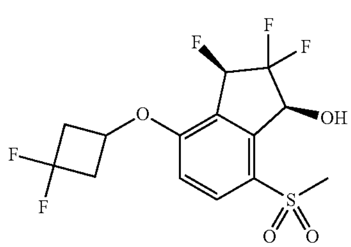 [SMILES: CS(=O)(=O)c1ccc(OC2CC(F)(F)C2)c2c1[C@H](O)C(F)(F)[C@@H]2F] | 373 (M + H) | |
| 575 | 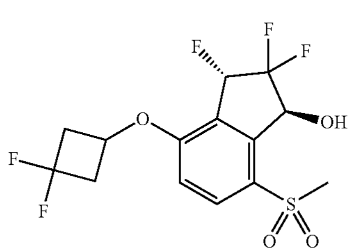 [SMILES: CS(=O)(=O)c1ccc(OC2CC(F)(F)C2)c2c1[C@H](O)C(F)(F)[C@H]2F] | 373 (M + H) | |

TABLE 1-continued

| No. | Structure | Mass Characterization | ¹H NMR Data |
|---|---|---|---|
| 576 | 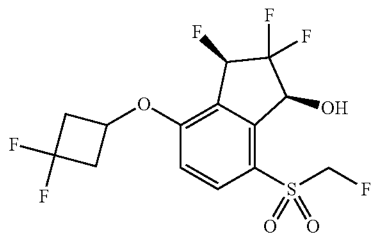 [SMILES: O=S(=O)(CF)c1ccc(OC2CC(F)(F)C2)c2c1[C@H](O)C(F)(F)[C@@H]2F] | (M + H) 391 | |
| 577 | 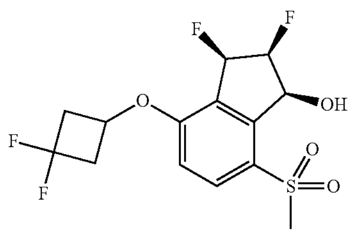 [SMILES: CS(=O)(=O)c1ccc(OC2CC(F)(F)C2)c2c1[C@H](O)[C@H](F)[C@@H]2F] | (M + NH4) 372 | |
| 578 | 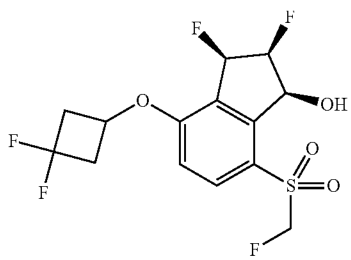 [SMILES: O=S(=O)(CF)c1ccc(OC2CC(F)(F)C2)c2c1[C@H](O)[C@H](F)[C@@H]2F] | (M + NH4) 390 | |
| 579 | 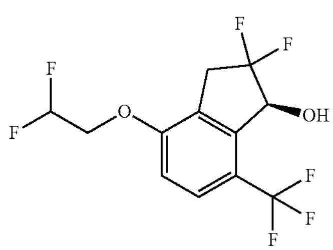 [SMILES: O[C@H]1c2c(C(F)(F)F)ccc(OCC(F)F)c2CC1(F)F] | [M − H + formate] 363 | |
| 580 | 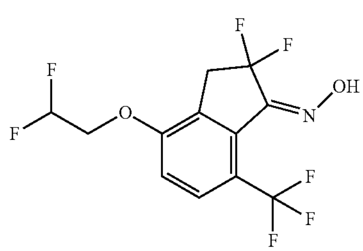 [SMILES: O/N=C1/c2c(C(F)(F)F)ccc(OCC(F)F)c2CC1(F)F] | [M + H] 332 | |
| 581 | 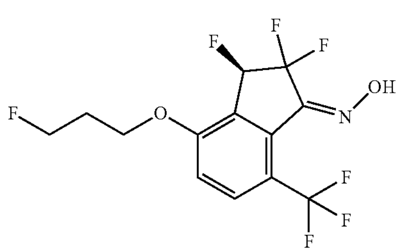 [SMILES: O/N=C1/c2c(C(F)(F)F)ccc(OCCCF)c2[C@@H](F)C1(F)F] | | (400 MHz, CDCl$_3$): δ 8.33 (d, 1H), 7.88-7.84 (m, 1H), 7.04 (d, 1H), 5.82 (dd, 1H), 4.67 (dt, 2H), 4.33-4.24 (m, 2H), 2.32-2.20 (m, 2H) |

TABLE 1-continued

| No. | Structure | Mass Characterization | ¹H NMR Data |
|---|---|---|---|
| 582 | 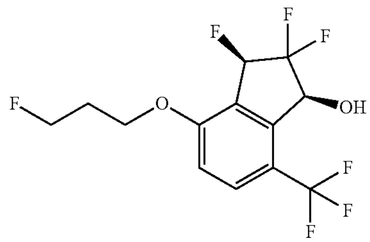 [SMILES: O[C@H]1c2c(C(F)(F)F)ccc(OCCCF)c2[C@@H](F)C1(F)F] | | (400 MHz, CDCl₃): δ 7.80-7.77 (m, 1H), 7.05 (d, 1H), 5.74 (dd, 1H), 5.25-5.20 (m, 1H), 4.66 (dt, 2H), 4.33-4.22 (m, 2H), 2.52 (d, 1H), 2.32-2.19 (m, 2H) |
| 583 | 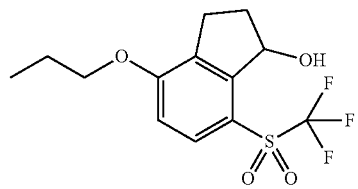 [SMILES: CCCOc1ccc(S(=O)(=O)C(F)(F)F)c2c1CCC2O] | | (300 MHz, CDCl₃): δ 7.87 (d, 1H), 6.95 (d, 1H), 5.58 (d, 1H), 4.08 (m, 2H), 2.06-3.17 (m, 2H), 2.84-2.94 (m, 1H), 2.37 (m, 1H), 2.27 (m, 1H), 1.86 (m, 2H), 1.07 (t, 3H) |
| 584 | 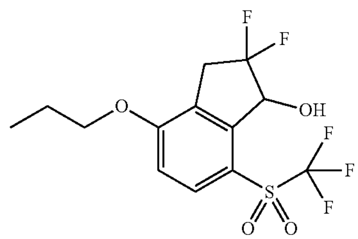 [SMILES: CCCOc1ccc(S(=O)(=O)C(F)(F)F)c2c1CC(F)(F)C2O] | 359 (M − H) | |
| 585 | 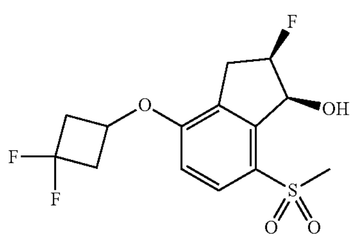 [SMILES: CS(=O)(=O)c1ccc(OC2CC(F)(F)C2)c2c1[C@H](O)[C@H](F)C2] | 337 (M + H) | |
| 586 | 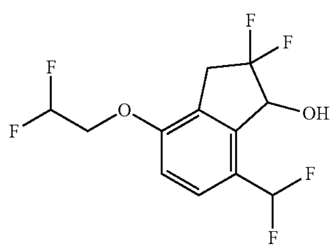 [SMILES: OC1c2c(C(F)F)ccc(OCC(F)F)c2CC1(F)F] | 345 (M − H + HCOOH) | |
| 587 | 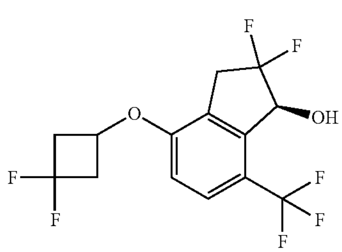 [SMILES: O[C@H]1c2c(C(F)(F)F)ccc(OC3CC(F)(F)C3)c2CC1(F)F] | 389 (M − H + HCOOH) | |

TABLE 1-continued

| No. | Structure | Mass Characterization | ¹H NMR Data |
|---|---|---|---|
| 588 | 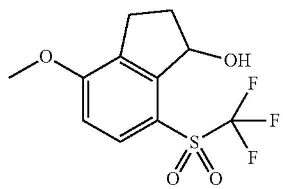 [SMILES: COc1ccc(S(=O)(=O)C(F)(F)F)c2c1CCC2O] | | (300 MHz, CDCl$_3$): δ 7.90 (d, 1H), 6.97 (d, 1H), 5.58 (m, 1H), 3.97 (s, 3H), 3.17 (m, 1H), 3.12 (m, 1H), 2.87 (m, 1H), 2.37 (m, 1H), 2.27 (m, 1H). |
| 589 | 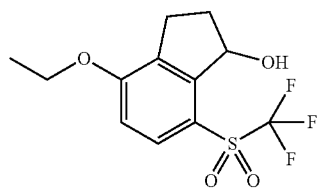 [SMILES: CCOc1ccc(S(=O)(=O)C(F)(F)F)c2c1CCC2O] | | (300 MHz, CDCl$_3$): δ 7.86 (d, 1H), 6.94 (d, 1H), 5.58 (m, 1H), 4.20 (m, 2H), 3.17 (m, 1H), 3.09 (m, 1H), 2.89 (m, 1H), 2.35 (m, 1H), 2.26 (m, 1H), 1.47 (t, 3H). |
| 590 | 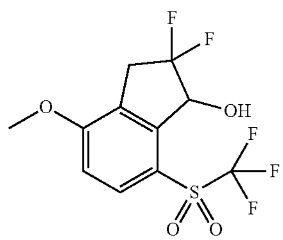 [SMILES: COc1ccc(S(=O)(=O)C(F)(F)F)c2c1CC(F)(F)C2O] | 331 (M − H) | |
| 591 | 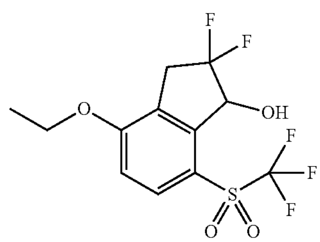 [SMILES: CCOc1ccc(S(=O)(=O)C(F)(F)F)c2c1CC(F)(F)C2O] | 345 (M − H) | |
| 592 | 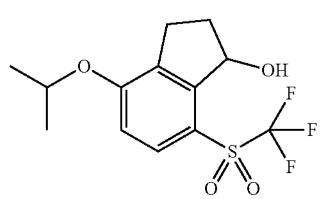 [SMILES: CC(C)Oc1ccc(S(=O)(=O)C(F)(F)F)c2c1CCC2O] | | (300 MHz, CDCl$_3$): δ 7.85 (d, 1H), 6.94 (d, 1H), 5.57 (m, 1H), 4.72 (m, 1H), 3.18 (m, 1H), 3.11 (m, 1H), 2.86 (m, 1H), 2.35 (m, 1H), 2.25 (m, 1H), 1.41 (d, 6H). |
| 593 | 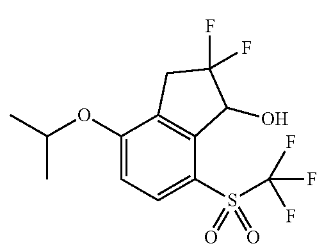 [SMILES: CC(C)Oc1ccc(S(=O)(=O)C(F)(F)F)c2c1CC(F)(F)C2O] | 359 (M − H) | |
| 594 | 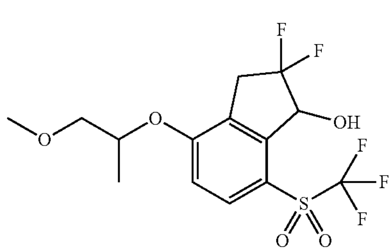 [SMILES: COCC(C)Oc1ccc(S(=O)(=O)C(F)(F)F)c2c1CC(F)(F)C2O] | 389 (M − H) | |

TABLE 1-continued

| No. | Structure | Mass Characterization | $^1$H NMR Data |
|---|---|---|---|
| 595 | 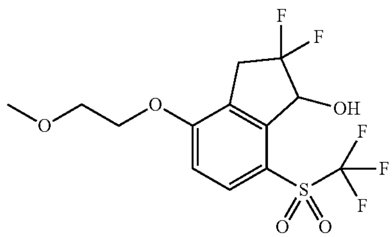 [SMILES: COCCOc1ccc(S(=O)(=O)C(F)(F)F)c2c1CC(F)(F)C2O] | 375 (M − H) | |
| 596 | 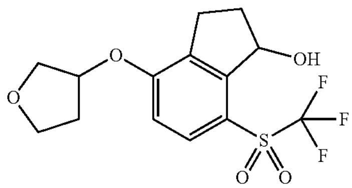 [SMILES: O=S(=O)(c1ccc(OC2CCOC2)c2c1C(O)CC2)C(F)(F)F] | | (300 MHz, CD$_3$OD): δ 7.89 (d, 1H), 7.28 (d, 1H), 5.44 (m, 1H), 5.27 (m, 1H), 5.14 (d, 1H), 3.77-3.96 (m 4H), 2.93 (m, 1H), 2.76 (m, 1H), 2.29 (m, 1H), 2.15 (m, 1H), 1.97 (m, 2H). |
| 597 | 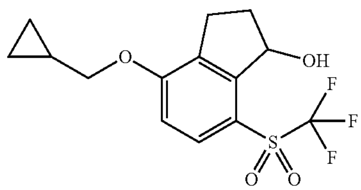 [SMILES: O=S(=O)(c1ccc(OCC2CC2)c2c1C(O)CC2)C(F)(F)F] | | (300 MHz, CDCl$_3$): δ 7.85 (d, 1H), 6.92 (d, 1H), 5.57 (m, 1H), 3.96 (m, 2H), 3.17 (m, 1H), 3.08 (m, 1H), 2.94 (m, 1H), 2.36 (m, 1H), 2.26 (m, 1H), 1.28 (m, 1H), 0.68 (m, 2H), 0.39 (m, 2H). |
| 598 | 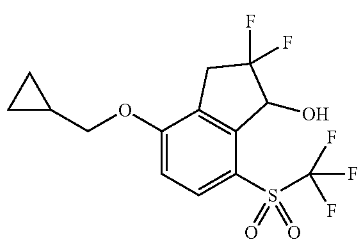 [SMILES: O=S(=O)(c1ccc(OCC2CC2)c2c1C(O)C(F)(F)C2)C(F)(F)F] | 371 (M − H) | |
| 599 | 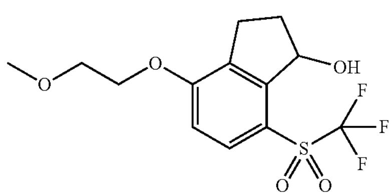 [SMILES: COCCOc1ccc(S(=O)(=O)C(F)(F)F)c2c1CCC2O] | | (300 MHz, CDCl$_3$): δ 7.87 (d, 1H), 6.99 (d, 1H), 5.57 (m, 1H), 4.27 (m, 2H), 3.80 (m, 2H), 3.45 (s, 3H), 3.15 (m, 1H), 3.11 (m, 1H), 2.93 (m, 1H), 2.36 (m, 1H), 2.27 (m, 1H) |
| 600 | 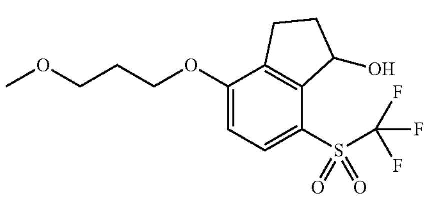 [SMILES: COCCCOc1ccc(S(=O)(=O)C(F)(F)F)c2c1CCC2O] | 372 (M + NH$_4$) | |
| 601 | 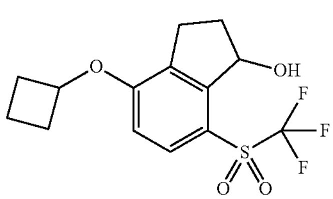 [SMILES: O=S(=O)(c1ccc(OC2CCC2)c2c1C(O)CC2)C(F)(F)F] | | (300 MHz, CDCl$_3$): δ 7.82 (d, 1H), 6.79 (d, 1H), 5.57 (m, 1H), 4.78 (m, 1H), 3.17 (m, 1H), 3.09 (m, 1H), 2.89 (m, 1H), 2.50 (m, 2H), 2.20-2.28 (m, 4H), 1.77 (m, 1H), 1.55 (m, 1H). |

TABLE 1-continued

| No. | Structure | Mass Characterization | ¹H NMR Data |
|---|---|---|---|
| 602 | 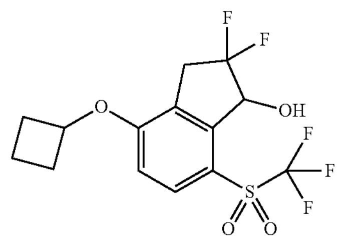 [SMILES: O=S(=O)(c1ccc(OC2CCC2)c2c1C(O)C(F)(F)C2)C(F)(F)F] | 371 (M − H) | |
| 603 | 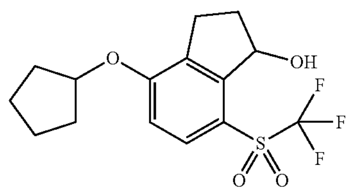 [SMILES: O=S(=O)(c1ccc(OC2CCCC2)c2c1C(O)CC2)C(F)(F)F] | | (300 MHz, CDCl₃): δ 7.85 (d, 1H), 6.95 (d, 1H), 5.56 (m, 1H), 4.91 (m, 1H), 3.18 (m, 1H), 3.10 (m, 1H), 2.87 (m, 1H), 2.32 (m, 1H), 2.25 (m, 1H), 1.56-1.99 (m, 8H). |
| 604 | 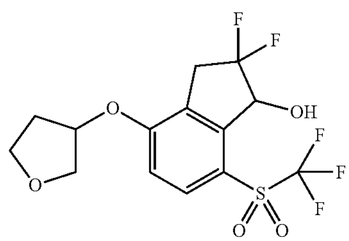 | 387 (M − H) | |
| 605 | 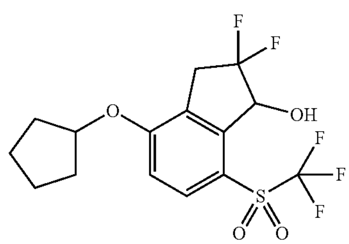 [SMILES: O=S(=O)(c1ccc(OC2CCCC2)c2c1C(O)C(F)(F)C2)C(F)(F)F] | 385 (M − H) | |
| 606 | 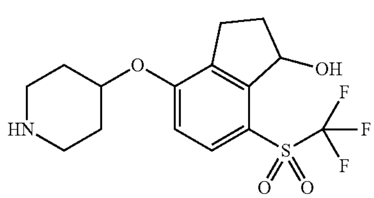 [SMILES: O=S(=O)(c1ccc(OC2CCNCC2)c2c1C(O)CC2)C(F)(F)F] | | (300 MHz, CDCl₃): δ 7.92 (d, 1H), 7.04 (d, 1H), 5.36 (d, 1H), 4.60 (m, 1H), 3.46 (m, 1H), 3.39 (m, 1H), 3.14 (m, 2H), 2.80 (m, 2H), 2.05 (m, 2H), 1.76 (m, 2H), 1.55 (m, 4H) |
| 607 | 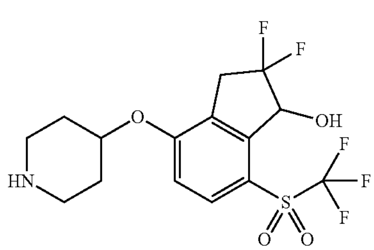 [SMILES: O=S(=O)(c1ccc(OC2CCNCC2)c2c1C(O)C(F)(F)C2)C(F)(F)F] | 402 (M + H) | |

TABLE 1-continued

| No. | Structure | Mass Characterization | ¹H NMR Data |
|---|---|---|---|
| 608 | 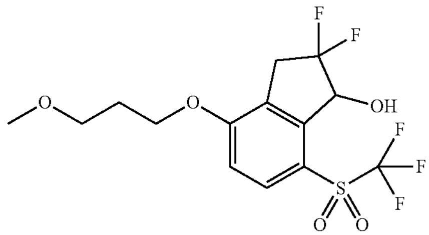 [SMILES: COCCCOc1ccc(S(=O)(=O)C(F)(F)F)c2c1CC(F)(F)C2O] | 389 (M − H) | |
| 609 | 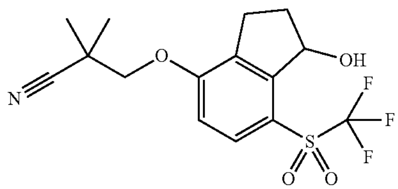 [SMILES: CC(C)(C#N)COc1ccc(S(=O)(=O)C(F)(F)F)c2c1CCC2O] | | (300 MHz, CDCl$_3$): δ 7.90 (d, 1H), 6.94 (d, 1H), 5.60 (m, 1H), 4.04 (m, 2H), 3.20 (m, 1H), 3.15 (m, 1H), 2.98 (m, 1H), 2.40 (m, 1H), 2.31 (m, 1H), 1.54 (s, 3H), 1.53 (s, 3H) |
| 610 | 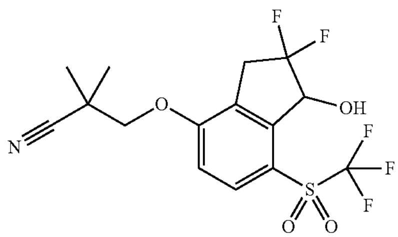 [SMILES: CC(C)(C#N)COc1ccc(S(=O)(=O)C(F)(F)F)c2c1CC(F)(F)C2O] | 398 (M − H) | |
| 611 | 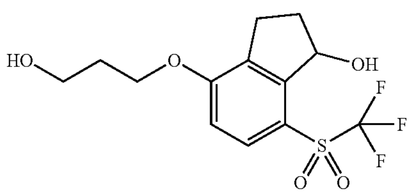 [SMILES: O=S(=O)(c1ccc(OCCCO)c2c1C(O)CC2)C(F)(F)F] | | (300 MHz, CDCl$_3$): δ 7.90 (d, 1H), 6.94 (d, 1H), 5.60 (m, 1H), 4.04 (m, 2H), 3.20 (m, 1H), 3.15 (m, 1H), 2.98 (m, 1H), 2.40 (m, 1H), 2.31 (m, 1H), 1.54 (s, 3H), 1.53 (s, 3H) |
| 612 | 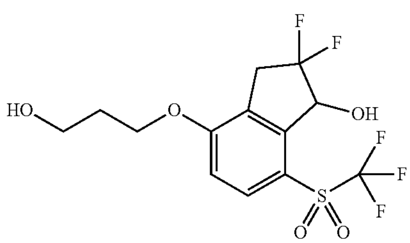 [SMILES: O=S(=O)(c1ccc(OCCCO)c2c1C(O)C(F)(F)C2)C(F)(F)F] | 377 (M + H) | |
| 613 | 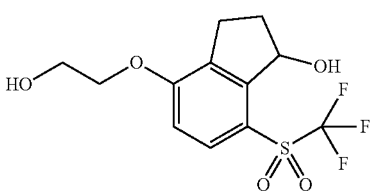 [SMILES: O=S(=O)(c1ccc(OCCO)c2c1C(O)CC2)C(F)(F)F] | 371 (M − H + HCOOH) | |
| 614 | 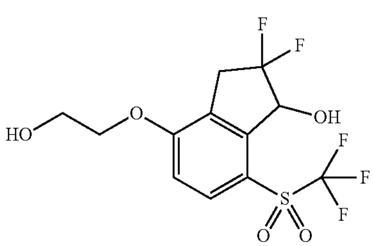 [SMILES: O=S(=O)(c1ccc(OCCO)c2c1C(O)C(F)(F)C2)C(F)(F)F] | 363 (M + H) | |

TABLE 1-continued

| No. | Structure | Mass Characterization | ¹H NMR Data |
|---|---|---|---|
| 615 | 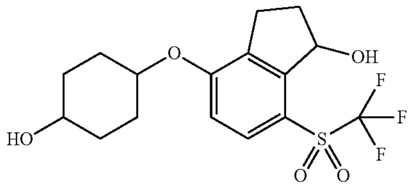 [SMILES: O=S(=O)(c1ccc(OC2CCC(O)CC2)c2c1C(O)CC2)C(F)(F)F] | 425 (M − H + HCOOH) | |
| 616 | 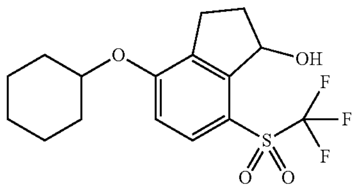 [SMILES: O=S(=O)(c1ccc(OC2CCCCC2)c2c1C(O)CC2)C(F)(F)F] | 382 (M + NH$_4^+$) | |
| 617 | 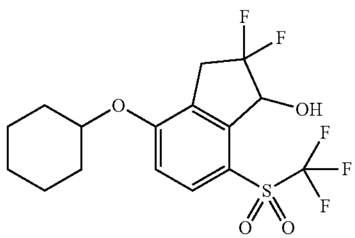 [SMILES: O=S(=O)(c1ccc(OC2CCCCC2)c2c1C(O)C(F)(F)C2)C(F)(F)F] | 399 (M − H) | |
| 618 | 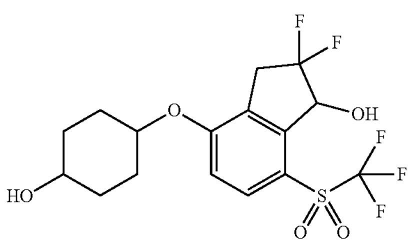 [SMILES: O=S(=O)(c1ccc(OC2CCC(O)CC2)c2c1C(O)C(F)(F)C2)C(F)(F)F] | 415 (M − H) | |
| 619 | 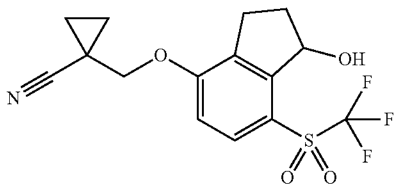 [SMILES: N#CC1(COc2ccc(S(=O)(=O)C(F)(F)F)c3c2CCC3O)CC1] | 406 (M − H + HCOOH) | |
| 620 | 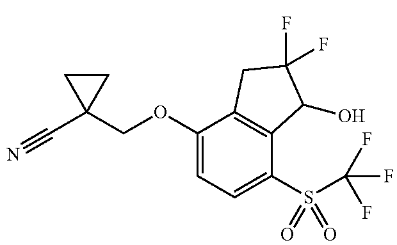 [SMILES: N#CC1(COc2ccc(S(=O)(=O)C(F)(F)F)c3c2CC(F)(F)C3O)CC1] | 398 (M + H) | |
| 621 | 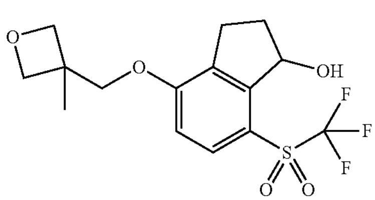 [SMILES: CC1(COc2ccc(S(=O)(=O)C(F)(F)F)c3c2CCC3O)COC1] | 411 (M − H + HCOOH) | |

TABLE 1-continued

| No. | Structure | Mass Characterization | $^1$H NMR Data |
|---|---|---|---|
| 622 | 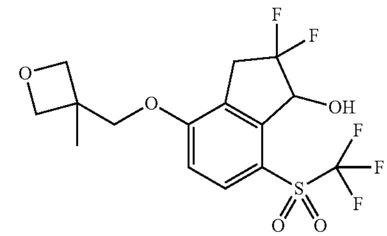 [SMILES: CC1(COc2ccc(S(=O)(=O)C(F)(F)F)c3c2CC(F)(F)C3O)COC1] | 401 (M − H) | |
| 623 | 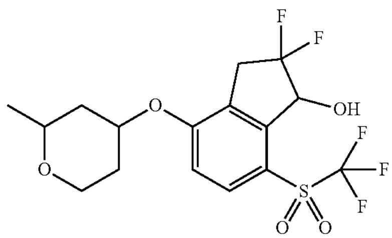 [SMILES: CC1CC(Oc2ccc(S(=O)(=O)C(F)(F)F)c3c2CC(F)(F)C3O)CCO1] | 415 (M − H) | |
| 624 | 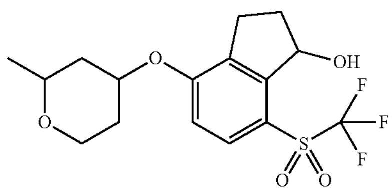 [SMILES: CC1CC(Oc2ccc(S(=O)(=O)C(F)(F)F)c3c2CCC3O)CCO1] | 425 (M − H + HCOOH) | |
| 625 | 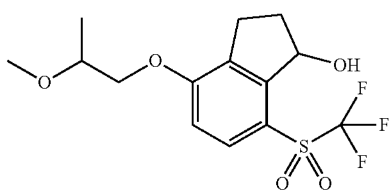 [SMILES: COC(C)COc1ccc(S(=O)(=O)C(F)(F)F)c2c1CCC2O] | 372 (M + NH$_4$) | |
| 626 | 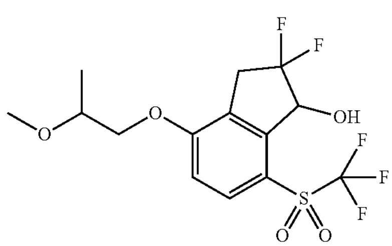 [SMILES: COC(C)COc1ccc(S(=O)(=O)C(F)(F)F)c2c1CC(F)(F)C2O] | 389 (M − H) | |
| 627 | 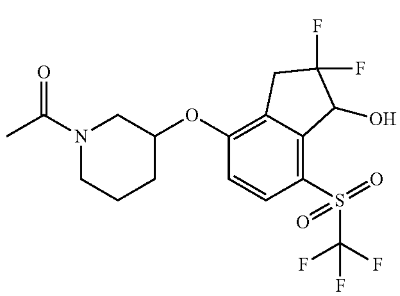 [SMILES: CC(=O)N1CCCC(Oc2ccc(S(=O)(=O)C(F)(F)F)c3c2CC(F)(F)C3O)C1] | 444 (M + H) | |

TABLE 1-continued

| No. | Structure | Mass Characterization | ¹H NMR Data |
|---|---|---|---|
| 628 | 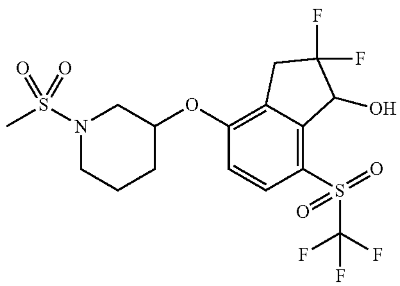 [SMILES: CS(=O)(=O)N1CCCC(Oc2ccc(S(=O)(=O)C(F)(F)F)c3c2CC(F)(F)C3O)C1] | 480 (M + H) | |
| 629 | 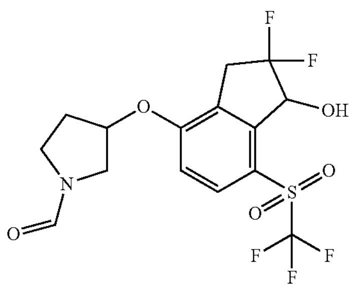 [SMILES: O=CN1CCC(Oc2ccc(S(=O)(=O)C(F)(F)F)c3c2CC(F)(F)C3O)C1] | 430 (M + H) | |
| 630 | 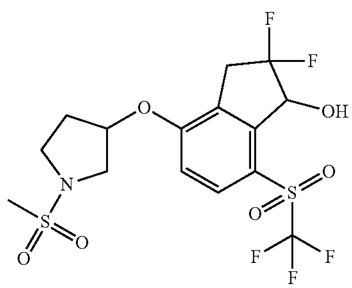 [SMILES: CS(=O)(=O)N1CCC(Oc2ccc(S(=O)(=O)C(F)(F)F)c3c2CC(F)(F)C3O)C1] | 466 (M + H) | |
| 631 | 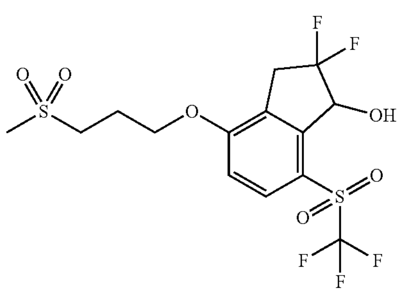 [SMILES: CS(=O)(=O)CCCOc1ccc(S(=O)(=O)C(F)(F)F)c2c1CC(F)(F)C2O] | 439 (M + H) | |
| 632 | 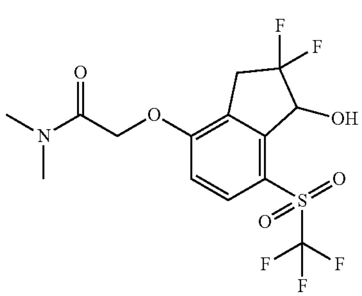 [SMILES: CN(C)C(=O)COc1ccc(S(=O)(=O)C(F)(F)F)c2c1CC(F)(F)C2O] | 404 (M + H) | |

TABLE 1-continued

| No. | Structure | Mass Characterization | ¹H NMR Data |
|---|---|---|---|
| 633 | 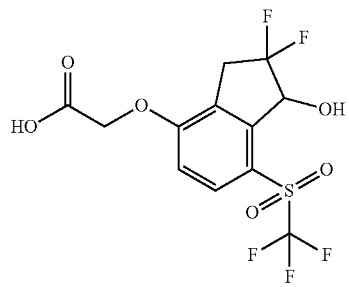 [SMILES: O=C(O)COc1ccc(S(=O)(=O)C(F)(F)F)c2c1CC(F)(F)C2O] | 377 (M + H) | |
| 634 | 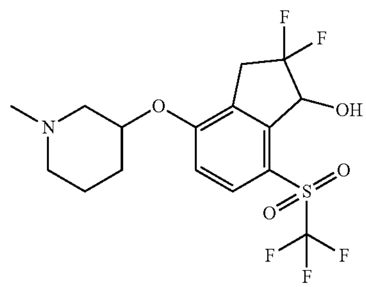 [SMILES: CN1CCCC(Oc2ccc(S(=O)(=O)C(F)(F)F)c3c2CC(F)(F)C3O)C1] | 416 (M + H) | |
| 635 | 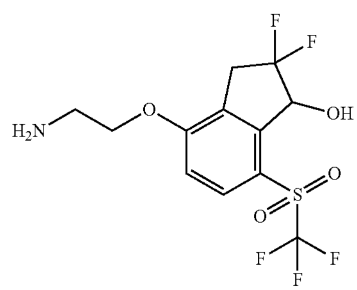 [SMILES: NCCOc1ccc(S(=O)(=O)C(F)(F)F)c2c1CC(F)(F)C2O] | 362 (M + H) | |
| 636 | 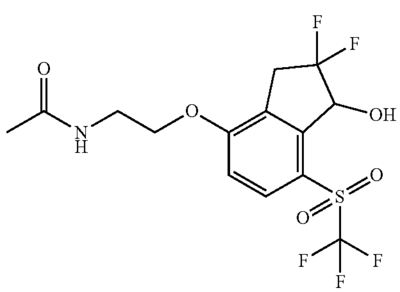 [SMILES: CC(=O)NCCOc1ccc(S(=O)(=O)C(F)(F)F)c2c1CC(F)(F)C2O] | 404 (M + H) | |
| 637 | 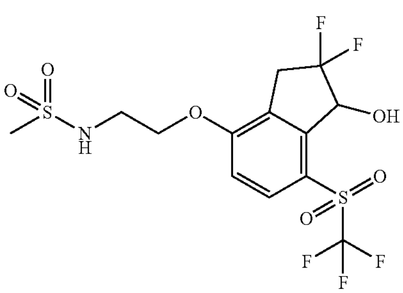 [SMILES: CS(=O)(=O)NCCOc1ccc(S(=O)(=O)C(F)(F)F)c2c1CC(F)(F)C2O] | 440 (M + H) | |

TABLE 1-continued

| No. | Structure | Mass Characterization | ¹H NMR Data |
|---|---|---|---|
| 638 | 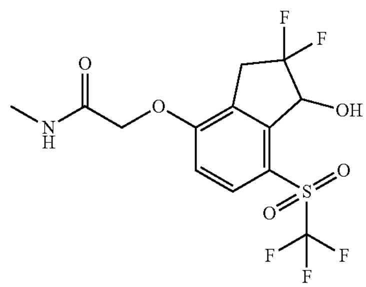 [SMILES: CNC(=O)COc1ccc(S(=O)(=O)C(F)(F)F)c2c1CC(F)(F)C2O] | 390 (M + H) | |
| 639 | 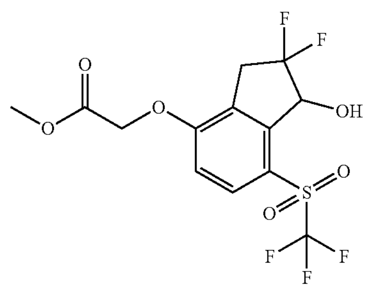 [SMILES: COC(=O)COc1ccc(S(=O)(=O)C(F)(F)F)c2c1CC(F)(F)C2O] | 389 (M − H) | |
| 640 | 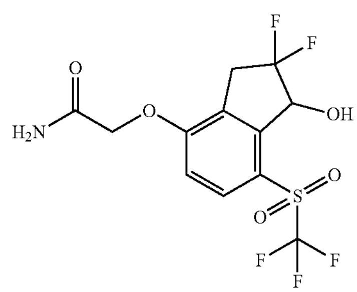 [SMILES: NC(=O)COc1ccc(S(=O)(=O)C(F)(F)F)c2c1CC(F)(F)C2O] | 374 (M − H) | |
| 641 | 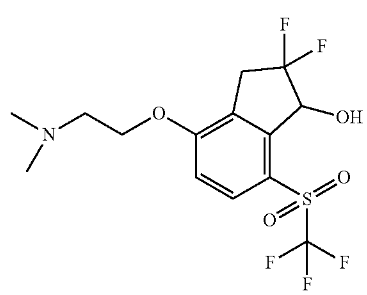 [SMILES: CN(C)CCOc1ccc(S(=O)(=O)C(F)(F)F)c2c1CC(F)(F)C2O] | 390 (M + H) | |
| 642 | 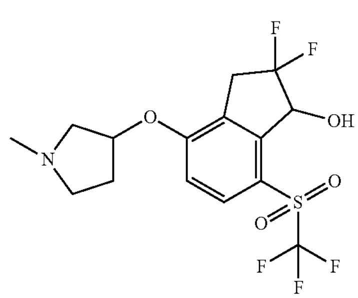 [SMILES: CN1CCC(Oc2ccc(S(=O)(=O)C(F)(F)F)c3c2CC(F)(F)C3O)C1] | | (300 MHz, CDCl$_3$): δ 7.93 (d, 1H), 6.94 (d, 1H), 5.35 (m, 1H), 4.96 (m, 1H), 3.38-3.47 (m, 3H), 2.82-2.92 (m 3H), 2.52 (m, 1H), 2.43 (m 1H), 2.42 (s, 3H), 2.04 (m 1H) |

TABLE 1-continued

| No. | Structure | Mass Characterization | ¹H NMR Data |
|---|---|---|---|
| 643 | 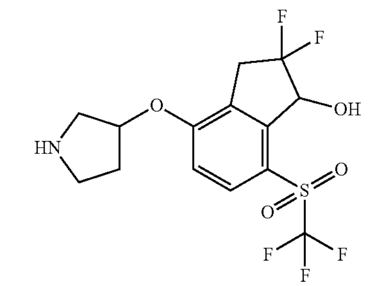 [SMILES: O=S(=O)(c1ccc(OC2CCNC2)c2c1C(O)C(F)(F)C2)C(F)(F)F] | 388 (M + H) | |
| 644 | 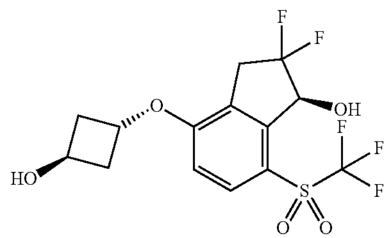 | 433 (M − H + HCOOH) | |
| 645 | 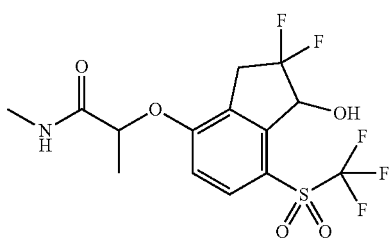 [SMILES: CNC(=O)C(C)Oc1ccc(S(=O)(=O)C(F)(F)F)c2c1CC(F)(F)C2O] | 402 (M − H) | |
| 646 | 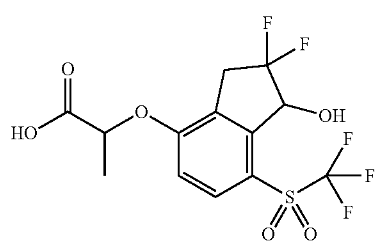 [SMILES: CC(Oc1ccc(S(=O)(=O)C(F)(F)F)c2c1CC(F)(F)C2O)C(=O)O] | 389 (M − H) | |
| 647 | 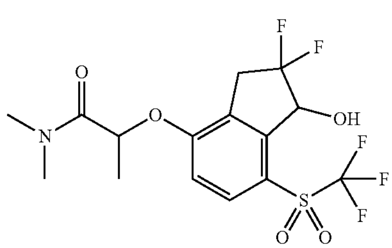 [SMILES: CC(Oc1ccc(S(=O)(=O)C(F)(F)F)c2c1CC(F)(F)C2O)C(=O)N(C)C] | 418 (M + H) | |
| 648 | 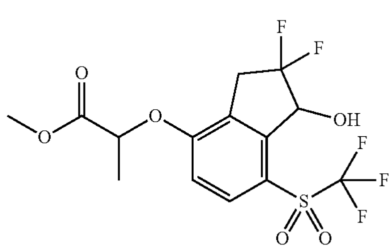 [SMILES: COC(=O)C(C)Oc1ccc(S(=O)(=O)C(F)(F)F)c2c1CC(F)(F)C2O] | | (300 MHz, CDCl$_3$): δ 7.92 (d, 1H), 6.87 (d, 1H), 5.36 (m, 1H), 4.93 (m, 1H), 3.80 (s, 3H), 3.44-3.60 (m, 2H), 3.22 (m, 1H), 1.71 (d, 3H) |

TABLE 1-continued

| No. | Structure | Mass Characterization | ¹H NMR Data |
|---|---|---|---|
| 649 | 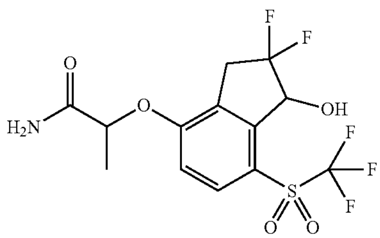 [SMILES: CC(Oc1ccc(S(=O)(=O)C(F)(F)F)c2c1CC(F)(F)C2O)C(N)=O] | 388 (M − H) | |
| 650 | 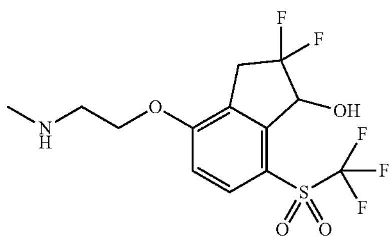 [SMILES: CNCCOc1ccc(S(=O)(=O)C(F)(F)F)c2c1CC(F)(F)C2O] | 376 (M + H) | |
| 651 | 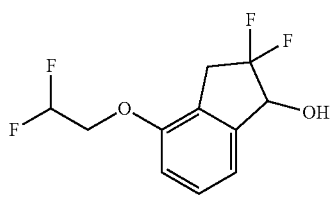 [SMILES: OC1c2cccc(OCC(F)F)c2CC1(F)F] | | (400 MHz, CDCl$_3$): δ 7.31 (m, 1H), 7.17(d, 1H), 6.82 (d, 1H), 6.09 (t, 1H), 5.15 (m, 1H), 4.20 (m, 2H), 3.45 (m, 1H), 3.27 (m, 1H), 2.27 (m, 1H) |
| 652 | 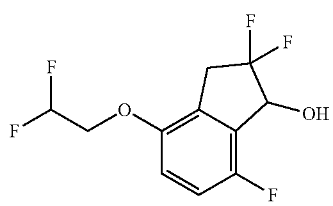 [SMILES: OC1c2c(F)ccc(OCC(F)F)c2CC1(F)F] | 313 (M − H + HCOOH) | |
| 653 | 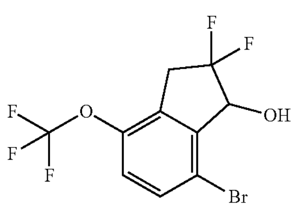 [SMILES: OC1c2c(Br)ccc(OC(F)(F)F)c2CC1(F)F] | | (400 MHz, CDCl$_3$): δ 7.56 (d, 1H), 7.17 (d, 1H), 5.13 (m, 1H), 3.56 (m, 2H), 2.50 (s, 1H) |
| 654 | 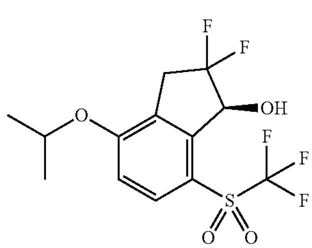 [SMILES: CC(C)Oc1ccc(S(=O)(=O)C(F)(F)F)c2c1CC(F)(F)[C@H]2O] | 359 (M − H) | |

TABLE 1-continued

| No. | Structure | Mass Characterization | $^1$H NMR Data |
|---|---|---|---|
| 655 | 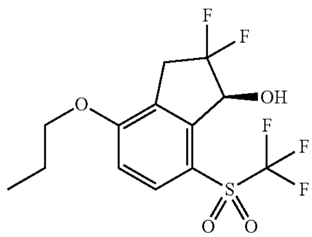 [SMILES: CCCOc1ccc(S(=O)(=O)C(F)(F)F)c2c1CC(F)(F)[C@H]2O] | 359 (M − H) | |
| 656 | 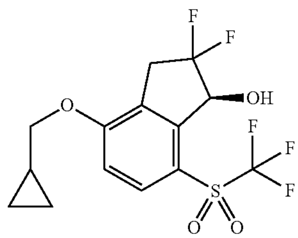 [SMILES: O=S(=O)(c1ccc(OCC2CC2)c2c1[C@H](O)C(F)(F)C2)C(F)(F)F] | 371 (M − H) | |
| 657 | 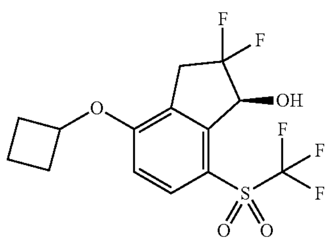 [SMILES: O=S(=O)(c1ccc(OC2CCC2)c2c1[C@H](O)C(F)(F)C2)C(F)(F)F] | 371 (M − H) | |
| 658 | 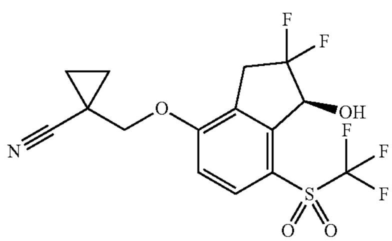 [SMILES: N#CC1(COc2ccc(S(=O)(=O)C(F)(F)F)c3c2CC(F)(F)[C@H]3O)CC1] | 442 (M + HCO$_2^-$) | |
| 659 | 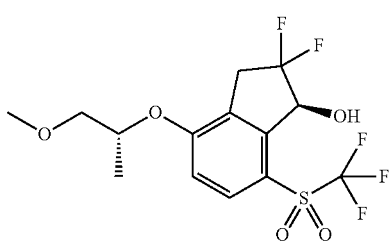 [SMILES: COC[C@@H](C)Oc1ccc(S(=O)(=O)C(F)(F)F)c2c1CC(F)(F)[C@H]2O] | 389 (M − H) | |
| 660 | 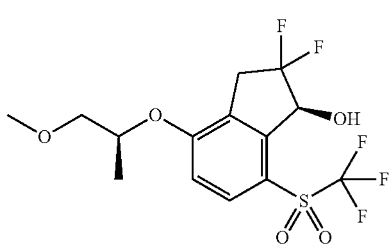 [SMILES: COC[C@H](C)Oc1ccc(S(=O)(=O)C(F)(F)F)c2c1CC(F)(F)[C@H]2O] | 389 (M − H) | |

TABLE 1-continued

| No. | Structure | Mass Characterization | ¹H NMR Data |
|---|---|---|---|
| 661 | 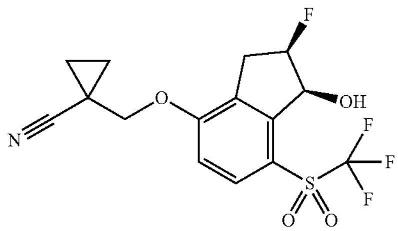 [SMILES: N#CC1(COc2ccc(S(=O)(=O)C(F)(F)F)c3c2C[C@@H](F)[C@H]3O)CC1] | 424 (M + HCO₂⁻) | |
| 662 | 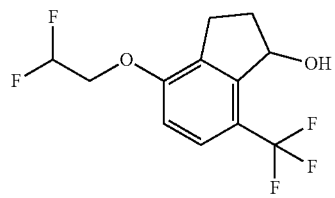 [SMILES: OC1CCc2c(OCC(F)F)ccc(C(F)(F)F)c21] | 265 (M − OH) | |
| 663 | 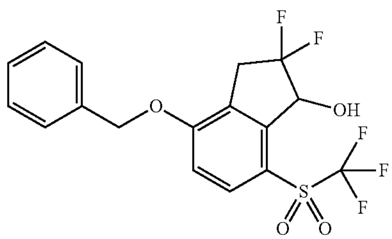 [SMILES: O=S(=O)(c1ccc(OCc2ccccc2)c2c1C(O)C(F)(F)C2)C(F)(F)F] | (M + NH4) 426 | |
| 664 | 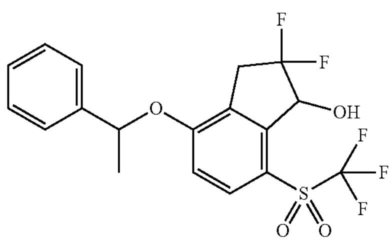 [SMILES: CC(Oc1ccc(S(=O)(=O)C(F)(F)F)c2c1CC(F)(F)C2O)c1ccccc1] | (M − H) 421 | |
| 665 | 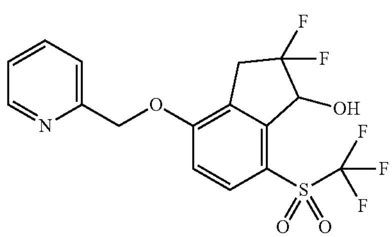 [SMILES: O=S(=O)(c1ccc(OCc2ccccn2)c2c1C(O)C(F)(F)C2)C(F)(F)F] | (M + H) 410 | |
| 666 | 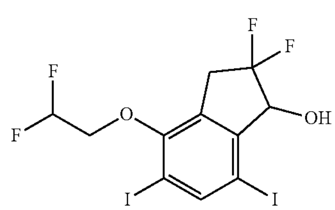 [SMILES: OC1c2c(I)cc(I)c(OCC(F)F)c2CC1(F)F] | | (400 MHz, CDCl$_3$): δ 8.15 (s, 1H), 6.12 (t, 1H), 4.96-4.87 (1H), 4.22-4.09 (2H), 3.62-3.50 (2H), 2.49 (1H) |
| 667 | 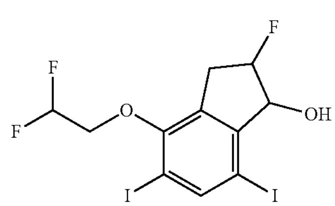 [SMILES: OC1c2c(I)cc(I)c(OCC(F)F)c2CC1F] | (M − OH) 467 | |

TABLE 1-continued

| No. | Structure | Mass Characterization | ¹H NMR Data |
|---|---|---|---|
| 668 | 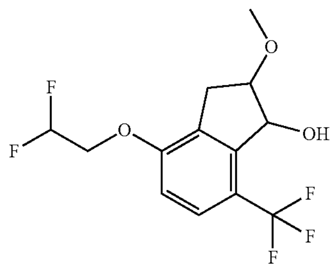 [SMILES: COC1Cc2c(OCC(F)F)ccc(C(F)(F)F)c2C1O] | (M + NH4) 330 | |
| 669 | 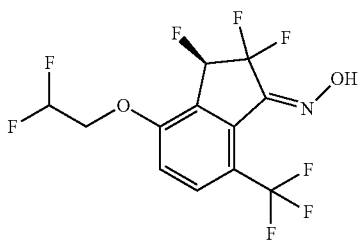 [SMILES: O/N=C1/c2c(C(F)(F)F)ccc(OCC(F)F)c2[C@@H](F)C1(F)F] | (M + H) 350 | |
| 670 | 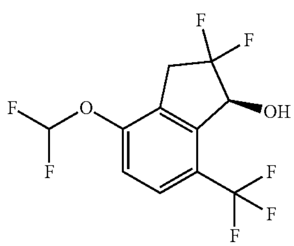 [SMILES: O[C@H]1c2c(C(F)(F)F)ccc(OC(F)F)c2CC1(F)F] | | (400 MHz, CDCl₃): δ 7.63 (d, 1H), 7.25 (d, 1H), 6.62 (t, 1H), 5.30-5.25 (m, 1H), 3.58-3.37 (m, 2H), 2.54-2.51 (m, 1H) |
| 671 | 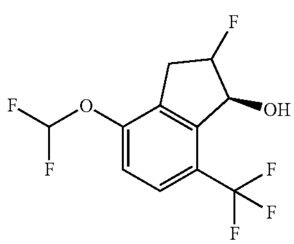 [SMILES: O[C@H]1c2c(C(F)(F)F)ccc(OC(F)F)c2CC1F] | | (400 MHz, CDCl₃): δ 7.59 (d, 1H), 7.18 (d, 1H), 6.60 (t, 1H), 5.40-5.23 (m, 2H), 3.40-3.12 (m, 2H), 2.55-2.51 (m, 1H) |
| 672 | 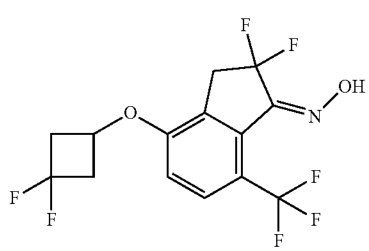 [SMILES: O/N=C1/c2c(C(F)(F)F)ccc(OC3CC(F)(F)C3)c2CC1(F)F] | (M + H) 358 | |
| 673 | 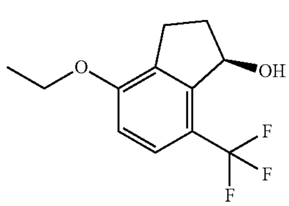 [SMILES: CCOc1ccc(C(F)(F)F)c2c1CC[C@H]2O] | [M − OH]⁺ 229 | |

| No. | Structure | Mass Characterization | $^1$H NMR Data |
|---|---|---|---|
| 674 | 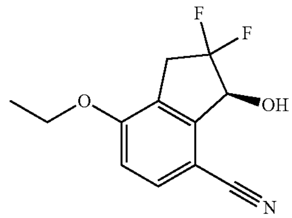 [SMILES: CCOc1ccc(C#N)c2c1CC(F)(F)[C@H]2O] | 284 | |
| 675 | 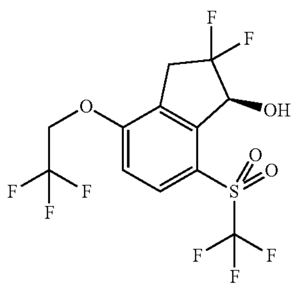 [SMILES: O=S(=O)(c1ccc(OCC(F)(F)F)c2c1[C@H](O)C(F)(F)C2)C(F)(F)F] | [M − H + HCOOH]$^-$ 445 | |
| 676 | 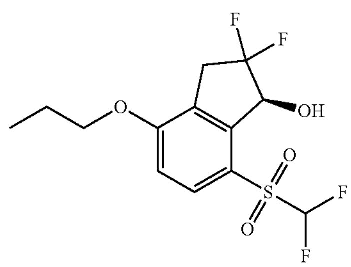 [SMILES: CCCOc1ccc(S(=O)(=O)C(F)F)c2c1CC(F)(F)[C@H]2O] | [M + NH4]$^+$ 360 | |
| 677 | 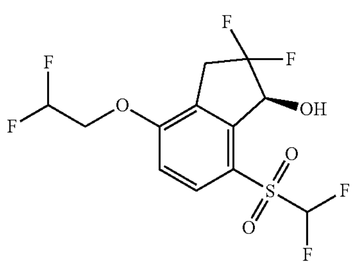 [SMILES: O=S(=O)(c1ccc(OCC(F)F)c2c1[C@H](O)C(F)(F)C2)C(F)F] | [M + NH4]$^+$ 382 | |
| 678 | 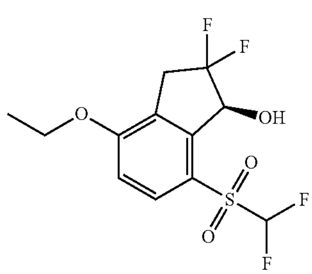 [SMILES: CCOc1ccc(S(=O)(=O)C(F)F)c2c1CC(F)(F)[C@H]2O] | [M + NH4]$^+$ 346 | |
| 679 | 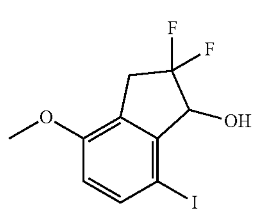 | | (400 MHz, CDCl$_3$): δ 7.62 (d, 1H), 6.63 (d, 1H), 4.94 (dd, 1H), 3.81 (s, 3H), 3.46-3.38 (m, 2H), 2.43-2.40 (m, 1H) |

TABLE 1-continued

| No. | Structure | Mass Characterization | ¹H NMR Data |
|---|---|---|---|
| 680 | 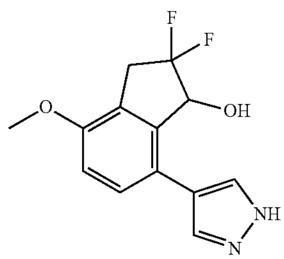 [SMILES: COc1ccc(-c2cn[nH]c2)c2c1CC(F)(F)C2O] | [M + Na]⁺ 289 | |
| 681 | 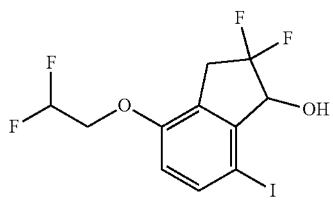 [SMILES: OC1c2c(I)ccc(OCC(F)F)c2CC1(F)F] | | (400 MHz, CDCl₃): δ 7.64 (d, 1H), 6.61 (d, 1H), 6.07 (tt, 1H), 4.94 (d, 1H), 4.19 (td, 2H), 3.50-3.42 (m, 2H), 2.41 (brs, 1H) |
| 682 | 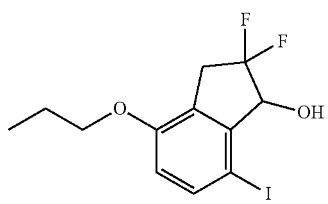 [SMILES: CCCOc1ccc(I)c2c1CC(F)(F)C2O] | | (400 MHz, CDCl₃): δ 7.59 (d, 1H), 6.61 (d, 1H), 4.98-4.91 (m, 1H), 3.92 (td, 2H), 3.48-3.39 (m, 2H), 2.40 (brs, 1H), 1.84-1.76 (m, 2H), 1.02 (t, 3H) |
| 683 | 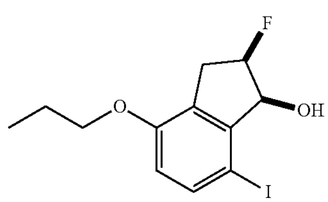 | | (400 MHz, CDCl₃): δ 7.58 (d, 1H), 6.57 (d, 1H), 5.26 (dq, 1H), 5.06-5.01 (m, 1H), 3.91 (t, 2H), 3.21 (dd, 2H), 2.42-2.38 (m, 1H), 1.84-1.74 (m, 2H), 1.03 (t, 3H) |
| 684 | 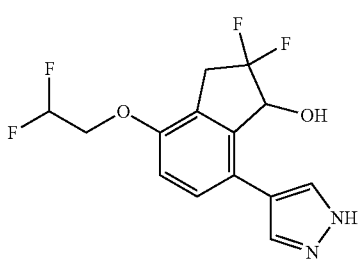 [SMILES: OC1c2c(-c3cn[nH]c3)ccc(OCC(F)F)c2CC1(F)F] | [M + H]⁺ 317 | |
| 685 | 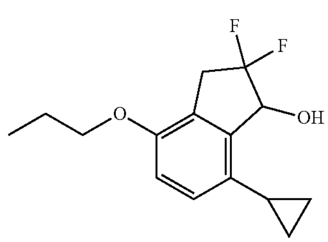 [SMILES: CCCOc1ccc(C2CC2)c2c1CC(F)(F)C2O] | [M + NH4]⁻ 251 | |

TABLE 1-continued

| No. | Structure | Mass Characterization | ¹H NMR Data |
|---|---|---|---|
| 686 | 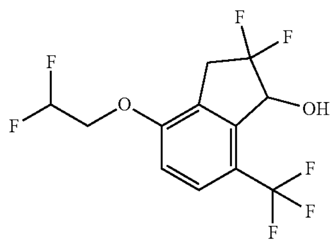 [SMILES: OC1c2c(C(F)(F)F)ccc(OCC(F)F)c2CC1(F)F] | [M − H + HCOOH]⁻ 363 | |
| 687 | 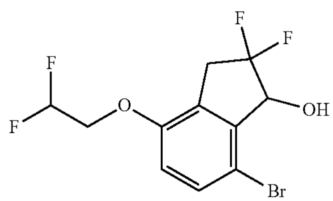 [SMILES: OC1c2c(Br)ccc(OCC(F)F)c2CC1(F)F] | | (400 MHz, CDCl₃): δ 7.42 (d, 1H), 6.73 (d, 1H), 6.07 (tt, 1H), 5.08 (d, 1H), 4.23-4.17 (m, 2H), 3.54-3.35 (m, 2H), 2.49 (brs, 1H) |
| 688 | 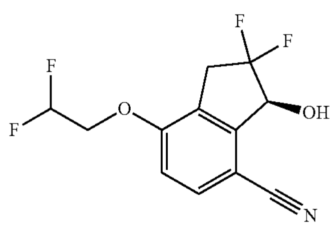 [SMILES: N#Cc1ccc(OCC(F)F)c2c1[C@H](O)C(F)(F)C2] | [M + H]⁺ 276 | |
| 689 | 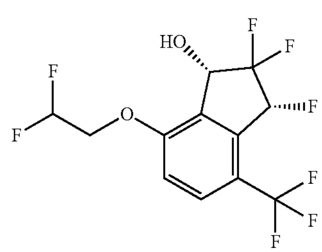 [SMILES: O[C@H]1c2c(OCC(F)F)ccc(C(F)(F)F)c2[C@@H](F)C1(F)F] | | (400 MHz, CDCl₃): δ 7.78 (d, 1H), 7.09 (d, 1H), 6.17 (tt, 1H), 5.79 (dd, 1H), 5.24-5.18 (m, 1H), 4.42-4.31 (m, 2H), 2.47-2.44 (m, 1H) |
| 690 | 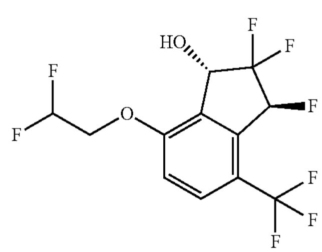 [SMILES: O[C@H]1c2c(OCC(F)F)ccc(C(F)(F)F)c2[C@H](F)C1(F)F] | | (400 MHz, CDCl₃): δ 7.74 (d, 1H), 7.05 (d, 1H), 6.16 (tt, 1H), 6.02 (dd, 1H), 5.54-5.48 (m, 1H), 4.35 (td, 2H), 2.68 (brd, 1H) |
| 691 | 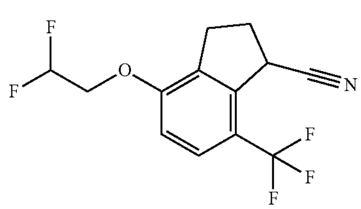 [SMILES: N#CC1CCc2c(OCC(F)F)ccc(C(F)(F)F)c21] | [M − H]⁻ 290 | |

TABLE 1-continued

| No. | Structure | Mass Characterization | ¹H NMR Data |
|---|---|---|---|
| 692 | 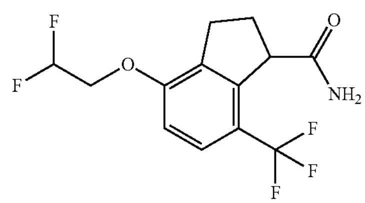 [SMILES: NC(=O)C1CCc2c(OCC(F)F)ccc(C(F)(F)F)c21] | [M + H]⁺ 310 | |
| 693 | 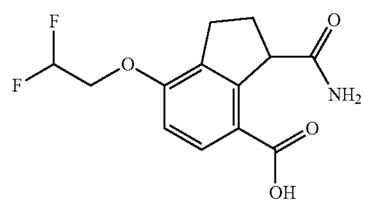 [SMILES: NC(=O)C1CCc2c(OCC(F)F)ccc(C(=O)O)c21] | [M + H]⁺ 286 | |
| 694 | 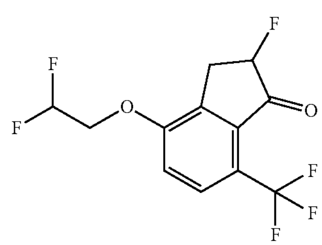 [SMILES: O=C1c2c(C(F)(F)F)ccc(OCC(F)F)c2CC1F] | [M − H + HCOOH]⁻ 343 | |
| 695 | 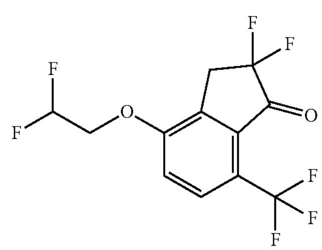 [SMILES: O=C1c2c(C(F)(F)F)ccc(OCC(F)F)c2CC1(F)F] | [M + H]⁺ 317 | |
| 696 | 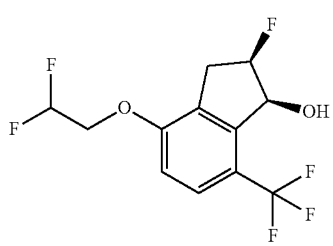 [SMILES: O[C@H]1c2c(C(F)(F)F)ccc(OCC(F)F)c2C[C@H]1F] | | (400 MHz, CDCl$_3$): δ 7.56 (d, 1H), 6.84 (d, 1H), 6.11 (tt, 1H), 5.38-5.22 (m, 2H), 4.26 (td, 2H), 3.33-3.07 (m, 2H), 2.52-2.48 (m, 1H) |
| 697 | 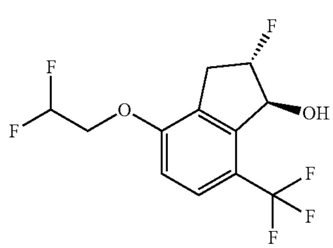 [SMILES: O[C@H]1c2c(C(F)(F)F)ccc(OCC(F)F)c2C[C@@H]1F] | | (400 MHz, CDCl$_3$): δ 7.56 (d, 1H), 6.87 (d, 1H), 6.12 (tt, 1H), 5.49-5.22 (m, 2H), 4.31-4.23 (m, 2H), 3.48-3.06 (m, 2H), 2.48 (brs, 1H) |

TABLE 1-continued

| No. | Structure | Mass Characterization | ¹H NMR Data |
|---|---|---|---|
| 698 | 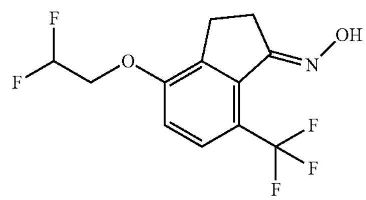 [SMILES: O/N=C1\CCc2c(OCC(F)F)ccc(C(F)(F)F)c21] | | (400 MHz, CDCl$_3$): δ 7.62 (d, 1H), 7.61 (s, 1H), 6.81 (d, 1H), 6.13 (tt, 1H), 4.28 (td, 2H), 3.09-2.97 (m, 4H) |
| 699 | 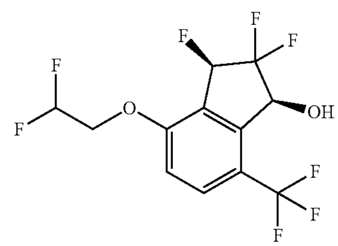 [SMILES: O[C@H]1c2c(C(F)(F)F)ccc(OCC(F)F)c2[C@@H](F)C1(F)F] | [M − H + HCOOH]$^-$ 381 | |
| 700 | 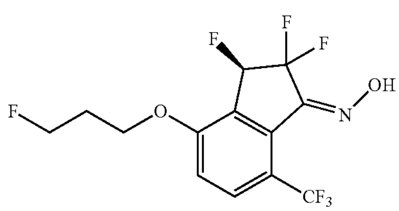 [SMILES: O/N=C1/c2c(C(F)(F)F)ccc(OCCCF)c2[C@@H](F)C1(F)F] | [M − H]$^-$ 344 | |
| 701 | 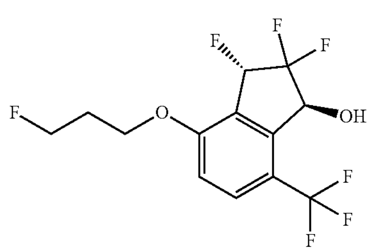 [SMILES: O[C@H]1c2c(C(F)(F)F)ccc(OCCCF)c2[C@H](F)C1(F)F] | [M − H + HCOOH]$^-$ 377 | |
| 702 | 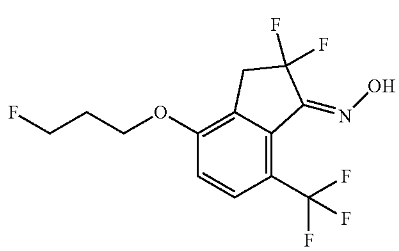 [SMILES: O/N=C1/c2c(C(F)(F)F)ccc(OCCCF)c2CC1(F)F] | [M + H]$^+$ 328 | |
| 703 | 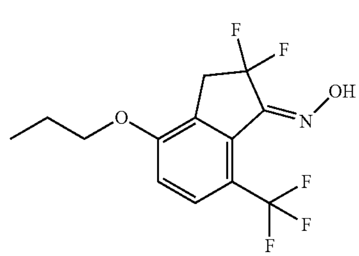 [SMILES: CCCOc1ccc(C(F)(F)F)c2c1CC(F)(F)/C2=N\O] | [M + H]$^+$ 310 | |

TABLE 1-continued

| No. | Structure | Mass Characterization | ¹H NMR Data |
|---|---|---|---|
| 704 | 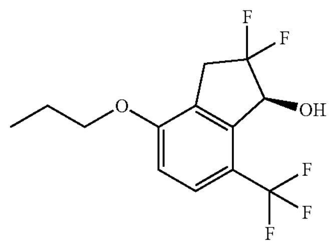 [SMILES: CCCOc1ccc(C(F)(F)F)c2c1CC(F)(F)[C@H]2O] | [M + Na]⁺ 320 | |
| 705 | 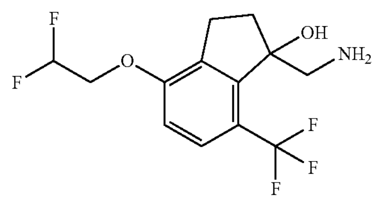 [SMILES: NCC1(O)CCc2c(OCC(F)F)ccc(C(F)(F)F)c21] | [M + H]⁺ 312 | |
| 706 | 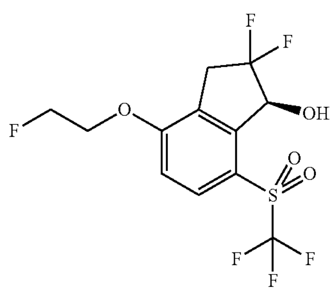 [SMILES: O=S(=O)(c1ccc(OCCF)c2c1[C@H](O)C(F)(F)C2)C(F)(F)F] | 363 (M − H)⁻ | |
| 707 | 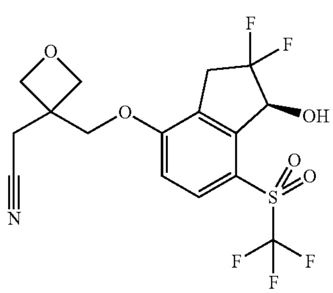 [SMILES: N#CCC1(COc2ccc(S(=O)(=O)C(F)(F)F)c3c2CC(F)(F)[C@H]3O)COC1] | 472 (M + HCO₂)⁻ | |
| 708 | 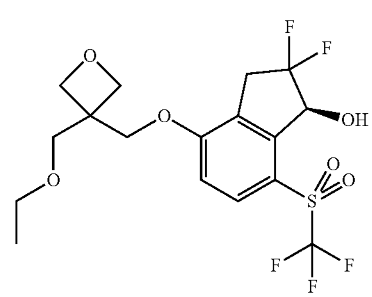 | 491 (M + HCO₂)⁻ | |

TABLE 1-continued

| No. | Structure | Mass Characterization | ¹H NMR Data |
|---|---|---|---|
| 709 | 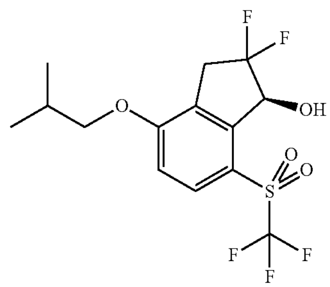 [SMILES: CC(C)COc1ccc(S(=O)(=O)C(F)(F)F)c2c1CC(F)(F)[C@H]2O] | 373 (M − H)⁻ | |
| 710 | 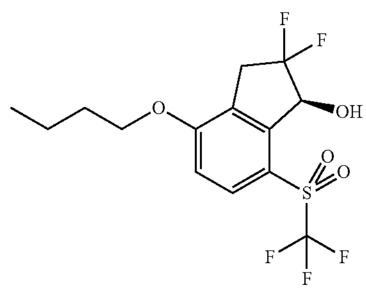 [SMILES: CCCCOc1ccc(S(=O)(=O)C(F)(F)F)c2c1CC(F)(F)[C@H]2O] | 373 (M − H)⁻ | |
| 711 | 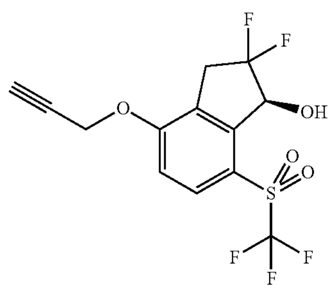 [SMILES: C#CCOc1ccc(S(=O)(=O)C(F)(F)F)c2c1CC(F)(F)[C@H]2O] | 355 (M − H)⁻ | |
| 712 | 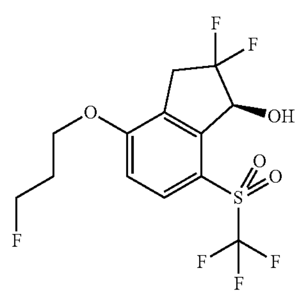 [SMILES: O=S(=O)(c1ccc(OCCCF)c2c1[C@H](O)C(F)(F)C2)C(F)(F)F] | 377 (M − H)⁻ | |
| 713 | 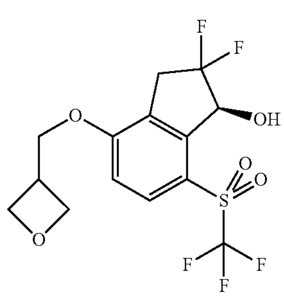 [SMILES: O=S(=O)(c1ccc(OCC2COC2)c2c1[C@H](O)C(F)(F)C2)C(F)(F)F] | 387 (M − H)⁻ | |

TABLE 1-continued

| No. | Structure | Mass Characterization | ¹H NMR Data |
|---|---|---|---|
| 714 | 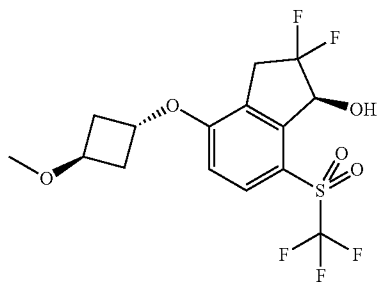 [SMILES: CO[C@H]1C[C@H](Oc2ccc(S(=O)(=O)C(F)(F)F)c3c2CC(F)(F)[C@H]3O)C1] | 401 (M − H)⁻ | |
| 715 | 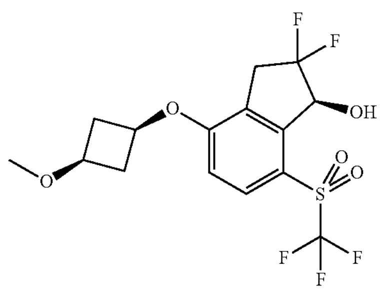 [SMILES: CO[C@H]1C[C@@H](Oc2ccc(S(=O)(=O)C(F)(F)F)c3c2CC(F)(F)[C@H]3O)C1] | 401 (M − H)⁻ | |
| 716 | 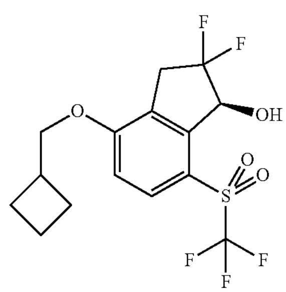 [SMILES: O=S(=O)(c1ccc(OCC2CCC2)c2c1[C@H](O)C(F)(F)C2)C(F)(F)F] | 385 (M − H)⁻ | |
| 717 | 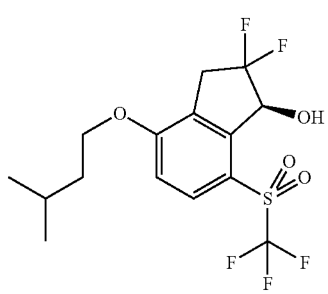 [SMILES: CC(C)CCOc1ccc(S(=O)(=O)C(F)(F)F)c2c1CC(F)(F)[C@H]2O] | 387 (M − H)⁻ | |
| 718 | 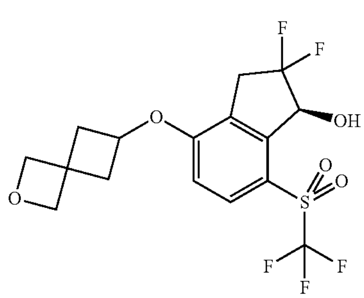 [SMILES: O=S(=O)(c1ccc(OC2CC3(COC3)C2)c2c1[C@H](O)C(F)(F)C2)C(F)(F)F] | 413 (M − H)⁻ | |

TABLE 1-continued

| No. | Structure | Mass Characterization | ¹H NMR Data |
|---|---|---|---|
| 719 | 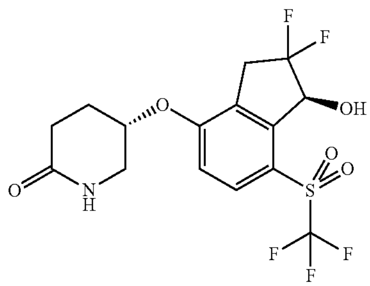 [SMILES: O=C1CC[C@H](Oc2ccc(S(=O)(=O)C(F)(F)F)c3c2CC(F)(F)[C@H]3O)CN1] | 416 (M + H)⁺ | |
| 720 | 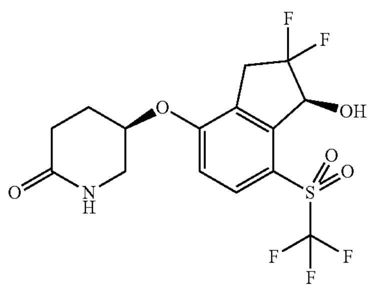 [SMILES: O=C1CC[C@@H](Oc2ccc(S(=O)(=O)C(F)(F)F)c3c2CC(F)(F)[C@H]3O)CN1] | 416 (M + H)⁺ | |
| 721 | 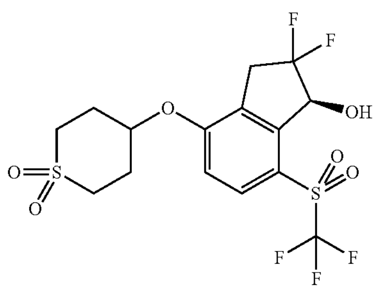 [SMILES: O=S1(=O)CCC(Oc2ccc(S(=O)(=O)C(F)(F)F)c3c2CC(F)(F)[C@H]3O)CC1] | 495 (M + HCO₂)⁻ | |
| 722 | 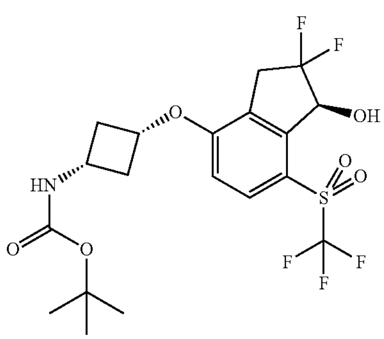 [SMILES: CC(C)(C)OC(=O)N[C@H]1C[C@@H](Oc2ccc(S(=O)(=O)C(F)(F)F)c3c2CC(F)(F)[C@H]3O)C1] | 388 (M + H − CO₂ − C₄H₈)⁺ | |
| 723 | 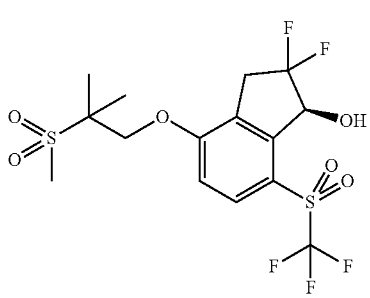 [SMILES: CC(C)(COc1ccc(S(=O)(=O)C(F)(F)F)c2c1CC(F)(F)[C@H]2O)S(C)(=O)=O] | 451 (M − H)⁻ | |

TABLE 1-continued

| No. | Structure | Mass Characterization | $^1$H NMR Data |
|---|---|---|---|
| 724 | 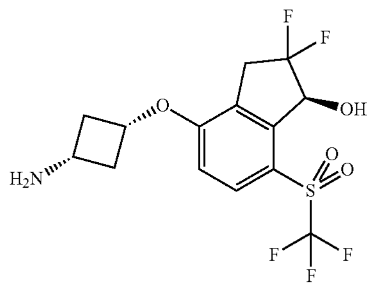 [SMILES: N[C@H]1C[C@@H](Oc2ccc(S(=O)(=O)C(F)(F)F)c3c2CC(F)(F)[C@H]3O)C1] | 388 (M + H)$^+$ | |
| 725 | 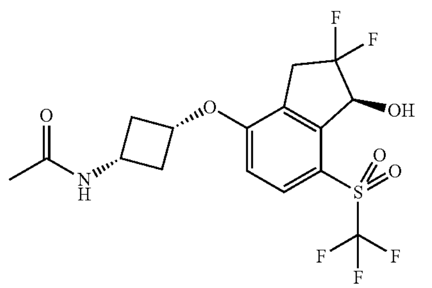 [SMILES: CC(=O)N[C@H]1C[C@@H](Oc2ccc(S(=O)(=O)C(F)(F)F)c3c2CC(F)(F)[C@H]3O)C1] | 430 (M + H)$^+$ | |
| 726 | 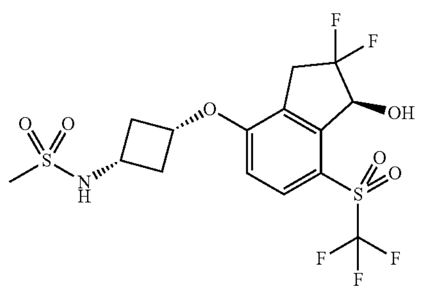 | 510 (M + HCO$_2$)$^-$ | |
| 727 | 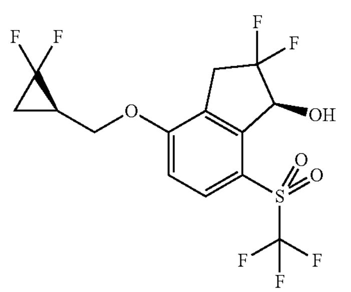 [SMILES: O=S(=O)(c1ccc(OC[C@H]2CC2(F)F)c2c1[C@H](O)C(F)(F)C2)C(F)(F)F] | 407 (M − H)$^-$ | |
| 728 | 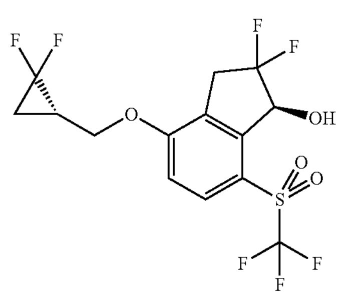 [SMILES: O=S(=O)(c1ccc(OC[C@@H]2CC2(F)F)c2c1[C@H](O)C(F)(F)C2)C(F)(F)F] | 407 (M − H) | |

TABLE 1-continued

| No. | Structure | Mass Characterization | $^1$H NMR Data |
|---|---|---|---|
| 729 | 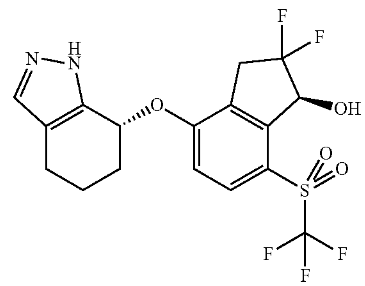 [SMILES: O=S(=O)(c1ccc(O[C@@H]2CCCc3cn[nH]c32)c2c1[C@H](O)C(F)(F)C2)C(F)(F)F] | 439 (M + H)+ | |
| 730 | 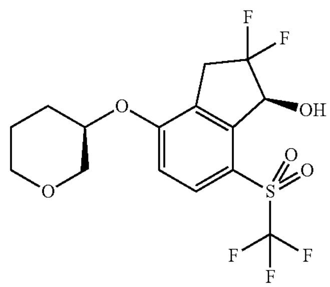 [SMILES: O=S(=O)(c1ccc(O[C@@H]2CCCOC2)c2c1[C@H](O)C(F)(F)C2)C(F)(F)F] | 401 (M − H)− | |
| 731 | 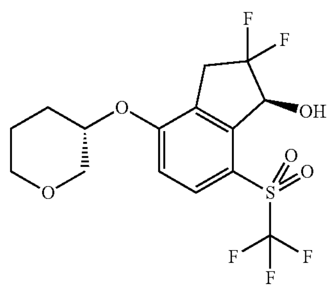 [SMILES: O=S(=O)(c1ccc(O[C@H]2CCCOC2)c2c1[C@H](O)C(F)(F)C2)C(F)(F)F] | 401 (M − H)− | |
| 732 | 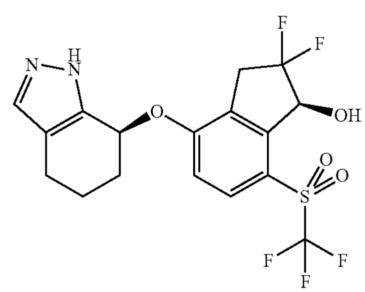 [SMILES: O=S(=O)(c1ccc(O[C@H]2CCCc3cn[nH]c32)c2c1[C@H](O)C(F)(F)C2)C(F)(F)F] | 439 (M + H)+ | |
| 733 | 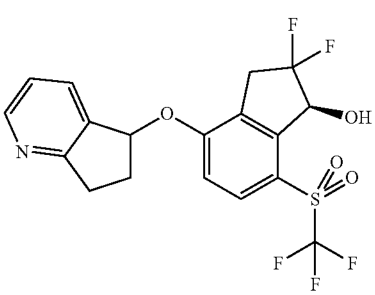 [SMILES: O=S(=O)(c1ccc(OC2CCc3ncccc32)c2c1[C@H](O)C(F)(F)C2)C(F)(F)F] | 436 (M + H)+ | |

TABLE 1-continued

| No. | Structure | Mass Characterization | ¹H NMR Data |
|---|---|---|---|
| 734 | 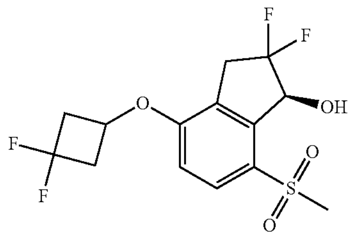 [SMILES: CS(=O)(=O)c1ccc(OC2CC(F)(F)C2)c2c1[C@H](O)C(F)(F)C2] | 355 (M + H)+ | |
| 735 | 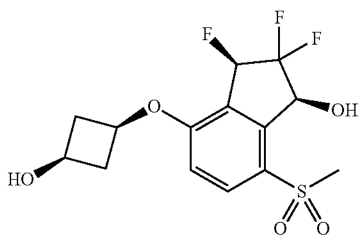 [SMILES: CS(=O)(=O)c1ccc(O[C@H]2C[C@@H](O)C2)c2c1[C@H](O)C(F)(F)[C@@H]2F] | 353 (M + H)+ | |
| 736 | 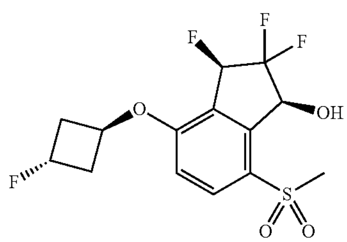 [SMILES: CS(=O)(=O)c1ccc(O[C@H]2C[C@H](F)C2)c2c1[C@H](O)C(F)(F)[C@@H]2F] | 355 (M + H)+ | |
| 737 | 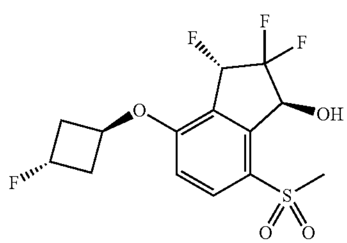 [SMILES: CS(=O)(=O)c1ccc(O[C@H]2C[C@H](F)C2)c2c1[C@H](O)C(F)(F)[C@H]2F] | 355 (M + H)+ | |
| 738 | 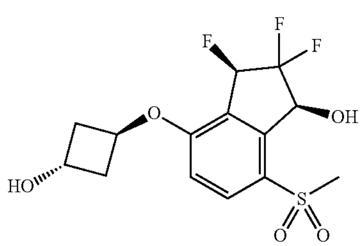 [SMILES: CS(=O)(=O)c1ccc(O[C@H]2C[C@H](O)C2)c2c1[C@H](O)C(F)(F)[C@@H]2F] | 353 (M + H)+ | |
| 739 | 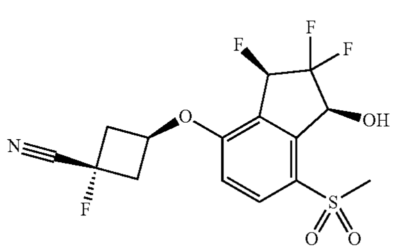 [SMILES: CS(=O)(=O)c1ccc(O[C@H]2C[C@@](F)(C#N)C2)c2c1[C@H](O)C(F)(F)[C@@H]2F] | 402 (M + Na)+ | |

TABLE 1-continued

| No. | Structure | Mass Characterization | ¹H NMR Data |
|---|---|---|---|
| 740 | 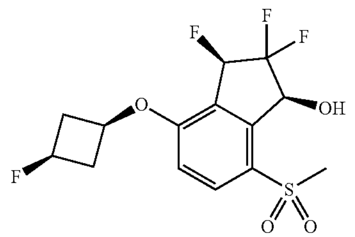 [SMILES: CS(=O)(=O)c1ccc(O[C@H]2C[C@@H](F)C2)c2c1[C@H](O)C(F)(F)[C@@H]2F] | 355 (M + H)⁺ | |
| 741 | 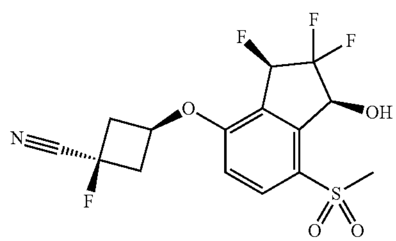 [SMILES: CS(=O)(=O)c1ccc(O[C@H]2C[C@](F)(C#N)C2)c2c1[C@H](O)C(F)(F)[C@@H]2F] | 380 (M + H)⁺ | |
| 742 | 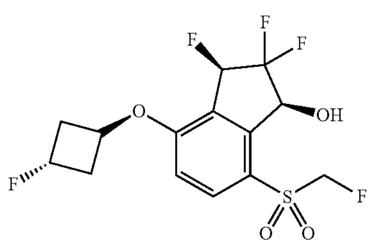 | 390 (M + NH₄)⁺ | |
| 743 | 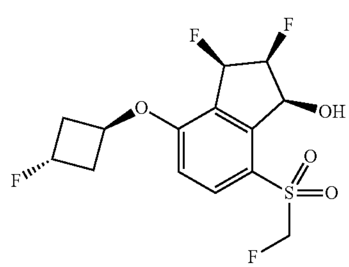 [SMILES: O=S(=O)(CF)c1ccc(O[C@H]2C[C@H](F)C2)c2c1[C@H](O)[C@H](F)[C@@H]2F] | 372 (M + NH₄)⁺ | |
| 744 | 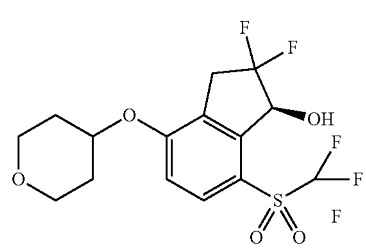 | [M + NH₄]⁺ 420 | |
| 745 | 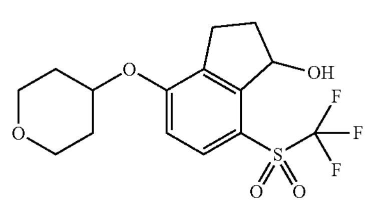 [SMILES: O=S(=O)(c1ccc(OC2CCOCC2)c2c1C(O)CC2)C(F)(F)F] | [M + NH₄]⁺ 384 | |

TABLE 1-continued

| No. | Structure | Mass Characterization | $^1$H NMR Data |
|---|---|---|---|
| 746 | 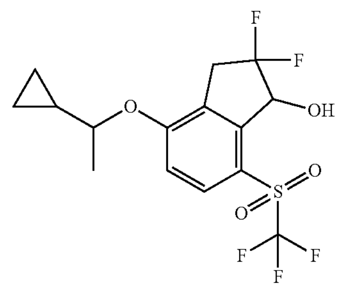 [SMILES: CC(Oc1ccc(S(=O)(=O)C(F)(F)F)c2c1CC(F)(F)C2O)C1CC1] | [M + NH$_4$]$^+$ 404 | |
| 747 | 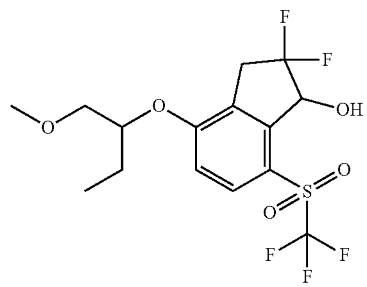 [SMILES: CCC(COC)Oc1ccc(S(=O)(=O)C(F)(F)F)c2c1CC(F)(F)C2O] | [M + NH$_4$]$^+$ 422 | |
| 748 | 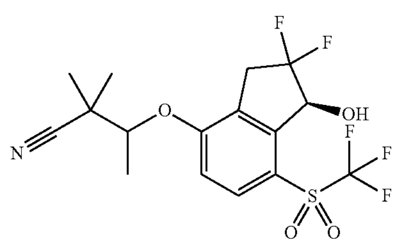 [SMILES: CC(Oc1ccc(S(=O)(=O)C(F)(F)F)c2c1CC(F)(F)[C@H]2O)C(C)(C)C#N] | [M + NH$_4$]$^+$ 429 | |
| 749 | 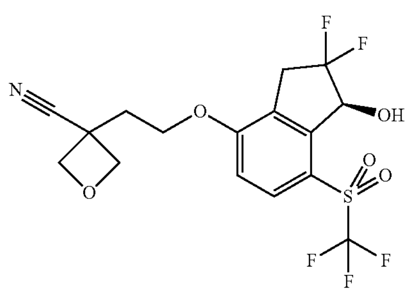 [SMILES: N#CC1(CCOc2ccc(S(=O)(=O)C(F)(F)F)c3c2CC(F)(F)[C@H]3O)COC1] | [M + NH$_4$]$^+$ 445 | |
| 750 | 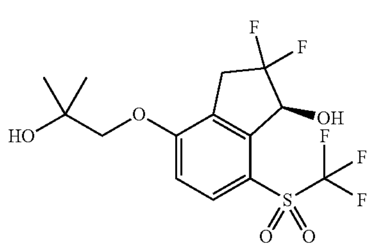 [SMILES: CC(C)(O)COc1ccc(S(=O)(=O)C(F)(F)F)c2c1CC(F)(F)[C@H]2O] | [M + NH$_4$]$^+$ 408 | |

TABLE 1-continued

| No. | Structure | Mass Characterization | ¹H NMR Data |
|---|---|---|---|
| 751 | 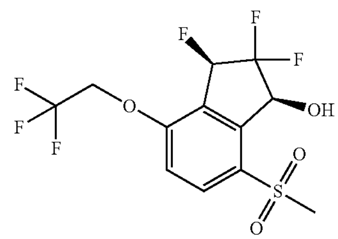 [SMILES: CS(=O)(=O)c1ccc(OCC(F)(F)F)c2c1[C@H](O)C(F)(F)[C@@H]2F] | [M + NH₄]⁺ 382 | |
| 752 | 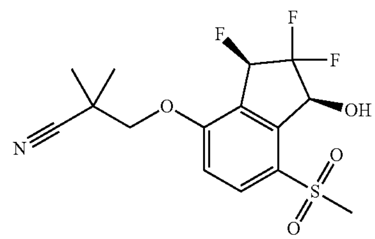 [SMILES: CC(C)(C#N)COc1ccc(S(C)(=O)=O)c2c1[C@@H](F)C(F)(F)[C@H]2O] | [M + NH₄]⁺ 381 | |
| 753 | 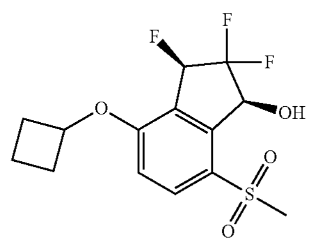 [SMILES: CS(=O)(=O)c1ccc(OC2CCC2)c2c1[C@H](O)C(F)(F)[C@@H]2F] | [M + NH₄]⁺ 354 | |
| 754 | 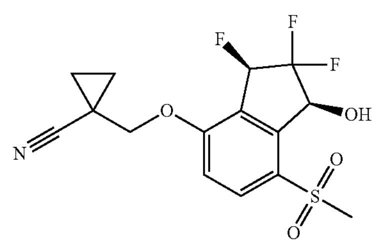 [SMILES: CS(=O)(=O)c1ccc(OCC2(C#N)CC2)c2c1[C@H](O)C(F)(F)[C@@H]2F] | [M + NH₄]⁺ 379 | |
| 755 | 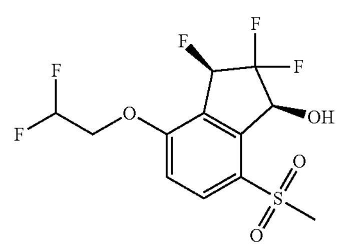 [SMILES: CS(=O)(=O)c1ccc(OCC(F)F)c2c1[C@H](O)C(F)(F)[C@@H]2F] | [M + NH₄]⁺ 364 | |
| 756 | 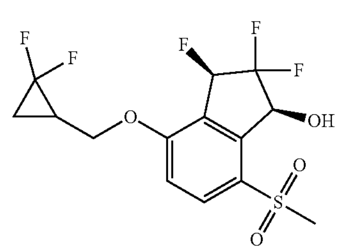 [SMILES: CS(=O)(=O)c1ccc(OCC2CC2(F)F)c2c1[C@H](O)C(F)(F)[C@@H]2F] | [M + NH₄]⁺ 390 | |

TABLE 1-continued

| No. | Structure | Mass Characterization | ¹H NMR Data |
|---|---|---|---|
| 757 | 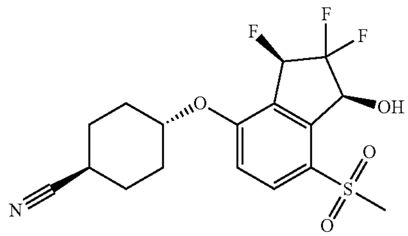 [SMILES: CS(=O)(=O)c1ccc(O[C@H]2CC[C@H](C#N)CC2)c2c1[C@H](O)C(F)(F)[C@@H]2F] | [M + NH₄]⁺ 407 | (400 MHz, CDCl₃): δ 8.09 (d, 1H), 7.07(d, 1H), 5.82-5.66 (m, 1H), 5.61-5.57 (m, 1H), 4.73 (m, 1H), 3.41 (d, 1H), 3.20 (s, 3H), 2.87 (m, 1H), 2.17-1.80 (m, 8H) |
| 758 | 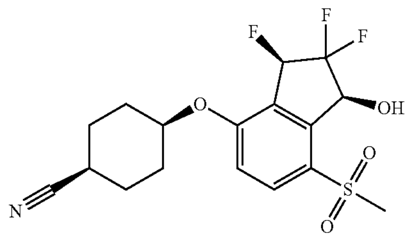 [SMILES: CS(=O)(=O)c1ccc(O[C@H]2CC[C@@H](C#N)CC2)c2c1[C@H](O)C(F)(F)[C@@H]2F] | [M + NH₄]⁺ 407 | (400 MHz, CDCl₃): δ 8.07 (dd, 1H), 7.04 (d, 1H), 5.85-5.70 (m, 1H), 5.62-5.58 (m, 1H), 4.65 (m, 1H), 3.25 (d, 1H), 3.20 (s, 3H), 2.76-2.74 (m, 1H), 2.12-1.55 (m, 8H) |
| 759 | 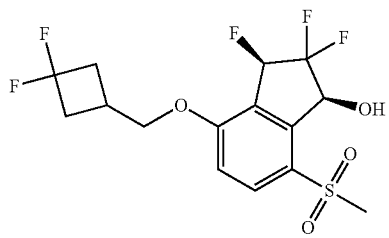 [SMILES: CS(=O)(=O)c1ccc(OCC2CC(F)(F)C2)c2c1[C@H](O)C(F)(F)[C@@H]2F] | [M + NH₄]⁺ 404 | |
| 760 | 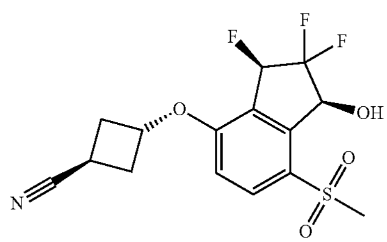 | [M + NH₄]⁺ 379 | (400 MHz, CDCl₃): δ 8.10 (dd, 1H), 6.86 (d, 1H), 5.82-5.66 (m, 1H), 5.61-5.58 (m, 1H), 5.17-5.14 (m, 1H), 3.32-3.29 (m, 1H), 3.24 (d, 1H), 3.20 (s, 3H), 2.99-2.93 (m, 2H), 2.76-2.70 (m, 2H) |
| 761 | 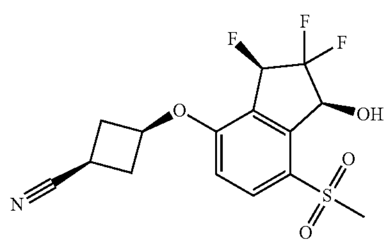 [SMILES: CS(=O)(=O)c1ccc(O[C@H]2C[C@@H](C#N)C2)c2c1[C@H](O)C(F)(F)[C@@H]2F] | [M + NH₄]⁺ 379 | (400 MHz, CDCl₃): δ 8.08 (dd, 1H), 6.84 (d, 1H), 5.85-5.69 (m, 1H), 5.62-5.58 (m, 1H), 4.86-4.79 (m, 1H), 3.24 (d, 1H), 3.20 (s, 3H), 3.07-3.00 (m, 2H), 2.96-2.87 (m, 1H), 2.76-2.66 (m, 2H) |
| 762 | 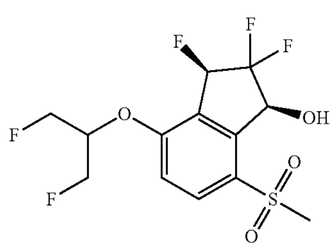 [SMILES: CS(=O)(=O)c1ccc(OC(CF)CF)c2c1[C@H](O)C(F)(F)[C@@H]2F] | [M + NH₄]⁺ 378 | |

| No. | Structure | Mass Characterization | ¹H NMR Data |
|---|---|---|---|
| 763 | 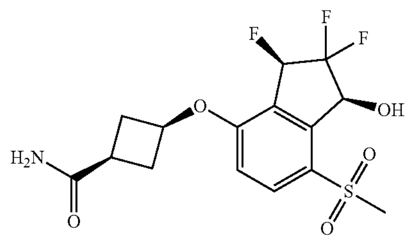 [SMILES: CS(=O)(=O)c1ccc(O[C@H]2C[C@@H](C(N)=O)C2)c2c1[C@H](O)C(F)(F)[C@@H]2F] | [M + NH$_4$]$^+$ 397 | (400 MHz, CDCl$_3$): δ 8.06 (dd, 1H), 6.90 (d, 1H), 5.85-5.70 (m, 1H), 5.59-5.56 (m, 1H), 5.39-5.32 (m, 2H), 4.79-4.76 (m, 1H), 3.24 (d, 1H), 3.20 (s, 3H), 2.83-2.74 (m, 3H), 2.63-2.55 (m, 2H) |
| 764 | 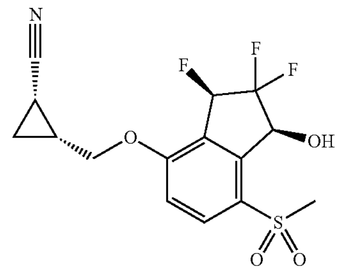 [SMILES: CS(=O)(=O)c1ccc(OC[C@@H]2C[C@@H]2C#N)c2c1[C@H](O)C(F)(F)[C@@H]2F] | [M + NH$_4$]$^+$ 379 | (400 MHz, CDCl$_3$): δ 8.10 (dd, 1H), 7.09 (d, 1H), 5.91-5.76 (m, 1H), 5.58-5.55 (m, 1H), 4.48-4.44 (m, 1H), 4.14-4.10 (m, 1H), 3.41 (d, 1H), 3.20 (s, 3H), 1.94-1.91 (m, 1H), 1.81-1.76 (m, 1H), 1.46-1.41 (m, 1H), 1.20-1.18 (m, 1H) |
| 765 | 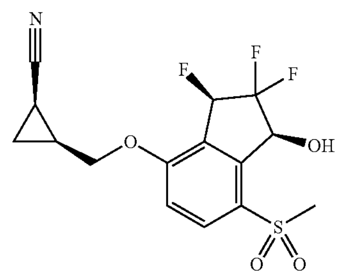 [SMILES: CS(=O)(=O)c1ccc(OC[C@H]2C[C@H]2C#N)c2c1[C@H](O)C(F)(F)[C@@H]2F] | [M + NH$_4$]$^+$ 379 | (400 MHz, CDCl$_3$): δ 8.12 (dd, 1H), 7.10 (d, 1H), 5.91-5.75 (m, 1H), 5.62-5.58 (m, 1H), 4.39-4.29 (m, 2H), 3.26 (d, 1H), 3.21 (s, 3H), 1.90-1.86 (m, 1H), 1.79-1.76 (m, 1H), 1.45-1.39 (m, 1H), 1.26-1.22 (m, 1H) |
| 766 | 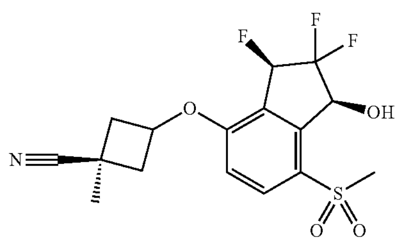 | [M + NH$_4$]$^+$ 393 | (400 MHz, CDCl$_3$): δ 8.10 (dd, 1H), 6.88 (d, 1H), 5.82-5.66 (m, 1H), 5.61-5.58 (m, 1H), 5.08-5.02 (m, 1H), 3.29 (d, 1H), 3.20 (s, 3H), 3.19-3.14 (m, 2H), 2.42-2.32 (m, 2H), 1.65 (s, 3H) |
| 767 | 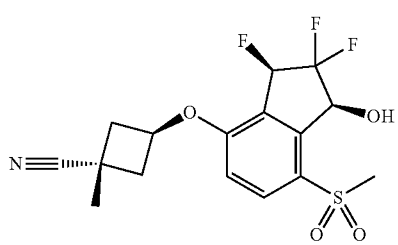 [SMILES: CS(=O)(=O)c1ccc(O[C@H]2C[C@](C)(C#N)C2)c2c1[C@H](O)C(F)(F)[C@@H]2F] | [M + NH$_4$]$^+$ 393 | (400 MHz, CDCl$_3$): δ 8.05 (d, 1H), 6.81 (d, 1H), 5.87-5.71 (m, 1H), 5.61-5.58 (m, 1H), 4.97-4.91 (m, 1H), 3.25 (d, 1H), 3.20 (s, 3H), 2.92-2.76 (m, 2H), 2.74-2.70 (m, 2H), 1.65 (s, 3H) |
| 768 | 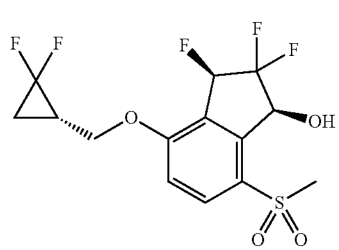 [SMILES: CS(=O)(=O)c1ccc(OC[C@@H]2CC2(F)F)c2c1[C@H](O)C(F)(F)[C@@H]2F] | [M + NH$_4$]$^+$ 390 | (400 MHz, CDCl$_3$): δ 8.11 (dd, 1H), 7.07 (d, 1H), 5.85-5.69 (m, 1H), 5.62-5.58 (m, 1H), 4.36-4.32 (m, 1H), 4.21-4.17 (m, 1H), 3.27 (d, 1H), 3.20 (s, 3H), 2.18-2.10 (m, 1H), 1.72-1.67 (m, 2H), 1.41-1.33 (m, 1H) |

TABLE 1-continued

| No. | Structure | Mass Characterization | ¹H NMR Data |
|---|---|---|---|
| 769 | 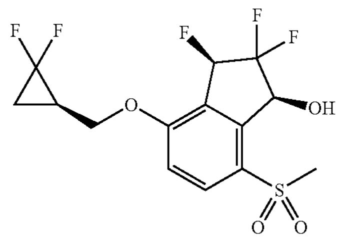 [SMILES: CS(=O)(=O)c1ccc(OC[C@H]2CC2(F)F)c2c1[C@H](O)C(F)(F)[C@@H]2F] | [M + NH₄]⁺ 390 | (400 MHz, CDCl₃): δ 8.11 (dd, 1H), 7.06 (d, 1H), 5.87-5.72 (m, 1H), 5.61-5.57 (m, 1H), 4.25-4.23 (m, 2H), 3.27 (d, 1H), 3.20 (s, 3H), 2.22-2.10 (m, 1H), 1.73-1.70 (m, 2H), 1.39-1.36 (m, 1H) |
| 770 | 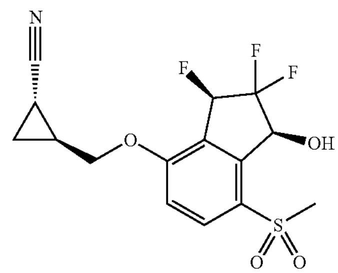 [SMILES: CS(=O)(=O)c1ccc(OC[C@H]2C[C@@H]2C#N)c2c1[C@H](O)C(F)(F)[C@@H]2F] | [M + NH₄]⁺ 379 | (400 MHz, CDCl₃): δ 8.10 (dd, 1H), 7.02 (d, 1H), 5.83-5.67 (m, 1H), 5.61-5.58 (m, 1H), 4.25-4.22 (m, 1H), 4.14-4.09 (m, 1H), 3.32-3.29 (m, 1H), 3.21 (s, 3H), 2.06-2.04 (m, 1H), 1.59-1.55 (m, 1H), 1.47-1.44 (m, 1H), 1.28-1.25 (m, 1H) |
| 771 | 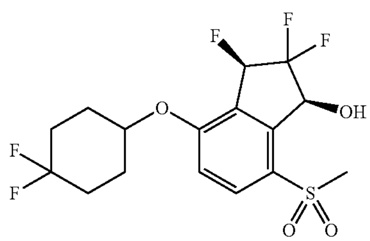 [SMILES: CS(=O)(=O)c1ccc(OC2CCC(F)(F)CC2)c2c1[C@H](O)C(F)(F)[C@@H]2F] | [M + NH₄]⁺ 418 | |
| 772 | 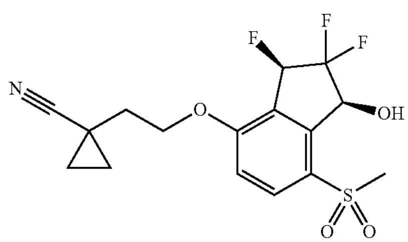 [SMILES: CS(=O)(=O)c1ccc(OCCC2(C#N)CC2)c2c1[C@H](O)C(F)(F)[C@@H]2F] | [M + NH₄]⁺ 393 | |
| 773 | 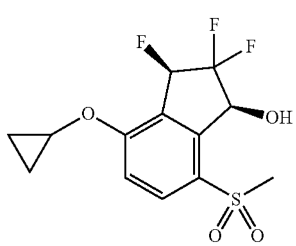 [SMILES: CS(=O)(=O)c1ccc(OC2CC2)c2c1[C@H](O)C(F)(F)[C@@H]2F] | [M + NH₄]⁺ 340 | |
| 774 | 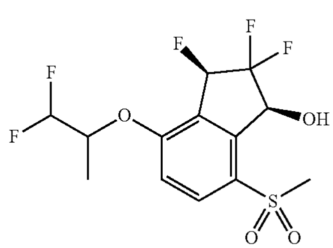 [SMILES: CC(Oc1ccc(S(C)(=O)=O)c2c1[C@@H](F)C(F)(F)[C@H]2O)C(F)F] | [M + NH₄]⁺ 378 | |

TABLE 1-continued

| No. | Structure | Mass Characterization | ¹H NMR Data |
|---|---|---|---|
| 775 | 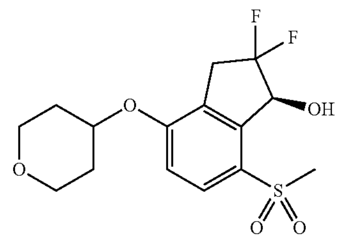 [SMILES: CS(=O)(=O)c1ccc(OC2CCOCC2)c2c1[C@H](O)C(F)(F)C2] | [M + NH₄]⁺ 366 | |
| 776 | 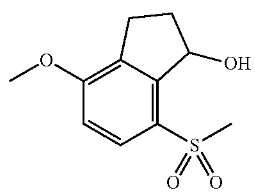 | [M + NH₄]⁺ 260 | |
| 777 | 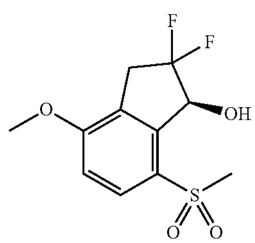 | [M + NH₄]⁺ 296 | |
| 778 | 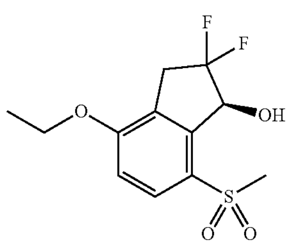 [SMILES: CCOc1ccc(S(C)(=O)=O)c2c1CC(F)(F)[C@H]2O] | [M + NH₄]⁺ 310 | |
| 779 | 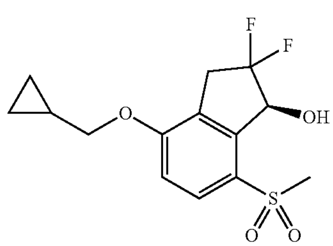 [SMILES: CS(=O)(=O)c1ccc(OCC2CC2)c2c1[C@H](O)C(F)(F)C2] | [M + NH₄]⁺ 336 | |
| 780 | 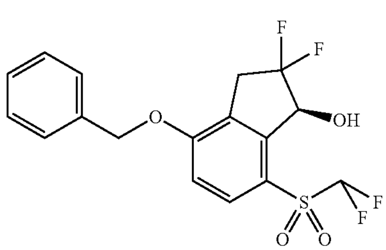 [SMILES: O=S(=O)(c1ccc(OCc2ccccc2)c2c1[C@H](O)C(F)(F)C2)C(F)F] | [M + NH₄]⁺ 408 | |

TABLE 1-continued

| No. | Structure | Mass Characterization | ¹H NMR Data |
|---|---|---|---|
| 781 | 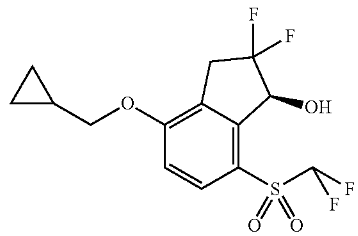 [SMILES: O=S(=O)(c1ccc(OCC2CC2)c2c1[C@H](O)C(F)(F)C2)C(F)F] | [M + NH₄]⁺ 372 | |
| 782 | 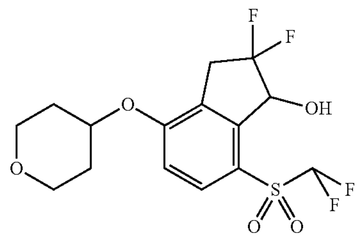 [SMILES: O=S(=O)(c1ccc(OC2CCOCC2)c2c1C(O)C(F)(F)C2)C(F)F] | | (400 MHz, CDCl₃): δ 7.89 (d, 1H), 6.98 (d, 1H), 6.55 (t, J = 54 Hz, 1H), 5.41 (d, 1H), 4.68 (m, 1H), 3.98-3.88 (m, 2H), 3.66-3.54 (m, 2H), 3.48-3.26 (m, 2H), 1.87-1.74 (m, 2H), 1.62-1.51 (m, 2H) |
| 783 | 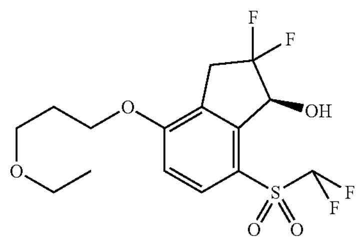 [SMILES: CCOCCCOc1ccc(S(=O)(=O)C(F)F)c2c1CC(F)(F)[C@H]2O] | [M + NH₄]⁺ 402 | |
| 784 | 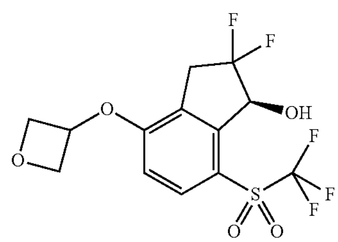 [SMILES: O=S(=O)(c1ccc(OC2COC2)c2c1[C@H](O)C(F)(F)C2)C(F)(F)F] | [M + NH₄]⁺ 392 | |
| 785 | 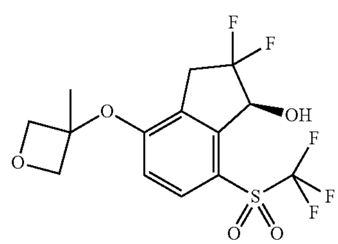 [SMILES: CC1(Oc2ccc(S(=O)(=O)C(F)(F)F)c3c2CC(F)(F)[C@H]3O)COC1] | [M + NH₄]⁺ 406 | |
| 786 | 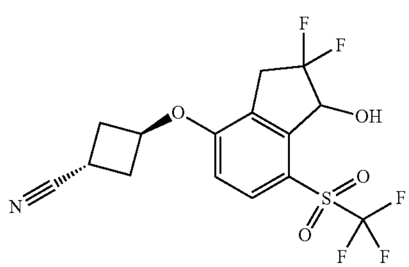 [SMILES: N#C[C@H]1C[C@H](Oc2ccc(S(=O)(=O)C(F)(F)F)c3c2CC(F)(F)C3O)C1] | [M + NH₄]⁺ 415 | |

TABLE 1-continued

| No. | Structure | Mass Characterization | ¹H NMR Data |
|---|---|---|---|
| 787 | 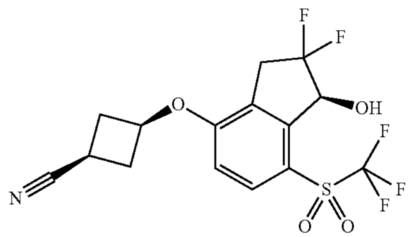 [SMILES: N#C[C@H]1C[C@@H](Oc2ccc(S(=O)(=O)C(F)(F)F)c3c2CC(F)(F)[C@H]3O)C1] | [M + NH₄]⁺ 415 | |
| 788 | 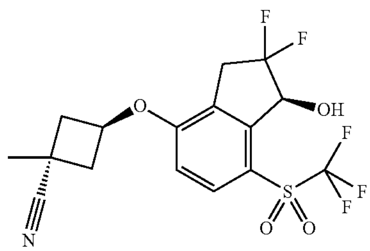 [SMILES: C[C@]1(C#N)C[C@H](Oc2ccc(S(=O)(=O)C(F)(F)F)c3c2CC(F)(F)[C@H]3O)C1] | [M + NH₄]⁺ 429 | |
| 789 | 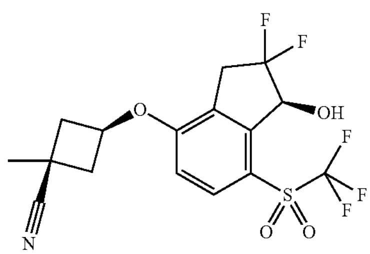 [SMILES: C[C@]1(C#N)C[C@@H](Oc2ccc(S(=O)(=O)C(F)(F)F)c3c2CC(F)(F)[C@H]3O)C1] | [M + NH₄]⁺ 429 | |
| 790 | 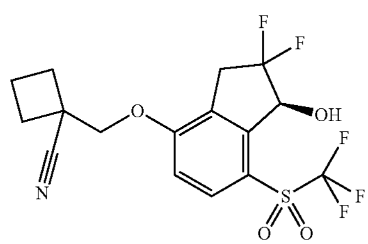 [SMILES: N#CC1(COc2ccc(S(=O)(=O)C(F)(F)F)c3c2CC(F)(F)[C@H]3O)CCC1] | [M + NH₄]⁺ 429 | |
| 791 | 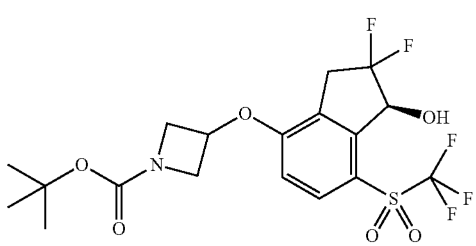 [SMILES: CC(C)(C)OC(=O)N1CC(Oc2ccc(S(=O)(=O)C(F)(F)F)c3c2CC(F)(F)[C@H]3O)C1] | [M + HCl − H]⁻ 508 | |
| 792 | 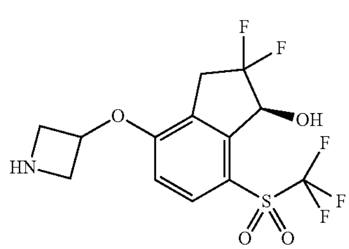 [SMILES: O=S(=O)(c1ccc(OC2CNC2)c2c1[C@H](O)C(F)(F)C2)C(F)(F)F] | [M + H]⁺ 374 | |

TABLE 1-continued

| No. | Structure | Mass Characterization | ¹H NMR Data |
|---|---|---|---|
| 793 | 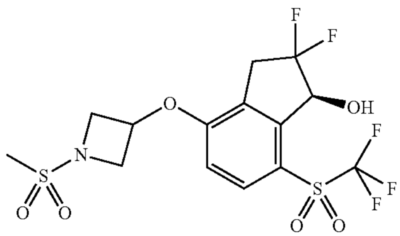 [SMILES: CS(=O)(=O)N1CC(Oc2ccc(S(=O)(=O)C(F)(F)F)c3c2CC(F)(F)[C@H]3O)C1] | [M + NH$_4$]$^+$ 469 | |
| 794 | 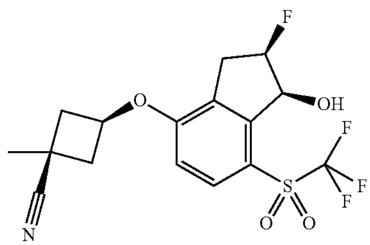 [SMILES: C[C@]1(C#N)C[C@@H](Oc2ccc(S(=O)(=O)C(F)(F)F)c3c2C[C@@H](F)[C@H]3O)C1] | [M + NH$_4$]$^+$ 411 | |
| 795 | 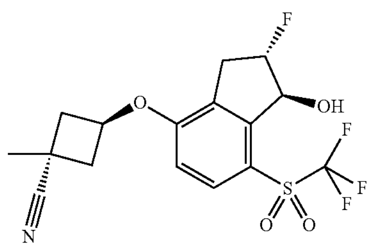 [SMILES: C[C@]1(C#N)C[C@H](Oc2ccc(S(=O)(=O)C(F)(F)F)c3c2C[C@H](F)[C@H]3O)C1] | [M + NH$_4$]$^+$ 411 | |
| 796 | 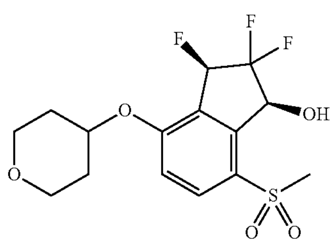 [SMILES: CS(=O)(=O)c1ccc(OC2CCOCC2)c2c1[C@H](O)C(F)(F)[C@@H]2F] | [M + NH$_4$]$^+$ 384 | |
| 797 | 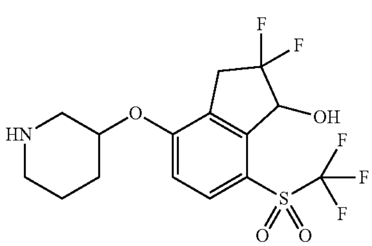 [SMILES: O=S(=O)(c1ccc(OC2CCCNC2)c2c1C(O)C(F)(F)C2)C(F)(F)F] | 402 (M + H) | |
| 798 | 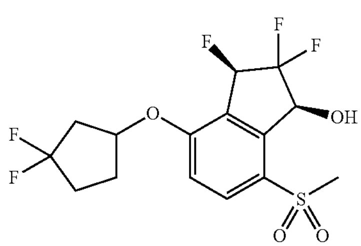 [SMILES: CS(=O)(=O)c1ccc(OC2CCC(F)(F)C2)c2c1[C@H](O)C(F)(F)[C@@H]2F] | [M + NH$_4$]$^+$ 404 | |

TABLE 1-continued

| No. | Structure | Mass Characterization | ¹H NMR Data |
|---|---|---|---|
| 799 | 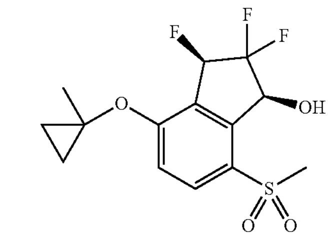 [SMILES: CC1(Oc2ccc(S(C)(=O)=O)c3c2[C@@H](F)C(F)(F)[C@H]3O)CC1] | [M + NH₄]⁺ 354 | |
| 800 | 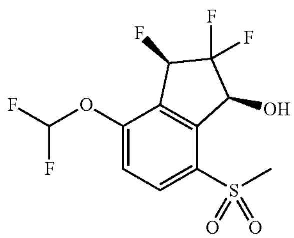 [SMILES: CS(=O)(=O)c1ccc(OC(F)F)c2c1[C@H](O)C(F)(F)[C@@H]2F] | [M + NH₄]⁺ 350 | |
| 801 | 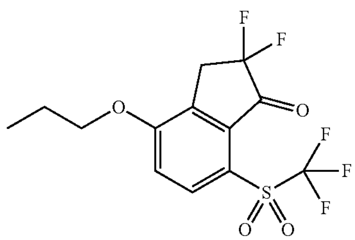 [SMILES: CCCOc1ccc(S(=O)(=O)C(F)(F)F)c2c1CC(F)(F)C2=O] | | (300 MHz, CDCl₃): δ 8.25 (d, 1H), 7.27 (d, 1H), 4.18 (t, 2H), 3.50 (t, 2H), 1.94 (m, 2H), 1.11 (t, 3H) |
| 802 | 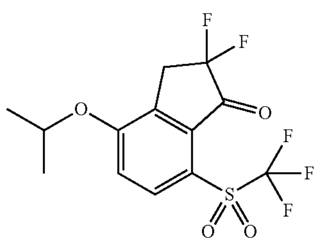 [SMILES: CC(C)Oc1ccc(S(=O)(=O)C(F)(F)F)c2c1CC(F)(F)C2=O] | | (300 MHz, CDCl₃): δ 8.23 (d, 1H), 7.25 (d, 1H), 4.83 (m, 1H), 3.47 (t, 2H), 1.48 (d, 6H) |
| 803 | 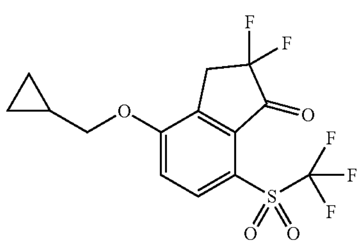 [SMILES: O=C1c2c(S(=O)(=O)C(F)(F)F)ccc(OCC3CC3)c2CC1(F)F] | | |
| 804 | 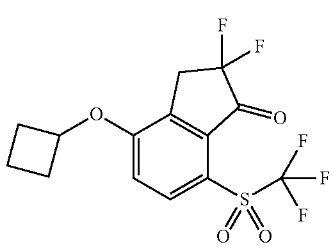 [SMILES: O=C1c2c(S(=O)(=O)C(F)(F)F)ccc(OC3CCC3)c2CC1(F)F] | | |

TABLE 1-continued

| No. | Structure | Mass Characterization | ¹H NMR Data |
|---|---|---|---|
| 805 | Isomer 1 | | (400 MHz, CDCl₃): δ 8.21 (d, 1H), 7.40 (d, 1H), 4.88-4.83 (m, 1H), 3.67-3.39 (m, 7H), 1.43 (d, 3H) |
| 806 | Isomer 2 | | (400 MHz, CDCl₃): δ 8.13 (d, 1H), 7.34 (d, 1H), 4.82-4.76 (m, 1H), 3.60-3.31 (m, 7H), 1.36 (d, 3H) |
| 807 | 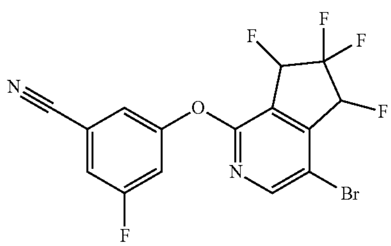 [SMILES: N#Cc1cc(F)cc(Oc2ncc(Br)c3c2C(F)C(F)(F)C3F)c1] | 405/407 (M + H) | (400 MHz, CDCl₃): δ 8.38 (d, 1H), 7.37-7.36 (m, 1H), 7.30 (ddd, 1H), 7.24 (dt, 1H), 6.09 (dddd, 1H), 6.00 (dddd, 1H) |
| 808 | 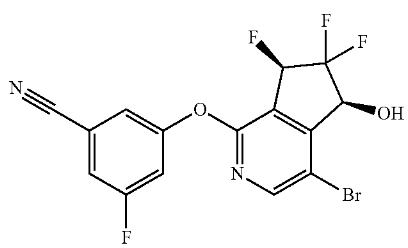 [SMILES: N#Cc1cc(F)cc(Oc2ncc(Br)c3c2[C@@H](F)C(F)(F)[C@H]3O)c1] | 403/405 (M + H) | (400 MHz, CDCl₃): δ 8.36 (d, 1H), 7.37-7.35 (m, 1H), 7.29 (ddd, 1H), 7.25 (dt, 1H), 5.86 (dd, 1H), 5.11 (ddd, 1H), 2.73 (d, 1H) |
| 809 | 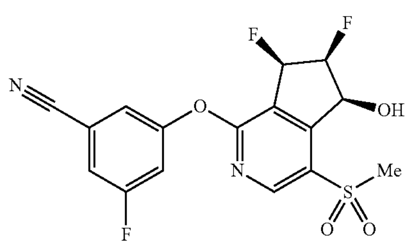 [SMILES: CS(=O)(=O)c1cnc(Oc2cc(F)cc(C#N)c2)c2c1[C@H](O)[C@H](F)[C@@H]2F] | 385 (M + H) | (400 MHz, CDCl₃): δ 8.75 (d, 1H), 7.39-7.37 (m, 1H), 7.34 (ddd, 1H), 7.29-7.25 (m, 1H), 6.25 (ddd, 1H), 5.94-5.87 (m, 1H), 5.44 (ddd, 1H), 3.66-3.58 (m, 1H), 3.29 (s, 3H) |
| 810 | 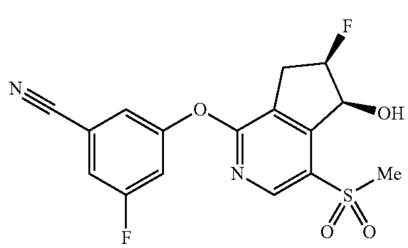 [SMILES: CS(=O)(=O)c1cnc(Oc2cc(F)cc(C#N)c2)c2c1[C@H](O)[C@H](F)C2] | 367 (M + H) | (400 MHz, CDCl₃): δ 8.60-8.59 (m, 1H), 7.35-7.33 (m, 1H), 7.31 (ddd, 1H), 7.24 (dt, 1H), 5.63 (ddd, 1H), 5.51 (dtd, 1H), 3.76 (dd, 1H), 3.47-3.35 (m, 1H), 3.31 (s, 3H), 3.29-3.15 (m, 1H) |

TABLE 1-continued

| No. | Structure | Mass Characterization | ¹H NMR Data |
|-----|-----------|----------------------|-------------|
| 811 | 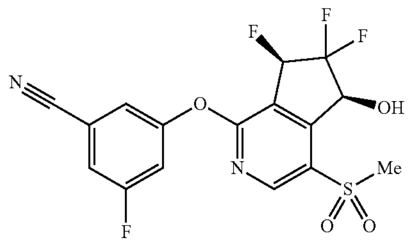 [SMILES: CS(=O)(=O)c1cnc(Oc2cc(F)cc(C#N)c2)c2c1[C@H](O)C(F)(F)[C@@H]2F] | 403 (M + H) | (400 MHz, CDCl$_3$): δ 8.80 (d, 1H), 7.40-7.38 (m, 1H), 7.36 (ddd, 1H), 7.28 (dt, 1H), 5.88 (dd, 1H), 5.66-5.60 (m, 1H), 3.52 (dd, 1H), 3.28 (s, 3H) |
| 812 | 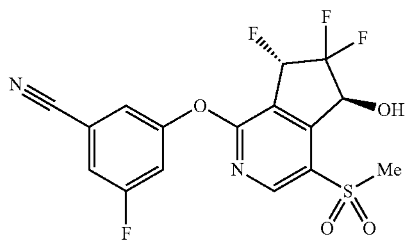 [SMILES: CS(=O)(=O)c1cnc(Oc2cc(F)cc(C#N)c2)c2c1[C@H](O)C(F)(F)[C@H]2F] | 403 (M + H) | (400 MHz, CDCl$_3$): δ 8.77 (d, 1H), 7.39-7.37 (m, 1H), 7.35 (ddd, 1H), 7.27 (dt, 1H), 6.00 (dd, 1H), 5.83 (tdd, 1H), 3.97 (d, 1H), 3.29 (s, 3H) |
| 813 | 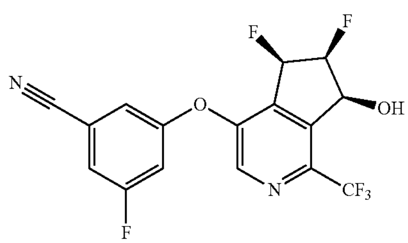 [SMILES: N#Cc1cc(F)cc(Oc2cnc(C(F)(F)F)c3c2[C@@H](F)[C@@H](F)[C@H]3O)c1] | 375 (M + H) | (400 MHz, CDCl$_3$): δ 8.42 (s, 1H), 7.28 (ddd, 1H), 7.20-7.18 (m, 1H), 7.09 (dt, 1H), 5.92 (dt, 1H), 5.53-5.46 (m, 1H), 5.19 (ddt, 1H), 2.66 (ddd, 1H) |
| 814 | 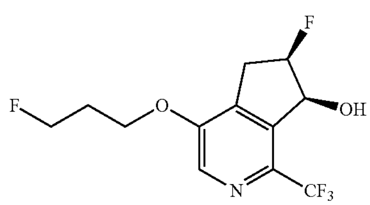 [SMILES: O[C@H]1c2c(C(F)(F)F)ncc(OCCCF)c2C[C@H]1F] | 298 (M + H) | |
| 815 | 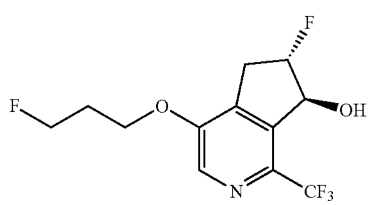 | 298 (M + H) | |
| 816 | 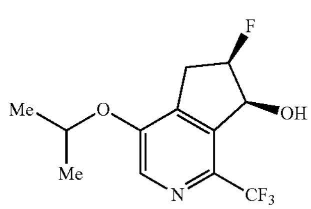 [SMILES: CC(C)Oc1cnc(C(F)(F)F)c2c1C[C@@H](F)[C@H]2O] | 280 (M + H) | |
| 817 | 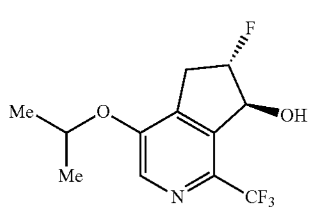 [SMILES: CC(C)Oc1cnc(C(F)(F)F)c2c1C[C@H](F)[C@H]2O] | 280 (M + H) | |

TABLE 1-continued

| No. | Structure | Mass Characterization | $^1$H NMR Data |
|---|---|---|---|
| 818 | 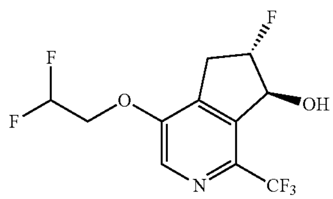 | 302 (M + H) | |
| 819 | 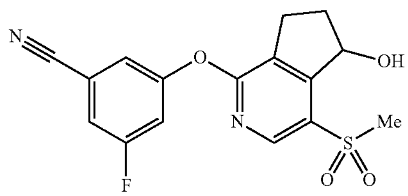 [SMILES: CS(=O)(=O)c1cnc(Oc2cc(F)cc(C#N)c2)c2c1C(O)CC2] | 349 (M + H) | (400 MHz, CDCl$_3$): δ 8.52-8.51 (m, 1H), 7.33 (ddd, 1H), 7.29 (ddd, 1H), 7.23 (dt, 1H), 5.71-5.66 (m, 1H), 3.64 (d, 1H), 3.26-3.17 (m, 1H), 3.22 (s, 3H), 2.99-2.90 (ddd, 1H), 2.66-2.56 (m, 1H), 2.32-2.22 (m, 1H) |
| 820 | 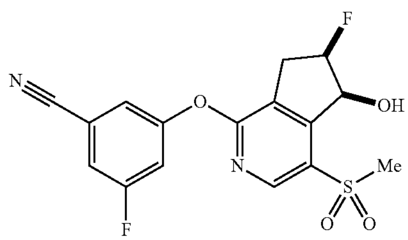 [SMILES: CS(=O)(=O)c1cnc(Oc2cc(F)cc(C#N)c2)c2c1[C@H](O)[C@H](F)C2] | 367 (M + H) | (400 MHz, CDCl$_3$): δ 8.60-8.59 (m, 1H), 7.35-7.33 (m, 1H), 7.31 (ddd, 1H), 7.24 (dt, 1H), 5.63 (ddd, 1H), 5.52 (dtd, 1H), 3.76 (dd, 1H), 3.47-3.35 (m, 1H), 3.31 (s, 3H), 3.29-3.15 (m, 1H) |
| 821 | 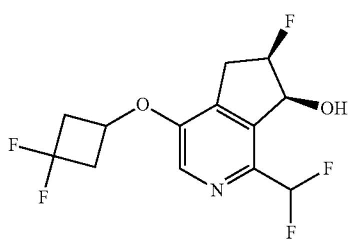 [SMILES: O[C@H]1c2c(C(F)F)ncc(OC3CC(F)(F)C3)c2C[C@H]1F] | 310 (M + H) | |
| 822 | 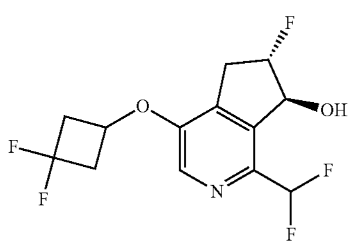 [SMILES: O[C@H]1c2c(C(F)F)ncc(OC3CC(F)(F)C3)c2C[C@@H]1F] | 310 (M + H) | |
| 823 | 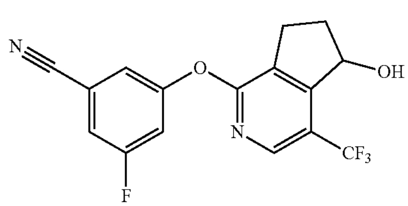 [SMILES: N#Cc1cc(F)cc(Oc2ncc(C(F)(F)F)c3c2CCC3O)c1] | 339 (M + H) | (400 MHz, CDCl$_3$): δ 8.29-8.27 (m, 1H), 7.34-7.32 (m, 1H), 7.26 (ddd, 1H), 7.22 (dt, 1H), 5.57-5.10 (m, 1H), 3.22 (dt, 1H), 2.96 (ddd, 1H), 2.56-2.45 (m, 1H), 2.33-2.25 (m, 1H), 2.22-2.18 (m, 1H) |

TABLE 1-continued

| No. | Structure | Mass Characterization | ¹H NMR Data |
|---|---|---|---|
| 824 | 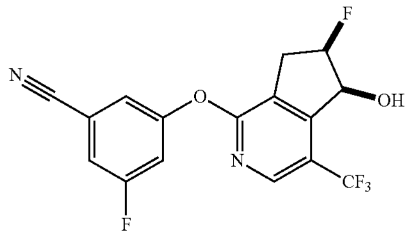 [SMILES: N#Cc1cc(F)cc(Oc2ncc(C(F)(F)F)c3c2C[C@@H](F)[C@H]3O)c1] | 357 (M + H) | (400 MHz, CDCl$_3$): δ 8.36-8.34 (m, 1H), 7.35-7.32 (m, 1H), 7.28 (ddd, 1H), 7.23 (dt, 1H), 5.53-5.35 (m, 2H), 3.40 (ddd, 1H), 3.22 (ddd, 1H), 2.73-2.68 (m, 1H) |
| 825 | 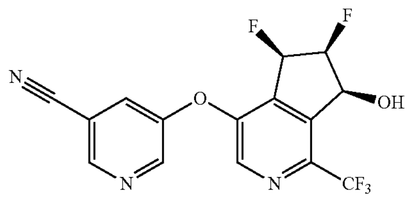 [SMILES: N#Cc1cncc(Oc2cnc(C(F)(F)F)c3c2[C@@H](F)[C@@H](F)[C@H]3O)c1] | 358 (M + H) | (400 MHz, CDCl$_3$): δ 8.79 (dd, 1H), 8.71 (d, 1H), 8.41 (s, 1H), 7.67 (dd, 1H), 5.94 (dt, 1H), 5.53-5.46 (m, 1H), 5.21 (ddt, 1H), 2.73 (ddd, 1H) |
| 826 | 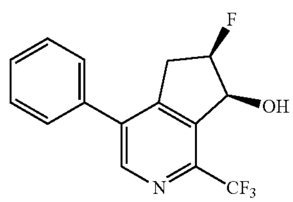 [SMILES: O[C@H]1c2c(C(F)(F)F)ncc(-c3ccccc3)c2C[C@H]1F] | 298 (M + H) | (400 MHz, CDCl$_3$): δ 8.68 (s, 1H), 7.55-7.45 (m, 3H), 7.44-7.40 (m, 2H), 5.54-5.46 (m, 1H), 5.31 (ddt, 1H), 3.46 (ddd, 1H), 3.24 (ddd, 1H), 2.61 (dd, 1H) |
| 827 | 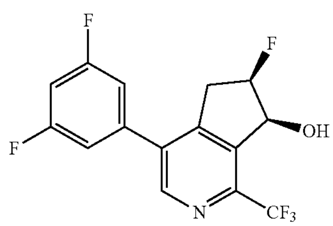 [SMILES: O[C@H]1c2c(C(F)(F)F)ncc(-c3cc(F)cc(F)c3)c2C[C@H]1F] | 334 (M + H) | (400 MHz, CDCl$_3$): δ 8.65 (s, 1H), 6.99-6.91 (m, 3H), 5.54-5.47 (m, 1H), 5.33 (ddt, 1H), 3.44 (ddd, 1H), 3.23 (ddd, 1H), 2.63 (dd, 1H) |
| 828 | 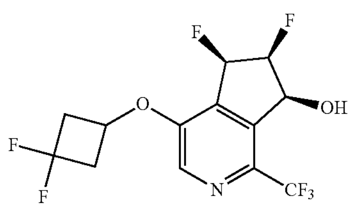 [SMILES: O[C@H]1c2c(C(F)(F)F)ncc(OC3CC(F)(F)C3)c2[C@@H](F)[C@H]1F] | 346 (M + H) | (400 MHz, CDCl$_3$): δ 8.24 (s, 1H), 5.95 (ddd, 1H), 5.47-5.41 (m, 1H), 5.07 (ddt, 1H), 4.97-4.88 (m, 1H), 3.30-3.15 (m, 2H), 2.99-2.79 (m, 2H), 2.54-2.49 (m, 1H) |
| 829 | 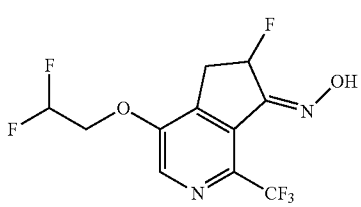 | 315 (M + H) | (400 MHz, DMSO-d$_6$): δ 8.30 (s, 1H), 6.26 (tt, 1H), 6.15 (ddd, 1H), 4.55 (td, 2H), 3.46-3.32 (m, 1H), 3.13 (ddd, 1H) |
| 830 | 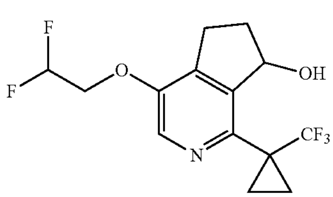 [SMILES: OC1CCc2c(OCC(F)F)cnc(C3(C(F)(F)F)CC3)c21] | 324 (M + H) | (400 MHz, CDCl$_3$): δ 8.14 (s, 1H), 6.10 (tt, 1H), 5.58-5.30 (m, 1H), 4.39-4.24 (m, 2H), 3.10 (dt, 1H), 2.87 (ddd, 1H), 2.37-2.27 (m, 1H), 2.20-2.12 (m, 1H), 1.90-1.86 (m, 1H), 1.47-1.39 (m, 2H), 1.27-1.21 (m, 2H) |

TABLE 1-continued

| No. | Structure | Mass Characterization | ¹H NMR Data |
|---|---|---|---|
| 831 | (structure) | 351 (M + H) | |
| 832 | (structure) | 351 (M + H) | (400 MHz, CDCl$_3$): δ 8.75 (d, 1H), 8.65-8.62 (m, 1H), 6.17 (tt, 1H), 5.83 (dd, 1H), 4.83-4.64 (m, 2H) |
| 833 | (structure) | 340 (M + H) | (400 MHz, CDCl$_3$): δ 7.43-7.41 (m, 1H), 7.33 (dt, 1H), 7.33-7.29 (m, 1H), 5.67-5.62 (m, 1H), 3.36-3.26 (m, 1H), 3.05 (ddd, 1H), 2.63-2.53 (m, 1H), 2.40-2.30 (m, 2H) |

In some embodiments, a method of the disclosure provides an effective dose of a HIF-2α inhibitor. An effective dose refers to an amount sufficient to effect the intended application, including but not limited to, disease treatment, as defined herein. Also contemplated in the subject methods is the use of a sub-therapeutic amount of a HIF-2α inhibitor for treating an intended disease condition.

The amount of the HIF-2α inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

A subject being treated with a HIF-2α inhibitor may be monitored to determine the effectiveness of treatment, and the treatment regimen may be adjusted based on the subject's physiological response to treatment. For example, if inhibition of a biological effect of HIF-2α inhibition is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with a HIF-2α inhibitor is discontinued if inhibition of the biological effect is above or below a threshold, such as in a lack of response or an adverse reaction. The biological effect may be a change in any of a variety of physiological indicators.

The effectiveness of treatment (or, alternatively, "therapeutic efficacy" or "clinically beneficial response") is measured based on an effect of treating a cancer. In general, therapeutic efficacy of the methods of the disclosure, with regard to the treatment of a cancer (whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

Several parameters as described herein may be considered by the clinician in determining if a subject having cancer exhibits a clinically beneficial response. In some desirable embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the inventive method in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the inventive method can be determined by a number of secondary parameters. Examples of secondary parameters include, but are not limited to, detection of new tumors, detection of tumor antigens or markers (e.g., CEA, PSA, EPO, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), erythropoietin (EPO), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932,412).

In additional desirable embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the disclosure can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, the disclosure provides a pharmaceutical composition comprising an amount of a HIF-2α inhibitor formulated for administration to a subject in need thereof. In some embodiments, the pharmaceutical composition comprises between about 0.0001-500 g, 0.001-250 g, 0.01-100 g, 0.1-50 g, or 1-10 g of HIF-2α inhibitor. In some embodiments, the pharmaceutical composition comprises about or more than about 0.0001 g, 0.001 g, 0.01 g, 0.1, 0.5 g, 1 g, 2 g, 3 g, 4 g, 5 g, 6 g, 7 g, 8 g, 9 g, 10 g, 15 g, 20 g, 25 g, 50 g, 100 g, 200 g, 250 g, 300 g, 350 g, 400 g, 450 g, 500 g, or more of a HIF-2α inhibitor. In some embodiments, the pharmaceutical composition comprises between 0.001-2 g of a HIF-2α inhibitor in a single dose. In some embodiments, the pharmaceutical composition comprises an amount between about 50-150 g of a HIF-2α inhibitor. In some embodiments, the therapeutic amount can be an amount between about 0.001-0.1 g of a HIF-2α inhibitor. In some embodiments, the therapeutic amount can be an amount between about 0.01-30 g of a HIF-2α inhibitor.

In some embodiments, the HIF-2α inhibitor can be administered as part of a therapeutic regimen that comprises administering one or more second agents (e.g. 1, 2, 3, 4, 5, or more second agents), either simultaneously or sequentially with the HIF-2α inhibitor. When administered sequentially, the HIF-2α inhibitor may be administered before or after the one or more second agents. When administered simultaneously, the HIF-2α inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising a HIF-2α inhibitor and one or more second agents).

In yet another aspect, the disclosure provides a method of identifying biomarkers for sensitivity to a HIF-2α inhibitor. In one embodiment, the method comprises (a) administering the HIF-2α inhibitor to a plurality of non-human subjects having a proliferative disorder; (b) measuring an expression level of a plurality of genes in the subjects; and (c) generating a biomarker profile for responsiveness to the HIF-2α inhibitor, wherein the biomarker profile comprises genes, and optionally associated expression levels, that are expressed at higher levels among non-human subjects in which cancer was most ameliorated by the HIF-2α inhibitor relative to corresponding levels among non-human subjects in which cancer was least ameliorated.

At least one of the biomarkers provided herein may be assayed for after HIF-2α inhibitor administration in order to determine if the patient remains sensitive to the HIF-2α inhibitor treatment. In addition, at least one biomarker can be assayed for in multiple time points after a single HIF-2α inhibitor administration. For example, an initial dose of a HIF-2α inhibitor is administered, at least one biomarker described herein is assayed for at 1 hour, 2 hours, 3 hours, 4 hours, 8 hours, 16 hours, 24 hours, 48 hours, 3 days, 1 week or 1 month or several months after the initial treatment. Alternatively, more than one (e.g., all) of the biomarkers described herein may be assayed for as a single set.

It is also within the scope of the methods of the disclosure that different biomarkers are assayed for at different time points. Without being bound to any one theory, due to a mechanism of action of the HIF-2α inhibitor or of the biomarker, the response to the HIF-2α inhibitor may be delayed and at least one biomarker described herein may be assayed for at any time after administration to determine if the patient remains sensitive to HIF-2α inhibitor administration. An assay for at least one biomarker as described herein after each administration of HIF-2α inhibitor will provide guidance as to the means, dosage and course of treatment. Alternatively, more than one (e.g., all) of the biomarkers described herein may be assayed for as a single set.

Kits for assessing the activity of any HIF-2α inhibitor can be made. For example, a kit comprising nucleic acid primers for PCR or for microarray hybridization for the biomarkers described herein may be used for assessing HIF-2α inhibitor sensitivity. Alternatively, a kit supplied with antibodies for at least one of the biomarkers described herein may be used for assessing HIF-2α inhibitor sensitivity.

It is well known in the art that cancers can become resistant to chemotherapeutic treatment, especially when that treatment is prolonged. Assaying for differential expression of at least one of the biomarkers described herein may be done after prolonged treatment with any chemotherapeutic to determine if the cancer is sensitive to a HIF-2α inhibitor. If the patient has been previously treated with another chemotherapeutic, it is useful information for the patient to assay for at least one of the biomarkers described herein to determine if the tumor is sensitive to treatment with a HIF-2α inhibitor.

EXAMPLES

The following examples are given for the purpose of illustrating various embodiments of the disclosure and are not meant to limit the present disclosure in any fashion. The present examples, along with the methods described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Synthesis of 3-[(1S)-7-(difluoromethyl-sulfonyl)-2,2-difluoro-1-hydroxy-indan-4-yl]oxy-5-fluoro-benzonitrile (Compound 15)

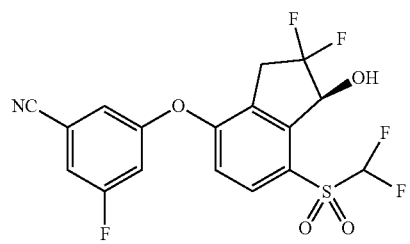 [SMILES: N#Cc1cc(F)cc(Oc2ccc(S(=O)(=O)C(F)F)c3c2CC(F)(F)[C@H]3O)c1]

Step A: Preparation of 3-((7-((difluoromethyl)sulfonyl)-2,3-dihydrospiro[indene-1,2'-[1,3]dioxolan]-4-yl)oxy)-5-fluorobenzonitrile: A mixture of 3-fluoro-5-hydroxy-benzonitrile (1.33 g, 9.7 mmol), 7'-(difluoromethylsulfonyl)-4'-fluoro-spiro[1,3-dioxolane-2,1'-indane] (1.0 g, 3.24 mmol), and cesium bicarbonate (1.26 g, 6.5 mmol) in 1-methyl-2-pyrrolidone (1.8 mL) was heated under N₂ at 110° C. (microwave) for 1 hour and 5 minutes. The reaction was repeated ten times. The reaction mixtures were combined, diluted with EtOAc, and washed twice with 1 N NaOH. The combined aqueous layer was extracted with EtOAc. The EtOAc extracts were combined and washed with brine, dried over Na₂SO₄, filtered, and concentrated to about 100 mL to give a suspension. The suspension was filtered to give 3-((7-((difluoromethyl)sulfonyl)-2,3-dihydrospiro[indene-1,2'-[1,3]dioxolan]-4-yl)oxy)-5-fluorobenzonitrile as an off-white solid (6.25 g). The filtrate was diluted with EtOAc, washed with brine (3×), dried over Na₂SO₄, filtered, and concentrated. The residue was purified by flash column chromatography on silica gel with EtOAc/hexane (0% to 40%) to give additional 3-((7-((difluoromethyl)sulfonyl)-2,2-difluoro-2,3-dihydrospiro[indene-1,2'-[1,3]dioxolan]-4-yl)oxy)-5-fluorobenzonitrile (3.3 g, 69% combined yield) as a white solid. LCMS ESI (+) m/z 426 (M+H).

Step B: Preparation of 3-((7-((difluoromethyl)sulfonyl)-1-oxo-2,3-dihydro-1H-inden-4-yl)oxy)-5-fluorobenzonitrile: A mixture of 3-((7-((difluoromethyl)sulfonyl)-2,3-dihydrospiro[indene-1,2'-[1,3]dioxolan]-4-yl)oxy)-5-fluorobenzonitrile (10.9 g, 25.6 mmol) and PPTS (667 mg, 2.66 mmol) in acetone (100 mL)/water (15 mL) was heated at 82° C. for 5 hours and then 75° C. overnight. The reaction mixture was cooled to room temperature, concentrated under reduced pressure, diluted with EtOAc, washed with saturated aqueous NaHCO₃, dried over MgSO₄, filtered, and concentrated. The residue was filtered and washed with water. The solid obtained was briefly dried under vacuum at 50° C. and then triturated with EtOAc/hexane to give 3-((7-((difluoromethyl)sulfonyl)-1-oxo-2,3-dihydro-1H-inden-4-yl)oxy)-5-fluorobenzonitrile (8 g). Flash column chromatography of the mother liquor on silica gel with EtOAc/hexane (0% to 80%) provided additional 3-((7-((difluoromethyl)sulfonyl)-1-oxo-2,3-dihydro-1H-inden-4-yl)oxy)-5-fluorobenzonitrile (1.3 g, combined 9.3 g, quant. yield). LCMS ESI (+) m/z 382 (M+H).

Step C: Preparation of (E, Z)-3-((1-(butylimino)-7-((difluoromethyl)sulfonyl)-2,3-dihydro-1H-inden-4-yl)oxy)-5-fluorobenzonitrile: A mixture of 3-((7-((difluoromethyl)sulfonyl)-1-oxo-2,3-dihydro-1H-inden-4-yl)oxy)-5-fluorobenzonitrile (1.42 g, 3.72 mmol), butylamine (6.0 mL) and 5 drops of trifluoroacetic acid (~0.1 mL) in benzene (40 mL) was refluxed overnight with removal of water using a Dean-Stark trap. The reaction mixture was concentrated under reduced pressure, diluted with methyl tert-butyl ether, washed with saturated aqueous NaHCO₃ and brine, dried over Na₂SO₄, filtered, and concentrated. The residue was used in the next step without further purification.

Step D: Preparation of 3-((7-((difluoromethyl)sulfonyl)-2,2-difluoro-1-oxo-2,3-dihydro-1H-inden-4-yl)oxy)-5-fluorobenzonitrile: A mixture of (E, Z)-3-((1-(butylimino)-7-((difluoromethyl)sulfonyl)-2,3-dihydro-1H-inden-4-yl)oxy)-5-fluorobenzonitrile (1.29 g, 3 mmol, crude from step C), Selectfluor® (2.62 g, 7.4 mmol) and sodium sulfate (4 g, 28.2 mmol) under N₂ was heated at 82° C. for 4 hours. After cooling to room temperature, concentrated HCl (37%, 3 mL) was added. The mixture was stirred at room temperature for 15 minutes and then concentrated under reduced pressure. The residue was diluted with methyl t-butyl ether, washed with half saturated aqueous NaHCO₃ and then brine, dried over Na₂SO₄, filtered, and triturated with EtOAc/hexane to give 3-((7-((difluoromethyl)sulfonyl)-2,2-difluoro-1-oxo-2,3-dihydro-1H-inden-4-yl)oxy)-5-fluorobenzonitrile as an off-white solid (0.5 g). The mother liquor was purified by flash column chromatography with EtOAc/hexane (5% to 40%) to give additional 3-((7-((difluoromethyl)sulfonyl)-2,2-difluoro-1-oxo-2,3-dihydro-1H-inden-4-yl)oxy)-5-fluorobenzonitrile (0.13 g, 51% combined yield). LCMS ESI (+) m/z 418 (M+H) and 435 (M+NH₄).

Step E: Preparation of (S)-3-((7-((difluoromethyl)sulfonyl)-2,2-difluoro-1-hydroxy-2,3-dihydro-1H-inden-4-yl)oxy)-5-fluorobenzonitrile (Compound 15): An ice cold solution of RuCl(p-cymene)[(R,R)-Ts-DPEN] (0.6 mg) in dichloromethane (0.2 mL) was added by syringe under nitrogen to an ice cold solution of 3-[7-(difluoromethylsulfonyl)-2,2-difluoro-1-oxo-indan-4-yl]oxy-5-fluoro-benzonitrile (28 mg, 0.07 mmol), triethylamine (18.7 μL, 0.13 mmol) and formic acid (7.6 μL, 0.2 mmol) in dichloromethane (0.5 mL) and then placed in a refrigerator at 4° C. overnight. The reaction mixture was directly purified on preparative TLC with EtOAc/hexane (40%) to give Compound 15 (23.4 mg, 0.06 mmol, 83% yield). The ee was determined to be greater than 95% by ¹⁹F NMR analysis of the corresponding Mosher ester. LCMS ESI (+) m/z 420 (M+H); ¹H NMR (400 MHz, CDCl₃): δ 7.94 (d, 1H), 7.33-6.98 (m, 4H), 6.44 (t, 1H), 5.51 (d, 1H), 3.61-3.45 (m, 2H).

Example 2: Synthesis of (S)-3-((2,2-Difluoro-1-hydroxy-7-(methylsulfonyl)-2,3-dihydro-1H-inden-4-yl)oxy)-5-fluorobenzonitrile (Compound 163)

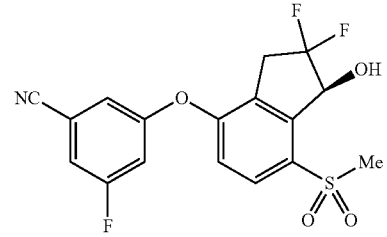 [SMILES: CS(=O)(=O)c1ccc(Oc2cc(F)cc(C#N)c2)c2c1[C@H](O)C(F)(F)C2]

Step A: Preparation of 4'-(3-bromo-5-fluoro-phenoxy)-7'-methylsulfonyl-spiro[1,3-dioxolane-2,1'-indane]: Cesium hydrogen carbonate (142 mg, 0.73 mmol) was added all at once to 4'-fluoro-7'-methylsulfonyl-spiro[1,3-dioxolane-2,1'-indane] (100 mg, 0.37 mmol) and 3-bromo-5-fluorophenol (105 mg, 0.55 mmol) in 1-methyl-2-pyrrolidone (1.5 mL) at room temperature in a microwave reaction vial equipped with a stir bar. The flask was flushed with nitrogen then sealed with a crimp cap. The reaction was heated to 150° C. for 7 hours, cooled to ambient temperature then purified directly on reverse phase silica gel (25+M, 14 CV, 20-100% MeCN/water) affording 4'-(3-bromo-5-fluoro-phenoxy)-7'-methylsulfonyl-spiro[1,3-dioxolane-2,1'-indane] (118 mg, 0.26 mmol, 72% yield).

Step B: Preparation of 3-fluoro-5-(7'-methylsulfonylspiro[1,3-dioxolane-2,1'-indane]-4'-yl)oxy-benzonitrile: Dichloro[1;1'-bis(diphenylphosphino)ferrocene]palladium (II) dichloromethane adduct (784 mg, 0.97 mmol) was quickly added to a degassed mixture of 4'-(3-bromo-5-fluoro-phenoxy)-7'-methylsulfonyl-spiro[1,3-dioxolane-2, 1'-indane] (4.3 g, 9.7 mmol), zinc cyanide (1.14 g, 9.7 mmol) and zinc powder (761 mg, 11.6 mmol) in DMF (60 mL) under nitrogen. The reaction mixture was then warmed to 110° C. for 2 hours. After cooling, the mixture was filtered through a pad of celite. The filtrate was diluted with water (100 mL), extracted with MTBE (5×100 mL), washed with brine (100 mL), dried over MgSO$_4$, filtered and concentrated in vacuo. The crude product was purified on silica gel (100 g SNAP, 14 CV, 15-100% EtOAc/hexanes) then purified again on silica gel (25 g Ultra SNAP, 14 CV, 0-20% dichloromethane/EtOAc) affording 3-fluoro-5-(7'-methylsulfonylspiro[1,3-dioxolane-2,1'-indane]-4'-yl)oxy-benzonitrile (3.77 g, 9.7 mmol, 100% yield).

Step C: Preparation of 3-fluoro-5-(7-methylsulfonyl-1-oxo-indan-4-yl)oxy-benzonitrile: Pyridinium para-toluenesulfonate (354 mg, 1.4 mmol) was added all at once to a solution of 3-fluoro-5-(7'-methylsulfonylspiro[1,3-dioxolane-2,1'-indane]-4'-yl)oxy-benzonitrile (550 mg, 1.4 mmol) in acetone (6 mL)/water (2 mL) at room temperature and then warmed to reflux until completion. The mixture was concentrated in vacuo then purified on silica gel (10 g SNAP, 14 CV, 20-100% EtOAc/hexane) affording 3-fluoro-5-(7-methylsulfonyl-1-oxo-indan-4-yl)oxy-benzonitrile (450 mg, 1.3 mmol, 92% yield).

Step D: Preparation of 3-[-(E, Z)-1-butylimino-7-methylsulfonyl-indan-4-yl]oxy-5-fluoro-benzonitrile: Butan-1-amine (5.15 mL, 52 mmol) was added to 3-fluoro-5-(7-methylsulfonyl-1-oxo-indan-4-yl)oxy-benzonitrile (450 mg, 1.3 mmol) and trifluoroacetic acid (19.96 µL, 0.26 mmol) in benzene (10 mL) at room temperature then warmed to reflux with the azeotropic removal of water by a Dean-Stark apparatus. Progress of the reaction was monitored by $^1$H-NMR. When complete, the reaction was cooled to room temperature then concentrated in vacuo. The residue was diluted with water (10 mL), extracted with MTBE (3×10 mL), washed with brine and dried over Na$_2$SO$_4$, filtered and concentrated. Crude 3-[(E, Z)-1-butylimino-7-methylsulfonyl-indan-4-yl]oxy-5-fluoro-benzonitrile was used immediately without purification in the next step.

Step E: Preparation of 3-(2,2-difluoro-7-methylsulfonyl-1-oxo-indan-4-yl)oxy-5-fluoro-benzonitrile: Selectfluor® (1.15 g, 3.25 mmol) was added to crude 3-[(E, Z)-1-butylimino-7-methylsulfonyl-indan-4-yl]oxy-5-fluoro-benzonitrile (520 mg, 1.3 mmol) and sodium sulfate (369 mg, 2.6 mmol) in acetonitrile (10 mL) then warmed to reflux for 6 hours. The reaction was cooled to room temperature, concentrated HCl (1.0 mL, 12 mmol) was added and stirred for 15 minutes. The mixture was diluted with water (10 mL), extracted with EtOAc (3×10 mL), washed with brine (10 mL), dried over MgSO$_4$, filtered and concentrated in vacuo. The residue was purified on silica gel (25 g SNAP, 14 CV, 20-100% EtOAc/hexane) afforded 3-(2,2-difluoro-7-methylsulfonyl-1-oxo-indan-4-yl)oxy-5-fluoro-benzonitrile (437 mg, 1.2 mmol, 88% yield).

Step F: Preparation of (S)-3-((2,2-difluoro-1-hydroxy-7-(methylsulfonyl)-2,3-dihydro-1H-inden-4-yl)oxy)-5-fluorobenzonitrile (Compound 163): An ice cold solution of RuCl(p-cymene)[(R,R)-Ts-DPEN] (40.7 mg, 0.06 mmol) in CH$_2$Cl$_2$ (30 mL) was added by syringe under nitrogen to an ice cold solution of 3-(2,2-difluoro-7-methylsulfonyl-1-oxo-indan-4-yl)oxy-5-fluoro-benzonitrile (2.44 g, 6.4 mmol), triethylamine (1.78 mL, 12.8 mmol) and formic acid (724 µL, 19.2 mmol) in CH$_2$Cl$_2$ (30 mL). The reaction was placed in a refrigerator at 4° C. for 16 hours. The mixture was concentrated to 10 mL then purified directly on silica gel (25 g SNAP ULTRA, 14 CV, 10-50% EtOAc/hexane) affording Compound 163 (2.15 g, 5.6 mmol, 87% yield). Enantiomeric excess (98%) was determined by chiral HPLC. Retention time for (S)-enantiomer: 1.93 minutes; retention time for (R)-enantiomer: 2.32 minutes. LCMS ESI (−) 428 (M+HCO$_2^+$). $^1$HNMR (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H).

Example 3: Synthesis of 3-[(1S,2S,3R)-2,3-difluoro-1-hydroxy-7-methylsulfonyl-indan-4-yl]oxy-5-fluoro-benzonitrile (Compound 289)

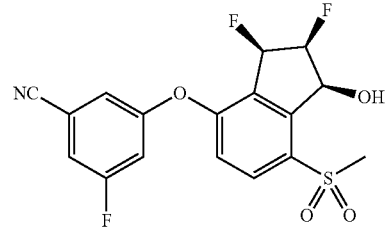 [SMILES: CS(=O)(=O)c1ccc(Oc2cc(F)cc(C#N)c2)c2c1[C@H](O)[C@H](F)[C@@H]2F]

Step A: [(1S,2R)-4-(3-cyano-5-fluoro-phenoxy)-2-fluoro-7-methylsulfonyl-indan-1-yl] acetate: To a stirred solution of 3-fluoro-5-[(1S,2R)-2-fluoro-1-hydroxy-7-methylsulfonyl-indan-4-yl]oxy-benzonitrile (2.00 g, 5.47 mmol) in DCM (27 mL) was added 4-(dimethylamino)pyridine (0.2 g, 1.64 mmol) and triethylamine (1.53 mL, 10.9 mmol). Acetic anhydride (1.00 mL, 10.9 mmol) was added dropwise at 0° C. under nitrogen. The reaction mixture was stirred at ambient temperature overnight. The reaction mixture was diluted with DCM, washed with saturated aqueous NaHCO$_3$ and brine, dried and concentrated. The residue was purified by flash chromatography on silica gel (20-40% EtOAc/hexane) to give [(1S,2R)-4-(3-cyano-5-fluoro-phenoxy)-2-fluoro-7-methylsulfonyl-indan-1-yl] acetate (1.95 g, 87%). LCMS ESI (+) m/z 408 (M+H).

Step B: [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate: To a stirred solution of [(1S,2R)-4-(3-cyano-5-fluoro-phenoxy)-2-fluoro-7-methylsulfonyl-indan-1-yl] acetate (1.95 g, 4.79 mmol) in 1,2-dichloroethane (24 mL) was added N-bromosuccinimide (0.94 g, 5.27 mmol) and 2,2'-azobisisobutyronitrile (8 mg, 0.05 mmol). The reaction mixture was heated at 80° C. for 3 hours. After cooling, the reaction mixture was diluted with DCM, washed with saturated aqueous NaHCO$_3$ and brine, dried and concentrated. The residue was purified by column chromatography on silica gel (20-30% EtOAc/hexane) to give [(1S,2S,3S)-3-bromo-4-(3-cyano-5-fluoro-phenoxy)-2-fluoro-7-methylsulfonyl-indan-1-yl] acetate (1.52 g, 65%). LCMS ESI (+) m/z 486, 488 (M+H). Further elution with 30-50% EtOAc/hexane gave the more polar product [(1S,2S,3R)-3-bromo-4-(3-cyano-5-fluoro-phenoxy)-2-fluoro-7-methylsulfonyl-indan-1-yl] acetate (0.583 g, 25%). LCMS ESI (+) m/z 486, 488 (M+H).

Step C: [(1S,2R,3S)-4-(3-cyano-5-fluoro-phenoxy)-2-fluoro-3-hydroxy-7-methylsulfonyl-indan-1-yl] acetate: To a combined mixture of [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate prepared in Step B (2.05 g, 4.22 mmol) were added 1,2-dimethoxyethane (28 mL) and water (0.050 mL) followed by silver perchlorate hydrate (1.42 g, 6.32 mmol). The reaction mixture was heated at 70° C. for 2 hours. After cooling, the reaction mixture was diluted with EtOAc and filtered through Celite. The filtrate was washed with water and brine, dried and concentrated. The residue was purified by flash chromatography on silica gel (20-50%) to give [(1S,2R,3S)-4-(3-cyano-5-fluoro-phenoxy)-2-fluoro-3-hydroxy-7-methylsulfonyl-indan-1-yl] acetate (0.416 g, 23%) as the less polar product. LCMS ESI (+) m/z 441 (M+NH$_4$+). Further elution with 60% EtOAc/hexane gave [(1S,2R,3R)-4-(3-cyano-5-fluoro-phenoxy)-2-fluoro-3-hydroxy-7-methylsulfonyl-indan-1-yl] acetate (0.58 g, 32%). LCMS ESI (+) m/z 441 (M+NH$_4$+).

Step D: [(1S,2S,3R)-4-(3-cyano-5-fluoro-phenoxy)-2,3-difluoro-7-methylsulfonyl-indan-1-yl] acetate: To a stirred solution of [(1S,2R,3S)-4-(3-cyano-5-fluoro-phenoxy)-2-fluoro-3-hydroxy-7-methylsulfonyl-indan-1-yl] acetate (416 mg, 0.98 mmol) in DCM (10 mL) was added (diethylamino)sulfur trifluoride (DAST) (0.26 mL, 2.0 mmol) at −78° C. under nitrogen. The reaction mixture was allowed to warm to 0° C. and stirred for 15 minutes. The reaction was quenched by saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-40% EtOAc/hexane) to give [(1S,2S,3R)-4-(3-cyano-5-fluoro-phenoxy)-2,3-difluoro-7-methylsulfonyl-indan-1-yl] acetate (310 mg, 74%). LCMS ESI (+) m/z 426 (M+H).

Step E: 3-[(1S,2S,3R)-2,3-difluoro-1-hydroxy-7-methylsulfonyl-indan-4-yl]oxy-5-fluoro-benzonitrile (Compound 289): To a stirred solution of [(1S,2S,3R)-4-(3-cyano-5-fluoro-phenoxy)-2,3-difluoro-7-methylsulfonyl-indan-1-yl] acetate (0.23 mmol) in tetrahydrofuran (1.5 mL) was added 0.5 N LiOH solution (0.68 mL, 0.34 mmol) at 0° C. under nitrogen. The reaction mixture was stirred at 0° C. for 1 hour. The reaction was then partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give Compound 289. LCMS ESI (+) m/z 384 (M+H); $^1$H NMR (400 MHz, CDCl$_3$): δ 8.13 (d, 1H), 7.31-7.25 (m, 1H), 7.23-7.19 (m, 1H), 7.14-7.09 (m, 1H), 7.04 (d, 1H), 6.09-5.91 (m, 1H), 5.87-5.80 (m, 1H), 5.25-5.05 (m, 1H), 3.32 (s, 3H), 2.95 (d, 1H).

Example 4: Synthesis of (R)-3-((4-(Difluoromethyl)-2,2-difluoro-3-hydroxy-1,1-dioxido-2,3-dihydrobenzo[b]thiophen-5-yl)oxy)-5-fluorobenzonitrile (Compound 349)

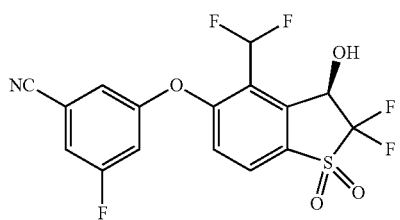 [SMILES: N#Cc1cc(F)cc(Oc2ccc3c(c2C(F)F)[C@@H](O)C(F)(F)S3(=O)=O)c1]

Step A: Preparation of 2-bromo-3-(difluoromethyl)-1,4-difluorobenzene: A solution of 2-bromo-3,6-difluorobenzaldehyde (40.0 g, 181 mmol) dissolved in dichloromethane (800 mL) was cooled to 0° C., then treated with (diethylamino)sulfur trifluoride (70.0 g, 454 mmol). After the addition, the reaction mixture was warmed to ambient temperature and stirred at this temperature for 4 hours. Saturated aqueous sodium bicarbonate solution was added slowly until the pH was 8-9. The organic layer was separated, dried over sodium sulfate, filtered and concentrated under reduced pressure to give 2-bromo-3-(difluoromethyl)-1,4-difluorobenzene (44.0 g, quant.) as solid which was used immediately in the next step without purification. $^1$H NMR (400 MHz, CDCl$_3$): δ 7.28-7.22 (m, 1H), 7.17-7.10 (m, 1H), 7.04 (t, 1H).

Step B: Preparation of 2-(difluoromethyl)-3,6-difluorobenzonitrile: A suspension of 2-bromo-3-(difluoromethyl)-1,4-difluorobenzene (44.0 g, 181 mmol) and copper (I) cyanide (21.1 g, 235 mmol) in 1-methyl-2-pyrrolidinone (400 mL) was heated to 180° C. for 2 hours. After cooling to ambient temperature, the reaction mixture was poured into water and extracted with diethyl ether. The organic layer was washed with brine, dried over sodium sulfate, filtered and then concentrated under reduced pressure. The crude product was purified by flash chromatography on silica gel eluting with hexane/ethyl acetate to give 2-(difluoromethyl)-3,6-difluorobenzonitrile as a solid (23 g, 67%). $^1$H NMR (400 MHz, CDCl$_3$): δ 7.48-7.35 (m, 2H), 6.98 (t, 1H).

Step C: Preparation of 2-(difluoromethyl)-3-fluoro-6-(methylthio)benzonitrile: A solution of 2-(difluoromethyl)-3,6-difluorobenzonitrile (31.3 g, 65.5 mmol) in acetonitrile (500 mL) was cooled to −30° C., then treated with sodium methanethiolate (12.8 g, 174 mmol). After addition of the solid, the reaction mixture was stirred for 7 hours while maintaining the temperature between −30° C. and −40° C. A mixture of water (200 mL) and methyl t-butyl ether (500 mL) were added and the reaction mixture was warmed to ambient temperature. The organic layer was separated, washed with brine, dried over sodium sulfate, filtered and concentrated under reduced pressure to give 2-(difluoromethyl)-3-fluoro-6-methylsulfanyl-benzonitrile as yellow solid (36.3 g, 150 mmol, 91%). $^1$H NMR (400 MHz, CDCl$_3$): δ 7.47-7.44 (m, 1H), 7.36-7.32 (m, 1H), 6.99 (t, 1H), 2.58 (s, 3H).

Step D: Preparation of 2-(difluoromethyl)-3-fluoro-6-(methylsulfonyl)benzonitrile: A slurry of 2-(difluoromethyl)-3-fluoro-6-methylsulfanyl-benzonitrile (36.3 g, 167 mmol) in acetonitrile (350 mL) and water (175 mL) was treated with Oxone® (257 g, 418 mmol), then the mixture was heated at 56° C. for 4 hours. After cooling to ambient temperature, the remaining solids were removed by filtration and washed with dichloromethane (300 mL). The filtrate was concentrated in vacuo to remove volatile solvents. The resulting aqueous solution was extracted with dichloromethane (400 mL). The organic layer was dried over sodium sulfate, filtered and concentrated under reduced pressure. The resulting solid was suspended in 4:1 hexane/methyl t-butyl ether (200 mL) and stirred for 10 minutes at ambient temperature. The undissolved solid was collected by filtration and air-dried to give 2-(difluoromethyl)-3-fluoro-6-(methylsulfonyl)benzonitrile (29.9 g, 71%). $^1$H NMR (400 MHz, CDCl$_3$): δ 8.41-8.37 (m, 1H), 7.66-7.61 (m, 1H), 7.11 (t, 1H), 3.34 (s, 3H).

Step E: Preparation of 3-(3-cyano-5-fluorophenoxy)-2-(difluoromethyl)-6-(methylsulfonyl)benzonitrile: A suspension of 2-(difluoromethyl)-3-fluoro-6-(methylsulfonyl)benzonitrile (9.52 g, 38.2 mmol), 3-fluoro-5-hydroxybenzonitrile (5.23 g, 38.2 mmol), and cesium carbonate (7.77 g, 40.1 mmol) in N, N-dimethylformamide (76 mL) was heated to 45° C. for 3 hours. Additional cesium carbonate (0.46 g, 1.4 mmol) was added and the reaction mixture was heated at 45° C. for three hours, then stirred at ambient temperature for 54 hours. The reaction mixture was vigorously stirred while water (800 mL) was added. The resulting suspension was stirred for 30 minutes, then the solids were collected by filtration, washed with water (1.2 L), and dried under high vacuum to give 3-(3-cyano-5-fluorophenoxy)-2-(difluoromethyl)-6-(methylsulfonyl)benzonitrile as a white solid (13.3 g, 96%). LCMS ESI (+) m/z 384 (M+NH$_4$). $^1$H NMR (400 MHz, DMSO-d$_6$): δ 8.22 (d, 1H), 7.86-7.82 (m, 1H), 7.72-7.62 (m, 3H), 7.49 (t, 1H), 3.44 (s, 3H).

Step F: Preparation of 3-((4-(difluoromethyl)-1,1-dioxido-3-oxo-2,3-dihydrobenzo[b]thiophen-5-yl)oxy)-5-fluorobenzonitrile: A solution of 3-(3-cyano-5-fluorophenoxy)-2-(difluoromethyl)-6-(methylsulfonyl)benzonitrile (13.3 g, 36 mmol) was dissolved in tetrahydrofuran (380 mL) and treated with sodium hydride (60% in mineral oil, 2.26 g, 56 mmol) in two equal portions at five minute intervals. The resulting suspension was stirred at ambient temperature for 60 minutes. The reaction mixture was quenched by addition of a mixture of 4:1 methanol/10% aqueous HCl (200 mL) and the resulting suspension was stirred for 1 hour. The mixture was concentrated to remove volatile solvents, then the remaining slurry was diluted with additional water (800 mL) and stirred for an additional 30 minutes. The solids were recovered by filtration and washed with additional water and the resulting beige solid was dried under high vacuum in the presence of solid NaOH. 3-((4-(Difluoromethyl)-1,1-dioxido-3-oxo-2,3-dihydrobenzo[b] thiophen-5-yl)oxy)-5-fluorobenzonitrile was obtained as a beige solid (13.3 g, quant.) and was used without further purification. LCMS ESI (–) m/z 366 (M–H). $^1$H NMR (400 MHz, DMSO-d$_6$): δ 8.35 (d, 1H), 7.79 (d, 1H), 7.76 (t, 1H), 7.76-7.72 (m, 1H), 7.56-7.50 (m, 2H), 4.72 (s, 2H).

Step G: Preparation of 3-((4-(difluoromethyl)-2,2-difluoro-1,1-dioxido-3-oxo-2,3-dihydrobenzo[b]thiophen-5-yl)oxy)-5-fluorobenzonitrile: A solution of 3-((4-(difluoromethyl)-1,1-dioxido-3-oxo-2,3-dihydrobenzo[b]thiophen-5-yl)oxy)-5-fluorobenzonitrile (1.40 g, 3.82 mmol) dissolved in acetonitrile (38 mL) was treated at ambient temperature with sodium carbonate (890 mg, 8.4 mmol) followed by Selectfluor® (2.98 g, 8.4 mmol). The reaction mixture was stirred at ambient temperature for 90 minutes. The reaction mixture was concentrated in vacuo to remove volatile solvents, then the residue was diluted with water (100 mL) and extracted three times with ethyl acetate (50 mL portions). The combined organic layers were washed with saturated NaCl, dried over MgSO$_4$, filtered and concentrated in vacuo to give 3-((4-(difluoromethyl)-2,2-difluoro-1,1-dioxido-3-oxo-2,3-dihydrobenzo[b]thiophen-5-yl)oxy)-5-fluorobenzonitrile as a solid (1.48 g, quant.). $^1$H NMR (400 MHz, DMSO-d$_6$, sample exists as hydrate): δ 8.81 (s, 2H), 8.29 (d, 1H), 7.80-7.76 (m, 1H), 7.74 (t, 1H), 7.57-7.50 (m, 3H).

Step H: Preparation of 3-((4-(difluoromethyl)-2,2-difluoro-3-hydroxy-1,1-dioxido-2,3-dihydrobenzo[b]thiophen-5-yl)oxy)-5-fluorobenzonitrile: A solution of 3-((4-(difluoromethyl)-2,2-difluoro-1,1-dioxido-3-oxo-2,3-dihydrobenzo[b]thiophen-5-yl)oxy)-5-fluorobenzonitrile (1.48 g, 3.67 mmol) in methanol (37 mL) was cooled to 0° C., then treated with sodium borohydride (139 mg, 3.7 mmol) and stirred for 1 hour. The reaction was quenched by addition of water (0.5 mL) and saturated NH$_4$Cl (0.25 mL). The reaction mixture was concentrated in vacuo to remove volatile solvents, then diluted with 0.5 M NaOH (10 mL). The aqueous was extracted three times with ethyl acetate and the combined organic layers were washed with saturated NaCl, dried over MgSO$_4$, filtered and concentrated in vacuo. The crude product was chromatographed on SiO$_2$ eluting with a gradient of ethyl acetate/hexane to give 3-((4-(difluoromethyl)-2,2-difluoro-3-hydroxy-1,1-dioxido-2,3-dihydrobenzo[b]thiophen-5-yl)oxy)-5-fluorobenzonitrile as a white solid (1.24 g, 83%).

Step I: Preparation of (R)-3-((4-(difluoromethyl)-2,2-difluoro-3-hydroxy-1,1-dioxido-2,3-dihydrobenzo[b]thiophen-5-yl)oxy)-5-fluorobenzonitrile: 3-((4-(Difluoromethyl)-2,2-difluoro-3-hydroxy-1,1-dioxido-2,3-dihydrobenzo[b]thiophen-5-yl)oxy)-5-fluorobenzonitrile was resolved using preparative SFC chromatography under the following conditions: ChiralPak AS(-H) (2×15 cm) column, 20% ethanol with carbon dioxide at 100 bar, 60 mL/min flow rate, injection volume was 0.5 mL of a 20 mg/mL solution in ethanol, peak detection at 220 nm. Compound 349 was recovered as the first peak (1.50 minutes) to elute from the column. LCMS ESI (–) m/z 404 (M–H). $^1$H NMR (400 MHz, CDCl$_3$): δ 7.98 (d, 1H), 7.33-7.30 (m, 1H), 7.23 (t, 1H), 7.22-7.18 (m, 2H), 7.10-7.06 (m, 1H), 5.69-5.65 (m, 1H), 3.23 (d, 1H).

Example 5: Synthesis of (6R,7S)-4-(3,3-difluorocyclobutoxy)-6-fluoro-1-(trifluoromethyl)-6,7-dihydro-5H-cyclopenta[c]pyridin-7-ol (Compound 465) and (R)-4-(3,3-difluorocyclobutoxy)-1-(trifluoromethyl)-6,7-dihydro-5H-cyclopenta[c]pyridin-7-ol (Compound 466)

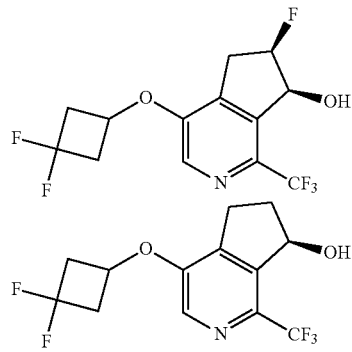

Step A: Preparation of 4-bromo-1-(trifluoromethyl)-5,6-dihydro-7H-cyclopenta[c]pyridin-7-one: A suspension of 4-bromo-5,6-dihydrocyclopenta[c]pyridin-7-one (1.0 g, 4.72 mmol) and bis(((trifluoromethyl)sulfinyl)oxy)zinc (4.69 g, 14.15 mmol) in a mixture of dichloromethane (30 mL) and water (15 mL) at 0° C. was treated with tert-butyl hydroperoxide (~70% in water, 2.58 mL, 18.86 mmol, added via pipette using a plastic tip) and stirred overnight. Additional portions of bis(((trifluoromethyl)sulfinyl)oxy)zinc (2.35 g, 7.07 mmol) and tert-butyl hydroperoxide (2.58 mL, 18.86 mmol) were added sequentially to drive the reaction to completion. After stirring for an additional day, the reaction vessel was placed into a water bath and carefully quenched by the addition of saturated NaHCO$_3$. Once effervescence ceased, the reaction mixture filtered through a pad of celite to remove. The pad of celite was rinsed with additional dichloromethane. The filtrate was separated and the aqueous portion extracted further with 2×20 mL CH$_2$Cl$_2$. The combined organics were rinsed with 10 mL of brine, dried with MgSO$_4$, filtered, and concentrated to dryness. Purification was achieved by chromatography on silica using 30-90% CH$_2$Cl$_2$/hexane to afford 4-bromo-1-(trifluoromethyl)-5,6-dihydro-7H-cyclopenta[c]pyridin-7-one as an off-white solid (390 mg, 30%). The desired regioisomer elutes first. LCMS ESI (+) (M+H) m/z 280/282.

Step B: Preparation of 4-bromo-1-(trifluoromethyl)-5,6-dihydrospiro[cyclopenta[c]pyridine-7,2'-[1,3]dioxolane] and 4-bromo-1-(trifluoromethyl)-7-(2-((trimethylsilyl)oxy)ethoxy)-5H-cyclopenta[c]pyridine: Trimethylsilyl trifluoromethanesulfonate (75.9 uL, 0.42 mmol) was added to a solution of 4-bromo-1-(trifluoromethyl)-5,6-dihydrocyclopenta[c]pyridin-7-one (389 mg, 1.39 mmol) and trimethyl(2-trimethylsilyloxyethoxy)silane (1.37 mL, 5.56 mmol) in dichloromethane (13.6 mL) cooled in an ice bath. The mixture was allowed to slowly warm to ambient temperature. After 5 h, an additional 1.3 mL of trimethyl(2-trimethylsilyloxyethoxy)silane and 76 uL of trimethylsilyl trifluoromethanesulfonate were added. After another 16 h, the reaction mixture was treated with triethylamine (770 uL, 5.56 mmol), stirred for 10 min, and then concentrated. The residue was treated with 20 mL EtOAc and 20 mL of water and the layers separated. The aqueous portion was extracted further with 2×20 mL of EtOAc. The combined organic extracts were washed with brine, dried over MgSO$_4$, filtered, and evaporated. Purification was achieved by chromatography on silica using 5-20% EtOAc/hexane to afford 4-bromo-1-(trifluoromethyl)-5,6-dihydrospiro[cyclopenta[c]pyridine-7,2'-[1,3]dioxolane] as a shite solid (262 mg, 58%) and 4-bromo-1-(trifluoromethyl)-7-(2-((trimethylsilyl)oxy)ethoxy)-5H-cyclopenta[c]pyridine as a white solid (170 mg, 31%). Data for 4-bromo-1-(trifluoromethyl)-5,6-dihydrospiro[cyclopenta[c]pyridine-7,2'-[1,3]dioxolane]: LCMS ESI (+) (M+H) m/z 324/326. Data for 4-bromo-1-(trifluoromethyl)-7-(2-((trimethylsilyl)oxy)ethoxy)-5H-cyclopenta[c]pyridine: $^1$H NMR (400 MHz, CDCl$_3$): δ 8.56 (s, 1H), 5.59 (t, 1H), 4.10 (t, 2H), 3.96 (t, 2H), 3.36 (d, 2H), 0.15 (s, 9H).

Step C: Preparation of 4-bromo-6-fluoro-1-(trifluoromethyl)-5,6-dihydrospiro[cyclopenta[c]pyridine-7,2'-[1,3]dioxolane]: A solution of 2-[[4-bromo-1-(trifluoromethyl)-5H-cyclopenta[c]pyridin-7-yl]oxy]ethoxy-trimethyl-silane (146.6 mg, 0.37 mmol) and sodium sulfate (262.7 mg, 1.85 mmol) in acetonitrile (3.7 mL) was stirred for 10 min and then treated with Selectfluor® (145.2 mg, 0.41 mmol) and stirred at 25° C. for 1 h. Volatiles were removed by concentration under reduced pressure. The reaction mixture was poured into 30 mL of water and extracted with 3×15 mL EtOAc. The combined organics were rinsed with 10 mL of brine, dried with MgSO$_4$, filtered, and concentrated to dryness. Purification was achieved by chromatography on silica using 5-20% EtOAc/hexane to afford 4-bromo-6-fluoro-1-(trifluoromethyl)-5,6-dihydrospiro[cyclopenta[c]pyridine-7,2'-[1,3]dioxolane] as a white solid (96.2 mg, 76%). LCMS ESI (+) (M+H) m/z 342/344.

Step D: Preparation of 6-fluoro-1-(trifluoromethyl)-5,6-dihydrospiro[cyclopenta[c]pyridine-7,2'-[1,3]dioxolan]-4-ol and 1-(trifluoromethyl)-5,6-dihydrospiro[cyclopenta[c]pyridine-7,2'-[1,3]dioxolan]-4-ol: A solution of 4'-bromo-6'-fluoro-1'-(trifluoromethyl)spiro[1,3-dioxolane-2,7'-5,6-dihydrocyclopenta[c]pyridine](96.2 mg, 0.2800 mmol) and 2-(di-t-butylphosphino)-3,6-dimethoxy-2',4',6'-tri-i-propyl-1,1'-biphenyl (3.4 mg, 0.007 mmol) in 1,4-dioxane (5.0 mL) was sparged with nitrogen for 3 mins. The reaction mixture was then treated sequentially with potassium hydroxide (47.3 mg, 0.84 mmol), water (101 uL, 5.62 mmol) and [2-(2-aminophenyl)phenyl]-methylsulfonyloxy-palladium; di-t-butyl-[3,6-dimethoxy-2-(2,4,6-triisopropylphenyl)phenyl]phosphane (6.0 mg, 0.007 mmol) under continuous nitrogen stream. The vessel was sealed and heated to 80 C for 1 h and 30 min. The reaction mixture was quenched by the addition of acetic acid (64.3 uL, 1.13 mmol). The reaction mixture was poured into 75 mL of water and extracted with 4×20 mL EtOAc. The combined organics were dried with MgSO$_4$, filtered, and concentrated to dryness. The product was used without further purification (87 mg). During the reaction, some of the hydrodefluorinated product formed as an impurity. Data for 6-fluoro-1-(trifluoromethyl)-5,6-dihydrospiro[cyclopenta[c]pyridine-7,2'-[1,3]dioxolan]-4-ol: LCMS ESI (+) (M+H) m/z 280. Data for 1-(trifluoromethyl)-5,6-dihydrospiro[cyclopenta[c]pyridine-7,2'-[1,3]dioxolan]-4-ol: LCMS ESI (+) (M+H) m/z 262.

Step E: Preparation of 4-(3,3-difluorocyclobutoxy)-6-fluoro-1-(trifluoromethyl)-5,6-dihydrospiro[cyclopenta[c]pyridine-7,2'-[1,3]dioxolane] and 4-(3,3-difluorocyclobutoxy)-1-(trifluoromethyl)-5,6-dihydrospiro[cyclopenta[c]pyridine-7,2'-[1,3]dioxolane]: A solution of impure 6'-fluoro-1'-(trifluoromethyl)spiro[1,3-dioxolane-2,7'-5,6-dihydrocyclopenta[c]pyridine]-4'-ol (44.0 mg, 0.16 mmol), polymer supported triphenylphosphine (~2.06 mmol/g, 306.2 mg, 0.63 mmol), and 3,3-difluoro-cyclobutanol (68.1 mg, 0.63 mmol) in tetrahydrofuran (3.2 mL) was treated with diisopropyl azodicarboxylate (120 uL, 0.61 mmol) and stirred at 60° C. for 2 h. The reaction mixture was filtered and the filter cake rinsed with 20 mL EtOAc. The filtrate was concentrated and purified by chromatography on silica using 10-30% EtOAc/hexane to afford a clear solid (39.0 mg, 67%) that was a 2:1 mixture of the fluorinated and hydrodefluorinated products. LCMS ESI (+) (M+H) m/z 370. Data for 4-(3,3-difluorocyclobutoxy)-6-fluoro-1-(trifluoromethyl)-5,6-dihydrospiro[cyclopenta[c]pyridine-7,2'-[1,3]dioxolane]: LCMS ESI (+) (M+H) m/z 370. Data for 4-(3,3-difluorocyclobutoxy)-1-(trifluoromethyl)-5,6-dihydrospiro[cyclopenta[c]pyridine-7,2'-[1,3]dioxolane]: LCMS ESI (+) (M+H) m/z 352.

Step F: Preparation of 4-(3,3-difluorocyclobutoxy)-6-fluoro-1-(trifluoromethyl)-5,6-dihydro-7H-cyclopenta[c]pyridin-7-one and 4-(3,3-difluorocyclobutoxy)-1-(trifluoromethyl)-5,6-dihydro-7H-cyclopenta[c]pyridin-7-one: A solution of impure 4'-(3,3-difluorocyclobutoxy)-6'-fluoro-1'-(trifluoromethyl)spiro[1,3-dioxolane-2,7'-5,6-dihydrocyclopenta[c]pyridine] (39.0 mg, 0.106 mmol) in dichloromethane (2.0 mL) at 0 C was treated with perchloric acid (70% in water, 200 uL) and stirred at 0 C for 3 h. The reaction mixture was quenched by the addition of 5 mL of saturated aqueous NaHCO$_3$. The resulting mixture was extracted with 3×15 mL CH$_2$Cl$_2$. The combined organics were rinsed with 10 mL of brine, dried with MgSO$_4$, filtered, and concentrated to dryness. The product was used without further purification as a 2:1 mixture of fluorinated and hydrodefluorinated ketones. LCMS ESI (+) (M+H) m/z 326. Data for 4-(3,3-difluorocyclobutoxy)-6-fluoro-1-(trifluoromethyl)-5,6-dihydro-7H-cyclopenta[c]pyridin-7-one: LCMS ESI (+) (M+H) m/z 326. Data for 4-(3,3-difluorocyclobutoxy)-1-(trifluoromethyl)-5,6-dihydro-7H-cyclopenta[c]pyridin-7-one: LCMS ESI (+) (M+H) m/z 308.

Step G: Preparation of (6R,7S)-4-(3,3-difluorocyclobutoxy)-6-fluoro-1-(trifluoromethyl)-6,7-dihydro-5H-cyclopenta[c]pyridin-7-ol (Compound 465) and (R)-4-(3,3-difluorocyclobutoxy)-1-(trifluoromethyl)-6,7-dihydro-5H-cyclopenta[c]pyridin-7-ol (Compound 466): A solution of impure 4-(3,3-difluorocyclobutoxy)-6-fluoro-1-(trifluoromethyl)-5,6-dihydrocyclopenta[c]pyridin-7-one (33.8 mg, 0.10 mmol) in dichloromethane (4.0 mL) was cooled to 0° C. and sparged with nitrogen for 5 min. During this time formic acid (11.8 uL, 0.31 mmol) and triethylamine (28.8 uL, 0.21 mmol) were sequentially added. Once sparging was complete, RuCl(p-cymene)[(R,R)-Ts-DPEN] (1.3 mg, 0.002 mmol) was added under a continuous stream of nitrogen. The reaction vessel was sealed and placed into the refrigerator to react overnight. Volatiles were removed by concentration under reduced pressure. The residue was purified by chromatography on silica using 4-18% EtOAc/$CH_2Cl_2$ to afford (6R,7S)-4-(3,3-difluorocyclobutoxy)-6-fluoro-1-(trifluoromethyl)-6,7-dihydro-5H-cyclopenta[c]pyridin-7-ol (Compound 465) as a clear solid (5.4 mg, 16%) and (R)-4-(3,3-difluorocyclobutoxy)-1-(trifluoromethyl)-6,7-dihydro-5H-cyclopenta[c]pyridin-7-ol (Compound 466) as a clear solid (7.4 mg, 23%). Data for (6R,7S)-4-(3,3-difluorocyclobutoxy)-6-fluoro-1-(trifluoromethyl)-6,7-dihydro-5H-cyclopenta[c]pyridin-7-ol (Compound 465): Retention time HPLC (14 min)=3.59 min; LCMS ESI (+) (M+H) m/z 328; $^1$H NMR (400 MHz, $CDCl_3$): δ 8.04 (s, 1H), 5.46-5.26 (m, 2H), 4.89-4.79 (m, 1H), 3.36-3.08 (m, 4H), 2.91-2.74 (m, 2H), 2.60 (dd, 1H). Data for (R)-4-(3,3-difluorocyclobutoxy)-1-(trifluoromethyl)-6,7-dihydro-5H-cyclopenta[c]pyridin-7-ol (Compound 466): Retention time HPLC (14 min)=3.95 min; LCMS ESI (+) (M+H) m/z 310; $^1$H NMR (400 MHz, $CDCl_3$): δ 7.98 (s, 1H), 5.59-5.54 (m, 1H), 4.88-4.79 (m, 1H), 3.24-3.07 (m, 3H), 2.89 (dd, 1H), 2.89-2.74 (m, 2H), 2.44-2.34 (m, 1H), 2.28-2.21 (m, 1H), 2.12-2.09 (m, 1H).

Example 6: Synthesis of 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 467)

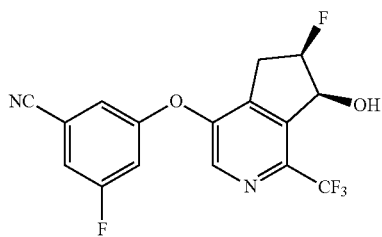 [SMILES: N#Cc1cc(F)cc(Oc2cnc(C(F)(F)F)c3c2C[C@@H](F)[C@H]3O)c1]

Step A: Preparation of 1-(trifluoromethyl)-5,6-dihydrospiro[cyclopenta[c]pyridine-7,2'-[1,3]dioxolan]-4-ol: A solution of 4'-bromo-1'-(trifluoromethyl)spiro[1,3-dioxolane-2,7'-5,6-dihydrocyclopenta[c]pyridine] (226.4 mg, 0.70 mmol) and 2-(di-t-butylphosphino)-3,6-dimethoxy-2',4',6'-tri-i-propyl-1,1'-biphenyl (8.5 mg, 0.017 mmol) in 1,4-dioxane (7.0 mL) was sparged with nitrogen for 3 mins. The reaction mixture was then treated sequentially with potassium hydroxide (117.6 mg, 2.10 mmol), water (252 uL, 13.97 mmol) and [2-(2-aminophenyl)phenyl]-methylsulfonyloxy-palladium; ditert-butyl-[3,6-dimethoxy-2-(2,4,6-triisopropylphenyl)phenyl]phosphane (14.9 mg, 0.017 mmol) under continuous nitrogen stream. The vessel was sealed and heated to 80 C for 1 h and 30 min. The reaction mixture was quenched by the addition of acetic acid (160 uL, 2.79 mmol). The reaction mixture was poured into 75 mL of water and extracted with 4×20 mL EtOAc. The combined organics were dried with $MgSO_4$, filtered, and concentrated to dryness. The brown solid was used without further purification. LCMS ESI (−) (M−H) m/z 260.

Step B: Preparation of 3-fluoro-5-((1-(trifluoromethyl)-5,6-dihydrospiro[cyclopenta[c]pyridine-7,2'-[1,3]dioxolan]-4-yl)oxy)benzonitrile: A suspension of potassium tert-butoxide (28.4 mg, 0.25 mmol) in tetrahydrofuran (1.5 mL) at 0 C was treated with 1'-(trifluoromethyl)spiro[1,3-dioxolane-2,7'-5,6-dihydrocyclopenta[c]pyridine]-4'-ol (60.0 mg, 0.23 mmol) and stirred at 0 C for 15 min. The resulting mixture was treated with (3-cyano-5-fluoro-phenyl)-(4-methoxyphenyl)iodonium; 4-methylbenzenesulfonate (144.8 mg, 0.28 mmol) and heated to 40 C. The reaction mixture was filtered through a plastic filter cup using EtOAc to rinse. Volatiles were removed by concentration under reduced pressure. Purification was achieved by chromatography on silica using 10-40% EtOAc/hexane to afford a solid (42 mg, 48%). LCMS ESI (+) (M+H) m/z 381.

Step C: Preparation of 3-fluoro-5-((7-oxo-1-(trifluoromethyl)-6,7-dihydro-5H-cyclopenta[c]pyridin-4-yl)oxy)benzonitrile: A solution of 3-fluoro-5-[1'-(trifluoromethyl)spiro[1,3-dioxolane-2,7'-5,6-dihydrocyclopenta[c]pyridine]-4'-yl]oxy-benzonitrile (42.0 mg, 0.11 mmol) in dichloromethane (2.0 mL) at 0 C was treated with perchloric acid (70% in water, 240 uL) and stirred at 0 C for 30 min. The reaction mixture was carefully quenched by the addition of 15 mL of saturated $NaHCO_3$ and extracted with 3×15 mL $CH_2Cl_2$. The combined organics were rinsed with 10 mL of brine, dried with $MgSO_4$, filtered, and concentrated to dryness. The solid residue was used immediately in the next step without further purification. LCMS ESI (+) (M+H) m/z 337.

Step D: Preparation of 3-((7-((tert-butyldimethylsilyl)oxy)-1-(trifluoromethyl)-5H-cyclopenta[c]pyridin-4-yl)oxy)-5-fluorobenzonitrile: A solution of triethylamine (122 uL, 0.88 mmol) and 3-fluoro-5-[[7-oxo-1-(trifluoromethyl)-5,6-dihydrocyclopenta[c]pyridin-4-yl]oxy]benzonitrile (37.0 mg, 0.11 mmol) in dichloromethane (2.2 mL) at 0° C. was treated with tert-butyldimethylsilyl triflate (152 ul, 0.66 mmol). The ice bath was removed and the reaction mixture left to stir for 2 h. The reaction mixture was poured into 30 mL of saturated $NaHCO_3$ and extracted with 3×20 mL $CH_2Cl_2$. The combined organics were rinsed with 10 mL of brine, dried with $MgSO_4$, filtered, and concentrated to dryness. The product was used without further purification. LCMS ESI (+) (M+H) m/z 451.

Step E: Preparation of 3-fluoro-5-((6-fluoro-7-oxo-1-(trifluoromethyl)-6,7-dihydro-5H-cyclopenta[c]pyridin-4-yl)oxy)benzonitrile: A solution of 3-[[7-[tert-butyl(dimethyl)silyl]oxy-1-(trifluoromethyl)-5H-cyclopenta[c]pyridin-4-yl]oxy]-5-fluoro-benzonitrile (49.56 mg, 0.110 mmol) in acetonitrile (2.2 mL) at 25° C. was treated with Selectfluor® (42.9 mg, 0.12 mmol) and stirred at 25° C. for 1 h. Volatiles were removed by concentration under reduced pressure The reaction mixture was poured into 30 mL of water and extracted with 3×10 mL EtOAc. The combined organics were rinsed with 10 mL of brine, dried with $MgSO_4$, filtered, and concentrated to dryness. Purification was achieved by chromatography on silica using 10-25% EtOAc/hexane to afford a thin film (37.8 mg, 97%). LCMS ESI (+) (M+H) m/z 355.

Step F: Preparation of 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 467): A solution of 3-fluoro-5-[[6-fluoro-7-oxo-1-(trifluoromethyl)-5,6-dihydrocyclopenta[c]pyridin-4-yl]oxy]benzonitrile (15.3 mg, 0.043 mmol) in dichloromethane (1.5 mL) was cooled to 0° C. and sparged with nitrogen for 5 min. During this time formic acid (4.9 uL, 0.13 mmol) and triethylamine (12.0 uL, 0.086 mmol) were sequentially added. Once the sparging was complete, RuCl(p-cymene)[(R,R)-Ts-DPEN] (0.5 mg, 0.00086 mmol) was added under a continuous stream of nitrogen. The reaction vessel was sealed and placed into the refrigerator to react overnight. Volatiles were removed by concentration under reduced pressure. The residue was purified by chromatography on silica using 10-30% EtOAc/hexane to afford 3-fluoro-5-((((6R,7S)-6-fluoro-7-hydroxy-1-(trifluoromethyl)-6,7-dihydro-5H-cyclopenta[c]pyridin-4-yl)oxy)benzonitrile (Compound 467) as a clear solid (11.8 mg, 77%). Retention time HPLC (14 min)=4.19 min; LCMS ESI (+) (M+H) m/z 357; $^1$H NMR (400 MHz, CDCl$_3$): δ 8.33 (s, 1H), 7.22 (ddd, 1H), 7.10-7.08 (m, 1H), 6.99 (dt, 1H), 5.54-5.46 (m, 1H), 5.46-5.28 (m, 1H), 3.26 (ddd, 1H), 3.11 (ddd, 1H), 2.67 (dd, 1H).

Example 7: Synthesis of 3-fluoro-5-((((6R,7S)-6-fluoro-7-hydroxy-1-(methylsulfonyl)-6,7-dihydro-5H-cyclopenta[c]pyridin-4-yl)oxy)benzonitrile (Compound 468)

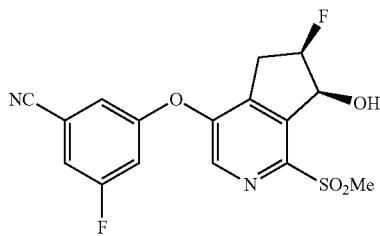 [SMILES: CS(=O)(=O)c1ncc(Oc2cc(F)cc(C#N)c2)c2c1[C@H](O)[C@H](F)C2]

Step A: Preparation of 5-bromo-2-(methylthio)nicotinic acid: A solution of 5-bromo-2-fluoro-pyridine-3-carboxylic acid (3.50 g, 15.91 mmol) in DMF (62 mL) at 0° C. was treated with potassium carbonate (2.42 g, 17.5 mmol) and vigorously stirred at 0° C. for 7 minutes. During this time, nitrogen was sparged through the solution. Then sodium thiomethoxide (1.23 g, 16.7 mmol) was added in one portion to the reaction vessel under continuous nitrogen stream. The reaction vessel was sealed and the ice bath removed. The solution turned from a tan color to faint yellow. The reaction mixture was left to stir overnight. The reaction mixture was poured onto 10% citric acid solution inducing precipitation of a white solid. The solid was filtered and rinsed exhaustively with water. Finally, the white solid was dried overnight under high vacuum in the presence of solid NaOH and used without further purification (3.63 g, 92%). LCMS ESI (+) (M+H) m/z 248/250.

Step B: Preparation of 5-bromo-4-formyl-2-(methylthio) nicotinic acid: A solution of 2,2,6,6-tetramethyl-piperidine (3.26 mL, 19.35 mmol) in tetrahydrofuran (40.3 mL) at −50 C was treated with n-butyllithium (~2.5M in hexanes, 7.09 mL, 17.73 mmol) and stirred for 5 min. Then 5-bromo-2-methylsulfanyl-pyridine-3-carboxylic acid (2.00 g, 8.06 mmol) was added via cannula over 30 min as a solution in 60 mL of THF. The resulting mixture stirred for 30 min at −50 C. The reaction mixture was quenched by the addition of N,N-dimethylformamide (0.94 mL, 12.09 mmol). 15 minutes following addition of the DMF, the reaction mixture was quenched by the addition of 40 mL of 10% citric acid solution (aqueous) and the reaction warmed to room temperature. After stirring for 30 min, excess THF removed by concentration under reduced pressure. The leftover mixture was poured into 120 mL of 3% citric acid (aqueous) and extracted with 3×50 mL EtOAc. The combined organics were dried with MgSO$_4$, filtered, and concentrated to dryness. 2.41 g of an orange solid was isolated and used without further purification. The material was contaminated with about 22% citric acid based on proton integration of the unpurified NMR spectra. LCMS ESI (+) (M+H) m/z 276/278.

Step C: Preparation of methyl (E)-5-bromo-4-(3-ethoxy-3-oxoprop-1-en-1-yl)-2-(methylthio)nicotinate: A solution of 7-bromo-1-hydroxy-4-methylsulfanyl-1H-furo[3,4-c]pyridin-3-one (2.21 g, 8.00 mmol), lithium chloride (anhydrous, 339.1 mg, 8.00 mmol) and ethyl 2-diethoxyphosphorylacetate (1.60 mL, 8.00 mmol) in acetonitrile (80 mL) at 25 C was treated with 1;8-Diazabicyclo[5.4.0]undec-7-ene (2.87 mL, 19.20 mmol) and stirred at 25 C for 2 h. Initially, the solution is heterogenous with the pyridine being insoluble. Upon addition of the DBU the solution becomes homogenous and darkens in color. After 1 h, the reaction appears to be mostly complete. In addition a precipitate has formed. Volatiles were removed by concentration under reduced pressure. The product residue was solubilized with 25 mL of DMF and treated with dimethyl sulfate (1.89 mL, 20.00 mmol). After 2 h, the reaction mixture was poured into 300 mL of water and extracted with 4×40 mL Et$_2$O. The combined organics were rinsed with 20 mL of brine, dried with MgSO$_4$, filtered, and concentrated to dryness. Purification was achieved by chromatography on silica using 5-20% EtOAc/hexane to afford methyl (E)-5-bromo-4-(3-ethoxy-3-oxoprop-1-en-1-yl)-2-(methylthio)nicotinate as a white solid (1.90 g, 66%). LCMS ESI (+) (M+H) m/z 360/362.

Step D: Preparation of methyl 5-bromo-4-(3-ethoxy-3-oxopropyl)-2-(methylthio)nicotinate: A solution of methyl 5-bromo-4-[(E)-3-ethoxy-3-oxo-prop-1-enyl]-2-methylsulfanyl-pyridine-3-carboxylate (1.87 g, 5.19 mmol) and cobalt (ii) chloride hexahydrate (123.5 mg, 0.52 mmol) in methanol (20.8 mL) at 0° C. was sparged with nitrogen for 3 min and treated with sodium borohydride (98.2 mg, 2.60 mmol) under continuous nitrogen stream. The vessel was sealed and the contents stirred at 0° C. for 10 min. LCMS at this time indicated partial consumption of the olefin. An additional portion of sodium borohydride (98.2 mg, 2.60 mmol) was added to drive the reaction to completion. The reaction mixture was quenched by the addition of 30 mL of saturated aqueous NH$_4$Cl. Volatiles were removed by concentration under reduced pressure. The reaction mixture was poured into 30 mL of water and extracted with 3×40 mL EtOAc. The combined organics were rinsed with 10 mL of brine, dried with MgSO$_4$, filtered, and concentrated to dryness. Purification was achieved by chromatography on silica using 5-15% EtOAc/hexane to afford the desired product as a solid (1.08 g, 57%). LCMS ESI (+) (M+H) m/z 362/364.

Step E: Preparation of ethyl 4-bromo-1-(methylthio)-5,6-dihydro-7H-cyclopenta[c]pyridin-7-one: A solution of methyl 5-bromo-4-(3-ethoxy-3-oxo-propyl)-2-methylsulfanyl-pyridine-3-carboxylate (1.08 g, 2.98 mmol) in tetrahydrofuran (29.8 mL) at −78° C. was treated with lithium bis(trimethylsilyl)amide (~1.0 M in THF, 7.16 mL, 7.16 mmol) by dropwise addition over 30 minutes. Once the addition was complete, LCMS indicated a small amount of starting material remained so an additional 1 mL of lithium bis(trimethylsilyl)amide was added and the reaction allowed to stir for a further 15 minutes. The reaction mixture was quenched by the addition of 30 mL of saturated aqueous NH$_4$Cl. THF was removed by concentration under reduced pressure. The reaction mixture diluted with 60 mL of EtOAc and an additional 30 mL of water. A thick precipitate formed that can be eliminated by the addition of 10% citric acid solution. The reaction mixture was extracted with 3×30 mL EtOAc. The combined organics were rinsed with 10 mL of brine, dried with MgSO$_4$, filtered, and concentrated to dryness. The intermediate product was transferred into a microwave tube using 9.1 mL of DMSO. The resulting mixture was diluted with 900 uL of water. The vessel was sealed and heated to 150 C by microwave irradiation for 40 min. The reaction mixture was diluted with 120 mL of water to induce precipitation of the product and vigorously stirred for 30 min. The precipitate was collected, dried overnight under high vacuum in the presence of solid NaOH, and used without further purification. Beige solid (705 mg, 92%). LCMS ESI (+) (M+H) m/z 258/260.

Step F: Preparation of 4-bromo-1-(methylsulfonyl)-5,6-dihydro-7H-cyclopenta[c]pyridin-7-one: A solution of 4-bromo-1-methylsulfanyl-5,6-dihydrocyclopenta[c]pyridin-7-one (364.5 mg, 1.41 mmol) in methanol (11.3 mL) at 0° C. was treated with a solution of Oxone® (1.91 g, 3.11 mmol) in water (11.3 mL). The reaction was left to stir for 24 h. Volatiles were removed by concentration under reduced pressure. The reaction mixture was poured into 40 mL of water and extracted with 3×20 mL EtOAc. The combined organics were rinsed with 10 mL of brine, dried with MgSO₄, filtered, and concentrated to dryness. The off white solid was used without further purification. LCMS ESI (+) (M+H) m/z 290/292.

Step G: Preparation of 4-bromo-1-(methylsulfonyl)-5,6-dihydrospiro[cyclopenta[c]pyridine-7,2'-[1,3]dioxolane]: Trimethylsilyl trifluoromethanesulfonate (331 uL, 1.83 mmol) was added to a solution of 4-bromo-1-methylsulfonyl-5,6-dihydrocyclopenta[c]pyridin-7-one (354 mg, 1.22 mmol) and trimethyl(2-trimethylsilyloxyethoxy)silane (1.20 mL, 4.88 mmol) in dichloromethane (14 mL) cooled in an ice bath. The ice bath was removed. After 3 h, an additional portion of trimethyl(2-trimethylsilyloxyethoxy)silane (1.20 mL, 4.88 mmol) was added. The reaction was left to stir overnight. After stirring, for the rest of the day, the reaction was quenched by the addition of triethylamine (1.02 mL, 7.32 mmol). The reaction mixture stirred for 10 min. Volatiles were removed and the residue suspended into 30 mL of saturated aqueous NaHCO₃ and extracted with 3×20 mL EtOAc. The combined organics were rinsed with 10 mL of brine, dried with MgSO₄, filtered, and concentrated to dryness. Purification was achieved by chromatography on silica using 15-50% EtOAc/hexane to afford 4-bromo-1-(methylsulfonyl)-5,6-dihydrospiro[cyclopenta[c]pyridine-7,2'-[1,3]dioxolane] as a white solid (74.5 mg, 18%). LCMS ESI (+) (M+H) m/z 334/336. The bulk of the product was isolated as the enol ether (295 mg, 59%).

Step H: Preparation of 1-(methylsulfonyl)-5,6-dihydrospiro[cyclopenta[c]pyridine-7,2'-[1,3]dioxolan]-4-ol: A solution of 4'-bromo-1'-methylsulfonyl-spiro[1,3-dioxolane-2,7'-5,6-dihydrocyclopenta[c]pyridine] (74.5 mg, 0.22 mmol) and 2-(di-t-butylphosphino)-3,6-dimethoxy-2',4',6'-tri-i-propyl-1,1'-biphenyl (5.4 mg, 0.011 mmol) in 1,4-dioxane (1.5 mL) was sparged with nitrogen for 3 mins. The reaction mixture was then treated sequentially with potassium hydroxide (37.5 mg, 0.67 mmol), water (80.3 uL, 4.46 mmol) and [2-(2-aminophenyl)phenyl]-methylsulfonyloxy-palladium; ditert-butyl-[3,6-dimethoxy-2-(2,4,6-triisopropylphenyl)phenyl]phosphane (9.5 mg, 0.011 mmol) under continuous nitrogen stream. The vessel was sealed and heated to 80 C for 1 h and 30 min. The reaction mixture was quenched by the addition of acetic acid (51.0 uL, 0.89 mmol). The reaction mixture was poured into 75 mL of water and extracted with 4×20 mL EtOAc. The combined organics were dried with MgSO₄, filtered, and concentrated to dryness. The product was used without further purification (77.9 mg). LCMS ESI (+) (M+H) m/z 272.

Step I: Preparation of 3-fluoro-5-((1-(methylsulfonyl)-5,6-dihydrospiro[cyclopenta[c]pyridine-7,2'-[1,3]dioxolan]-4-yl)oxy)benzonitrile: A suspension of potassium carbonate (30.6 mg, 0.22 mmol) in acetonitrile (1.5 mL) at 25 C was treated with 1'-methylsulfonylspiro[1,3-dioxolane-2,7'-5,6-dihydrocyclopenta[c]pyridine]-4'-ol (40.0 mg, 0.15 mmol) and stirred at 25 C for 10 min. The resulting mixture was treated with (3-cyano-5-fluoro-phenyl)-(4-methoxyphenyl)iodonium; 4-methylbenzenesulfonate (116.2 mg, 0.22 mmol) and heated to 50 C for 3 h. Volatiles were removed by concentration under reduced pressure. The reaction mixture was poured into 20 mL of water and extracted with 3×15 mL EtOAc. The combined organics were rinsed with 10 mL of brine, dried with MgSO₄, filtered, and concentrated to dryness. Purification was achieved by chromatography on silica using 20-50% EtOAc/hexane to afford (3-fluoro-5-((1-(methylsulfonyl)-5,6-dihydrospiro[cyclopenta[c]pyridine-7,2'-[1,3]dioxolan]-4-yl)oxy)benzonitrile as a solid (25.1 mg, 44%). LCMS ESI (+) (M+H) m/z 391.

Step J: Preparation of 3-fluoro-5-((1-(methylsulfonyl)-7-oxo-6,7-dihydro-5H-cyclopenta[c]pyridin-4-yl)oxy)benzonitrile: A solution of 4'-(3,3-difluorocyclobutoxy)-6'-fluoro-1'-methylsulfonyl-spiro[1,3-dioxolane-2,7'-5,6-dihydrocyclopenta[c]pyridine] (25.1 mg, 0.064 mmol) in dichloromethane (3.0 mL) at 0 C was treated with perchloric acid (70% in water, 330 uL) and stirred at 0 C for 2 h and then at room temperature for 30 min. The reaction mixture was carefully quenched with 5 mL of saturated NaHCO₃/10 mL of water and extracted with 3×15 mL CH₂Cl₂. The combined organics were rinsed with 10 mL of brine, dried with MgSO₄, filtered, and concentrated to dryness. The product was used without further purification. LCMS ESI (+) (M+H) m/z 347.

Step K: Preparation of 3-((7-((tert-butyldimethylsilyl)oxy)-1-(methylsulfonyl)-5H-cyclopenta[c]pyridin-4-yl)oxy)-5-fluorobenzonitrile: A solution of triethylamine (71.4 uL, 0.51 mmol) and 3-fluoro-5-[[7-oxo-1-(trifluoromethyl)-5,6-dihydrocyclopenta[c]pyridin-4-yl]oxy]benzonitrile (22.2 mg, 0.064 mmol) in dichloromethane (3.0 mL) at 0° C. was treated with tert-butyldimethylsilyl trifluoromethanesulfonate (58.2 uL, 0.38 mmol). The ice bath was removed and the reaction mixture stirred for 2 h. The reaction mixture was poured into 30 mL of saturated NaHCO₃ and extracted with 3×20 mL CH₂Cl₂. The combined organics were rinsed with 10 mL of brine, dried with MgSO₄, filtered, and concentrated to dryness. The product was used without further purification. LCMS ESI (+) (M+H) m/z 461.

Step L: Preparation of 3-fluoro-5-((6-fluoro-1-(methylsulfonyl)-7-oxo-6,7-dihydro-5H-cyclopenta[c]pyridin-4-yl)oxy)benzonitrile: A solution of 3-[[7-[tert-butyl(dimethyl)silyl]oxy-1-(trifluoromethyl)-5H-cyclopenta[c]pyridin-4-yl]oxy]-5-fluoro-benzonitrile (29.5 mg, 0.064 mmol) in acetonitrile (2.6 mL) at 25° C. was treated with Selectfluor® (24.9 mg, 0.070 mmol) and stirred at 25° C. for 1 h. Volatiles were removed by concentration under reduced pressure. The reaction mixture was poured into 30 mL of water and extracted with 3×10 mL EtOAc. The combined organics were rinsed with 10 mL of brine, dried with MgSO₄, filtered, and concentrated to dryness. Purification was achieved by chromatography on silica using 10-25% EtOAc/hexane to afford 3-fluoro-5-((6-fluoro-1-(methylsulfonyl)-7-oxo-6,7-dihydro-5H-cyclopenta[c]pyridin-4-yl)oxy)benzonitrile as a thin film (11.1 mg, 48%). LCMS ESI (+) (M+H) m/z 365.

Step M: Preparation of 3-fluoro-5-(((6R,7S)-6-fluoro-7-hydroxy-1-(methylsulfonyl)-6,7-dihydro-5H-cyclopenta[c]pyridin-4-yl)oxy)benzonitrile (Compound 468): A solution of 6-fluoro-4-[(5-fluoro-3-pyridyl)oxy]-1-(trifluoromethyl)-

5,6-dihydrocyclopenta[c]pyridin-7-one (11.1 mg, 0.031 mmol) in dichloromethane (2.0 mL) was cooled to 0° C. and sparged with nitrogen for 5 min. During this time formic acid (3.4 uL, 0.091 mmol) and triethylamine (8.4 uL, 0.061 mmol) were sequentially added. Once the sparging was complete, RuCl(p-cymene)[(R,R)-Ts-DPEN] (0.4 mg, 0.0006 mmol) was added under a continuous stream of nitrogen. The reaction vessel was sealed and put into the refrigerator to react overnight. Volatiles were removed by concentration under reduced pressure. The residue was purified by chromatography on silica using 20-60% EtOAc/hexane to afford 3-fluoro-5-(((6R,7S)-6-fluoro-7-hydroxy-1-(methylsulfonyl)-6,7-dihydro-5H-cyclopenta[c]pyridin-4-yl)oxy)benzonitrile (Compound 468) as a white solid (7.0 mg, 63%). Retention time HPLC (14 min)=3.16 min; LCMS ESI (+) (M+H) m/z 367; $^1$H NMR (400 MHz, CDCl$_3$): δ 8.27 (s, 1H), 7.25 (ddd, 1H), 7.14 (m, 1H), 7.03 (dt, 1H), 5.69 (dt, 1H), 5.53-5.36 (m, 1H), 4.24 (d, 1H), 3.34 (s, 3H), 3.31-3.24 (m, 1H), 3.09 (ddd, 1H).

Example 8: Synthesis of racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 471)

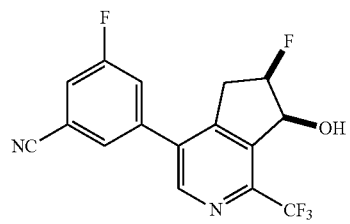 [SMILES: N#Cc1cc(F)cc(-c2cnc(C(F)(F)F)c3c2C[C@@H](F)[C@H]3O)c1]

Step A: Preparation of racemic (6R,7S)-4-bromo-6-fluoro-1-(trifluoromethyl)-6,7-dihydro-5H-cyclopenta[c]pyridin-7-ol: A solution of 4-bromo-6-fluoro-1-(trifluoromethyl)-5,6-dihydrocyclopenta[c]pyridin-7-one (6.7 mg, 0.022 mmol) in methanol (0.8 mL) at 0° C. was treated with sodium borohydride (0.9 mg, 0.022 mmol) and stirred at 0° C. for 10 min. The reaction mixture was quenched by the addition of 0.2 mL of saturated NH$_4$Cl. Volatiles were removed by concentration under reduced pressure. The reaction mixture was poured into 20 mL of water and extracted with 3×10 mL EtOAc. The combined organics were rinsed with 10 mL of brine, dried with MgSO$_4$, filtered, and concentrated to dryness. The product was used without further purification. LCMS ESI (+) (M+H) m/z 300/302.

Step B: Preparation of racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 471): A suspension of racemic (6R,7S)-4-bromo-6-fluoro-1-(trifluoromethyl)-6,7-dihydro-5H-cyclopenta[c]pyridin-7-ol (6.7 mg, 0.022 mmol), 3-cyano-5-fluorophenylboronic acid (5.5 mg, 0.033 mmol), cesium fluoride (10.5 mg, 0.069 mmol) and bis(di-tert-butyl(4-dimethylaminophenyl)phosphine)dichloropalladium(II) (0.8 mg, 0.0011 mmol) in a mixture 1,4-dioxane (0.8 mL) and water (80 uL) was sparged with nitrogen for 3 mins. The vessel was sealed and heated to 80° C. for 1 h. LCMS indicates product formation. The reaction mixture was poured into 60 mL of water and extracted with 3×20 mL EtOAc. The combined organics were rinsed with 10 mL of brine, dried with MgSO$_4$, filtered, and concentrated to dryness. Purification was achieved by chromatography on silica using 10-30% EtOAc/hexane to afford racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 471) as an orange solid (1.8 mg, 24%). Retention time HPLC (14 min)=3.80 min; LCMS ESI (+) (M+H) m/z 341; $^1$H NMR (400 MHz, CDCl$_3$): δ 8.65 (s, 1H), 7.53-7.48 (m, 2H), 7.40 (ddd, 1H), 5.56-5.48 (m, 1H), 5.35 (ddt, 1H), 3.41 (ddd, 1H), 3.21 (ddd, 1H), 2.65 (dd, 1H).

Example 9: (S)-3-((2,2-difluoro-1-hydroxy-7-((trifluoromethyl)sulfonyl)-2,3-dihydro-1H-inden-4-yl)amino)-5-fluorobenzonitrile (Compound 489)

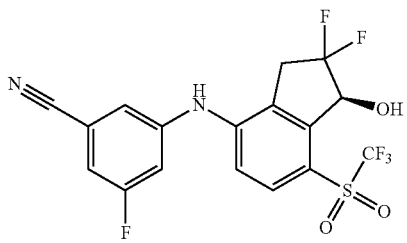 [SMILES: N#Cc1cc(F)cc(Nc2ccc(S(=O)(=O)C(F)(F)F)c3c2CC(F)(F)[C@H]3O)c1]

Step A: Preparation of 4-bromophenyl 3-chloropropanoate: A solution of 4-bromophenol (45.0 g, 260 mmol) in dichloromethane (1.0 L) was cooled to 0° C., treated with triethylamine (44.7 g, 442 mmol). A solution of 3-chloropropionyl chloride (36.3 g, 286 mmol) dissolved in dichloromethane (100 mL) was added dropwise to the reaction vessel. The reaction mixture was allowed to warm to ambient temperature and stirred overnight. Saturated NaCl was added to the reaction mixture, (300 mL). After stirring for 1 hour, the organic layer was separated. The aqueous layer was extracted with dichloromethane. The combined organics were washed with saturated NaCl, dried over Na$_2$SO$_4$, and concentrated in vacuo. The crude product was used without further purification.

Step B: Preparation of 4-bromo-7-hydroxy-2,3-dihydro-1H-inden-1-one: A flask containing crude (4-bromophenyl) 3-chloropropanoate (68.0 g, 258 mmol) was cooled to 0° C., then treated in several portions with aluminum trichloride (275 g, 2060 mmol). The reaction mixture was then heated at 155° C. under N$_2$ for 3 hours. Stirring became difficult as the reaction proceeded. HCl (g) which was generated from the reaction was trapped by a beaker containing 1 N NaOH. After cooling to ambient temperature, the reaction mixture was further cooled in an ice bath. Water was added very carefully (dropwise initially and then added in small volumes) to the reaction to quench excess AlCl$_3$. The mixture was then extracted with twice with ethyl acetate. The combined organic layers were washed with water and brine, dried and concentrated. The crude product was used without additional purification.

Step C: Preparation of O-(7-bromo-3-oxo-2,3-dihydro-1H-inden-4-yl) dimethylcarbamothioate: A mixture of 4-bromo-7-hydroxy-2,3-dihydro-1H-inden-1-one (900 mg, 4.0 mmol) dissolved in DMF (15 mL) was treated with DABCO 33LV (1.3 mL, 12 mmol) and N,N-dimethylcarbamothioyl chloride (1.5 g, 12 mmol) was stirred overnight at ambient temperature. The reaction was treated with water and ethyl acetate and separated. The aqueous layer was extracted with ethyl acetate then the combined organic layers were washed with water and saturated NaCl. After drying, the organic layer was concentrated in vacuo and purified by chromatography on SiO2 eluting with a gradient of ethyl acetate/hexanes, (670 mg, 54%). $^1$H NMR (400 MHz, CDCl$_3$): δ 7.78-7.76 (d, 1H), 6.97-6.95 (d, 1H), 3.44 (s, 3H), 3.41 (s, 3H), 3.08 (m, 2H), 2.76-2.69 (m, 2H).

Step D: Preparation of S-(7-bromo-3-oxo-2,3-dihydro-1H-inden-4-yl) dimethylcarbamothioate: A mixture of O-(7-bromo-3-oxo-2,3-dihydro-1H-inden-4-yl) dimethylcarbamothioate (670 mg, 2.1 mmol) and diphenyl ether (15 mL) was heated at 220° C. under N$_2$ for 30 minutes. After cooling to ambient temperature, the mixture was diluted with hexanes and the mixture was applied to a pad of SiO$_2$ and eluted with hexanes. After removal of the diphenyl ether, the desired product was eluted with ethyl acetate. After concentration in vacuo, the crude product was used without further purification.

Step E: Preparation of 4-bromo-7-mercapto-2,3-dihydro-1H-inden-1-one: A solution of S-(7-bromo-3-oxo-2,3-dihydro-1H-inden-4-yl) dimethylcarbamothioate (670 mg, 2.1 mmol) dissolved in ethanol (25 mL) was treated with 3N sodium hydroxide) 10.7 mL, 32.1 mmol). The mixture was heated to reflux for 1 hour then cooled to 0° C. Aqueous HCl (3M) was added dropwise to neutralize the reaction. Ethanol was removed by concentration in vacuo followed by addition of aqueous HCl (1M) to adjust to pH 3-4. The aqueous was extracted twice with ethyl acetate and the combined organic layers were washed with saturated NaCl, dried and concentrated in vacuo. The crude product was used without further purification.

Step F: Preparation of 4-bromo-7-((trifluoromethyl)thio)-2,3-dihydro-1H-inden-1-one: Methyl viologen dichloride hydrate (0.11 g, 0.41 mmol), 4-bromo-7-mercapto-2,3-dihydro-1H-inden-1-one (2.0 g, 8.2 mmol) and triethylamine (1.25 g, 12.3 mmol) were dissolved in DMF (50 mL) and cooled to −50° C. The flask was placed under gentle vacuum then trifluoromethyl iodide (3.2 g, 16 mmol) gas was introduced using a balloon. This reaction was warmed to ambient temperature and stirred at overnight. The reaction mixture was diluted with ethyl acetate and water, filtered through a celite pad, and the layers were partitioned. The organic layer was washed with water, brine, dried over Na$_2$SO$_4$, filtered, and evaporated. The crude oil was then purified by flash column chromatography on SiO$_2$ eluting with petroleum ether/ethyl acetate, (0.96 g, 51.7%). $^1$H NMR (400 MHz, CDCl$_3$): δ 7.72 (d, 1H), 7.41 (d, 1H), 3.10-3.07 (m, 2H), 2.79-2.77 (m, 2H).

Step G: Preparation of 4-bromo-7-((trifluoromethyl)sulfonyl)-2,3-dihydro-1H-inden-1-one: Ruthenium(III) chloride (19 mg, 0.09 mmol) was added to a mixture of 4-bromo-7-((trifluoromethyl)thio)-2,3-dihydro-1H-inden-1-one (0.96 g, 3.1 mmol) and sodium periodate (1.98 g, 9.26 mmol) in a mixture of carbon tetrachloride (20 mL), acetonitrile (20 mL), and water (40 mL). The mixture was stirred at ambient temperature for 3 hours. The reaction mixture was partitioned between dichloromethane and water. The organic layer was washed with brine, dried over MgSO$_4$, filtered, and concentrated in vacuo. The crude product was purified by flash column chromatography on SiO$_2$ eluting with petroleum ether/ethyl acetate, (1.7 g, 79%). $^1$H NMR (400 MHz, CDCl$_3$): δ 8.05-8.02 (m, 2H), 3.21-3.18 (m, 2H), 2.89-2.86 (m, 2H).

Step H: Preparation of 4-bromo-7-((trifluoromethyl)sulfonyl)-2,3-dihydrospiro[indene-1,2'-[1,3]dioxolane]: Trimethylsilyl trifluoromethanesulfonate (177 mg, 0.80 mmol) was added dropwise to a pre-cooled (−78° C.) solution of 4-bromo-7-((trifluoromethyl)sulfonyl)-2,3-dihydro-1H-inden-1-one and trimethyl(2-trimethylsilyloxyethoxy)silane (410 mg, 2.0 mmol) dissolved in dichloromethane (50 mL). The reaction mixture was warmed to ambient temperature and stirred for 2 hours. The reaction was quenched by addition of triethylamine then concentrated in vacuo. The residue was redissolved in ethyl acetate and washed twice with water, and saturated NaCl. The organic layer was separated, dried over Na$_2$SO$_4$ and concentrated in vacuo. The crude product was purified by chromatography on SiO$_2$ eluting with ethyl acetate/isohexane, (600 mg, 77%).

Step I: Preparation of 4-bromo-7-((trifluoromethyl)sulfonyl)-2,3-dihydro-1H-inden-1-one: 4-Bromo-7-((trifluoromethyl)sulfonyl)-2,3-dihydrospiro[indene-1,2'-[1,3]dioxolane] (3.5 g, 9.1 mmol) was dissolved in THF (72 mL) and treated with 10% aqueous HCl (27 mL, 27 mmol). The mixture was stirred for several minutes then warmed to 60° C. for 2 hours. The mixture was cooled, diluted with diethyl ether and separated. The aqueous was washed with diethyl ether and the combined organics were washed with water, saturated NaHCO$_3$, saturated NaCl, dried over Na$_2$SO$_4$ and concentrated in vacuo to a yellowish solid, (3.09 g, quant.). $^1$H NMR (400 MHz, CDCl$_3$): δ 8.05-8.02 (m, 2H), 3.21-3.18 (m, 2H), 2.89-2.86 (m, 2H).

Step J: Preparation of (E,Z)-3-((4-bromo-7-((trifluoromethyl)sulfonyl)-2,3-dihydro-1H-inden-1-ylidene)amino)propan-1-ol: 4-Bromo-7-(trifluoromethylsulfonyl)indan-1-one (3.09 g, 9.02 mmol] was slurried in toluene (35 mL) and cyclohexane (35 mL) then treated with 3-methoxypropylamine (2.15 mL, 27.1 mmol) and pivalic acid (46 mg, 0.45 mmol). The mixture was refluxed through a Dean-Stark trap (sidearm pre-filled with cyclohexane) for 8 hours. The reaction mixture was cooled and concentrated in vacuo. The crude material was taken directly into the fluorination.

Step K: Preparation of 4-bromo-2,2-difluoro-7-((trifluoromethyl)sulfonyl)-2,3-dihydro-1H-inden-1-one: Crude (E,Z)-3-((4-bromo-7-((trifluoromethyl)sulfonyl)-2,3-dihydro-1H-inden-1-ylidene)amino)propan-1-ol (3.75 g, 9.1 mmol) was dissolved in dry acetonitrile (23 mL) and added dropwise to a warm (60° C.), suspension of Selectfluor (9.6 g, 27.2 mmol) and sodium sulfate (12.9 g, 90.5 mmol) slurried in acetonitrile (10 mL). After the addition, the mixture was heated to 60° C. for 10 minutes then cooled to ambient temperature and treated with 10% HCl (15 mL) and stirred for 20 minutes. The mixture was adjusted to pH 8 with solid NaHCO$_3$ then diluted with ethyl acetate and separated. The aqueous was washed with ethyl acetate and the combined organics were washed with saturated NaHCO$_3$, saturated NaCl, dried over Na$_2$SO$_4$ filtered, and concentrated in vacuo to dark oil. The crude material was chromatographed on SiO$_2$ eluting with a gradient of ethyl acetate/hexanes. The desired product was concentrated to a light yellow solid, (2.27 g, 66%). $^1$H NMR (400 MHz, CDCl$_3$): δ 8.22-8.14 (m, 2H), 3.60-3.55 (t, 2H).

Step L: Preparation of (S)-4-bromo-2,2-difluoro-7-((trifluoromethyl)sulfonyl)-2,3-dihydro-1H-inden-1-ol: 4-Bromo-2,2-difluoro-7-((trifluoromethyl)sulfonyl)-2,3-dihydro-1H-inden-1-one_(1.65 g, 4.35 mmol) was dissolved in isopropanol (21 mL) and treated with triethylamine (1.2 mL, 8.7 mmol), formic acid (0.49 mL, 13.1 mmol) and RuCl(p-cymene)[(R,R)-Ts-DPEN] (27.7 mg, 0.040 mmol). The reaction mixture was stirred at ambient temperature for 4 hours. The solvent was removed in vacuo then the crude material was chromatographed on SiO$_2$ eluting with a gradient of ethyl acetate/hexanes. The product was isolated as a more pure fraction (1.83 g) and a slightly less pure fraction. Both of these fractions were successfully utilized in the coupling reaction. ¹H NMR (400 MHz, CDCl₃): δ 7.88-7.80 (m, 2H), 5.50-5.45 (m, 1H), 3.66-3.58 (m, 1H), 3.20 (m, 1H).

Step M: Preparation of (S)-3-((2,2-difluoro-1-hydroxy-7-((trifluoromethyl)sulfonyl)-2,3-dihydro-1H-inden-4-yl)amino)-5-fluorobenzonitrile: (S)-4-Bromo-2,2-difluoro-7-((trifluoromethyl)sulfonyl)-2,3-dihydro-1H-inden-1-ol (98 mg, 0.26 mmol) was dissolved in 1,4-dioxane (0.80 mL) and treated with benzonitrile, 3-amino-5-fluoro-(42 mg, 0.31 mmol), palladium (II) acetate (2.9 mg, 0.010 mmol), and Xantphos (14.9 mg, 0.030 mmol). The mixture was heated to 120° C. for 1.5 hours in the microwave reactor. The reaction mixture was cooled, diluted with ethyl acetate and water then separated. The aqueous was washed with ethyl acetate and the combined organics were washed with saturated NaHCO₃, saturated NaCl, dried over Na₂SO₄ and concentrated in vacuo. The crude dark oil was chromatographed on SiO₂ eluting with a gradient of ethyl acetate/hexanes. The desired material was recovered in a slightly impure form. This material was re-chromatographed on reversed-phase SiO₂ eluting with a gradient of MeCN/water. A single fraction was collected and to light tan solid, (35 mg, 31%). LCMS ESI (−) m/z (M−H) 435; ¹H NMR (400 MHz, CDCl₃): δ 7.87 (d, 1H), 7.31-7.29 (m, 2H), 7.21-7.19 (m, 2H), 6.18 (m, 1H), 5.42-5.38 (m, 1H), 3.52-3.41 (m, 1H), 3.32-3.24 (m, 1H).

Example 10: Synthesis of (1S,3R)-4-((3-chloro-5-fluorophenyl)thio)-2,2,3-trifluoro-7-(methylsulfonyl)-2,3-dihydro-1H-inden-1-ol (Compound 491)

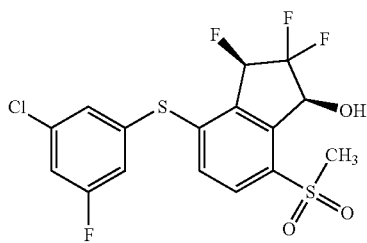 [SMILES: CS(=O)(=O)c1ccc(Sc2cc(F)cc(Cl)c2)c2c1[C@H](O)C(F)(F)[C@@H]2F]

Step A: Preparation of 4,7-difluoro-1H-indene-1,3(2H)-dione (0.52 g, 2.8 mmol) was slurried acetic anhydride (2.5 mL, 27 mmol) and treated with tert-butyl 3-oxobutanoate (0.52 mL, 3.1 mmol) and triethylamine (1.4 mL, 10 mmol). The mixture was stirred at ambient temperature for 60 hours. The reaction was cooled to 0° C. and treated with 10% aqueous hydrochloric acid (8.6 mL, 25 mmol) by dropwise addition. After the addition, the mixture was warmed to ambient temperature then heated to 75° C. for 10 minutes. After cooling, the mixture was diluted with water (20 mL) and extracted three times with methylene chloride (20 mL portions). The combined organics were dried over Na₂SO₄ and concentrated in vacuo to crude orange solid. This material was carried forward without purification.

Step B: Preparation of 2,2,4,7-tetrafluoro-1H-indene-1,3(2H)-dione: 4,7-difluoro-1H-indene-1,3(2H)-dione (0.51 g, 2.8 mmol) was dissolved in acetonitrile (27 mL), placed in an ambient temperature water bath then treated with solid sodium carbonate (950 mg, 9.0 mmol) followed by Selectfluor® (2.18 g, 6.2 mmol). The mixture was stirred at ambient temperature for 1 hour. The mixture was filtered to removed undissolved solids, the solids were washed with ethyl acetate and the filtrate was concentrated in vacuo. The residue was redissolved in water (ca. 20 mL) and extracted four times with ethyl acetate (20 mL each). The combined organics were washed with saturated NaCl, dried over Na₂SO₄ and concentrated in vacuo to orange solid. The crude solid was chromatographed on SiO₂ eluting with an aggressive gradient of ethyl acetate/hexanes. The desired material concentrated to orange solid, (493 mg, 81%). ¹H NMR (400 MHz, CDCl₃): δ 7.70-7.65 (2H).

Step C: Preparation of (S)-2,2,4,7-tetrafluoro-3-hydroxy-2,3-dihydro-1H-inden-1-one: 2,2,4,7-tetrafluoro-1H-indene-1,3(2H)-dione (5.81 g, 26.6 mmol) was suspended in methylene chloride (260 mL), cooled to 0° C., and treated with formic acid (1.01 mL, 26.6 mmol), triethylamine (2.60 mL, 18.6 mmol), then the reaction mixture was sparged with argon for 5 minutes. RuCl(p-cymene)[(S,S)-Ts-DPEN] (339 mg, 0.530 mmol) was added and the reaction was transferred to the refrigerator and allowed to stand at 4° C. for 20 hours. The cold reaction mixture was poured into cold 1N aqueous HCl (70 mL) and separated. The aqueous was washed twice with ethyl acetate then the combined organic layers were dried over Na₂SO₄ and concentrated in vacuo to a brown semi-solid. The crude material was chromatographed on SiO₂ eluting with a gradient of ethyl acetate/hexanes. The product was recovered as yellow solid, (3.48 g, 59%). ¹H NMR (400 MHz, CDCl₃): δ 7.86-7.80 (m, 1H), 7.60-7.54 (m, 1H), 5.79-5.74 (m, 1H), 3.23-3.18 (m, 1H).

Step D: Preparation of (S)-2,2,4-trifluoro-3-hydroxy-7-(methylthio)-2,3-dihydro-1H-inden-1-one: (S)-2,2,4,7-tetrafluoro-3-hydroxy-2,3-dihydro-1H-inden-1-one (0.40 g, 1.8 mmol) was dissolved in dry acetonitrile (18 mL), cooled to 0° C., and sparged with argon for 5 minutes. The solution was treated in a single portion with sodium thiomethoxide (144 mg, 2.06 mmol) and after 5 minutes, the ice bath was removed and the reaction was stirred at ambient temperature for 3 hours. The reaction mixture was concentrated in vacuo and the residue was redissolved in water and ethyl acetate. After separation, the aqueous was washed twice with ethyl acetate and the combined organics were washed with saturated NaCl, dried over Na₂SO₄ and concentrated in vacuo. The orange residue was chromatographed on SiO₂ eluting with a gradient of ethyl acetate/hexanes. The desired material was recovered as bright yellow solid, (314 mg, 70%). LCMS ESI (+) m/z (M+H) 249.

Step E: Preparation of (S)-2,2,4-trifluoro-3-hydroxy-7-(methylsulfonyl)-2,3-dihydro-1H-inden-1-one: (S)-2,2,4-trifluoro-3-hydroxy-7-(methylthio)-2,3-dihydro-1H-inden-1-one (0.40 g, 1.6 mmol) was dissolved in MeOH (10 mL) and the reaction was treated dropwise with a solution of Oxone® (2.2 g, 3.6 mmol) dissolved in water (10 mL). The mixture was stirred at ambient temperature for 14 hours. The reaction mixture was filtered, the solids were washed with ethyl acetate and the filtrate was concentrated in vacuo to remove volatile solvents. The aqueous filtrate was extracted three times with ethyl acetate then the combined organics were washed with saturated NaCl, dried over Na₂SO₄ and concentrated in vacuo to yellow solid, (467 mg, quant.). LCMS ESI (+) m/z (M+H) 281.

Step F: Preparation of (R)-2,2,3,4-tetrafluoro-7-(methylsulfonyl)-2,3-dihydro-1H-inden-1-one: (S)-2,2,4-trifluoro-3-hydroxy-7-(methylsulfonyl)-2,3-dihydro-1H-inden-1-one (0.45 g, 1.6 mmol) was dissolved in dichloromethane (16 mL), cooled to 0° C., and treated dropwise with diethylaminosulfur trifluoride (DAST) (0.32 mL, 2.4 mmol) and stirred at 0° C. for 14 hours. The reaction was treated with additional diethylaminosulfur trifluoride (0.32 mL, 2.4 mmol) and stirring continued for 6 hours at 0° C. The cold reaction was treated with saturated NaHCO₃ (10 mL) and stirred vigorously for 20 minutes. The mixture was diluted with additional methylene chloride and the layers were separated. The aqueous was re-extracted with methylene chloride and the combined organic layers were dried over Na$_2$SO$_4$ and concentrated in vacuo to a yellow solid. The crude material was chromatographed on SiO$_2$ eluting with a gradient of ethyl acetate/hexanes. The desired material was recovered as pale yellow solid, (258 mg, 53%). LCMS ESI (+) m/z (M+H) 283.

Step G: Preparation of (1S,3R)-2,2,3,4-tetrafluoro-7-(methylsulfonyl)-2,3-dihydro-1H-inden-1-ol: (R)-2,2,3,4-tetrafluoro-7-(methylsulfonyl)-2,3-dihydro-1H-inden-1-one: (0.098 g, 0.35 mmol) was suspended in methylene chloride (3.3 mL), cooled to 0° C., and treated with triethylamine (97 µL, 0.69 mmol), formic acid (39 µL, 1.0 mmol) and RuCl(p-cymene)[(R,R)-Ts-DPEN] (2.2 mg, 0.003 mmol). The solution was allowed to stand at 4° C. in the refrigerator for 60 hours. The reaction mixture was concentrated in a stream of nitrogen gas then chromatographed on SiO$_2$ eluting with a gradient of ethyl acetate/hexanes. The desired fractions were concentrated to colorless film, (53 mg, 53%). LCMS ESI (+) m/z (M+H) 285.

Step H: Preparation of (1S,3R)-4-((3-chloro-5-fluorophenyl)thio)-2,2,3-trifluoro-7-(methylsulfonyl)-2,3-dihydro-1H-inden-1-ol: (1S,3R)-2,2,3,4-tetrafluoro-7-(methylsulfonyl)-2,3-dihydro-1H-inden-1-ol (0.005 g, 0.02 mmol) was treated with cesium bicarbonate (17 mg, 0.090 mmol) and suspended in DMF (0.1 mL) then stirred at ambient temperature for 1 hour. 3-Chloro-5-fluorothiophenol (14 mg, 0.090 mmol) was added and the mixture was stirred at ambient temperature for 18 hours. The reaction was concentrated in a stream of nitrogen gas to remove DMF. The residue was chromatographed on SiO$_2$ eluting with a stepped gradient of ethyl acetate/hexanes. Compound 491 was concentrated to light pink oil, (7 mg, 93%). LCMS ESI (+) m/z (M+Na) 449; $^1$H NMR (400 MHz, CDCl$_3$): δ 7.99-7.95 (m, 1H), 7.33-7.32 (m, 1H), 7.24-7.19 (m, 2H), 7.16-7.13 (m, 1H), 5.75 (dd, 1H), 5.68-5.65 (m, 1H), 3.37-3.36 (m, 1H), 3.23 (s, 3H).

Example 11: Synthesis of (S)-2,2-difluoro-4-(2-hydroxyethyl)-7-((trifluoromethyl)sulfonyl)-2,3-dihydro-1H-inden-1-ol (Compound 496)

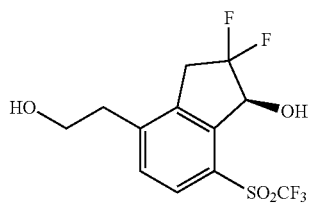

Step A: Borane dimethylsulfide complex (439.0 µL, 0.88 mmol) was added dropwise to 2-[7'-(trifluoromethylsulfonyl)spiro[1,3-dioxolane-2,1'-indane]-4'-yl]acetic acid (268.0 mg, 0.73 mmol) in tetrahydrofuran (7.0 mL) at 0° C. under nitrogen then slowly warmed to room temperature. Stirred until complete as judged by LC-MS. Quenched carefully with saturated sodium bicarbonate, extracted with ethyl acetate, washed with brine, dried over MgSO$_4$, filtered and concentrated in vacuo. Purified on silica gel (10 g SNAP Ultra, 14 CV, 40-100% ethyl acetate/hexanes) affording 2-[7'-(trifluoromethylsulfonyl)spiro[1,3-dioxolane-2,1'-indane]-4'-yl]ethanol (95.0 mg, 0.27 mmol, 37% yield).

Step B: HCl (1.0 mL, 1.0 mmol) was added all at once to 2-[7'-(trifluoromethylsulfonyl)spiro[1,3-dioxolane-2,1'-indane]-4'-yl]ethanol (95.0 mg, 0.27 mmol) in acetone (4.0 mL) at room temperature then stirred until complete as judged by LC-MS. Diluted with water, extracted with ethyl acetate, washed with saturated sodium bicarbonate, washed with brine, dried over MgSO$_4$, filtered and concentrated in vacuo. Used without further purification.

Step C: Tert-Butyldimethylsilyl chloride (46.9 mg, 0.31 mmol) was added all at once to a solution of 4-(2-hydroxyethyl)-7-(trifluoromethylsulfonyl)indan-1-one (80.0 mg, 0.26 mmol) and imidazole (53.0 mg, 0.78 mmol) in dichloromethane (2.0 mL) at room temperature then stirred overnight. Diluted with water, extracted with MTBE, washed with brine, dried over Na$_2$SO$_4$, filtered and concentrated in vacuo. Purified on silica gel (10 g SNAP, 12 CV, 5-60% ethyl acetate/hexanes) affording 4-[2-[tert-butyl(dimethyl)silyl]oxyethyl]-7-(trifluoromethylsulfonyl)indan-1-one (89.0 mg, 0.21 mmol, 81% yield).

Step D: Pivalic acid (2.2 mg, 0.02 mmol) was added to a mixture of 4-[2-[tert-butyl(dimethyl)silyl]oxyethyl]-7-(trifluoromethylsulfonyl)indan-1-one (89.0 mg, 0.21 mmol) and 3-methoxypropylamine (37.6 mg, 0.42 mmol) in cyclohexane (1.5 mL):toluene (1.5 mL) at room temperature then warmed to reflux with the azeotropic removal of water by Dean-Stark trap. Monitored by $^1$H-NMR. Cooled to room temperature then concentrated in vacuo. Used without further purification.

Step E: Crude 4-[2-[tert-butyl(dimethyl)silyl]oxyethyl]-N-(3-methoxypropyl)-7-(trifluoromethylsulfonyl)indan-1-imine (103.0 mg, 0.21 mmol) in acetonitrile (1.5 mL) was added to 1-chloromethyl-4-fluoro-1,4-diazoniabicyclo[2.2.2]octane bis(tetrafluoroborate) (184.8 mg, 0.52 mmol) and sodium Sulfate (59.3 mg, 0.42 mmol) in acetonitrile (1.5 mL) at 60° C. and stirred for 1 h. Cooled to room temperature then 1 N HCl (3.0 mL) was added and stirred overnight. Extracted with ethyl acetate, washed with brine, dried over MgSO$_4$, filtered and concentrated in vacuo. Purified on reverse phase silica gel (12+M, 14 CV, 20-100% acetonitrile/water) affording 2,2-difluoro-4-(2-hydroxyethyl)-7-(trifluoromethylsulfonyl)indan-1-one (40.0 mg, 0.12 mmol, 56% yield).

Step F: Chloro{[(1R,2R)-(−)-2-amino-1,2-diphenylethyl](4-toluenesulfonyl)amido}(p-cymene)ruthenium(II) (1.5 mg, 0.002 mmol) was added all at once to an ice cold solution of 2,2-difluoro-4-(2-hydroxyethyl)-7-(trifluoromethylsulfonyl)indan-1-one (40.0 mg, 0.12 mmol), triethylamine (32.4 µL, 0.23 mmol) and formic acid (13.2 µL, 0.35 mmol) in dichloromethane (1.0 mL) then sealed with a threaded teflon cap and placed in a 4° C. fridge over the weekend. Purified directly on silica gel (10 g SNAP Ultra, 14 CV, 25-100% ethyl acetate/hexanes) affording (1S)-2,2-difluoro-4-(2-hydroxyethyl)-7-(trifluoromethylsulfonyl)indan-1-ol (Compound 496) (28.0 mg, 0.081 mmol, 70% yield) as a clear oil. Swirled with hexanes to yield a white solid. LC-MS ESI (−) m/z 345 (M−H).

Example 12: Synthesis of (1S,3R)-4-(3,3-difluoro-cyclobutoxy)-2,2,3-trifluoro-7-(methylsulfonyl)-2,3-dihydro-1H-inden-1-ol (Compound 574) and (1S, 3S)-4-(3,3-difluorocyclobutoxy)-2,2,3-trifluoro-7-(methylsulfonyl)-2,3-dihydro-1H-inden-1-ol (Compound 575)

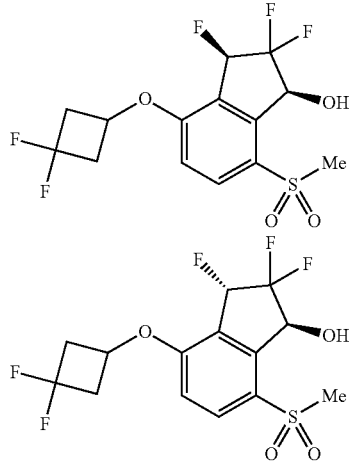

Step A: Preparation of 4,7-difluoro-1H-indene-1,3(2H)-dione: A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 h. The reaction mixture was cooled to 0° C. and treated with 10% hydrochloric acid (65 mL, 211 mmol) by dropwise addition. Once the addition was complete, the ice bath was removed and the mixture stirred at ambient for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL $CH_2Cl_2$. The combined organics were dried with $MgSO_4$, filtered, and concentrated to dryness. The product was used without further purification.

Step B: Preparation of 2,2,4,7-tetrafluoro-1H-indene-1,3 (2H)-dione: A solution of the unpurified 4,7-difluoro-1H-indene-1,3(2H)-dione (4.2 g, 23.1 mmol) in acetonitrile (100 mL) cooled in a 25° C. water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with $MgSO_4$, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. $^1$H NMR (400 MHz, $CDCl_3$): δ 7.70 (t, 2H).

Step C: Preparation of (S)-2,2,4,7-tetrafluoro-3-hydroxy-2,3-dihydro-1H-inden-1-one: To a solution of 2,2,4,7-tetrafluoro-1H-indene-1,3(2H)-dione (3.48 g, 16.0 mmol) in dichloromethane (150 mL) at 0° C. was added formic acid (600 μL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The $CH_2Cl_2$ layer was separated and the aqueous layer extracted with ethyl acetate (2×50 mL). The combined organics were dried with $Na_2SO_4$, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. $^1$H NMR (400 MHz, $CDCl_3$): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one: A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxice (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over $MgSO_4$, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+)[M+H]+m/z 249.

Step E: Preparation of (S)-2,2,4-trifluoro-3-hydroxy-7-(methylsulfonyl)-2,3-dihydro-1H-inden-1-one: (S)-2,2,4-trifluoro-3-hydroxy-7-(methylthio)-2,3-dihydro-1H-inden-1-one (400 mg, 1.6 mmol) was dissolved in MeOH (10 mL) and the reaction was treated dropwise with a solution of Oxone© (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over $Na_2SO_4$ and concentrated in vacuo to a yellow solid that was used without further purification (467 mg). LCMS ESI (+) [M+H]+m/z 281.

Step F: Preparation of (R)-2,2,3,4-tetrafluoro-7-(methyl-sulfonyl)-2,3-dihydro-1H-inden-1-one: (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylami-nosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 h at 0° C. The cold reaction was treated with saturated $NaHCO_3$ (10 mL) and stirred vigorously for 20 minutes. The mixture was diluted with additional methylene chloride and the layers were separated. The aqueous was re-extracted with methylene chloride and the combined organic layers were dried over $Na_2SO_4$ and concentrated in vacuo to a yellow solid. The crude material was chromatographed on $SiO_2$ (Biotage SNAP Ultra) and eluted with a gradient of ethyl acetate/hexane. The desired material was concentrated to a pale yellow solid (258 mg). LCMS ESI (+) [M+H]+m/z 283.

Step G: Preparation of (R)-2,2,3,4-tetrafluoro-7-(methyl-sulfonyl)-2,3-dihydrospiro[indene-1,2'-[1,3]dioxolane]: A solution of (3R)-2,2,3,4-tetrafluoro-7-methylsulfonyl-in-dan-1-one (2.03 g, 7.2 mmol) and 2-bromoethanol (1.53 mL, 21.6 mmol) in DMF (16 mL) at 25° C. was treated with potassium carbonate (2.98 g, 21.6 mmol) and stirred at 25° C. for 30 min. The reaction mixture was poured into 200 mL of water and extracted with 3×50 mL Et2O. The combined organics were rinsed with 30 mL of brine, dried with MgSO4, filtered, and concentrated to dryness. The off-white solid was used without further purification. LCMS ESI (+) [M+H]+m/z 327.

Step H: Preparation of (R)-4-(3,3-difluorocyclobutoxy)-2,2,3-trifluoro-7-(methylsulfonyl)-2,3-dihydrospiro[indene-1,2'-[1,3]dioxolane]: A solution of (3'R)-2',2',3',4'-tetrafluoro-7'-methylsulfonyl-spiro[1,3-dioxolane-2,1'-indane] (1.95 g, 5.98 mmol) and 3,3-difluoro-cyclobutanol (770 µL, 7.95 mmol) in acetonitrile (30 mL) at 25° C. was treated with potassium hydroxide (402.4 mg, 7.17 mmol) and stirred at 25° C. for 1 h. Excess acetonitrile was removed by concentration under reduced pressure. The reaction mixture was poured into 40 mL of water and extracted with 3×40 mL EtOAc. The combined organics were rinsed with 10 mL of brine, dried with MgSO$_4$, filtered, and concentrated to dryness. Purification was achieved by chromatography on silica using 15-45% EtOAc/hexane to afford a white solid (2.2 g, 89%). LCMS ESI (+) [M+H]+m/z 415.

Step I: Preparation of (R)-4-(3,3-difluorocyclobutoxy)-2,2,3-trifluoro-7-(methylsulfonyl)-2,3-dihydro-1H-inden-1-one: A solution of (3'R)-4'-(3,3-difluorocyclobutoxy)-2',2',3'-trifluoro-7'-methylsulfonyl-spiro[1,3-dioxolane-2,1'-indane] (2.2 g, 5.31 mmol) in dichloromethane (30 mL) at 25° C. was treated with perchloric acid (70% in water, 10 mL) and left to stir for 2 days. The reaction mixture was carefully quenched by the addition of 100 mL of saturated aqueous NaHCO$_3$ and extracted with 3×50 mL CH$_2$Cl$_2$. The combined organics were rinsed with 10 mL of brine, dried with MgSO$_4$, filtered, and concentrated to dryness. Purification was achieved by chromatography on silica using 25-65% EtOAc/hexane to afford a solid (1.41 g, 72%). LCMS ESI (+) [M+H]+m/z 371.

Step J: Preparation of (1S,3R)-4-(3,3-difluorocyclobutoxy)-2,2,3-trifluoro-7-(methylsulfonyl)-2,3-dihydro-1H-inden-1-ol (Compound 574) and (1S,3S)-4-(3,3-difluorocyclobutoxy)-2,2,3-trifluoro-7-(methylsulfonyl)-2,3-dihydro-1H-inden-1-ol (Compound 575): A solution of (3R)-4-(3,3-difluorocyclobutoxy)-2,2,3-trifluoro-7-methylsulfonyl-indan-1-one (1.41 g, 3.81 mmol) in dichloromethane (40 mL) was cooled to 0° C. and sparged with nitrogen for 5 minutes. During this time formic acid (430 µL, 11.42 mmol) and triethylamine (1.06 mL, 7.62 mmol) were sequentially added. Once the sparging was complete, RuCl(p-cymene)[(R,R)-Ts-DPEN] (48.5 mg, 0.076 mmol) was added under a continuous stream of nitrogen. The reaction vessel was sealed and put into the refrigerator to react overnight. Volatiles were removed by concentration under reduced pressure. The residue was purified by chromatography on silica using 25-55% EtOAc/hexane. Additional purifications by chromatography on silica using 20-50% EtOAc/hexane were necessary to isolate material of sufficient purity. A flash crystallization was preformed from CHCl$_3$. The sample was dissolved in a minimum of refluxing CHCl$_3$ and then cooled to 0° C. The collected solid was rinsed with CHCl$_3$ and dried under high vacuum overnight to afford Compound 574 as a white solid (550 mg, 39%). From the repeated purifications, Compound 575 was isolated as a white solid. Data for Compound 574: LCMS ESI (+) [M+H]+m/z 373; $^1$H NMR (400 MHz, (CD$_3$)$_2$CO): δ 8.11 (dd, 1H), 7.33 (d, 1H), 5.87 (dd, 1H), 5.65-5.59 (m, 1H), 5.17-5.08 (m, 1H), 3.40-3.26 (m, 2H), 3.27 (s, 3H), 2.98-2.81 (m, 2H), 2.80 (t, 1H). Data for Compound 575: LCMS ESI (+) [M+H]+m/z 373; $^1$H NMR (400 MHz, CDCl$_3$): δ 8.06 (dd, 1H), 6.87 (d, 1H), 5.92 (dd, 1H), 5.78 (td, 1H), 4.86-4.76 (m, 1H), 3.98 (d, 1H), 3.25-3.14 (m, 2H), 3.22 (s, 3H), 2.95-2.78 (m, 2H).

Example 13: Synthesis of 3-(((5R,6S,7S)-5,6-difluoro-7-hydroxy-1-(trifluoromethyl)-6,7-dihydro-5H-cyclopenta[c]pyridin-4-yl)oxy)-5-fluorobenzonitrile (Compound 813)

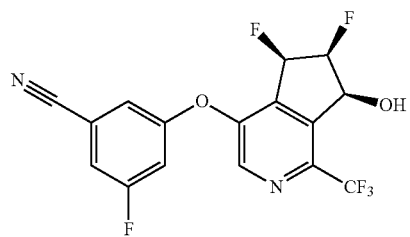 [SMILES: N#Cc1cc(F)cc(Oc2cnc(C(F)(F)F)c3c2[C@@H](F)[C@@H](F)[C@H]3O)c1]

Step A: Preparation of 3-((5-bromo-1-(trifluoromethyl)-5,6-dihydrospiro[cyclopenta[c]pyridine-7,2'-[1,3]dioxolan]-4-yl)oxy)-5-fluorobenzonitrile: A suspension of 3-fluoro-5-[1'-(trifluoromethyl)spiro[1,3-dioxolane-2,7'-5,6-dihydrocyclopenta[c]pyridine]-4'-yl]oxy-benzonitrile (1520 mg, 4 mmol), 2,2'-azobisisobutyronitrile (66 mg, 0.4 mmol), magnesium oxide (483 mg, 12 mmol) and N-bromosuccinimide (925 mg, 5.2 mmol) in 1,2-dichloroethane (40 mL) was sparged with nitrogen for 3 minutes. The vessel was sealed and heated to 80° C. for 3 h. Additional 2,2'-azobisisobutyronitrile (66 mg, 0.4 mmol) and N-bromosuccinimide (925 mg, 5.2 mmol) was added to help drive the reaction to completion. Heating was continued for an additional 1.5 h. The reaction mixture was left at room temperature overnight. MgO was removed by filtration through the celite and rinsing of the filter cake with CH$_2$Cl$_2$. The filtrate was treated with 30 mL of saturated aqueous NaHCO$_3$, stirred for 10 minutes, and extracted with 3×30 mL CH$_2$Cl$_2$. The combined organics were rinsed with 10 mL of brine, dried with MgSO$_4$, filtered, and concentrated to dryness. Purification was achieved by chromatography on silica using 5-25% EtOAc/hexane to afford 3-((5-bromo-1-(trifluoromethyl)-5,6-dihydrospiro[cyclopenta[c]pyridine-7,2'-[1,3]dioxolan]-4-yl)oxy)-5-fluorobenzonitrile as a yellow foam (931 mg, 51%). LCMS ESI (+) (M+H) m/z 459/461.

Step B: Preparation of 3-fluoro-5-((5-hydroxy-1-(trifluoromethyl)-5,6-dihydrospiro[cyclopenta[c]pyridine-7,2'-[1,3]dioxolan]-4-yl)oxy)benzonitrile: A solution of 3-[5'-bromo-1'-(trifluoromethyl)spiro[1,3-dioxolane-2,7'-5,6-dihydrocyclopenta[c]pyridine]-4'-yl]oxy-5-fluoro-benzonitrile (931 mg, 2 mmol) in a mixture of 1,2-dimethoxyethane (15 mL) and water (5 mL) at 25° C. was treated with silver(I) carbonate (1.12 g, 4.1 mmol) and stirred at 85° C. for 8 h. An additional portion of silver(I) carbonate (1.12 g, 4.05 mmol) was added and the reaction mixture left to heat at 85° C. overnight. The reaction mixture was diluted with EtOAc and filtered through celite. The filtrate was washed with water and brine, dried and concentrated. Purification was achieved by chromatography on silica using 20-55% EtOAc/hexane to afford 3-fluoro-5-((5-hydroxy-1-(trifluoromethyl)-5,6-dihydrospiro[cyclopenta[c]pyridine-7,2'-[1,3]dioxolan]-4-yl)oxy)benzonitrile as a yellow solid (295 mg, 37%). LCMS ESI (+) (M+H) m/z 397.

Step C: Preparation of 3-fluoro-5-((5-oxo-1-(trifluoromethyl)-5,6-dihydrospiro[cyclopenta[c]pyridine-7,2'-[1,3]dioxolan]-4-yl)oxy)benzonitrile: A solution of 3-fluoro-5-[5'- hydroxy-1'-(trifluoromethyl)spiro[1,3-dioxolane-2,7'-5,6-dihydrocyclopenta[c]pyridine]-4'-yl]oxy-benzonitrile (296 mg, 0.75 mmol) in dichloromethane (15 mL) at 25° C. was treated with Dess-Martin periodinane (396 mg, 0.93 mmol). After 1 h, an additional 20 mg of Dess-Martin periodinane was added. After stirring for another 30 minutes, the reaction was quenched by the addition of 6 mL of saturated $Na_2S_2O_3$ solution and 6 mL of saturated $NaHCO_3$ solution. The resulting biphase was stirred for 10 minutes. The reaction mixture was poured into 10 mL of water and extracted with 3×20 mL $CH_2Cl_2$. The combined organics were rinsed with 10 mL of brine, dried with $MgSO_4$, filtered, and concentrated to dryness. The product, 3-fluoro-5-((5-oxo-1-(trifluoromethyl)-5,6-dihydrospiro[cyclopenta[c]pyridine-7,2'-[1,3]dioxolan]-4-yl)oxy)benzonitrile (264 mg), was used without further purification. LCMS ESI (+) (M+H) m/z 395.

Step D: Preparation of 3-fluoro-5-((6-fluoro-5-oxo-1-(trifluoromethyl)-5,6-dihydrospiro[cyclopenta[c]pyridine-7,2'-[1,3]dioxolan]-4-yl)oxy)benzonitrile: A solution of 3-fluoro-5-[5'-oxo-1'-(trifluoromethyl)spiro[1,3-dioxolane-2,7'-6H-cyclopenta[c]pyridine]-4'-yl]oxy-benzonitrile (294 mg, 0.75 mmol) and triethylamine (520 μL, 3.7 mmol) in dichloromethane (15 mL) at 0° C. was treated with tert-butyldimethylsilyl trifluoromethane (690 μL, 2.98 mmol) and stirred at 0° C. for 30 minutes. The reaction mixture was left to stir for 5 h during which it was slowly warmed to room temperature. The reaction mixture was poured into 15 mL of saturated $NaHCO_3$, stirred for 10 minutes, and extracted with 3×15 mL $CH_2Cl_2$. The combined organics were rinsed with 10 mL of brine, dried with $MgSO_4$, filtered, and concentrated to dryness. The crude residue was dissolved in 4 mL of acetonitrile and treated with Selectfluor® (264 mg, 0.75 mmol). The reaction mixture was stirred for 3 h at room temperature. Volatiles were removed by concentration under reduced pressure. The mixture was poured into 30 mL of water and extracted with 3×15 mL EtOAc. The combined organics were rinsed with 10 mL of brine, dried with $MgSO_4$, filtered, and concentrated to dryness. Purification was achieved by chromatography on silica using 5-30% EtOAc/hexane to afford 3-fluoro-5-((6-fluoro-5-oxo-1-(trifluoromethyl)-5,6-dihydrospiro[cyclopenta[c]pyridine-7,2'-[1,3]dioxolan]-4-yl)oxy)benzonitrile as a white solid (206 mg, 67%). $^1$H NMR (400 MHz, $CDCl_3$): δ 8.51 (s, 1H), 7.32-7.28 (m, 1H), 7.21-7.18 (m, 1H), 7.13-7.08 (m, 1H), 5.20 (d, 1H), 4.51-4.31 (m, 4H).

Step E: Preparation of 3-fluoro-5-(((5R,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile: A solution of 3-fluoro-5-[6'-fluoro-5'-oxo-1'-(trifluoromethyl) spiro[1,3-dioxolane-2,7'-6H-cyclopenta[c]pyridine]-4'-yl] oxy-benzonitrile (206 mg, 0.5 mmol) in dichloromethane (10 mL) was cooled to 0° C. and sparged with nitrogen for 5 minutes. During this time, formic acid (57 μL, 1.50 mmol) and triethylamine (104 μL, 0.75 mmol) were sequentially added. Once sparging was complete, RuCl(p-cymene)[(S, S)-Ts-DPEN](6.4 mg, 0.01 mmol) was added under a continuous stream of nitrogen. The reaction vessel was sealed and put into the refrigerator to react overnight. Volatiles were removed by concentration under reduced pressure. Purification was achieved by chromatography on silica using 20-45% EtOAc/hexane to afford 3-fluoro-5-(((5R,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile as a clear solid (200 mg, 97%). LCMS ESI (+) (M+H) m/z 415.

Step F: Preparation of (5S,6R)-4-(3-cyano-5-fluorophenoxy)-6-fluoro-1-(trifluoromethyl)-5,6-dihydrospiro[cyclopenta[c]pyridine-7,2'-[1,3]dioxolan]-5-yl 4-nitrobenzoate: A solution of 3-fluoro-5-[(5'R,6'R)-6'-fluoro-5'-hydroxy-1'-(trifluoromethyl)spiro[1,3-dioxolane-2,7'-5,6-dihydrocyclopenta[c]pyridine]-4'-yl]oxy-benzonitrile (200 mg, 0.48 mmol), polymer supported triphenylphosphine (~2.06 mmol/g, 938 mg, 1.93 mmol), and 4-nitrobenzoic acid (323 mg, 1.93 mmol) in tetrahydrofuran (9.7 mL) at 25° C. was treated with diisopropyl azodicarboxylate (371 μL, 1.88 mmol) and stirred for 2 h. The reaction mixture was filtered and the filter cake rinsed with EtOAc. The filtrate was concentrated and purified by chromatography on silica using 10-35% EtOAc/hexane to afford (5S,6R)-4-(3-cyano-5-fluorophenoxy)-6-fluoro-1-(trifluoromethyl)-5,6-dihydrospiro [cyclopenta[c]pyridine-7,2'-[1,3]dioxolan]-5-yl 4-nitrobenzoate as a white solid (221 mg, 81%). LCMS ESI (+) (M+H) m/z 564.

Step G: Preparation of 3-fluoro-5-(((5S,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile: A solution of [(5'S,6'R)-4'-(3-cyano-5-fluoro-phenoxy)-6'-fluoro-1'-(trifluoromethyl)spiro[1,3-dioxolane-2,7'-5,6-dihydrocyclopenta[c]pyridine]-5'-yl] 4-nitrobenzoate (238 mg, 0.42 mmol) in tetrahydrofuran (8 mL) at 25° C. was treated with a solution of freshly prepared lithium hydroxide hydrate (19.5 mg, 0.46 mmol) in water (2.4 mL) and stirred at 25° C. for 30 minutes. An additional portion of lithium hydroxide hydrate (10 mg, 0.24 mmol) in water (1.2 mL) was added and the reaction mixture stirred for 30 minutes. 2.0 mL of saturated $NH_4Cl$ was added to the reaction mixture and volatiles were removed under reduced pressure. The reaction mixture was poured into 10 mL of saturated $NaHCO_3$ and extracted with 3×15 mL EtOAc. The combined organics were rinsed with 10 mL of brine, dried with $MgSO_4$, filtered, and concentrated to dryness. Purification was achieved by chromatography on silica using 5-10% EtOAc/dichloromethane to afford 3-fluoro-5-(((5S,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile as a white solid (137 mg, 78%). LCMS ESI (+) (M+H) m/z 415.

Step H: Preparation of 3-(((5R,6S)-5,6-difluoro-1-(trifluoromethyl)-5,6-dihydrospiro[cyclopenta[c]pyridine-7,2'-[1,3]dioxolan]-4-yl)oxy)-5-fluorobenzonitrile: A solution of 3-fluoro-5-[(5'S,6'R)-6'-fluoro-5'-hydroxy-1'-(trifluoromethyl)spiro[1,3-dioxolane-2,7'-5,6-dihydrocyclopenta[c] pyridine]-4'-yl]oxy-benzonitrile (137 mg, 0.33 mmol) in dichloromethane (6.6 mL) at 25° C. was treated with diethylaminosulfur trifluoride (87.4 μL, 0.66 mmol). The reaction mixture was allowed to stir for 30 minutes. The reaction mixture was quenched by the careful addition of 2 mL of aqueous saturated $NaHCO_3$. The resulting mixture vigorously stirred for 30 minutes. The reaction mixture was poured into 20 mL of water and extracted with 3×10 mL $CH_2Cl_2$. The combined organics were rinsed with 10 mL of brine, dried with $MgSO_4$, filtered, and concentrated to dryness. Purification was achieved by chromatography on silica using 10-30% EtOAc/hexane to afford 3-(((5R,6S)-5,6-difluoro-1-(trifluoromethyl)-5,6-dihydrospiro[cyclopenta[c]pyridine-7,2'-[1,3]dioxolan]-4-yl)oxy)-5-fluorobenzonitrile as a white solid (92.7 mg, 67%). LCMS ESI (+) (M+H) m/z 417.

Step I: Preparation of 3-(((5R,6S,7S)-5,6-difluoro-7-hydroxy-1-(trifluoromethyl)-6,7-dihydro-5H-cyclopenta[c] pyridin-4-yl)oxy)-5-fluorobenzonitrile (Compound 813): A solution of 3-[(5'R,6'S)-5',6'-difluoro-1'-(trifluoromethyl) spiro[1,3-dioxolane-2,7'-5,6-dihydrocyclopenta[c]pyridine]-4'-yl]oxy-5-fluoro-benzonitrile (93 mg, 0.22 mmol) in dichloromethane (5 mL) at 0 C was treated with 70% aqueous perchloric acid (1.0 mL) and stirred at 44 C for 3 h. The reaction mixture was cooled to 0° C., carefully quenched with a mixture of 10 mL of saturated NaHCO$_3$/10 mL of water and extracted with 3×15 mL CH$_2$Cl$_2$. The combined organics were rinsed with 10 mL of brine, dried with MgSO$_4$, filtered, and concentrated to dryness. The intermediate ketone product was used immediately without further purification by dissolving in 4 mL of MeOH, cooling to 0° C., and treating with sodium borohydride (8.4 mg, 0.22 mmol). The reaction stirred for 15 min and was then quenched by the addition of 1 mL of saturated NH$_4$Cl. Volatiles were removed by concentration under reduced pressure. The reaction mixture was poured into 20 mL of water and extracted with 3×10 mL EtOAc. The combined organics were rinsed with 10 mL of brine, dried with MgSO$_4$, filtered, and concentrated to dryness. Purification was achieved by chromatography on silica using 10-45% EtOAc/hexane to afford 3-(((5R,6S,7S)-5,6-difluoro-7-hydroxy-1-(trifluoromethyl)-6,7-dihydro-5H-cyclopenta[c]pyridin-4-yl)oxy)-5-fluorobenzonitrile as a white solid (60 mg, 72%). Retention time HPLC (14 min)=4.18 minutes; LCMS ESI (+) (M+H) m/z 375; $^1$H NMR (400 MHz, CDCl$_3$): δ 8.42 (s, 1H), 7.28 (ddd, 1H), 7.20-7.18 (m, 1H), 7.09 (dt, 1H), 5.92 (dt, 1H), 5.53-5.46 (m, 1H), 5.19 (ddt, 1H), 2.66 (ddd, 1H).

Example 14: Synthesis of (5R,6S,7S)-4-(3,3-difluorocyclobutoxy)-5,6-difluoro-1-(trifluoromethyl)-6,7-dihydro-5H-cyclopenta[c]pyridin-7-ol (Compound 828)

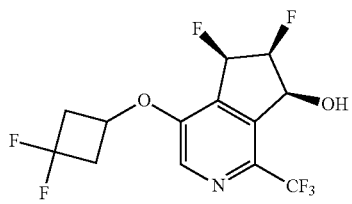 [SMILES: O[C@H]1c2c(C(F)(F)F)ncc(OC3CC(F)(F)C3)c2[C@@H](F)[C@H]1F]

Step A: Preparation of 4-(3,3-difluorocyclobutoxy)-1-(trifluoromethyl)-5,6-dihydrospiro[cyclopenta[c]pyridine-7,2'-[1,3]dioxolane]: A solution of 1'-(trifluoromethyl)spiro[1,3-dioxolane-2,7'-5,6-dihydrocyclopenta[c]pyridine]-4'-ol (1.9 g, 7.27 mmol), (3,3-difluorocyclobutyl) 4-methylbenzenesulfonate (2.86 g, 10.9 mmol), potassium iodide (1.81 g, 10.9 mmol) and potassium carbonate (2.0 g, 14.6 mmol) in acetonitrile (20 mL) was stirred at 100° C. overnight. The reaction mixture was concentrated to dryness, diluted with ethyl acetate (100 mL), washed with water (100 mL) and brine (20 mL). The organic phase was collected, dried over anhydrous Na$_2$SO$_4$, filtered and the filtrate was concentrated. Purification was achieved by chromatography on silica using 10-20% EtOAc/petroleum ether to afford 4'-(3,3-difluorocyclobutoxy)-1'-(trifluoromethyl)spiro[1,3-dioxolane-2,7'-5,6-dihydrocyclopenta[c]pyridine] as a white solid (1.00 g, 2.85 mmol, 39%). LCMS ESI (+) (M+H) m/z 352. (The Mitsunobu reaction can also be used to derivatize the 1'-(trifluoromethyl)spiro[1,3-dioxolane-2,7'-5,6-dihydrocyclopenta[c]pyridine]-4'-ol.)

Step B: Preparation of 5-bromo-4-(3,3-difluorocyclobutoxy)-1-(trifluoromethyl)-5,6-dihydrospiro[cyclopenta[c]pyridine-7,2'-[1,3]dioxolane]: A solution of 4'-(3,3-difluorocyclobutoxy)-1'-(trifluoromethyl)spiro[1,3-dioxolane-2,7'-5,6-dihydrocyclopenta[c]pyridine] (1.00 g, 2.85 mmol), 2,2'-azobisisobutyronitrile (94 mg, 0.57 mmol), NaHCO$_3$ (420 mg, 5.0 mmol) and 1-bromopyrrolidine-2,5-dione (1.27 g, 7.12 mmol) in 1,2-dichloroethane (20 mL) was sparged with nitrogen for 3 minutes. The vessel was sealed and heated to 80° C. for 1 h. The reaction mixture was poured into 30 mL of saturated aqueous Na$_2$SO$_3$ and extracted with 3×30 mL CH$_2$Cl$_2$. The combined organics were rinsed with 20 mL of brine, dried with MgSO$_4$, filtered, and concentrated to dryness. Purification was achieved by chromatography on silica using 5-25% EtOAc/hexane to afford 5'-bromo-4'-(3,3-difluorocyclobutoxy)-1'-(trifluoromethyl)spiro[1,3-dioxolane-2,7'-5,6-dihydrocyclopenta[c]pyridine] as an off-white solid (650 mg, 1.5 mmol, 53%). $^1$H NMR (400 MHz, CDCl$_3$): δ 8.11 (s, 1H), 5.36-5.31 (m, 1H), 4.98-4.88 (m, 1H), 4.36-4.21 (m, 2H), 4.16-4.07 (m, 2H), 3.26-3.13 (m, 2H), 2.96-2.71 (m, 4H).

Step C: Preparation of 4-(3,3-difluorocyclobutoxy)-1-(trifluoromethyl)-5,6-dihydrospiro[cyclopenta[c]pyridine-7,2'-[1,3]dioxolan]-5-ol: A solution of 5'-bromo-4'-(3,3-difluorocyclobutoxy)-1'-(trifluoromethyl)spiro[1,3-dioxolane-2,7'-5,6-dihydrocyclopenta[c]pyridine] (650 mg, 1.5 mmol) in a mixture of 1,2-dimethoxyethane (15 mL) and water (5 mL) was treated with silver carbonate (417 mg, 1.5 mmol) and stirred at 85° C. overnight. The mixture was diluted with EtOAc and filtered through celite. The filtrate was concentrated to remove the dimethoxyethane. The residue was re-suspended in 60 mL of 1:1 EtOAc/H$_2$O and extracted with 3×15 mL EtOAc. The combined organics were rinsed with 10 mL of brine, dried with MgSO$_4$, filtered, and concentrated to dryness. Purification was achieved by chromatography on silica using 10-30% EtOAc/hexane to afford 4'-(3,3-difluorocyclobutoxy)-1'-(trifluoromethyl)spiro[1,3-dioxolane-2,7'-5,6-dihydrocyclopenta[c]pyridine]-5'-ol as a solid (280 mg, 50%). $^1$H NMR (400 MHz, CDCl$_3$): δ 8.11 (s, 1H), 5.39-5.32 (m, 1H), 4.97-4.87 (m, 1H), 4.33-4.20 (m, 2H), 4.17-4.04 (m, 2H), 3.27-3.13 (m, 2H), 2.96-2.75 (m, 2H), 2.63 (dd, 1H), 2.53 (d, 1H), 2.28 (dd, 1H).

Step D: Preparation of 4-(3,3-difluorocyclobutoxy)-1-(trifluoromethyl)spiro[cyclopenta[c]pyridine-7,2'-[1,3]dioxolan]-5(6H)-one: A solution of 4'-(3,3-difluorocyclobutoxy)-1'-(trifluoromethyl)spiro[1,3-dioxolane-2,7'-5,6-dihydrocyclopenta[c]pyridine]-5'-ol (280 mg, 0.76 mmol) in dichloromethane (10 mL) at 25° C. was treated with Dess-Martin periodinane (500 mg, 1.18 mmol). After 2 h, the reaction was quenched by the addition of 10 mL of saturated Na$_2$S$_2$O$_3$ solution and 10 mL of saturated NaHCO$_3$ solution. The resulting biphase stirred for 10 minutes. The reaction mixture was poured into 20 mL of water and extracted with 3×20 mL CH$_2$Cl$_2$. The combined organics were rinsed with 10 mL of brine, dried with MgSO$_4$, filtered, and concentrated to dryness to afford 4'-(3,3-difluorocyclobutoxy)-1'-(trifluoromethyl)spiro[1,3-dioxolane-2,7'-6H-cyclopenta[c]pyridine]-5'-one as a solid (270 mg, 97%) that was used without further purification. LCMS ESI (+) (M+H) m/z 366.

Step E: Preparation of 4-(3,3-difluorocyclobutoxy)-6-fluoro-1-(trifluoromethyl)spiro[cyclopenta[c]pyridine-7,2'-[1,3]dioxolan]-5(6H)-one: A solution of 4'-(3,3-difluorocyclobutoxy)-1'-(trifluoromethyl)spiro[1,3-dioxolane-2,7'-6H-cyclopenta[c]pyridine]-5'-one (270 mg, 0.74 mmol) and triethylamine (410 µL, 3 mmol) in dichloromethane (10 mL) at 0° C. was treated with tert-butyl-dimethyl-(trifluoromethylsulfonyl)silane (480 µL, 2.2 mmol) and stirred at 0° C. for 30 minutes. The reaction mixture was left to stir overnight at room temperature. The reaction mixture was poured into 10 mL of saturated NaHCO$_3$, stirred for 10 minutes, and extracted with 3×15 mL CH$_2$Cl$_2$. The combined organics were rinsed with 10 mL of brine, dried with MgSO$_4$, filtered, and concentrated to dryness. The unpurified residue was dissolved in acetonitrile (10 mL) and treated with Selectfluor® (322 mg, 0.92 mmol). The reaction stirred for 6 h at room temperature. Volatiles were removed by concentration under reduced pressure. The reaction mixture was poured into 30 mL of water and extracted with 3×15 mL EtOAc. The combined organics were rinsed with 10 mL of brine, dried with MgSO$_4$, filtered, and concentrated to dryness. Purification was achieved by chromatography on silica using 5-20% EtOAc/hexane to afford 4'-(3,3-difluorocyclobutoxy)-6'-fluoro-1'-(trifluoromethyl)spiro[1,3-dioxolane-2,7'-6H-cyclopenta[c]pyridine]-5'-one as a white solid (180 mg, 56%). $^1$H NMR (400 MHz, CDCl$_3$): δ 8.35 (s, 1H), 5.13 (d, 1H), 5.01-4.91 (m, 1H), 4.47-4.38 (m, 1H), 4.38-4.26 (m, 3H), 3.30-3.14 (m, 2H), 3.04-2.86 (m, 2H).

Step F: Preparation of (5R,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-ol: A solution of 4'-(3,3-difluorocyclobutoxy)-6'-fluoro-1'-(trifluoromethyl) spiro[1,3-dioxolane-2,7'-6H-cyclopenta[c]pyridine]-5'-one (180 mg, 0.47 mmol) in dichloromethane (10 mL) was cooled to 0° C. and sparged with nitrogen for 5 minutes. During this time formic acid (53.1 μL, 1.4 mmol) and triethylamine (98.2 uL, 0.70 mmol) were sequentially added. Once sparging was complete, RuCl(p-cymene)[(S,S)-Ts-DPEN] (15 mg, 0.023 mmol) was added under a continuous stream of nitrogen. The reaction vessel was sealed and put into the refrigerator to react overnight. Volatiles were removed by concentration under reduced pressure. Purification was achieved by chromatography on silica using 10-30% EtOAc/hexane to afford (5'R,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-ol as a clear solid (152 mg, 84%). LCMS ESI (+) (M+H) m/z 386.

Step G: Preparation of (5S,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-yl 4-nitrobenzoate: A solution of (5'R,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-ol (124 mg, 0.32 mmol), polymer supported triphenylphosphine (~2.06 mmol/g, 627 mg, 1.29 mmol), and 4-nitrobenzoic acid (216 mg, 1.29 mmol) in tetrahydrofuran (3.3 mL) was treated with diisopropyl azodicarboxylate (248 μL, 1.26 mmol) and stirred at 25° C. for 2 h. The reaction mixture was filtered and the filter cake rinsed with 30 mL EtOAc. The filtrate was concentrated and purified by chromatography on silica using 10-25% EtOAc/hexane to afford (5S,6R)-4-(3,3-difluorocyclobutoxy)-6-fluoro-1-(trifluoromethyl)-5,6-dihydrospiro [cyclopenta[c]pyridine-7,2'-[1,3]dioxolan]-5-yl 4-nitrobenzoate as a white solid (160 mg, 93%). LCMS ESI (+) (M+H) m/z 535.

Step H: Preparation of (5S,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-ol: A solution of [(5'S,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-yl] 4-nitrobenzoate (194 mg, 0.36 mmol) in tetrahydrofuran (7 mL) at 25° C. was treated with a solution of freshly prepared hydroxylithium hydrate (16.8 mg, 0.4 mmol) in water (2.1 mL) and stirred at 25° C. for 30 minutes. An additional portion of hydroxylithium hydrate (8.4 mg, 0.20 mmol) in water (1.0 mL) was added and the reaction mixture stirred for another 30 minutes. Saturated NH$_4$Cl (0.5 mL) was added and volatiles were removed under reduced pressure. The reaction mixture was poured into 10 mL of saturated NaHCO$_3$ and extracted with 3×15 mL EtOAc. The combined organics were rinsed with 10 mL of brine, dried with MgSO$_4$, filtered, and concentrated to dryness. Purification was achieved by chromatography on silica using 10-35% EtOAc/hexane to afford (5S,6R)-4-(3, 3-difluorocyclobutoxy)-6-fluoro-1-(trifluoromethyl)-5,6-dihydrospiro[cyclopenta[c]pyridine-7,2'-[1,3]dioxolan]-5-ol as a white solid (74 mg, 53%). LCMS ESI (+) (M+H) m/z 386.

Step I: Preparation of (5R,6S)-4-(3,3-difluorocyclobutoxy)-5,6-difluoro-1-(trifluoromethyl)-5,6-dihydrospiro[cyclopenta[c]pyridine-7,2'-[1,3]dioxolane]: A solution of (5'S,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-ol (74 mg, 0.19 mmol) in dichloromethane (3.8 mL) at 25° C. was treated with diethylaminosulfur trifluoride (51 μL, 0.38 mmol). The reaction mixture was allowed to stir for 30 minutes. The reaction mixture was quenched by the careful addition of 1 mL of aqueous saturated NaHCO$_3$. The resulting mixture stirred for 30 minutes, poured into 20 mL of water and extracted with 3×15 mL CH$_2$Cl$_2$. The combined organics were rinsed with 10 mL of brine, dried with MgSO$_4$, filtered, and concentrated to dryness. Purification was achieved by chromatography on silica using 5-25% EtOAc/hexane to afford (5R,6S)-4-(3,3-difluorocyclobutoxy)-5,6-difluoro-1-(trifluoromethyl)-5,6-dihydrospiro[cyclopenta[c]pyridine-7,2'-[1,3]dioxolane] as a white solid (72 mg, 97%). LCMS ESI (+) (M+H) m/z 388.

Step J: Preparation of (5R,6S,7S)-4-(3,3-difluorocyclobutoxy)-5,6-difluoro-1-(trifluoromethyl)-6,7-dihydro-5H-cyclopenta[c]pyridin-7-ol (Compound 828): A solution of (5'R,6'S)-4'-(3,3-difluorocyclobutoxy)-5',6'-difluoro-1'-(trifluoromethyl)spiro[1,3-dioxolane-2,7'-5,6-dihydrocyclopenta[c]pyridine] (72 mg, 0.19 mmol) in dichloromethane (4.0 mL) at 0° C. was treated with 70% aqueous perchloric acid (800 μL). The reaction mixture was heated to 44° C. for 5 h. The reaction mixture was cooled to 0° C., carefully quenched with a mixture of 10 mL of saturated NaHCO$_3$/10 mL of water and extracted with 3×15 mL CH$_2$Cl$_2$. The combined organics were rinsed with 10 mL of brine, dried with MgSO$_4$, filtered, and concentrated to dryness. The product was used immediately without further purification by dissolving in 2 mL of MeOH, cooling to 0° C., and treating with sodium borohydride (7.0 mg, 0.19 mmol). The reaction stirred for 15 min and was then quenched by the addition of 1 mL of saturated NH$_4$Cl. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 10-40% EtOAc/hexane to afford (5R,6S,7S)-4-(3,3-difluorocyclobutoxy)-5,6-difluoro-1-(trifluoromethyl)-6,7-dihydro-5H-cyclopenta[c] pyridin-7-ol as a white solid (53 mg, 83%). Retention time HPLC (14 min)=3.37 minutes; LCMS ESI (+) (M+H) m/z 346; $^1$H NMR (400 MHz, CDCl$_3$): δ 8.24 (s, 1H), 5.95 (ddd, 1H), 5.47-5.41 (m, 1H), 5.07 (ddt, 1H), 4.97-4.88 (m, 1H), 3.30-3.15 (m, 2H), 2.99-2.79 (m, 2H), 2.54-2.49 (m, 1H).

Example 15: Identification of Predictive Biomarkers for Response to a HIF-2α Inhibitor Tumor fragments were surgically removed from human subjects, then propagated orthotopically under the renal capsule of 4-6 week old NOD/SCID mice. Tumors that achieved stable growth were used in efficacy studies, wherein fragments of ~64 mm³ were implanted subcutaneously in the left flank of NOC/SCID mice. When the xenografts reached about 300 to 500 mm³ in size, the tumor bearing mice were stratified into two groups (n=3-5) for each of 22 mouse xenografts derived from clear cell renal cell carinoma (ccRCC) patient specimens. Groups of 3 to 5 mice were then treated with vehicle (10% ethanol, 30% polyethylene glycol 400, 60% MCT (0.5% methyl cellulose, 0.5% Tween 80) or compound 15 (100 mg/kg in vehicle) administered by oral gavage twice daily for four weeks. Tumor sizes were measured twice a week in two dimensions using a digital caliper, and the volume expressed in mm³ using the formula Volume=l×w×h, where l is the largest dimension of the tumor, w is the largest diameter perpendicular to l, and h is maximal height of the tumor. Compound 15 was tested in a total of 22 groups of mouse xenografts derived from ccRCC patient specimens. Among these tumors, 10 models were highly sensitive to growth inhibition by Compound 15, with growth inhibition of between 90 and 150% observed (Table 2). Moderate sensitivity (40 to 65% growth inhibition) was found in an additional 5 models, while the remaining 7 models were insensitive (less than 40% growth inhibition) to Compound 15. Understanding the molecular basis for sensitivity or resistance of the tumor models to Compound 15 required the availability of the gene expression profiles of the tumors. To that end, 5 sensitive and 4 resistant models were subjected to RNA sequencing (RNA-seq). Tumors that were selected for the analysis are indicated in Table 2.

RNA was isolated from pairs of tumors treated with either vehicle or Compound 15 following the 28-day study. cDNA library preparation and sequencing was performed at the New York Genome Center. Sequencing was done on a HiSeq 2500 (Illumina) using SBS kit v4 as recommended by the manufacturer. Sequencing reads were aligned to a combined index of human and mouse sequences using STAR algorithm v2.4.0c (see Dobin A et al., Bioinformatics (2013) 29:15-21). This allowed the mouse sequences to be removed. The remaining human sequences were aligned to the NCBI human reference genome hg37 using STAR aligner v2.3.1z. The sequencing reads, mapped to GenCode v19, were then quantified using HTSeq (see Anders S et al., Bioinformatics (2014) 31:166-69). Analysis of differential gene expression between sensitive and resistant tumors was performed using the edgeR software package (see Robinson M D et al., Bioinformatics (2010) 26:139-40).

Table 2 shows a list of the tumor xenografts that were derived from patients with ccRCC and treated with either vehicle or a HIF-2α inhibitor (Compound 15). The tumors are categorized by their response to treatment with Compound 15. Tumors marked with "@" were derived from the same patient (a primary tumor or a lymph node metastasis). The mutation status of three genes that are frequently mutated in ccRCC (VHL, BRCA associated protein 1 (BAP1), and polybromo 1 (PBRM1)) is provided for each tumor sample. The tumors that were subjected to RNA sequencing are noted. Abbreviations used are wt=wild type; mut=mutant; unk=unknown; GI=growth inhibition; IHC=immunohistochemistry; tRCC=translocation renal cell carcinoma; and Y=yes.

TABLE 2

| Response | Tumor | Histology | VHL status | BAP1 (IHC) | PBRM1 (IHC) | Relative GI % (p value) | RNA-seq |
|---|---|---|---|---|---|---|---|
| Sensitive | 1 | ccRCC | mut | mut | wt | 87 (0.0003) | |
| | 2 | ccRCC | mut | wt | wt | 98 (<0.0001) | Y |
| | 3 | ccRCC | wt | wt | wt | 134 (<0.0001) | Y |
| | 4 | ccRCC | mut | wt | mut | 112 (<0.0001) | |
| | 5 | ccRCC | wt | mut | wt | 103 (<0.0001) | Y |
| | 6 | ccRCC | mut | wt | wt | 109 (<0.0001) | Y |
| | 7 | ccRCC | wt | wt | wt | 110 (<0.0001) | Y |
| | 8 | ccRCC | wt | mut | wt | 156 (0.0032) | |
| | 9 | ccRCC | mut | mut | mut | 91 (<0.0001) | |
| | 10 | ccRCC | mut | mut | unk | 129 (0.0007) | |
| Intermediate | 11 | tRCC | unk | wt | wt | 43 (0.0144) | |
| | 12 | ccRCC | mut | wt | mut | 45 (0.0018) | |
| | 13@ | ccRCC | wt | wt | wt | 44 (0.0273) | |
| | 14@ | ccRCC | wt | wt | wt | 54 (0.0206) | |
| | 15 | ccRCC | wt | mut | unk | 67 (0.0030) | |
| Resistant | 16 | Unclassified | wt | wt | wt | 0 (0.0119) | Y |
| | 17 | ccRCC | mut | mut | wt | 39 (0.11) | |
| | 18 | ccRCC | mut | wt | wt | 29 (0.30) | Y |
| | 19 | Unclassified | wt | wt | mut | 29 (0.11) | |
| | 20 | ccRCC | mut | wt | wt | 39 (0.89) | Y |
| | 21 | ccRCC | wt | wt | wt | 20 (0.76) | Y |
| | 22 | Unclassified | wt | unk | unk | 2 (0.68) | |

RNA samples were sequenced to a depth of more than 80 million reads, thus achieving sufficient coverage for the assessment of differential gene expression among the samples (Table 3). Analysis of the gene expression data of vehicle-treated tumors revealed that a total of 3,542 genes were differentially expressed between the tumors that are resistant or sensitive to Compound 15, with roughly equal numbers of genes that were expressed at higher or reduced levels in the two groups (Table 4). FIG. 1 illustrates relative read counts of four genes that are differentially expressed in tumors that are sensitive or resistant to Compound 15 (A074091.13, CORO6, C1QL1, and CPE). The vehicle-treated tumor samples of FIG. 1 are listed in the same order as the vehicle-treated samples shown in Table 3, wherein samples 1-12 (corresponding to 2-V4352 to 7-C5108) were sensitive to treatment and samples 13-23 (corresponding to 16-V5230 to 21-V4777) were resistant to treatment. Treatment with Compound 15 resulted in the down-regulation of 297 genes and the up-regulation of 195 genes in the tumors that are inhibited in growth.

Table 3 shows sequencing read counts from individual tumor samples subjected to sequencing. The samples are identified by their tumor model numbers (see Table 2), the treatment group assignment (V=vehicle; P=Compound 15), and identification numbers assigned to individual mice.

TABLE 3

| Samples | Read Count | Samples | Read Count |
|---|---|---|---|
| 2-P4340 | 131,078,351 | 16-P5231 | 150,980,881 |
| 2-P4342 | 127,945,953 | 16-P5240 | 146,751,739 |
| 3-P3281 | 121,045,606 | 16-P5241 | 144,959,159 |
| 3-P3287 | 128,070,443 | 18-P4512 | 151,324,826 |
| 3-P3297 | 138,586,535 | 18-P4531 | 144,982,512 |
| 5-P4241 | 162,092,320 | 20-P3207 | 142,380,928 |
| 5-P4244 | 146,116,441 | 20-P3210 | 164,412,241 |
| 5-P4250 | 140,629,410 | 20-P3214 | 169,970,555 |
| 6-P5172 | 88,374,928 | 21-P4734 | 165,472,466 |
| 7-P5103 | 120,921,569 | 21-P4735 | 154,474,148 |
| 7-P5104 | 108,148,316 | 21-P4736 | 173,988,590 |
| 7-P5109 | 117,009,388 | 16-V5230 | 159,863,685 |
| 2-V4352 | 128,119,810 | 16-V5235 | 146,783,488 |
| 2-V4377 | 148,456,002 | 16-V5239 | 144,377,378 |
| 3-V3290 | 144,464,174 | 18-V4519 | 146,536,970 |
| 3-V3294 | 161,750,684 | 18-V4524 | 148,798,769 |
| 3-V3298 | 152,823,172 | 20-V3211 | 162,273,604 |
| 5-V4232 | 156,310,574 | 20-V3218 | 123,559,977 |
| 5-V4236 | 150,155,973 | 20-V3224 | 151,672,989 |
| 5-V4237 | 148,496,505 | 21-V4743 | 181,173,536 |
| 6-V5170 | 130,903,402 | 21-V4745 | 156,598,756 |
| 7-V5105 | 123,966,544 | 21-V4777 | 164,427,358 |
| 7-V5107 | 123,347,998 | | |
| 7-V5108 | 112,341,672 | | |

Additional statistical filters were applied to the genes that were differentially expressed between resistant and sensitive tumors, yielding a list of 76 protein-encoding genes that meet a stringent cutoff for statistical significance (Wilcoxon $p<0.01$). The list includes genes that were expressed at 2-fold or greater in resistant or sensitive tumors. The expression data for these genes were inspected to ensure that they conformed to the selection criteria, and 25 genes were removed because the apparent differential expression or magnitude of regulation was caused by large absolute variation in a single sample. Further examination of the data set also resulted in the inclusion of 24 additional genes that missed the statistical cutoff, but that otherwise behaved in a manner comparable to that of most of the genes that resulted from the edgeR analysis, yielding a total of 75 genes (Table 4). The relative expression of these genes, or a subset of the genes, can be used to predict sensitivity of ccRCC patients to treatment with a HIF-2α inhibitor.

Table 4 provides a list of genes that are differentially expressed in ccRCC tumors. These genes, or a subset thereof, may be used to predict sensitivity or resistance to HIF-2α inhibition. The list includes genes that are more highly expressed in tumors that are sensitive (S) or resistant (R) to treatment with a HIF-2α inhibitor, e.g. Compound 15. The fold difference in expression of each gene is shown as log 2 of the ratio of expression in resistant (R) tumors relative to that in sensitive (S) tumors.

TABLE 4

| Gene | Up in | $\log_2(R/S)$ |
|---|---|---|
| AC074091.13 | R | 4.8 |
| ANO7 | R | 1.8 |
| AVPR2 | S | -7.4 |
| BCL2L11 | R | 1.3 |
| BRCC3 | R | 1.4 |
| C1QL1 | S | -3.0 |
| CAMK2D | R | 2.1 |
| CHRDL2 | S | -7.9 |

TABLE 4-continued

| Gene | Up in | $\log_2(R/S)$ |
|---|---|---|
| CHST1 | S | -6.0 |
| CORO6 | R | 4.0 |
| CPE | S | -5.1 |
| CRYM | R | 1.4 |
| CXCR4 | S | -2.7 |
| DEK | R | 1.2 |
| EPAS1 | S | -1.8 |
| EPO | S | -9.7 |
| EXOG | R | 1.3 |
| EZH2 | R | 1.1 |
| FAM180A | S | -6.6 |
| FAM65B | R | 7.6 |
| FAM65C | R | 6.1 |
| GFRA2 | S | -7.7 |
| GLI1 | S | -4.9 |
| HAGHL | R | 2.7 |
| HIF1A | R | 2.0 |
| HMGA1 | R | 3.2 |
| HRH2 | S | -8.4 |
| HSPB7 | S | -4.7 |
| IGFBP1 | S | -9.2 |
| INHBB | S | -4.9 |
| ITGB8 | R | 2.0 |
| KCNIP3 | R | 4.7 |
| KLHL3 | R | 4.2 |
| KNDC1 | S | -4.3 |
| LAMB1 | R | 2.0 |
| LOX | S | -2.8 |
| LYPD1 | R | 5.9 |
| MCAM | R | 5.7 |
| MCIDAS | R | 3.0 |
| MEST | R | 5.8 |
| MRS2 | R | 1.0 |
| NFASC | S | -6.6 |
| NPTX1 | S | -8.6 |
| PASK | R | 1.3 |
| PFN2 | R | 1.1 |
| PHYHIP | R | 3.0 |
| PICALM | R | 1.2 |
| PKNOX2 | S | -4.0 |
| PLAG1 | R | 3.6 |
| POSTN | S | -4.1 |
| PPA2 | R | 1.1 |
| PPAPDC3 | R | 9.0 |
| PRICKLE1 | R | 5.2 |
| PRR5 | R | 1.9 |
| PTHLH | S | -6.4 |
| PTPRJ | R | 1.3 |
| RASGEF1B | R | 4.2 |
| RDH13 | S | -2.5 |
| RGL2 | R | 1.0 |
| SLC36A4 | R | 1.5 |
| SLC6A3 | S | -7.6 |
| SLCO5A1 | R | 2.3 |
| SLITRK4 | R | 4.1 |
| SORCS3 | S | -11.0 |
| ST3GAL5 | R | 1.9 |
| SVIP | R | 2.2 |
| TBC1D4 | R | 1.9 |
| TMEM30B | S | -10.0 |
| TPST2 | S | -2.5 |
| VGLL4 | R | 1.2 |
| WFIKKN1 | S | -5.1 |
| ZKSCAN3 | R | 1.3 |
| ZKSCAN8 | R | 1.0 |
| ZSCAN16 | R | 1.7 |
| ZSCAN9 | R | 1.1 |

Table 5 provides a list of genes that are up-regulated in ccRCC tumors that are sensitive (5) to treatment with a HIF-2α inhibitor. These genes, or a subset thereof, may be used to predict sensitivity or resistance to HIF-2α inhibition.

TABLE 5

| Gene | Up in | log$_2$(R/S) |
| --- | --- | --- |
| AVPR2 | S | −7.4 |
| C1QL1 | S | −3.0 |
| CHRDL2 | S | −7.9 |
| CHST1 | S | −6.0 |
| CPE | S | −5.1 |
| CXCR4 | S | −2.7 |
| EPAS1 | S | −1.8 |
| EPO | S | −9.7 |
| FAM180A | S | −6.6 |
| GFRA2 | S | −7.7 |
| GLI1 | S | −4.9 |
| HRH2 | S | −8.4 |
| HSPB7 | S | −4.7 |
| IGFBP1 | S | −9.2 |
| INHBB | S | −4.9 |
| KNDC1 | S | −4.3 |
| LOX | S | −2.8 |
| NFASC | S | −6.6 |
| NPTX1 | S | −8.6 |
| PKNOX2 | S | −4.0 |
| POSTN | S | −4.1 |
| PTHLH | S | −6.4 |
| RDH13 | S | −2.5 |
| SLC6A3 | S | −7.6 |
| SORCS3 | S | −11.0 |
| TMEM30B | S | −10.0 |
| TPST2 | S | −2.5 |
| WFIKKN1 | S | −5.1 |

Table 6 provides a list of genes that are up-regulated in ccRCC tumors that are resistant (R) to treatment with a HIF-2α inhibitor. These genes, or a subset thereof, may be used to predict sensitivity or resistance to HIF-2α inhibition.

TABLE 6

| Gene | Up in | log$_2$(R/S) |
| --- | --- | --- |
| AC074091.13 | R | 4.8 |
| ANO7 | R | 1.8 |
| BCL2L11 | R | 1.3 |
| BRCC3 | R | 1.4 |
| CAMK2D | R | 2.1 |
| CORO6 | R | 4.0 |
| CRYM | R | 1.4 |
| DEK | R | 1.2 |
| EXOG | R | 1.3 |
| EZH2 | R | 1.1 |
| FAM65B | R | 7.6 |
| FAM65C | R | 6.1 |
| HAGHL | R | 2.7 |
| HIF1A | R | 2.0 |
| HMGA1 | R | 3.2 |
| ITGB8 | R | 2.0 |
| KCNIP3 | R | 4.7 |
| KLHL3 | R | 4.2 |
| LAMB1 | R | 2.0 |
| LYPD1 | R | 5.9 |
| MCAM | R | 5.7 |
| MCIDAS | R | 3.0 |
| MEST | R | 5.8 |
| MRS2 | R | 1.0 |
| PASK | R | 1.3 |
| PFN2 | R | 1.1 |
| PHYHIP | R | 3.0 |
| PICALM | R | 1.2 |
| PLAG1 | R | 3.6 |
| PPA2 | R | 1.1 |
| PPAPDC3 | R | 9.0 |
| PRICKLE1 | R | 5.2 |
| PRR5 | R | 1.9 |
| PTPRJ | R | 1.3 |
| RASGEF1B | R | 4.2 |
| RGL2 | R | 1.0 |
| SLC36A4 | R | 1.5 |
| SLCO5A1 | R | 2.3 |

TABLE 6-continued

| Gene | Up in | log$_2$(R/S) |
| --- | --- | --- |
| SLITRK4 | R | 4.1 |
| ST3GAL5 | R | 1.9 |
| SVIP | R | 2.2 |
| TBC1D4 | R | 1.9 |
| VGLL4 | R | 1.2 |
| ZKSCAN3 | R | 1.3 |
| ZKSCAN8 | R | 1.0 |
| ZSCAN16 | R | 1.7 |
| ZSCAN9 | R | 1.1 |

Table 7 provides a list of pathways that are associated with genes that predict sensitivity or resistance to HIF-2α inhibition. Pathway analysis was performed using CytoKegg (www.cytoscape.org) and refined by manual reference to published literature (www.ncbi.nlm.nih.gov/pubmed). These pathways, or a subset thereof, may be used to predict sensitivity or resistance to HIF-2α inhibition.

TABLE 7

| Pathway | Up in |
| --- | --- |
| Hypoxia signaling | S |
| DNA damage response | R |
| GPCR signaling | S |
| Insulin signaling | R |
| Non-canonical Wnt signaling | R |
| Dopaminiergic signaling | S |
| Ion and solute transport | R |
| Neurotrophic growth factor signaling | S |

Example 16: Selection of Treatment Following Gene Expression Analysis of a Tumor Sample RNA is extracted from a tumor biopsy, e.g., a fresh biopsy obtained from surgical resection or fine needle aspiration. In some examples, the tumor is fixed or paraffin-embedded. RNA is extracted using an established method, e.g., with the use of RNAlater (Invitrogen) to solubilize the RNA from a fresh or frozen sample, or with the use of a commercially available RNA extraction kit. The expression of one or more biomarkers described in Example 15 is detected and/or quantified using a suitable method known in the art, including, for example, quantitative polymerase chain reaction (qPCR), hybridization to a high-density array of synthesized oligonucleotide or cDNA probes immobilized on a solid matrix, or direct sequence determination. In some examples, the RNA is converted into complementary DNA (cDNA) sequences by reverse transcription using a recombinant reverse transcriptase. The cDNA prepared from the RNA samples may be subjected to amplification using the polymerase chain reaction before detection. Protein products encoded by one or more biomarkers described in Example 15 may be detected and/or quantified to assess expression levels. This is done using any protein detection method known in the art, including, for example, mass spectrometry, reverse phase chromatography, immunoblot, immunohistochemistry, immunofluorescence microscopy, or methods of antibody-mediated detection that involve mobilization of an antibody to the gene product to a solid support.

Expression of each of the analyzed biomarkers is quantified in accordance with a standard protocol appropriate to the detection method. A responder score or weighted probability is then calculated. In some examples, the responder score is calculated by taking the difference between the number of genes that predict sensitivity to treatment with a HIF-2α inhibitor that have increased expression in responders and the number of genes that predict the same that have decreased expression in non-responders. The score is then normalized against a range of 0 to 100 for comparison across tumor examples. Alternatively or additionally, gene expression data is used to classify a test sample according to a method described in van't Veer, L. J. et al., J Clin Oncol (2005) 23:1631-35; Parker, J. S. et al., J Clin Oncol (2009) 27:1160-67; or Nielsen, T. et al., BMC Cancer (2014) 14:177-91. If the tumor is predicted to respond to treatment with a HIF-2α inhibitor, then an effective dose of a suitable HIF-2α inhibitor is administered to the subject.

Many of the biomarkers described in Example 15 are expressed widely in many different types of cancer, including, for example, lung, colon, pancreatic, liver, head and neck, and stomach cancer. At least a subset of these biomarkers may be used to identify patients with other tumor types who will respond to treatment with a HIF-2α inhibitor.

Example 17: Use of a NanoString nCounter Assay to Measure Differential Gene Expression in Tumors that are Sensitive or Resistant to Treatment with Compound 15

Further evaluation of the gene expression signature derived from RNA sequencing (RNA-seq) was performed by analyzing mRNA isolated from untreated tumors using a NanoString nCounter code set. A custom code set for detecting mRNA encoded by the 75 candidate genes was prepared and the sequences used in the code set are listed in Table 8.

TABLE 8

Probes used in NanoString nCounter code set

| Gene symbol | Accession | Probe position |
|---|---|---|
| AC074091.13 | LN607913.1 | 1702-1801 |
| ANO7 | NM_001001666.3 | 491-590 |
| AVPR2 | NM_000054.4 | 1063-1162 |
| BCL2L11 | NM_138621.4 | 3079-3178 |
| BRCC3 | NM_024332.3 | 2814-2913 |
| C1QL1 | NM_006688.3 | 1259-1358 |
| CAMK2D | NM_001221.3 | 2349-2448 |
| CHRDL2 | NM_001278473.1 | 813-912 |
| CHST1 | NM_003654.5 | 2526-2625 |
| CORO6 | NM_032854.3 | 1068-1167 |
| CPE | NM_001873.2 | 1409-1508 |
| CRYM | NM_001014444.2 | 905-1004 |
| CXCR4 | NM_003467.2 | 1336-1435 |
| DEK | NM_003472.3 | 2301-2400 |
| EPAS1 | NM_001430.3 | 4247-4346 |
| EPO | NM_000799.2 | 1056-1155 |
| EXOG | NM_005107.3 | 1143-1242 |
| EZH2 | NM_004456.4 | 31-130 |
| FAM180A | NM_205855.3 | 1171-1270 |
| FAM65B | NM_014722.3 | 315-414 |
| FAM65C | NM_080829.2 | 4059-4158 |
| GFRA2 | NM_001495.4 | 73-172 |
| GLI1 | NM_005269.1 | 2886-2985 |
| HAGHL | NM_032304.2 | 472-571 |
| HIF1A | NM_001530.2 | 1986-2085 |
| HMGA1 | NM_145904.1 | 872-971 |
| HRH2 | NM_022304.2 | 1292-1391 |
| HSPB7 | NM_014424.4 | 1941-2040 |
| IGFBP1 | NM_000596.2 | 761-860 |
| INHBB | NM_002193.2 | 1970-2069 |
| ITGB8 | NM_002214.2 | 392-491 |
| KCNIP3 | NM_001034914.1 | 2086-2185 |
| KLHL3 | NM_017415.2 | 3271-3370 |
| KNDC1 | NM_152643.6 | 6335-6434 |
| LAMB1 | NM_002291.2 | 5605-5704 |

TABLE 8-continued

Probes used in NanoString nCounter code set

| Gene symbol | Accession | Probe position |
|---|---|---|
| LOX | NM_002317.5 | 311-410 |
| LYPD1 | NM_144586.5 | 301-400 |
| MCAM | NM_006500.2 | 1516-1615 |
| MCIDAS | NM_001190787.1 | 1877-1976 |
| MEST | NM_001253902.1 | 1172-1271 |
| MRS2 | NM_020662.2 | 2484-2583 |
| NFASC | NM_001160333.1 | 93-192 |
| NPTX1 | NM_002522.3 | 4786-4885 |
| PASK | NM_015148.3 | 2620-2719 |
| PFN2 | NM_002628.4 | 1121-1220 |
| PHYHIP | NM_014759.3 | 2817-2916 |
| PICALM | NM_001206946.1 | 2310-2409 |
| PKNOX2 | NM_022062.2 | 2661-2760 |
| PLAG1 | NM_001114635.1 | 2427-2526 |
| POSTN | NM_006475.2 | 488-587 |
| PPA2 | NM_006903.4 | 903-1002 |
| PPAPDC3 | NM_032728.3 | 1381-1480 |
| PRICKLE1 | NM_153026.1 | 1336-1435 |
| PRR5 | NM_015366.3 | 1636-1735 |
| PTHLH | NM_198965.1 | 686-785 |
| PTPRJ | NM_001098503.1 | 1716-1815 |
| RASGEF1B | NM_152545.2 | 96-195 |
| RDH13 | NM_138412.3 | 533-632 |
| RGL2 | NM_001243738.1 | 2765-2864 |
| SLC36A4 | NM_152313.3 | 2556-2655 |
| SLC6A3 | NM_001044.4 | 703-802 |
| SLCO5A1 | NM_030958.2 | 3544-3643 |
| SLITRK4 | NM_001184750.2 | 7440-7539 |
| SORCS3 | NM_014978.2 | 4684-4783 |
| ST3GAL5 | NM_001042437.1 | 311-410 |
| SVIP | NM_148893.1 | 47-146 |
| TBC1D4 | NM_014832.2 | 4155-4254 |
| TMEM30B | NM_001017970.2 | 2421-2520 |
| TPST2 | NM_001008566.1 | 1401-1500 |
| VGLL4 | NM_001128219.1 | 1611-1710 |
| WFIKKN1 | NM_053284.2 | 913-1012 |
| ZKSCAN3 | NM_001242895.1 | 1577-1676 |
| ZKSCAN8 | NM_001278119.1 | 3049-3148 |
| ZSCAN16 | NM_025231.1 | 97-196 |
| ZSCAN9 | NM_001199479.1 | 1519-1618 |

RNA prepared from a total of 21 tumor models were analyzed using the NanoString assay, and the RNA samples are listed in Table 9. The models are categorized according to their responses to treatment with Compound 15, as listed in Table 2. One of the tumors with intermediate sensitivity to Compound 15 (Tumor 14 in Table 2) was not analyzed because it was derived from the same patient as Tumor 13 (Table 2). The NanoString analysis included 5 sensitive, 4 intermediate, and 3 resistant tumors that had not been analyzed by RNA sequencing previously.

TABLE 9

Tumor RNA samples used in gene expression analyses using NanoString nCounter code set

| Sample for NanoString | Response to Compound 15 | Analyzed by RNA Sequencing | Tumor listed in Table 2 |
|---|---|---|---|
| 1 | Sensitive | Yes | 2 |
| 2 | Sensitive | Yes | 3 |
| 3 | Sensitive | No | 4 |
| 4 | Sensitive | No | 1 |
| 5 | Sensitive | Yes | 5 |
| 6 | Sensitive | Yes | 6 |
| 7 | Sensitive | Yes | 7 |
| 8 | Sensitive | No | 8 |
| 9 | Sensitive | No | 9 |
| 10 | Sensitive | No | 10 |
| 11 | Intermediate | No | 11 |
| 12 | Intermediate | No | 12 |

TABLE 9-continued

Tumor RNA samples used in gene expression analyses using NanoString nCounter code set

| Sample for NanoString | Response to Compound 15 | Analyzed by RNA Sequencing | Tumor listed in Table 2 |
|---|---|---|---|
| 13 | Intermediate | No | 13 |
| 14 | Intermediate | No | 15 |
| 15 | Resistant | Yes | 16 |
| 16 | Resistant | No | 17 |
| 17 | Resistant | Yes | 18 |
| 18 | Resistant | No | 19 |
| 19 | Resistant | Yes | 20 |
| 20 | Resistant | Yes | 21 |
| 21 | Resistant | No | 22 |

Figure 2:
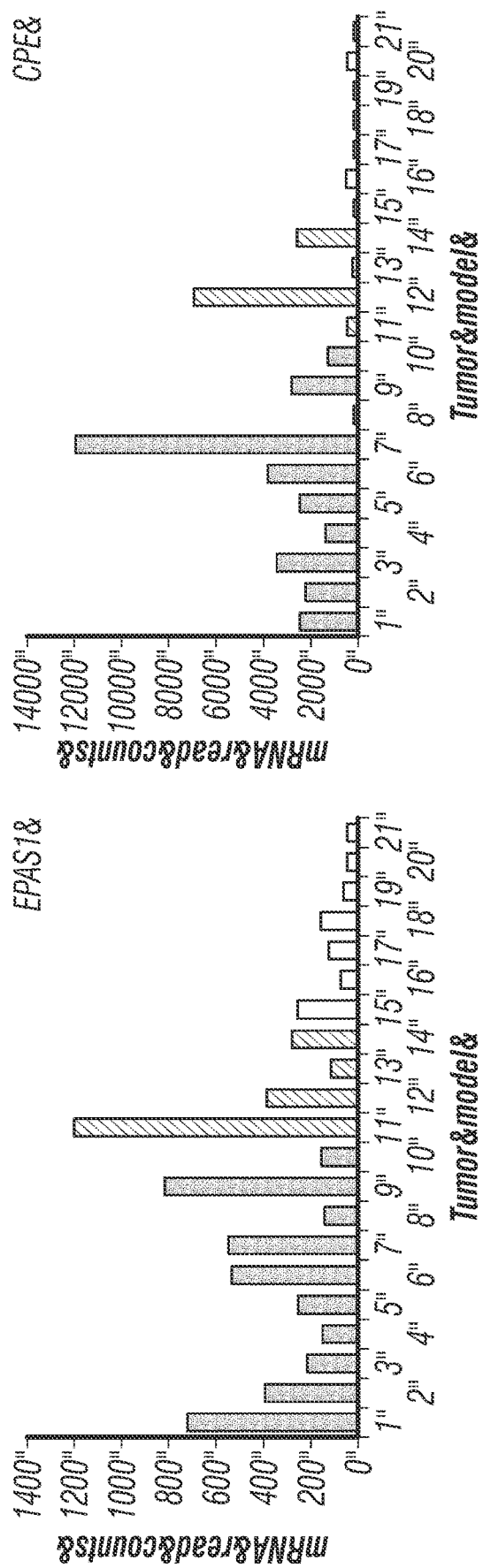
FIG. 2. Expression of genes that show higher relative expression in tumors that are sensitive to Compound 15. Tumors 1-10 (filled bars) are sensitive, whereas tumors 11-14 (hatched bars) and 15-21 (open bars) are intermediate and resistant tumors, respectively.
Figure 2:
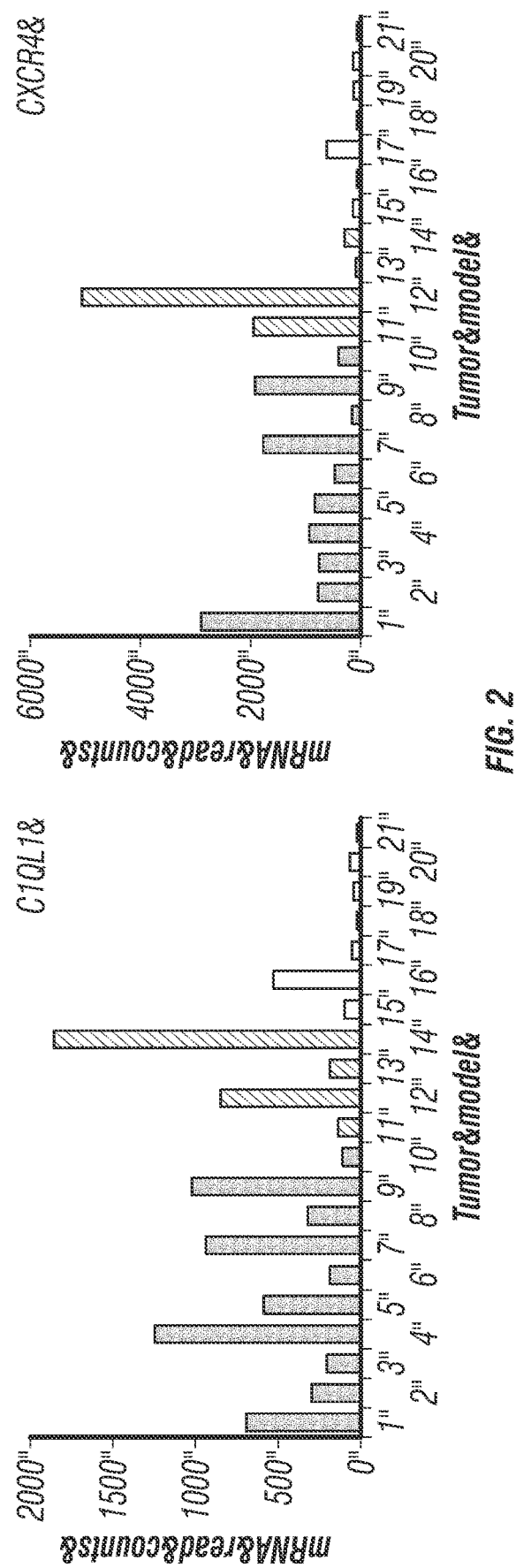
Figure 2:
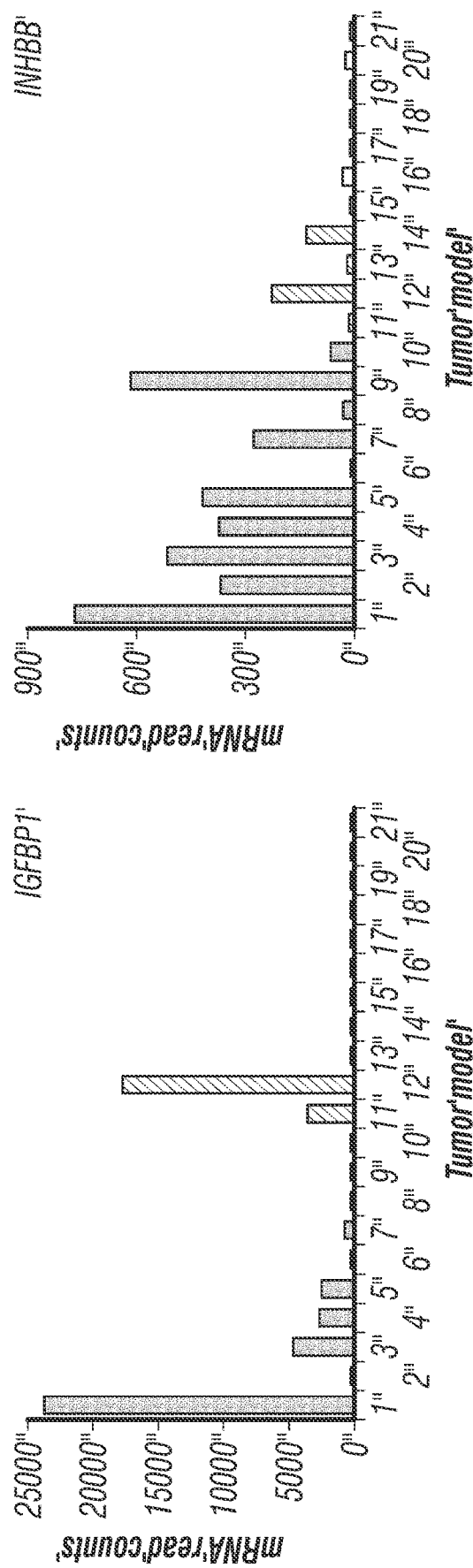
Figure 2:
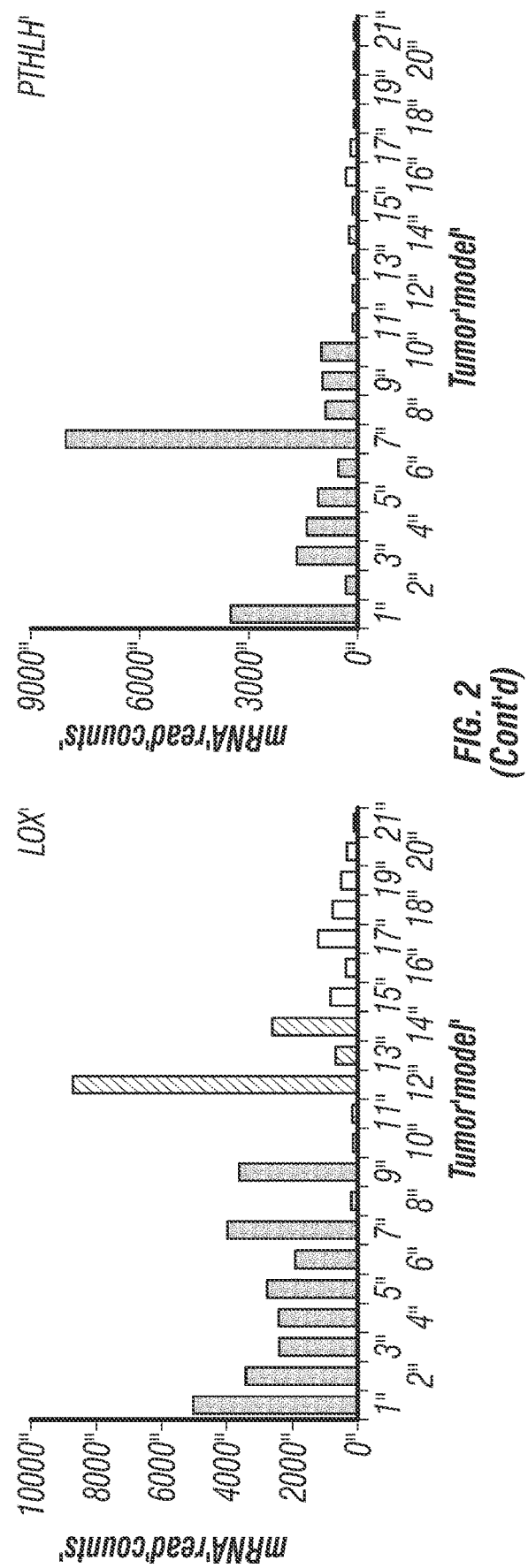
Figure 2:
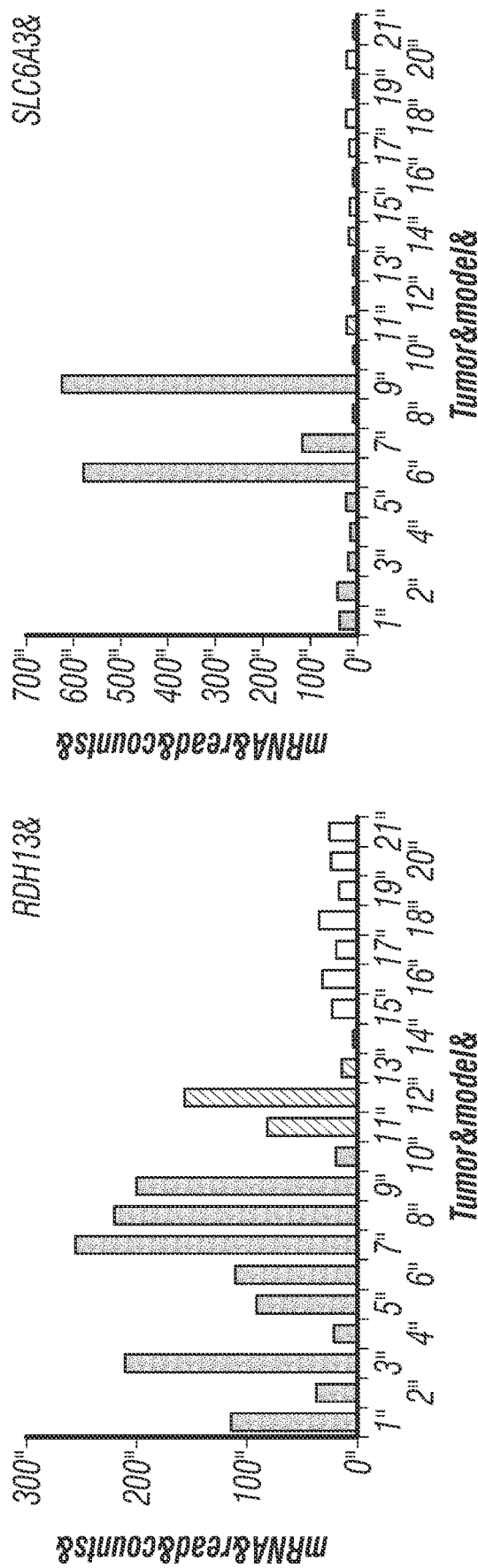
Figure 3:
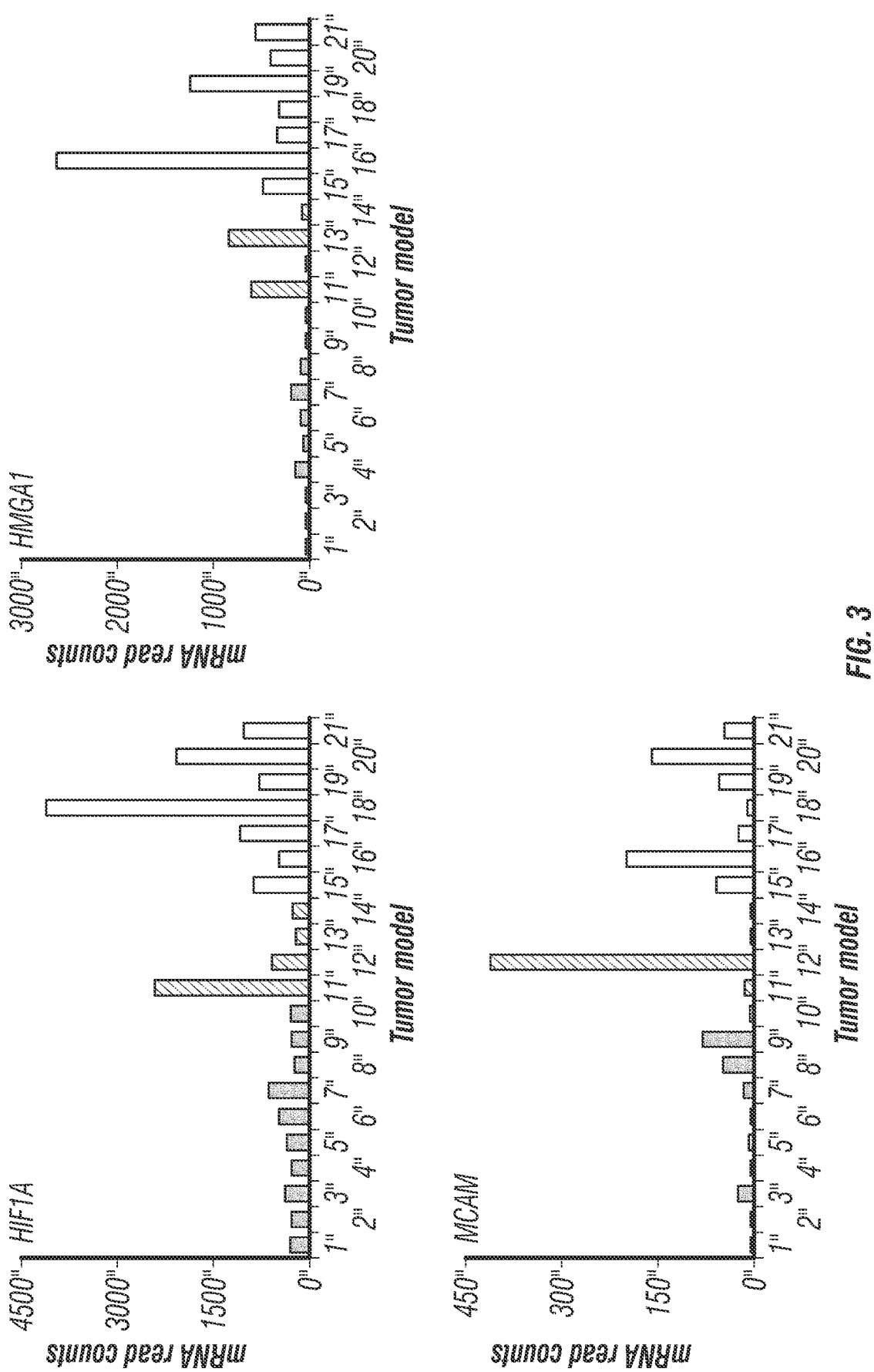
FIG. 3. Expression of genes that show higher relative expression in tumors that are resistant to treatment with Compound 15. Tumors 1-10 (filled bars) are sensitive, whereas tumors 11-14 (hatched bars) and 15-21 (open bars) are intermediate and resistant tumors, respectively.

Results of the NanoString analyses indicate that of the 75 genes in the signature, 14 genes have sufficient sensitivity and specificity for routine use in gene expression analyses using the NanoString nCounter methodology. The 14 genes are EPAS1, CPE, C1QL1, CXCR4, IGFBP1, INHBB, LOX, PTHLH, RDH13, SCL6A3, SORCS3, HIF1A, and HMGA1. FIG. 2 shows the NanoString data for the 11 genes that were expressed at high levels in the sensitivity tumors, compared to the resistant tumors. In FIG. 3 are the NanoString data for the 3 genes that show higher expression in the resistant tumors. The 14 genes show differential expression in the tumors that are sensitive or resistant to Compound 15, but not in the tumors with intermediate sensitivity to Compound 15.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods within the scope of these claims and their equivalents be covered thereby.

What is claimed is:

1. A method of treating a plurality of human renal cell carcinoma cells with a HIF-2α inhibitor, comprising:
    (a) assessing, by nucleic acid hybridization assay and/or protein assay, an expression level of EPAS1 in a biological sample comprising a cancer cell of the plurality of cells, or a portion thereof; and
    (b) administering an effective dose of the HIF-2α inhibitor to the plurality of cells if EPAS1 is present in the sample at an increased expression level as compared to a cancer cell that is resistant to an HIF-2α inhibitor.

2. The method of claim 1, wherein the expression level of the EPAS1 expression level is assessed by detecting a level of mRNA transcribed from the EPAS1.

3. The method of claim 1, wherein the expression level of the EPAS1 expression level is assessed by detecting a level of cDNA produced from reverse transcription of mRNA transcribed from EPAS1.

4. The method of claim 1, wherein the expression level of the EPAS1 expression level is assessed by detecting a level of polypeptide encoded by the at least one biomarker.

5. The method of claim 1, wherein the biological sample is a tissue sample.

* * * * *

UNITED STATES PATENT AND TRADEMARK OFFICE
CERTIFICATE OF CORRECTION

PATENT NO. : 12,234,516 B2
APPLICATION NO. : 17/206895
DATED : February 25, 2025
INVENTOR(S) : Min Soo Kim et al.

Page 1 of 1

It is certified that error appears in the above-identified patent and that said Letters Patent is hereby corrected as shown below:

In the Claims

In Claim 1, Column 438, Line 17, after "if" and before "EPAS1", insert --the--.

Signed and Sealed this
Second Day of September, 2025

Coke Morgan Stewart
*Acting Director of the United States Patent and Trademark Office*